United States Patent
Lee et al.

(10) Patent No.: US 11,512,105 B2
(45) Date of Patent: Nov. 29, 2022

(54) ORGANOMETALLIC COMPOUND, ORGANIC LIGHT-EMITTING DEVICE INCLUDING THE ORGANOMETALLIC COMPOUND, AND DIAGNOSTIC COMPOSITION INCLUDING THE ORGANOMETALLIC COMPOUND

(71) Applicant: Samsung Electronics Co., Ltd., Suwon-si (KR)

(72) Inventors: Kum Hee Lee, Suwon-si (KR); Seungyeon Kwak, Suwon-si (KR); Yoonhyun Kwak, Seoul (KR); Ohyun Kwon, Seoul (KR); Aram Jeon, Suwon-si (KR); Whail Choi, Seoul (KR); Kyuyoung Hwang, Anyang-si (KR); Byoungki Choi, Hwaseong-si (KR); Hyeonho Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/840,871

(22) Filed: Apr. 6, 2020

(65) Prior Publication Data

US 2020/0331940 A1 Oct. 22, 2020

(30) Foreign Application Priority Data

Apr. 16, 2019 (KR) .................. 10-2019-0044480

(51) Int. Cl.
| | | |
|---|---|---|
| C07F 15/00 | (2006.01) | |
| H01L 51/00 | (2006.01) | |
| C09K 11/06 | (2006.01) | |
| C07D 293/10 | (2006.01) | |
| C07D 329/00 | (2006.01) | |
| C07D 339/00 | (2006.01) | |
| C07D 419/02 | (2006.01) | |

(52) U.S. Cl.
CPC ........ *C07F 15/0033* (2013.01); *C07D 293/10* (2013.01); *C07D 329/00* (2013.01); *C07D 339/00* (2013.01); *C07D 419/02* (2013.01); *C09K 11/06* (2013.01); *H01L 51/0085* (2013.01); *C09K 2211/185* (2013.01)

(58) Field of Classification Search
CPC ...... C07F 15/0033; H01L 51/50; C09K 11/06
USPC .............. 546/10, 2; 313/504; 252/301.18
See application file for complete search history.

(56) References Cited

U.S. PATENT DOCUMENTS

| | | |
|---|---|---|
| 7,445,857 B2 | 11/2008 | Shen et al. |
| 9,359,549 B2 | 6/2016 | Rayabarapu et al. |
| 9,859,510 B2 | 1/2018 | Boudreault et al. |
| 10,003,035 B2 | 6/2018 | Hwang et al. |
| 10,205,106 B2 | 2/2019 | Stoessel et al. |
| 10,340,466 B2 | 7/2019 | Lin et al. |
| 2011/0285275 A1 | 11/2011 | Huang et al. |
| 2015/0097169 A1 | 4/2015 | Xia et al. |
| 2015/0171348 A1 | 6/2015 | Stoessel et al. |
| 2016/0164006 A1 | 6/2016 | Chao et al. |
| 2017/0294596 A1 | 10/2017 | Ishibe et al. |
| 2019/0112324 A1 | 4/2019 | Kim et al. |
| 2019/0326527 A1 | 10/2019 | Choi et al. |
| 2020/0328360 A1 | 10/2020 | Lee et al. |

FOREIGN PATENT DOCUMENTS

| | | |
|---|---|---|
| EP | 3173418 A1 | 5/2017 |
| EP | 3626724 A1 | 3/2020 |
| EP | 3637489 A1 | 4/2020 |
| KR | 1020120026486 A | 3/2012 |
| KR | 1020150039846 A | 4/2015 |
| KR | 1020160064951 A | 6/2016 |
| KR | 1020170115872 A | 10/2017 |
| KR | 1020190042459 A | 4/2019 |
| KR | 1020190123228 A | 10/2019 |
| KR | 1020200120185 A | 10/2020 |
| TW | I242999 B | 12/1993 |
| WO | 2014023377 A2 | 2/2014 |
| WO | 2018062758 A1 | 4/2018 |

OTHER PUBLICATIONS

Chemical Communications (Cambridge, United Kingdom) (2013), 49(15), 1497-1499.
Extended European search report issued by the European Patent Office dated Aug. 25, 2020 in the examination of the European Patent Application No. 20168152.5, which corresponds to the U.S. Application above.
Tian-Yi Li, et al., Coordination Chemistry Reviews, 374, (2018) 55-92.
English Abstract of KR 10-2020-0120185.

*Primary Examiner* — Charanjit Aulakh
(74) *Attorney, Agent, or Firm* — Cantor Colburn LLP

(57) ABSTRACT

An organometallic compound represented by Formula 1, an organic light-emitting device including the organometallic compound, and a diagnostic composition including the organometallic compound:

$$M(L_1)_{n1}(L_2)_{n2},\qquad \text{Formula 1}$$

wherein, in Formula 1, M, $L_1$, $L_2$, n1, and n2 are each independently the same as described herein.

16 Claims, 1 Drawing Sheet

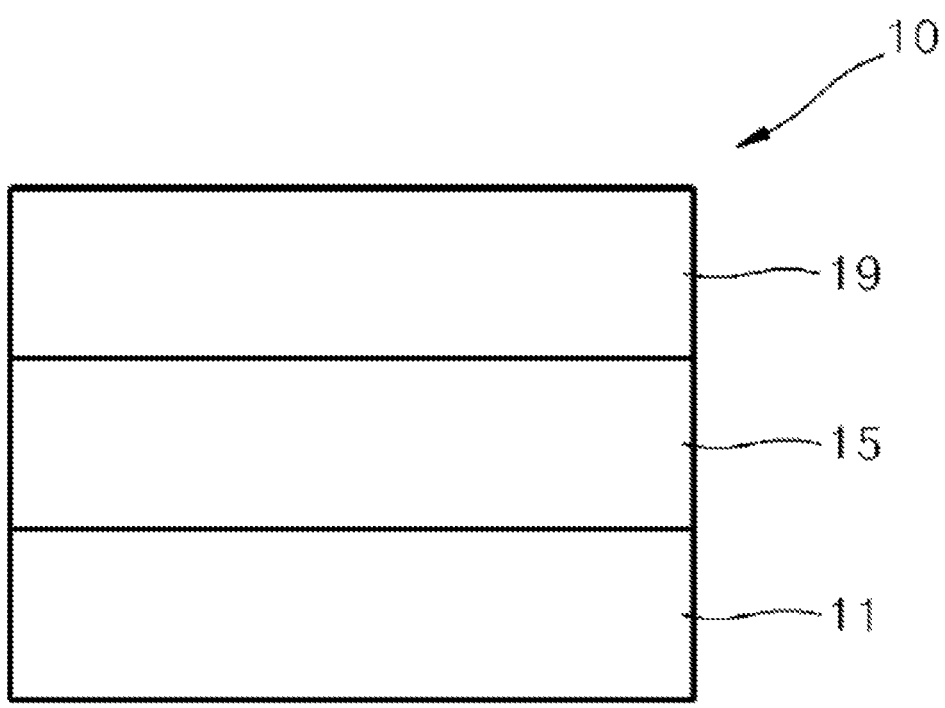

ORGANOMETALLIC COMPOUND, ORGANIC LIGHT-EMITTING DEVICE INCLUDING THE ORGANOMETALLIC COMPOUND, AND DIAGNOSTIC COMPOSITION INCLUDING THE ORGANOMETALLIC COMPOUND

CROSS-REFERENCE TO RELATED APPLICATION

This application claims the priority and the benefit of Korean Patent Application No. 10-2019-0044480, filed on Apr. 16, 2019, in the Korean Intellectual Property Office, and all the benefits accruing therefrom under 35 U.S.C. § 119, the contents of which in their entirety are herein incorporated by reference.

BACKGROUND

1. Field

An embodiment relates to an organometallic compound, an organic light-emitting device including the organometallic compound, and a diagnostic composition including the organometallic compound.

2. Description of the Related Art

Organic light-emitting devices are self-emission devices, which have excellent characteristics in terms of a viewing angle, response time, brightness, driving voltage, and response speed, and produce full-color images.

In an example, an organic light-emitting device includes an anode, a cathode, and an organic layer between the anode and the cathode, wherein the organic layer includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

Luminescent compounds may be used to monitor, sense, or detect a variety of biological materials including cells and proteins. An example of the luminescent compounds is a phosphorescent luminescent compound.

SUMMARY

Aspects of the present disclosure provide a novel organometallic compound, an organic light-emitting device including the same, and a diagnostic composition including the novel organometallic compound.

Additional aspects will be set forth in part in the description which follows and, in part, will be apparent from the description, or may be learned by practice of the presented embodiments.

An aspect of the present disclosure provides an organometallic compound represented by Formula 1 below:

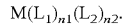
Formula 1

In Formula 1,
M may be a transition metal,
$L_1$ may be a ligand represented by Formula 2,
n1 may be 1, 2, or 3, wherein, when n1 is 2 or more, two or more $L_1$(s) may be identical to or different from each other,
$L_2$ may be a monodentate ligand, a bidentate ligand, a tridentate ligand, or a tetradentate ligand,
n2 may be 0, 1, 2, 3, or 4, wherein, when n2 is 2 or more, two or more $L_2$(s) may be identical to or different from each other, and
$L_1$ and $L_2$ may be different from each other:

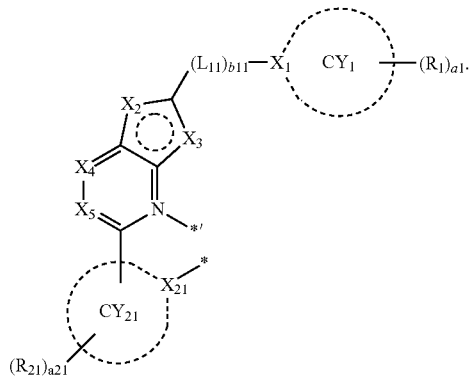
Formula 2

In Formula 2,
$X_1$ may be C, N, Si, or P,
$X_{21}$ may be C or N,
ring $CY_1$ and ring $CY_{21}$ may each independently be a $C_5$-$C_{30}$ carbocyclic group or a $C_2$-$C_{30}$ heterocyclic group,
$X_2$ and $X_3$ may each independently be O, S, Se, or C($R_2$), wherein $X_2$ or $X_3$ may be O, S, or Se,
$X_4$ may be N or C($R_4$),
$X_5$ may be N or C($R_5$),
$R_1$, $R_2$, $R_4$, $R_5$, and $R_{21}$ may each independently be hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group (e.g., a substituted or unsubstituted phenyl($C_1$-$C_{20}$ alkyl) group), a substituted or unsubstituted heteroaryl group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), —P(=O)($Q_8$)($Q_9$) or —P($Q_8$)($Q_9$),
a1 and a21 may each independently be an integer from 0 to 20,
ring $CY_1$ and $R_2$ may not be linked to each other, and $R_1$ and $R_2$ may not be linked to each other, $L_{11}$ may be a $C_5$-$C_{30}$ carbocyclic group that is unsubstituted or substituted with at least one $R_{10a}$ group or a $C_2$-$C_{30}$ heterocyclic group that is unsubstituted or substituted with at least one $R_{10a}$ group, b11 may be an integer from 0 to 10, wherein, when b11 is 0, a group represented by *-$(L_{11})_{b11}$-*' may be a single bond, and when b11 is 2 or more, two or more $L_{11}$(s) may be identical to or different from each other, two or more of a plurality of neighboring $R_{21}$(s) may optionally be linked to form a $C_5$-$C_{30}$ carbocyclic group that is unsubstituted or substituted with at least one $R_{10a}$ group or a $C_2$-$C_{30}$ heterocyclic group that is unsubstituted or substituted with at least one $R_{10a}$ group, $R_{10a}$ may be the same as defined in connection with $R_{21}$,

* and *' each indicate a binding site to M in Formula 1, a substituent(s) of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group (e.g., the substituted phenyl($C_1$-$C_{20}$ alkyl) group), the substituted $C_2$-$C_{60}$ heteroarylalkyl group, the substituted heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a phenyl($C_1$-$C_{20}$ alkyl) group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_{60}$ heteroaryl group, a monovalent non-aromatic condensed polycyclic group, or a monovalent non-aromatic condensed heteropolycyclic group, a $C_6$-$C_{60}$ arylthio group, a $C_7$-$C_{60}$ arylalkyl group (e.g., a phenyl($C_1$-$C_{20}$ alkyl) group), a $C_{60}$ heteroaryl group, a monovalent non-aromatic condensed polycyclic group, or a monovalent non-aromatic condensed heteropolycyclic group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group, or any combination thereof, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_1$-$C_{60}$ heteroaryl group, a monovalent non-aromatic condensed polycyclic group, or a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{28})(Q_{29})$, or any combination thereof;

—$N(Q_{31})(Q_{32})$, —$Si(Q_{33})(Q_{34})(Q_{35})$, —$B(Q_{36})(Q_{37})$, or —$P(=O)(Q_{38})(Q_{39})$; or any combination thereof, and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group, or any combination thereof, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_1$-$C_{60}$ heteroaryl group, a monovalent non-aromatic condensed polycyclic group, or a monovalent non-aromatic condensed heteropolycyclic group.

Another aspect of the present disclosure provides an organic light-emitting device including: a first electrode; a second electrode; and an organic layer between the first electrode and the second electrode and including an emission layer, wherein the organic layer includes at least one organometallic compound represented by Formula 1.

The organometallic compound represented by Formula 1 included in the emission layer of the organic layer may act as a dopant.

Another aspect of the present disclosure provides a diagnostic composition including at least one organometallic compound represented by Formula 1.

BRIEF DESCRIPTION OF THE DRAWING

These and/or other aspects will become apparent and more readily appreciated from the following description of the embodiments, taken in conjunction with FIGURE which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer, or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of another feature, region, integer, step, operation, element, component, and/or groups thereof.

Furthermore, relative terms, such as "lower" or "bottom" and "upper" or "top," may be used herein to describe one element's relationship to another element as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An aspect of the present disclosure provides an organometallic compound represented by Formula 1 below:

$$M(L_1)_{n1}(L_2)_{n2}.$$ Formula 1

M in Formula 1 may be a transition metal.

For example, M may be a first-row transition metal, a second-row transition metal, or a third-row transition metal of the Periodic Table of Elements.

In an embodiment, M may be iridium (Ir), platinum (Pt), osmium (Os), titanium (Ti), zirconium (Zr), hafnium (Hf), europium (Eu), terbium (Tb), thulium (Tm), or rhodium (Rh).

In an embodiment, M may be Ir, Pt, Os, or Rh, but embodiments of the present disclosure are not limited thereto.

$L_1$ in Formula 1 may be a ligand represented by Formula 2, and n1 in Formula 1 indicates the number of $L_1$ in Formula 1 and may be 1, 2, or 3. When n1 is 2 or more, two or more $L_1$(s) may be identical to or different from each other:

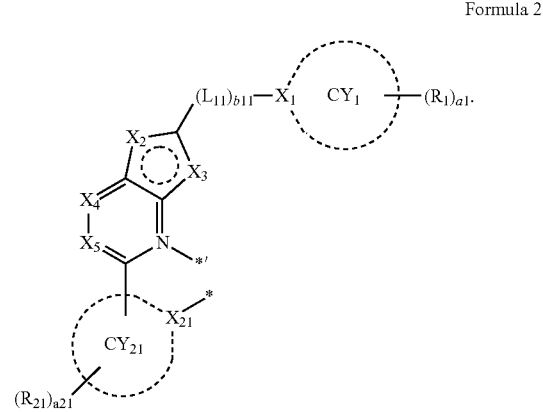

Formula 2

Formula 2 may be the same as described below.

For example, n1 may be 1 or 2.

$L_2$ in Formula 1 may be a monodentate ligand, a bidentate ligand, a tridentate ligand, or a tetradentate ligand, and n2 in Formula 1 indicates the number of $L_2$ and may be 0, 1, 2, 3, or 4. When n2 is 2 or more, two or more $L_2$(s) may be identical to or different from each other. $L_2$ may be the same as described below.

For example, n2 in Formula 1 may be 1 or 2.

In Formula 1, $L_1$ and $L_2$ may be different from each other.

In an embodiment, M may be Ir or Os, and the sum of n1 and n2 may be 3 or 4; or M may be Pt, and the sum of n1 and n2 may be 2.

In Formula 2, $X_1$ may be C, N, Si, or P, and $X_{21}$ may be C or N.

For example, in Formula 2, $X_{21}$ may be C.

In Formula 2, ring $CY_1$ and ring $CY_{21}$ may each independently be a $C_5$-$C_{30}$ carbocyclic group or a $C_2$-$C_{30}$ heterocyclic group.

For example, ring $CY_1$ and ring $CY_{21}$ may each independently be i) a first ring, ii) a second ring, iii) a condensed ring in which at least two first rings are condensed with each other, iv) a condensed ring in which at least two second rings are condensed with each other, or v) a condensed ring in which at least one first ring and at least one second ring are condensed with each other.

The first ring may be a cyclopentane group, a cyclopentadiene group, a furan group, a thiophene group, a pyrrole group, a silole group, an indene group, a benzofuran group, a benzothiophene group, an indole group, a benzosilole group, an oxazole group, an isoxazole group, an oxadiazole group, an isoxadiazole group, an oxatriazole group, an isoxatriazole group, a thiazole group, an isothiazole group, a thiadiazole group, an isothiadiazole group, a thiatriazole group, an isothiatriazole group, a pyrazole group, an imidazole group, a triazole group, a tetrazole group, an azasilole group, a diazasilole group, or a triazasilole group.

The second ring may be an admantane group, a norbornane group, a norbornene group, a cyclohexane group, a cyclohexene group, a benzene group, a pyridine group, a pyrimidine group, a pyrazine group, a pyridazine group, or a triazine group.

In an embodiment, ring $CY_1$ and ring $CY_{21}$ may each independently be a cyclopentene group, a cyclohexene group, a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, but embodiments of the present disclosure are not limited thereto.

In an embodiment, ring $CY_1$ may be a cyclopentane group, a cyclohexane group, a cycloheptane group, a cyclooctane group, an adamantane group, a norbornane group, a norbornene group, a cyclopentene group, a cyclohexene group, a cycloheptene group, a benzene group, a naphthalene group, a fluorene group, a phenanthrene group, an anthracene group, a fluoranthene group, a triphenylene group, a pyrene group, a chrysene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an isoindole group, an indole group, an indazole group, a purine group, a quinoline group, an isoquinoline group, a benzoquinoline group, a quinoxaline group, a quinazoline group, a cinnoline group, a carbazole group, a phenanthroline group, a benzimidazole group, a benzofuran group, a benzothiophene group, an isobenzothiazole group, a benzoxazole group, an isobenzoxazole group, a triazole group a tetrazole group, an oxadiazole group, a triazine group, a dibenzofuran group, a dibenzothiophene group, a dibenzosilole group, a benzocarbazole group, a dibenzocarbazole group, an imidazopyridine group, or an imidazopyrimidine group, but embodiments of the present disclosure are not limited thereto.

In Formula 2, $X_2$ and $X_3$ may each independently be O, S, Se, or $C(R_2)$, wherein $X_2$ or $X_3$ may be O, S, or Se.

For example, in Formula 2, i) $X_2$ may be O, S, or Se, and $X_3$ may be $C(R_2)$; or ii) $X_2$ may be $C(R_2)$, and $X_3$ may be O, S, or Se.

In Formula 2, $X_4$ may be N or $C(R_4)$, and $X_5$ may be N or $C(R_5)$.

For example, $X_4$ may be $C(R_4)$, and $X_5$ may be $C(R_5)$.

In Formula 2, $R_1$, $R_2$, $R_4$, $R_5$, $R_{21}$, and $R_{10a}$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group (e.g., a substituted or unsubstituted phenyl($C_1$-$C_{20}$ alkyl) group), a substituted or unsubstituted $C_1$-$C_{60}$ heteroaryl group, substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), —P(=O)($Q_8$)($Q_9$) or —P($Q_8$)($Q_9$), wherein $Q_1$ to $Q_9$ are each the same as described above.

For example, $R_1$, $R_2$, $R_4$, $R_5$, $R_{21}$, and $R_{10a}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, or any combination thereof; a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a cyclooctenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a cyclooctenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —Si($Q_{33}$)($Q_{34}$)($Q_{35}$), or any combination thereof; or —N($Q_1$)($Q_2$), —Si($Q_3$)($Q_4$)($Q_5$), —B($Q_6$)($Q_7$), —P(=O)($Q_8$)($Q_9$), or —P($Q_8$)($Q_9$), and $Q_1$ to $Q_9$ and $Q_{33}$ to $Q_{35}$ may each independently be:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each unsubstituted or substituted with deuterium, a $C_1$-$C_{10}$ alkyl group, a phenyl group, or any combination thereof, but embodiments of the present disclosure are not limited thereto.

In Formula 2, a1 and a21 each indicate the number of $R_1$ and the number of $R_{21}$, respectively, and may each independently be an integer from 0 to 20 (for example, an integer from 0 to 10 or an integer from 0 to 5). When a1 is 2 or more, two or more $R_1$(s) may be identical to or different from each other, and when a21 is 2 or more, two or more $R_{21}$(s) may be identical to or different from each other.

In Formula 2, ring $CY_1$ and $R_2$ are not linked to each other, and $R_1$ and $R_2$ are not linked to each other.

In an embodiment, a group represented by

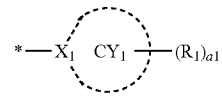

in Formula 2 may be a $C_{53}$-$C_{10}$ cycloalkenyl group, a $C_2$-$C_{10}$ heterocycloalkenyl group, a $C_6$-$C_{30}$ aryl group, a $C_2$-$C_{30}$ heteroaryl group, a monovalent non-aromatic condensed polycyclic group, or a monovalent non-aromatic condensed heteropolycyclic group, each unsubstituted or substituted with $R_1$(s) in the number of a1.

In Formula 2, $R_1$ and $R_2$ may each independently be:
hydrogen, deuterium, —F, —Cl, —Br, —I, a cyano group, or —$SF_5$; or a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, or a $C_2$-$C_{10}$ heterocycloalkenyl group, each unsubstituted or substituted with deuterium, —F, —Cl, —Br, —I, —$CD_3$, —$CD_2H$, —$CDH_2$, —$CF_3$, —$CF_2H$, —$CFH_2$, a cyano group, a $C_1$-$C_{20}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or any combination thereof, and a1 may be an integer from 0 to 10.

Detailed descriptions of a1, $R_1$, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{30}$ aryl group, a $C_2$-$C_{30}$ heteroaryl group, a monovalent non-aromatic condensed polycyclic group, and a monovalent non-aromatic condensed heteropolycyclic group are the same as described above.

In an embodiment, a group represented by

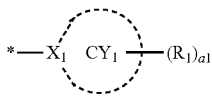

in Formula 2 may be a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with $R_1$(s) in the number of a1.

In Formula 2, $R_1$ and $R_2$ may each independently be:

hydrogen, deuterium, —F, —Cl, —Br, —I, a cyano group, or —$SF_5$; or a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonanyl group (an n-nonyl group), an isononanyl group (an isononyl group), a sec-nonanyl group (a sec-nonyl group), a tert-nonanyl group (a tert-nonyl group), an n-decanyl group, an isodecanyl group, a sec-decanyl group, a tert-decanyl group, a $C_1$-$C_{10}$ alkoxy, a cyclopentyl group, a cyclohexyl group, a cycloheptyl group, a cyclooctyl group, an adamantyl group, a norbornyl group, a norbornenyl group, a cyclopentenyl group, a cyclohexenyl group, or a cycloheptenyl group, each unsubstituted or substituted with deuterium, —F, —Cl, —Br, —I, —$CD_3$, —$CD_2H$, —$CDH_2$, —$CF_3$, —$CF_2H$, —$CFH_2$, a cyano group, a $C_1$-$C_{20}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or any combination thereof, and a1 may be an integer from 0 to 5, but embodiments of the present disclosure are not limited thereto.

In an embodiment, a group represented by

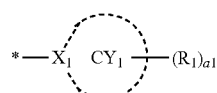

in Formula 2 may be a group represented by one of Formulae 10-13(1) to 10-13(18) or 10-13:

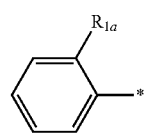

10-13(1)

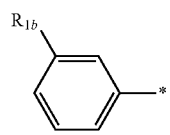

10-13(2)

10-13(3)

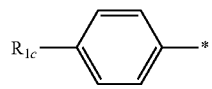

10-13(4)

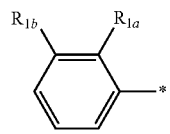

10-13(5)

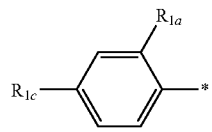

10-13(6)

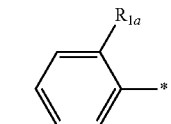

10-13(7)

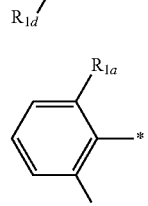

10-13(8)

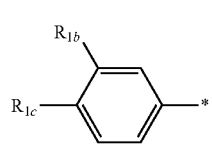

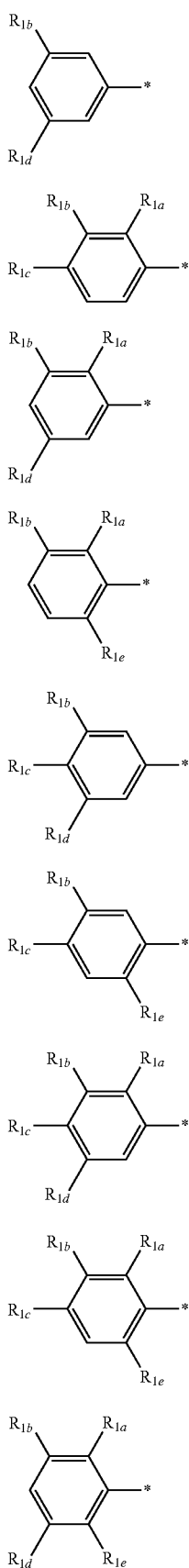

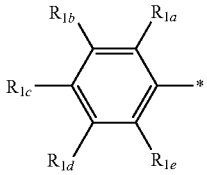

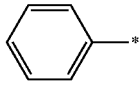

In Formulae 10-13(1) to 10-13(18) and 10-13, $R_{1a}$ to $R_{1e}$ are each independently the same as defined in connection with $R_1$, wherein $R_{1a}$ to $R_{1e}$ are not each hydrogen, and * indicates a binding site to a neighboring atom (e.g., carbon atom).

For example, a group represented by

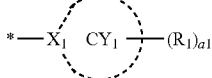

in Formula 2 may be a group represented by one of Formulae 10-13 to 10-240, wherein $R_1$, $R_2$, $R_4$, $R_5$, $R_{21}$, and $R_{10a}$ may each independently be hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, a group represented by one of Formulae 9-1 to 9-19, a group represented by one of Formulae 10-1 to 10-240, or —Si(Q$_3$)(Q$_4$)(Q$_5$) (wherein Q$_3$ to Q$_5$ are the same as described above), but embodiments of the present disclosure are not limited thereto:

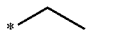

9-1

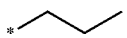

9-2

9-3

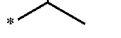

9-4

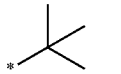

9-5

9-6

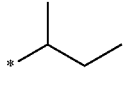

9-7


9-8

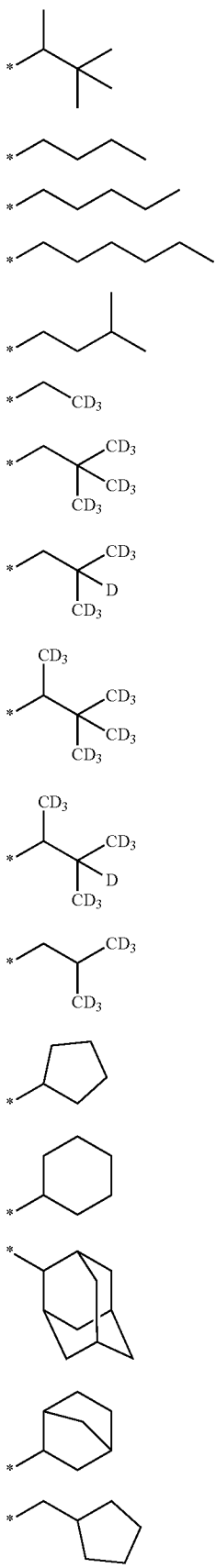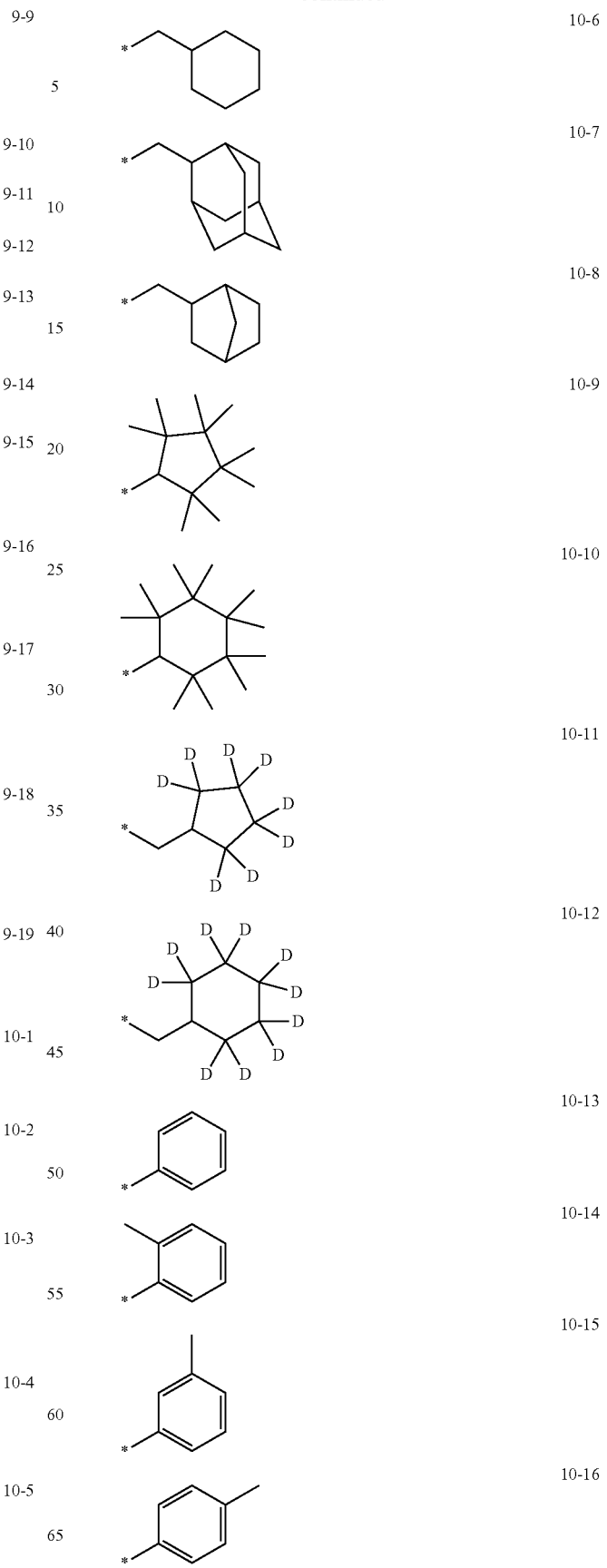

-continued
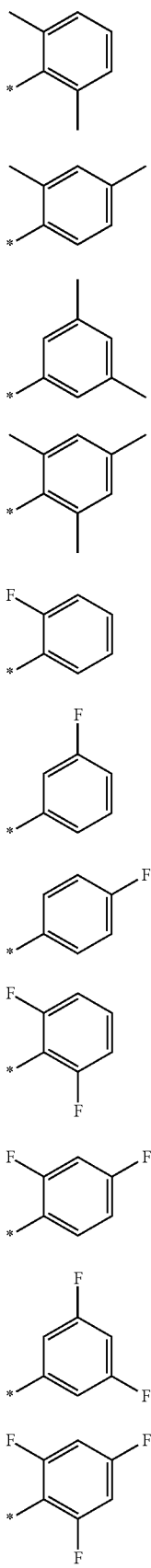
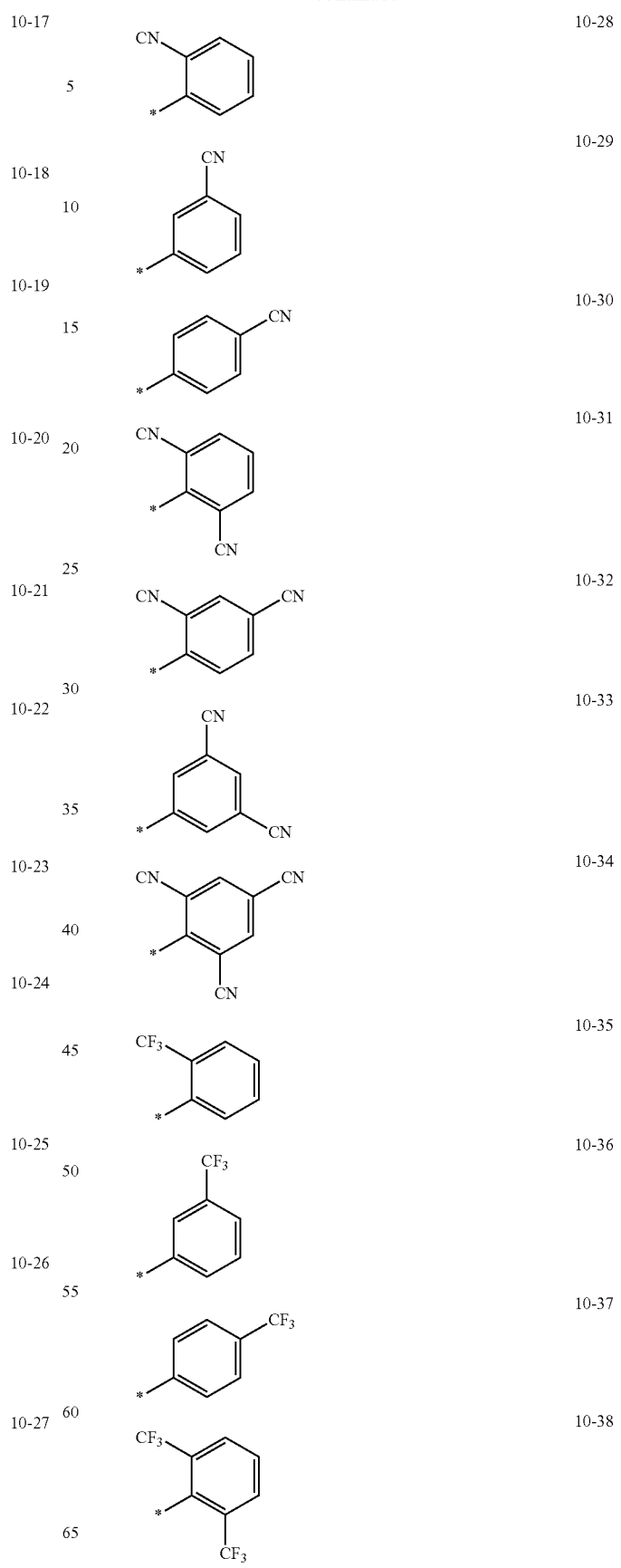

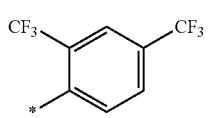
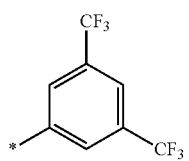
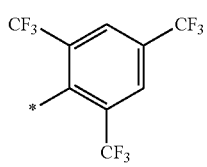
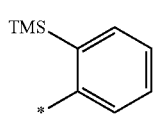
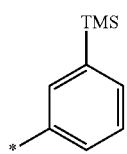
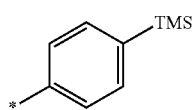
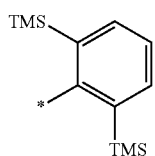
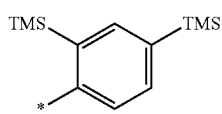
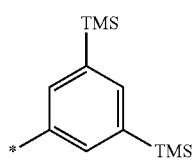
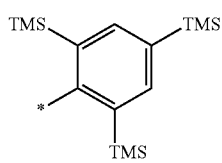
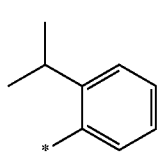
10-39
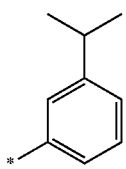
10-40
10-41
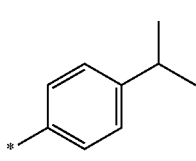
10-42
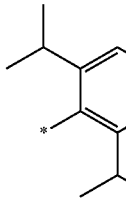
10-43
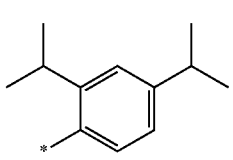
10-44
10-45
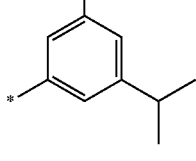
10-46
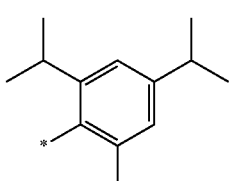
10-47
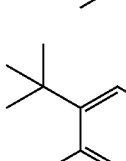
10-48
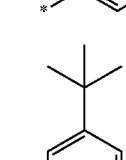
10-49
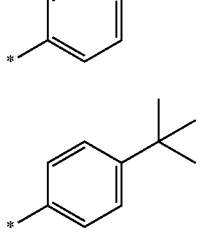
10-50
10-51
10-52
10-53
10-54
10-55
10-56
10-57
10-58

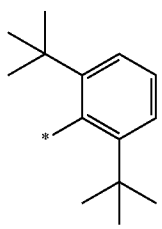
10-59
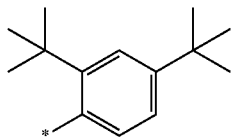
10-60
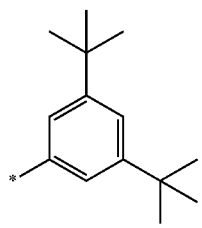
10-61
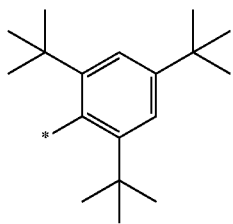
10-62
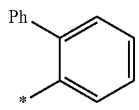
10-63
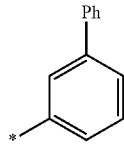
10-64
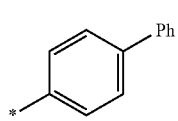
10-65
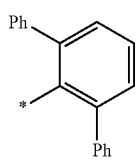
10-66
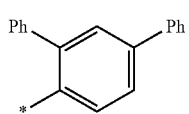
10-67
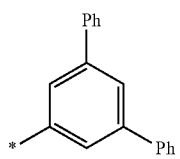
10-68

10-69
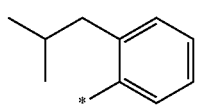
10-70
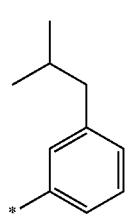
10-71
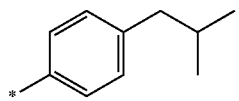
10-72
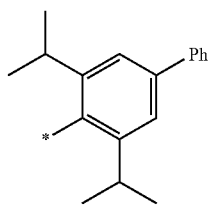
10-73
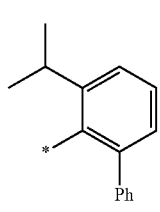
10-74
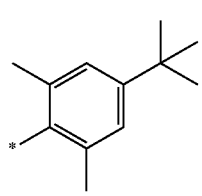
10-75

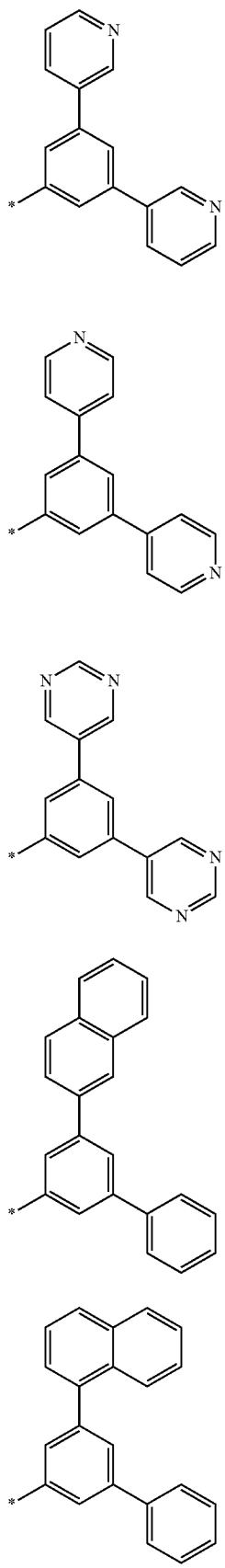

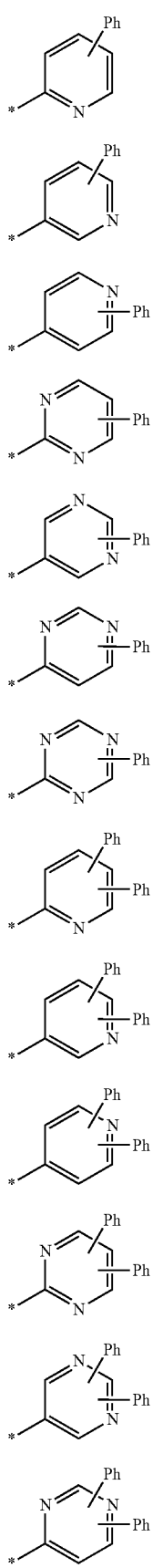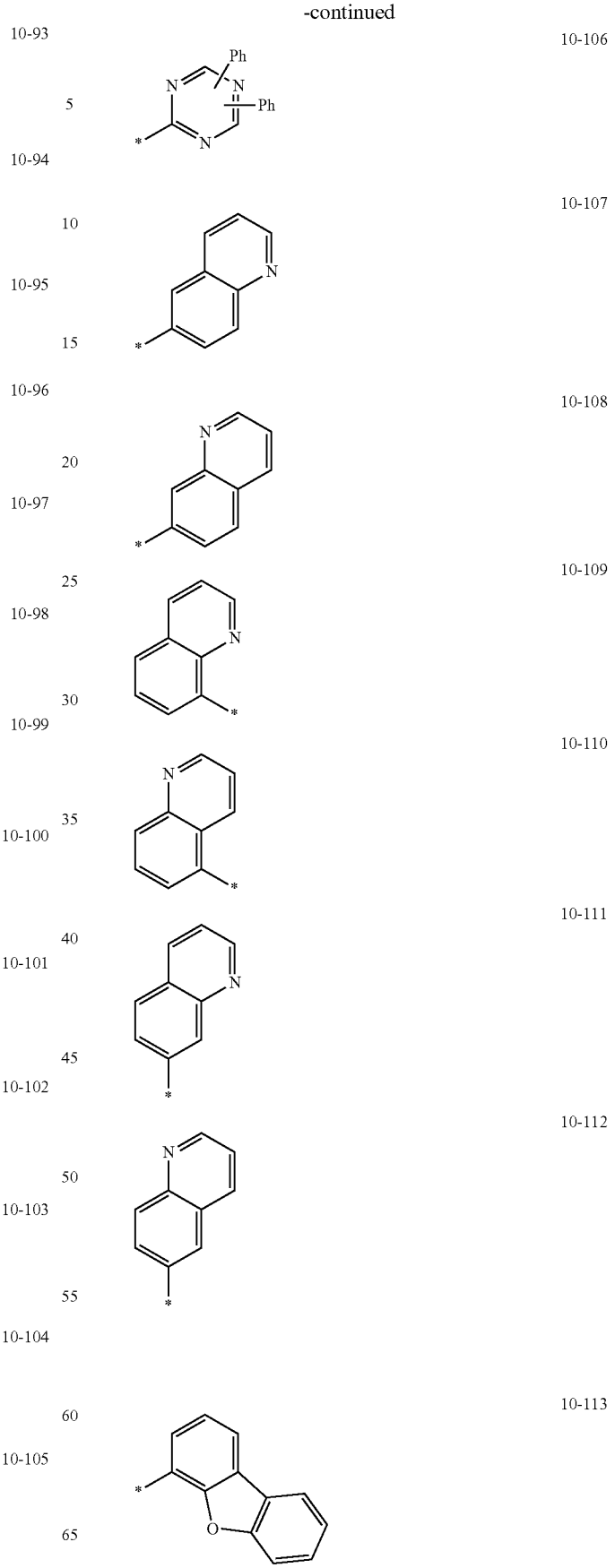

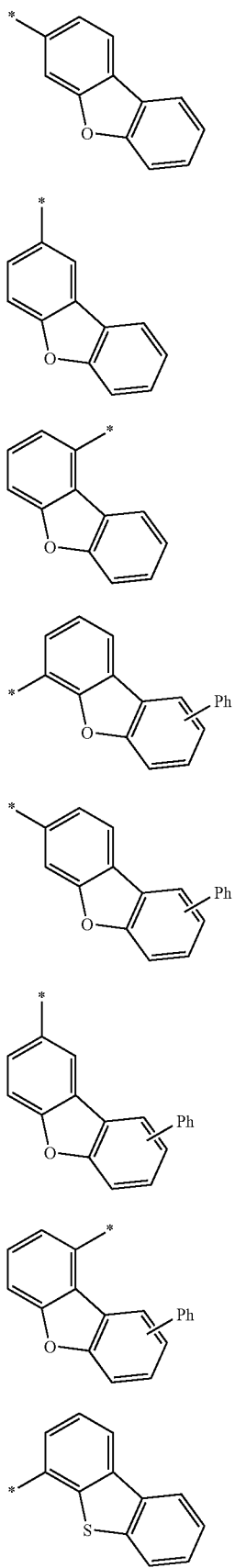
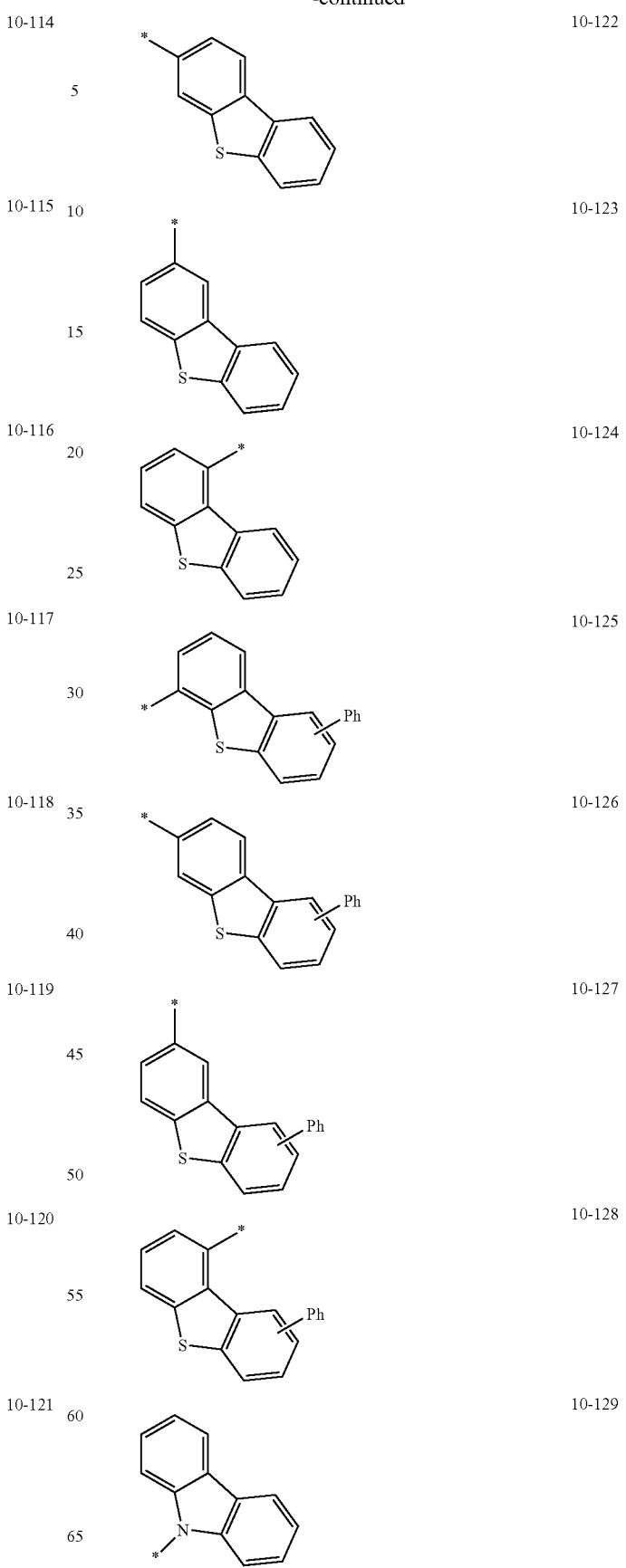

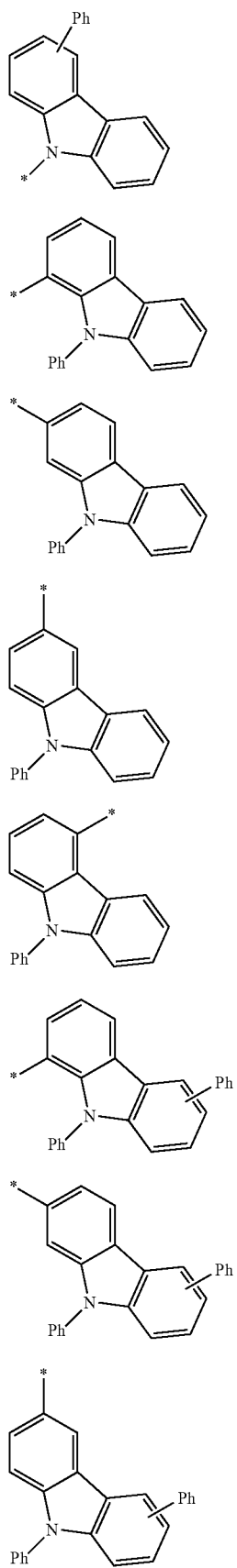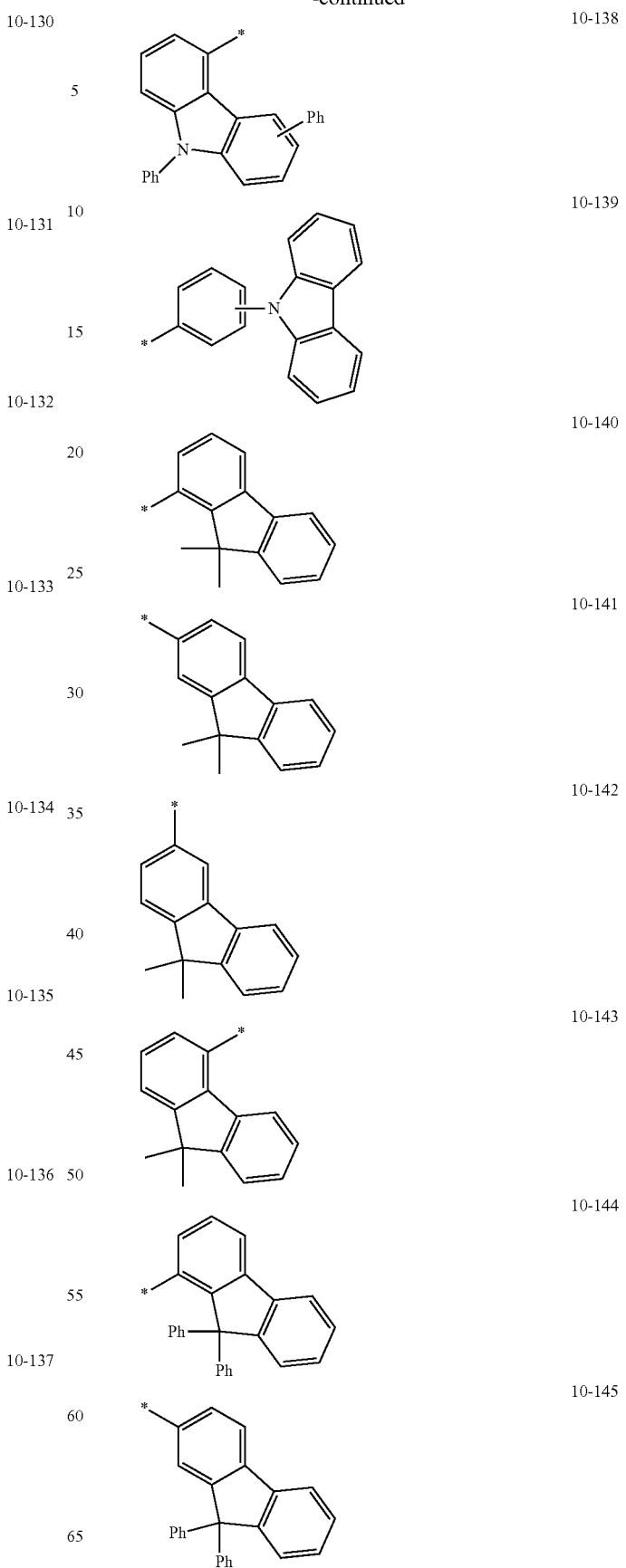

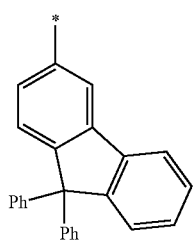
10-146
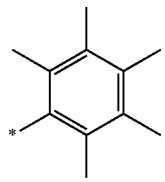
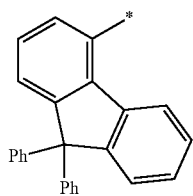
10-147
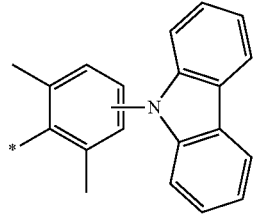
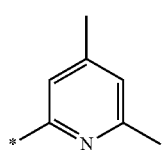
10-148
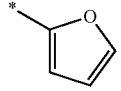
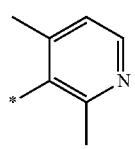
10-149
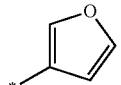
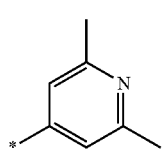
10-150
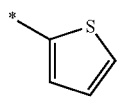
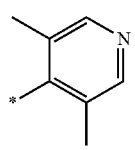
10-151
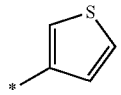
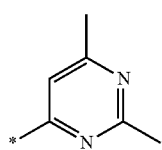
10-152
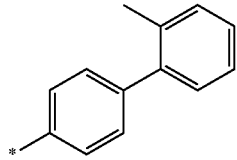
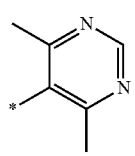
10-153
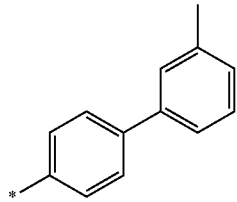
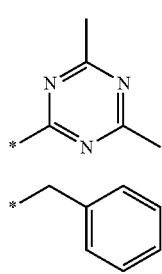
10-154
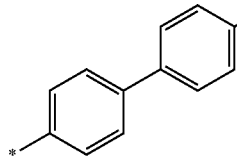
10-155
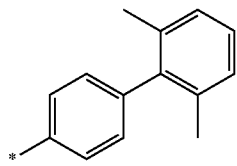

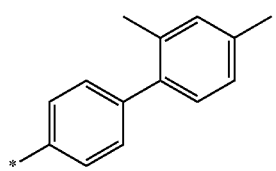
10-166
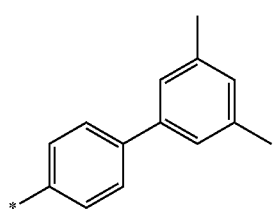
10-167
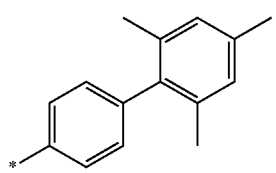
10-168
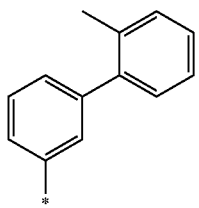
10-169
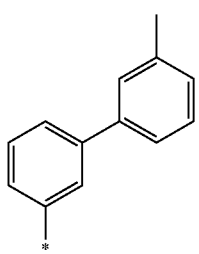
10-170
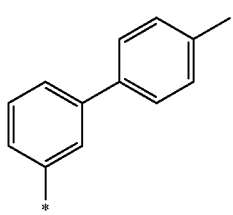
10-171
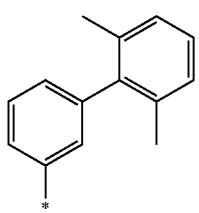
10-172
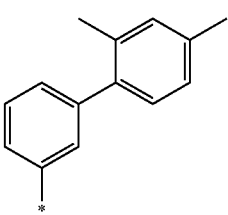
10-173
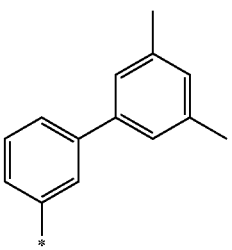
10-174
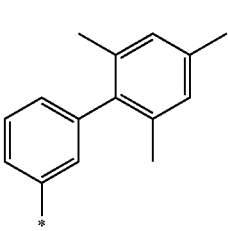
10-175
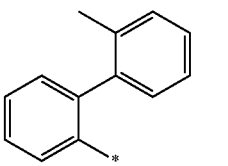
10-176
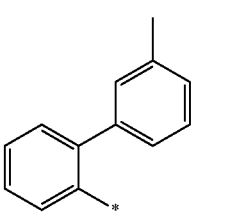
10-177
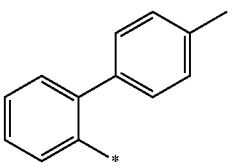
10-178
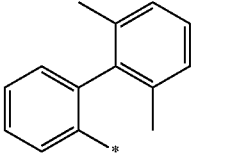
10-179
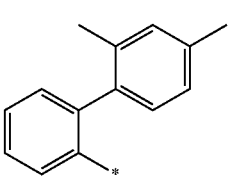
10-180

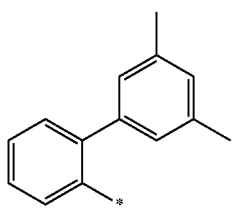
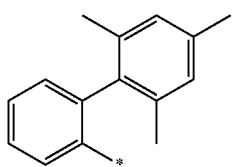
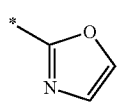
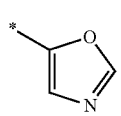
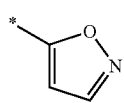
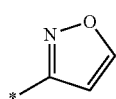
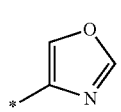
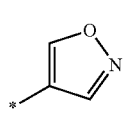
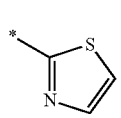
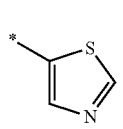
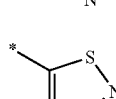
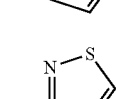
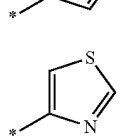
10-181
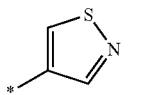
10-182
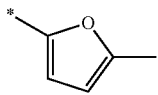
10-183
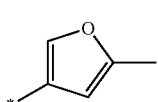
10-184
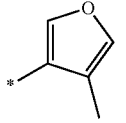
10-185
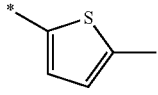
10-186
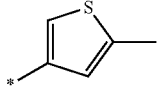
10-187
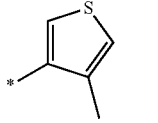
10-188
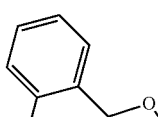
10-189
10-190
10-191
10-192
10-193
10-194
10-195
10-196
10-197
10-198
10-199
10-200
10-201
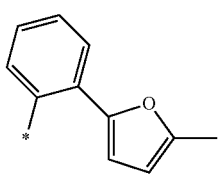
10-202
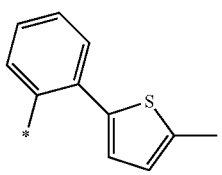
10-203
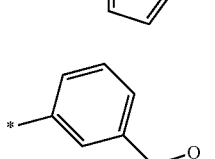
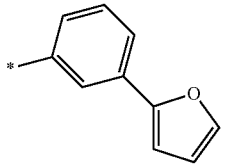
10-204
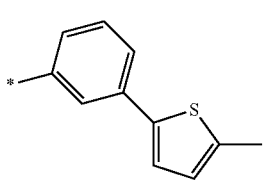

10-205 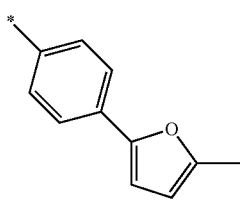
10-206 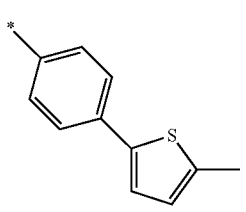
10-207 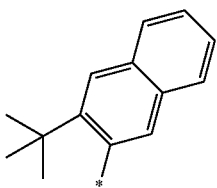
10-208 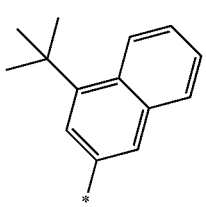
10-209 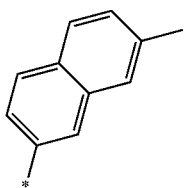
10-210 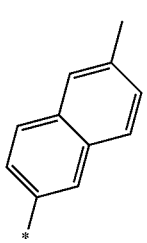
10-211 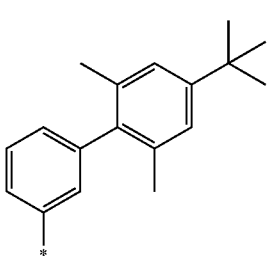
10-212 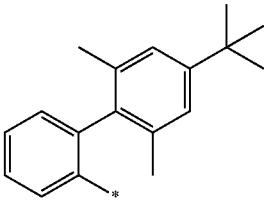
10-213 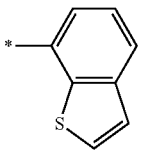
10-214 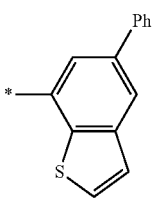
10-215 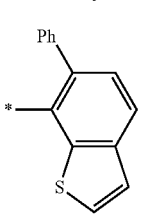
10-216 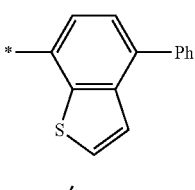
10-217 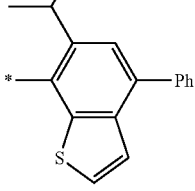
10-218 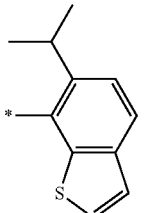
10-219

-continued
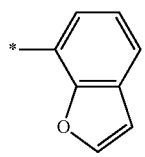
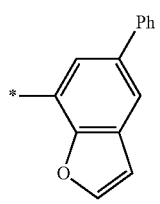
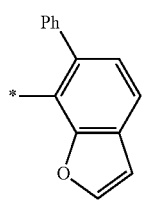
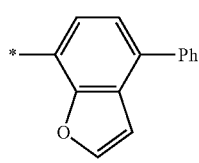
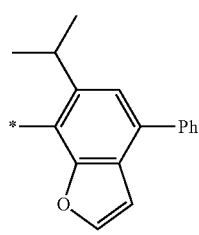
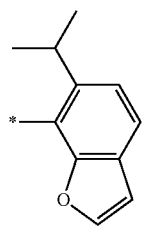
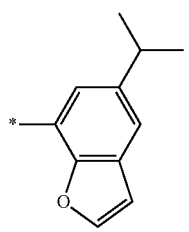
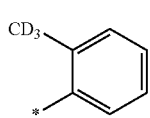
-continued
10-220
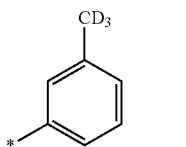
10-221
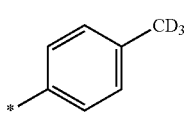
10-222
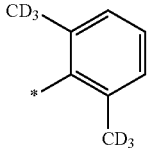
10-223
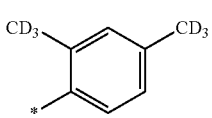
10-224
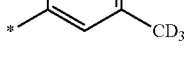
10-225
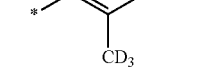
10-226
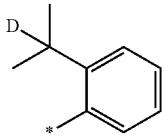
10-227
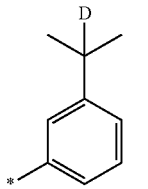
10-228
10-229
10-230
10-231
10-232
10-233
10-234
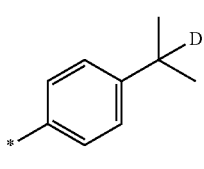
10-235
10-236
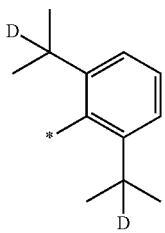
10-237

-continued

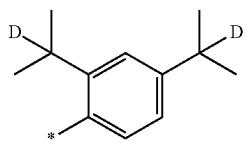
10-238

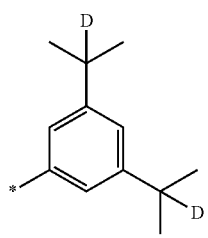
10-239

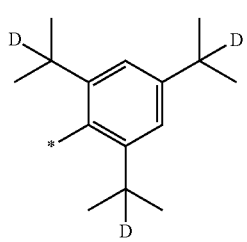
10-240

In Formulae 9-1 to 9-19 and 10-1 to 10-240, * indicates a binding site to a neighboring atom, Ph indicates a phenyl group, and TMS indicates a trimethylsilyl group.

In Formula 2, $L_{11}$ may be a $C_5$-$C_{30}$ carbocyclic group that is unsubstituted or substituted with at least one $R_{10a}$ or a $C_2$-$C_{30}$ heterocyclic group that is unsubstituted or substituted with at least one $R_{10a}$, wherein $R_{10a}$ is the same as described above.

For example, $L_{11}$ may be a benzene group, a naphthalene group, an anthracene group, a phenanthrene group, a triphenylene group, a pyrene group, a chrysene group, a cyclopentadiene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, or a benzothiadiazole group, each unsubstituted or substituted with at least one $R_{10a}$ group, but embodiments of the present disclosure are not limited thereto.

In Formula 2, b11 indicates the number of $L_{11}$, and may be an integer from 0 to 10, wherein, when b11 is 0, a group represented by *-$(L_{11})_{b11}$-*' may be a single bond, and when b11 is 2 or more, two or more $L_{11}$(s) may be identical to or different from each other. For example, b11 may be 0, 1, 2, or 3, but embodiments of the present disclosure are not limited thereto.

In Formula 2, two or more of a plurality of neighboring $R_{21}$(s) may optionally be linked to form a $C_5$-$C_{30}$ carbocyclic group that is unsubstituted or substituted with at least one $R_{10a}$ group or a $C_2$-$C_{30}$ heterocyclic group that is unsubstituted or substituted with at least one $R_{10a}$ group (for example, a benzene group, a cyclopentane group, a cyclopentadiene group, a furan group, a thiophene group, a pyrrole group, a silole group, an indene group, a benzofuran group, a benzothiophene group, an indole group, or a benzosilole group, each unsubstituted or substituted with at least one $R_{10a}$ group), wherein $R_{10a}$ is the same as defined in connection with $R_{21}$. Detailed descriptions of a $C_5$-$C_{30}$ carbocyclic group and a $C_2$-$C_{30}$ heterocyclic group are the same as described above.

In Formula 2, * and *' each indicate a binding site to M in Formula 1.

In an embodiment, a group represented by

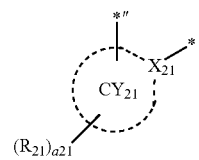

in Formula 2 may be a group represented by one of Formulae CY21-1 to CY21-25:

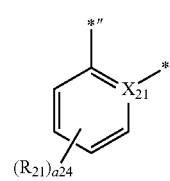
CY21-1

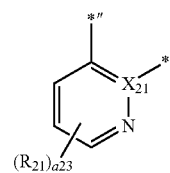
CY21-2

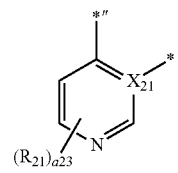
CY21-3

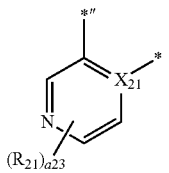 CY21-4
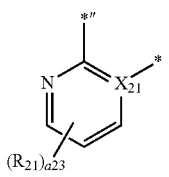 CY21-5
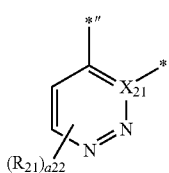 CY21-6
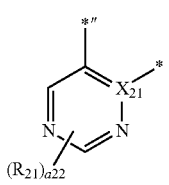 CY21-7
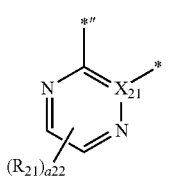 CY21-8
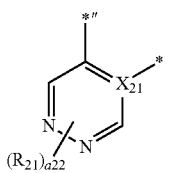 CY21-9
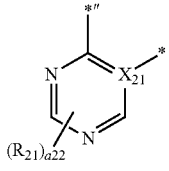 CY21-10
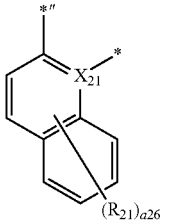 CY21-11
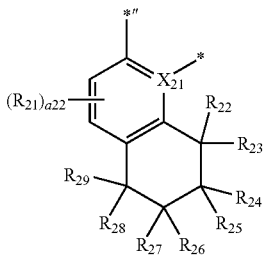 CY21-12
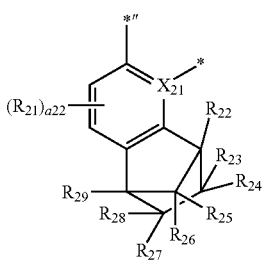 CY21-13
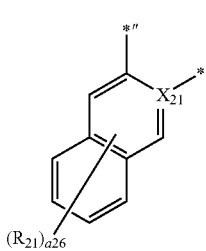 CY21-14
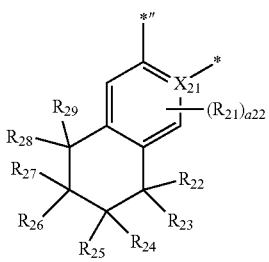 CY21-15
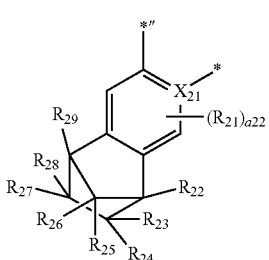 CY21-16
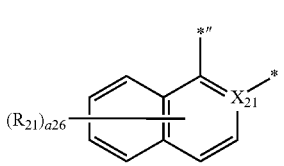 CY21-17

-continued

CY21-18
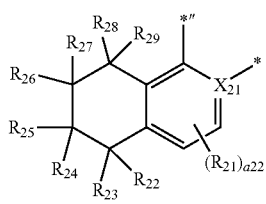

CY21-19
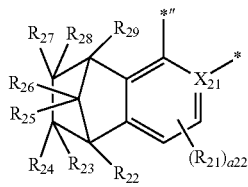

CY21-20
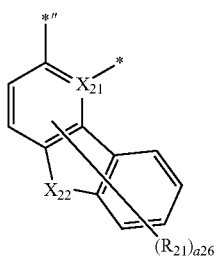

CY21-21
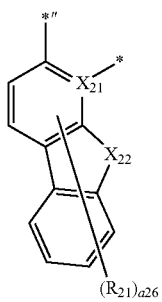

CY21-22
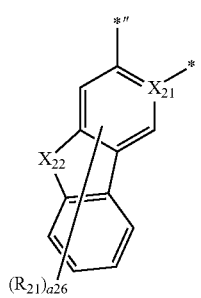

CY21-23
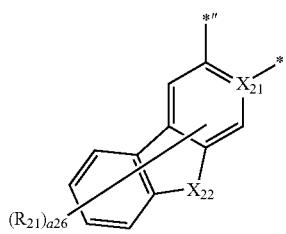

-continued

CY21-24
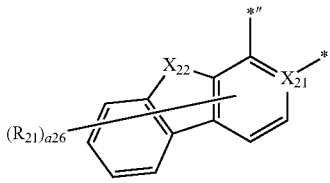

CY21-25
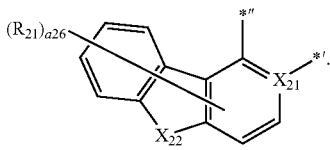

In Formulae CY21-1 to CY21-25, $X_{21}$ and $R_{21}$ may each independently be the same as described herein, $X_{22}$ may be $C(R_{22})(R_{23})$, $N(R_{22})$, O, S, or $Si(R_{22})(R_{23})$, $R_{22}$ to $R_{29}$ may each independently be the same as defined in connection with $R_{21}$, a26 may be an integer from 0 to 6, a24 may be an integer from 0 to 4, a23 may be an integer from 0 to 3, a22 may be an integer from 0 to 2,

*" indicates a binding site to a carbon atom of a neighboring 6-membered ring in Formula 2, and

* indicates a binding site to M in Formula 1.

In an embodiment, a group represented by

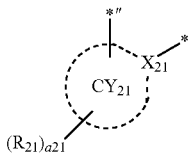

in Formula 2 may be a group represented by one of Formulae CY21(1) to CY21(56) or a group represented by one of Formulae CY21-20 to CY21-25:

CY21(1)
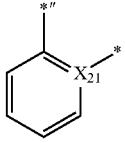

CY21(2)
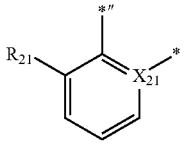

CY21(3)
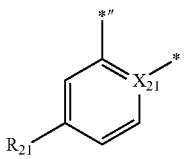

-continued
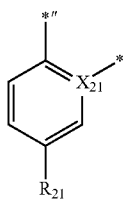
CY21(4)
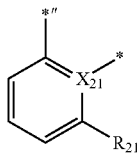
CY21(5)
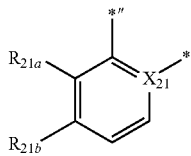
CY21(6)
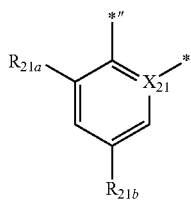
CY21(7)
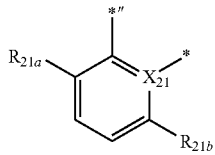
CY21(8)
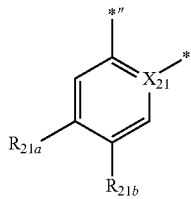
CY21(9)
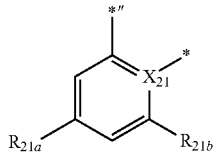
CY21(10)
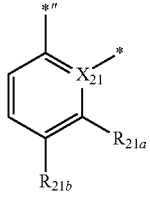
CY21(11)
-continued
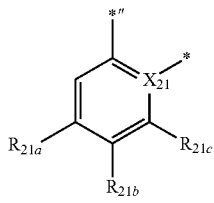
CY21(12)
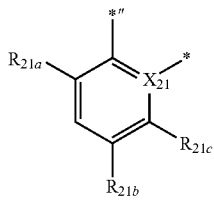
CY21(13)
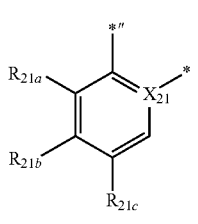
CY21(14)
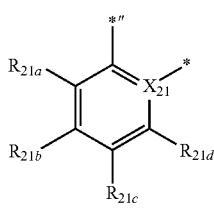
CY21(15)
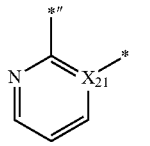
CY21(16)
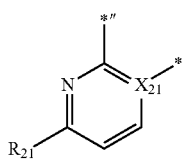
CY21(17)
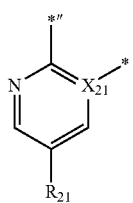
CY21(18)
CY21(19)

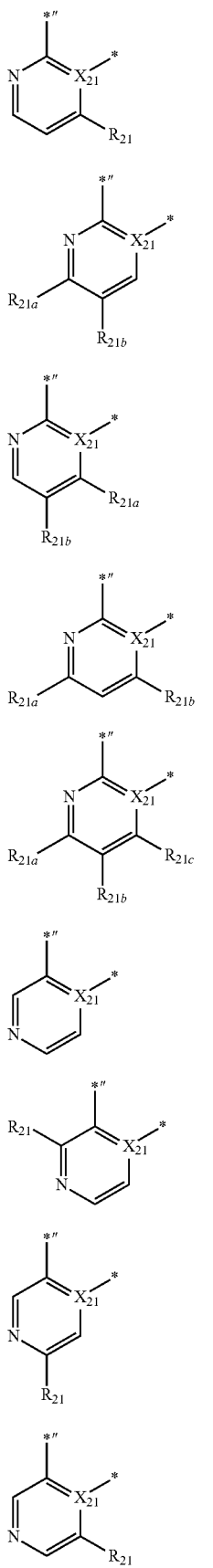
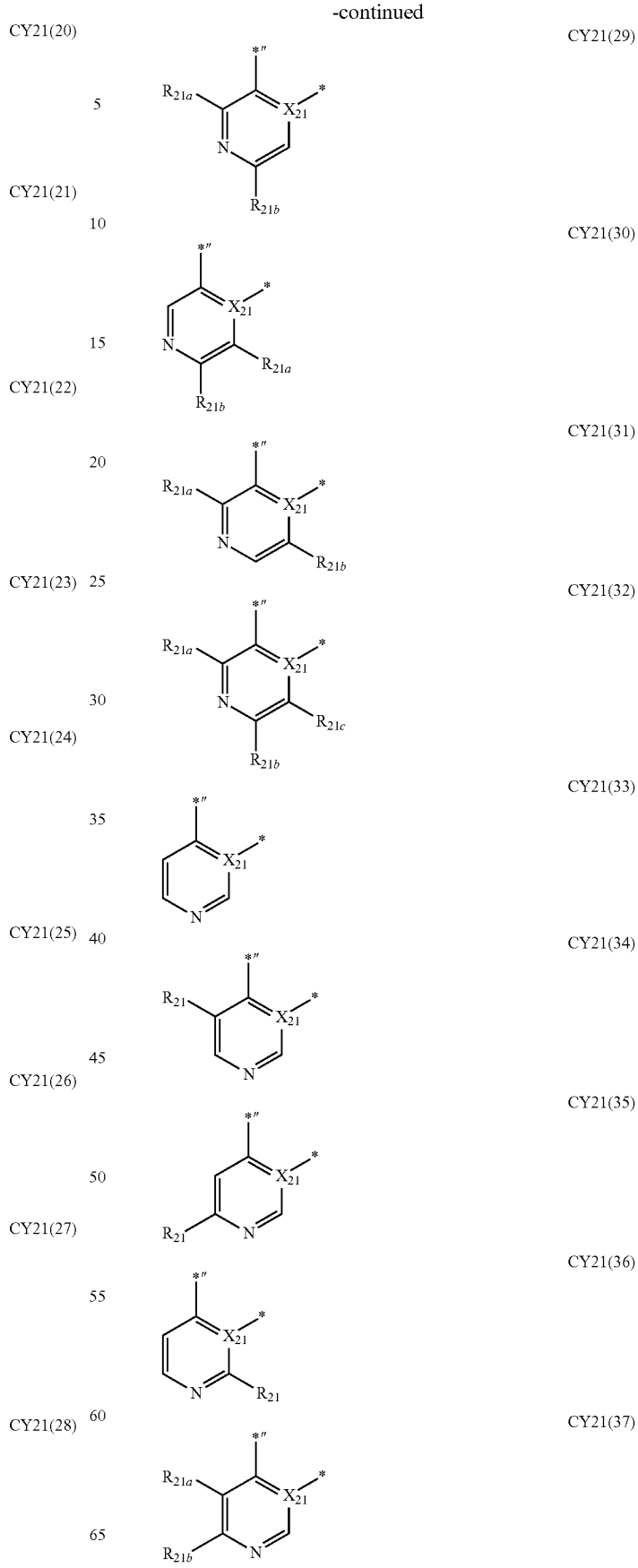

CY21(38)
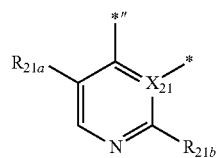
CY21(39)
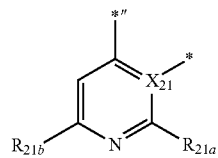
CY21(40)
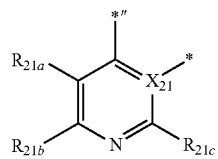
CY21(41)
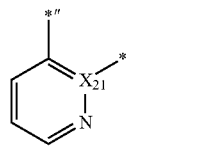
CY21(42)
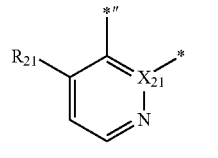
CY21(43)
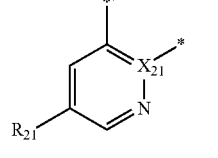
CY21(44)
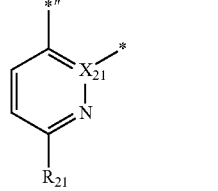
CY21(45)
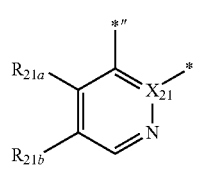
CY21(46)
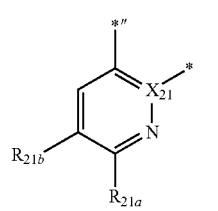
CY21(47)
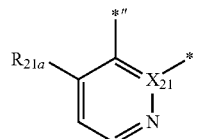
CY21(48)
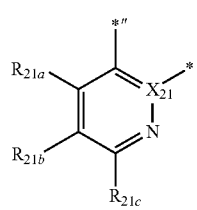
CY21(49)
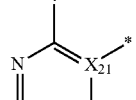
CY21(50)
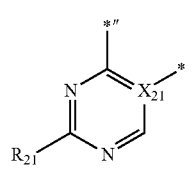
CY21(51)
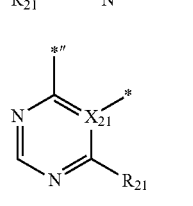
CY21(52)
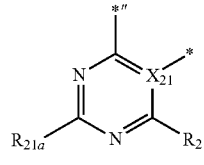
CY21(53)
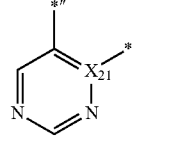
CY21(54)
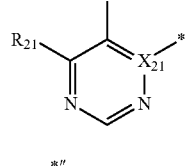
CY21(55)
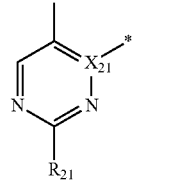

CY21(56)

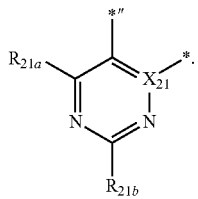

In Formulae CY21(1) to CY21(56), $X_{21}$ and $R_{21}$ may each independently be the same as described herein, $R_{21a}$ to $R_{21d}$ may each independently be the same as defined in connection with $R_{21}$, wherein $R_{21}$ and $R_{21a}$ to $R_{21d}$ are not each hydrogen,

*″ indicates a binding site to a carbon atom of a neighboring 6-membered ring in Formula 2, and

* indicates a binding site to M in Formula 1.

In an embodiment, a group represented by

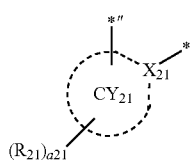

in Formula 2 may be a group represented by one of Formulae CY21(1), CY21(3), or CY21(10) or a group represented by one of Formulae CY21-20 to CY21-25, but embodiments of the present disclosure are not limited thereto. For example, in Formula CY21(10), $R_{21a}$ and $R_{21b}$ may be identical to or different from each other. In an embodiment, in Formula CY21(10), $R_{21a}$ and $R_{21b}$ may be different from each other, and the number of carbon atoms included in $R_{21a}$ may be larger than the number of carbon atoms included in $R_{21b}$.

In an embodiment, in Formula 1, $L_1$ may be a ligand represented by Formula 2A or 2B, but embodiments of the present disclosure are not limited thereto:

Formula 2A

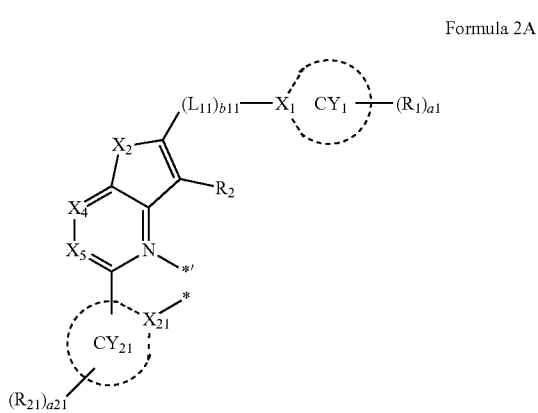

Formula 2B

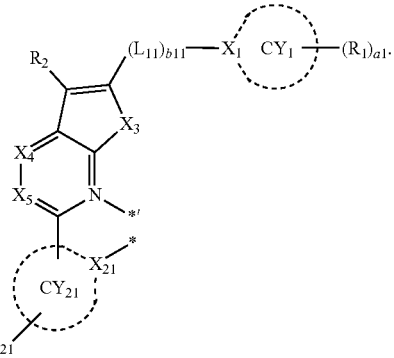

In Formulae 2A and 2B, $X_1$, $X_{21}$, ring $CY_1$, ring $CY_{21}$, $X_4$, $X_5$, $R_1$, $R_2$, $R_{21}$, a1, a21, $L_{11}$, b11, *, and *′ may each independently be the same as described herein, wherein $X_2$ and $X_3$ may each independently be O, S, or Se.

In Formula 1, $L_2$ may be a bidentate ligand linked to M of Formula 1 via O, S, N, C, P, Si, or As.

In an embodiment, in Formula 1, $L_2$ may be a bidentate ligand represented by Formula 3:

Formula 3

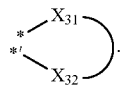

In Formula 3, $X_{31}$ and $X_{32}$ may each independently be O, S, N, C, P, Si, or As, ⌣ indicates an arbitrary atom group linking $X_{31}$ and $X_{32}$ to each other, and

* and *′ each indicate a binding site to M in Formula 1.

For example, in Formula 3, i) $X_{31}$ and $X_{32}$ may each be O; ii) $X_{31}$ may be O, and $X_{32}$ may be N, or iii) $X_{31}$ may be N, and $X_{32}$ may be C, but embodiments of the present disclosure are not limited thereto.

In an embodiment, in Formula 1, $L_2$ may be a monodentate ligand, for example, I⁻, Br⁻, $C_1^-$, sulfide, nitrate, azide, hydroxide, cyanate, isocyanate, thiocyanate, water, acetonitrile, pyridine, ammonia, carbon monoxide, P(Ph)$_3$, P(Ph)$_2$CH$_3$, PPh(CH$_3$)$_2$, P(CH$_3$)$_3$, or any combination thereof, but embodiments of the present disclosure are not limited thereto.

In an or more embodiment, in Formula 1, $L_2$ may be a bidentate ligand, for example, oxalate, acetylacetonate, picolinic acid, 1,2-bis(diphenylphosphino)ethane, 1,1-bis(diphenylphosphino)methane, glycinate, ethylenediamine, or any combination thereof, but embodiments of the present disclosure are not limited thereto.

In an or more embodiment, in Formula 1, $L_2$ may be a group represented by one of Formulae 3A to 3F:

3A

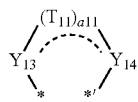

-continued

3B
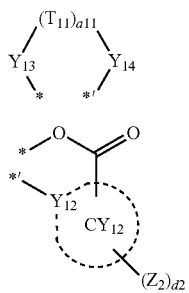

3C
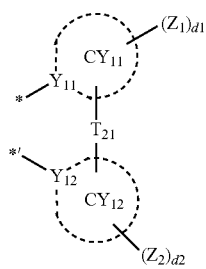

3D
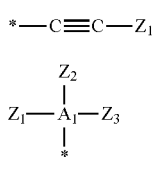

3E
*—C≡C—Z$_1$

3F
$$Z_1\text{—}A_1\text{—}Z_3$$
with Z$_2$ above and * below A$_1$

In Formulae 3A to 3F,

Y$_{13}$ may be O, N, N(Z$_1$), P(Z$_1$)(Z$_2$), or As(Z$_1$)(Z$_2$),

Y$_{14}$ may be O, N, N(Z$_3$), P(Z$_3$)(Z$_4$), or As(Z$_3$)(Z$_4$),

T$_{11}$ may each independently be a single bond, a double bond, *—C(Z$_{11}$)(Z$_{12}$)—*', *—C(Z$_{11}$)=C(Z$_{12}$)—*', *=C(Z$_{11}$)—*', *—C(Z$_{11}$)=*', *=C(Z$_{11}$)—C(Z$_{12}$)=C(Z$_{13}$)—*', *—C(Z$_{11}$)=C(Z$_{12}$)—C(Z$_{13}$)=*', *—N(Z$_{11}$)—*', or a C$_5$-C$_{30}$ carbocyclic group that is unsubstituted or substituted with at least one Z$_{11}$ group, a11 may be an integer from 1 to 10, Y$_{11}$ and Y$_{12}$ may each independently be C or N, T$_{21}$ may be a single bond, a double bond, O, S, C(Z$_{11}$)(Z$_{12}$), Si(Z$_{11}$)(Z$_{12}$), or N(Z$_{11}$), ring CY$_{11}$ and ring CY$_{12}$ may each independently be a C$_5$-C$_{30}$ carbocyclic group or a C$_2$-C$_{30}$ heterocyclic group, A$_1$ may be P or As, Z$_1$ to Z$_4$ and Z$_{11}$ to Z$_{13}$ may each independently be the same as defined in connection with R$_{21}$, d1 and d2 may each independently be an integer from 0 to 10, and

* and *' each indicate a binding site to M in Formula 1.

In Formulae 3A to 3F, the C$_5$-C$_{30}$ carbocyclic group and the C$_2$-C$_{30}$ heterocyclic group may each independently be the same as defined in connection with ring CY$_{21}$.

For example, a moiety represented by

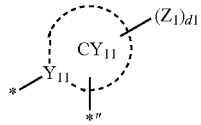

in Formula 3D may be a group represented by one of Formulae CY11-1 to CY11-34, and/or a moiety represented by

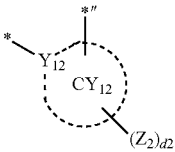

in Formulae 3C and 3D may be a group represented by one of Formulae CY12-1 to CY12-34:

CY11-1
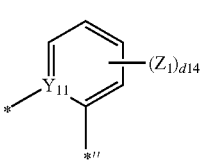

CY11-2
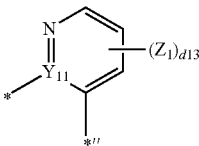

CY11-3
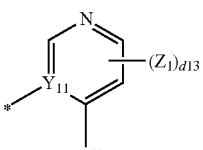

CY11-4
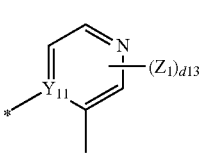

CY11-5
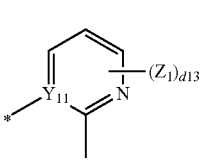

CY11-6
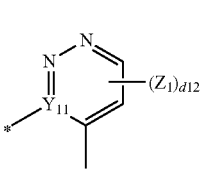

CY11-7
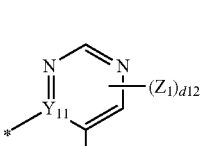

-continued
CY11-8
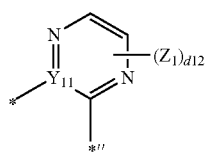
CY11-9
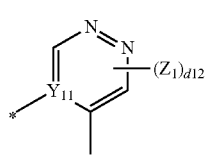
CY11-10
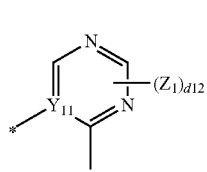
CY11-11
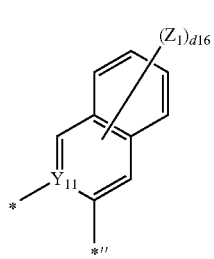
CY11-12
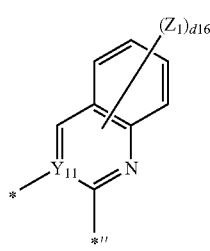
CY11-13
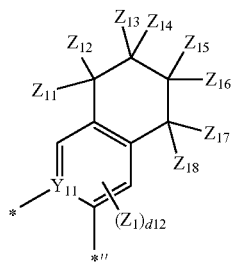
CY11-14
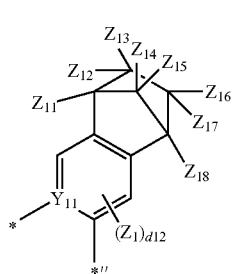
-continued
CY11-15
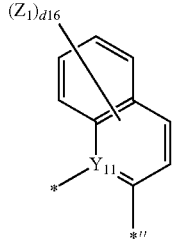
CY11-16
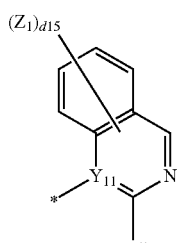
CY11-17
CY11-18
CY11-19
CY11-20
CY11-21
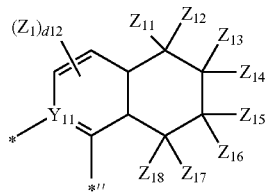

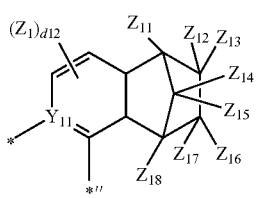
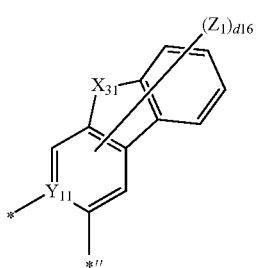
CY11-22
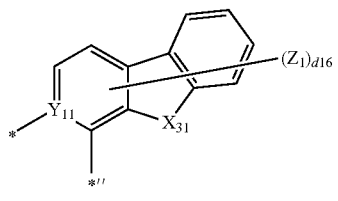
CY11-28
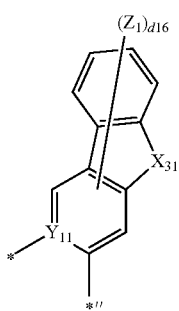
CY11-23
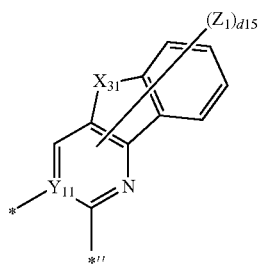
CY11-29
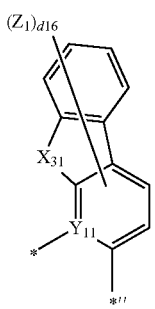
CY11-24
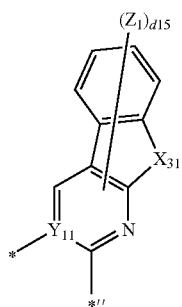
CY11-30
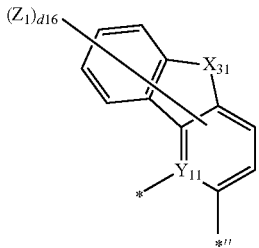
CY11-25
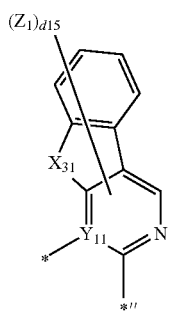
CY11-31
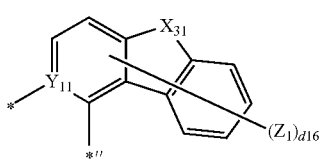
CY11-26
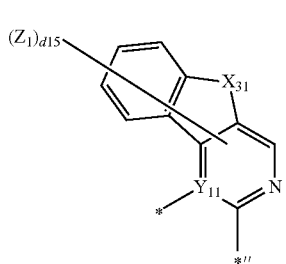
CY11-32
CY11-27
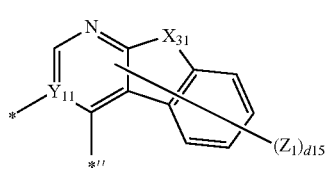
CY11-33

-continued
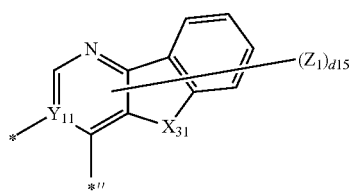
CY11-34
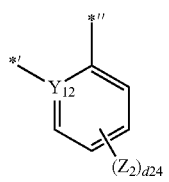
CY12-1
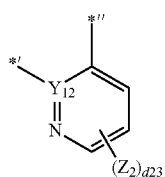
CY12-2
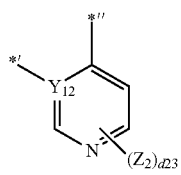
CY12-3
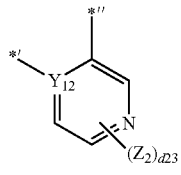
CY12-4
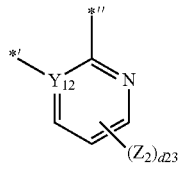
CY12-5
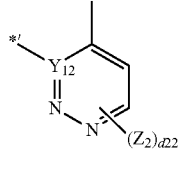
CY12-6
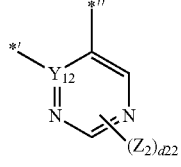
CY12-7
-continued
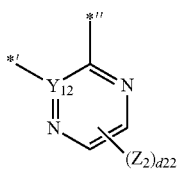
CY12-8
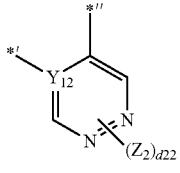
CY12-9
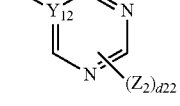
CY12-10
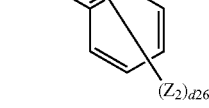
CY12-11
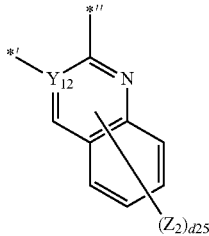
CY12-12
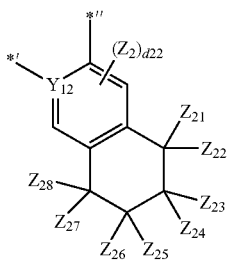
CY12-13
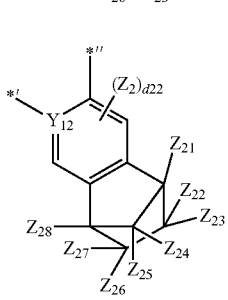
CY12-14

CY12-15
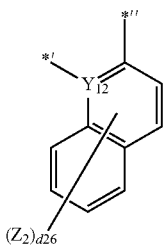
CY12-16
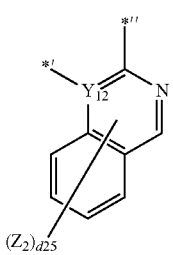
CY12-17
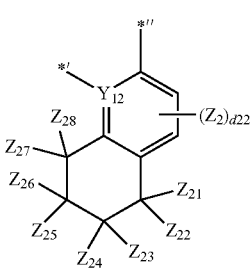
CY12-18
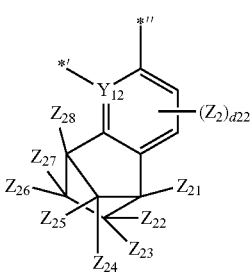
CY12-19
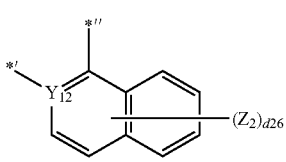
CY12-20
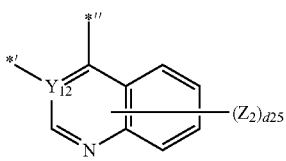
CY12-21
CY12-22
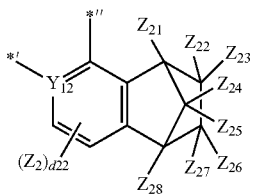
CY12-23
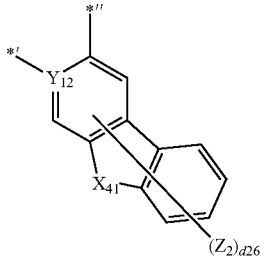
CY12-24
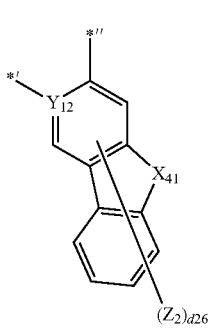
CY12-25
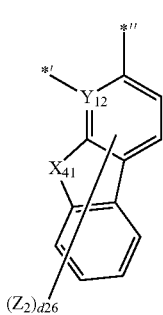
CY12-26
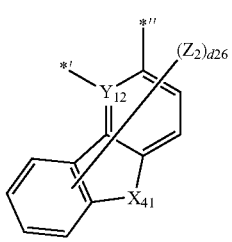
CY12-27
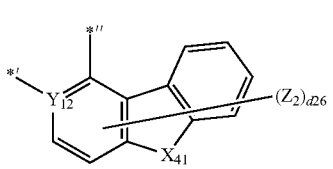

CY12-28

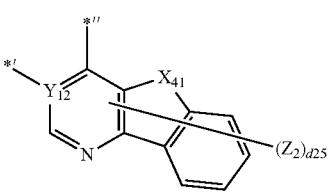

CY12-29

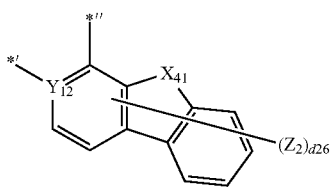

In Formulae CY11-1 to CY11-34 and CY12-1 to CY12-34, $X_{31}$ may be O, S, $N(Z_{11})$, $C(Z_{11})(Z_{12})$, or $Si(Z_{11})(Z_{12})$, $X_{41}$ may be O, S, $N(Z_{21})$, $C(Z_{21})(Z_{22})$, or $Si(Z_{21})(Z_{22})$, $Y_{11}$, $Y_{12}$, $Z_1$, and $Z_2$ may each independently be the same as described herein, $Z_{11}$ to $Z_{18}$ and $Z_{21}$ to $Z_{28}$ may each independently be the same as defined in connection with $R_{21}$, d12 and d22 may each independently be an integer from 0 to 2,

CY12-30 d13 and d23 may each independently be an integer from 0 to 3, d14 and d24 may each independently be an integer from 0 to 4, d15 and d25 may each independently be an integer from 0 to 5, d16 and d26 may each independently be an integer from 0 to 6, and in Formulae CY11-1 to CY11-34 and CY12-1 to CY12-34, * and *' each indicate a binding site to M in Formula 1, and *'' indicates a binding site to a neighboring atom in Formula 3C or a binding site to $T_{21}$ in Formula 3D.

CY12-31

In an embodiment, in Formula 1, $L_2$ may be a group represented by one of Formulae 3-1(1) to 3-1(66) or one of 3-1(301) to 3-1(309), but embodiments of the present disclosure are not limited thereto:

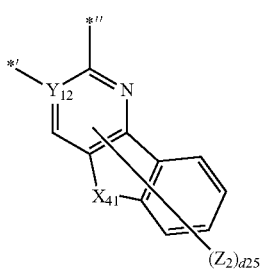

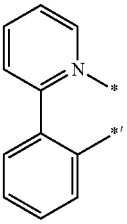

3-1(1)

CY12-32

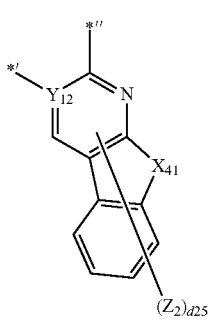

CY12-33

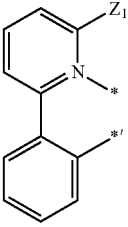

3-1(2)

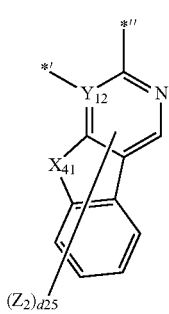

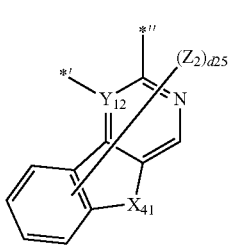

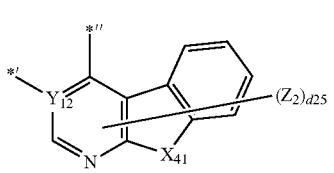

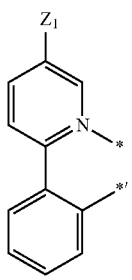
3-1(2)
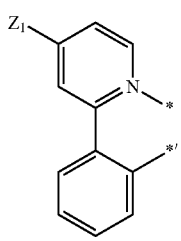 3-1(4)
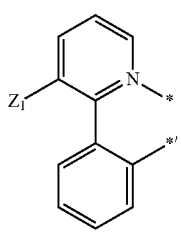 3-1(5)
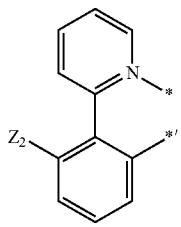 3-1(6)
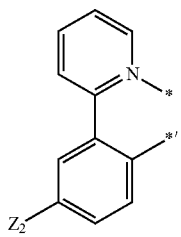 3-1(7)
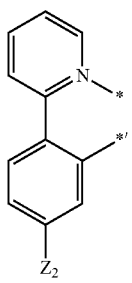
3-1(8)
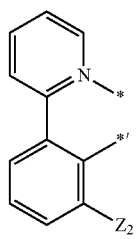 3-1(9)
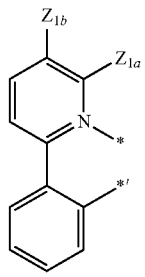 3-1(10)
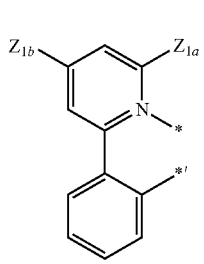 3-1(11)
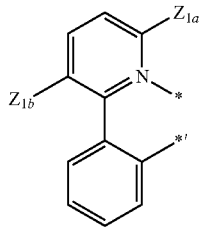 3-1(12)
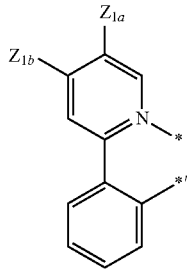 3-1(13)
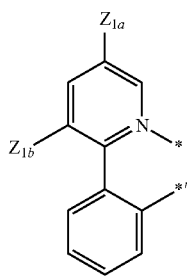 3-1(14)

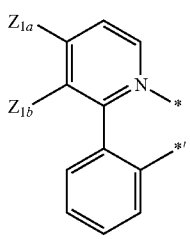
3-1(15)
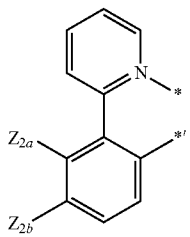
3-1(16)
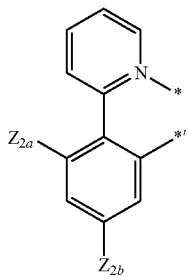
3-1(17)
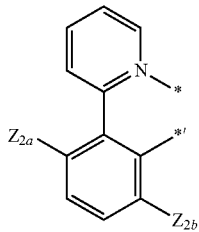
3-1(18)
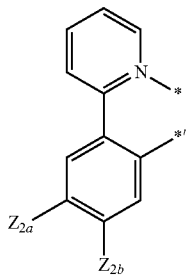
3-1(19)
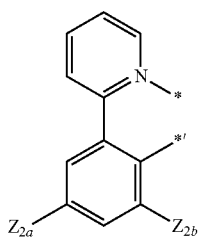
3-1(20)
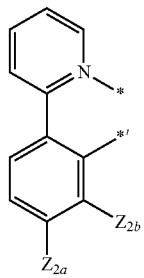
3-1(21)
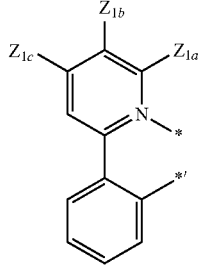
3-1(22)
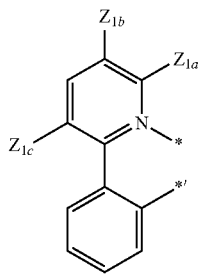
3-1(23)
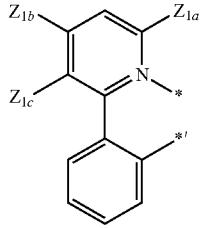
3-1(24)
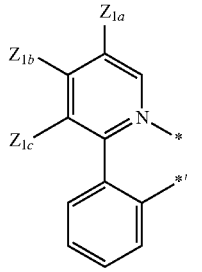
3-1(25)
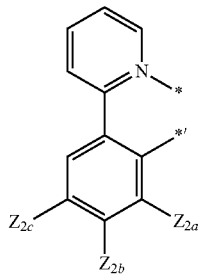
3-1(26)

-continued
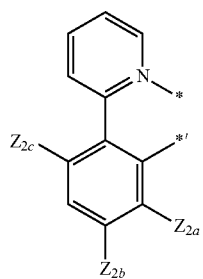
3-1(27)
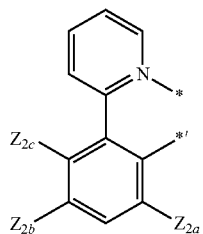
3-1(28)
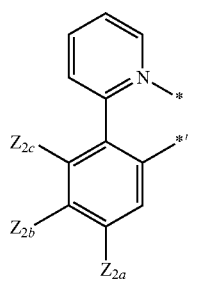
3-1(29)
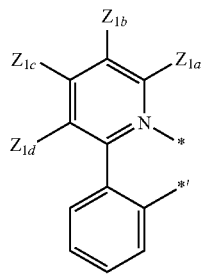
3-1(30)
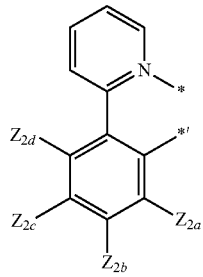
3-1(31)
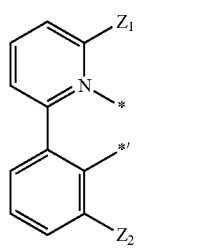
3-1(32)
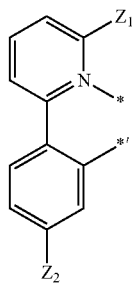
-continued
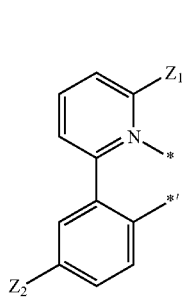
3-1(33)
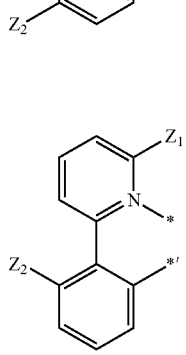
3-1(34)
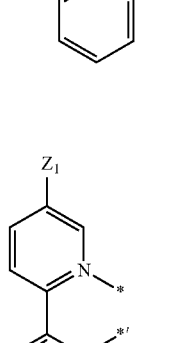
3-1(35)
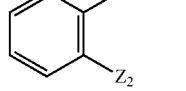
3-1(36)
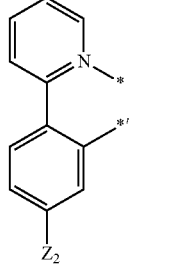
3-1(37)

-continued
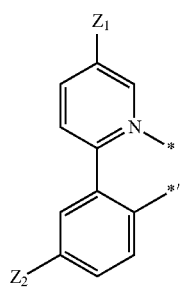 3-1(38)
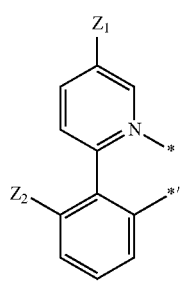 3-1(39)
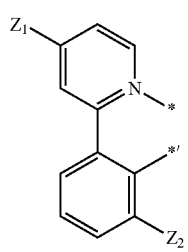 3-1(40)
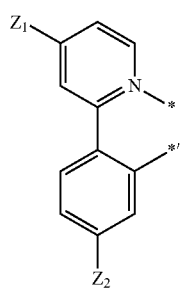 3-1(41)
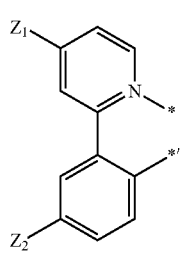 3-1(42)
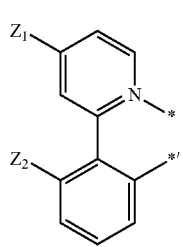 3-1(43)
-continued
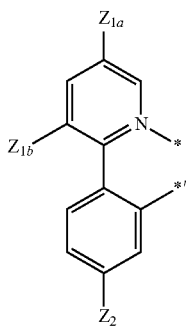 3-1(44)
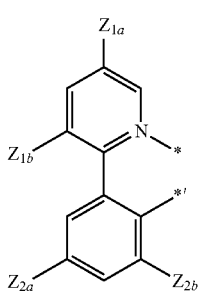 3-1(45)
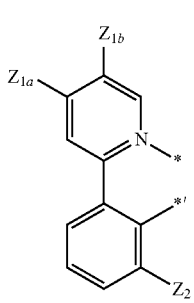 3-1(46)
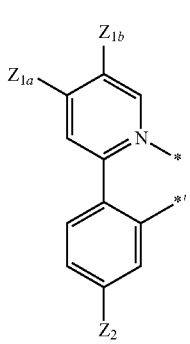 3-1(47)
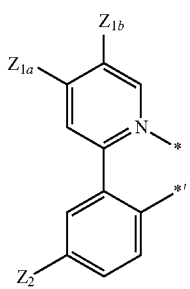 3-1(48)

3-1(49)
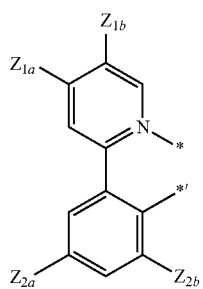
3-1(50)
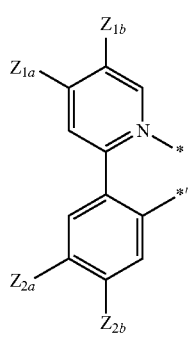
3-1(51)
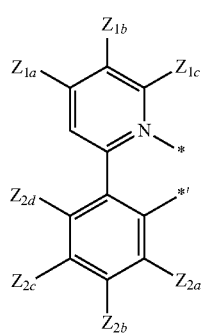
3-1(52)
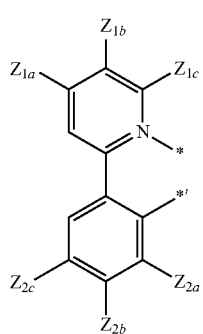
3-1(53)
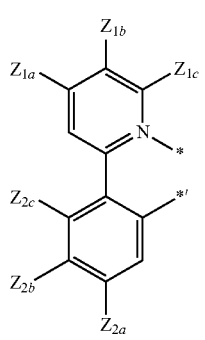
3-1(54)
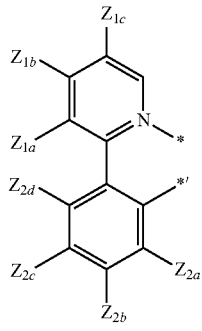
3-1(55)
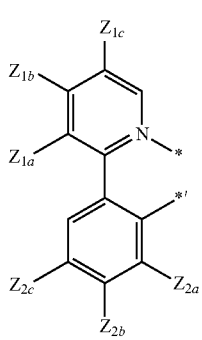
3-1(56)
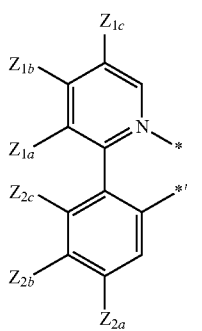
3-1(57)
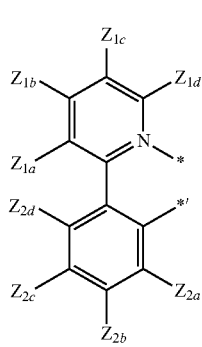
3-1(58)
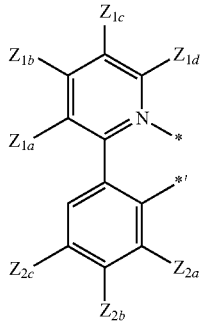

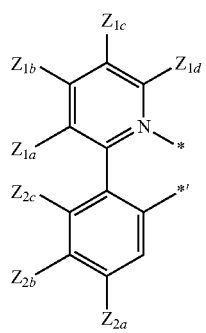
3-1(59)
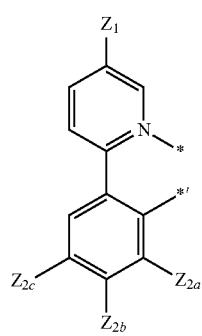
3-1(60)
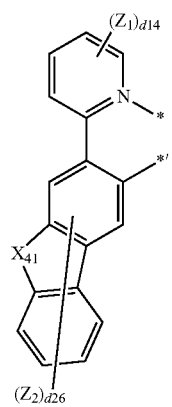
3-1(61)
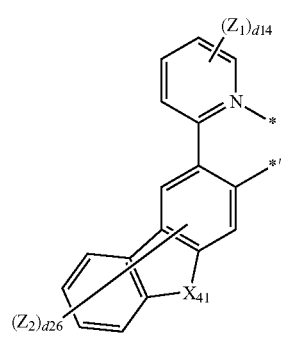
3-1(62)
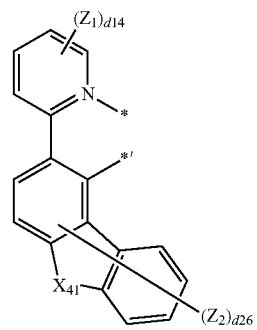
3-1(63)
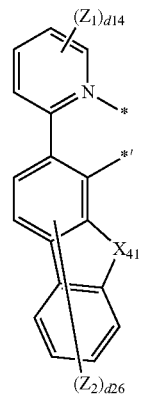
3-1(64)
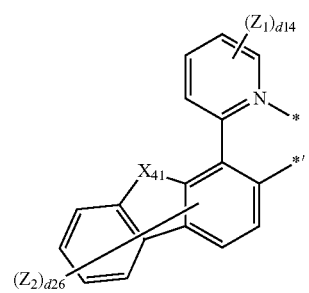
3-1(65)
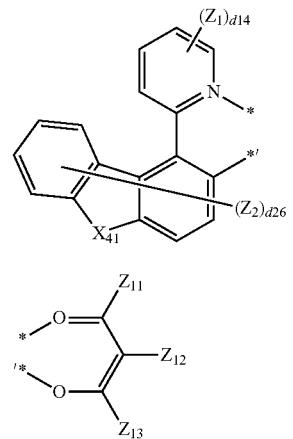
3-1(66)
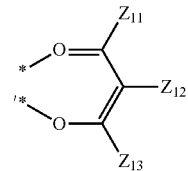
3-1(301)

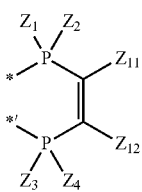
3-1(302)

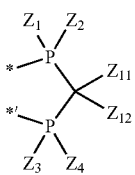
3-1(303)

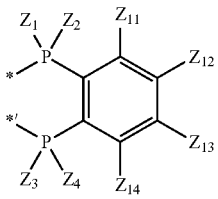
3-1(304)

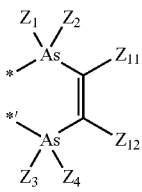
3-1(305)

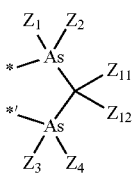
3-1(306)

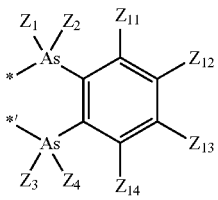
3-1(307)

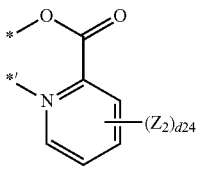
3-1(308)

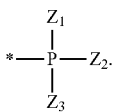
3-1(309)

In Formulae 3-1(1) to 3-1(66) and 3-1(301) to 3-1(309), $X_{41}$ may be O, S, $N(Z_{21})$, $C(Z_{21})(Z_{22})$, or $Si(Z_{21})(Z_{22})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, $Z_{21}$ and $Z_{22}$ may each independently be the same as defined in connection with $R_{21}$, d14 may be an integer from 0 to 4, d26 may be an integer from 0 to 6, and

* and *' each indicate a binding site to M in Formula 1.

In an embodiment, the organometallic compound represented by Formula 1 may emit red light or green light. In an embodiment, the organometallic compound represented by Formula 1 may emit red light or green light, each having a maximum emission wavelength of about 500 nm or more, for example, about 500 nm or more and about 650 nm or less.

The terms "an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, and an azadibenzothiophene 5,5-dioxide group" as used herein each refer to a heterocyclic group having the same backbone as "an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, and a dibenzothiophene 5,5-dioxide group" in which at least one carbon atom constituting the cyclic groups is substituted with N.

In an embodiment, the organometallic compound represented by Formula 1 may be one of Compounds 1 to 420, but embodiments of the present disclosure are not limited thereto:

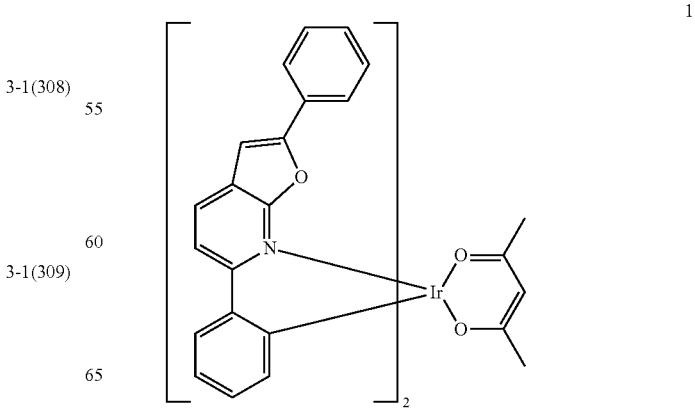
1

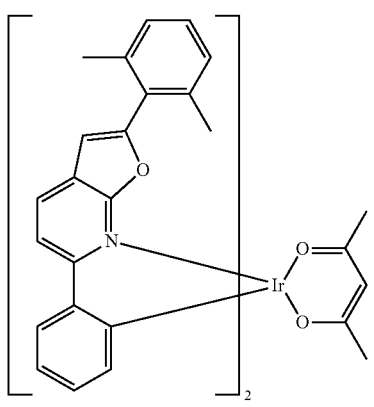
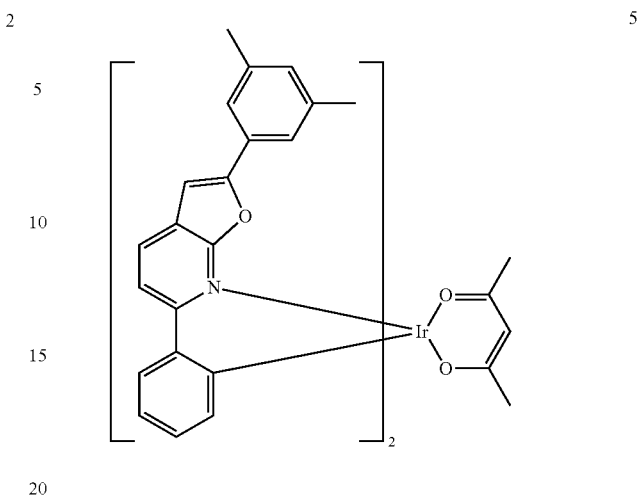
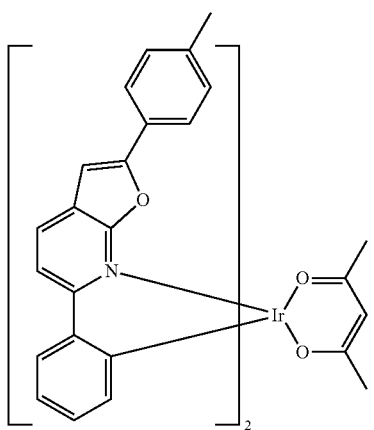
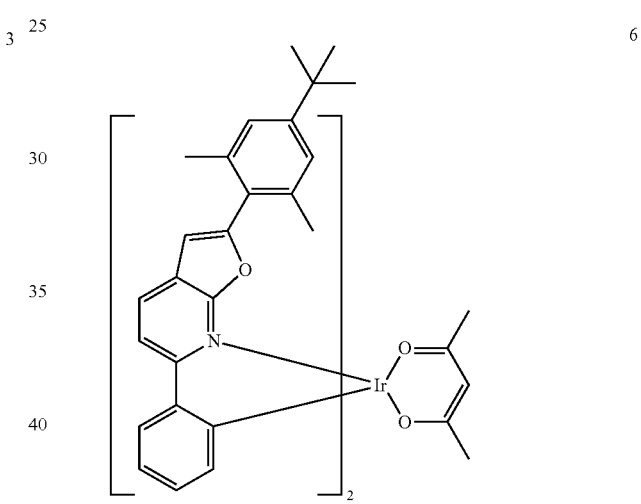
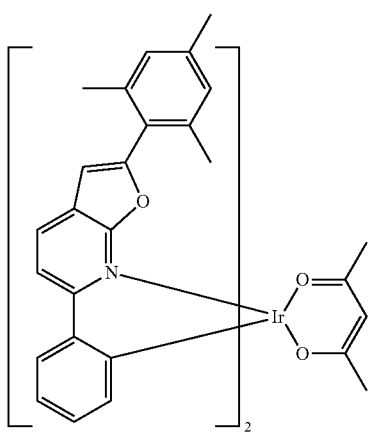
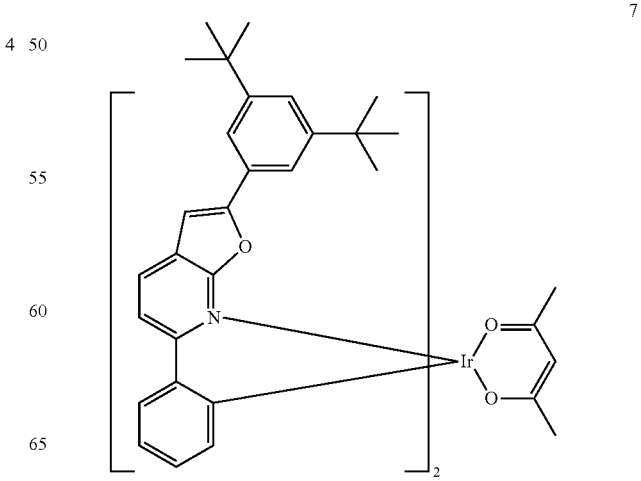

8
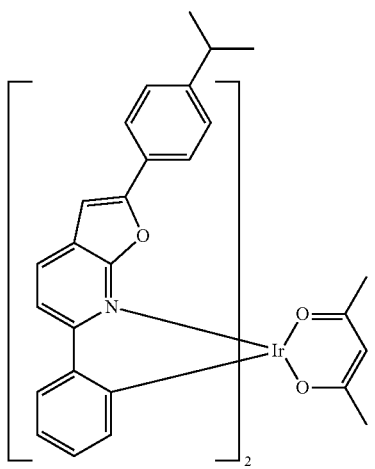
9
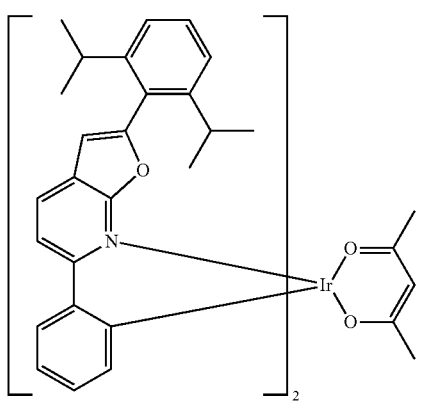
10
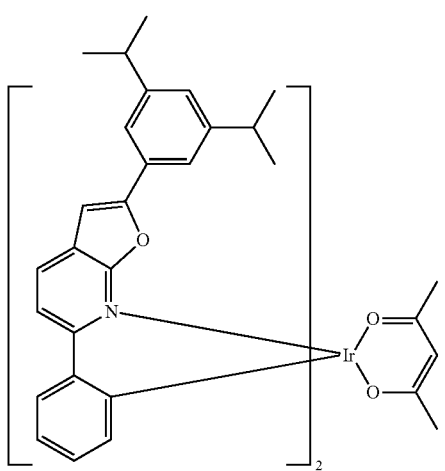
11
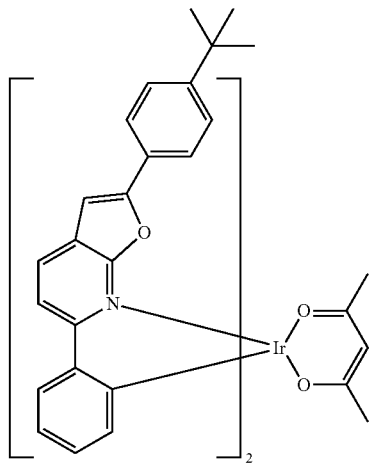
12
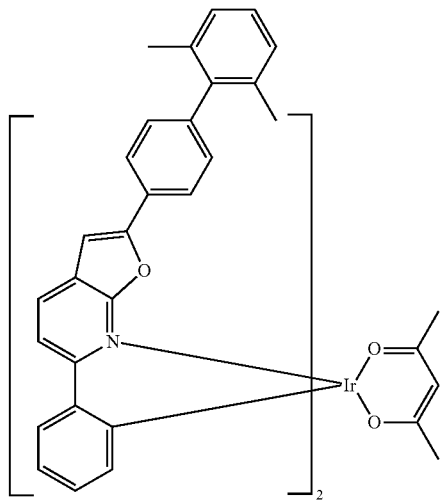
13
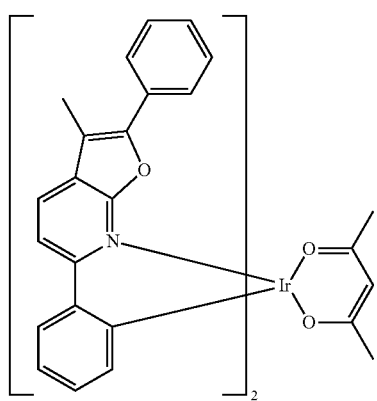

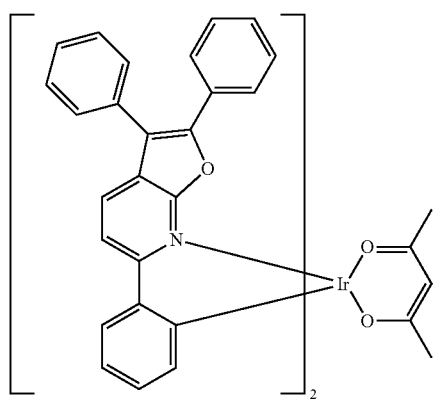
14
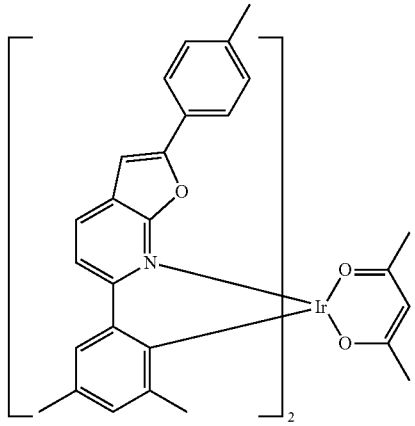
18
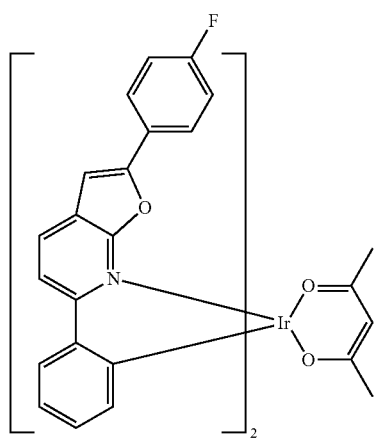
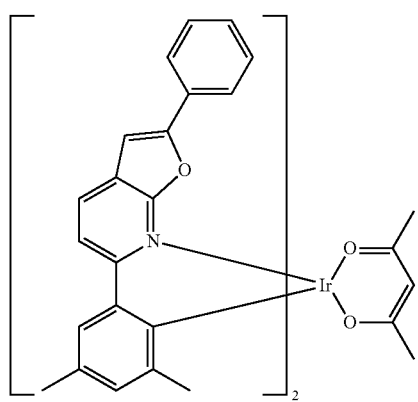
16
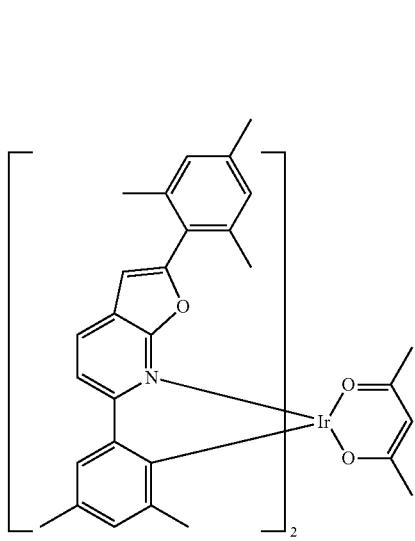
19
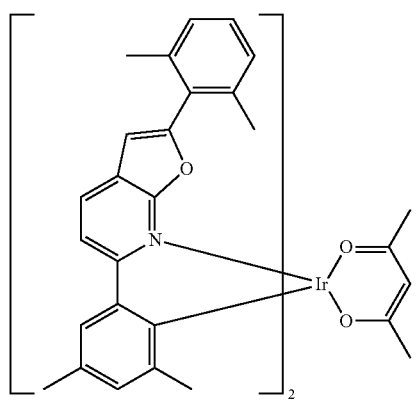
17

20

| 21 | 24 |
|---|---|
| 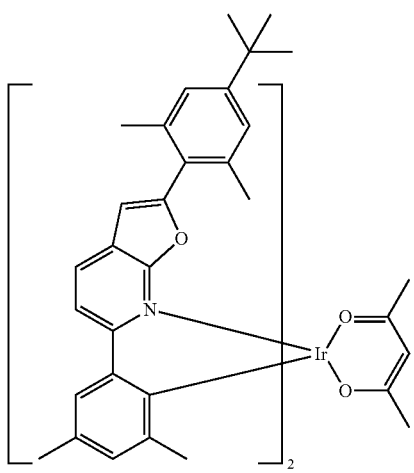 | 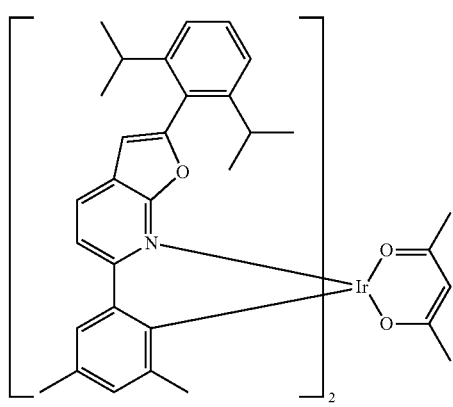 |
| 22 | 25 |
| 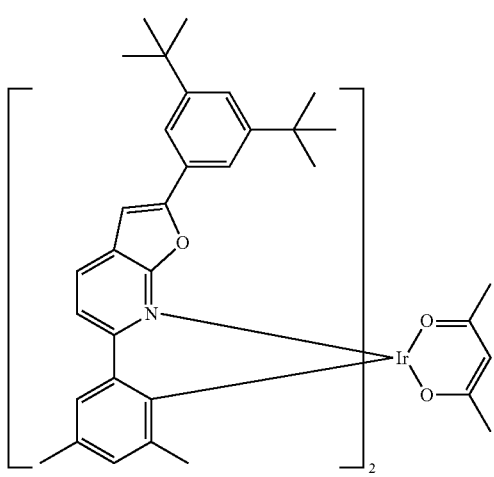 | 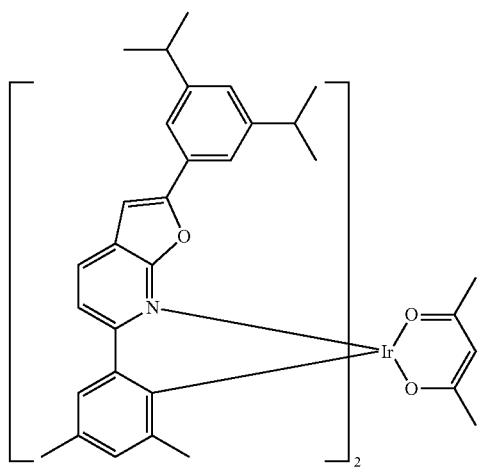 |
| 23 | 26 |
| 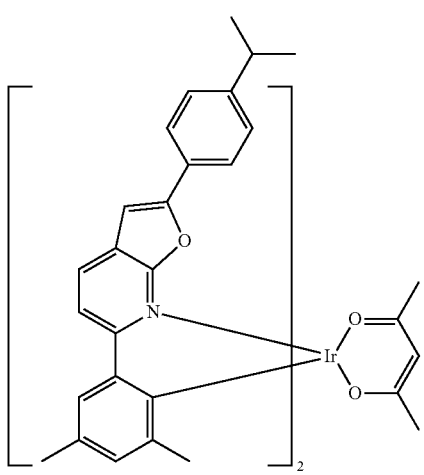 | 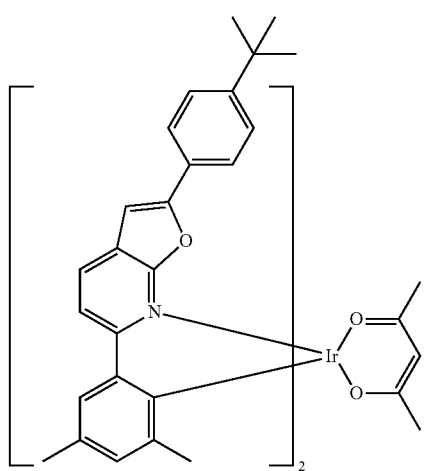 |

27
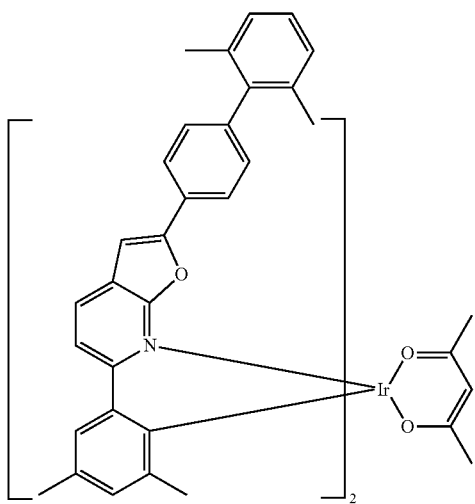
28
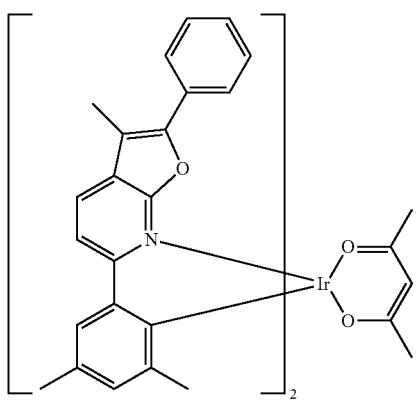
29
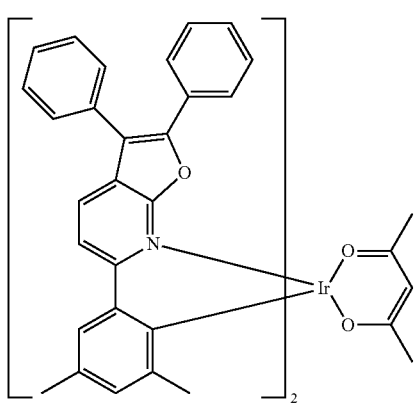
30
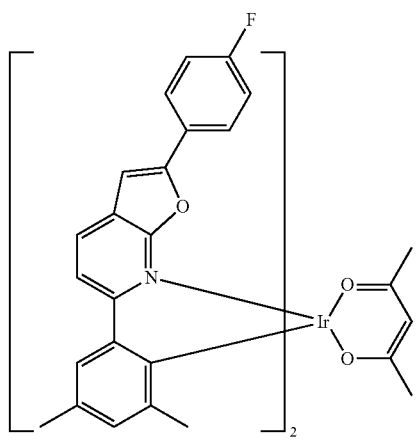
31
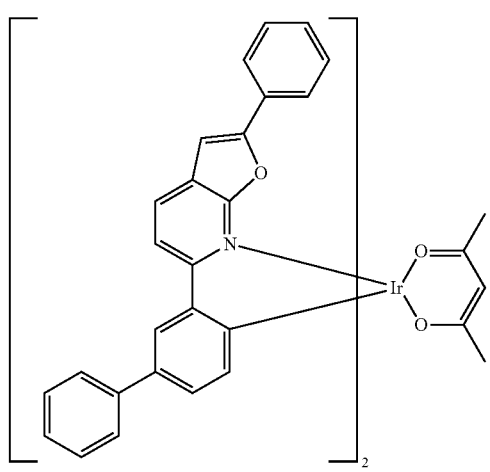
32
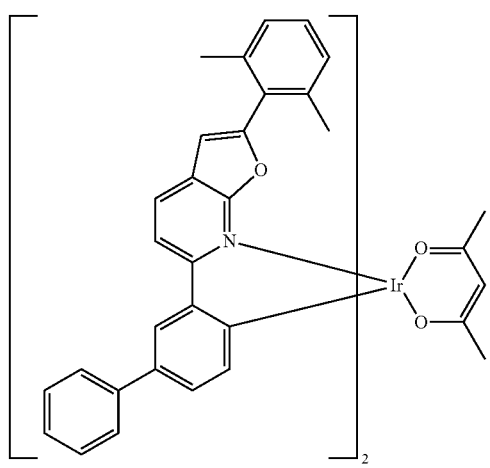

-continued
33
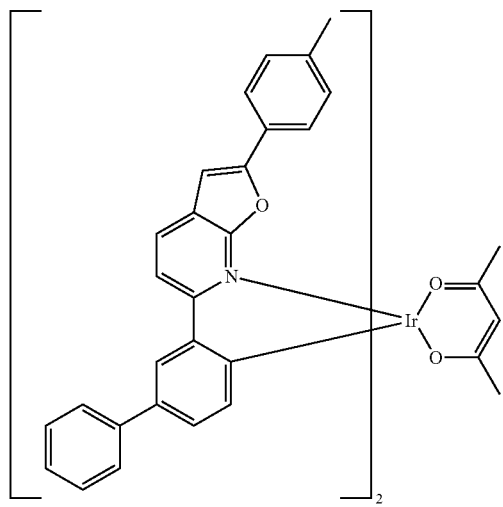
34
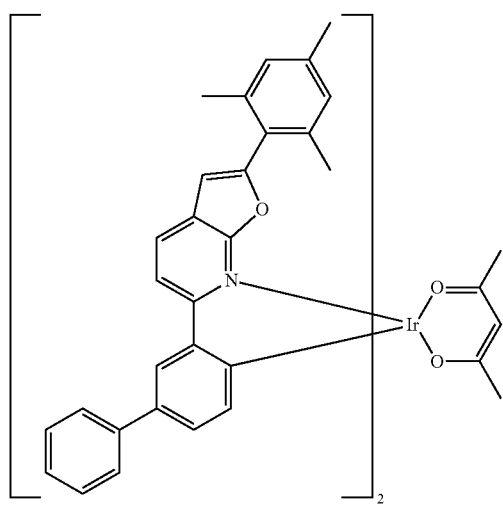
35
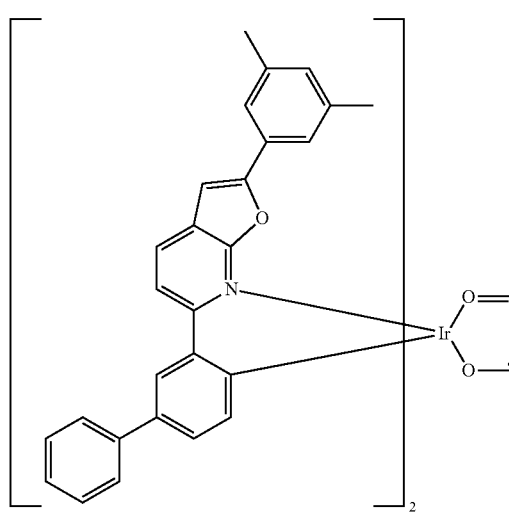
-continued
36
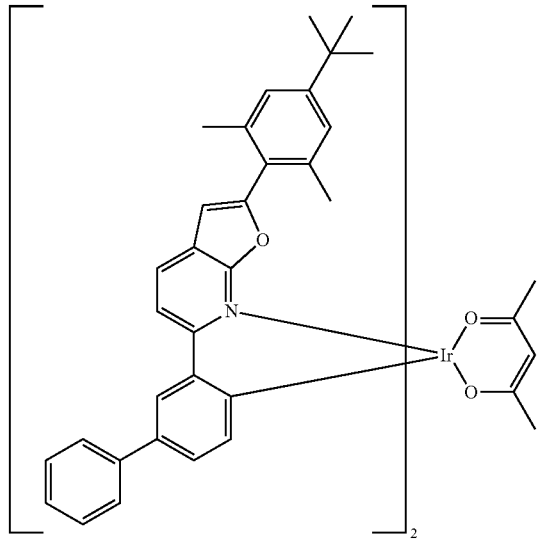
37
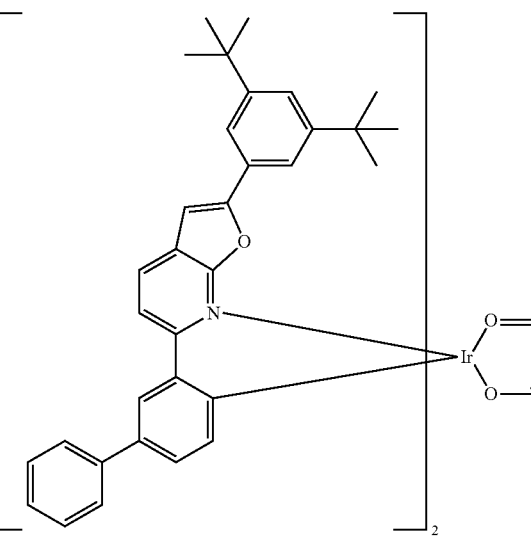

38
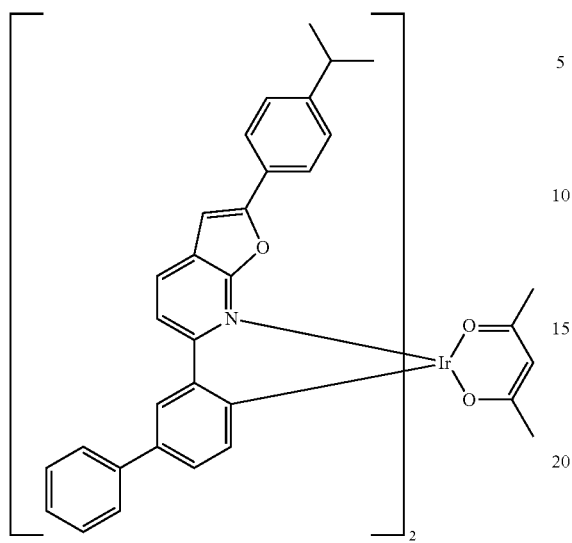
39
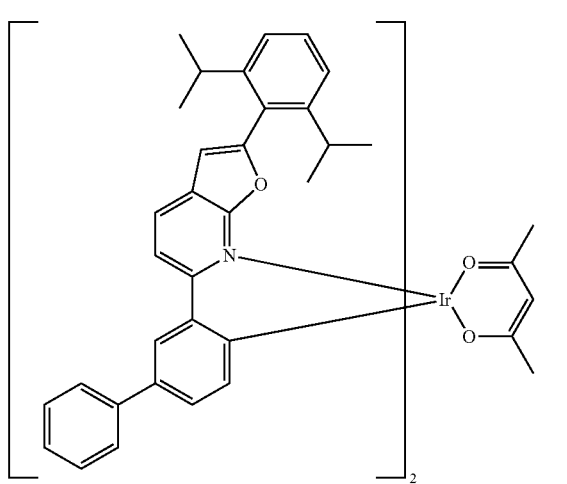
40
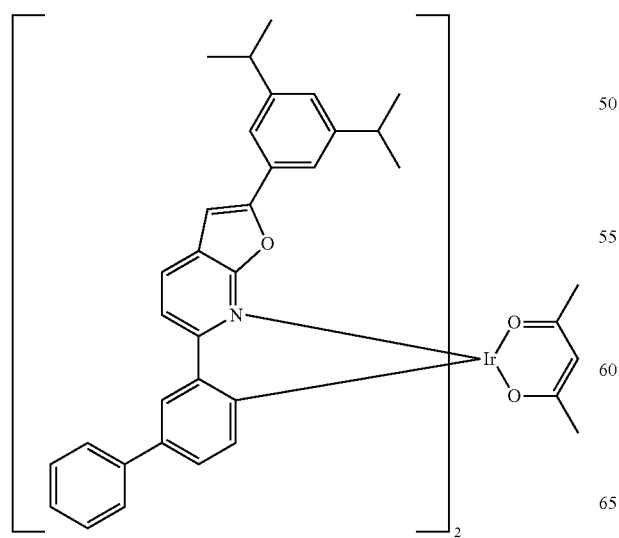
41
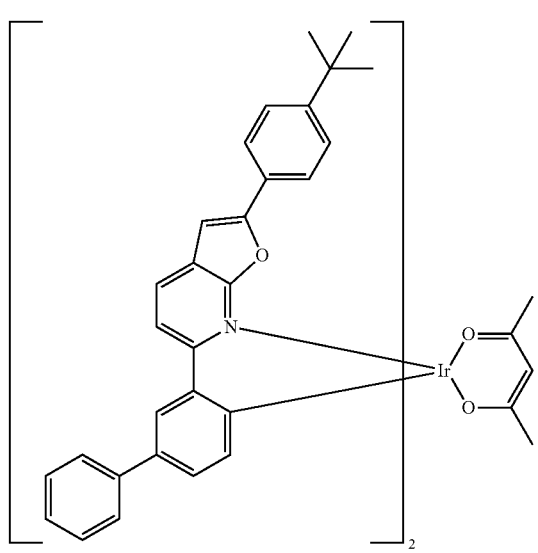
42
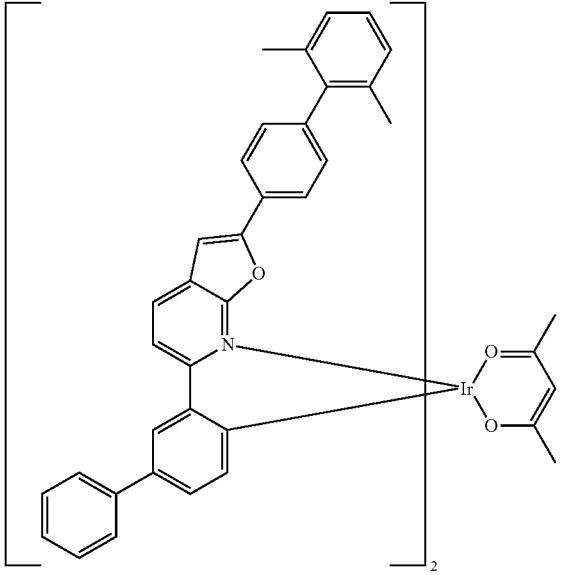
43
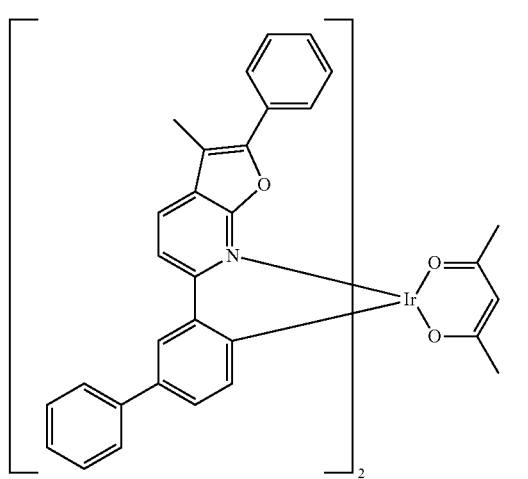

44
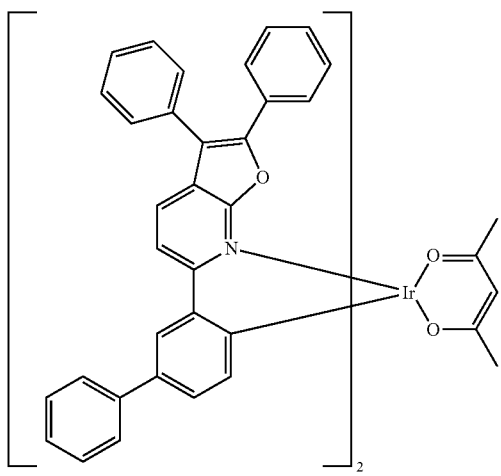
45
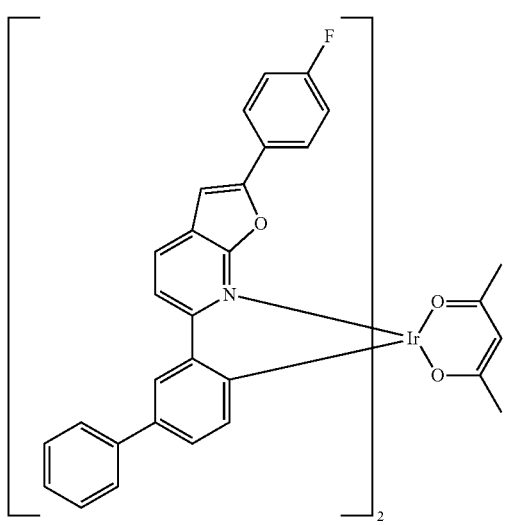
46
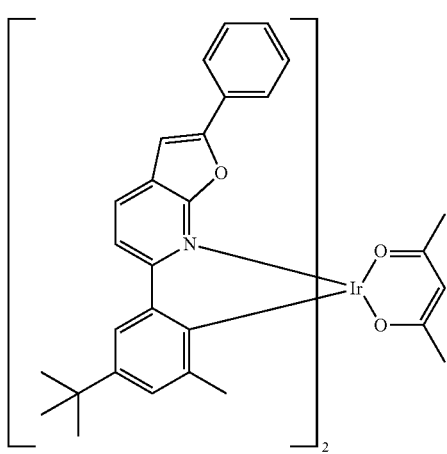
47
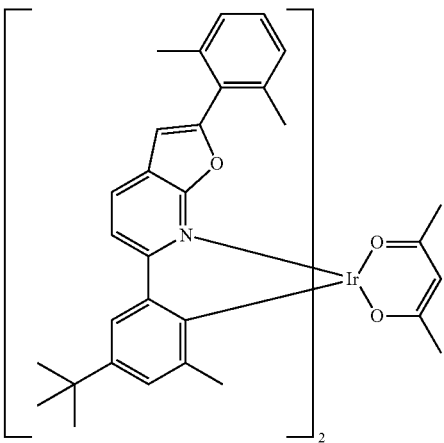
48
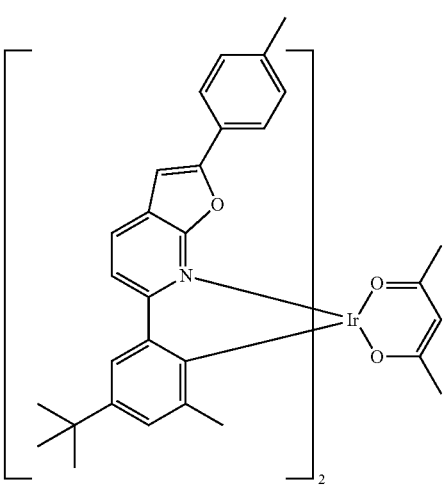
49
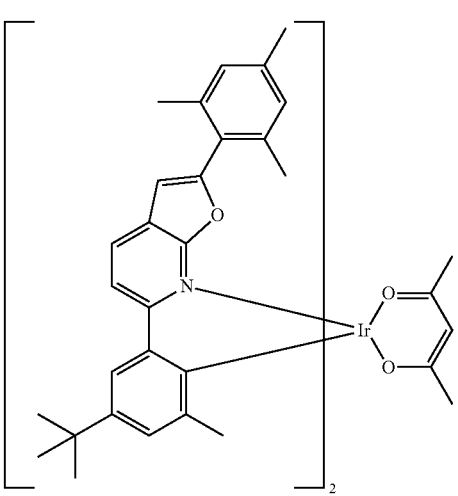

50
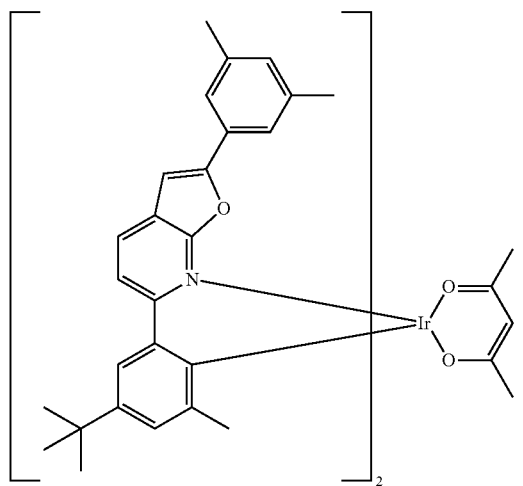
51
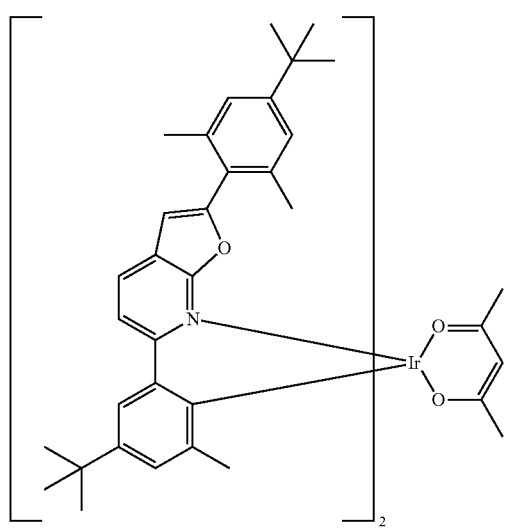
52
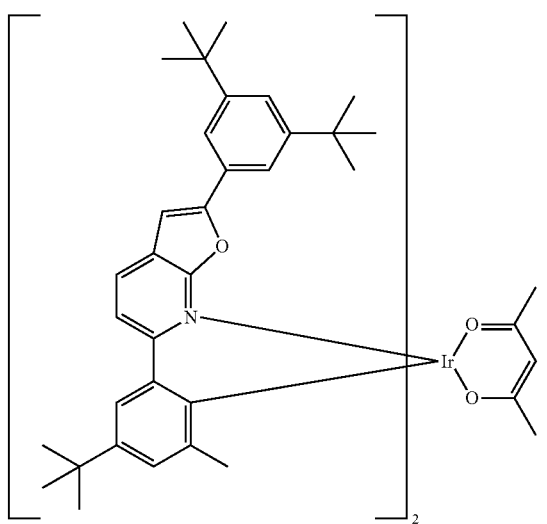
53
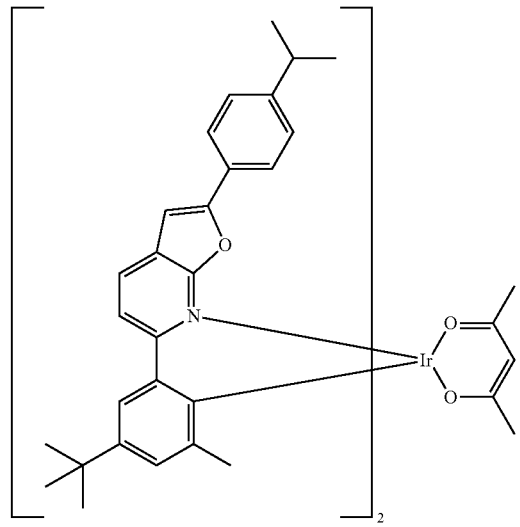
54
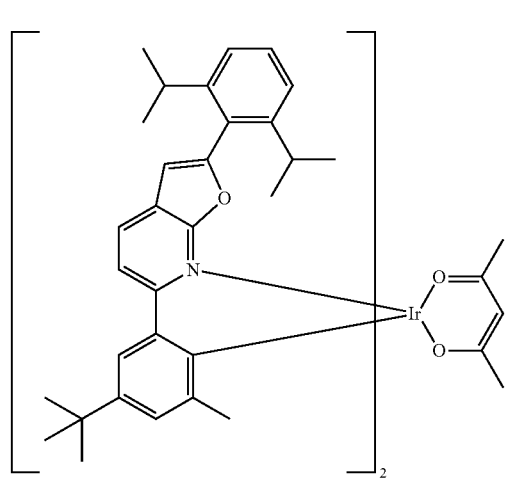
55
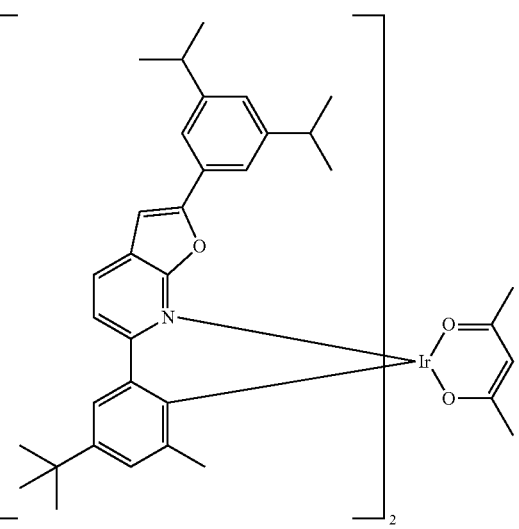

56
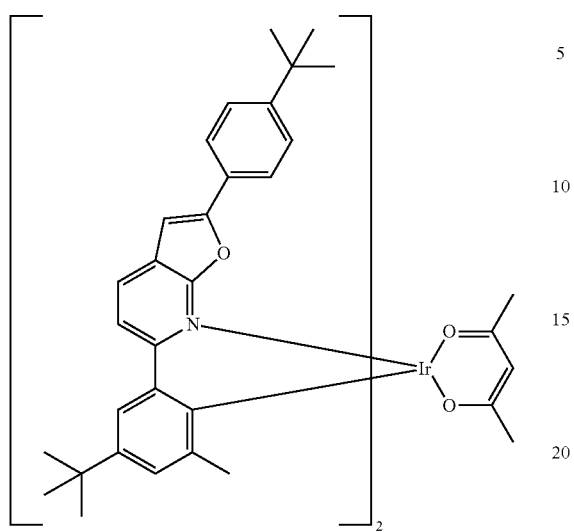
57
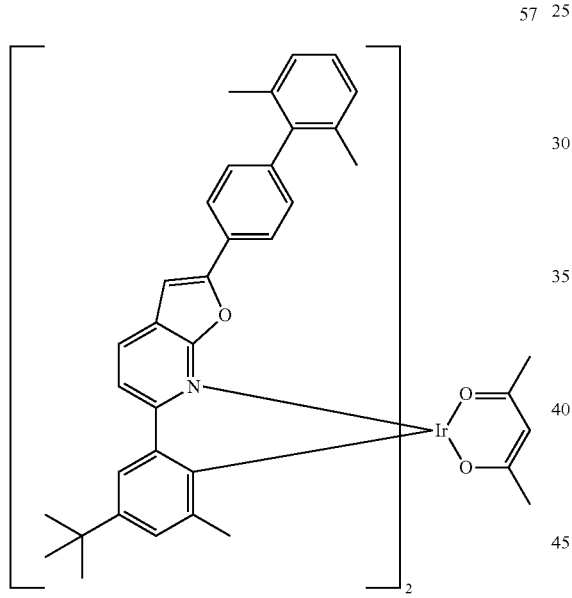
58
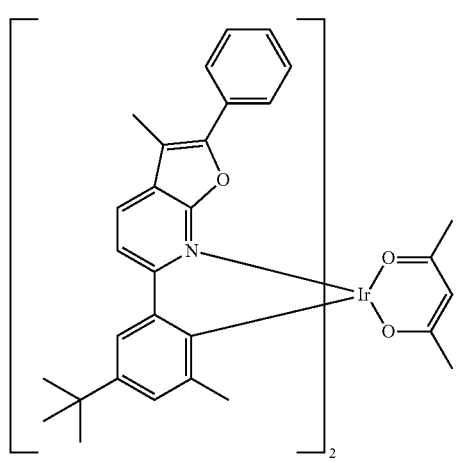
59
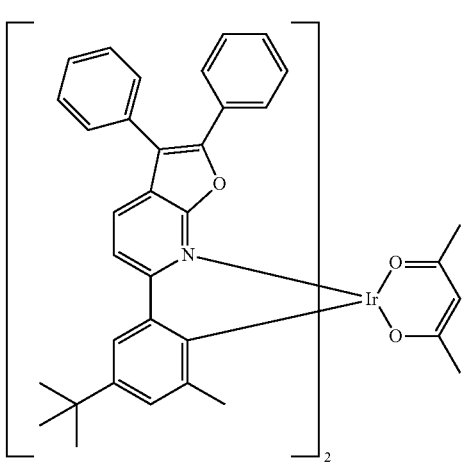
60
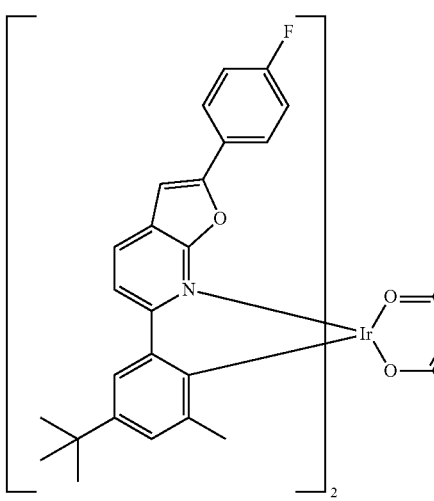
61
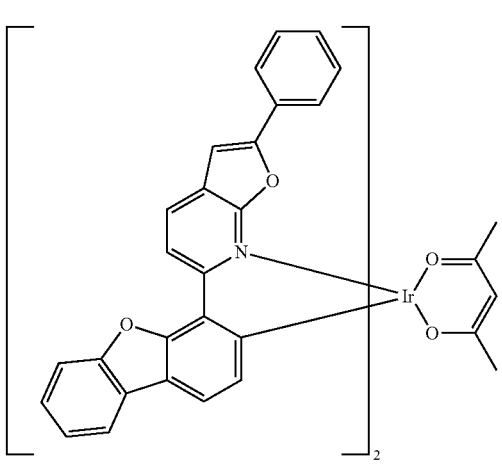

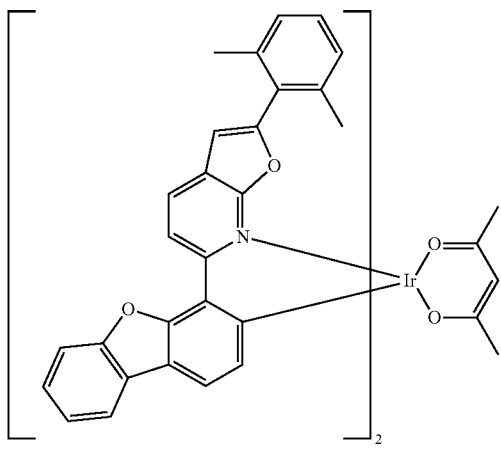
62
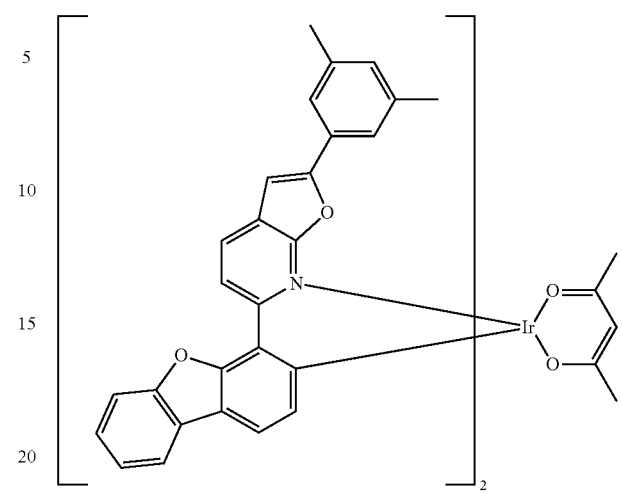
65
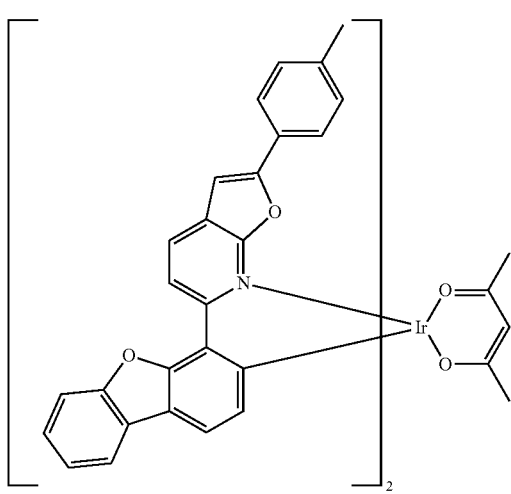
63
66
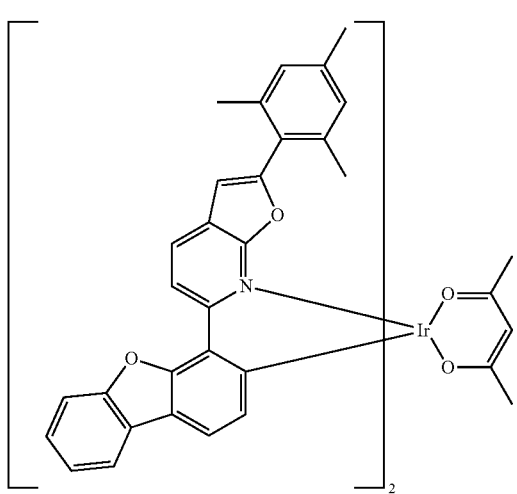
64
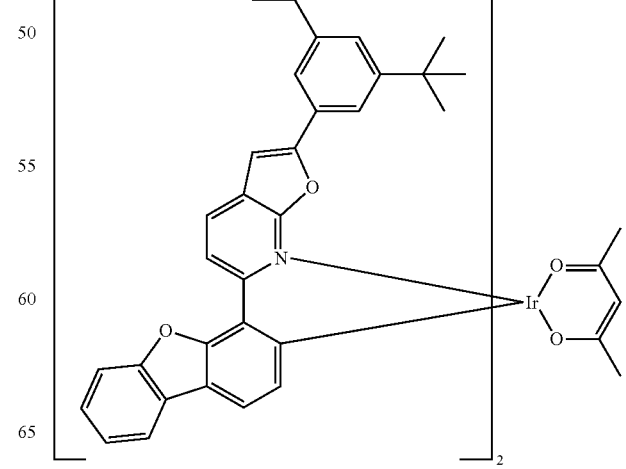
67

103 -continued
68
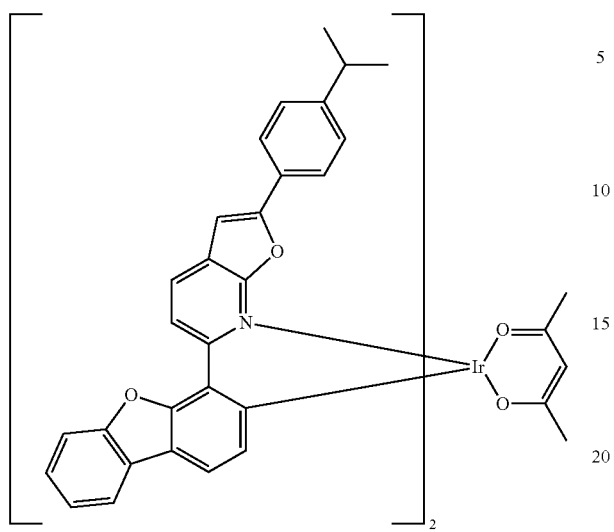
69
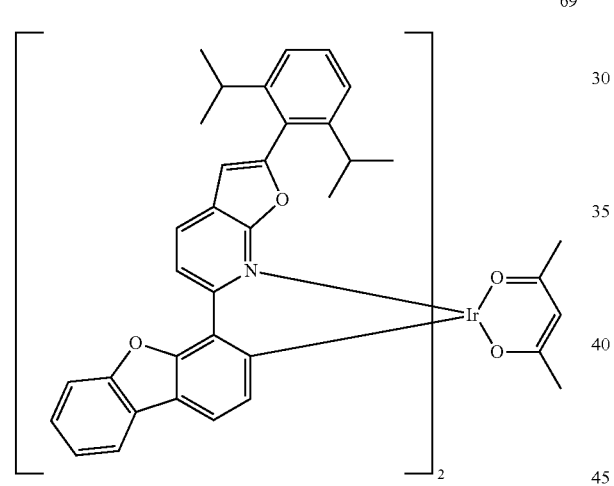
70
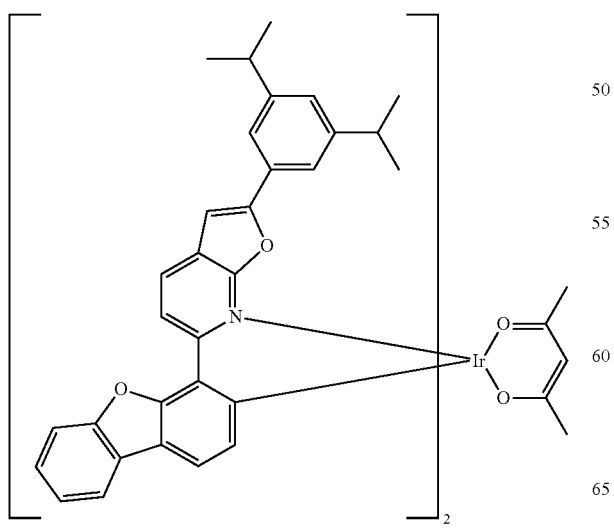
104 -continued
71
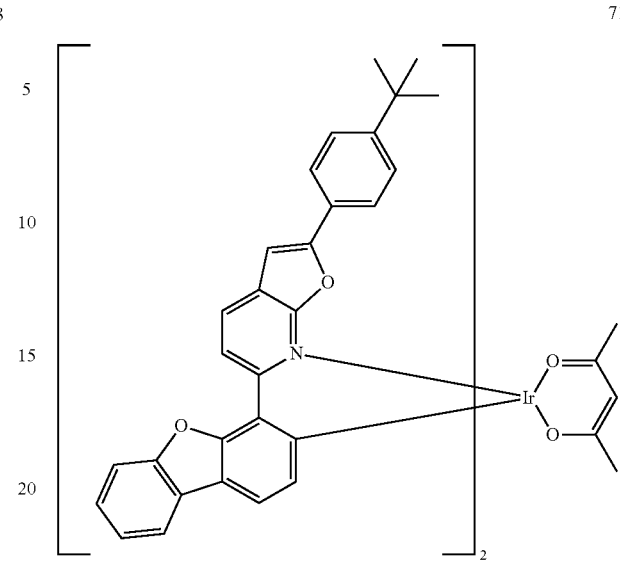
72
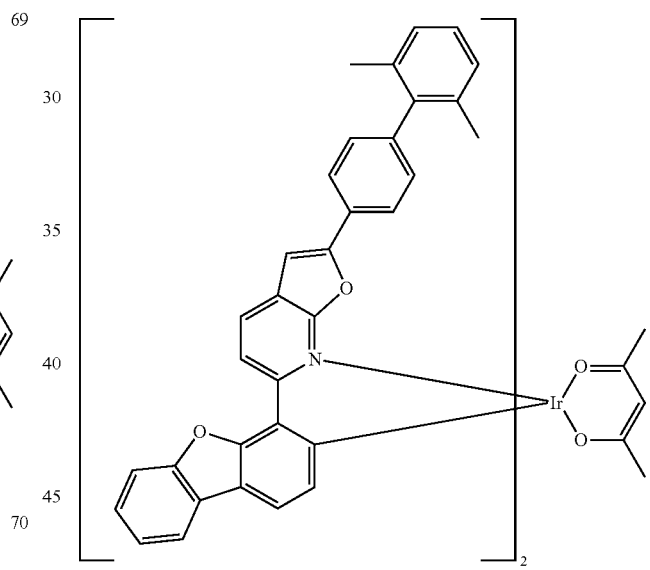
73
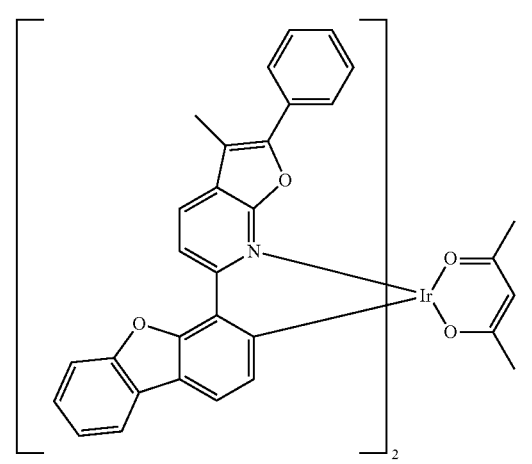

74
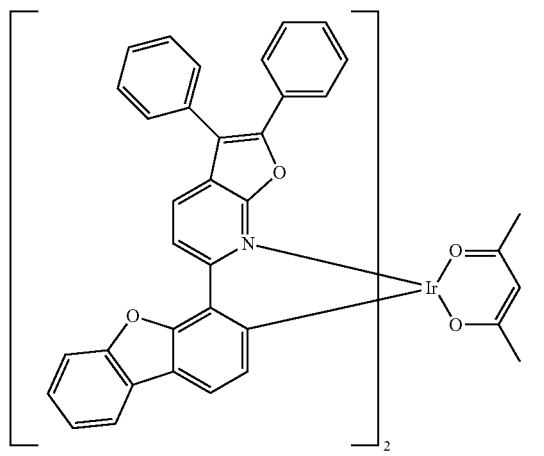
75
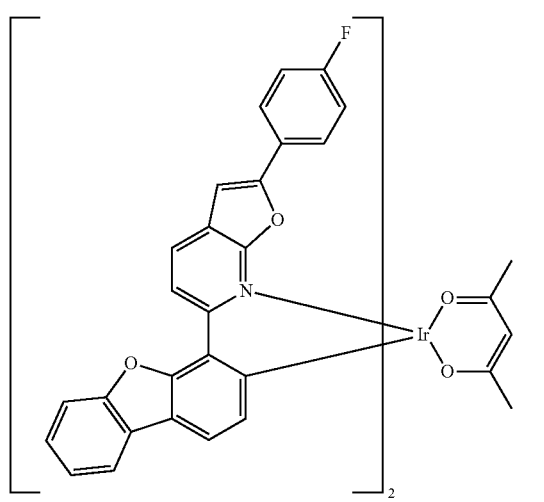
76
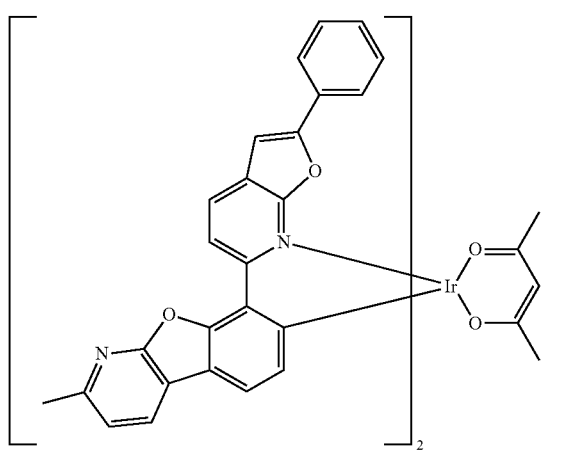
77
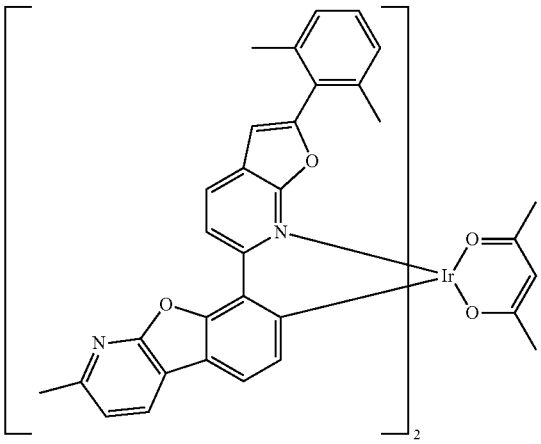
78
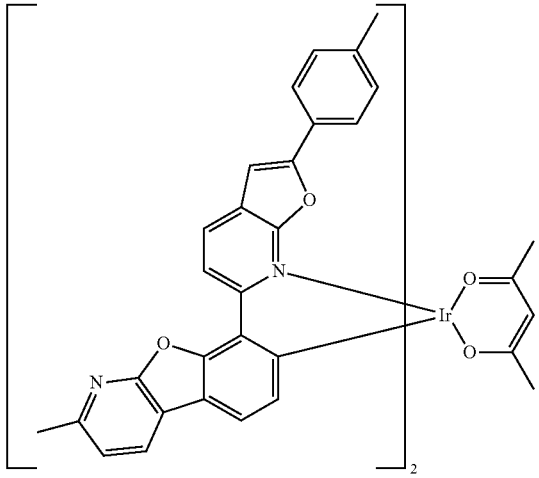
79
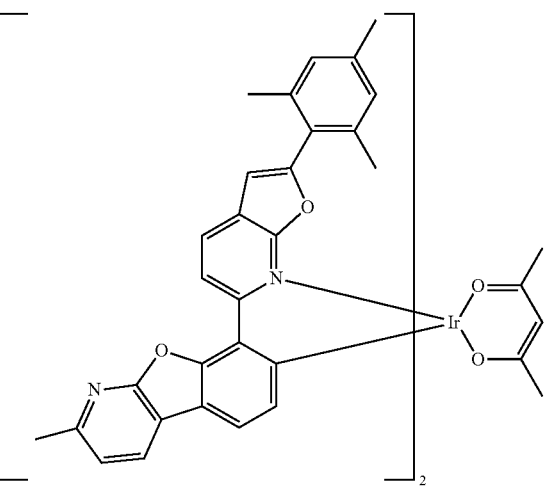

80
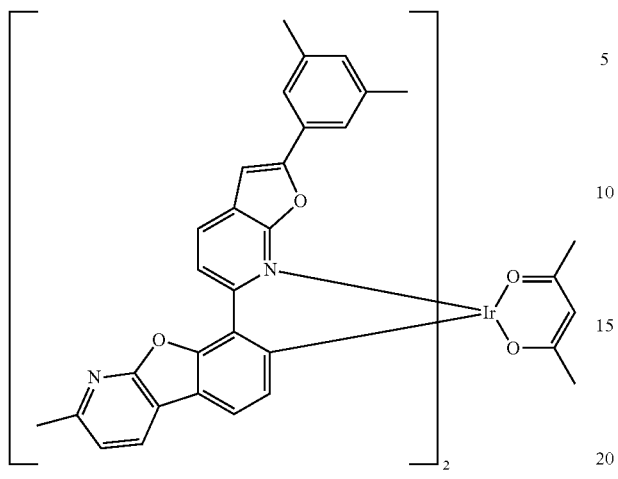
83
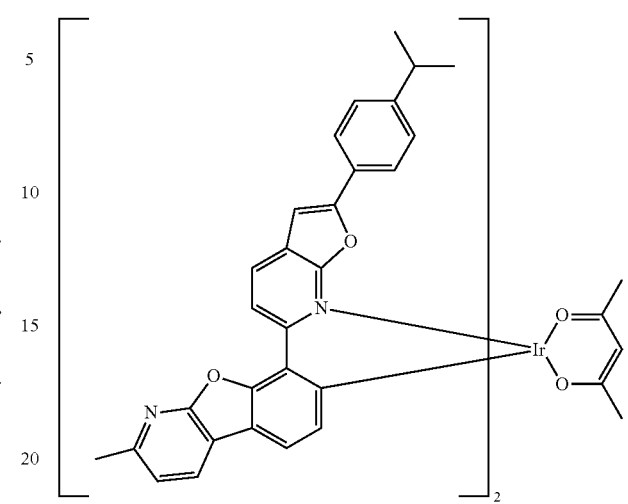
81
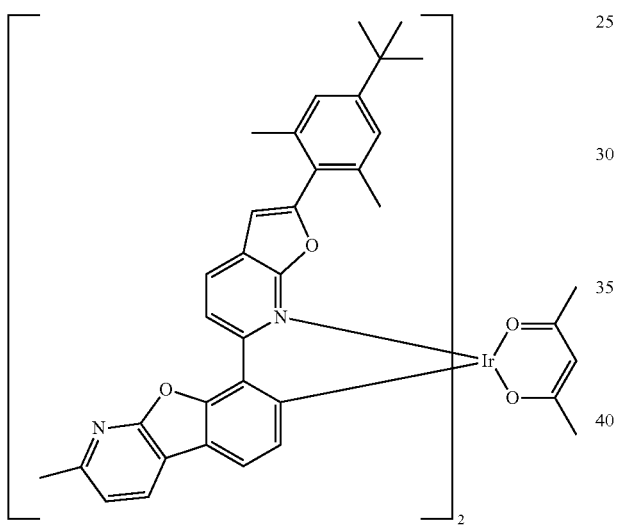
84
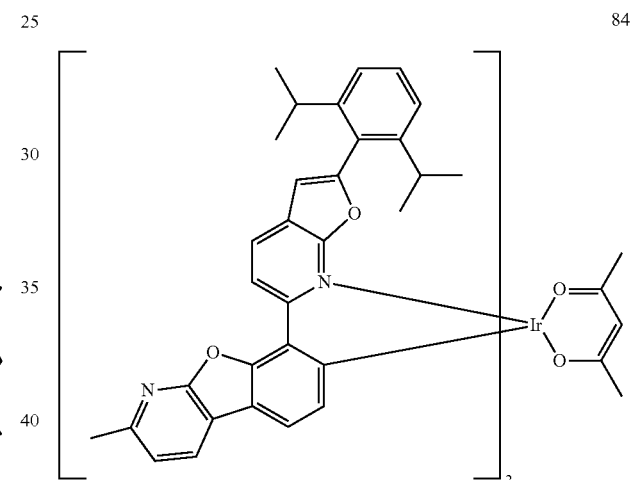
82
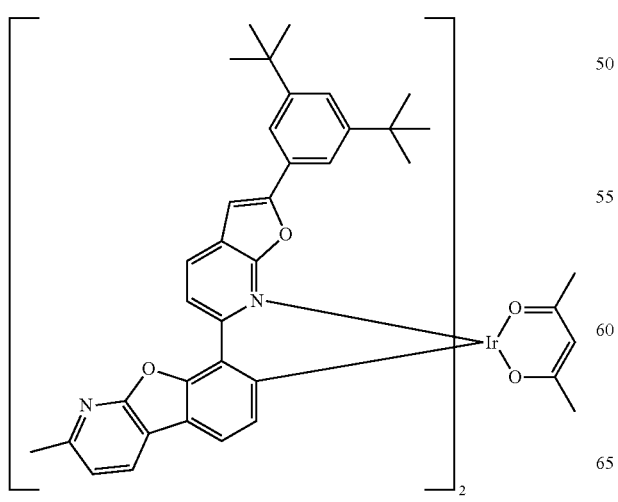
85

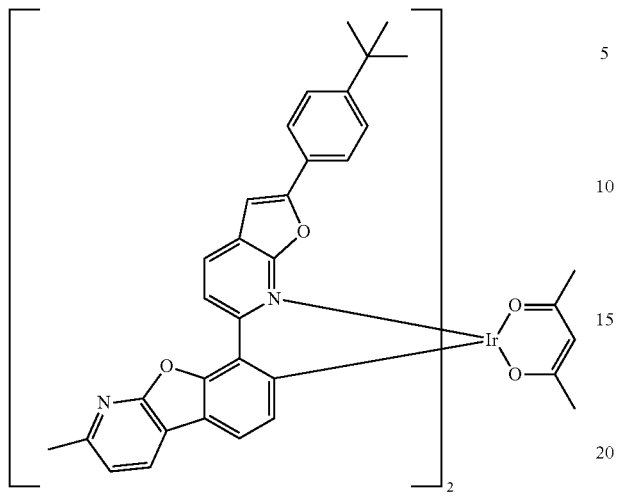
86
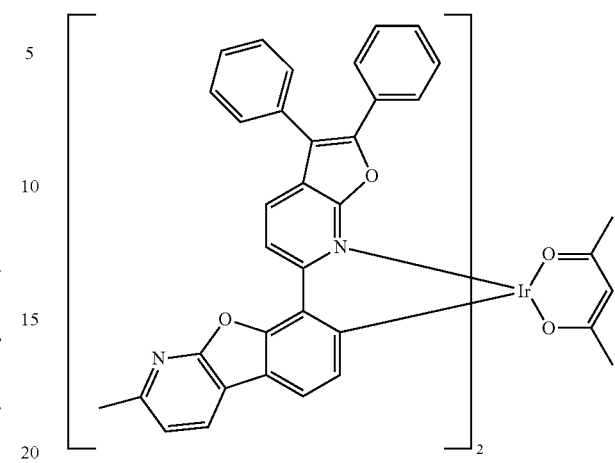
89
87
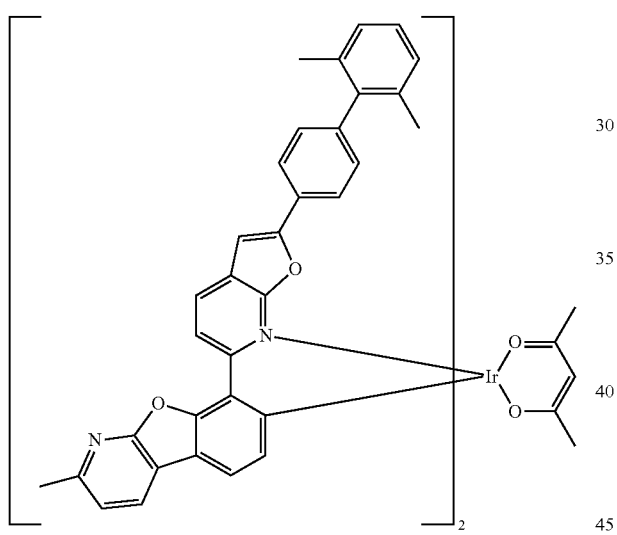
90
88
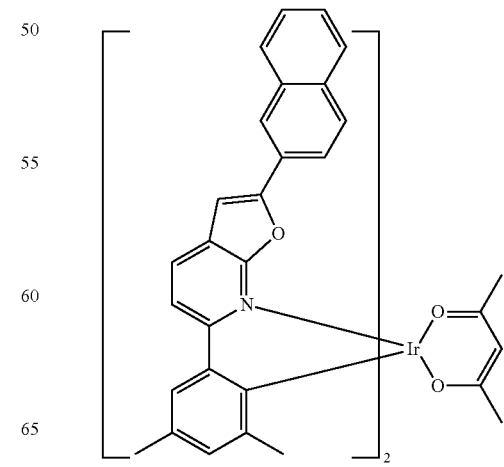
91

111
92
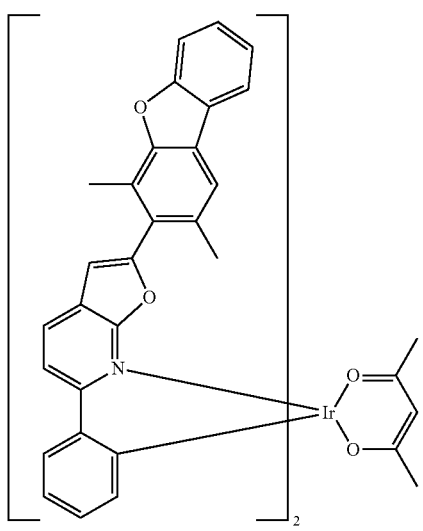
93
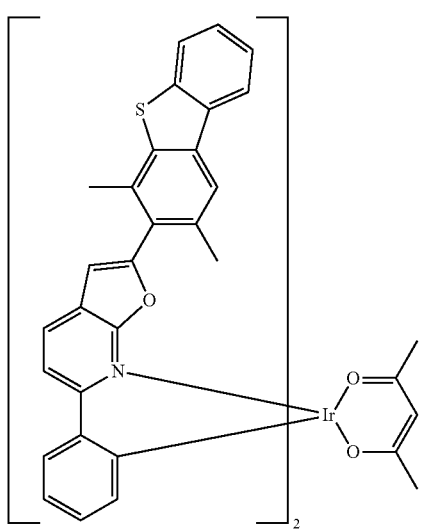
94
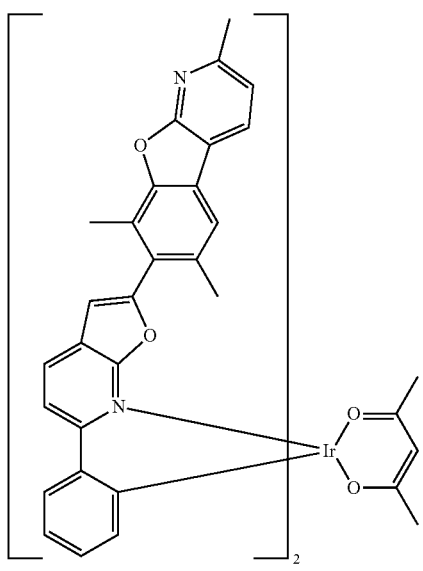
112
95
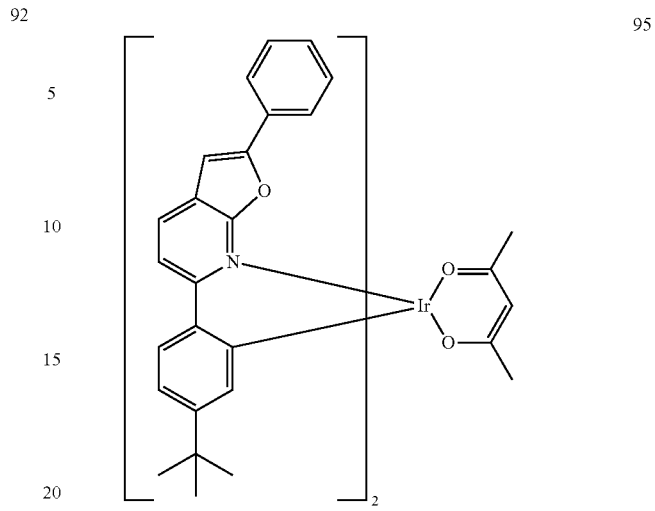
96
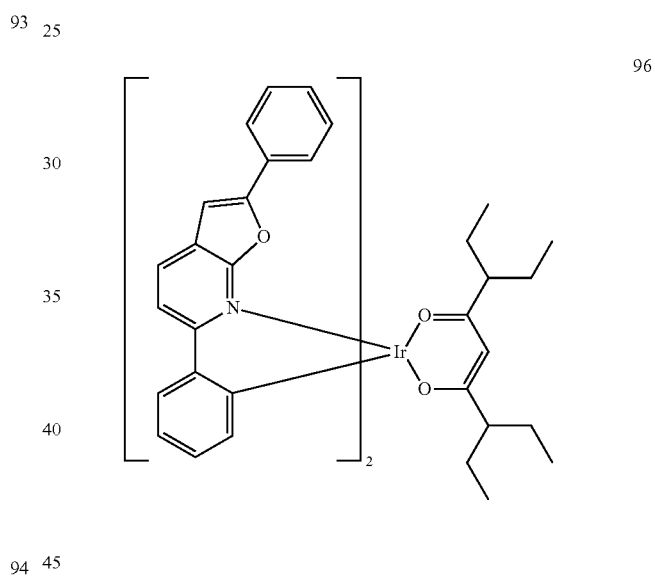
97
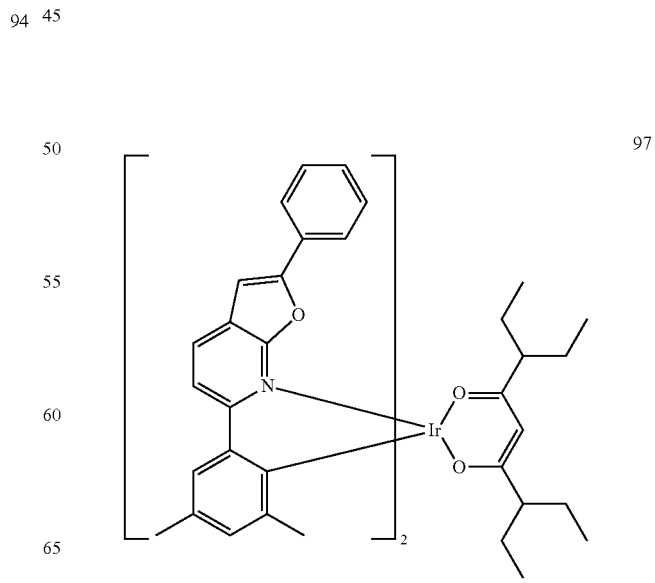

-continued
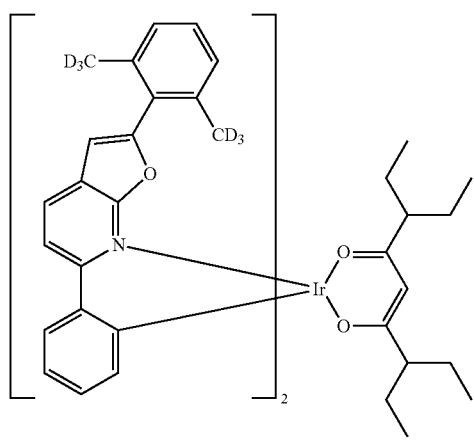
98
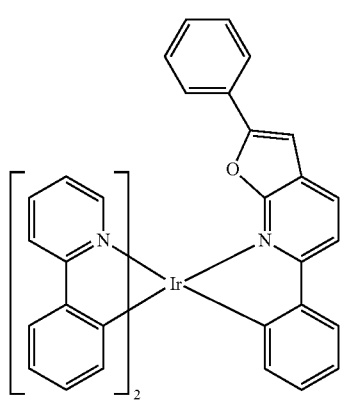
99
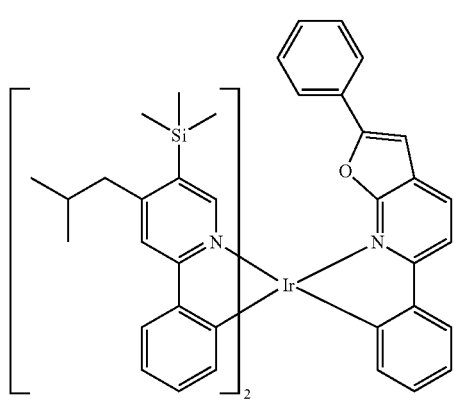
100
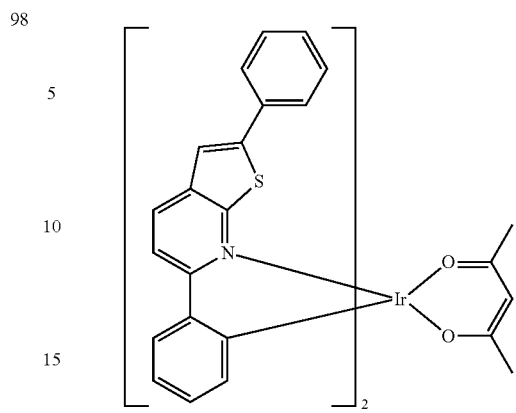
101
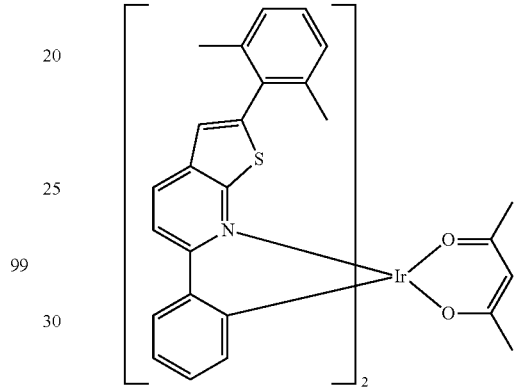
102
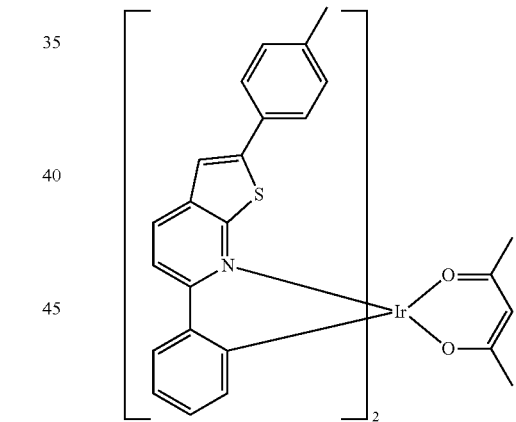
103
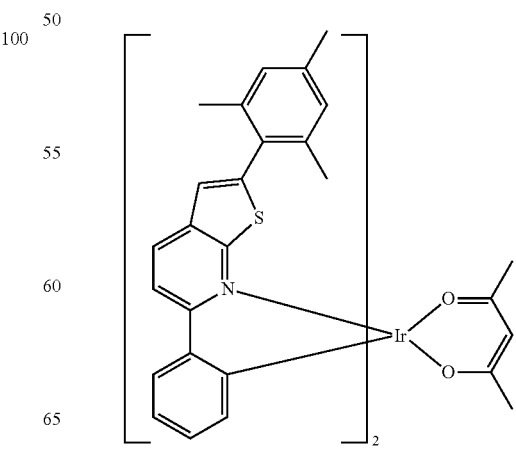
104

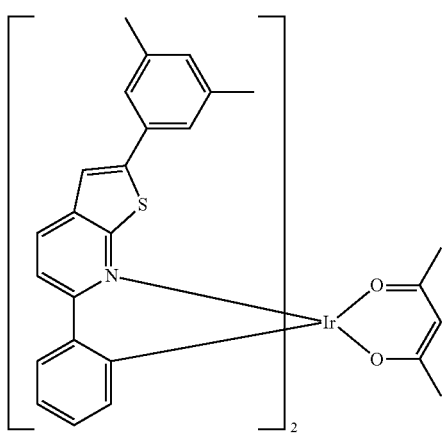
105
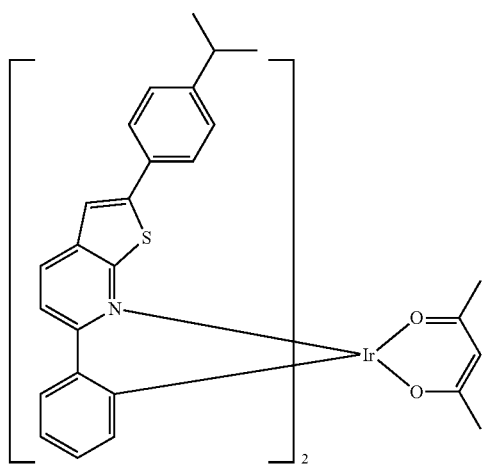
108
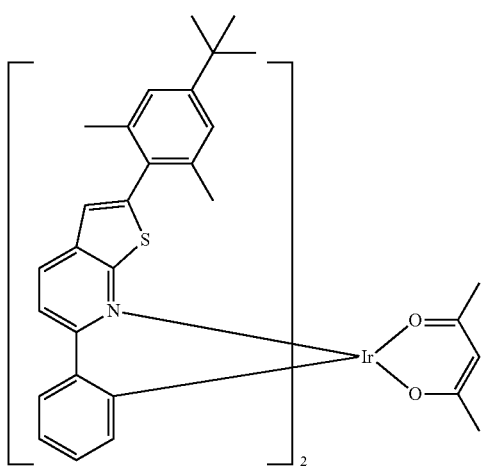
106
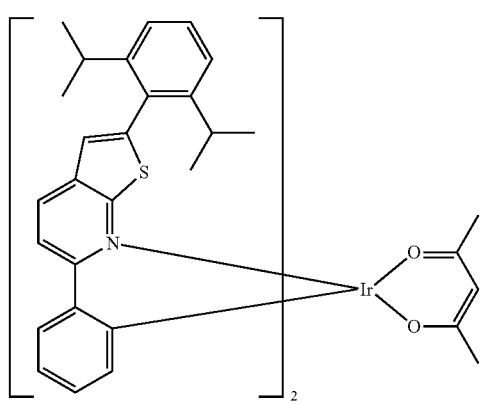
109
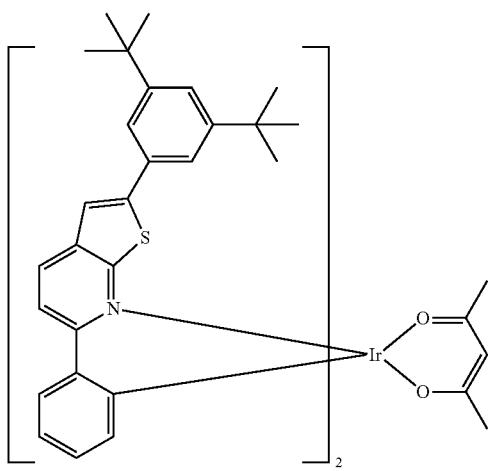
107
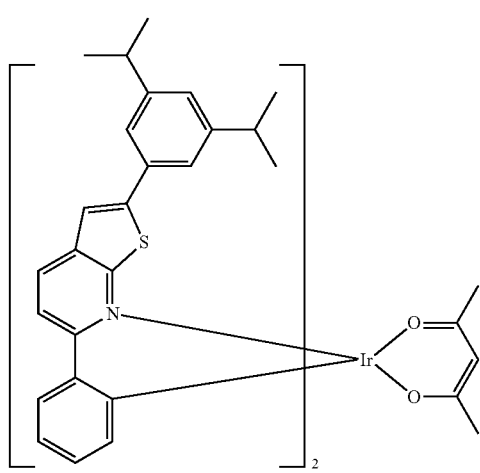
110

111 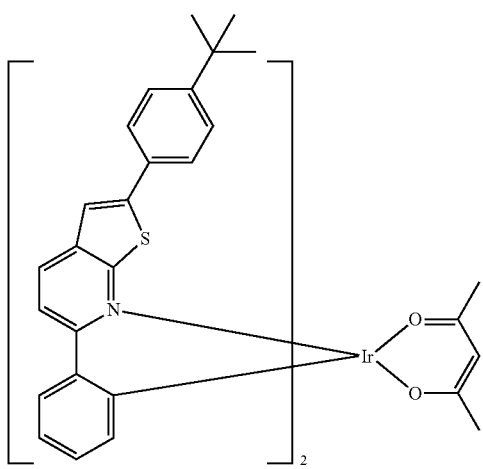
112 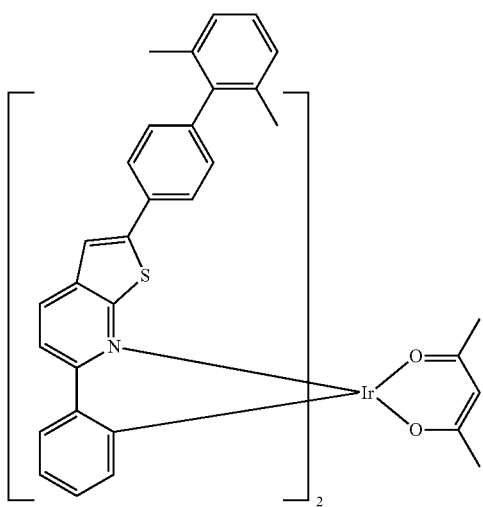
113 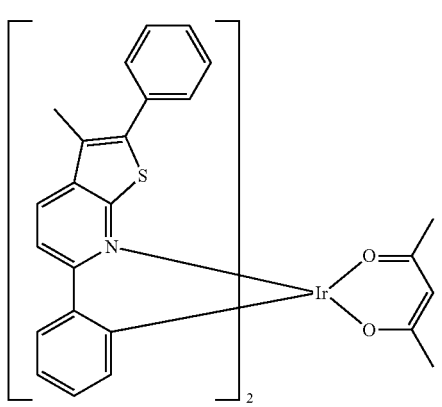
114 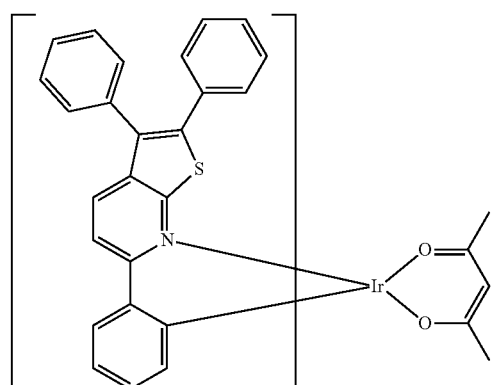
115 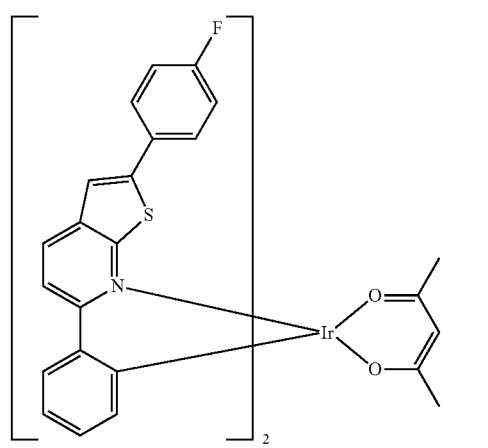
116 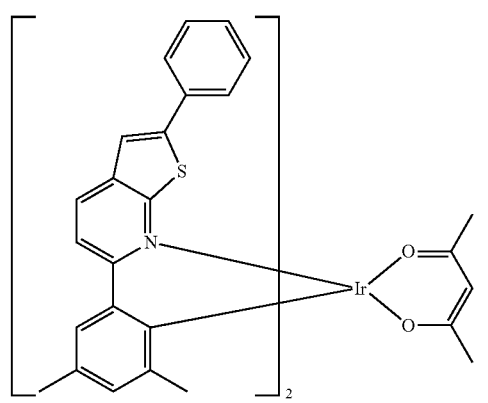
117 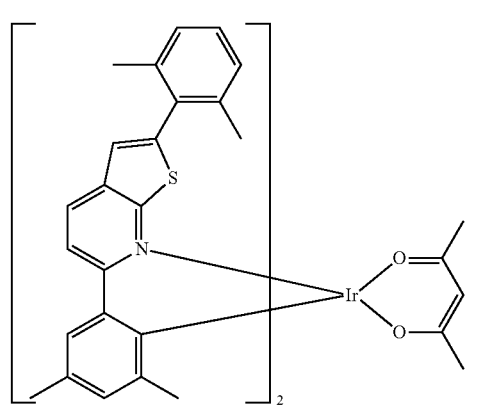

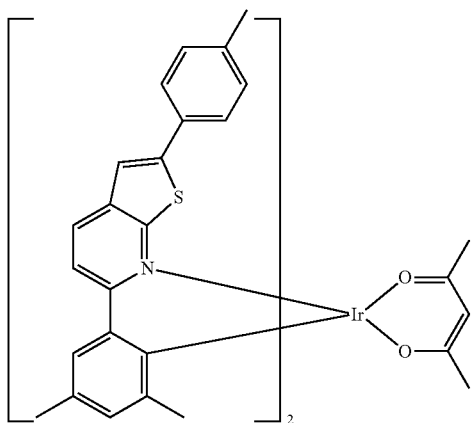
118
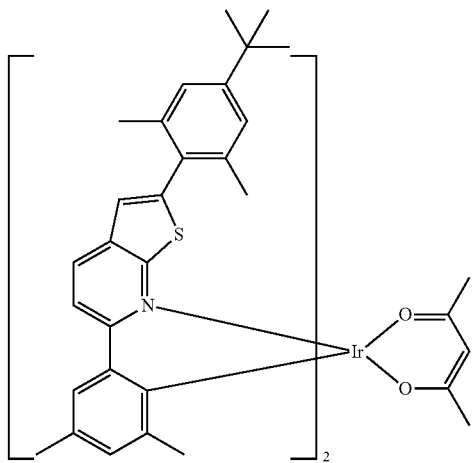
121
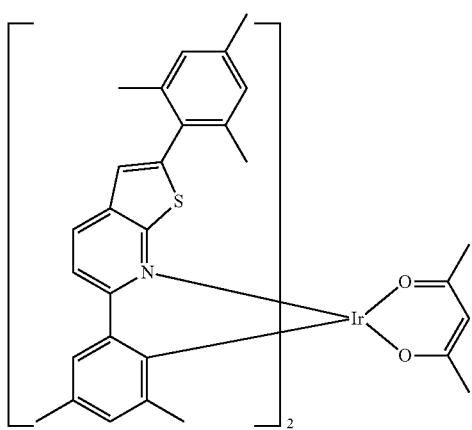
119
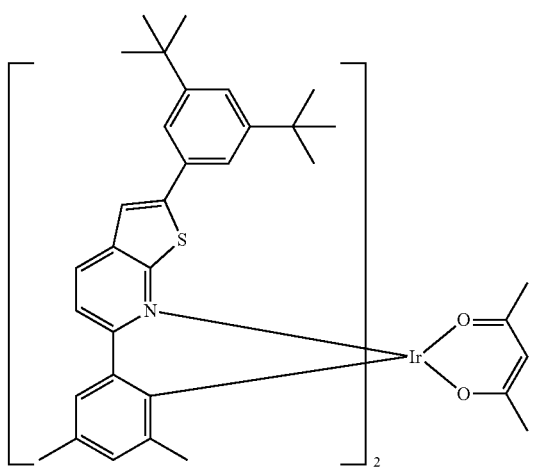
122
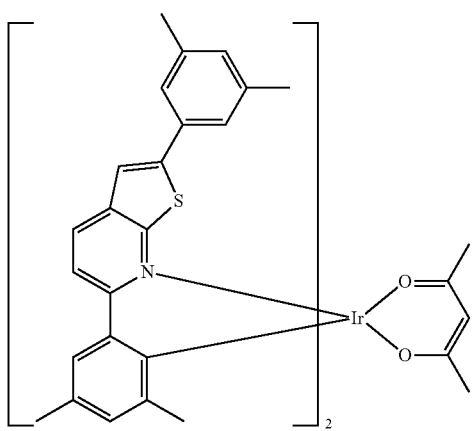
120
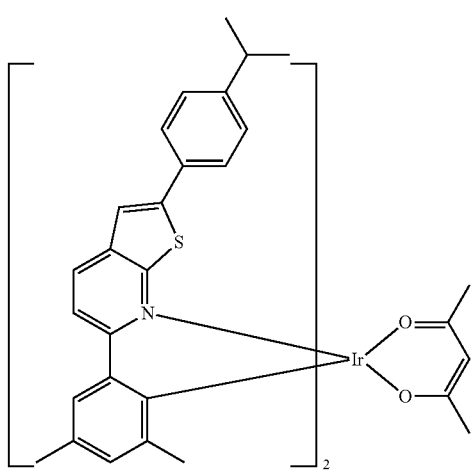
123

| 121 | 122 |
|---|---|
| 124 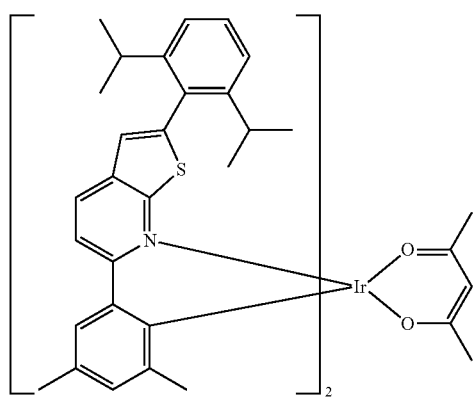 | 127 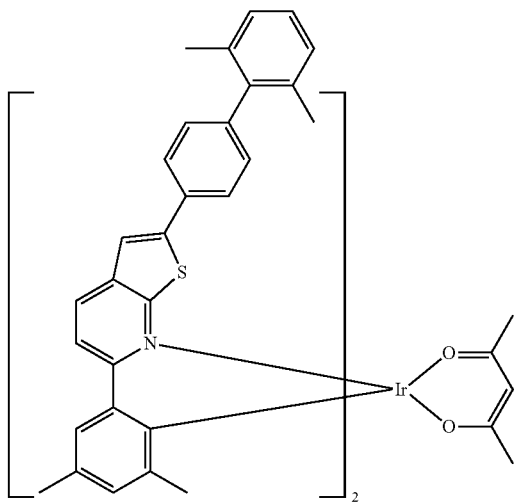 |
| 125 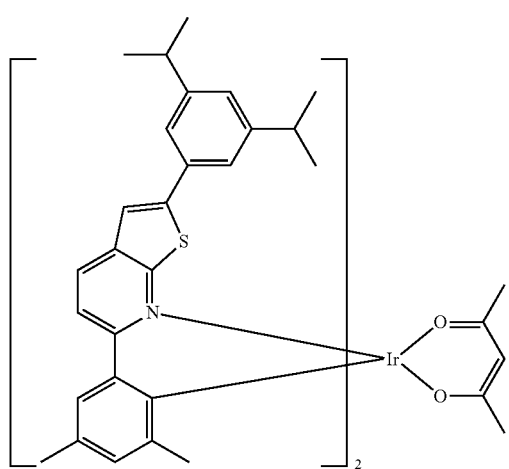 | 128 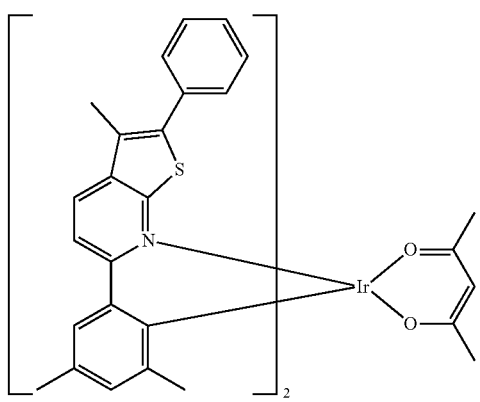 |
| 126 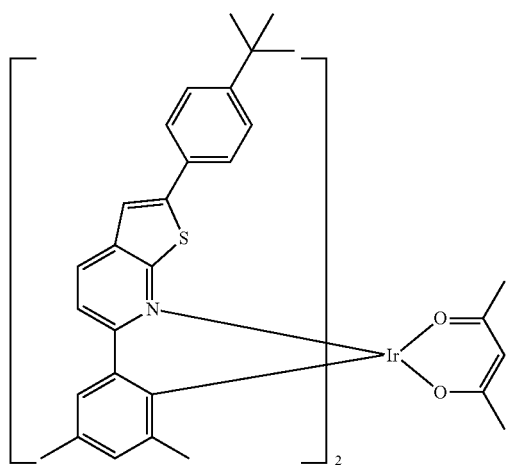 | 129 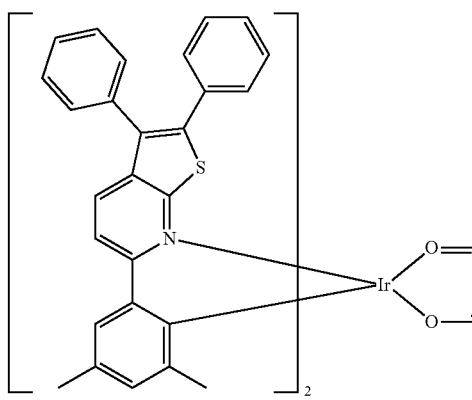 |

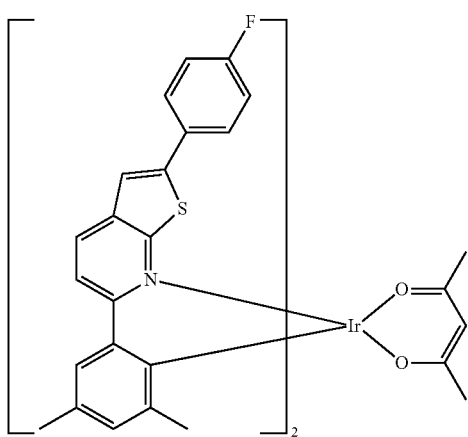
130
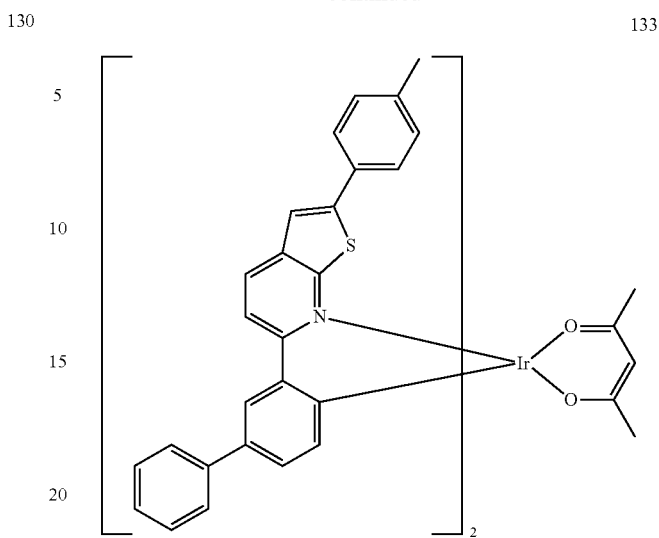
133
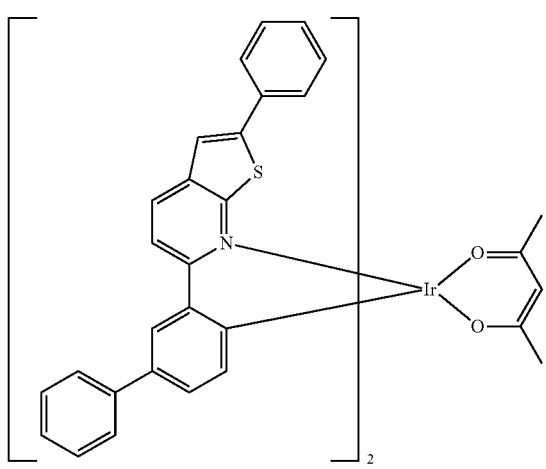
131
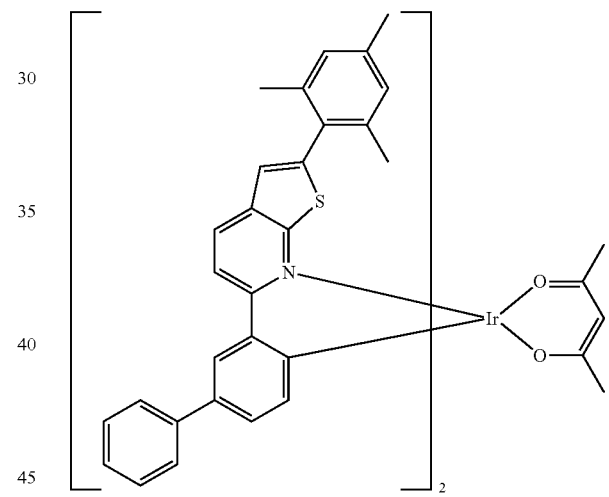
134
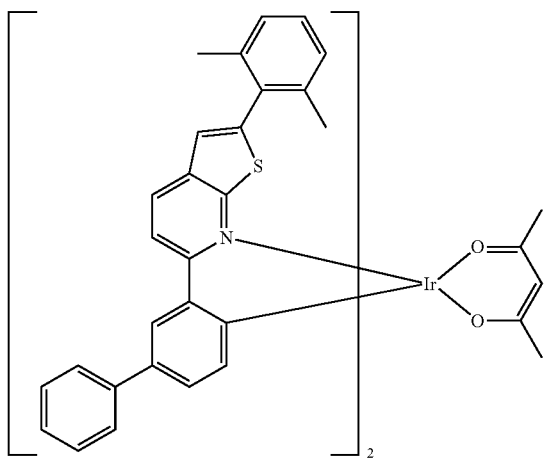
132
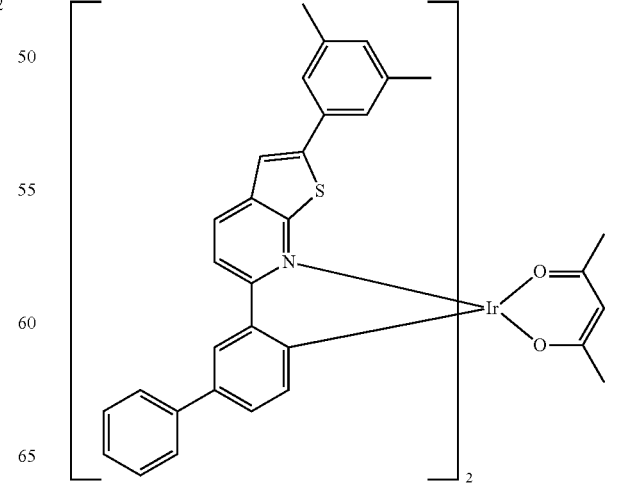
135

136
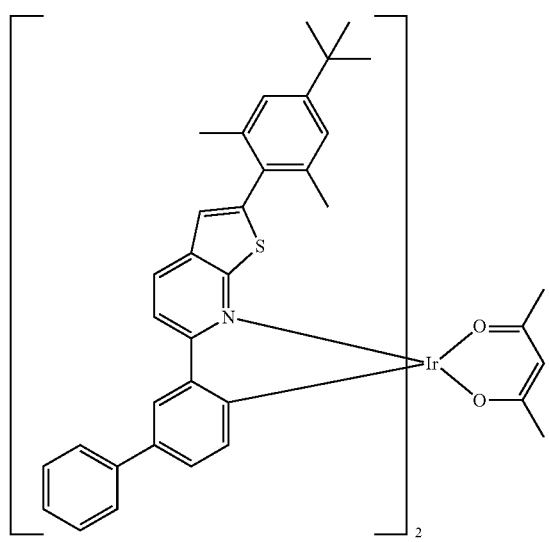
137
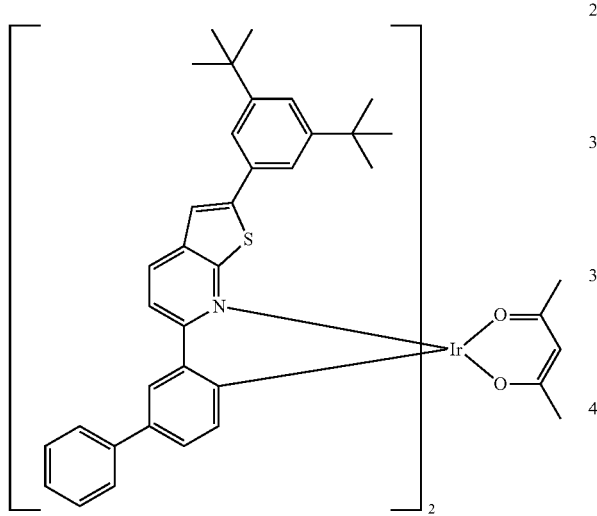
138
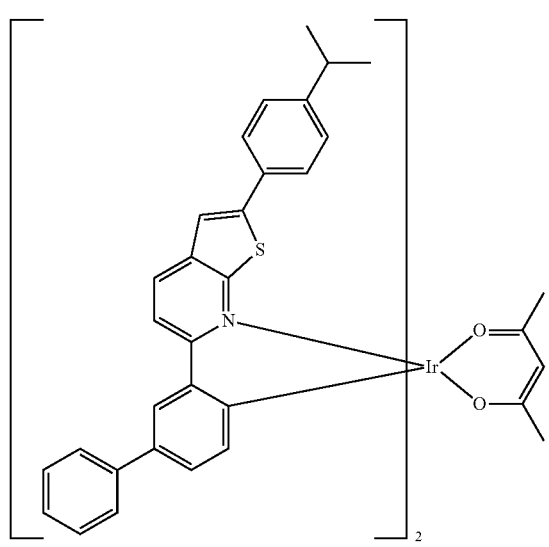
139
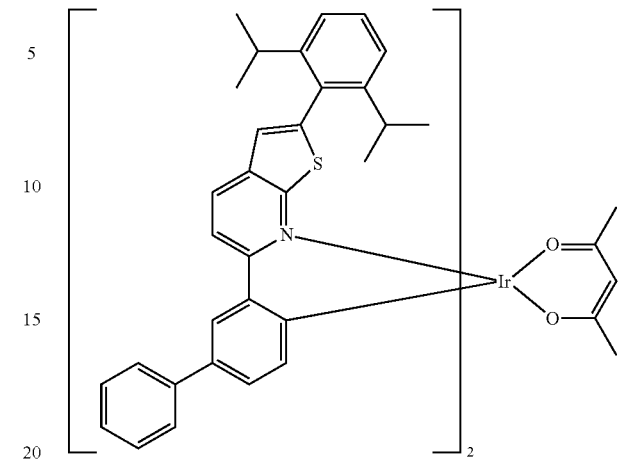
140
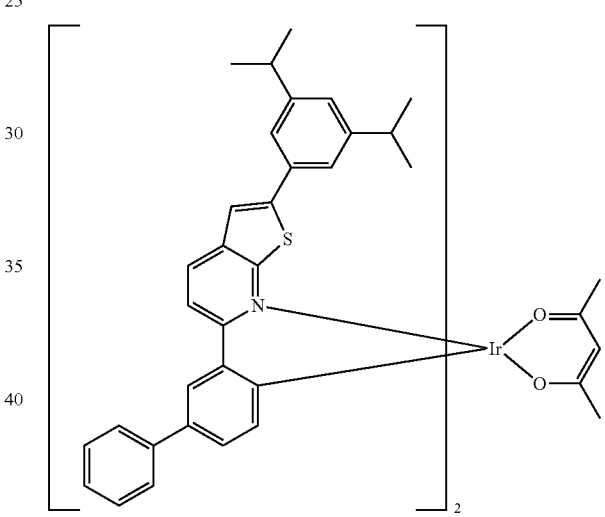
141
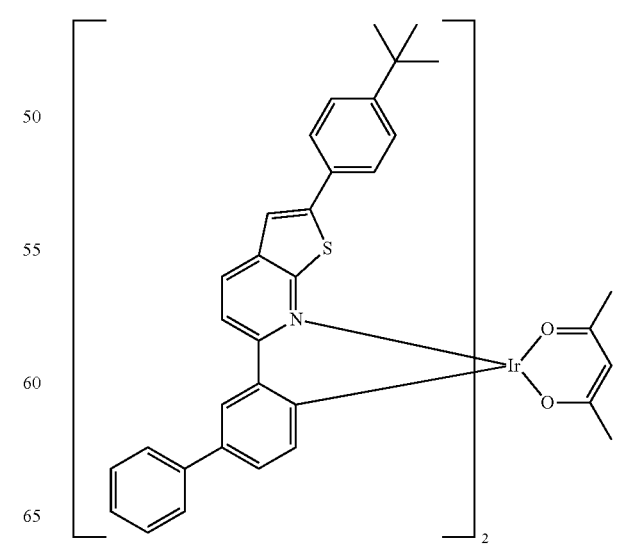

-continued
142
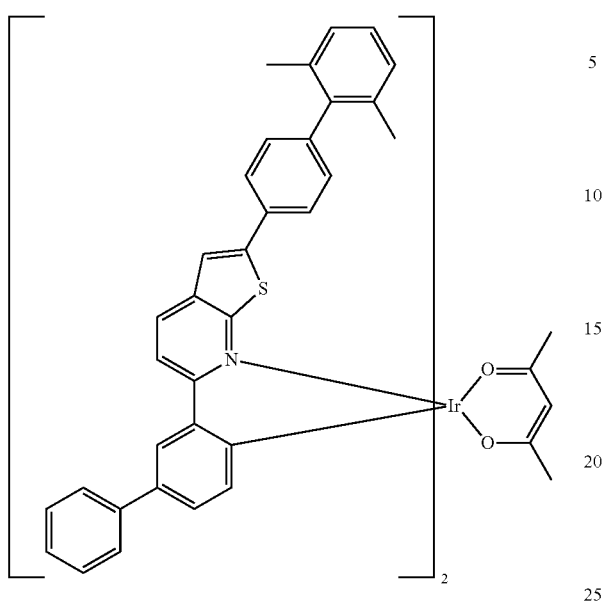
143
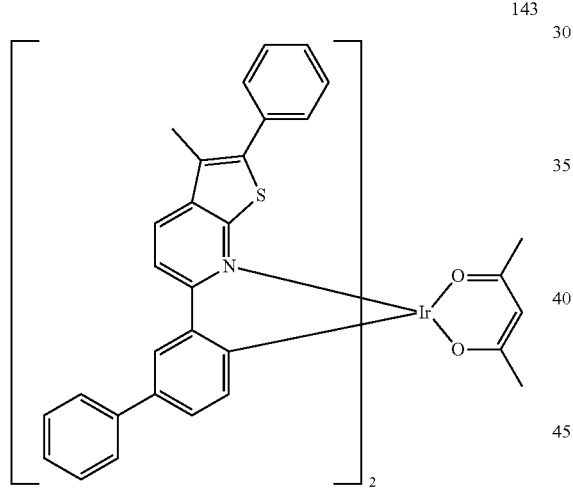
144
-continued
145
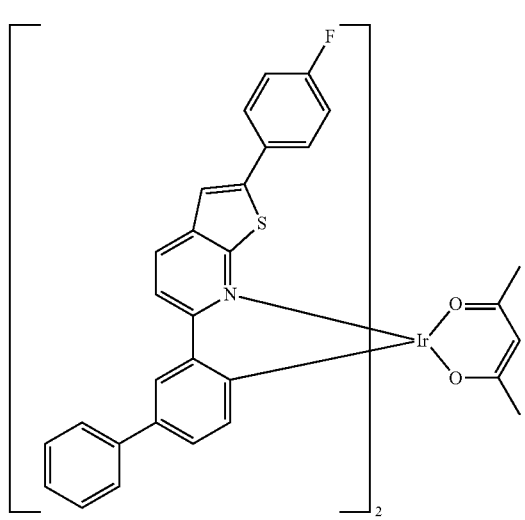
146
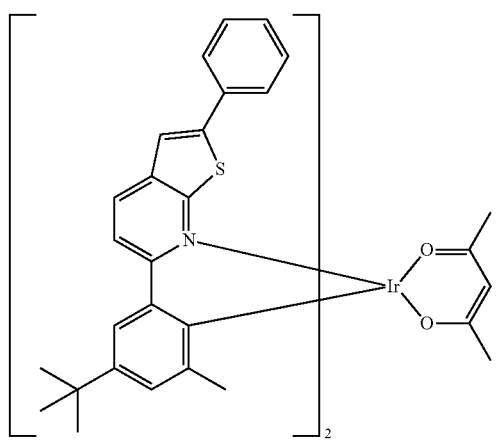
147
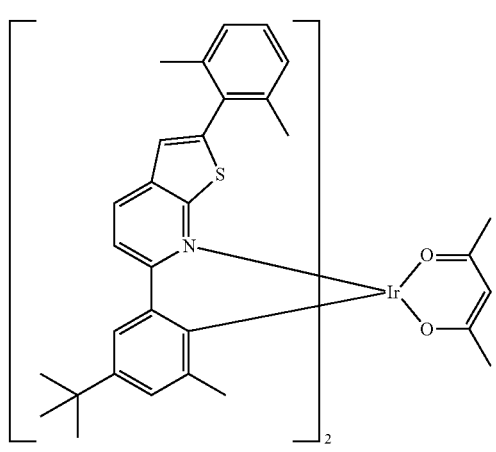

148
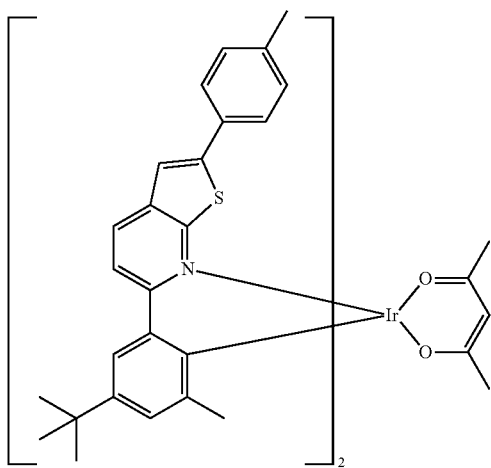
149
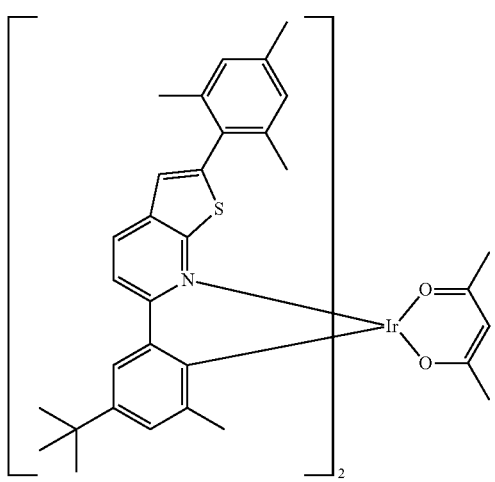
150
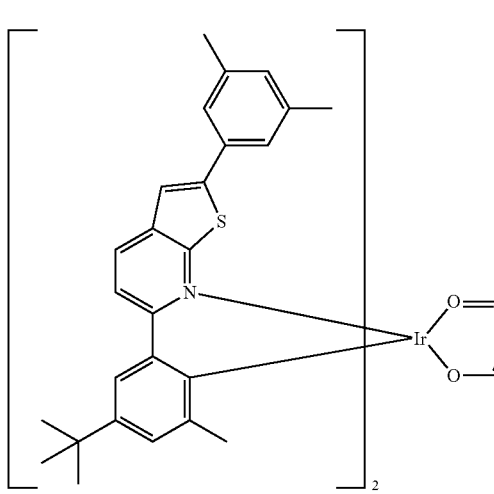
151
152
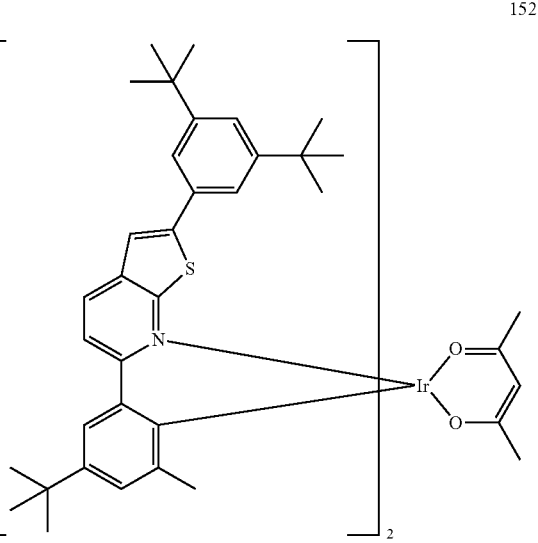
153
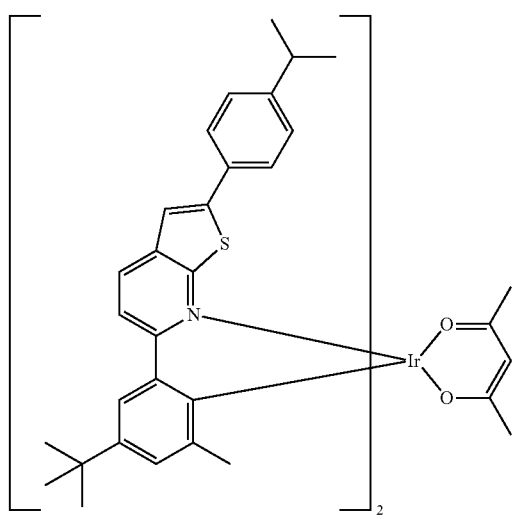

-continued
154
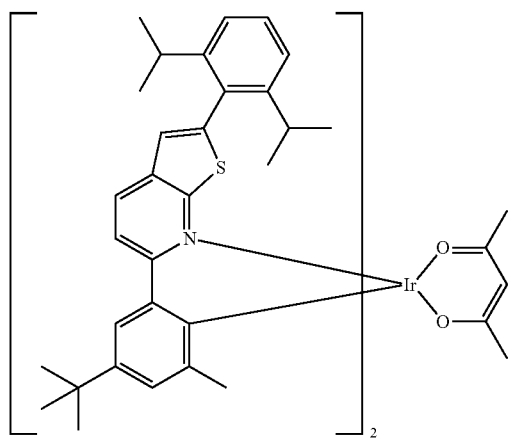
155
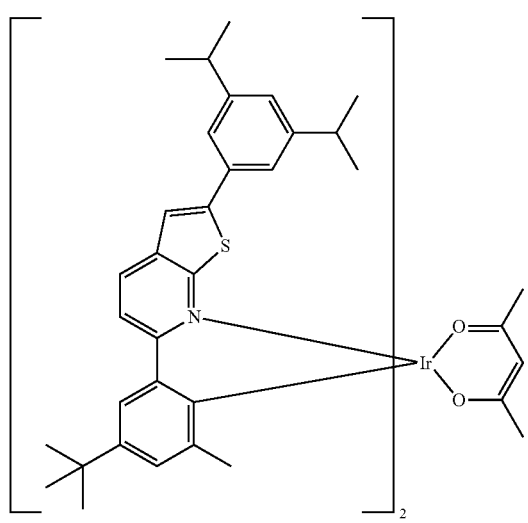
156
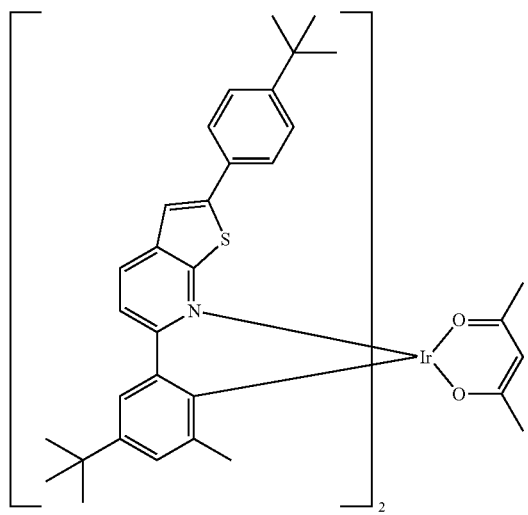
-continued
157
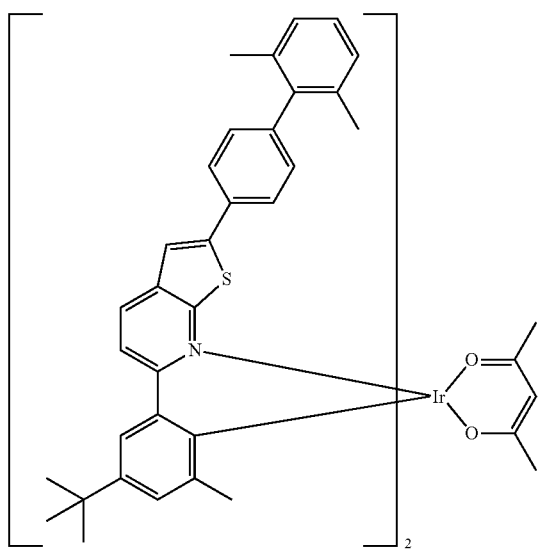
158
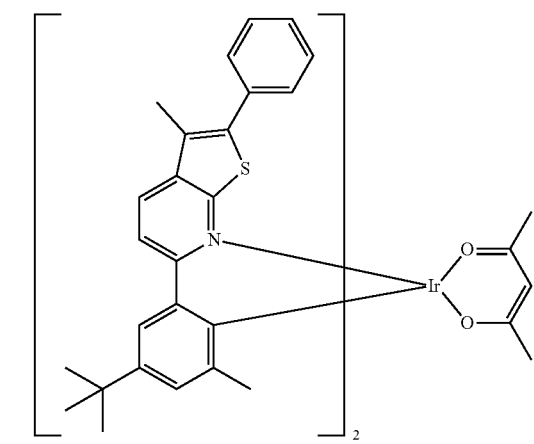
159
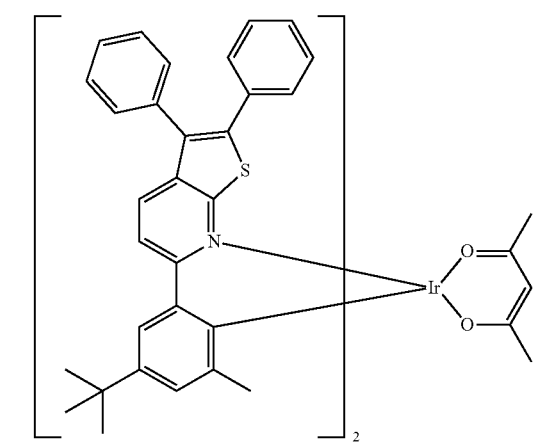

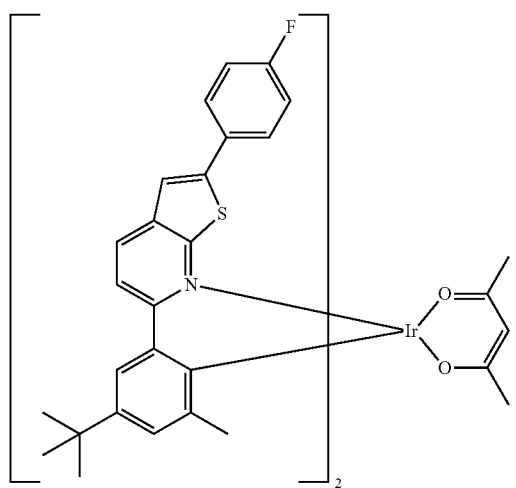
160
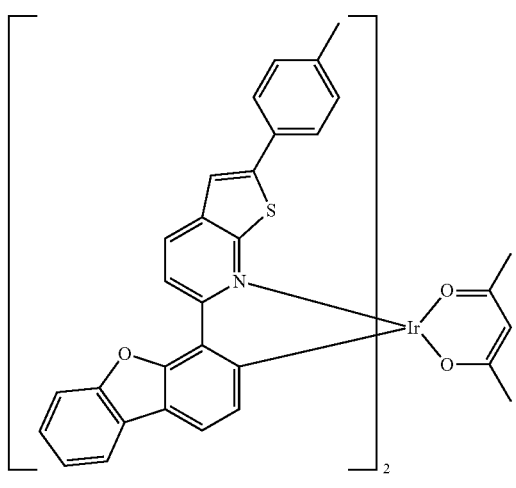
163
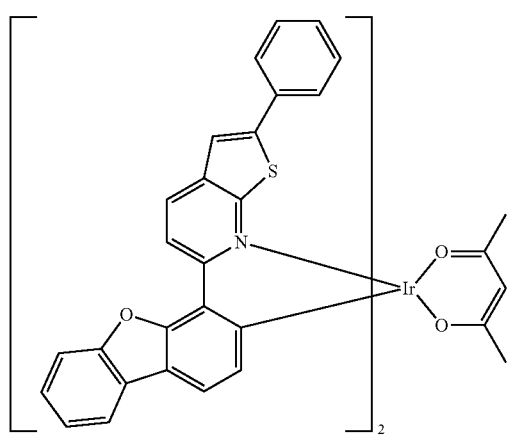
161
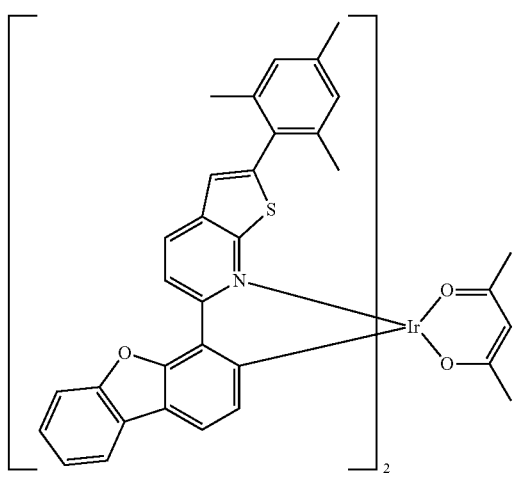
164
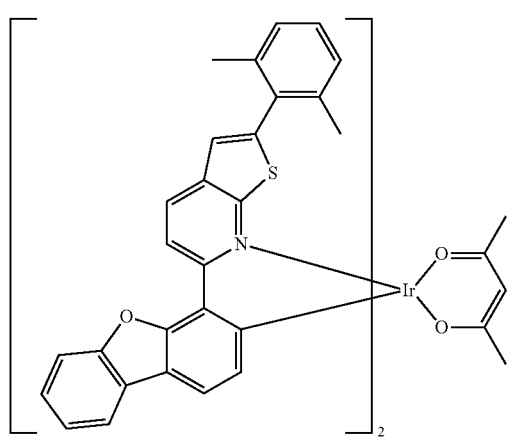
162
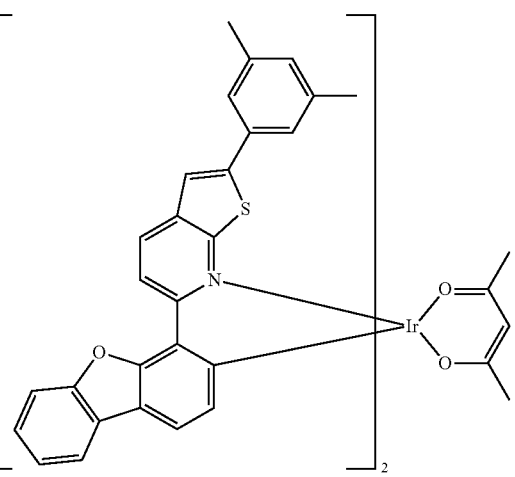
165

166
167
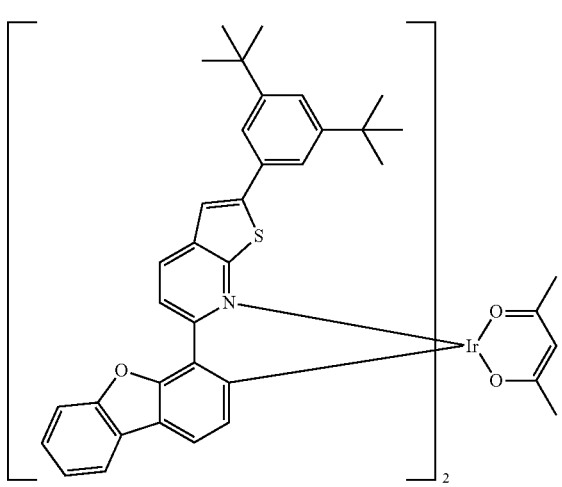
168
169
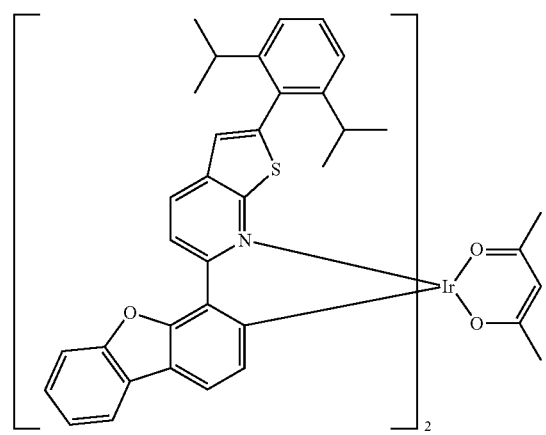
170
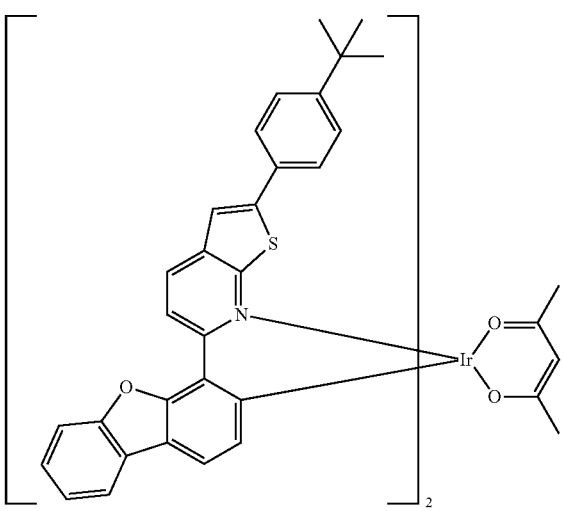
171

172
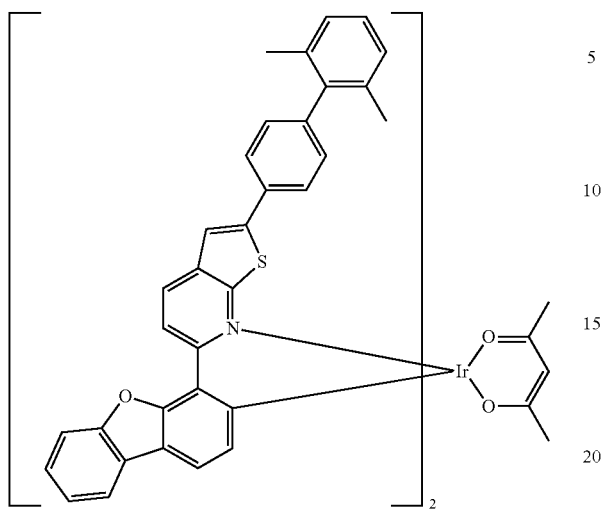
173
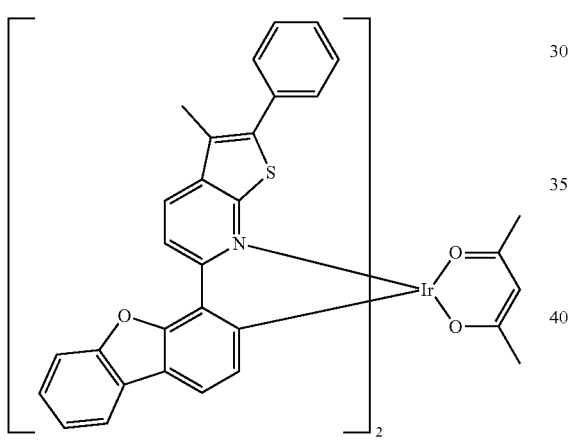
174
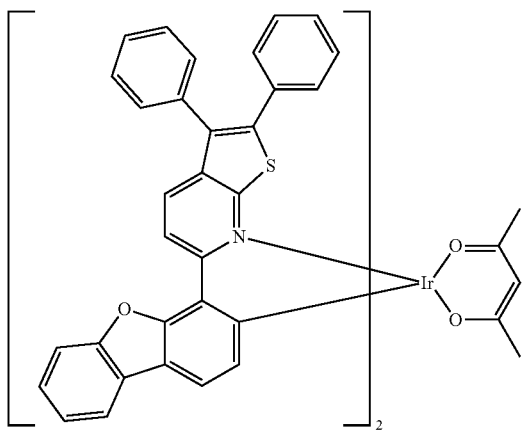
175
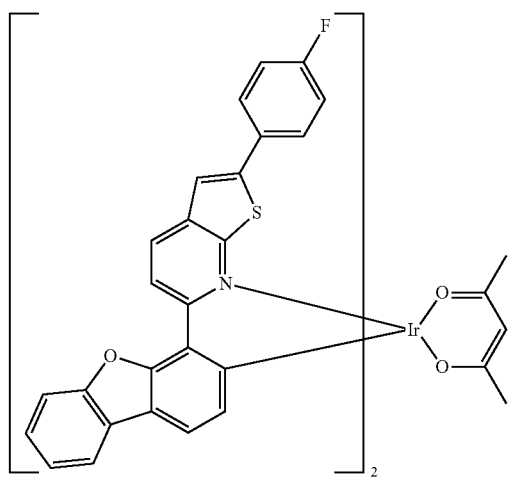
176
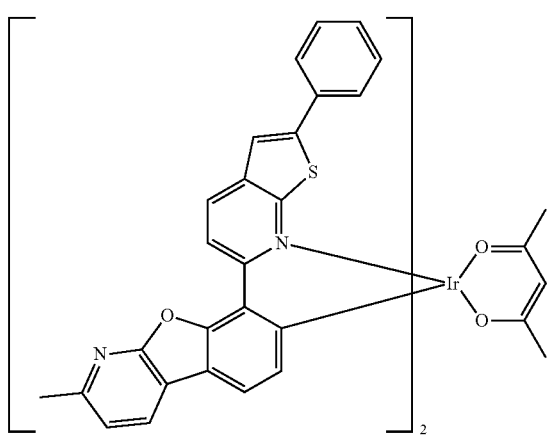
177
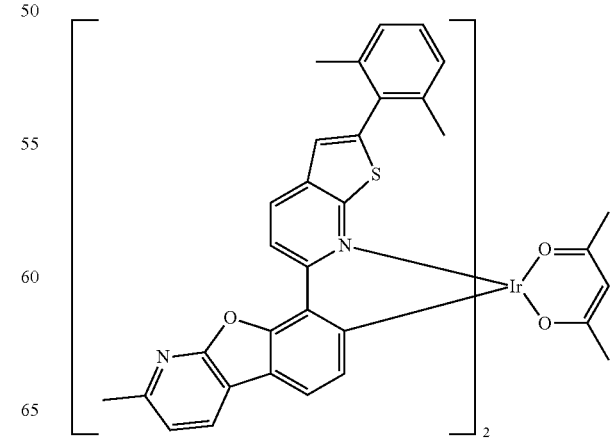

178
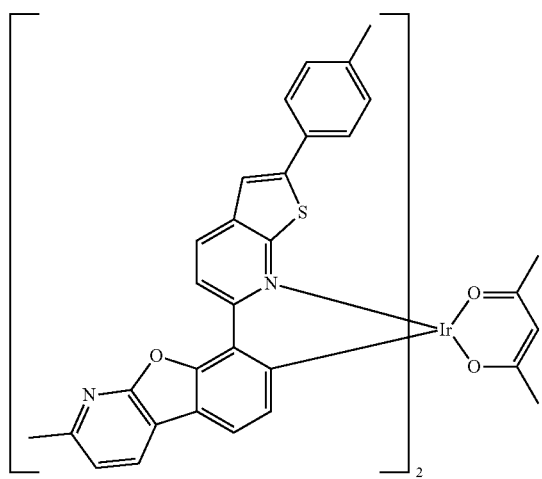
179
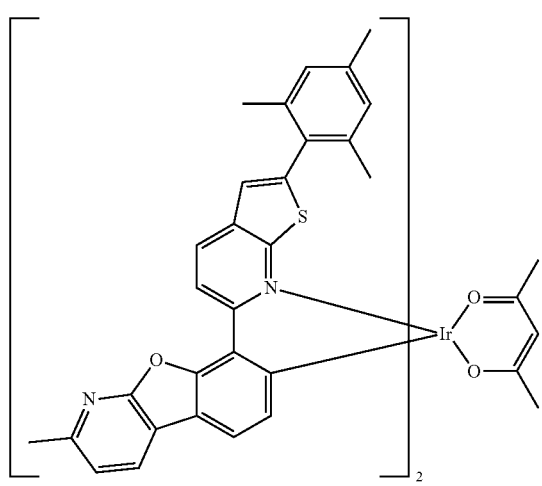
180
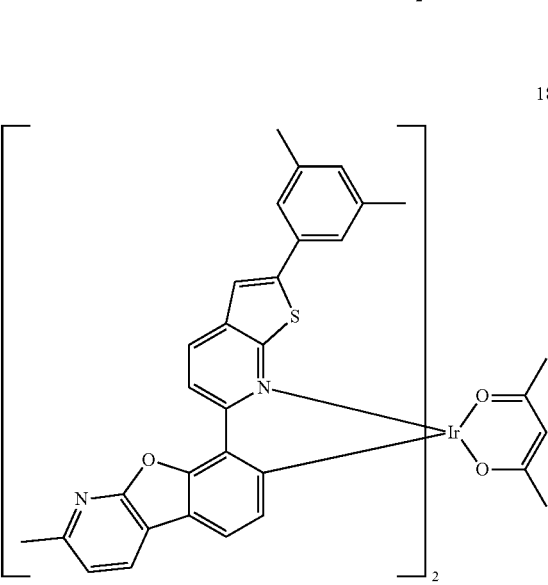
181
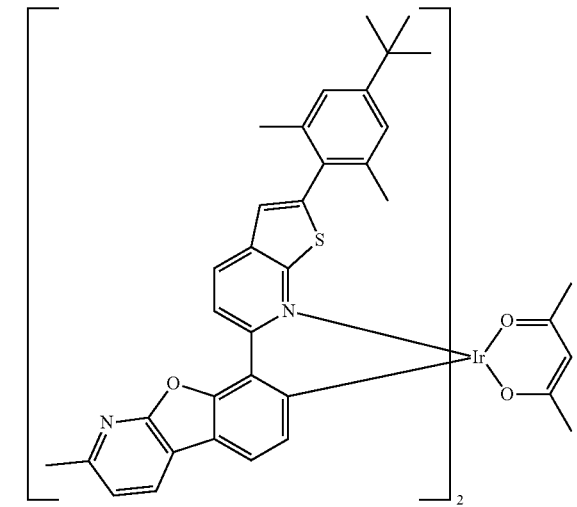
182
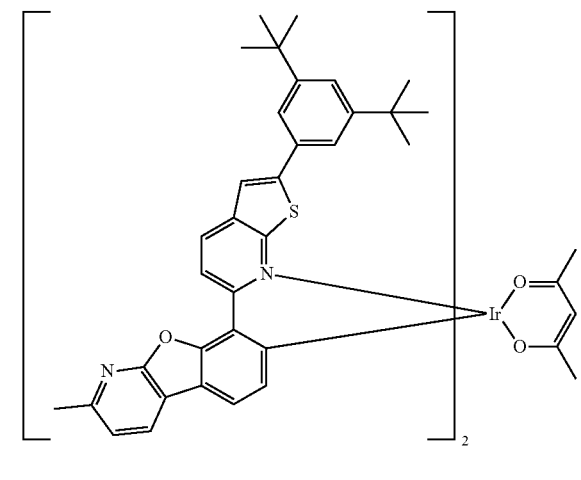
183
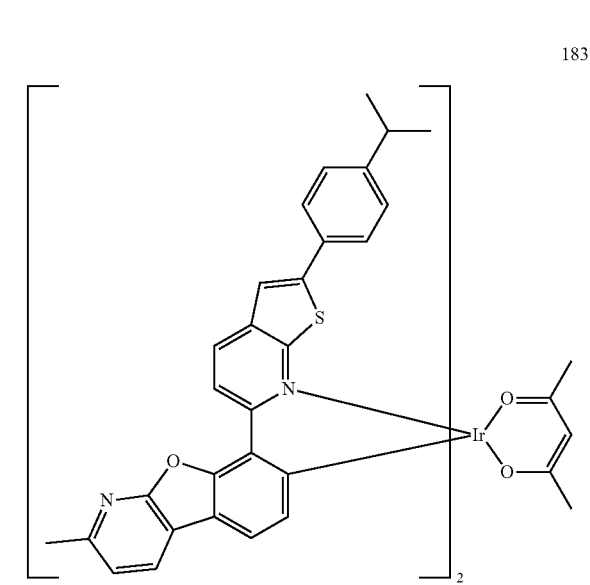

184
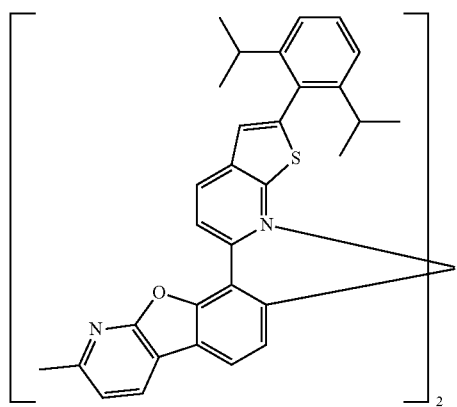
185
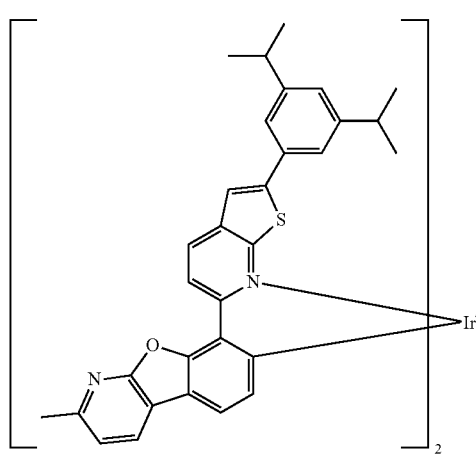
186
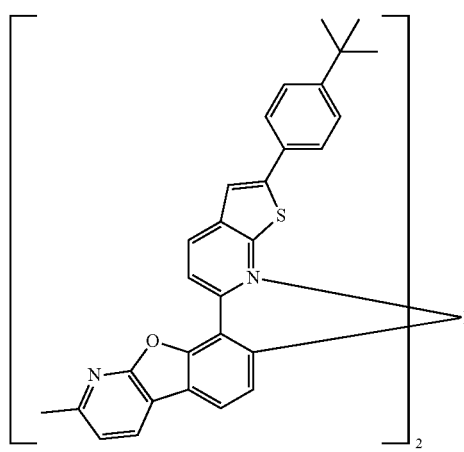
187
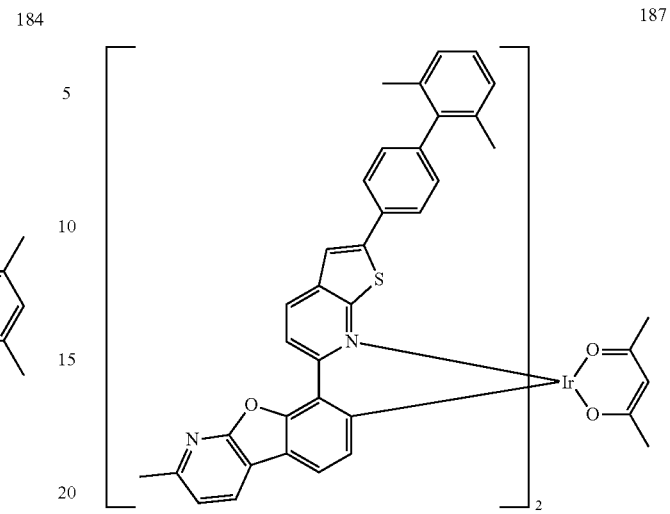
188
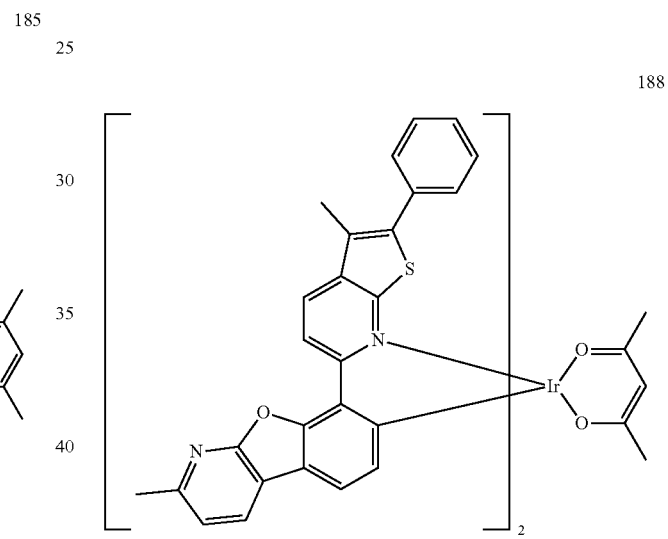
189
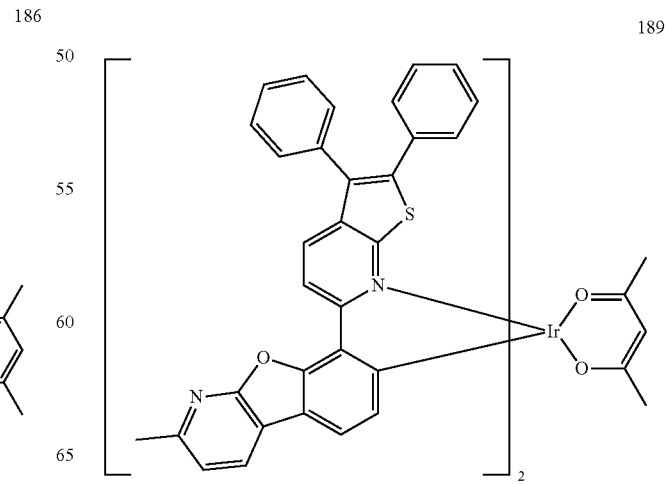

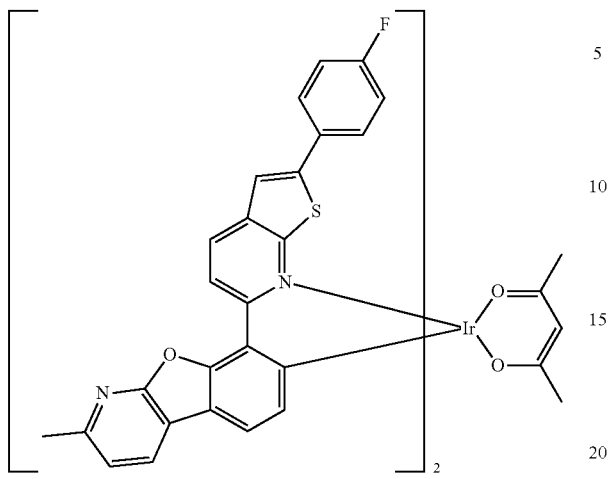
190
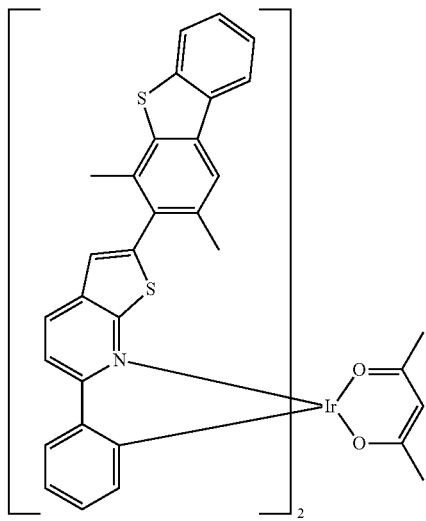
193
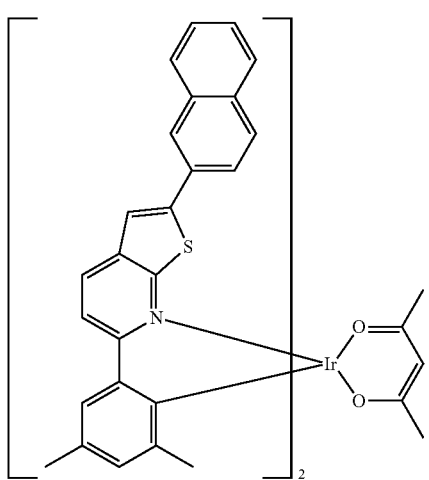
191
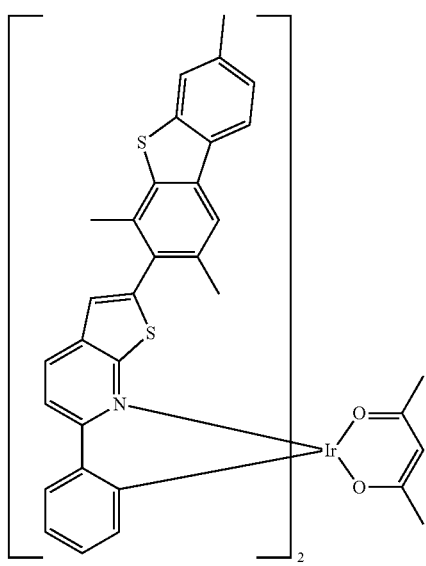
194
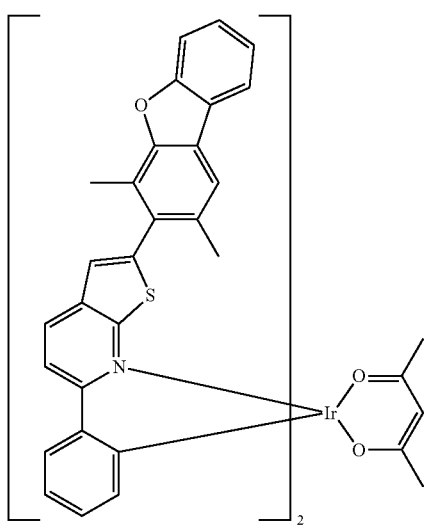
192
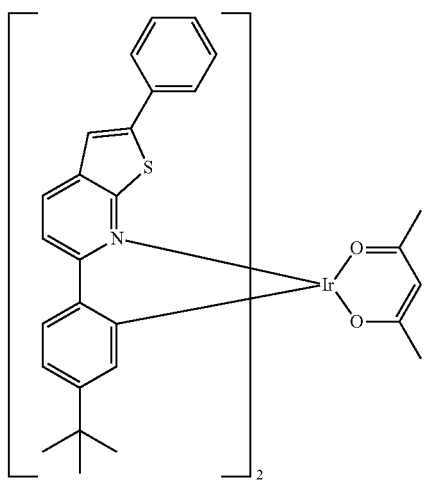
195

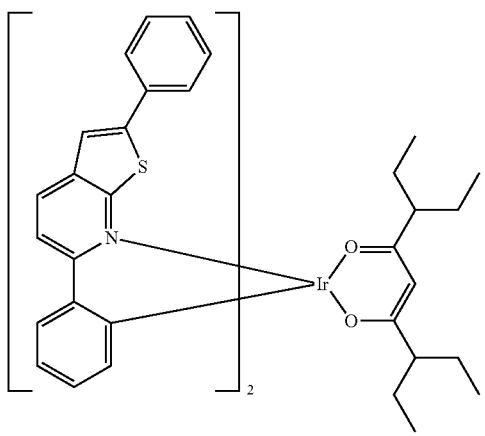
196
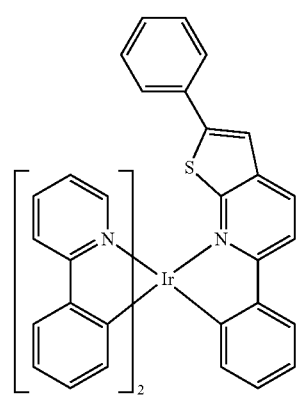
199
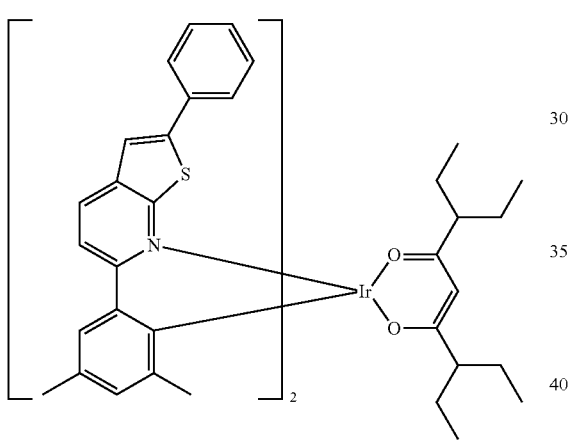
197
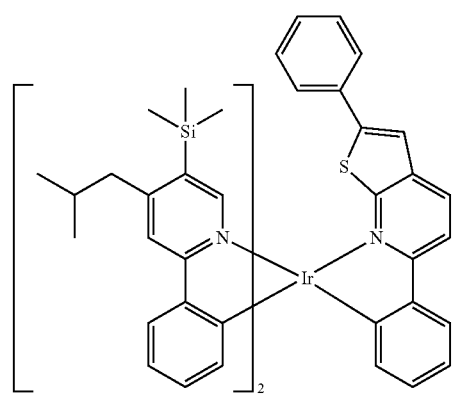
200
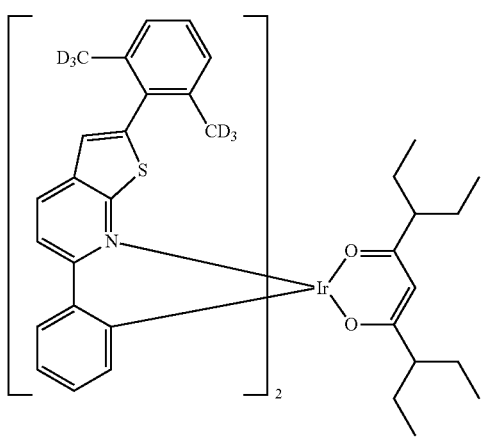
198
201

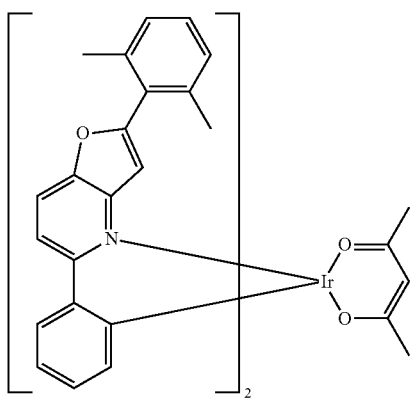
202
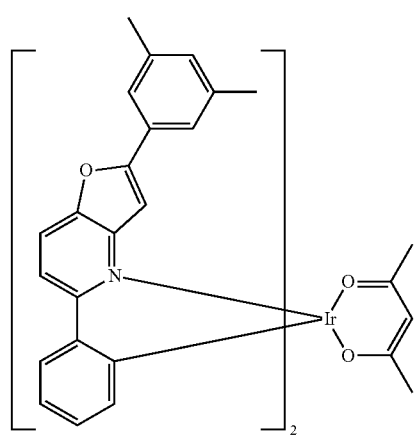
205
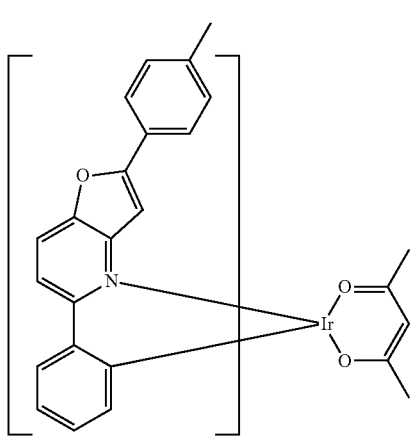
203
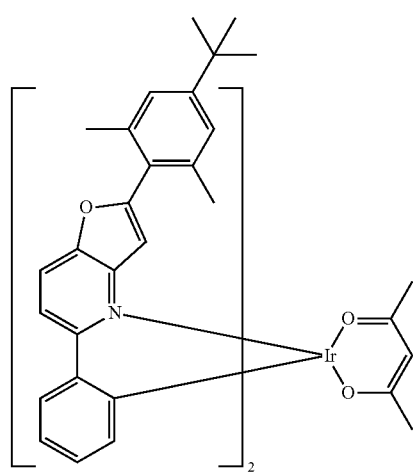
206
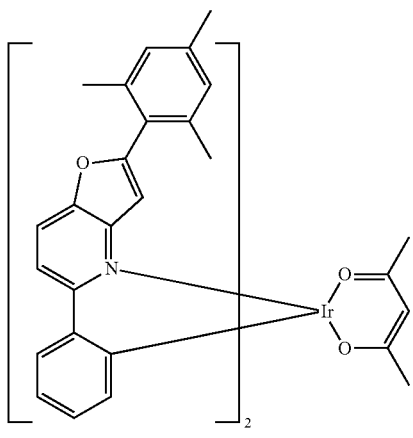
204
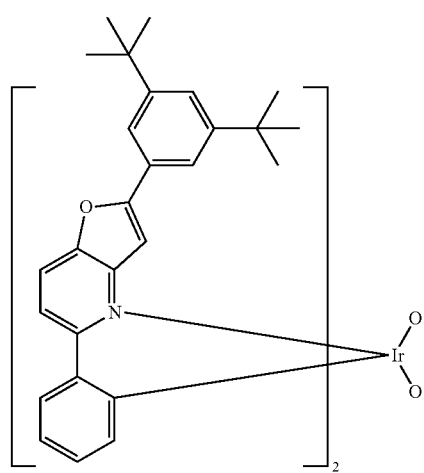
207

208
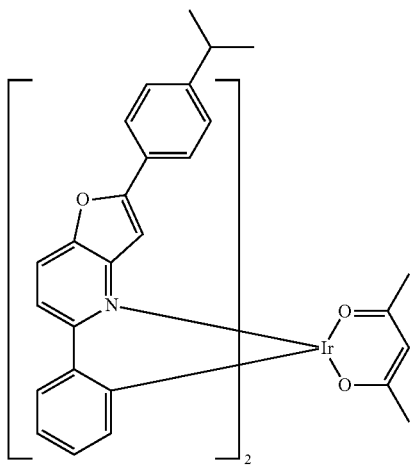
209
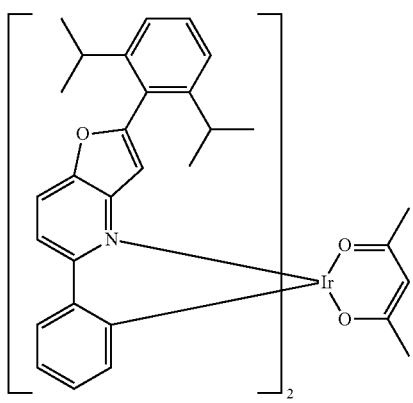
210
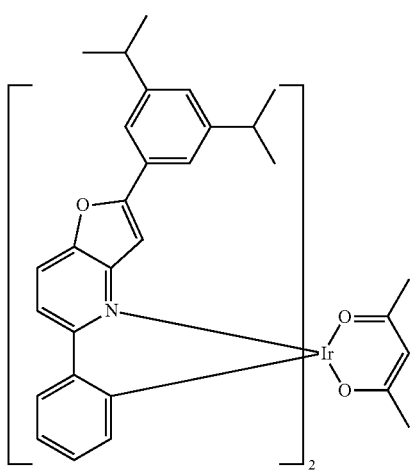
211
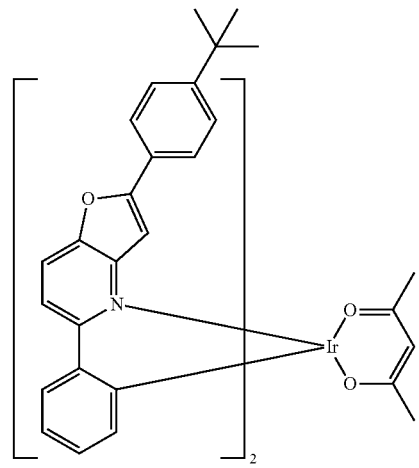
212
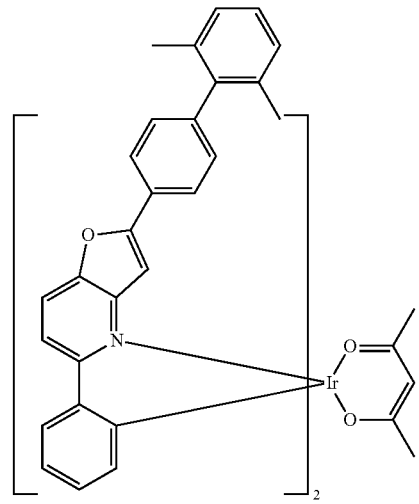
213
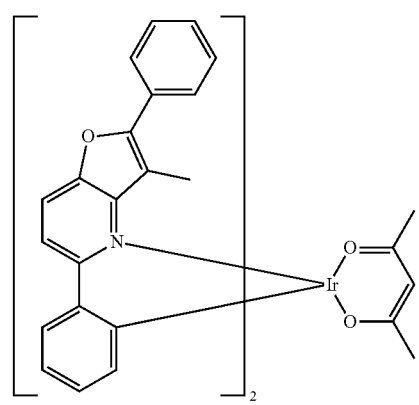

214
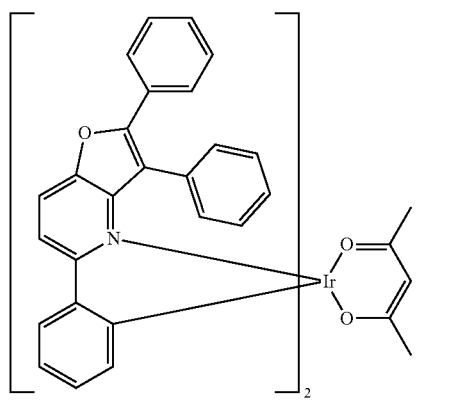
215
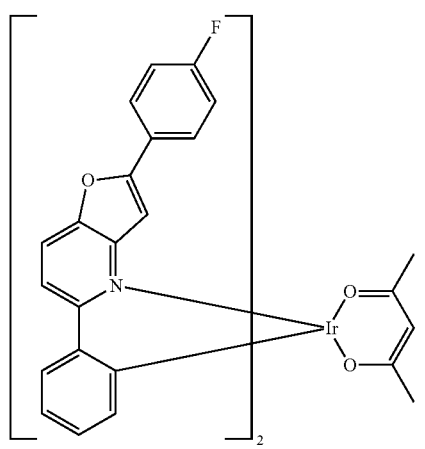
216
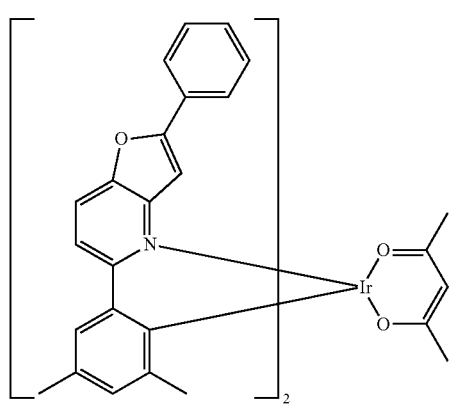
217
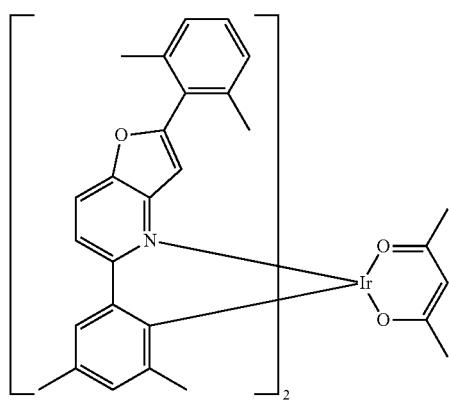
218
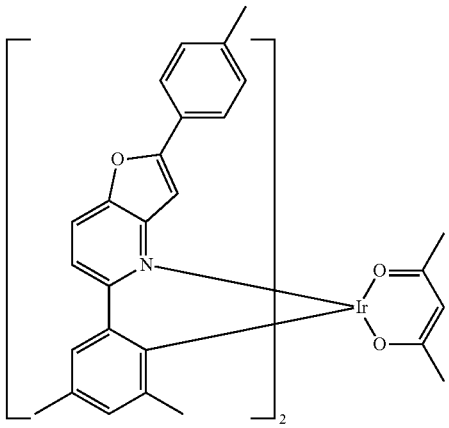
219
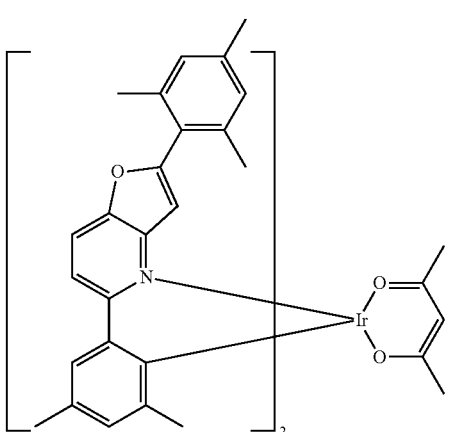
220
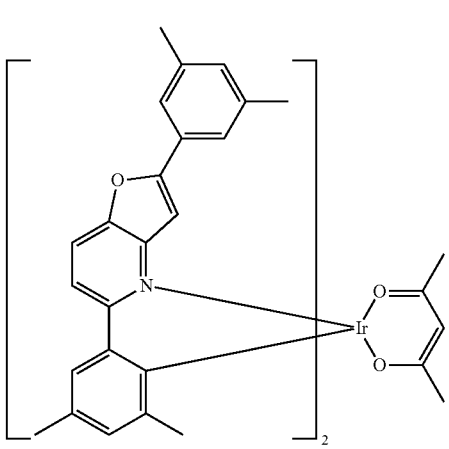

221
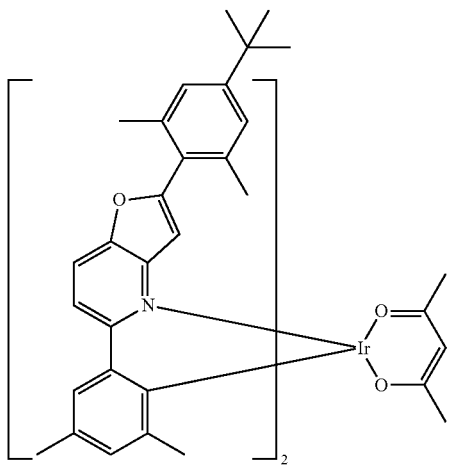
222
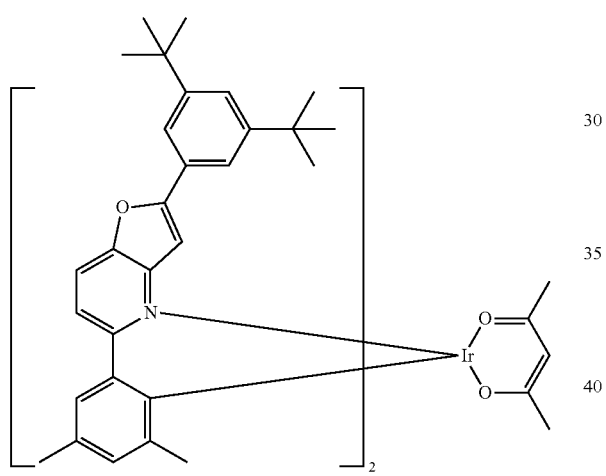
223

224
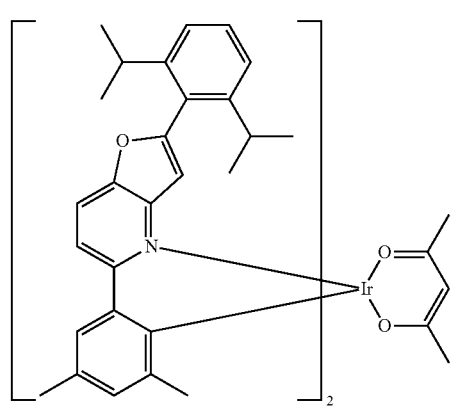
225
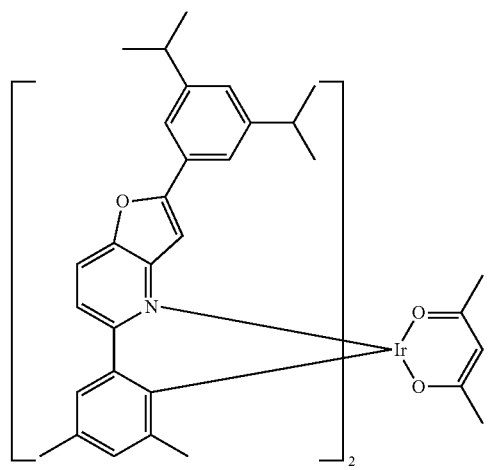
226
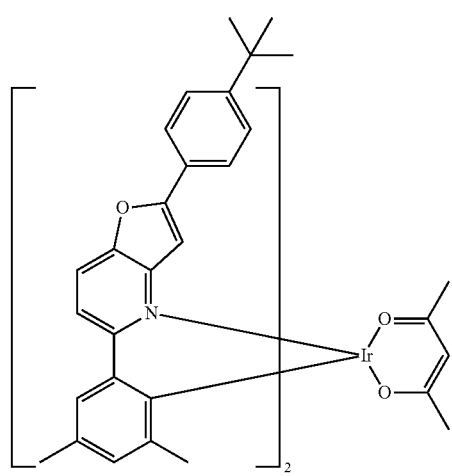

227
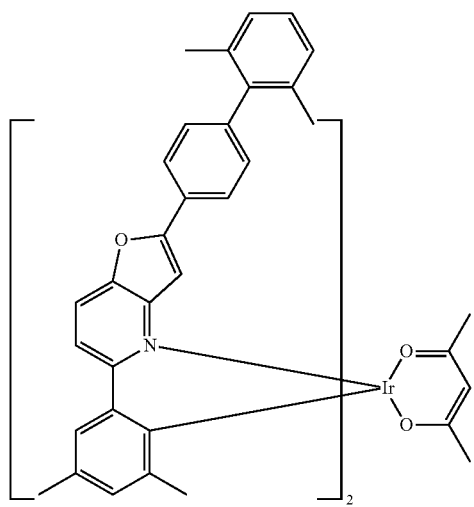
228
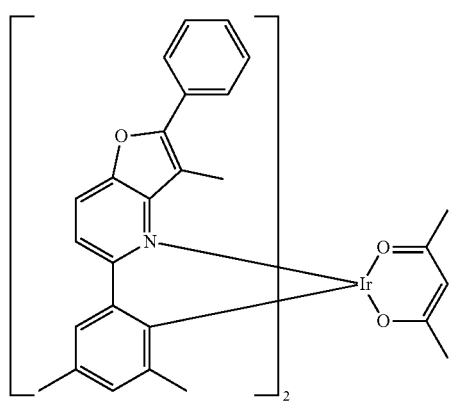
229
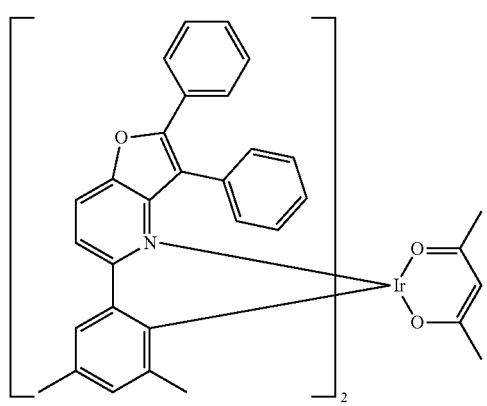
230
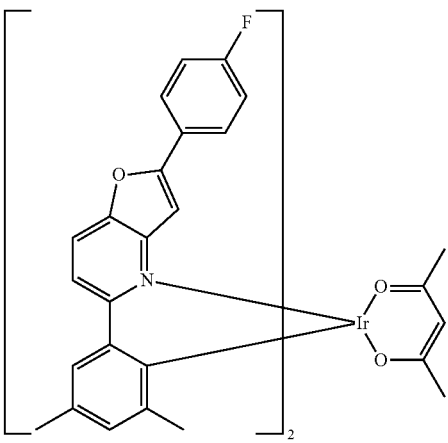
231
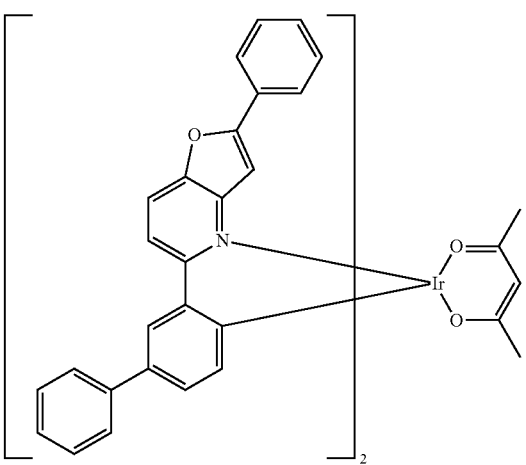
232
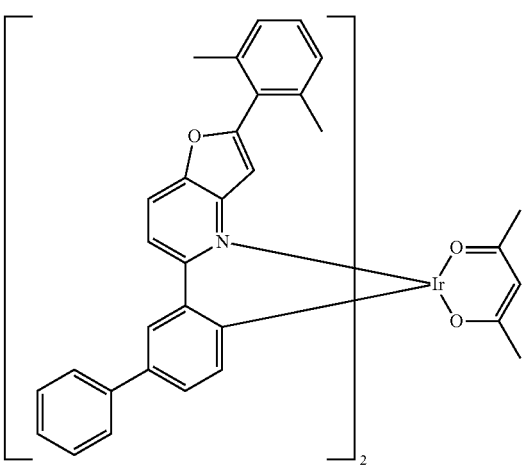

233
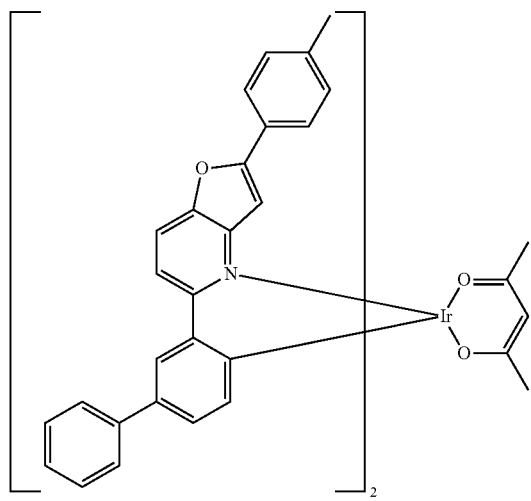
234
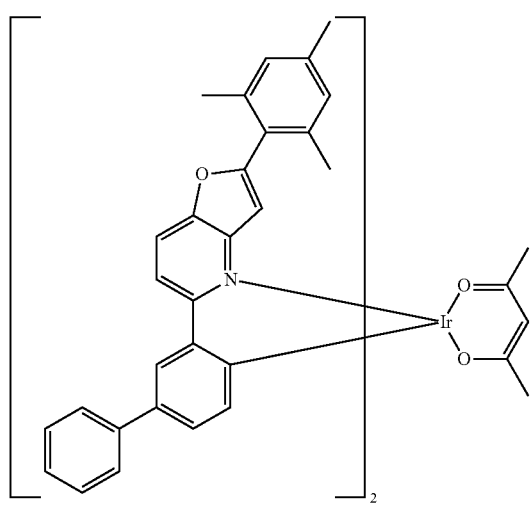
235
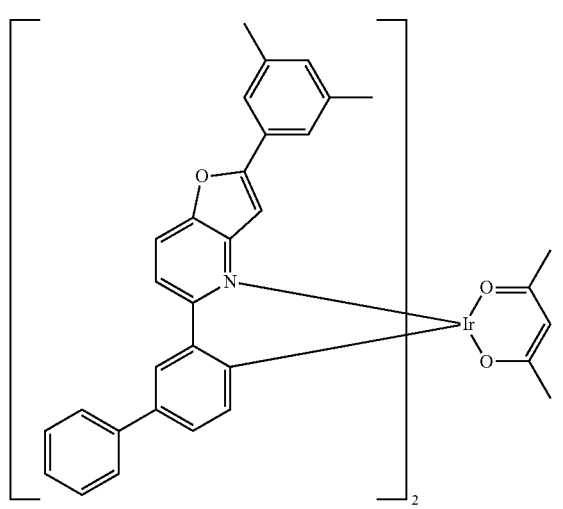
236
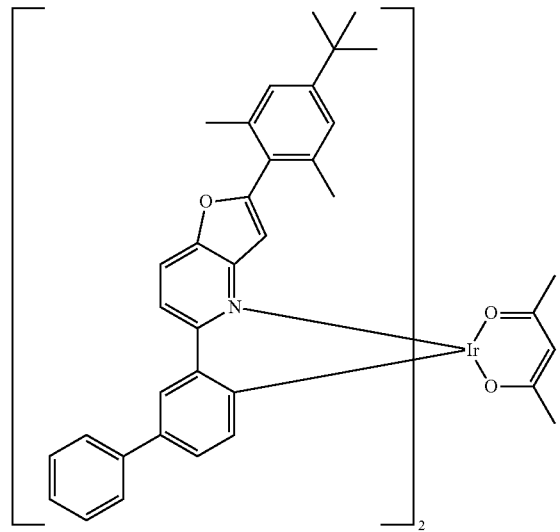
237
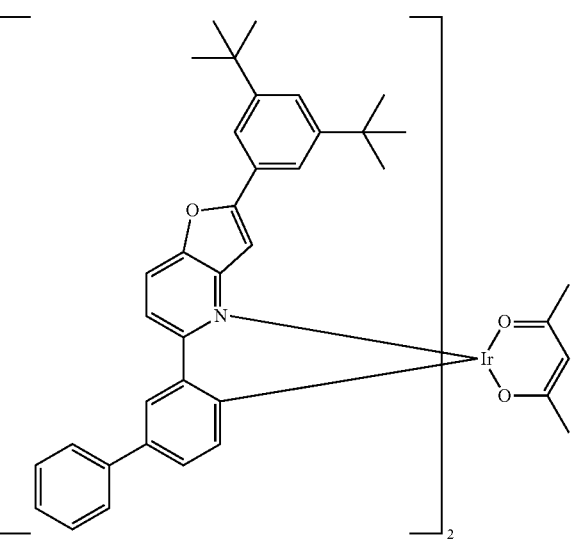
238
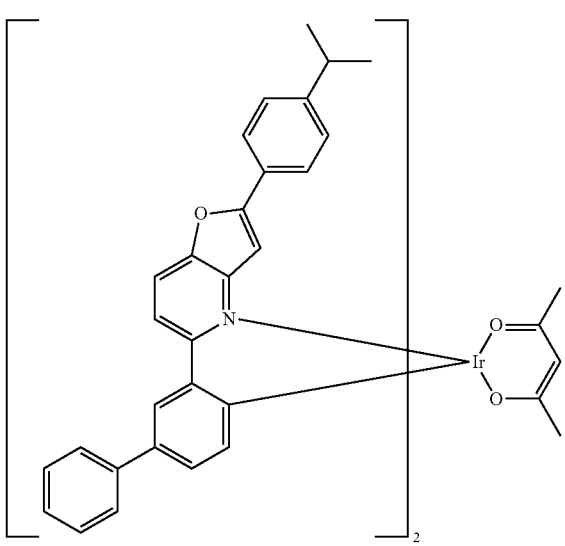

239
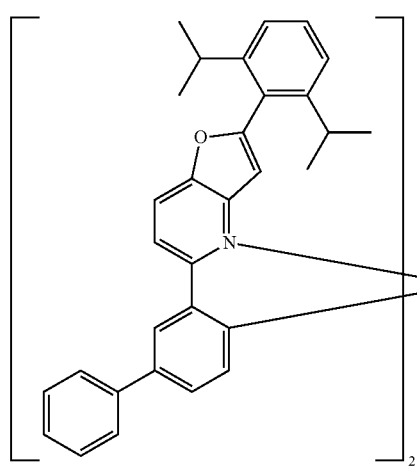
240
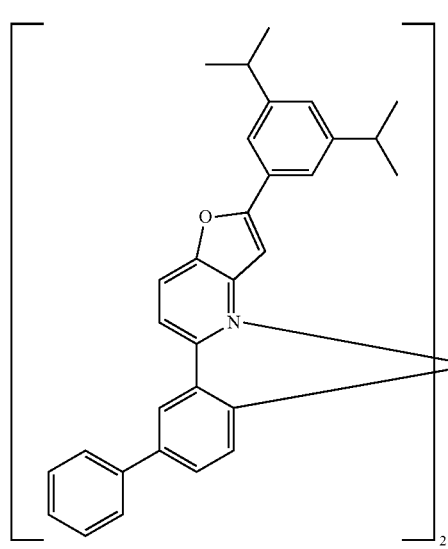
241
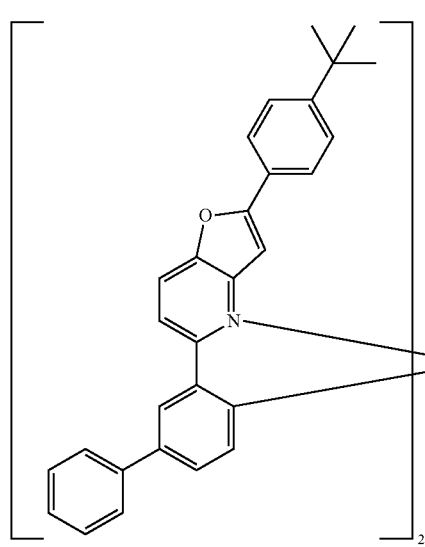
242
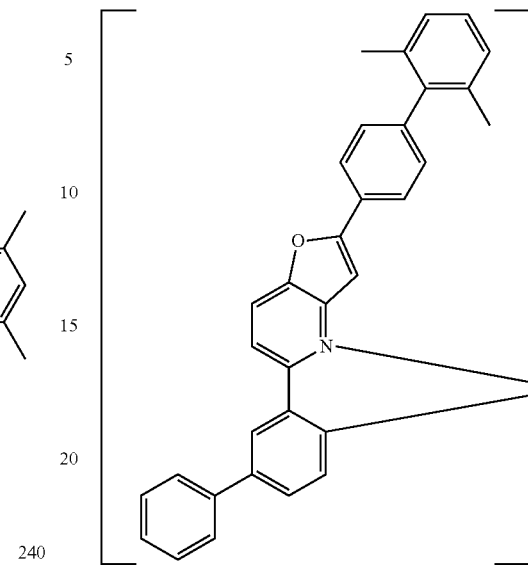
243
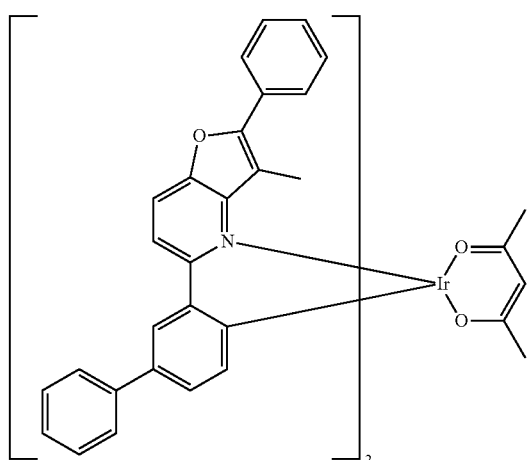
244
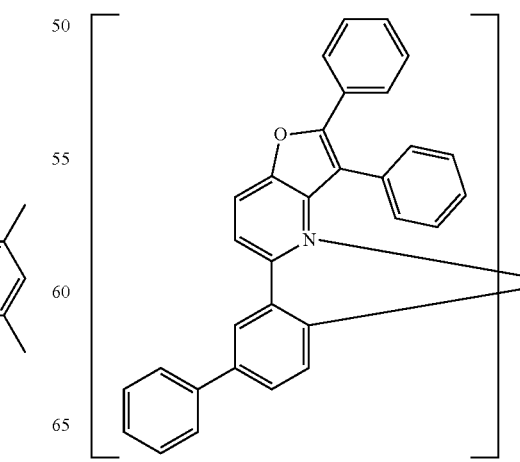

-continued
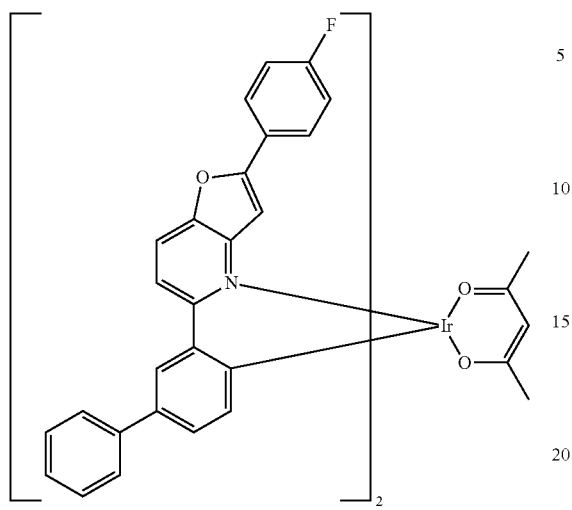
245
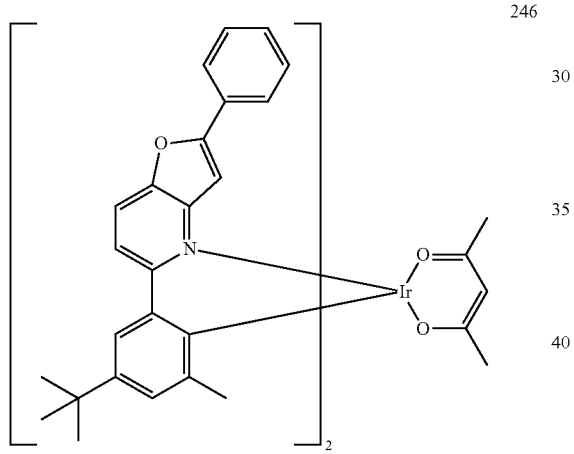
246
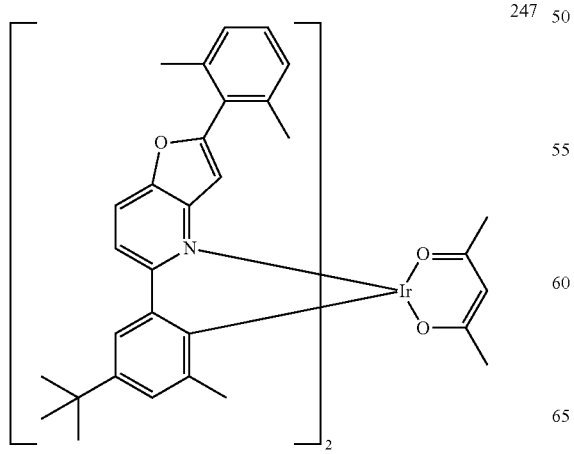
247
-continued
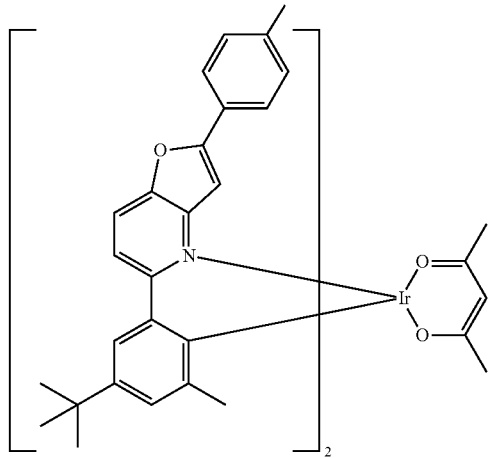
248
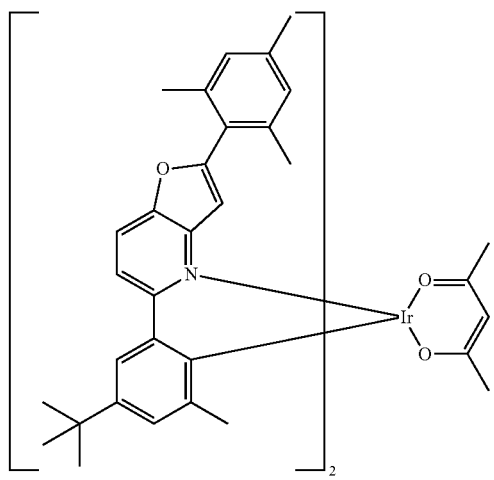
249
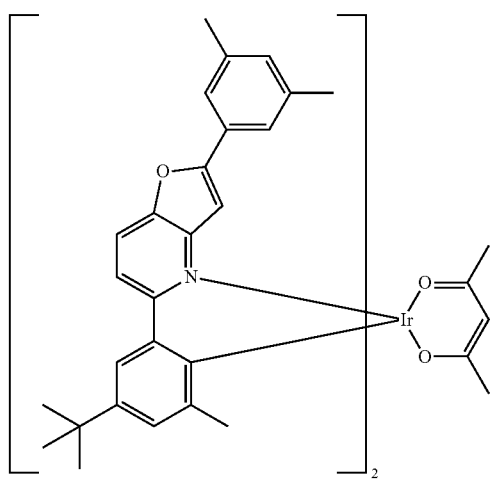
250

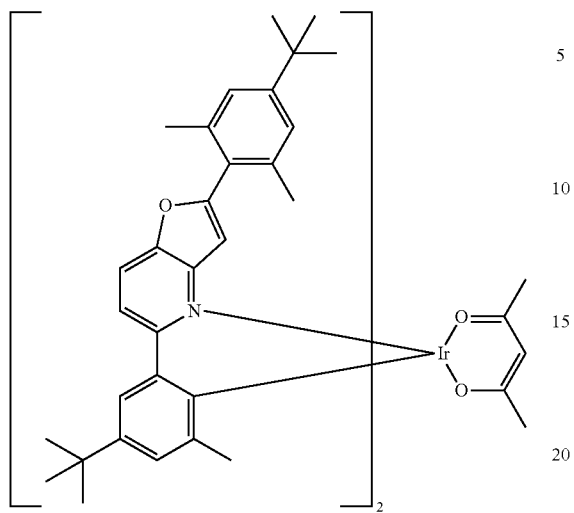
251
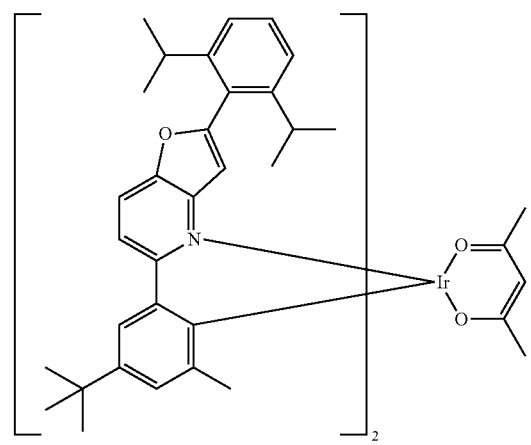
254
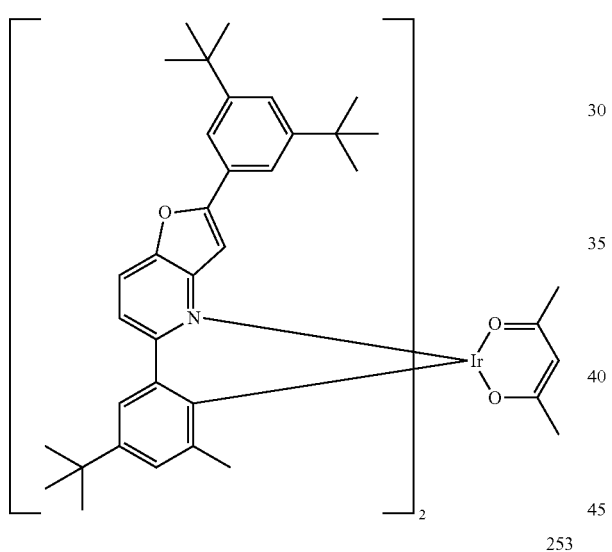
252
255
253
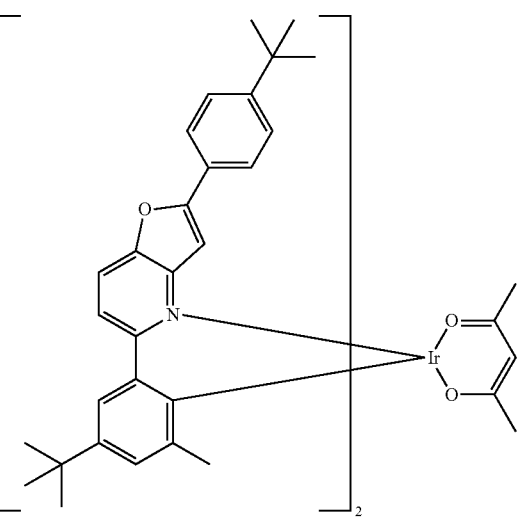
256

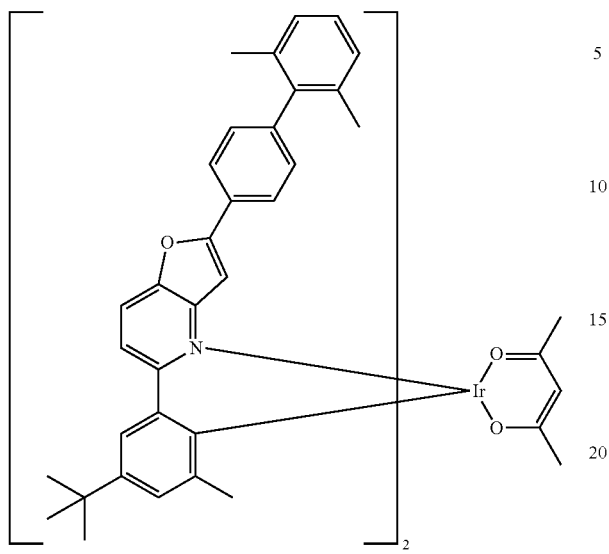
257
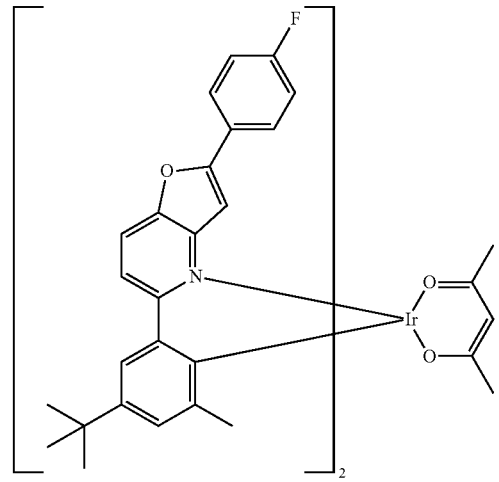
260
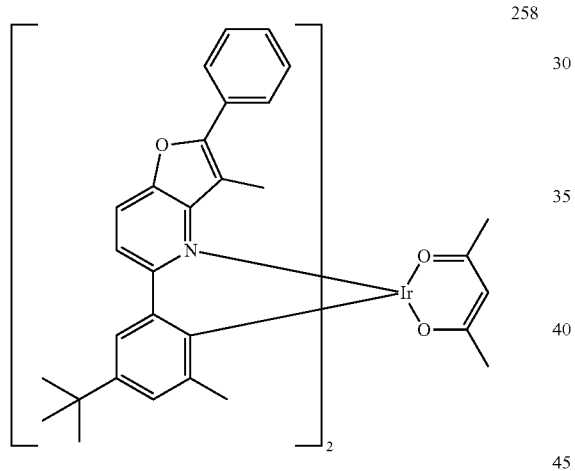
258
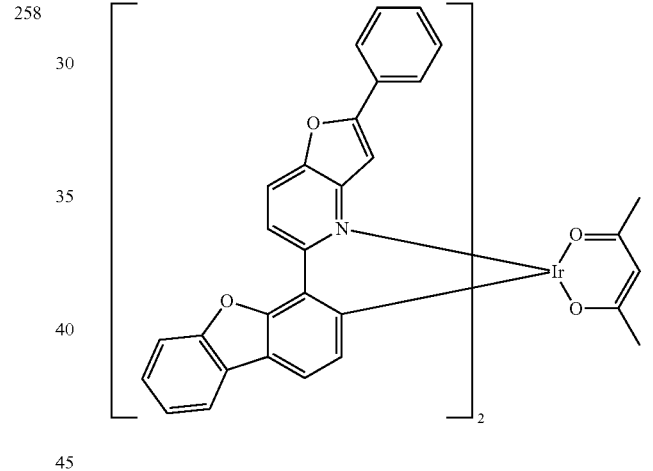
261
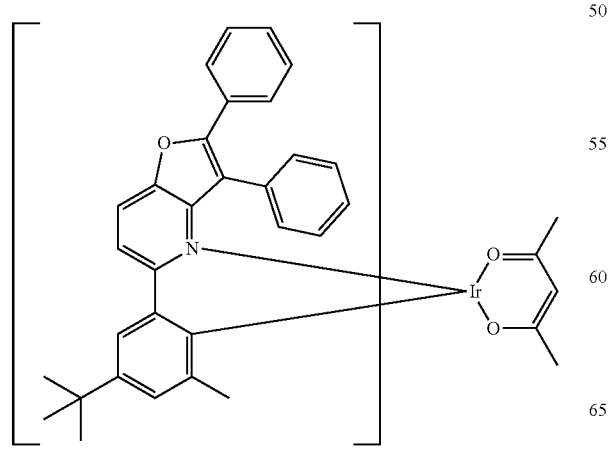
259
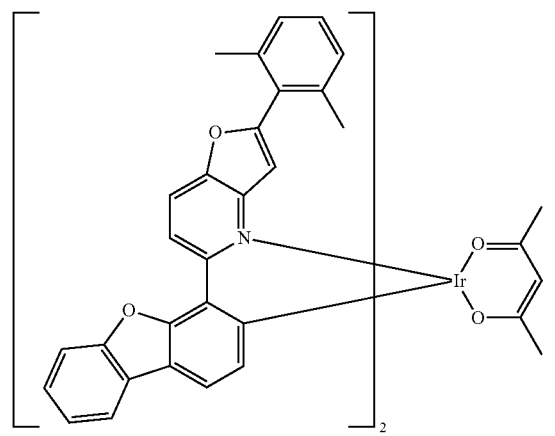
262

263
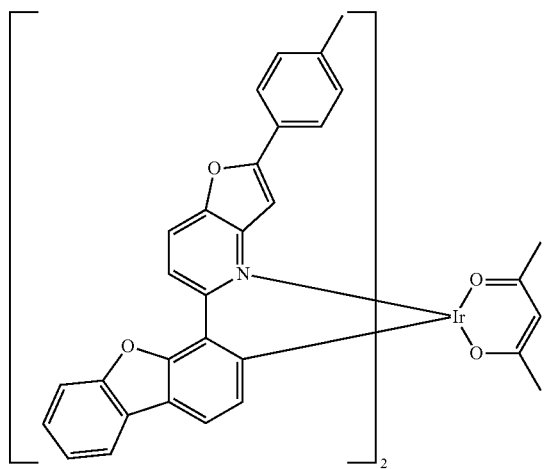
264
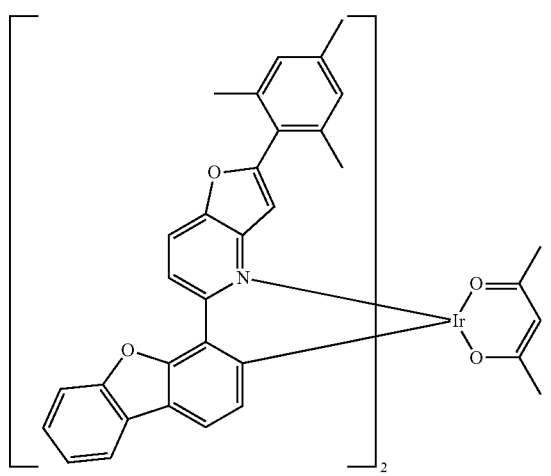
265
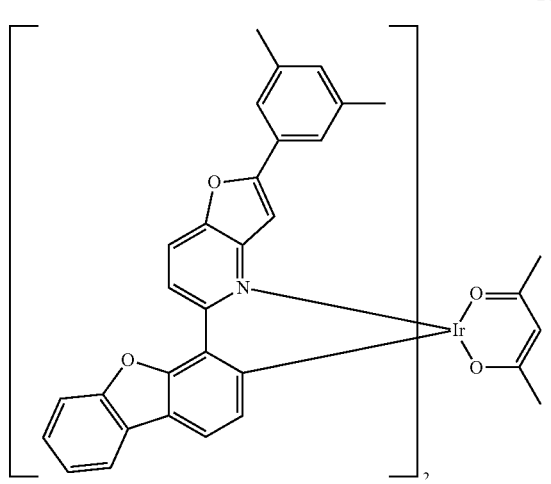
266
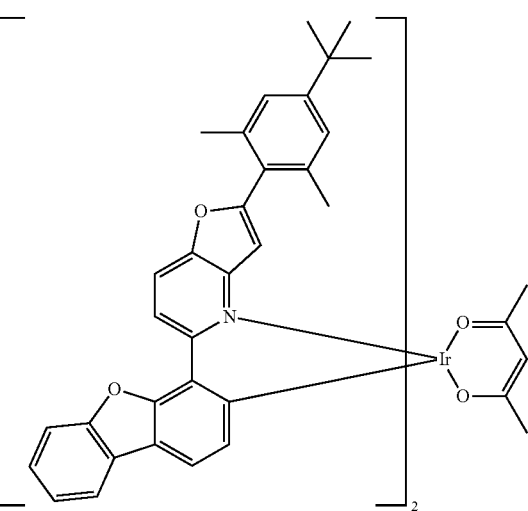
267
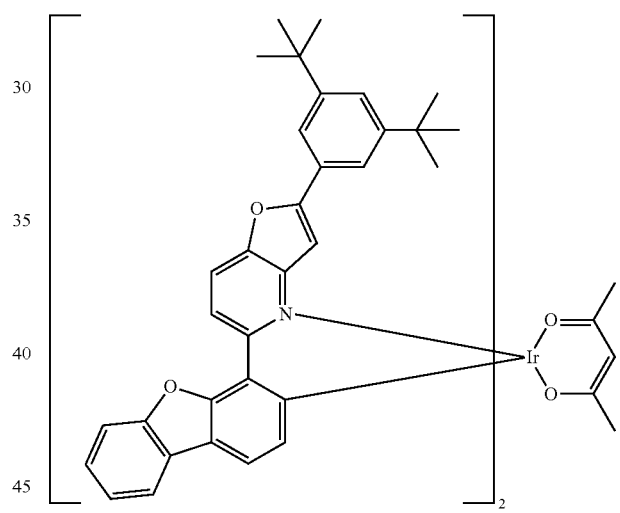
268
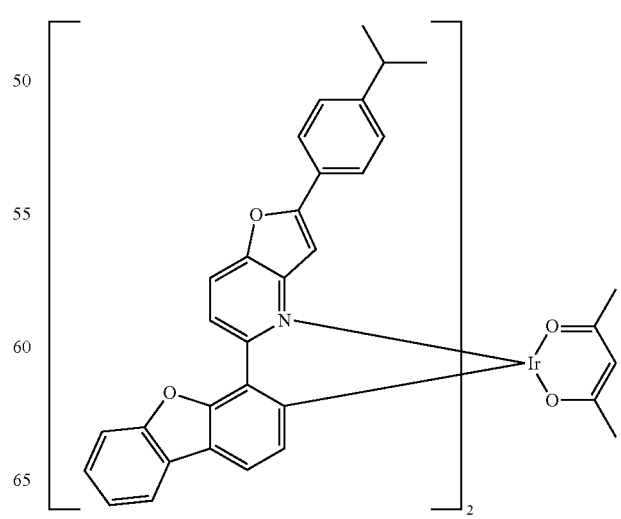

169
-continued
269
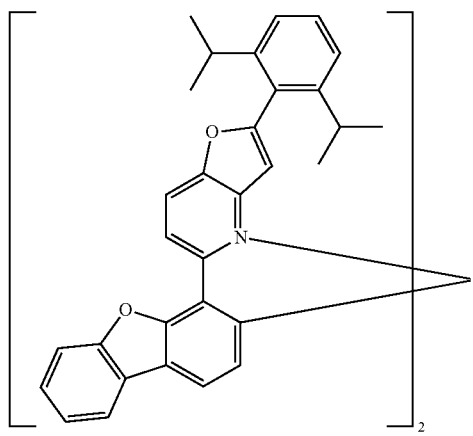
270
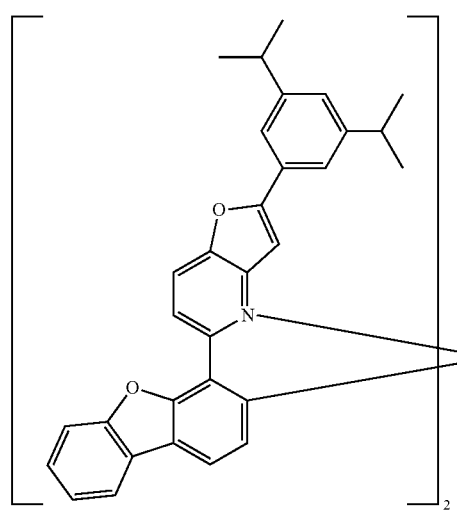
271
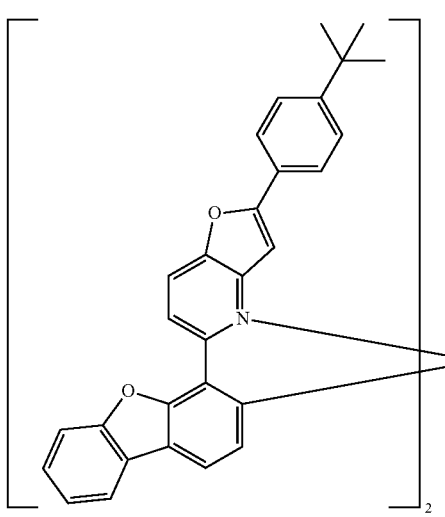
170
-continued
272
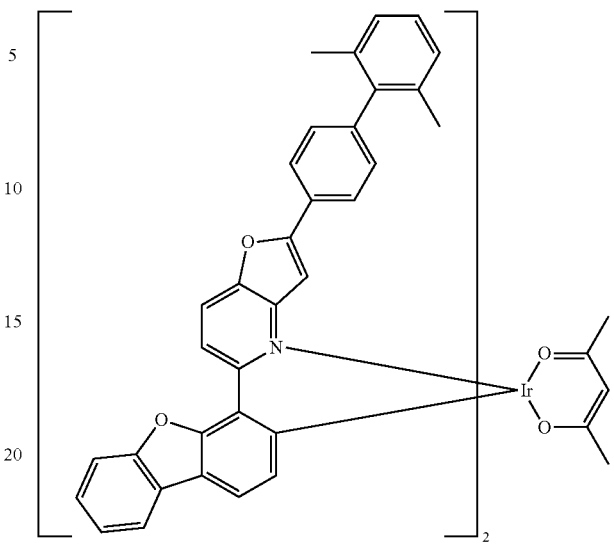
273
274
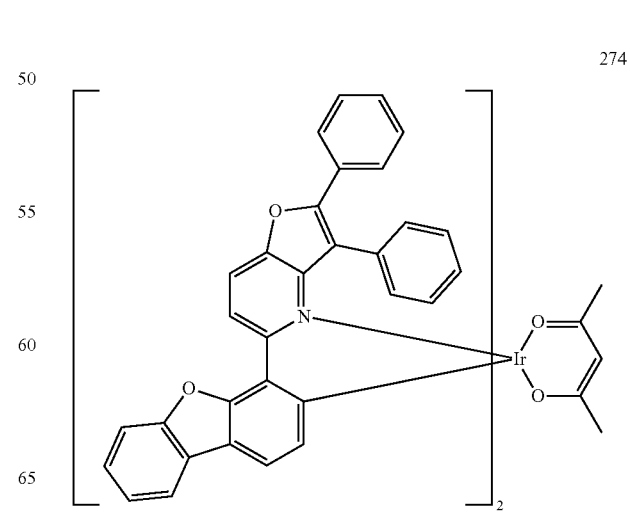

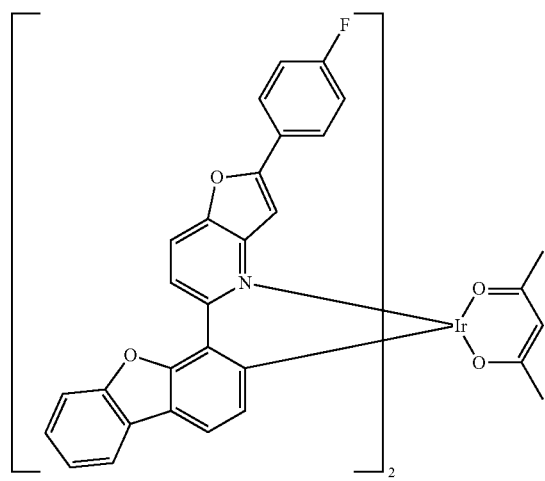
275
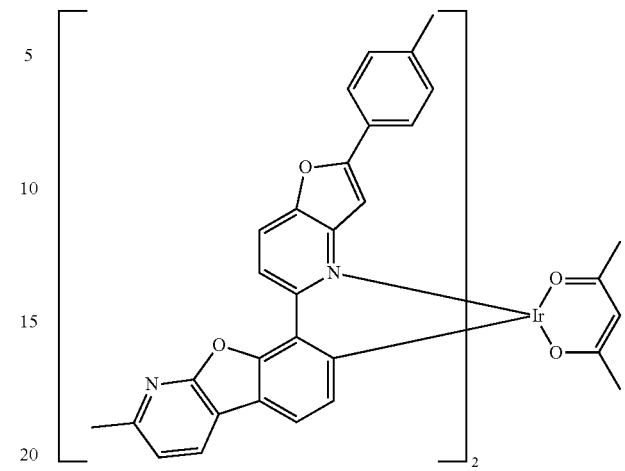
278
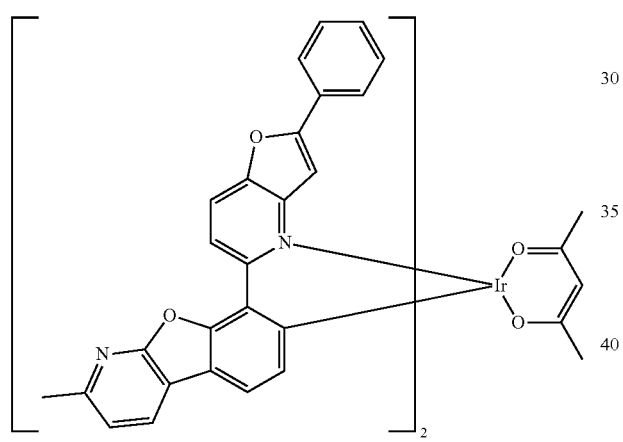
276
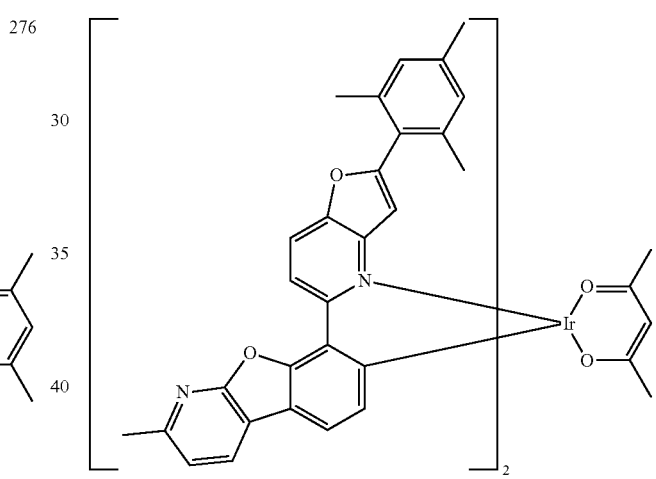
279
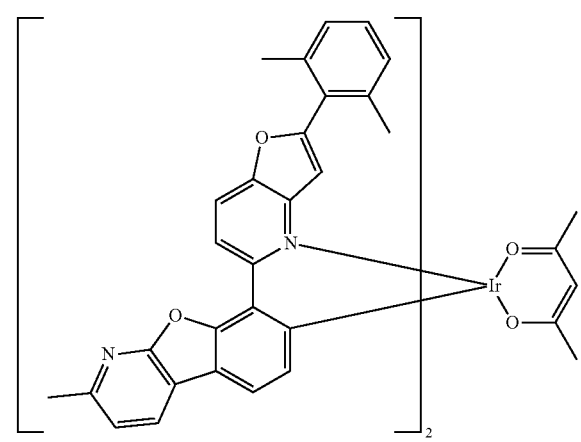
277
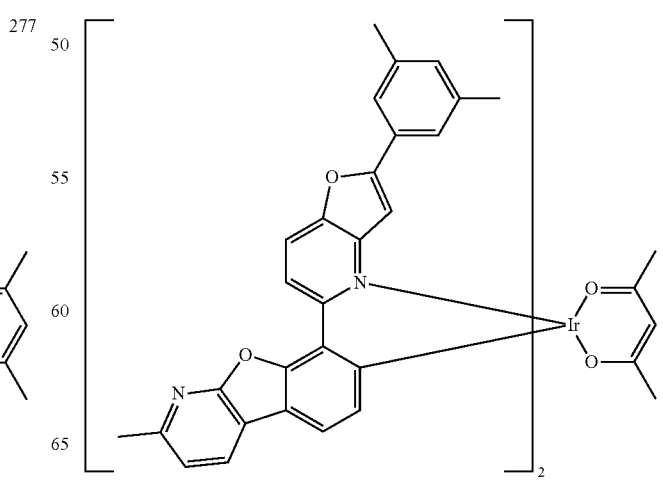
280

281
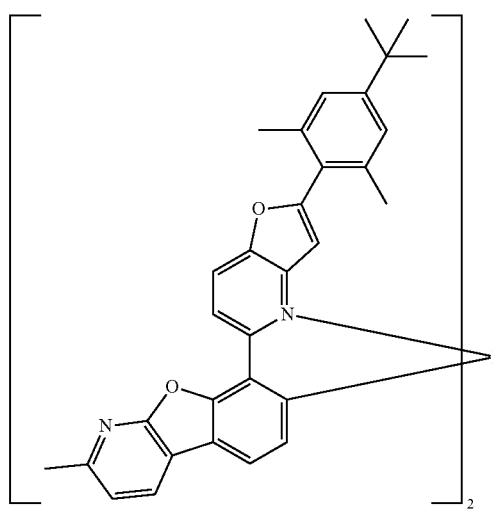
282
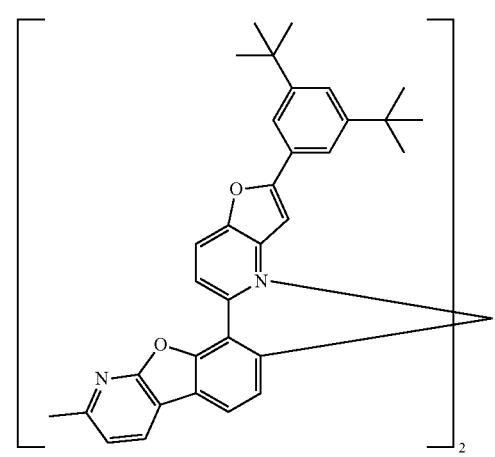
283
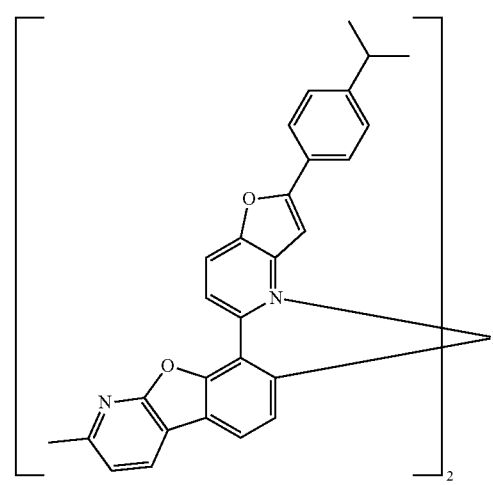
284
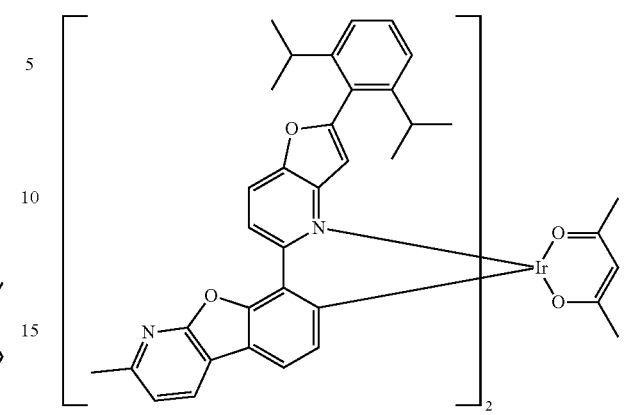
285
286

287
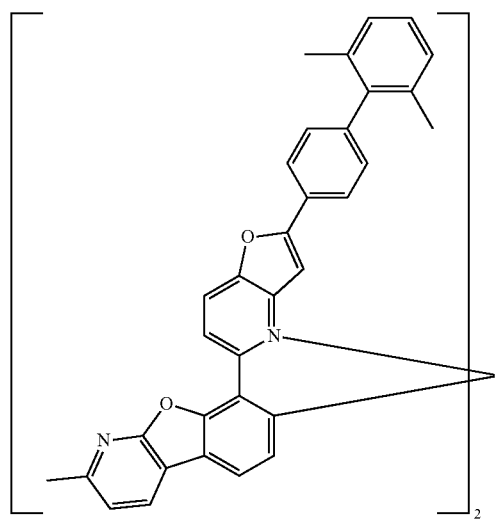
288
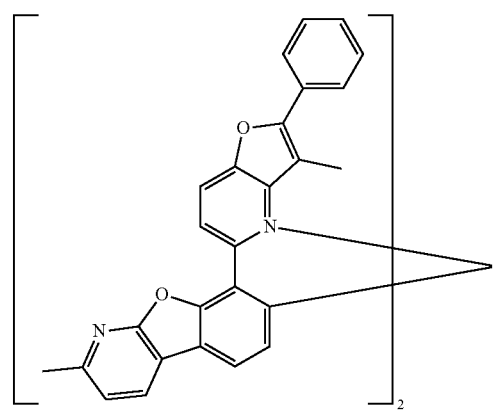
289
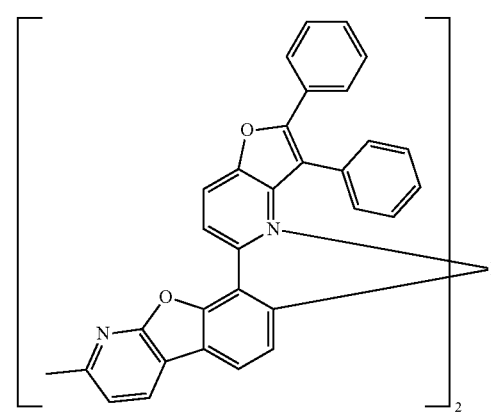
290
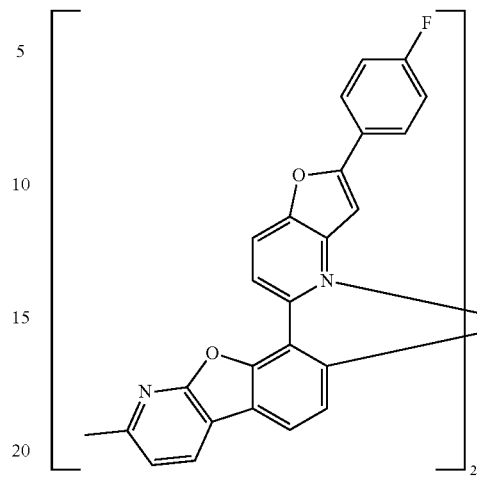
291
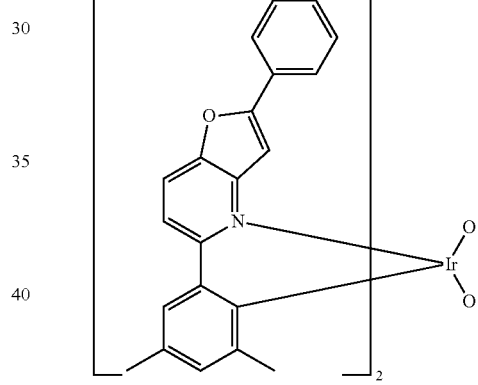
292
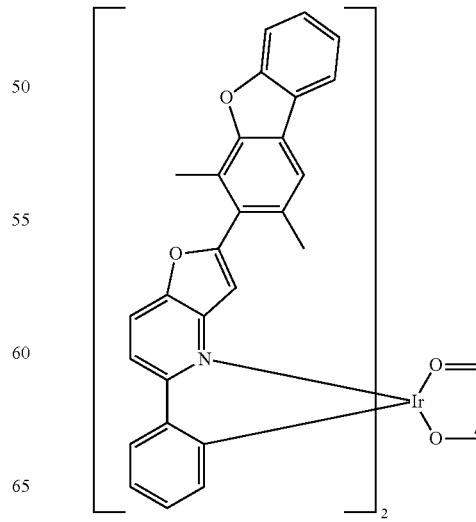

293
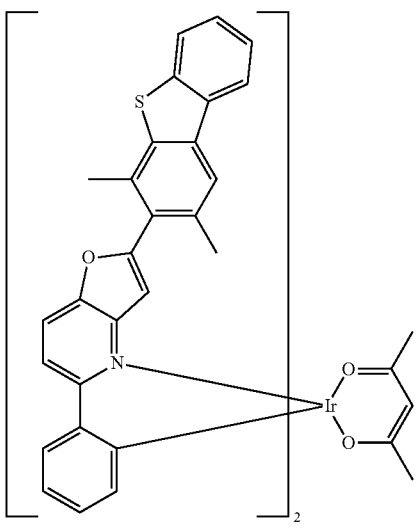
294
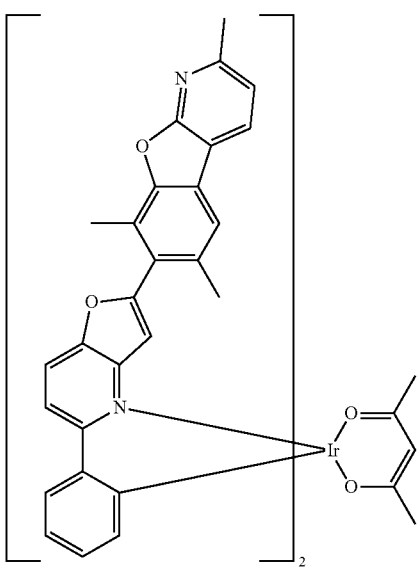
295
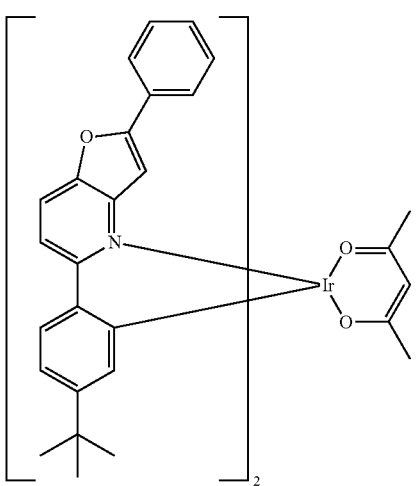
296
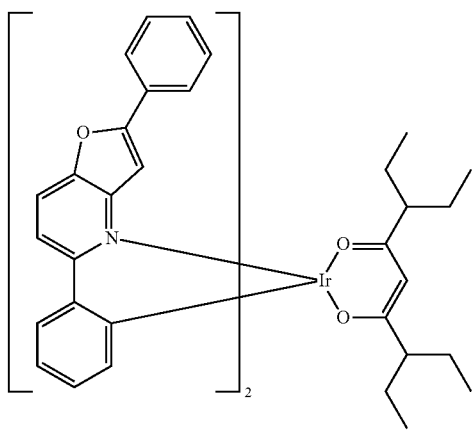
297
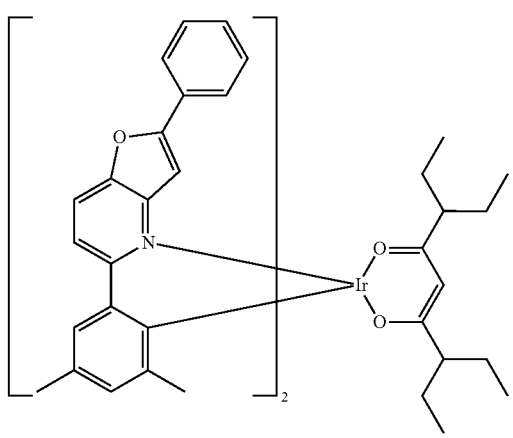
298
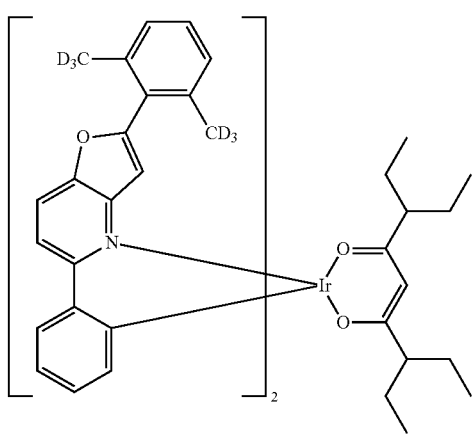

299
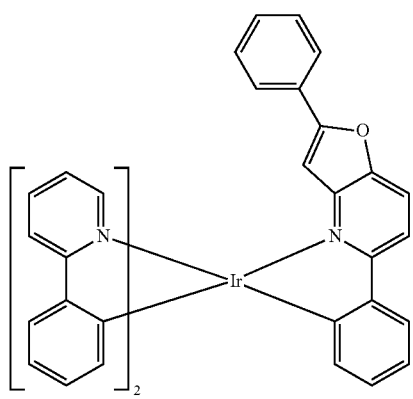
300
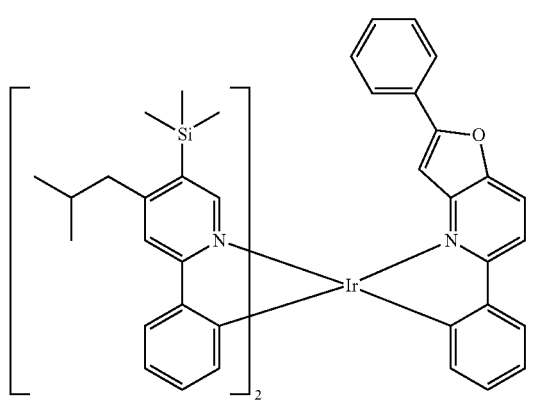
301
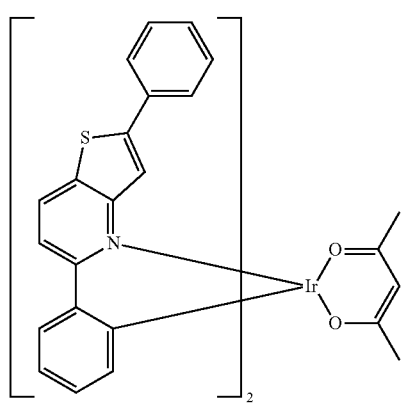
302
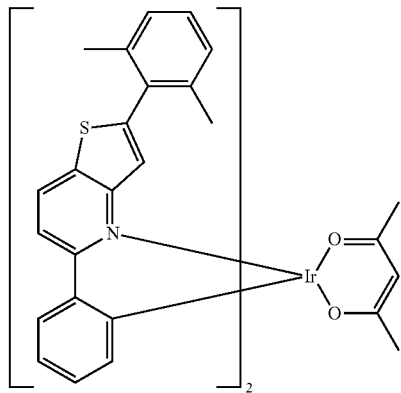
303
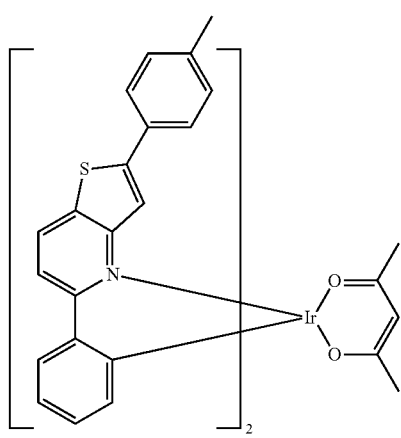
304
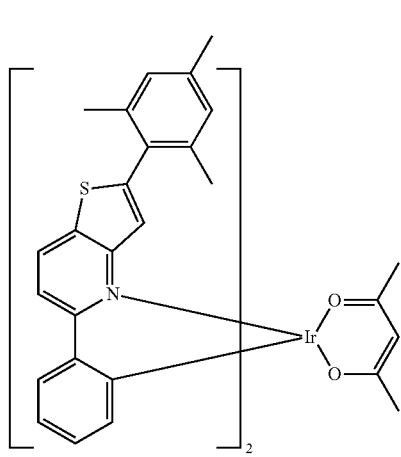

-continued
305
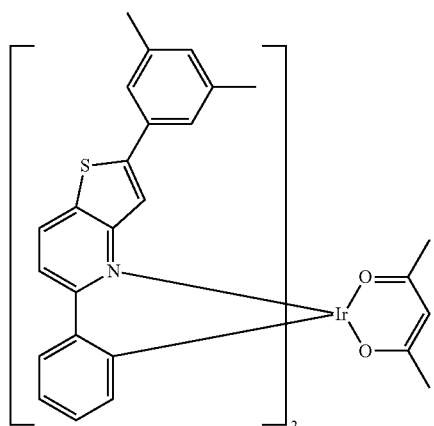
306
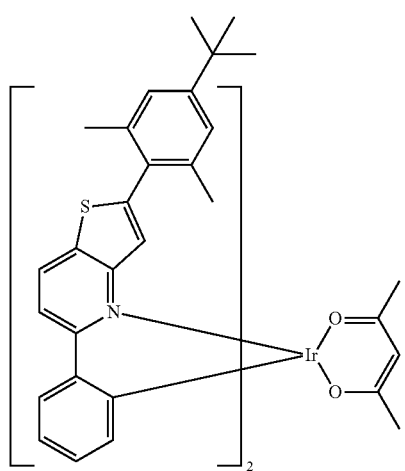
307
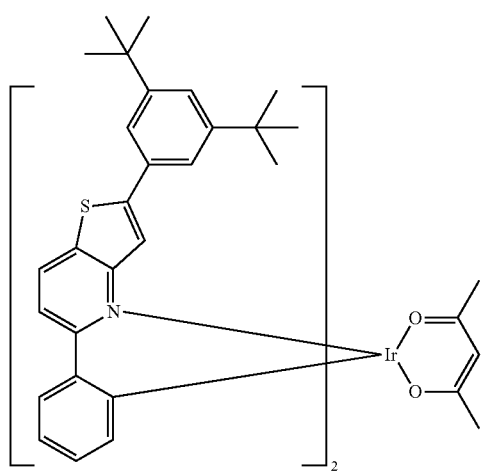
-continued
308
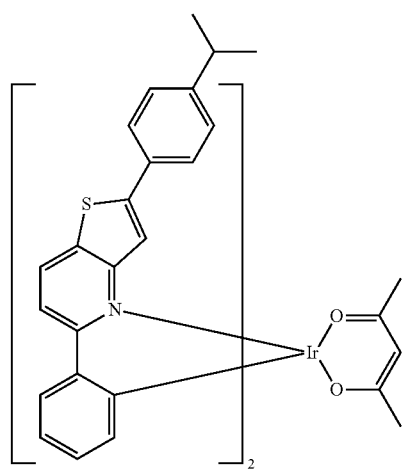
309
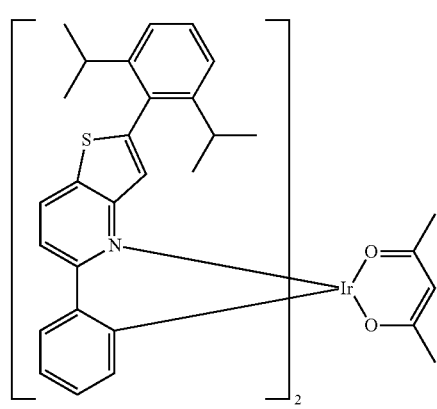
310
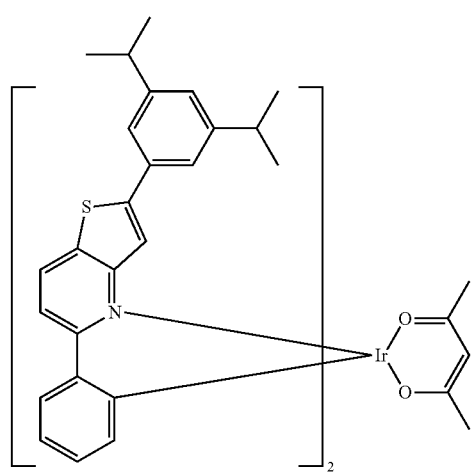

311
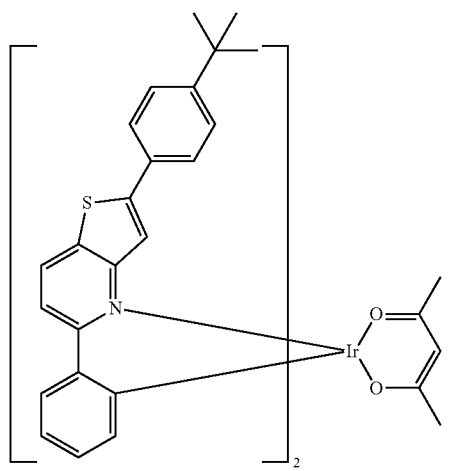
312
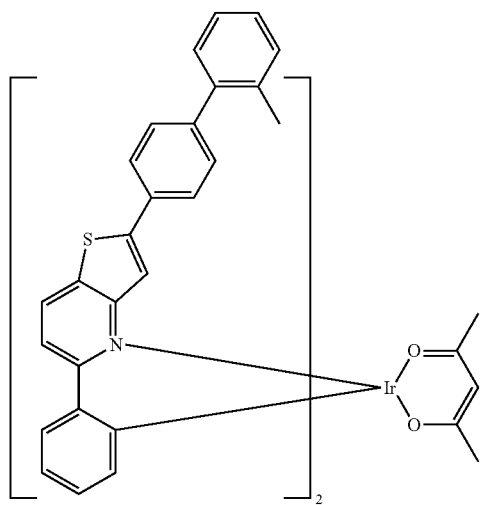
313
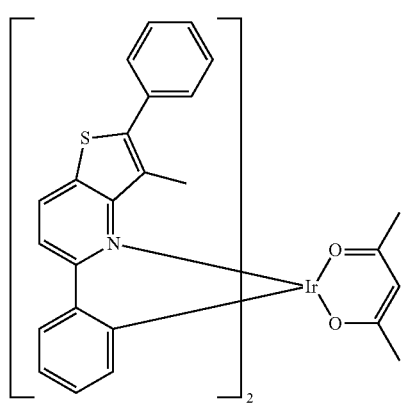
314
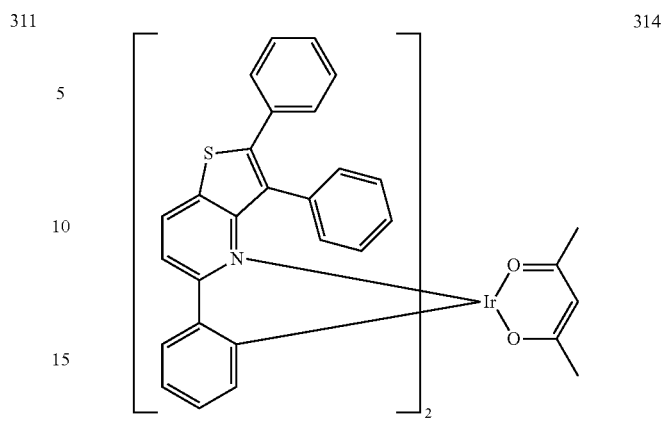
315
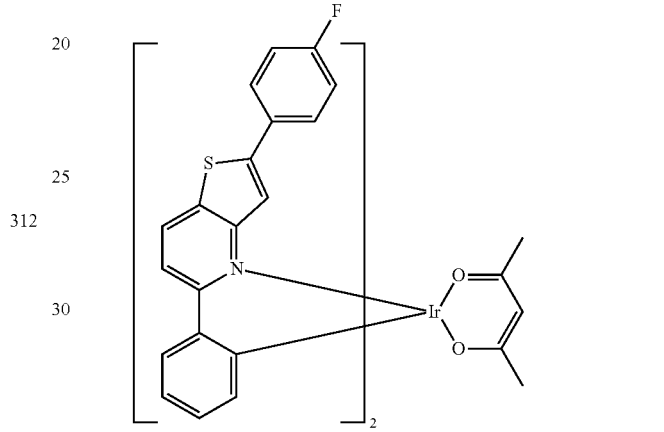
316
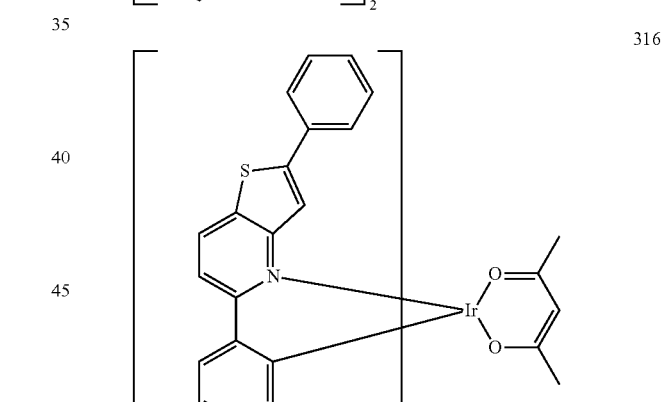
317
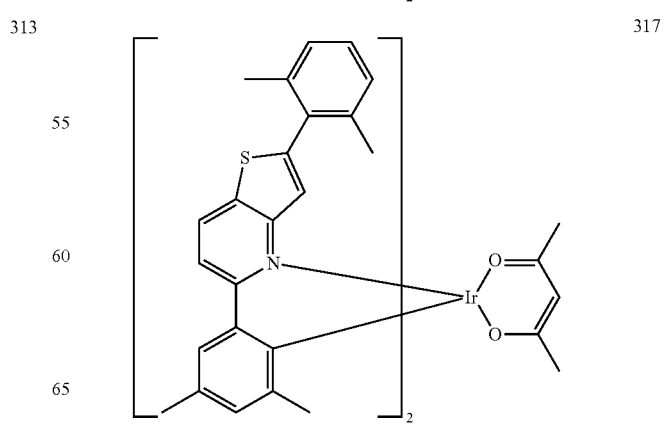

318
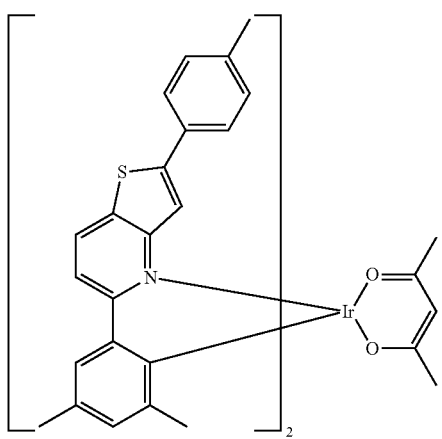
319
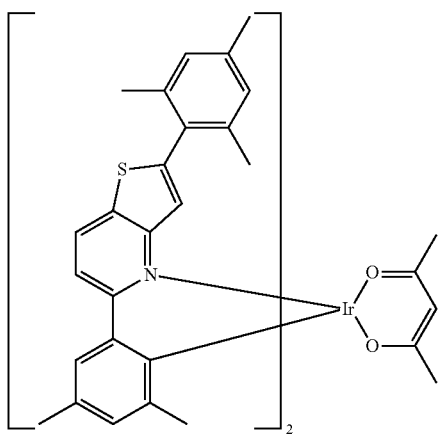
320
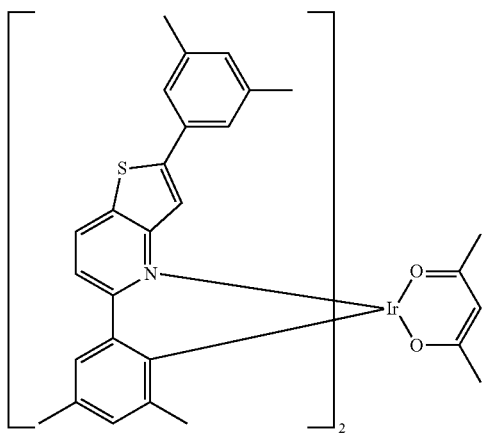
321
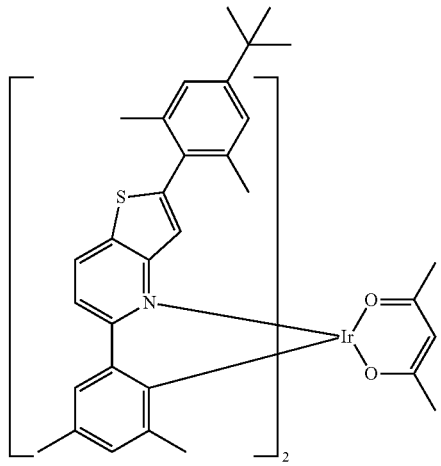
322
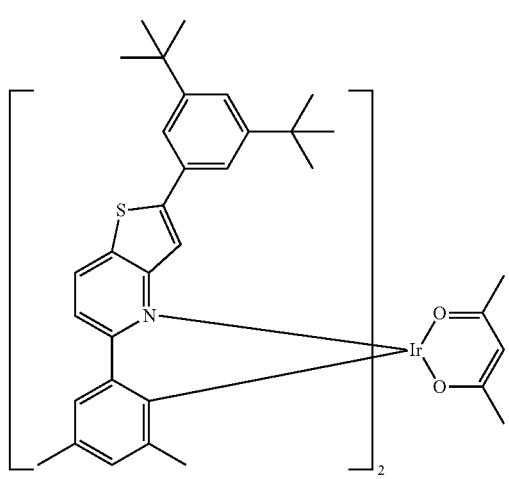
323
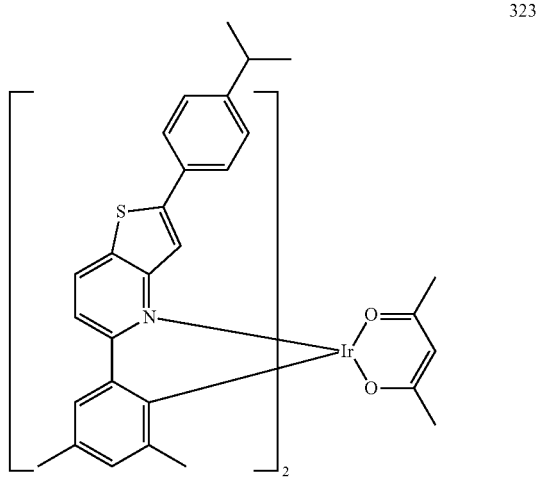

-continued
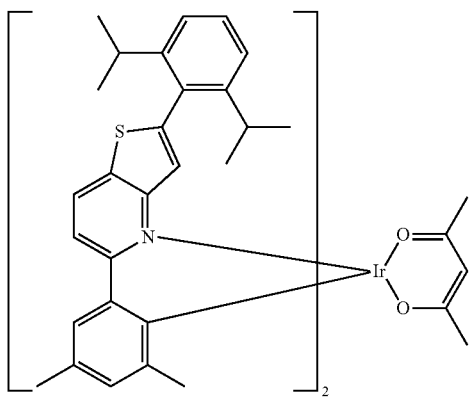
324
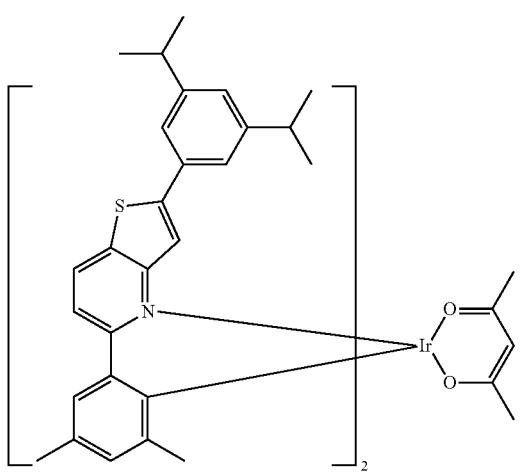
325
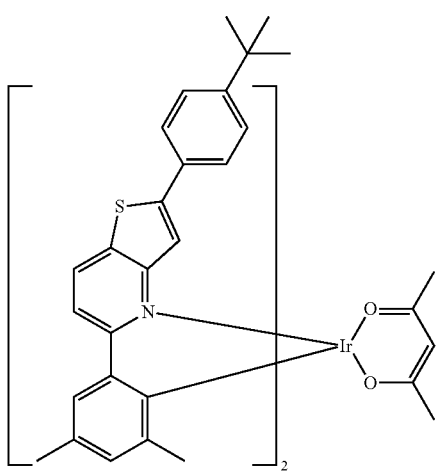
326
-continued
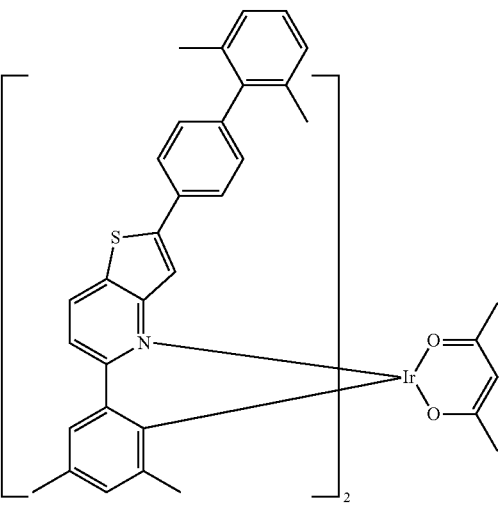
327
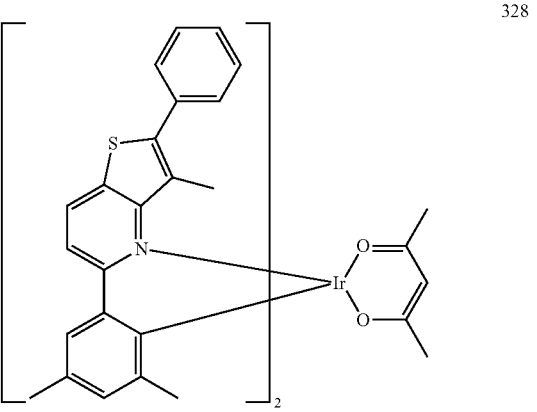
328
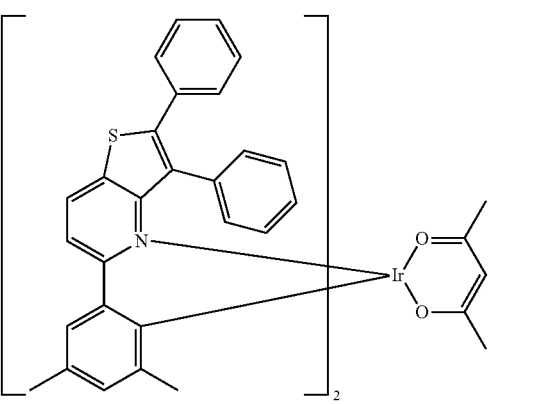
329

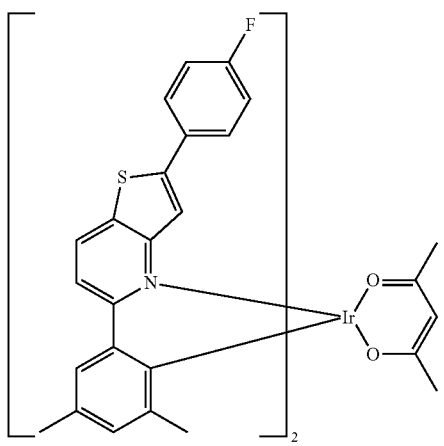
330
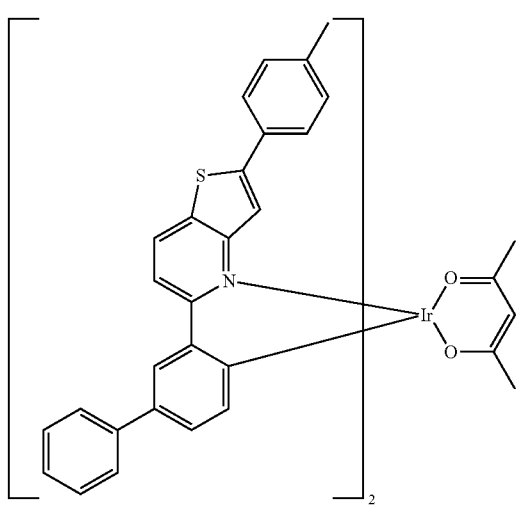
333
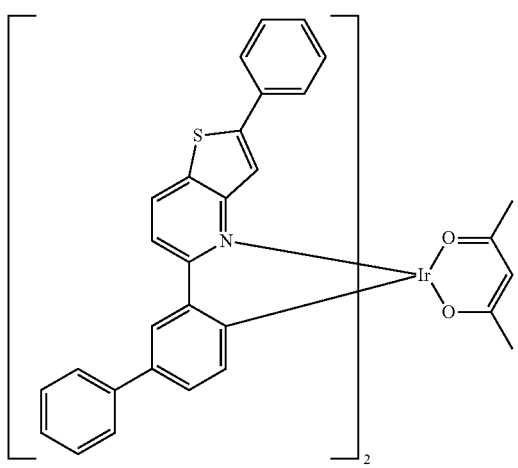
331
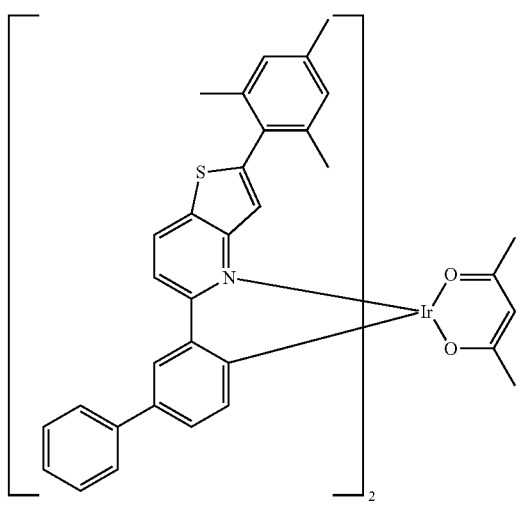
334
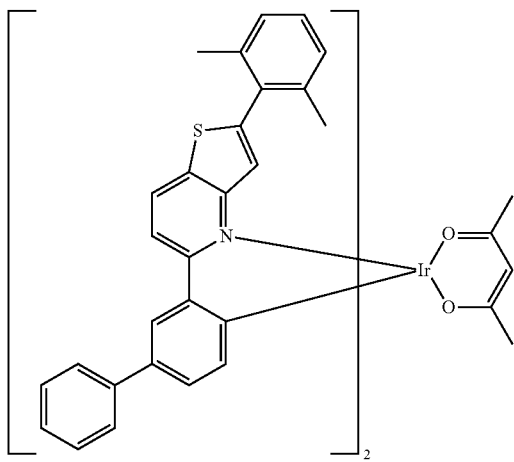
332
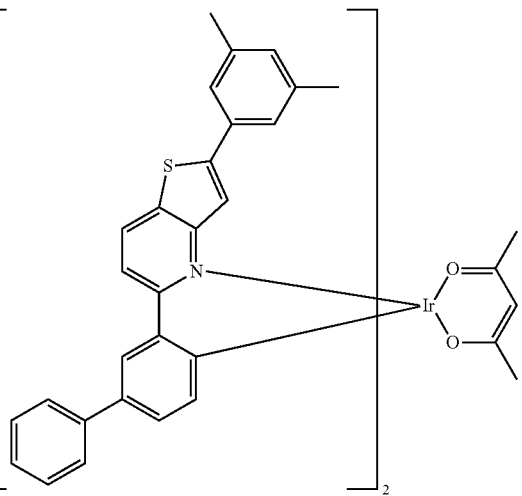
335

-continued
336
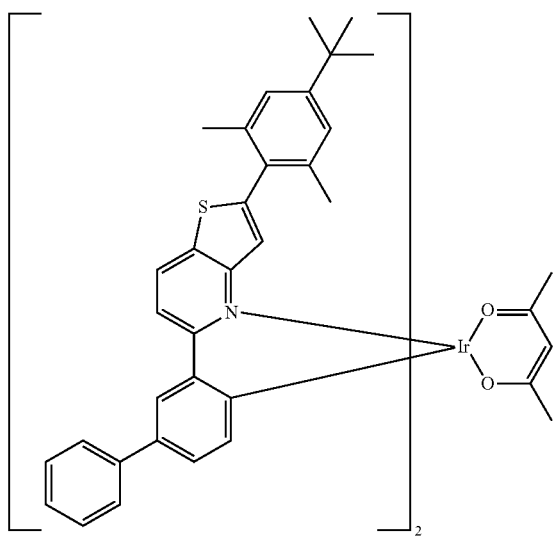
337
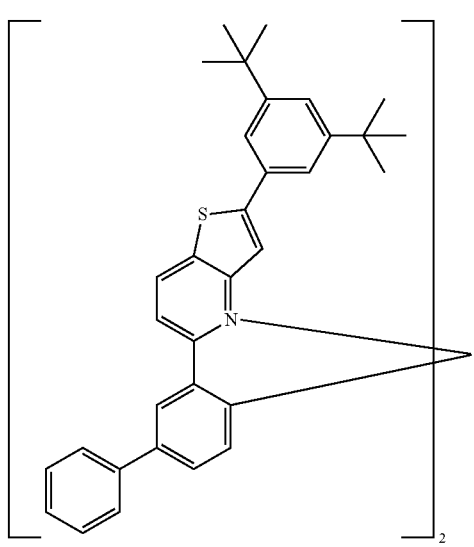
338
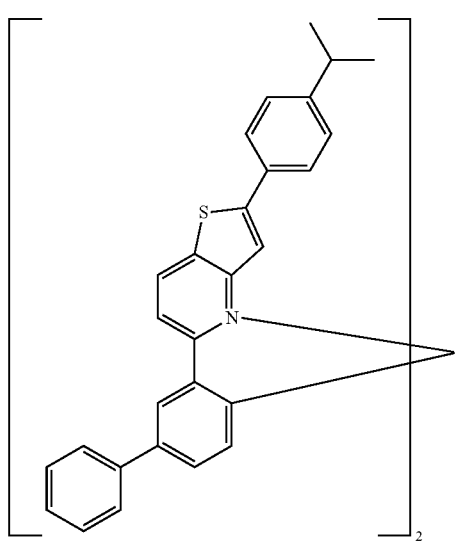
-continued
339
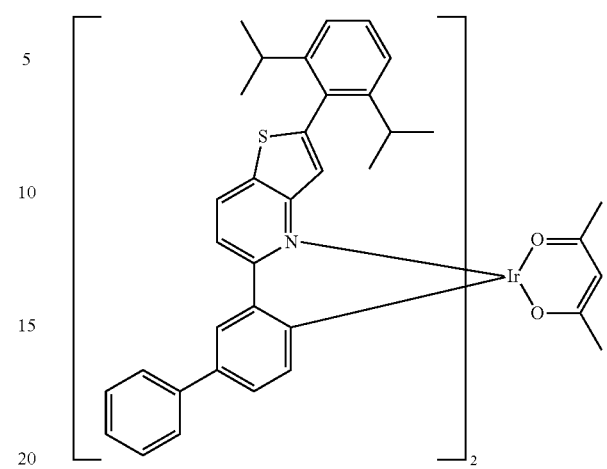
340
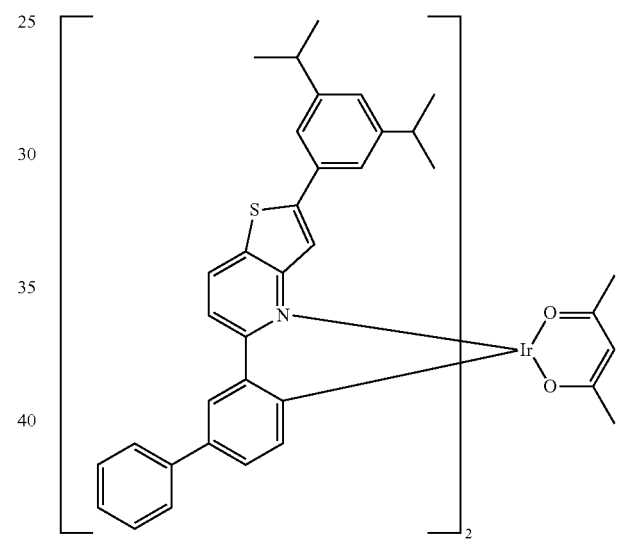
341
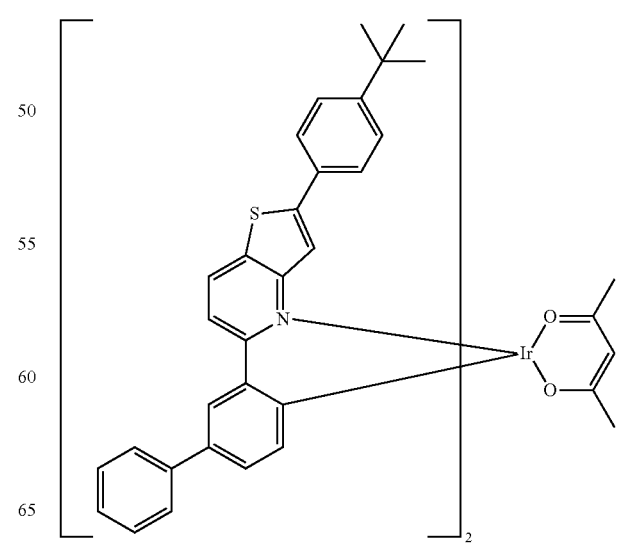

342
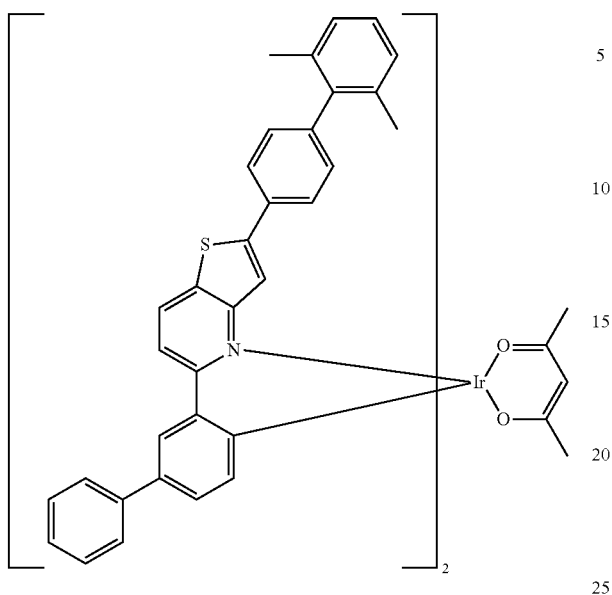
343
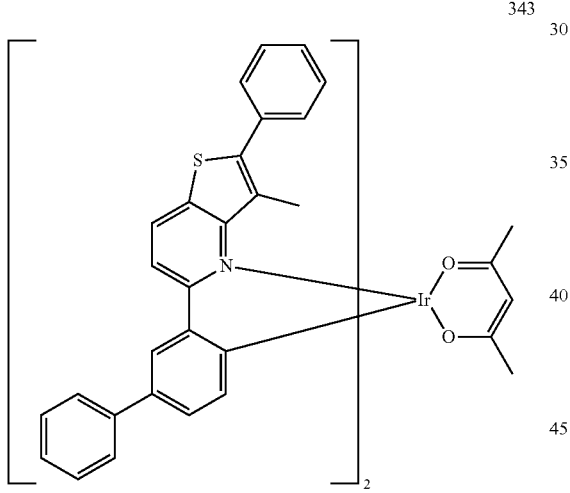
344
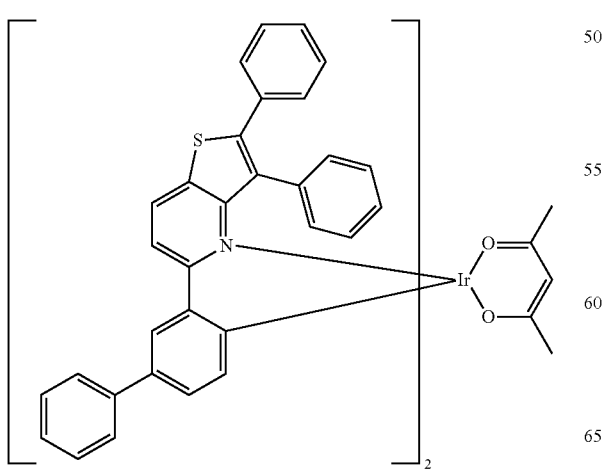
345
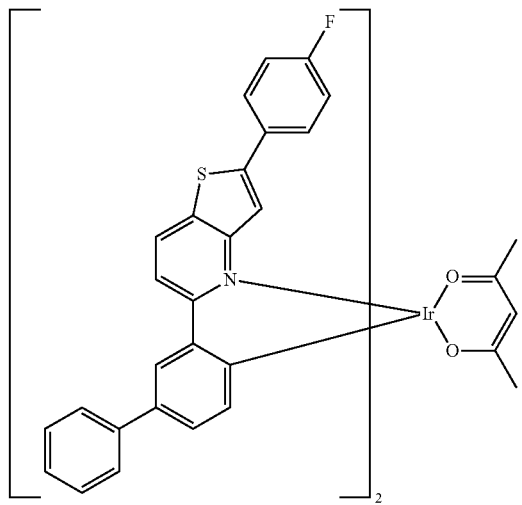
346
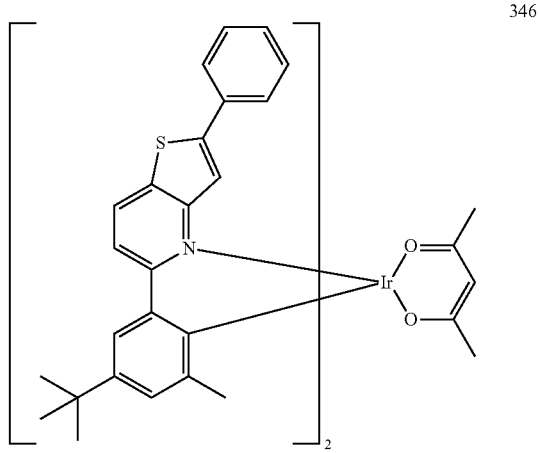
347
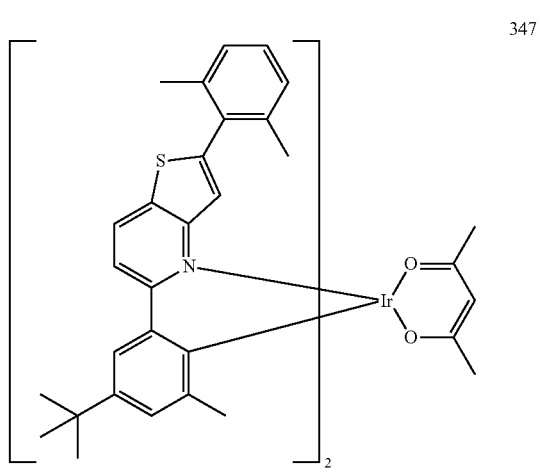

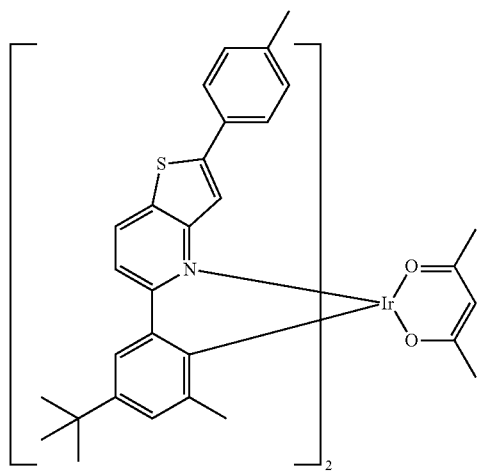
348
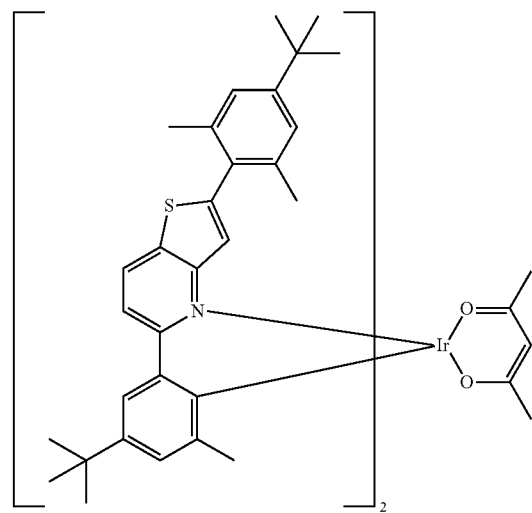
351
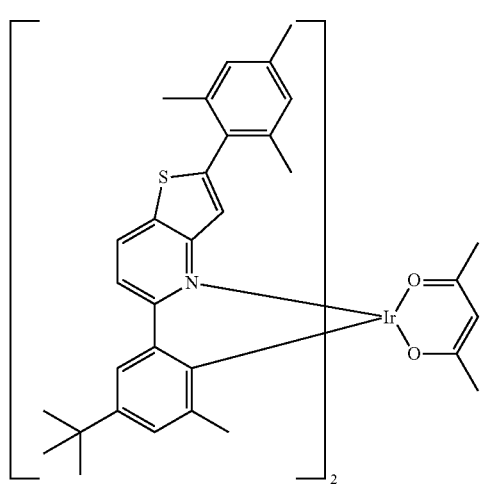
349
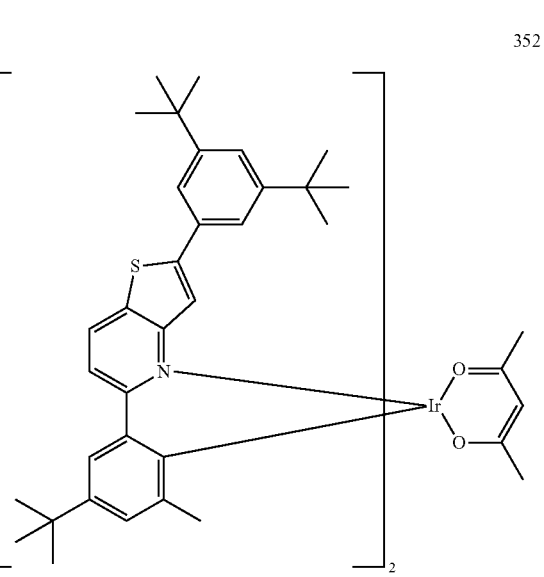
352
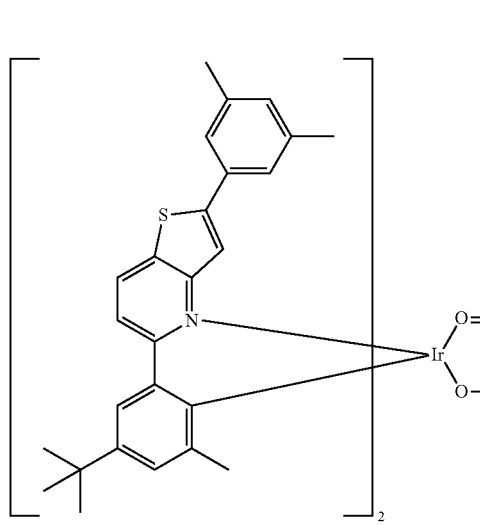
350
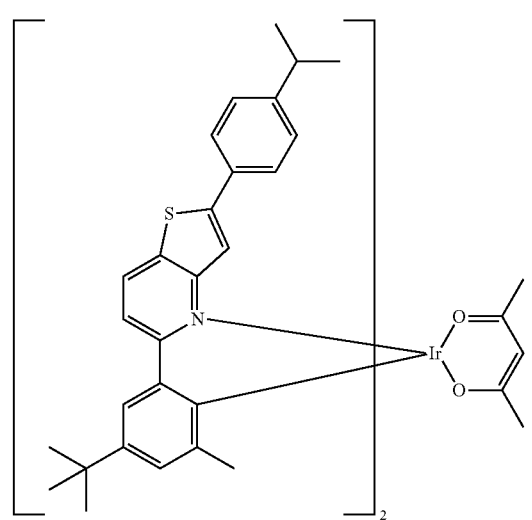
353

-continued
354
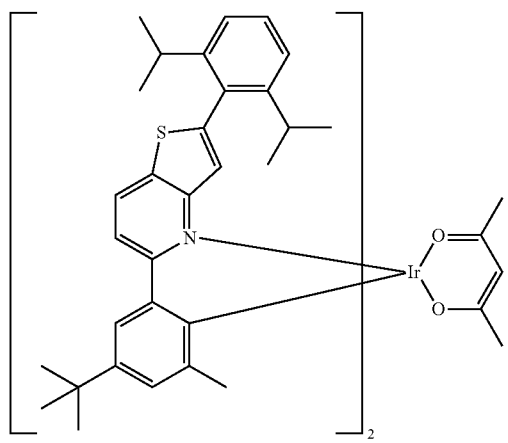
355
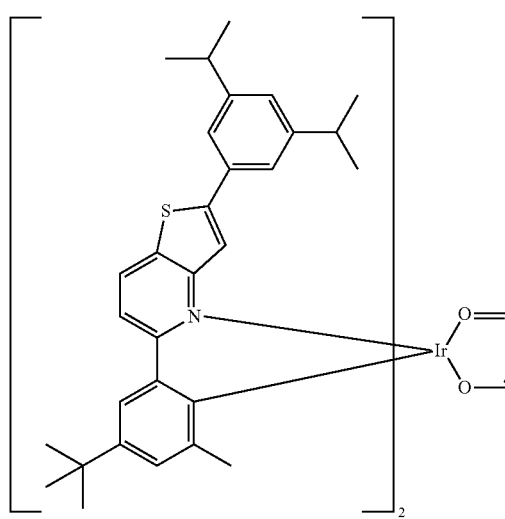
356
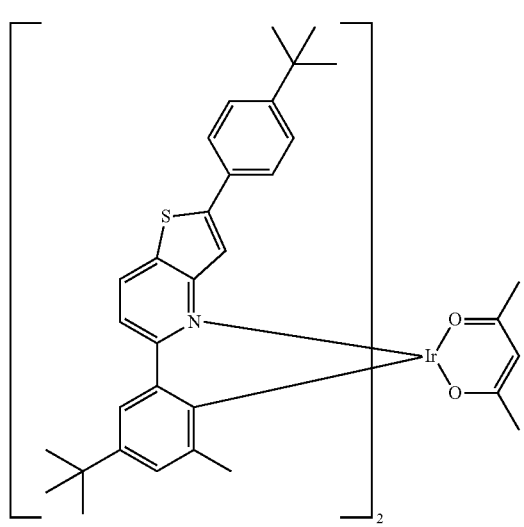
-continued
357
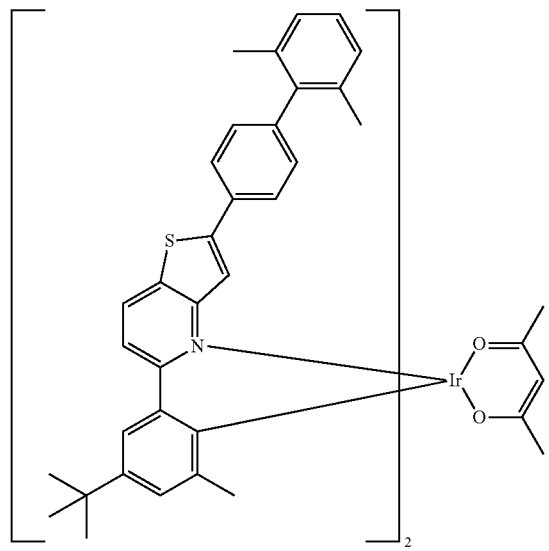
358
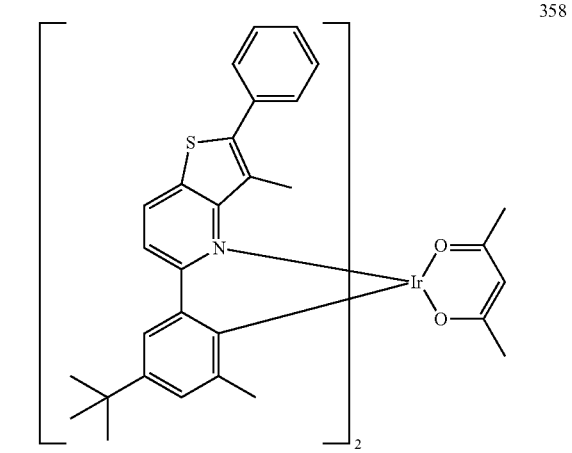
359
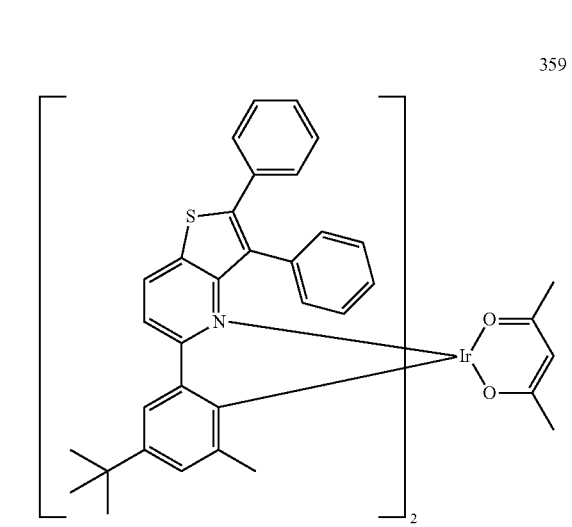

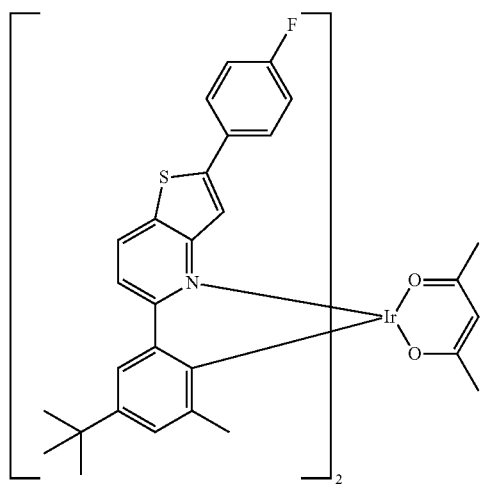
360
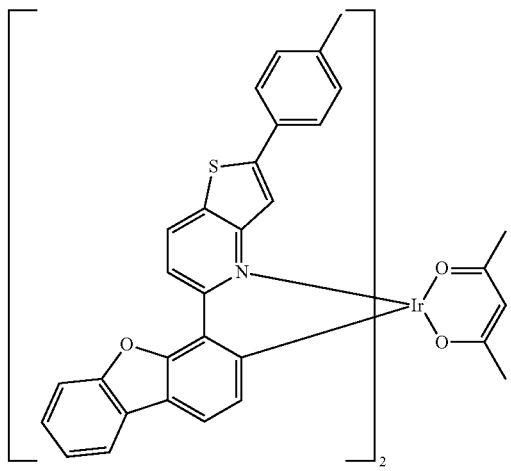
363
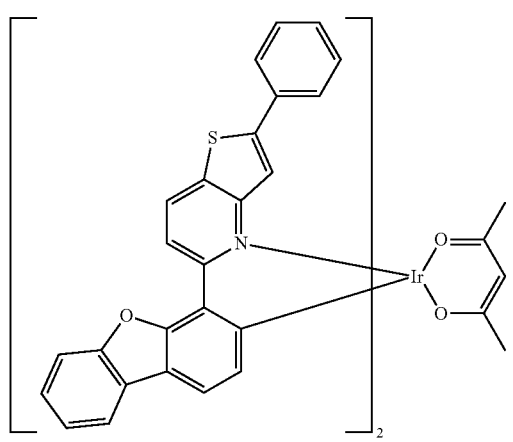
361
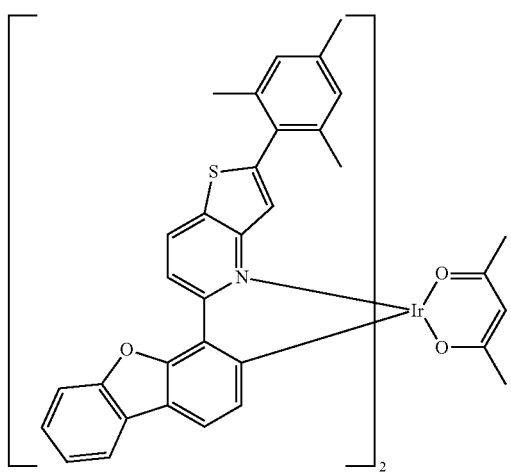
364
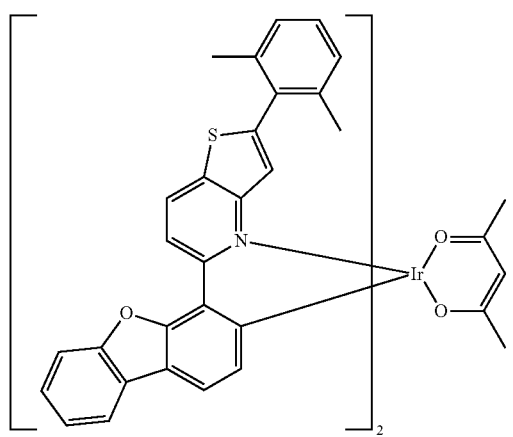
362
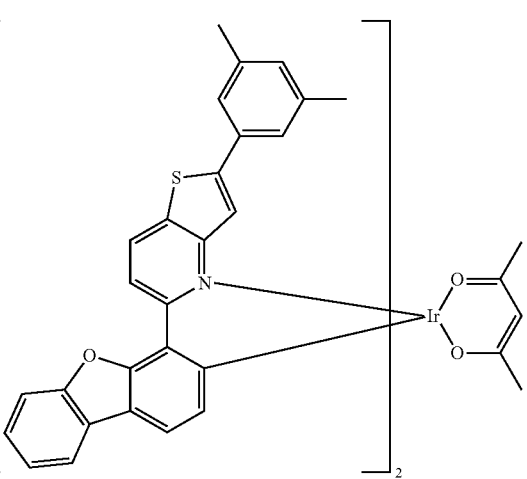
365

201
-continued
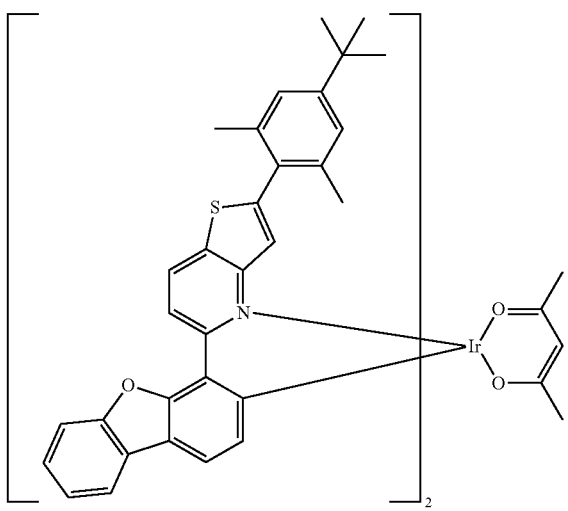
366
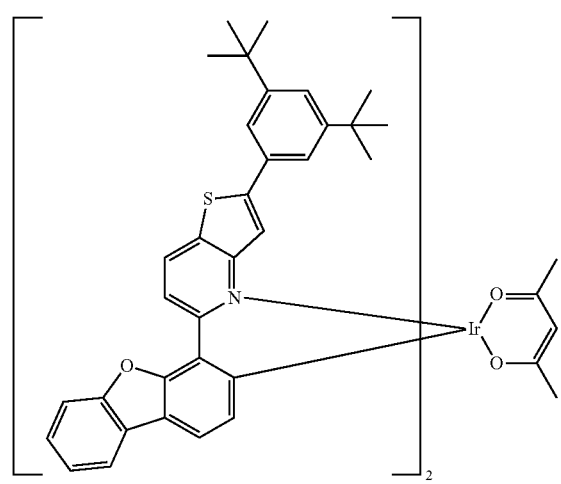
367
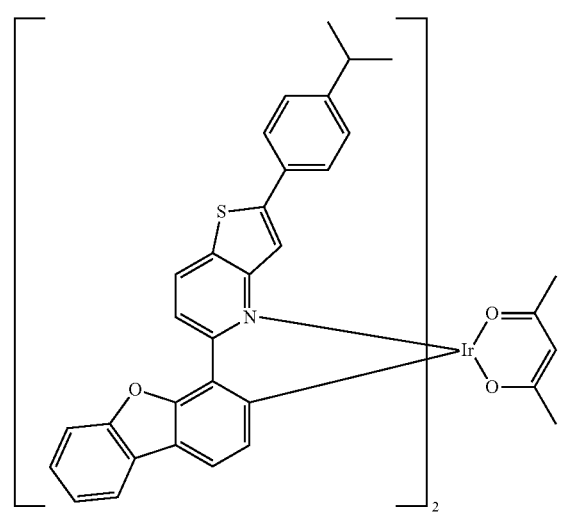
368
202
-continued
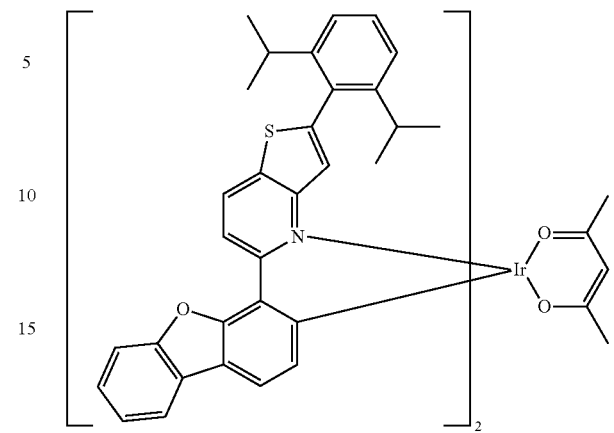
369
370
371

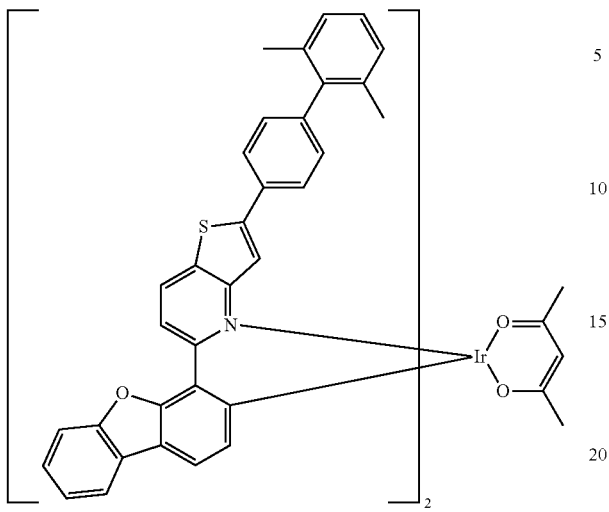
372
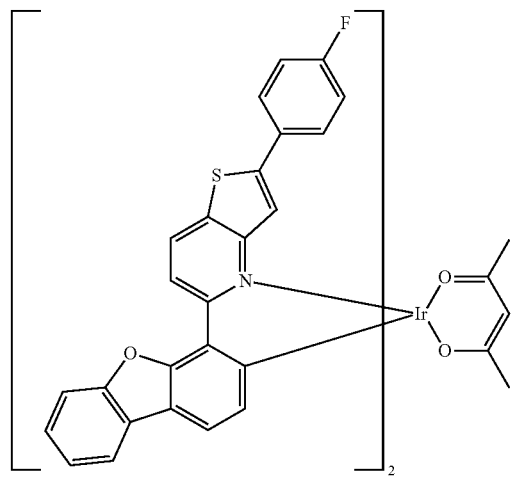
375
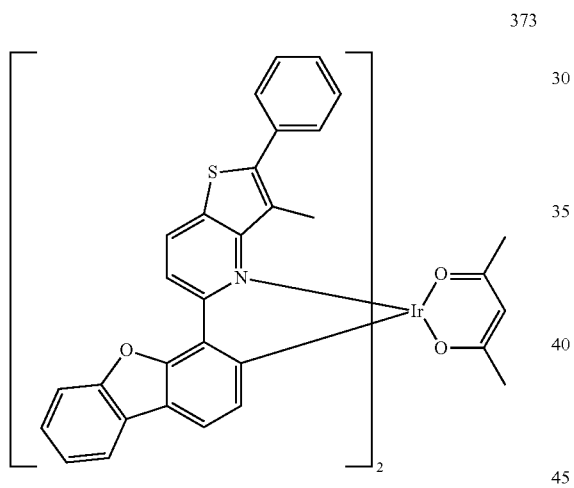
373
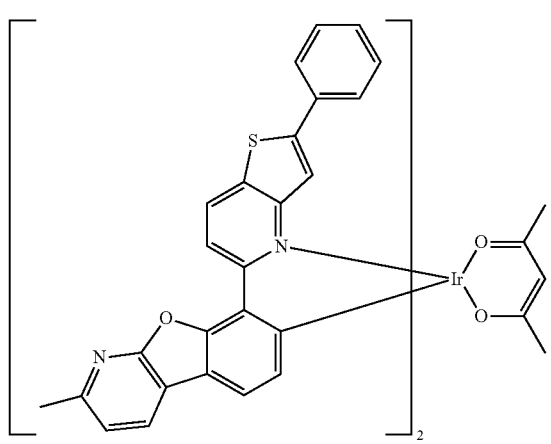
376
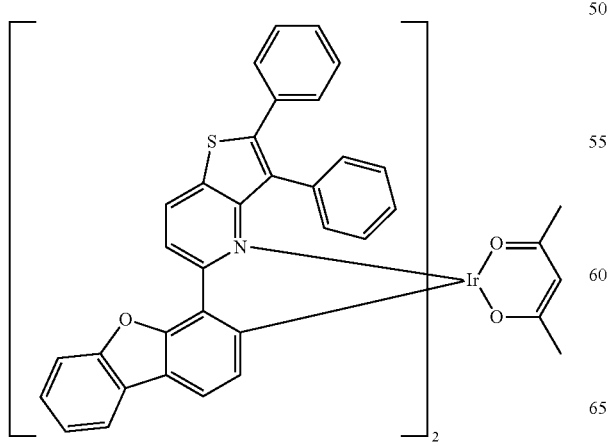
374
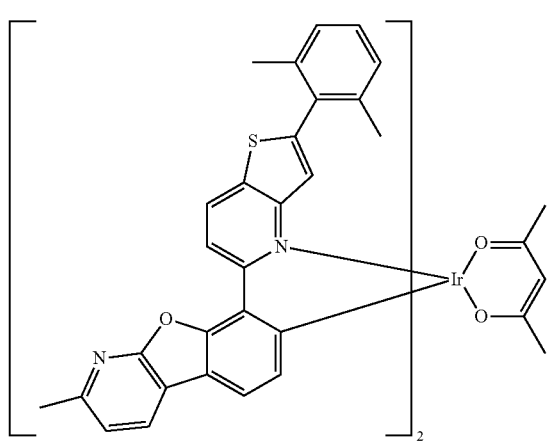
377

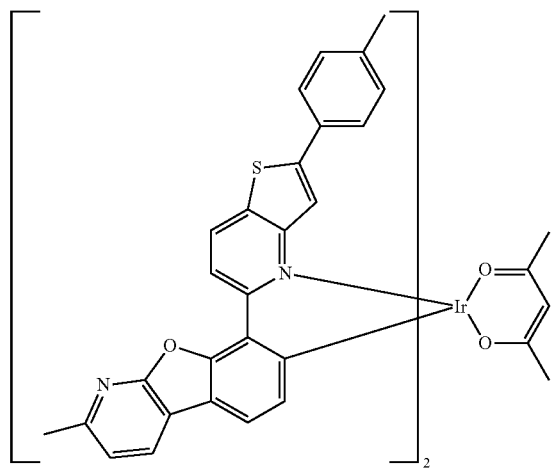
378
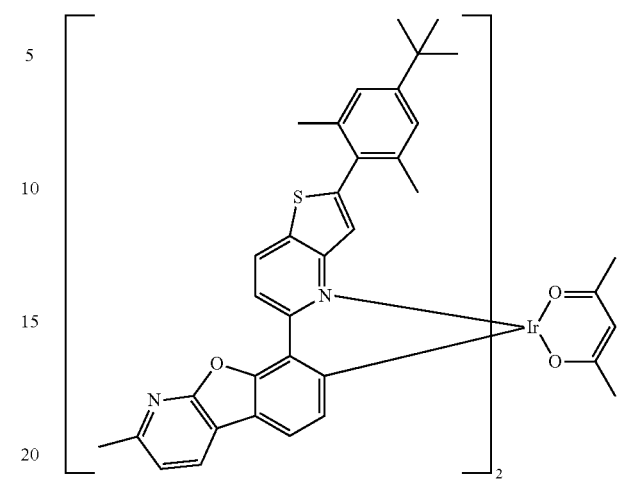
381
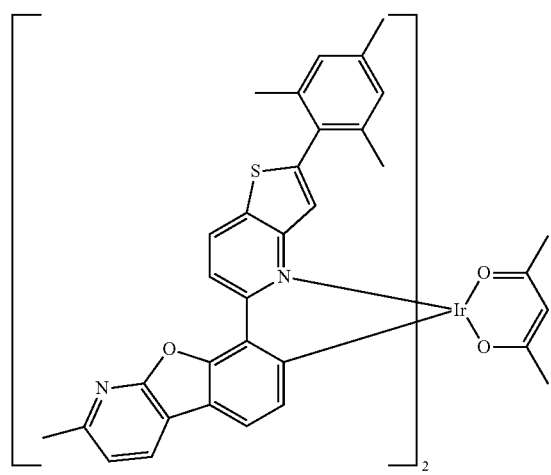
379
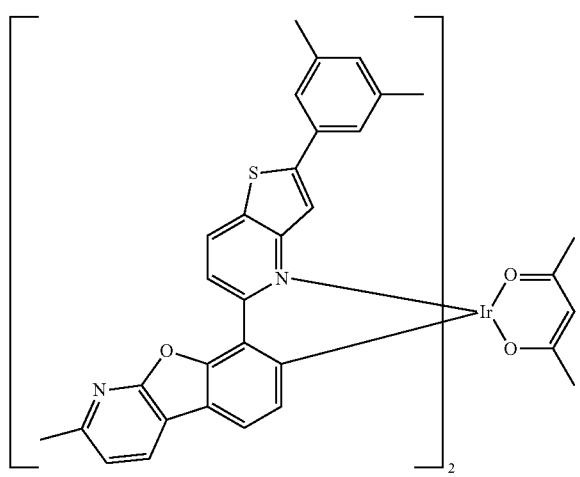
380

-continued
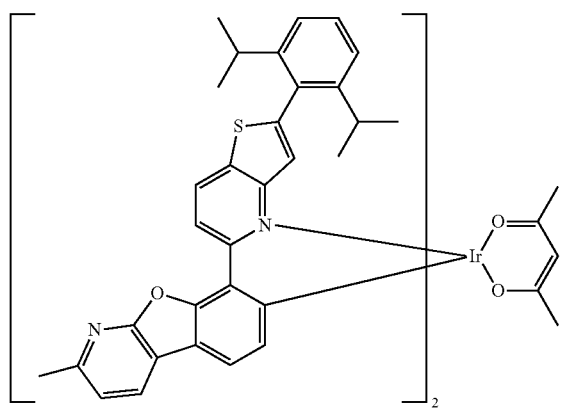
384
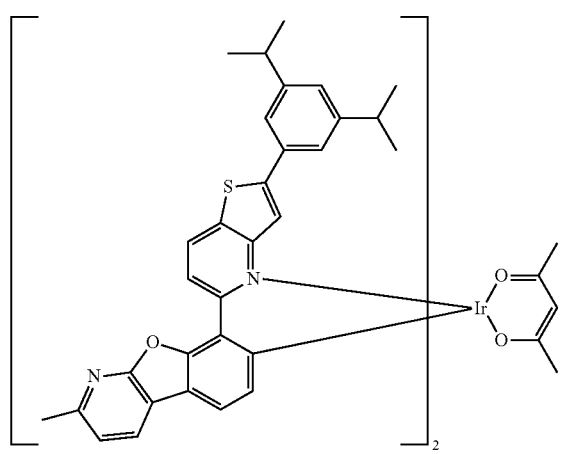
385
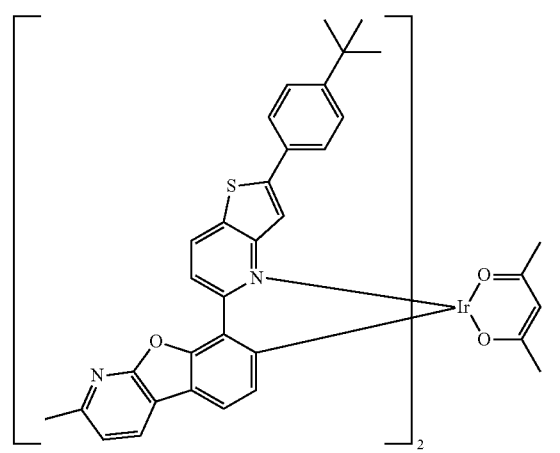
386
-continued
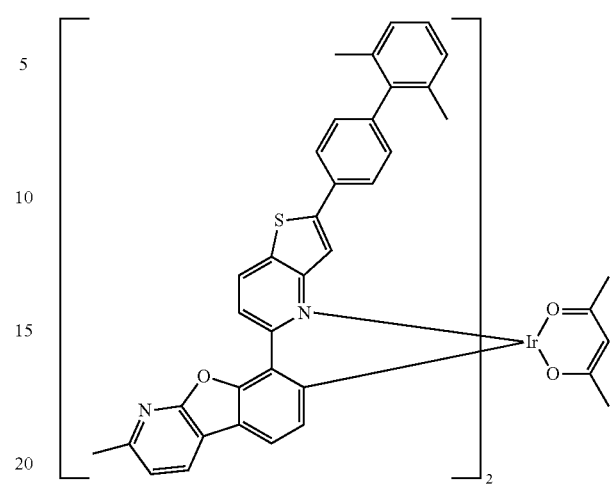
387
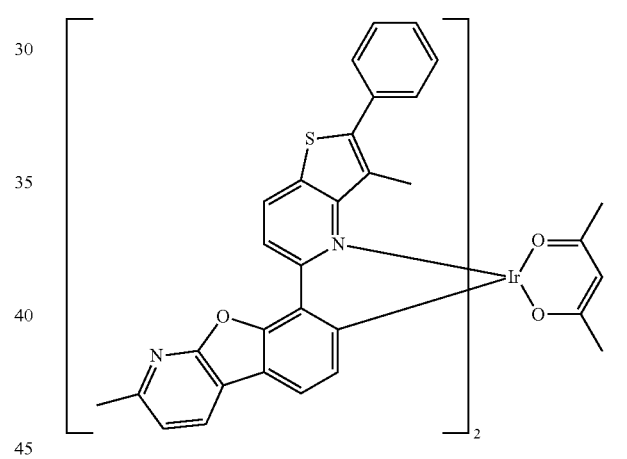
388
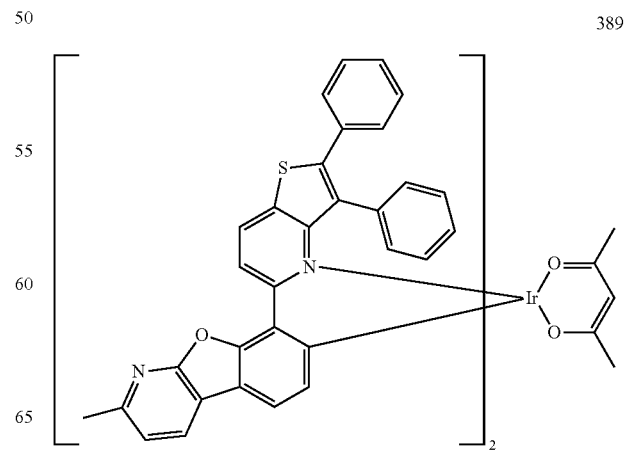
389

-continued
390
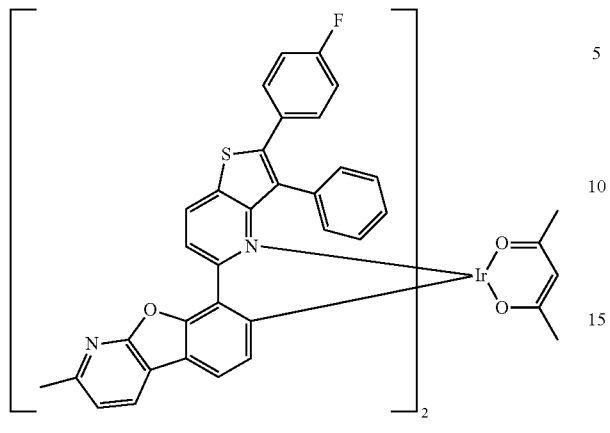
391
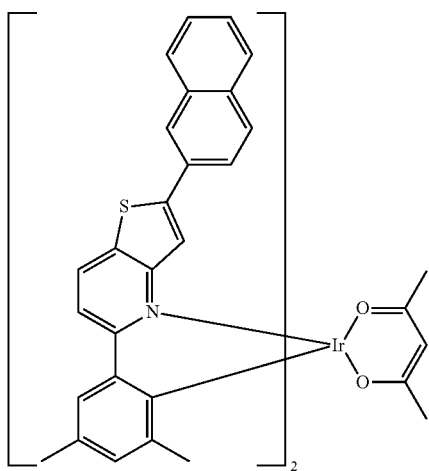
392
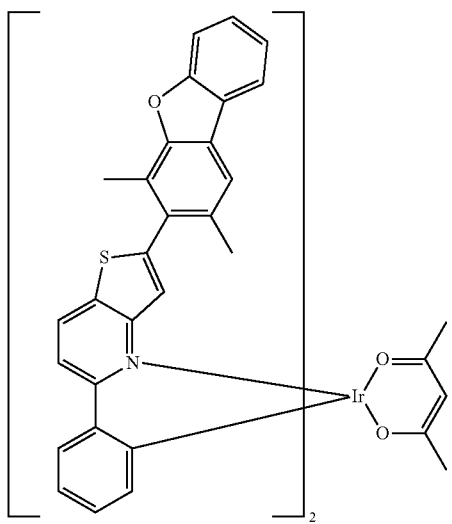
-continued
393
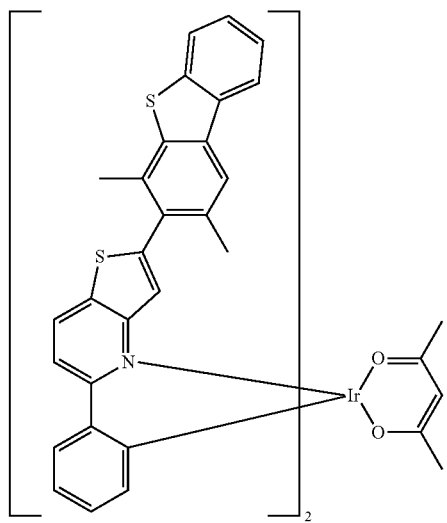
394
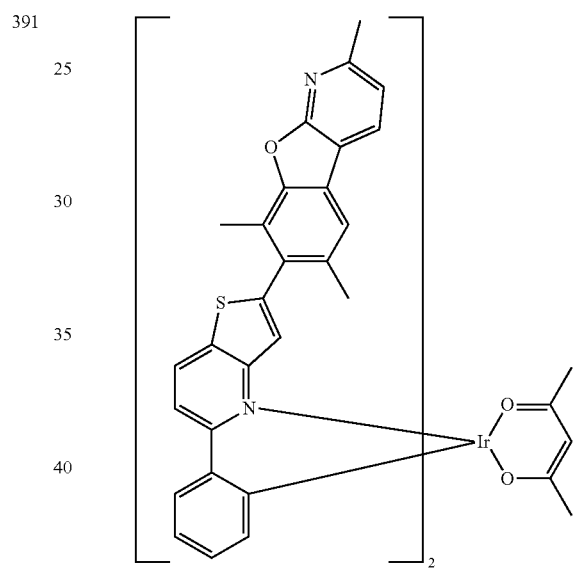
395
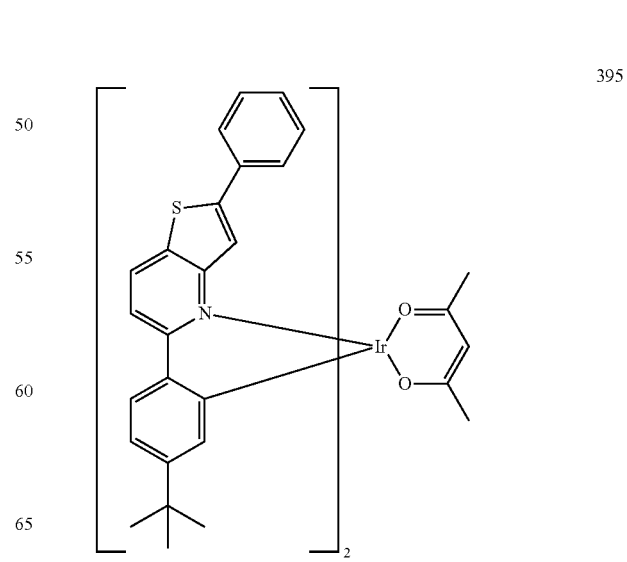

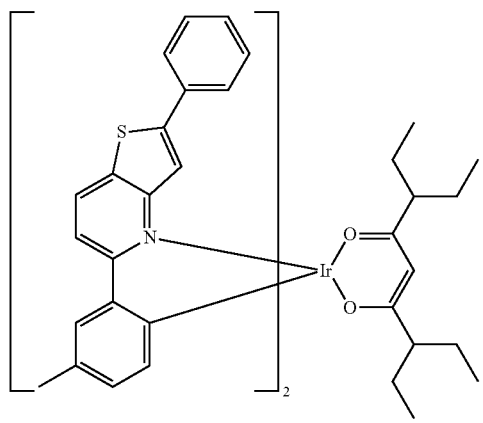
396
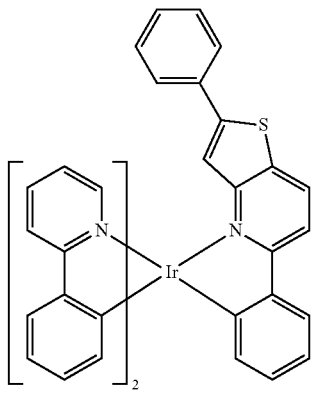
399
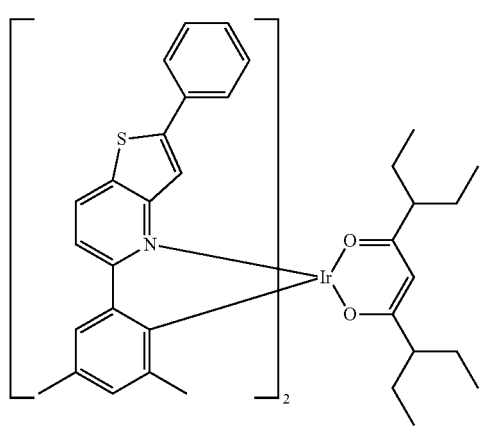
397
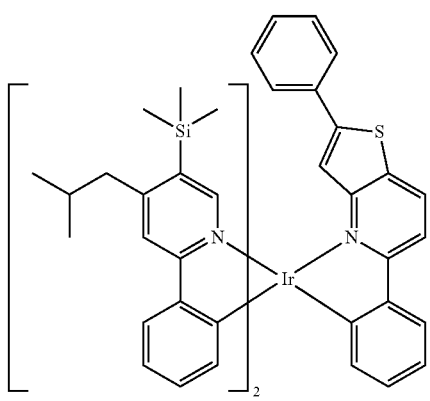
400
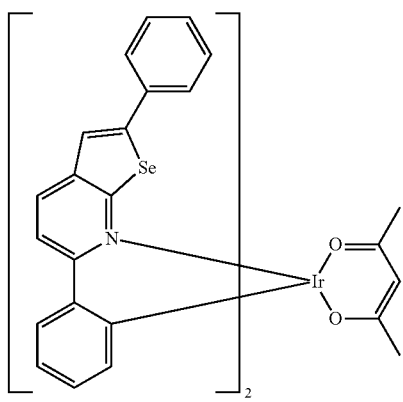
401
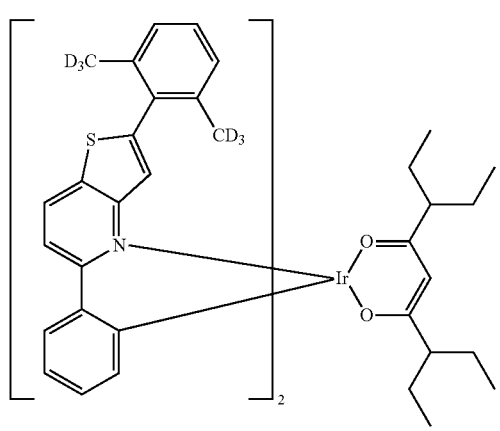
398
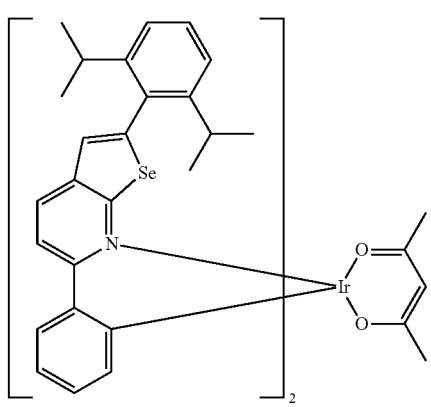
402

213
-continued
403
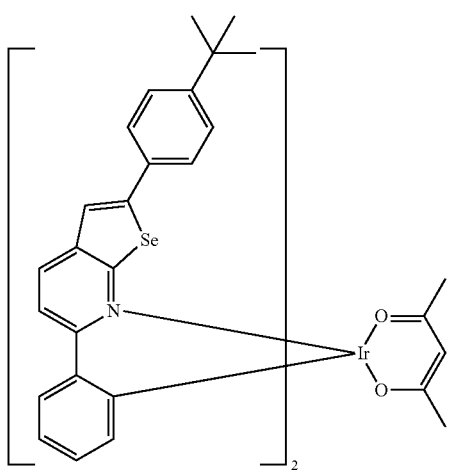
404
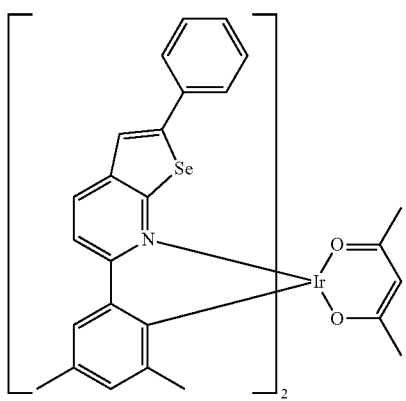
405
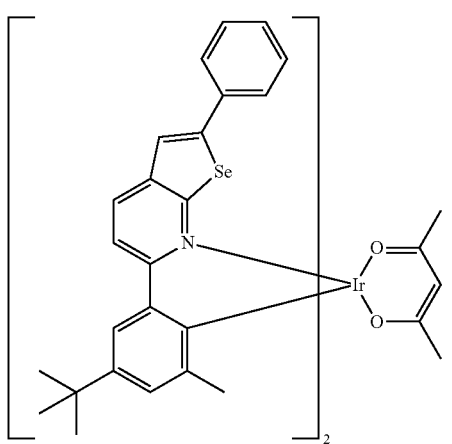
214
-continued
406
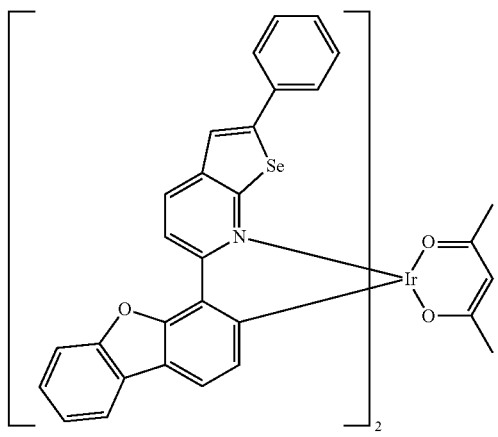
407
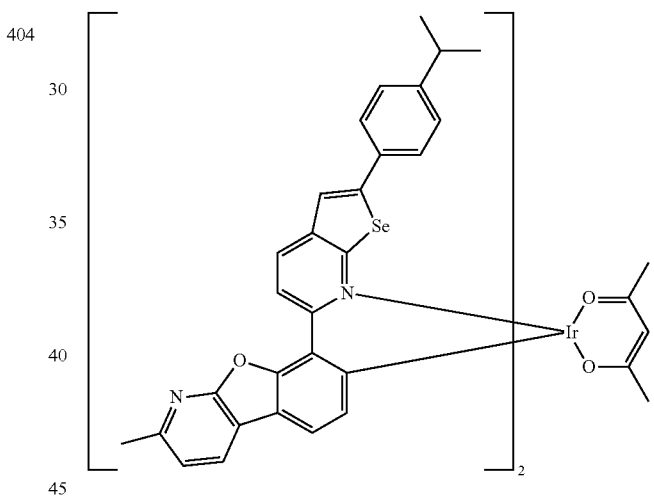
408
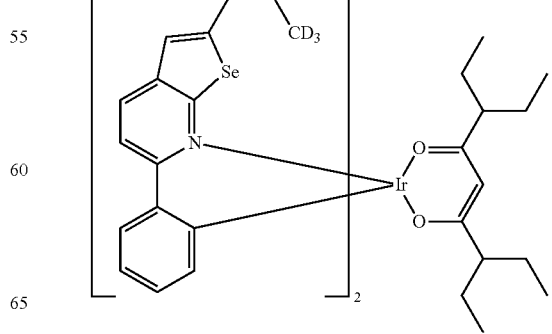

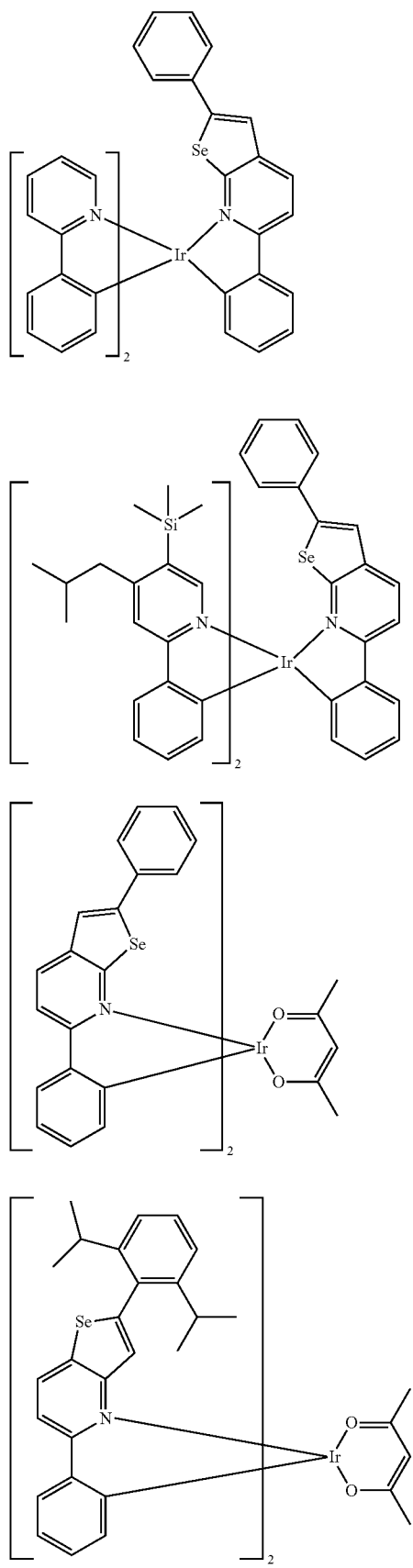
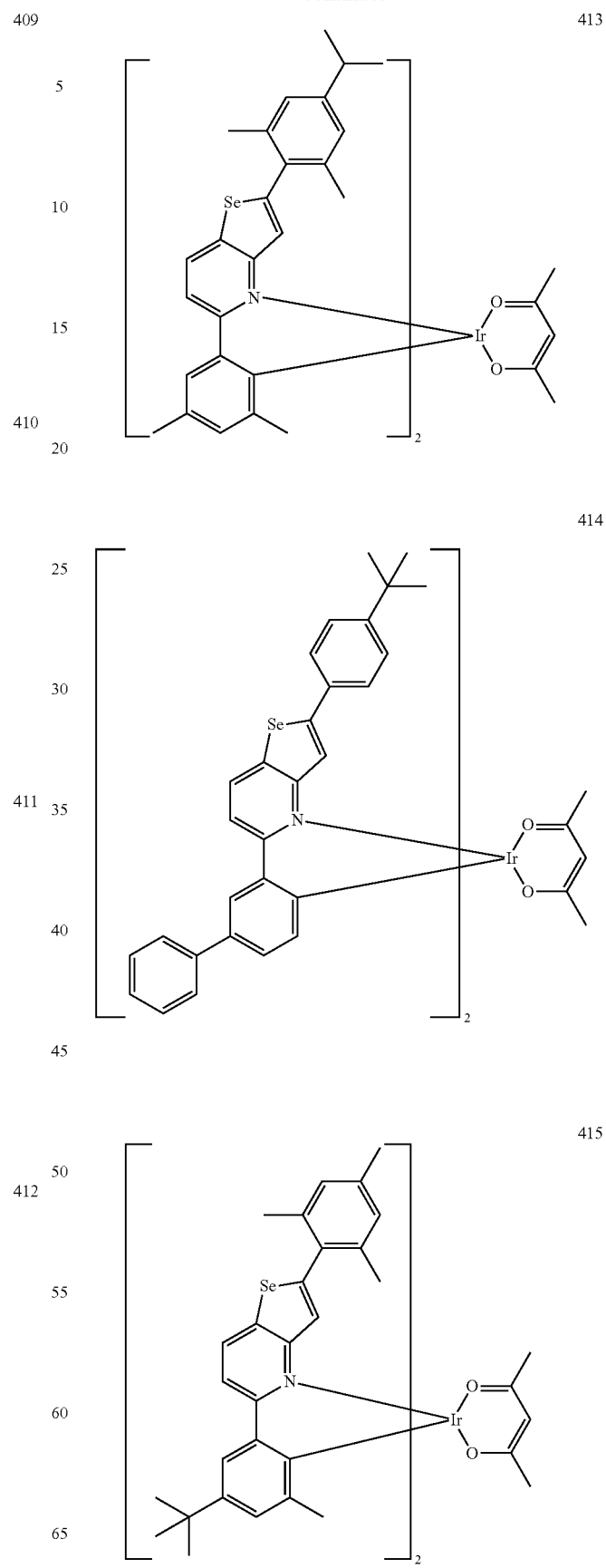

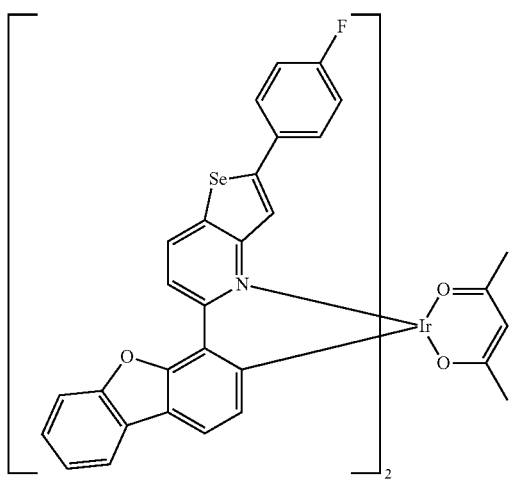

416

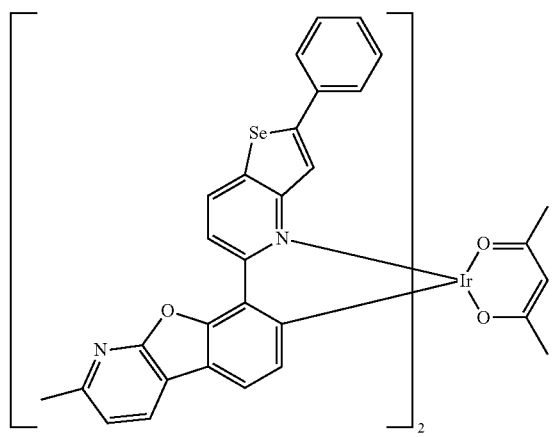

417

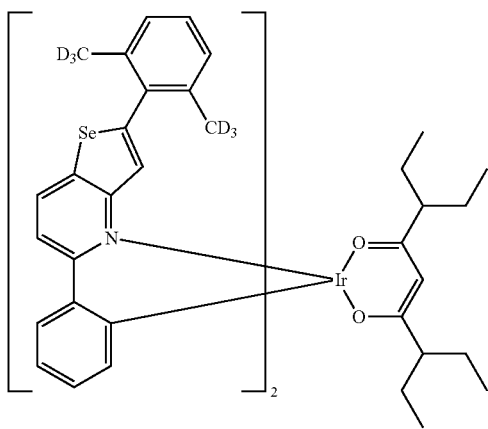

418

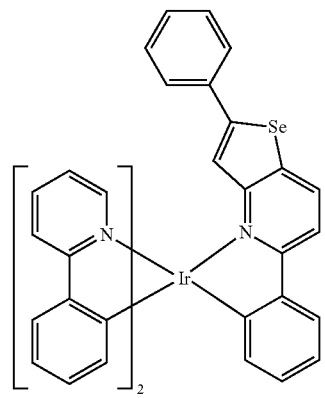

419

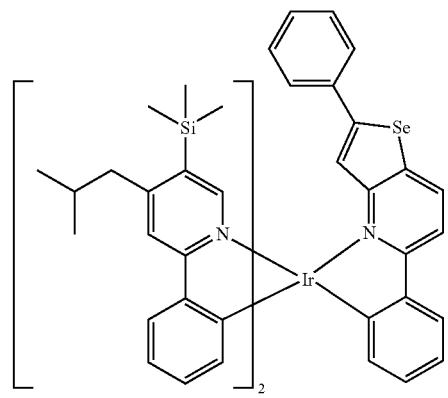

420

$L_1$ of the organometallic compound represented by Formula 1 may be a ligand represented by Formula 2, and n1 which indicates the number of $L_1$ may be 1, 2, or 3. That is, the organometallic compound essentially includes, as ligands linked to metal M, at least one ligand represented by Formula 2.

$X_2$ and $X_3$ in the ligand represented by Formula 2 are each independently O, S, Se, or $C(R_2)$, wherein $X_2$ or $X_3$ is O, S, or Se. That is, in Formula 2, the 5-membered ring (see Formula 2') does not include *=N—*' (* and *' each indicate a binding site to a neighboring atom) as a ring-forming atom, and includes O, S, or Se. In addition, in Formula 2, the 5-membered ring is condensed with the 6-membered ring while sharing carbon 1 and carbon 2 (see Formula 2'). A reduction in the intermolecular bonding force of the organometallic compound represented by Formula 1 may be prevented. Therefore, a reduction in the lifespan of an electronic device, for example, an organic light-emitting device, which includes the organometallic compound represented by Formula 1, may be prevented.

Formula 2'

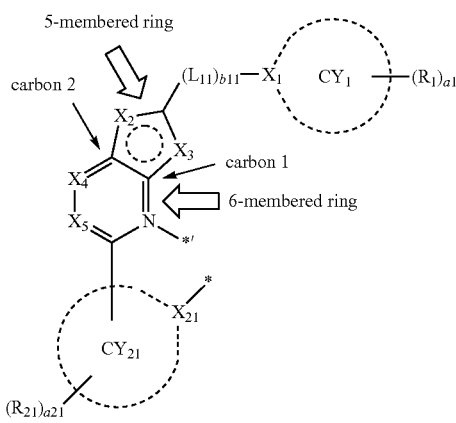

The ligand represented by Formula 2 includes "ring $CY_1$". Therefore, a transition dipole moment increases in an alignment axis direction of Formula 1, and the alignment of the organometallic compound represented by Formula 1 may be improved, thereby increasing the luminescence efficiency of an electronic device, for example, an organic light-emitting device, which includes the organometallic compound represented by Formula 1.

Meanwhile, in Formula 2, ring $CY_1$ and $R_2$ are not linked to each other, and $R_1$ and $R_2$ are not linked to each other. Therefore, it is possible to prevent a transition dipole moment of Formula 1 from deviating to a direction other than the alignment axis direction of Formula 1, thereby increasing the luminescence efficiency of an electronic device, for example, an organic light-emitting device, which includes the organometallic compound represented by Formula 1.

A highest occupied molecular orbital (HOMO) energy level, a lowest unoccupied molecular orbital (LUMO) energy level, and a triplet (Ti) energy level of some compounds of the organometallic compound represented by Formula 1 are evaluated by a density functional theory (DFT) of Gaussian program with molecular structure optimization based on B3LYP, and results are shown in Table 1.

TABLE 1

| Compound No. | HOMO (eV) | LUMO (eV) | $T_1$ (eV) |
|---|---|---|---|
| 16 | −4.542 | −1.694 | 2.008 |
| 101 | −4.749 | −1.682 | 2.177 |
| 116 | −4.600 | −1.671 | 2.081 |
| 146 | −4.687 | −1.651 | 2.150 |
| 216 | −4.576 | −1.747 | 2.075 |
| 316 | −4.633 | −1.747 | 2.116 |

TABLE 1-continued

| Compound No. | HOMO (eV) | LUMO (eV) | $T_1$ (eV) |
|---|---|---|---|

TABLE 1-continued

| Compound No. | HOMO (eV) | LUMO (eV) | T$_1$ (eV) |
|---|---|---|---|
| 216 | | | |
| 316 | | | |

Referring to Table 1, it is confirmed that the organometallic compound represented by Formula 1 has such electrical characteristics that are suitable for use in an electronic device, for example, an organic light-emitting device, for use as a dopant.

Synthesis methods of the organometallic compound represented by Formula 1 may be understood by one of ordinary skill in the art by referring to Synthesis Examples provided below.

Therefore, the organometallic compound represented by Formula 1 may be suitable for use in an organic layer of an organic light-emitting device, for example, for use as a dopant in an emission layer of the organic layer. Another aspect of the present disclosure provides an organic light-emitting device including: a first electrode, a second electrode, and an organic layer disposed between the first electrode and the second electrode and including an emission layer, wherein the organic layer includes at least one organometallic compound represented by Formula 1.

The organic light-emitting device may have, due to the inclusion of an organic layer including the organometallic compound represented by Formula 1, a low driving voltage, high external quantum luminescence efficiency, a low roll-off ratio, and a long lifespan.

The organometallic compound represented by Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host). The emission layer may emit, for example, green light or red light.

The expression "(an organic layer) includes at least one organometallic compound represented by Formula 1" as used herein may include a case in which "(an organic layer) includes identical organometallic compounds represented by Formula 1" and a case in which "(an organic layer) includes two or more different organometallic compounds represented by Formula 1".

For example, the organic layer may include, as the organometallic compound represented by Formula 1, only Compound 1. In this regard, Compound 1 may exist only in the emission layer of the organic light-emitting device. In an embodiment, the organic layer may include, as the organometallic compound represented by Formula 1, Compound 1 and Compound 2. In this regard, Compound 1 and Compound 2 may exist in an identical layer (for example, Compound 1 and Compound 2 all may exist in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, the organic light-emitting device, the first electrode is an anode, and the second electrode is a cathode, and the organic layer further includes a hole transport region disposed between the first electrode and the emission layer and an electron transport region disposed between the emission layer and the second electrode, and the hole transport region includes a hole injection layer, a hole transport layer, an electron blocking layer, or any combination thereof, and the electron transport region includes a hole blocking layer, an electron transport layer, an electron injection layer, or any combination thereof.

The term "organic layer" as used herein refers to a single layer and/or a plurality of layers disposed between the first electrode and the second electrode of an organic light-emitting device. The "organic layer" may include, in addition to an organic compound, an organometallic complex including metal.

FIGURE is a schematic cross-sectional view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in the organic light-emitting device art may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be a material with a high work function to facilitate hole injection. The first electrode 11 may be a reflective electrode, a semi-reflective electrode, or a transmissive electrode. The material for forming the first electrode may be, for example, indium tin oxide (ITO), indium zinc oxide (IZO), tin oxide (SnO$_2$), or zinc oxide (ZnO). In an embodiment, the material for forming the first electrode 11 may be a metal or a metal alloy, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In an embodiment, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer, the hole injection layer may be formed on the first electrode 11 by using a suitable method, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about 10$^{-8}$ torr to about 10$^{-3}$ torr, and a deposition rate of about 0.01 Å/sec to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 rpm to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include, for example, m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201 below, a compound represented by Formula 202 below, or any combination thereof:

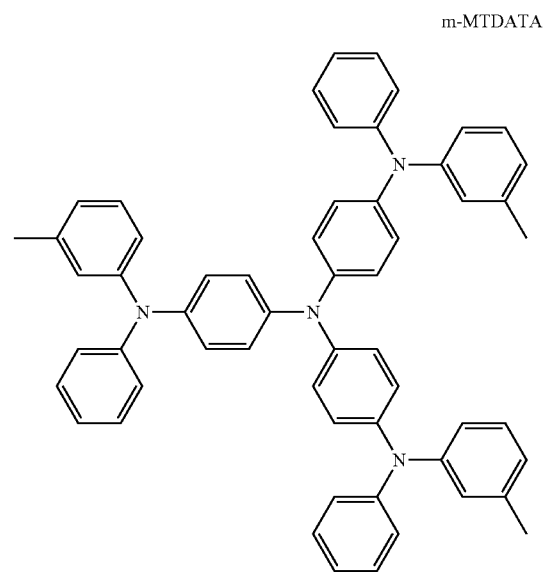

m-MTDATA

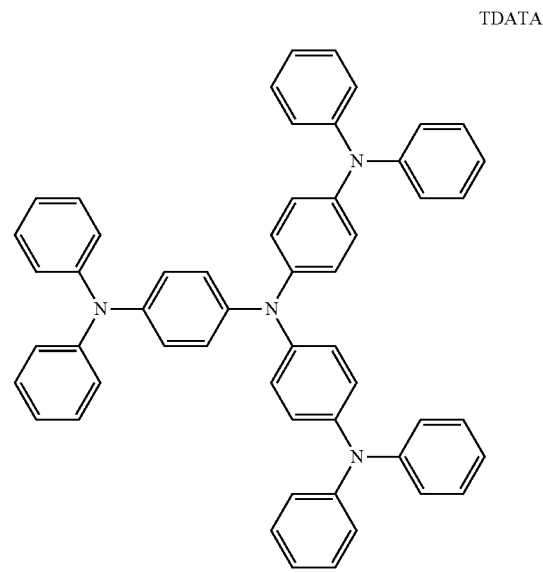

TDATA

2-TNATA
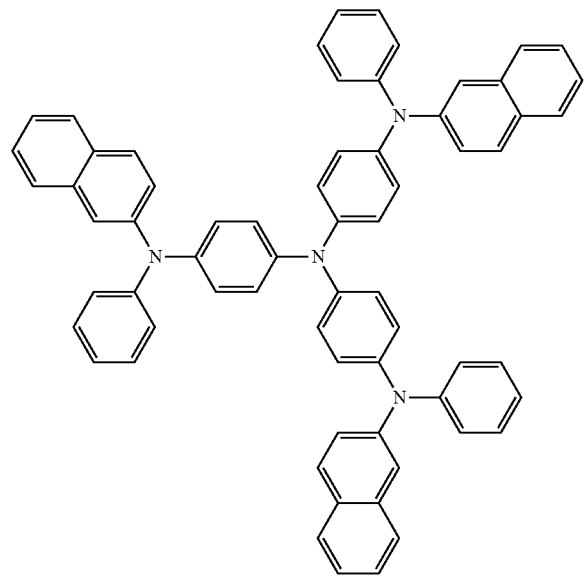
NPB
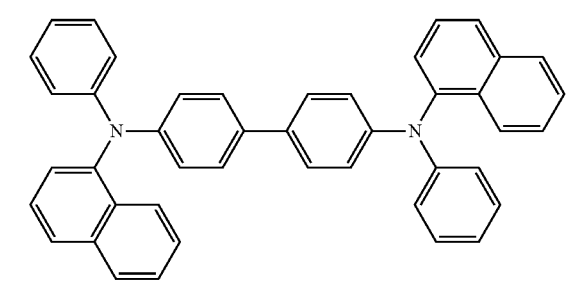
β-NPB
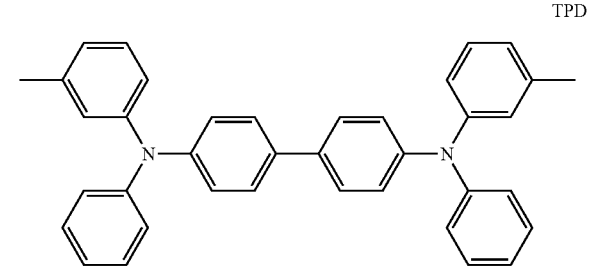
TPD
Spiro-TPD
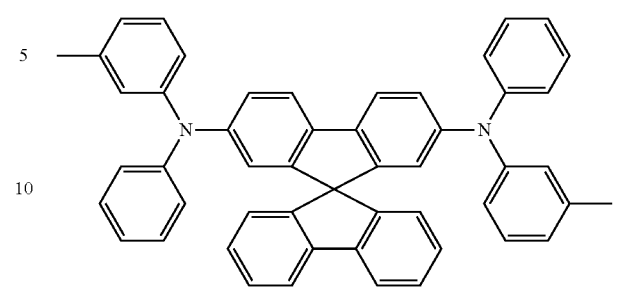
Spiro-NPB
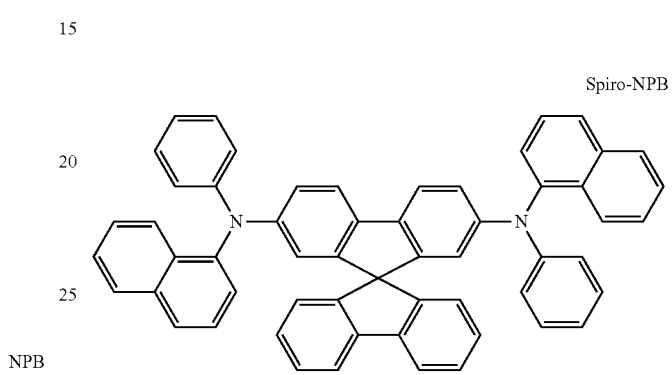
methylated NPB
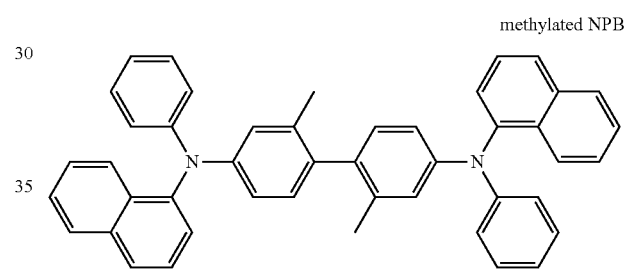
TAPC
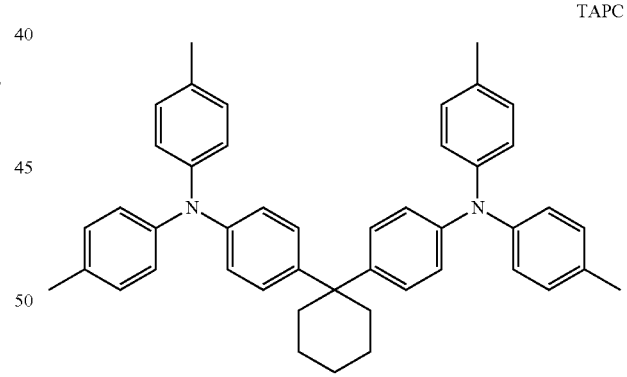
HMTPD
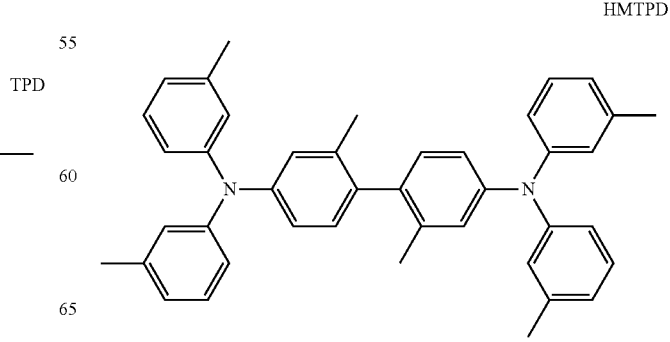

-continued

Formula 201

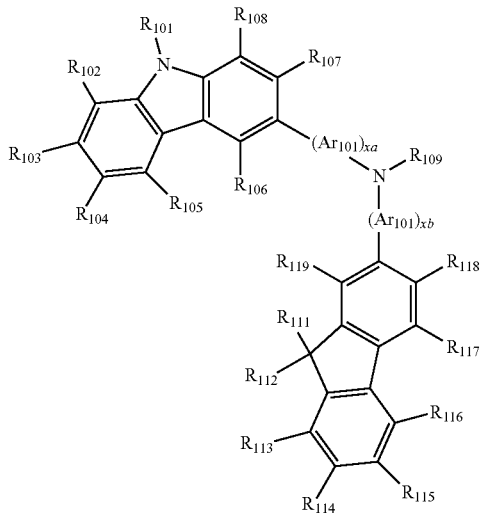

Formula 202

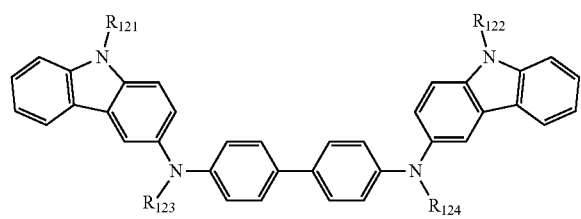

In Formula 201, $Ar_{101}$ and $Ar_{102}$ may each independently be a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_1$-$C_{60}$ heteroaryl group, a $C_2$-$C_{60}$ heteroarylalkyl group, a monovalent non-aromatic condensed polycyclic group, a monovalent non-aromatic condensed heteropolycyclic group, or any combination thereof.

In Formula 201, xa and xb may each independently be an integer from 0 to 5, or may be 0, 1, or 2. For example, xa may be 1, and xb may be 0, but embodiments of the present disclosure are not limited thereto.

In Formulae 201 and 202, $R_{101}$ to $R_{108}$, $R_{111}$ to $R_{119}$, and $R_{121}$ to $R_{124}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and the like), or a $C_1$-$C_{10}$ alkoxy group (for example, a methoxy group, an ethoxy group, a propoxy group, a butoxy group, a pentoxy group, and the like);

a $C_1$-$C_{10}$ alkyl group or a $C_1$-$C_{10}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or any combination thereof; or a phenyl group, a naphthyl group, an anthracenyl group, a fluorenyl group, or a pyrenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or any combination thereof, but embodiments of the present disclosure are not limited thereto.

In Formula 201, $R_{109}$ may be a phenyl group, a naphthyl group, an anthracenyl group, or a pyridinyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or any combination thereof.

In an embodiment, the compound represented by Formula 201 may be represented by Formula 201A below, but embodiments of the present disclosure are not limited thereto:

Formula 201A

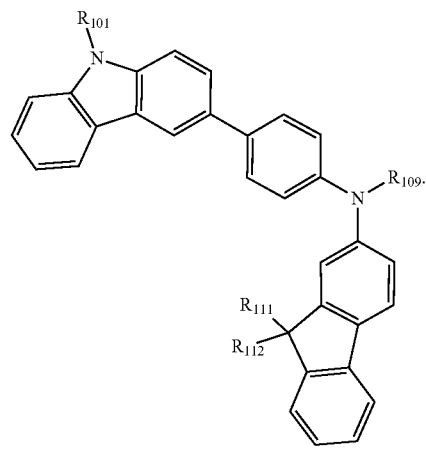

Detailed descriptions of $R_{101}$, $R_{111}$, $R_{112}$, and $R_{109}$ in Formula 201A are the same as described above.

For example, the compound represented by Formula 201, and the compound represented by Formula 202 may include Compounds HT1 to HT20 but are not limited thereto:

HT1
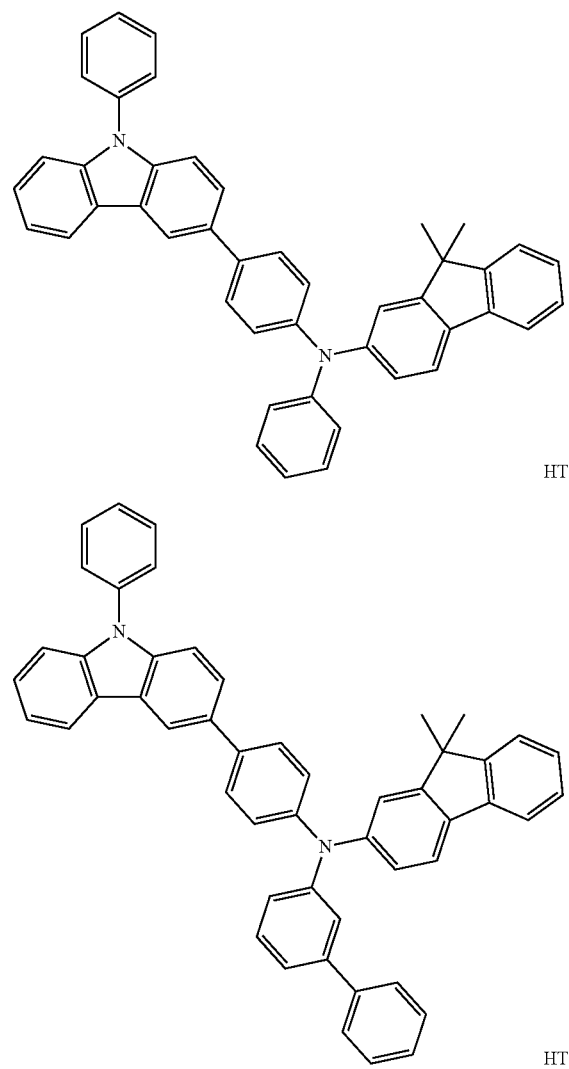
HT2
HT3
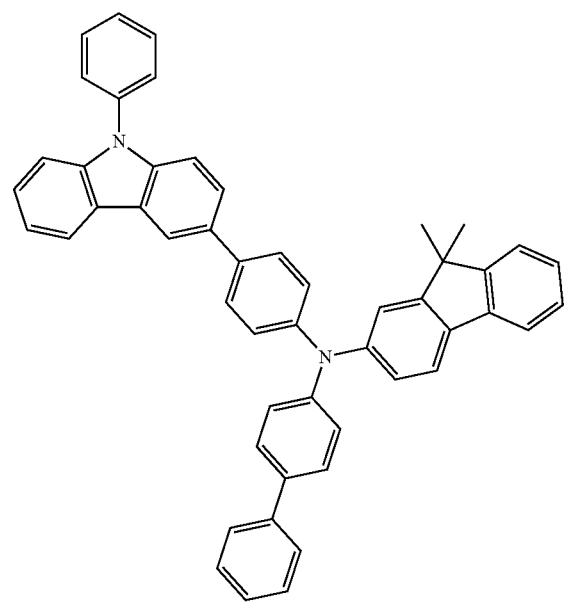
HT4
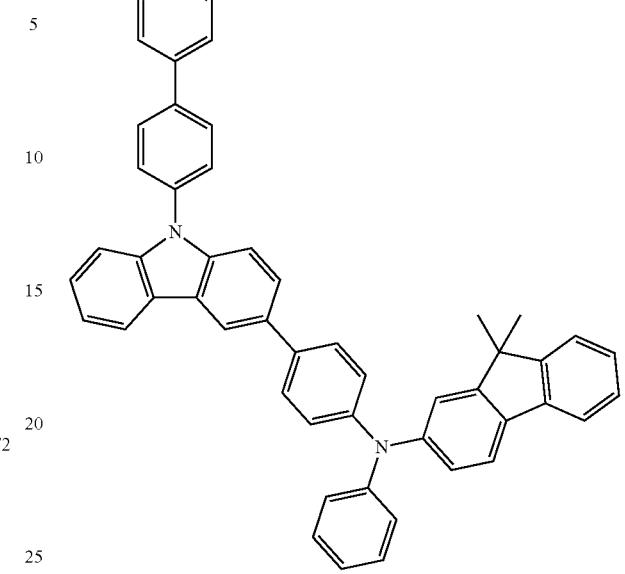
HT5
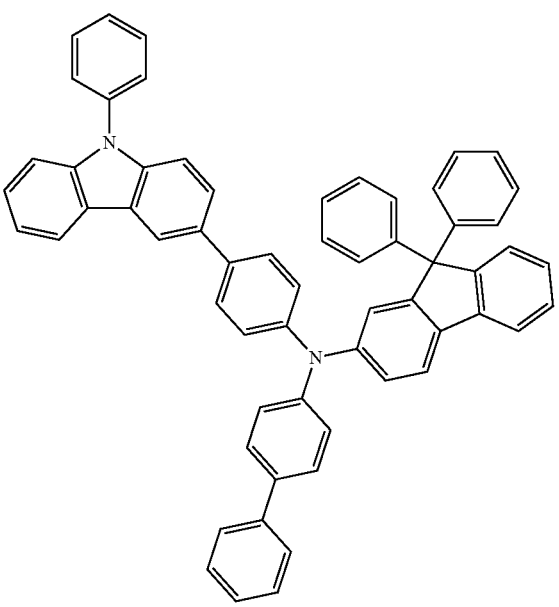

-continued
HT6
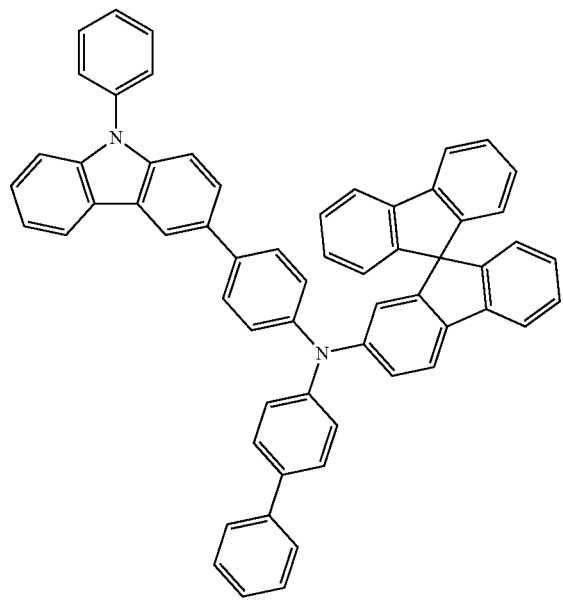
HT7
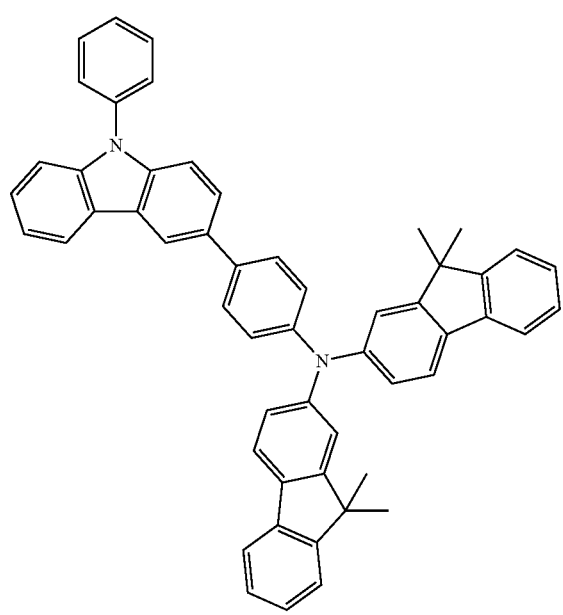
HT8
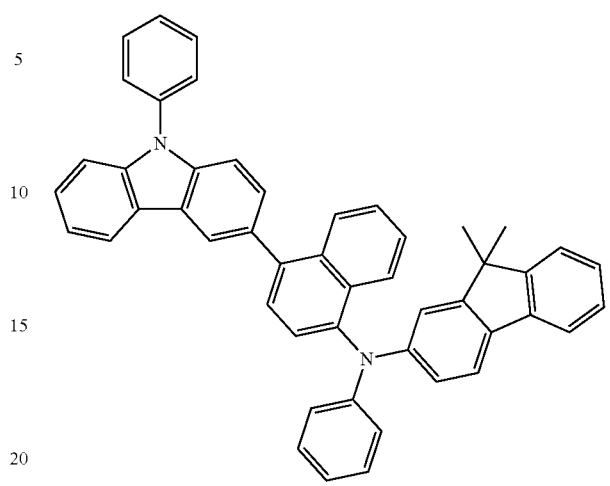
HT9
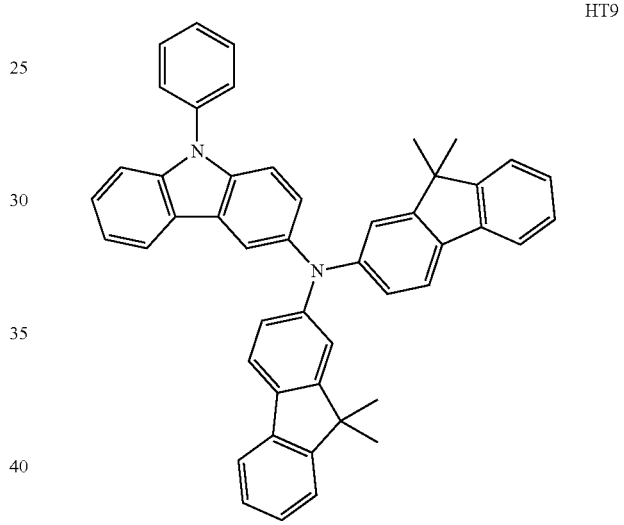
HT10
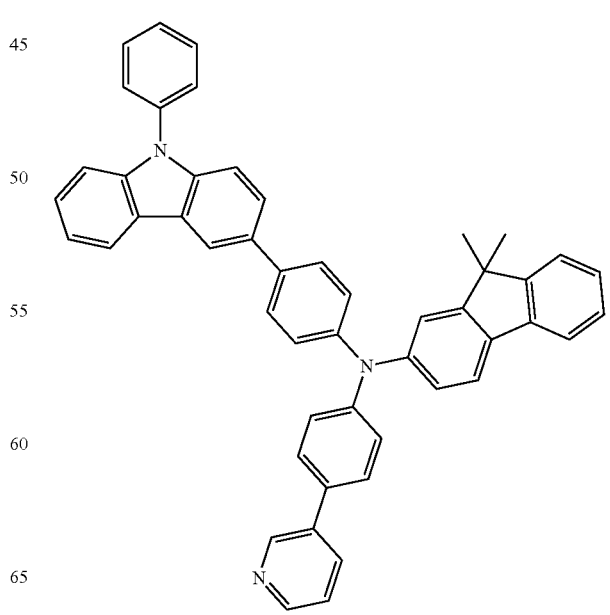

HT11
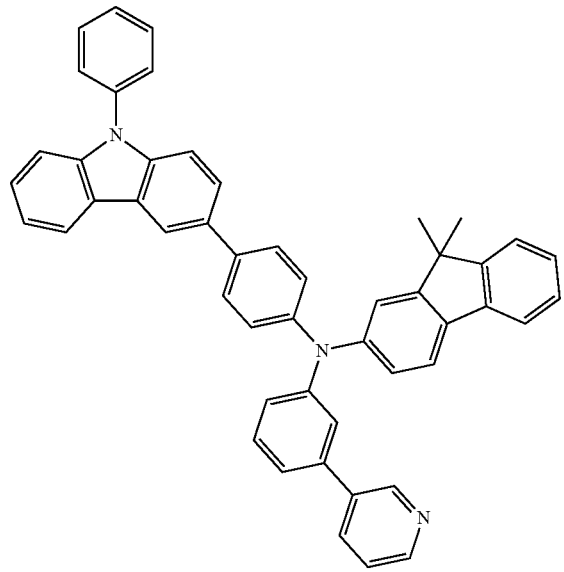
HT14
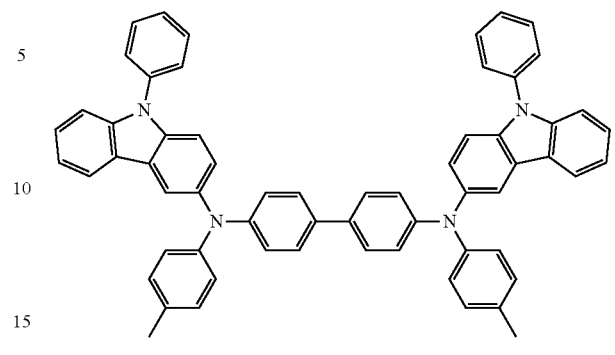
HT15
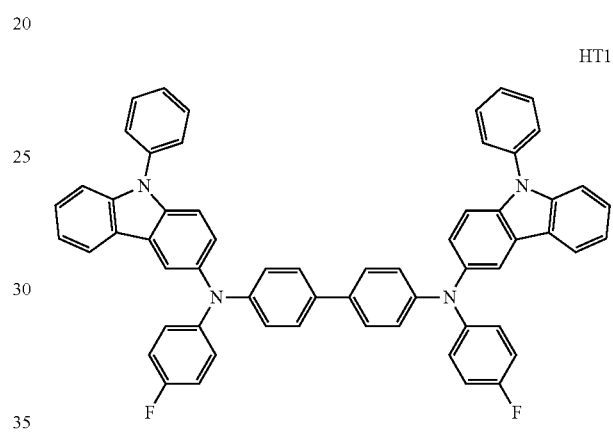
HT12
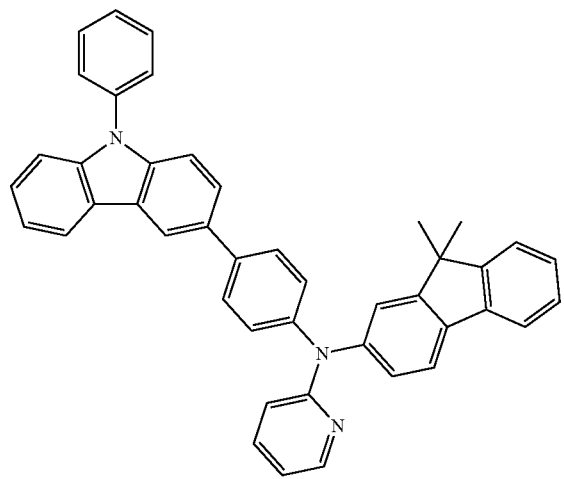
HT16
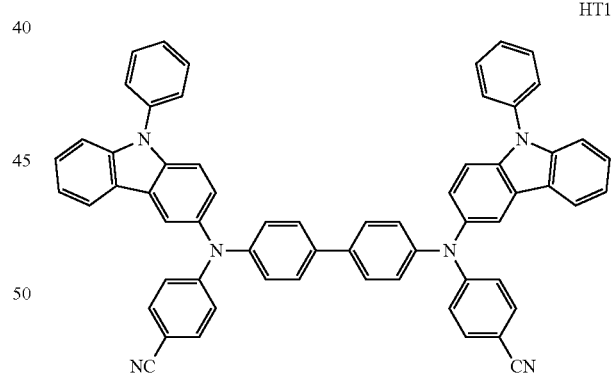
HT13
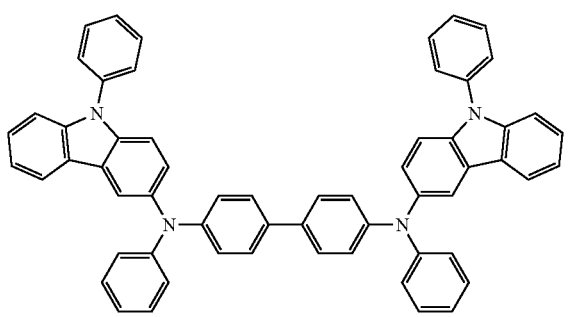
HT17
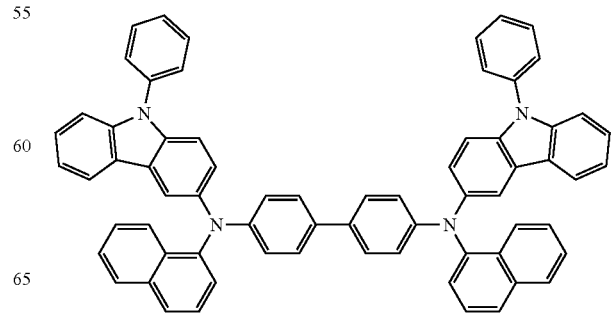

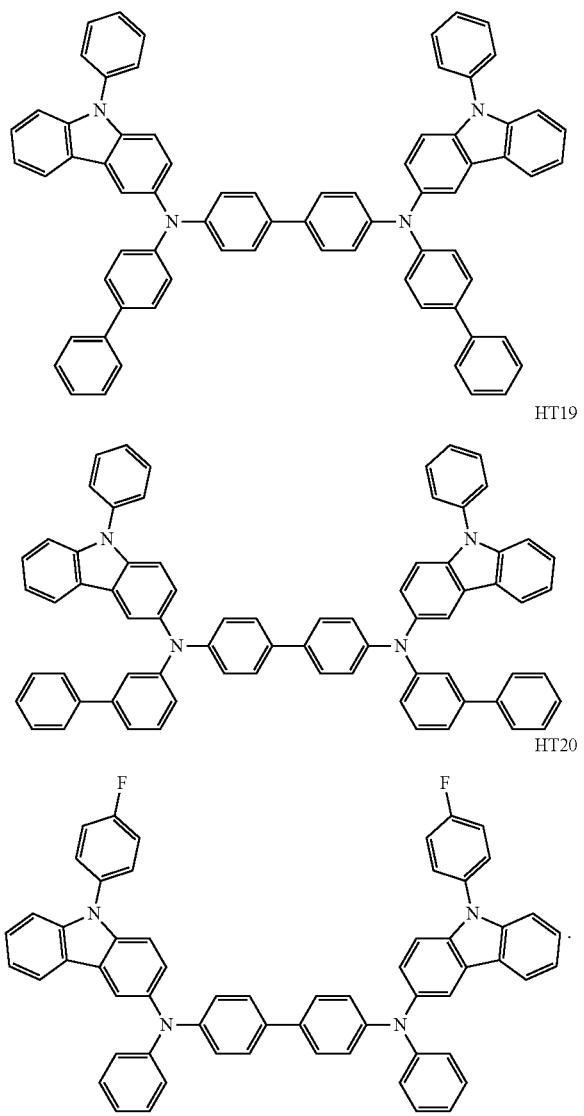

HT18

HT19

HT20

A thickness of the hole transport region may be from about 100 Å to about 10,000 Å, for example, about 100 Å to about 1,000 Å. When the hole transport region includes a hole injection layer, a hole transport layer, or any combination thereof, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, a cyano group-containing compound, or any combination thereof, but embodiments of the present disclosure are not limited thereto. Non-limiting examples of the p-dopant are a quinone derivative, such as tetracyanoquinodimethane (TCNQ) or 2,3,5,6-tetrafluoro-tetracyano-1,4-benzoquinodimethane (F4-TCNQ); a metal oxide, such as a tungsten oxide or a molybdenum oxide; and a cyano group-containing compound, such as Compound HT-D1 below, but are not limited thereto:

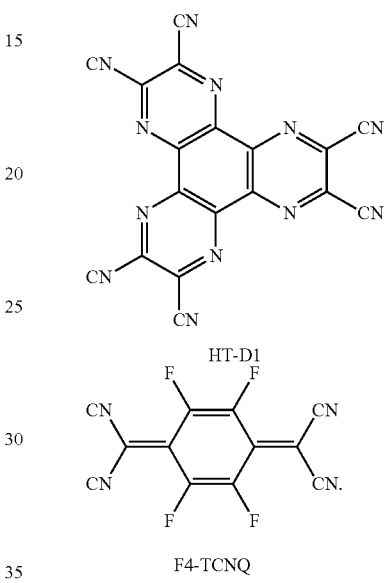

HT-D1

F4-TCNQ

The hole transport region may include a buffer layer.

Also, the buffer layer may compensate for an optical resonance distance according to a wavelength of light emitted from the emission layer, and thus, efficiency of a formed organic light-emitting device may be improved.

Meanwhile, when the hole transport region includes an electron blocking layer, a material for the electron blocking layer may be materials for the hole transport region described above, materials for a host to be explained later, or any combination thereof. However, the material for the electron blocking layer is not limited thereto. For example, when the hole transport region includes an electron blocking layer, a material for the electron blocking layer may be mCP, which will be explained later.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

The emission layer may include a host and a dopant, and the dopant may include the organometallic compound represented by Formula 1.

The host may include TPBi, TBADN, ADN (also referred to as "DNA"), CBP, CDBP, TCP, mCP, one of Compounds H50 to H52, or any combination thereof:

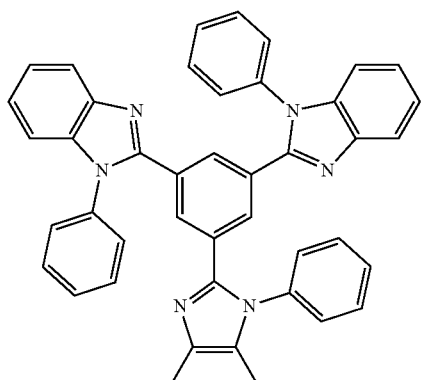
TPBi

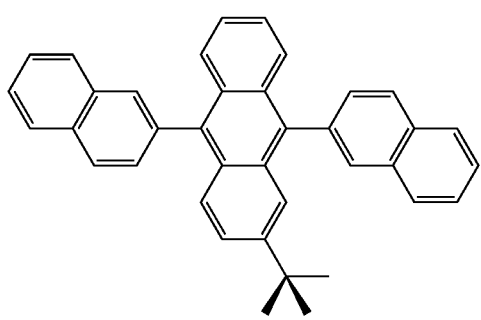
TBADN

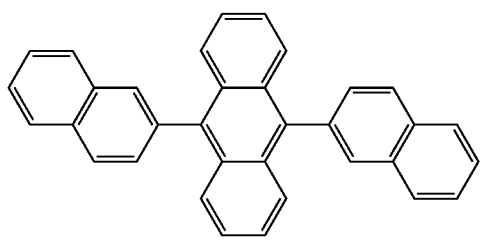
ADN

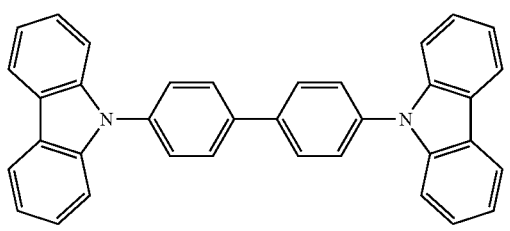
CBP

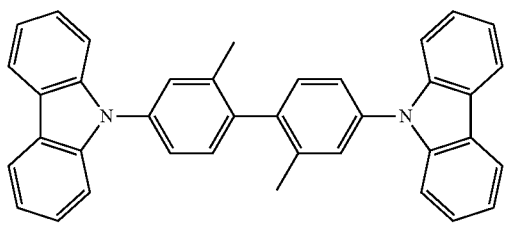
CDBP

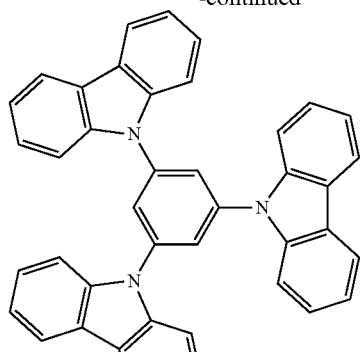
TCP

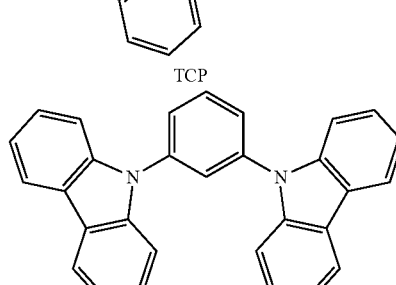
mCP

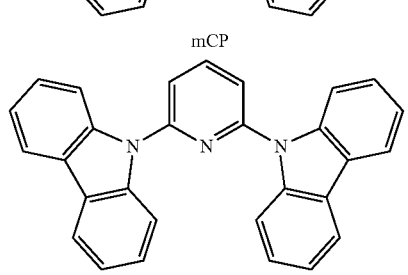
H50

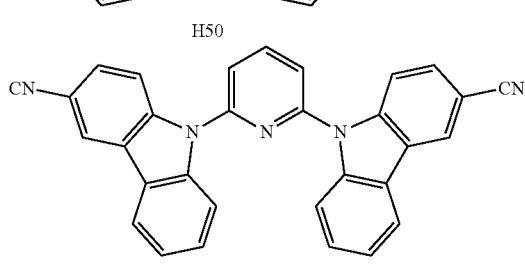
H51

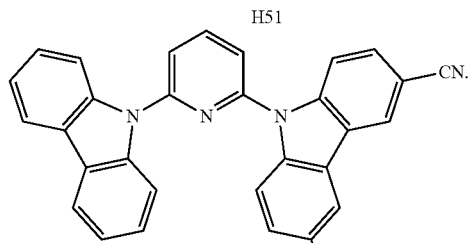
H52

When the organic light-emitting device is a full-color organic light-emitting device, the emission layer may be patterned into a red emission layer, a green emission layer, and/or a blue emission layer. In an embodiment, due to a stacked structure including a red emission layer, a green emission layer, and/or a blue emission layer, the emission layer may emit white light.

When the emission layer includes a host and a dopant, an amount of the dopant may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure, or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, BCP, Bphen, BAlq, or any combination thereof, but embodiments of the present disclosure are not limited thereto:

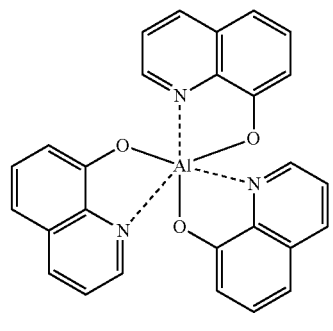

Alq$_3$

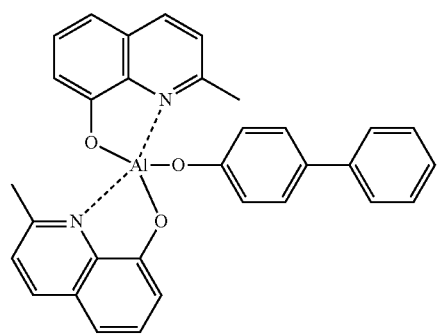

BAlq

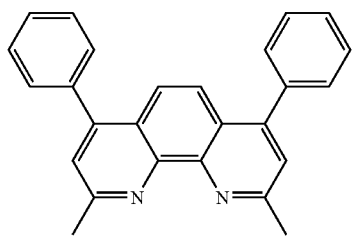

BCP

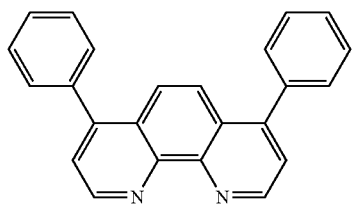

Bphen

A thickness of the hole blocking layer may be from about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may include BCP, Bphen, Alq$_3$, BAlq, TAZ, NTAZ, or any combination thereof:

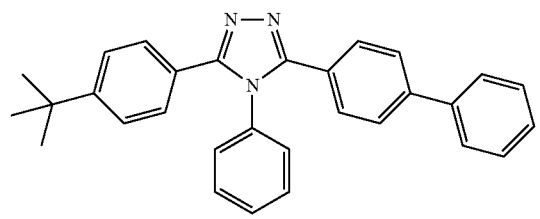

TAZ

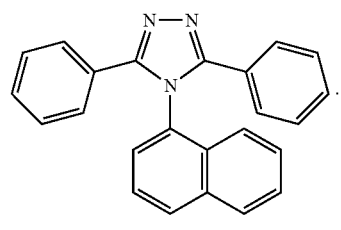

NTAZ

In an embodiment, the electron transport layer may include one of ET1 to ET25, but embodiments of the present disclosure are not limited thereto:

ET1
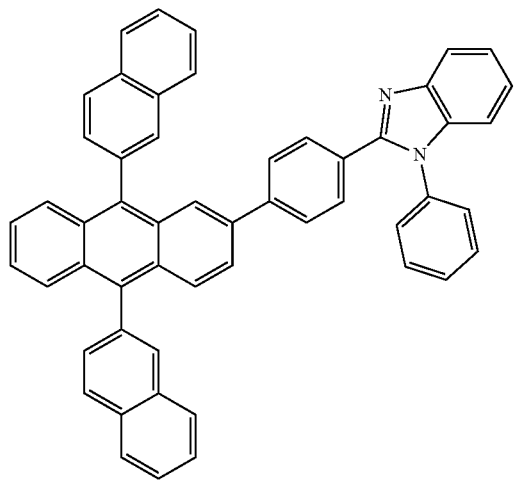
ET2
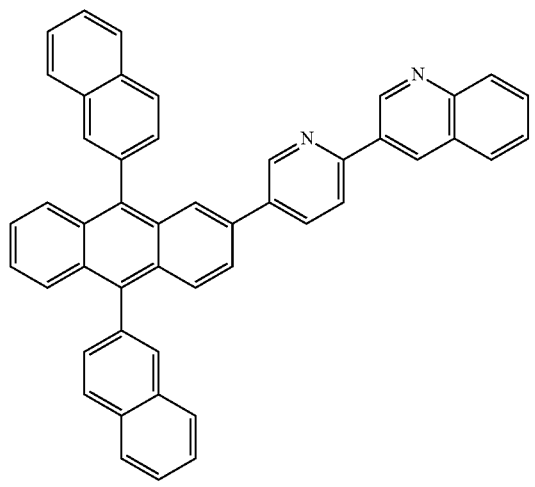
ET3
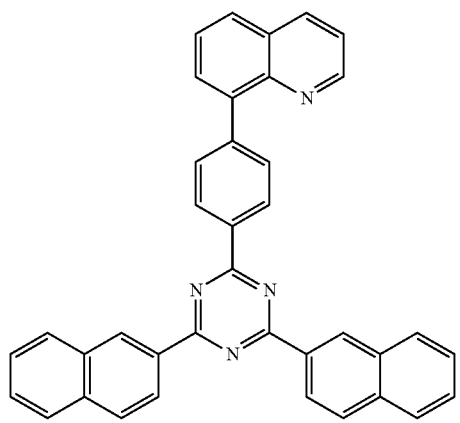
ET4
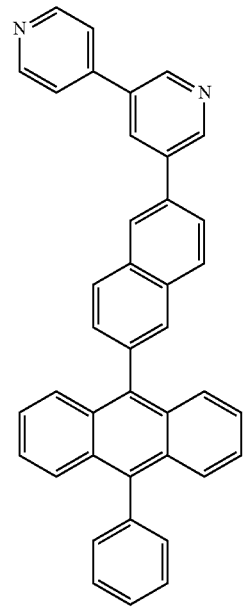
ET5
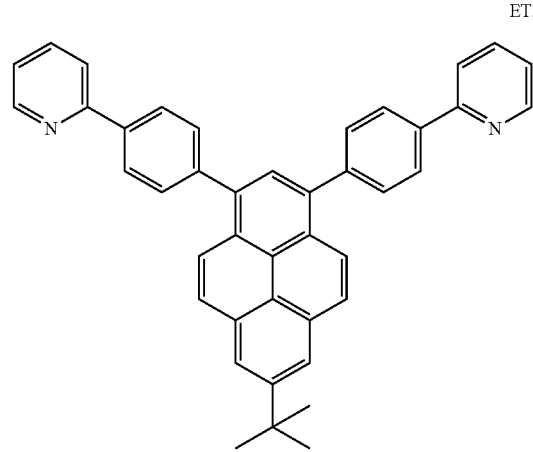
ET6
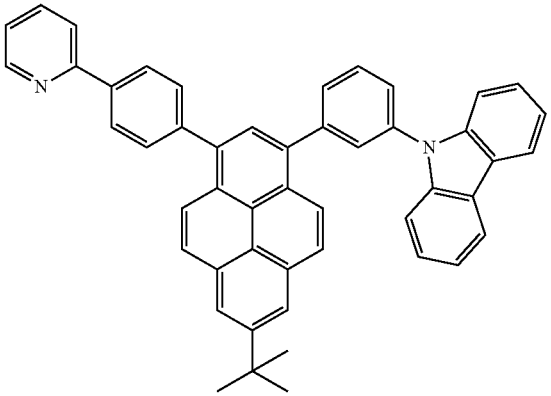

ET7
ET8
ET9
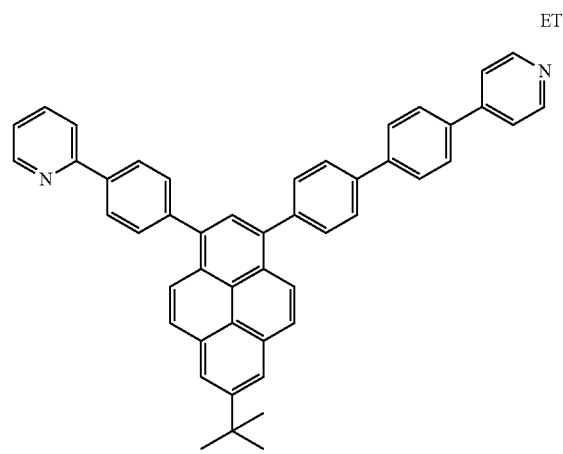
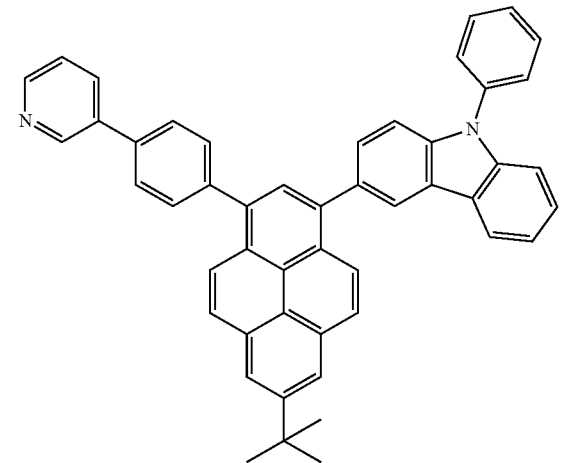
ET10
ET11
ET12
ET13
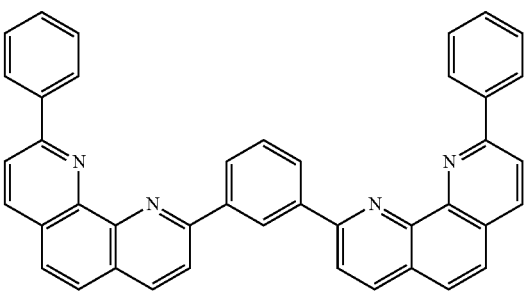
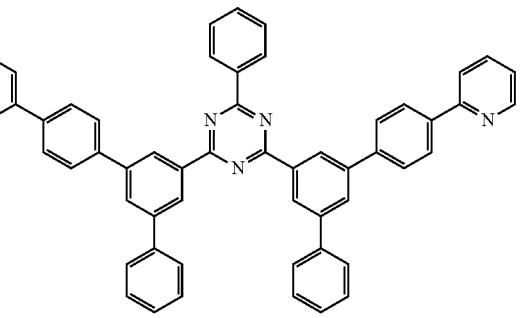
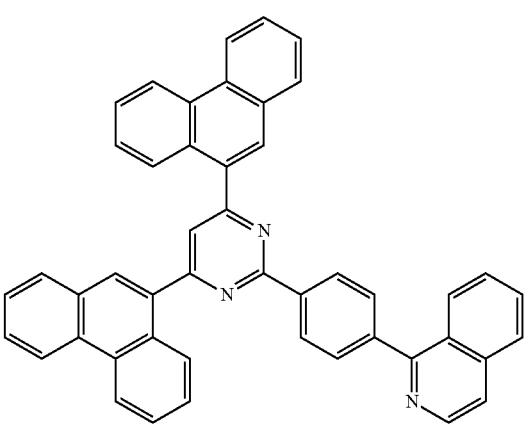

ET14
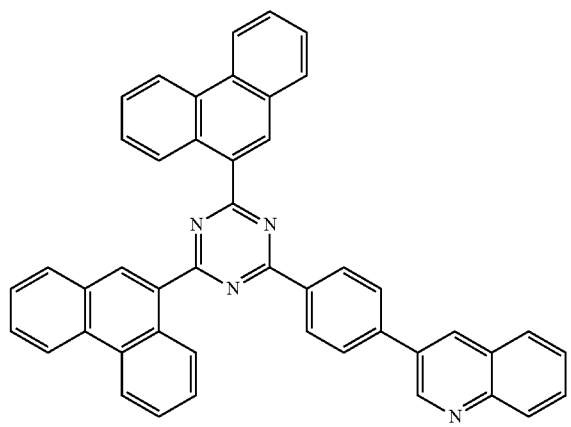
ET17
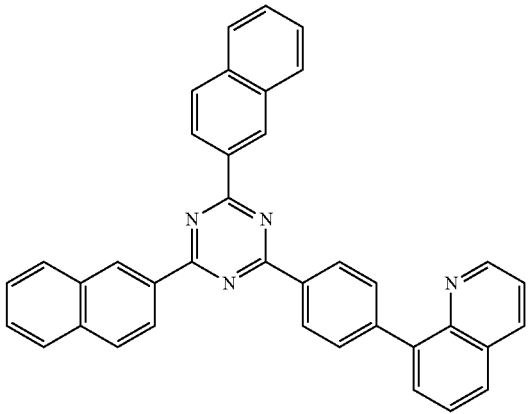
ET15
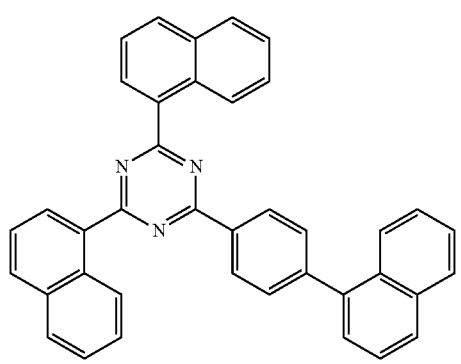
ET18
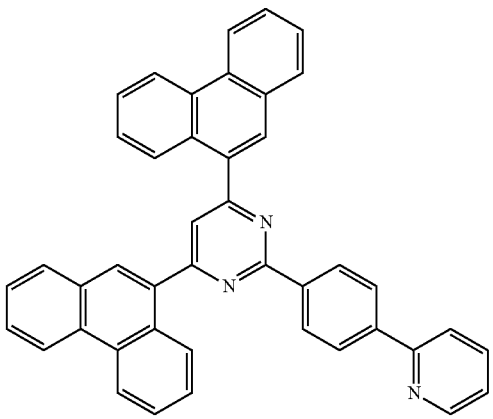
ET16
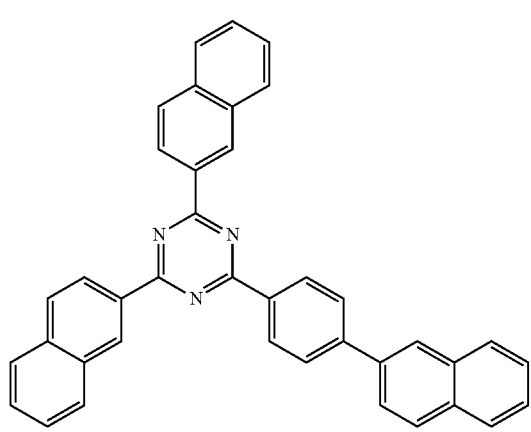
ET19
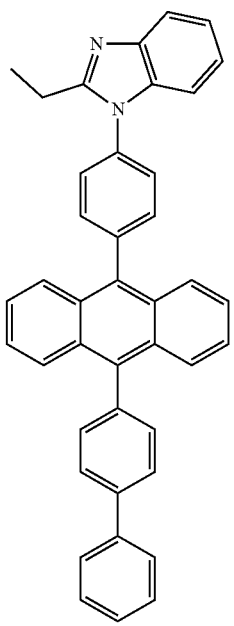

ET20
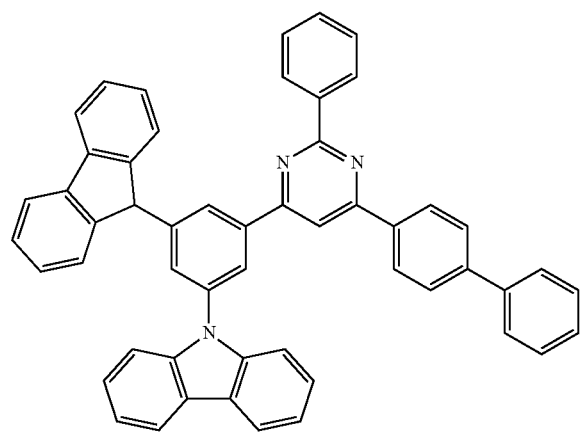
ET21
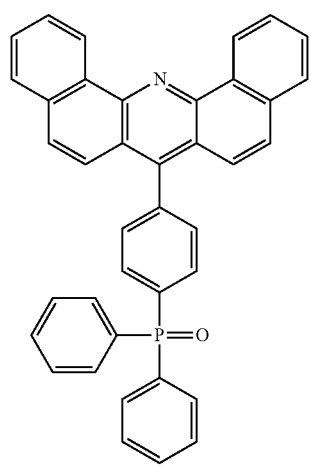
ET22
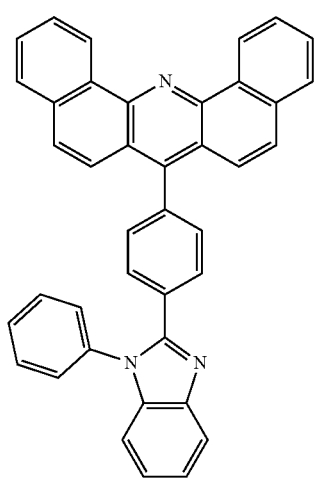
ET23
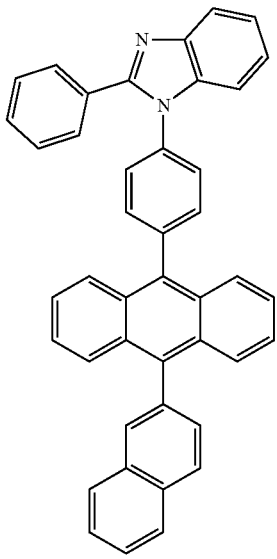
ET24
ET25
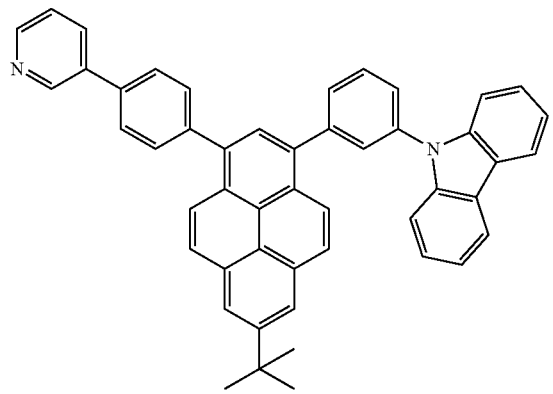
A thickness of the electron transport layer may be from about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (LiQ), ET-D2, or any combination thereof:

ET-D1

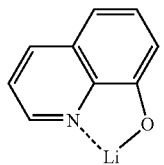

ET-D2

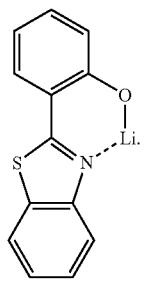

The electron transport region may include an electron injection layer that promotes flow of electrons from the second electrode 19 thereinto.

The electron injection layer may include LiF, NaCl, CsF, $Li_2O$, BaO, or any combination thereof.

A thickness of the electron injection layer may be from about 1 Å to about 100 Å, for example, about 3 Å to about 90 Å. When a thickness of the electron injection layer is within these ranges, satisfactory electron injection characteristics may be obtained without substantial increase in driving voltage.

The second electrode 19 is disposed on the organic layer 15. The second electrode 19 may be a cathode. A material for forming the second electrode 19 may be a metal, an alloy, an electrically conductive compound, or any combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode 19. To manufacture a top-emission type light-emitting device, a transmissive electrode formed using ITO or IZO may be used as the second electrode 19.

Hereinbefore, the organic light-emitting device according to an embodiment has been described in connection with the FIGURE.

Another aspect of the present disclosure provides a diagnostic composition including at least one organometallic compound represented by Formula 1.

The organometallic compound represented by Formula 1 provides high luminescence efficiency. Accordingly, a diagnostic composition including the organometallic compound may have high diagnostic efficiency.

The diagnostic composition may be used in various applications including a diagnosis kit, a diagnosis reagent, a biosensor, and a biomarker.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group having N, O, P, Si, Se, S, or a combination thereof and 2 to 10 carbon atoms as ring-forming atoms, and non-limiting examples thereof include a tetrahydrofuranyl group and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has N, O, P, Si, Se, S, or any combination thereof and 2 to 10 carbon atoms as ring-forming atoms, and at least one double bond in its ring. Examples of the $C_2$-$C_{10}$ heterocycloalkenyl group are a 2,3-dihydrofuranyl group, and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_7$-$C_{60}$ arylalkyl group" as used herein refers to an alkylene group substituted with an aryl group. A non-limiting example of a $C_7$-$C_{60}$ arylalkyl group includes a —$CH_2$-phenyl (i.e., benzyl) group and a $CH_2$-naphthyl group.

The term "phenyl($C_1$-$C_{20}$ alkyl) group" as used herein refers to an alkylene group substituted with a phenyl group. Non-limiting examples of a phenyl($C_1$-$C_{20}$ alkyl) group include a —$CH_2$-phenyl (i.e., benzyl) group and a $(CH_2)_3$-phenyl group.

The term "$C_1$-$C_{60}$ heteroaryl group" as used herein refers to a monovalent group having a heterocyclic aromatic system that has N, O, P, Si, Se, S, or any combination thereof and 1 to 60 carbon atoms as ring-forming atoms. The term "$C_1$-$C_{60}$ heteroarylene group" as used herein refers to a divalent group having a heterocyclic aromatic system that has N, O, P, Si, Se, S, or any combination thereof and 1 to 60 carbon atoms as ring-forming atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_2$-$C_{60}$ heteroarylalkyl group" as used herein refers to an alkylene group substituted with a heteroaryl group. A non-limiting example of a $C_2$-$C_{60}$ heteroarylalkyl group includes a —$CH_2$-pyridyl group.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The $C_5$-$C_{30}$ carbocyclic group may be a monocyclic group or a polycyclic group.

The term "$C_2$-$C_{30}$ heterocyclic group" as used herein refers to a saturated or unsaturated cyclic group having N, O, Si, P, Se, S, or any combination thereof and 1 to 30 carbon atoms as ring-forming atoms. The $C_2$-$C_{30}$ heterocyclic group may be a monocyclic group or a polycyclic group.

A substituent of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group (e.g., the substituted phenyl($C_1$-$C_{20}$ alkyl) group), the substituted $C_1$-$C_{60}$ heteroaryl group, the substituted $C_2$-$C_{60}$ heteroarylalkyl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_1$-$C_{60}$ heteroaryl group, $C_2$-$C_{60}$ heteroarylalkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_7$-$C_{60}$ arylalkyl group (e.g., a phenyl($C_1$-$C_{20}$ alkyl) group), a $C_6$-$C_{60}$ aryloxy group, a $C_6$-$C_{60}$ arylthio group, a $C_1$-$C_{60}$ heteroaryl group, a $C_2$-$C_{60}$ heteroarylalkyl group, a monovalent non-aromatic condensed polycyclic group, or a monovalent non-aromatic condensed heteropolycyclic group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_{60}$ heteroaryl group, $C_2$-$C_{60}$ heteroarylalkyl group, a monovalent non-aromatic condensed polycyclic group, or a monovalent non-aromatic condensed heteropolycyclic group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_7$-$C_{60}$ arylalkyl group (e.g., a phenyl($C_1$-$C_{20}$ alkyl) group), a $C_6$-$C_{60}$ aryloxy group, a $C_6$-$C_{60}$ arylthio group, a $C_1$-$C_{60}$ heteroaryl group, $C_2$-$C_{60}$ heteroarylalkyl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{28})(Q_{29})$, or any combination thereof;

—$N(Q_{31})(Q_{32})$, —$Si(Q_{33})(Q_{34})(Q_{35})$, —$B(Q_{36})(Q_{37})$, or —$P(=O)(Q_{38})(Q_{39})$; or any combination thereof.

In the present specification, $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group, or any combination thereof, a $C_6$-$C_{60}$ aryloxy group, a $C_6$-$C_{60}$ arylthio group, a $C_7$-$C_{60}$ arylalkyl group (e.g., a phenyl($C_1$-$C_{20}$ alkyl) group), a $C_1$-$C_{60}$ heteroaryl group, $C_2$-$C_{60}$ heteroarylalkyl group, a monovalent non-aromatic condensed polycyclic group, a monovalent non-aromatic condensed heteropolycyclic group, or any combination thereof.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1 (Compound 1)

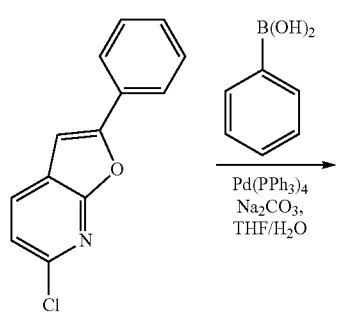

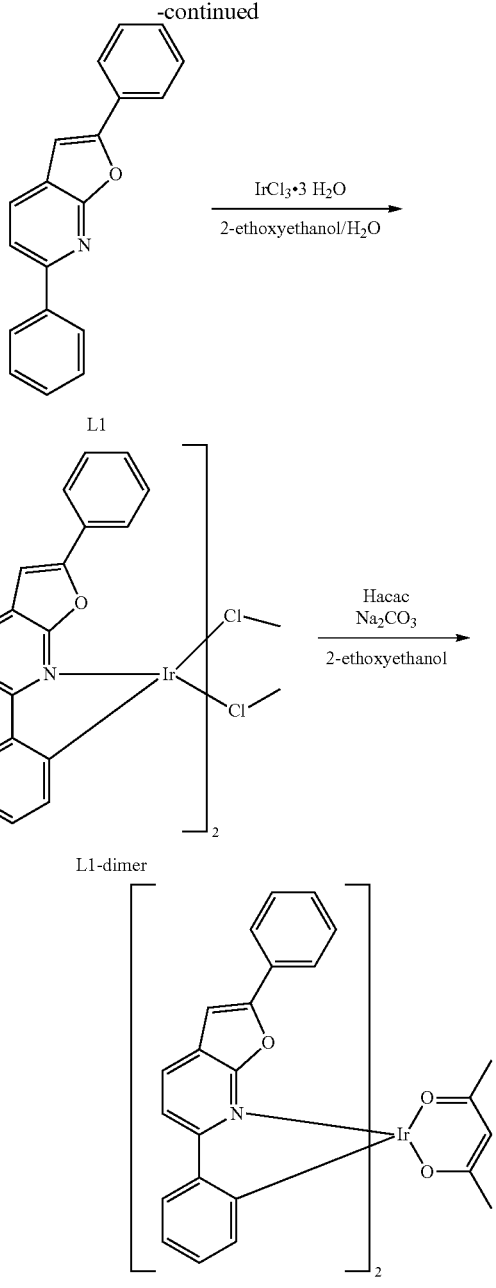

Synthesis of Intermediate L1

6-Chloro-2-phenylfuro[2,3-b]pyridine (2.55 g, 11.1 mmol), phenylboronic acid (2.603 g, 16.64 mmol), Pd(PPh$_3$)$_4$ (1.03 g, 0.89 mmol), and K$_2$CO$_3$ (3.83 g, 27.7 mmol) were mixed with 60 mL of tetrahydrofuran and 30 mL of distilled water, stirred at a temperature of 90° C. for 18 hours, and then cooled to room temperature. An organic layer was extracted from a result obtained therefrom by using ethyl acetate, dried by using anhydrous magnesium sulfate (MgSO$_4$), and filtered to obtain a filtrate. The filtrate was concentrated to obtain a residue. The residue was purified by column chromatography using ethyl acetate: hexane=1:2 (v/v) as an eluent to obtain Intermediate L1 (2.85 g, 83%).

LC-MS m/z=272 (M+H)$^+$.

Synthesis of Intermediate L1-Dimer

Intermediate L1 (1.99 g, 7.32 mmol) and iridium chloride hydrate (1.15 g, 3.25 mmol) were mixed with 21 mL of 2-ethoxyethanol and 7 mL of distilled water, stirred at a temperature of 120° C. for 24 hours under reflux, and then cooled to room temperature. A solid obtained therefrom was filtered, separated, and sufficiently washed in the order of water/methanol/hexane. The solid was dried in a vacuum oven to obtain Intermediate L1-dimer (1.95 g, 78%). The obtained compound was used in the next reaction without additional purification.

Synthesis of Compound 1

Thirty mL of 2-ethoxyethanol was added to Intermediate L1-dimer (1.94 g, 1.26 mmol), acetyl acetone (1.26 g, 12.6 mmol), and $Na_2CO_3$ (1.33 g, 12.6 mmol), and stirred at room temperature for 12 hours. An organic layer was extracted from a result obtained therefrom by using ethyl acetate, dried by using anhydrous magnesium sulfate ($MgSO_4$), and filtered to obtain a filtrate. The filtrate was concentrated to obtain a residue. The residue was purified by column chromatography using dichloromethane:hexane=1:4 (v/v) as an eluent to obtain Compound 1 (0.451 g, 22%). The obtained compound was identified by Mass spectroscopy (MS) and HPLC analysis.

HRMS(MALDI-TOF) calcd for $C_{43}H_{31}IrN_2O_4$: m/z 832.1913, Found: 832.1913.

Synthesis Example 2 (Compound 16)

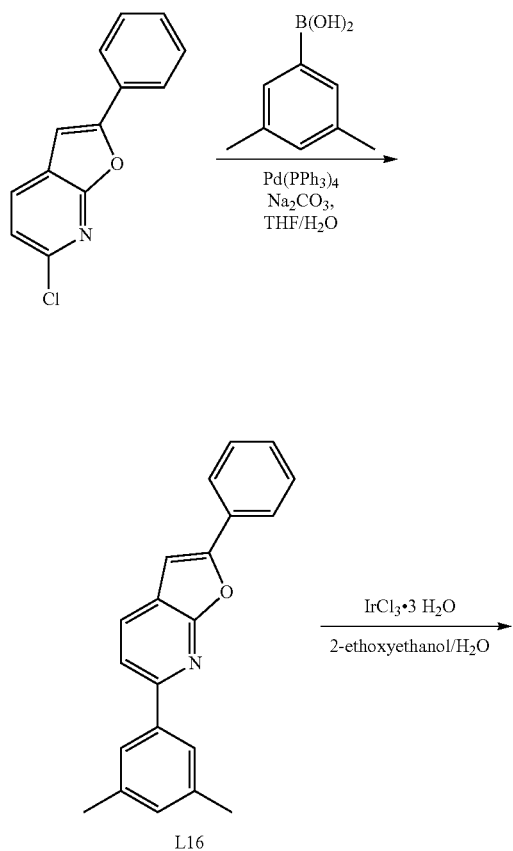

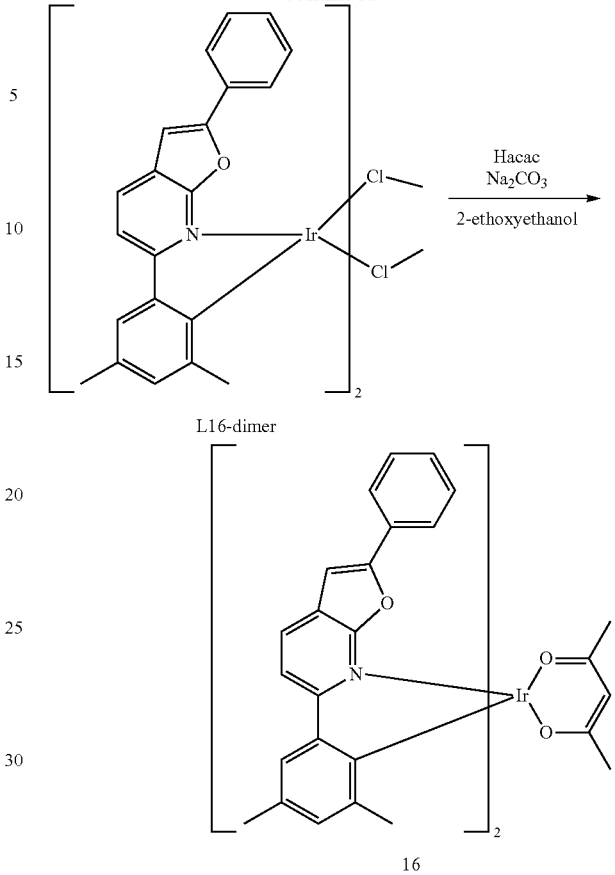

Synthesis of Intermediate L16

6-Chloro-2-phenylfuro[2,3-b]pyridine (2.69 g, 11.71 mmol), (3,5-dimethylphenyl)boronic acid (2.64 g, 17.56 mmol), $Pd(PPh_3)_4$ (1.08 g, 0.94 mmol), and $K_2CO_3$ (4.05 g, 29.3 mmol) were mixed with 60 mL of tetrahydrofuran and 30 mL of distilled water, stirred at a temperature of 90° C. for 18 hours, and then cooled to room temperature. An organic layer was extracted from a result obtained therefrom by using ethyl acetate, dried by using anhydrous magnesium sulfate ($MgSO_4$), and filtered to obtain a filtrate. The filtrate was concentrated to obtain a residue. The residue was purified by column chromatography using ethyl acetate:hexane=1:2 (v/v) as an eluent to obtain Intermediate L16 (1.97 g, 56%).

LC-MS m/z=300 $(M+H)^+$.

Synthesis of Intermediate L16-dimer

Intermediate L16 (1.97 g, 6.82 mmol) and iridium chloride hydrate (1.07 g, 3.03 mmol) were mixed with 21 mL of ethoxyethanol and 7 mL of distilled water, stirred at a temperature of 120° C. for 24 hours under reflux, and then cooled to room temperature. A solid obtained therefrom was filtered, separated, and sufficiently washed in the order of water/methanol/hexane. The solid was dried in a vacuum oven to obtain Intermediate L16-dimer (2.16 g, 86%). The obtained compound was used in a next reaction without additional purification.

Synthesis of Compound 16

Thirty mL of 2-ethoxyethanol was added to Intermediate L16-dimer (2.15 g, 1.31 mmol), acetyl acetone (1.31 g, 13.1 mmol), and $Na_2CO_3$ (1.38 g, 13.1 mmol), and stirred at room temperature for 12 hours. An organic layer was extracted from a result obtained therefrom by using ethyl acetate, dried by using anhydrous magnesium sulfate (MgSO$_4$), and filtered to obtain a filtrate. The filtrate was concentrated to obtain a residue. The residue was purified by column chromatography using dichloromethane:hexane=1:4 (v/v) as an eluent to obtain Compound 16 (0.47 g, 20%). The obtained compound was identified by MS and HPLC analysis.

HRMS(MALDI-TOF) calcd for C$_{47}$H$_{39}$IrN$_2$O$_4$: m/z 888.2539, Found: 888.2538.

Synthesis Example 3 (Compound 101)

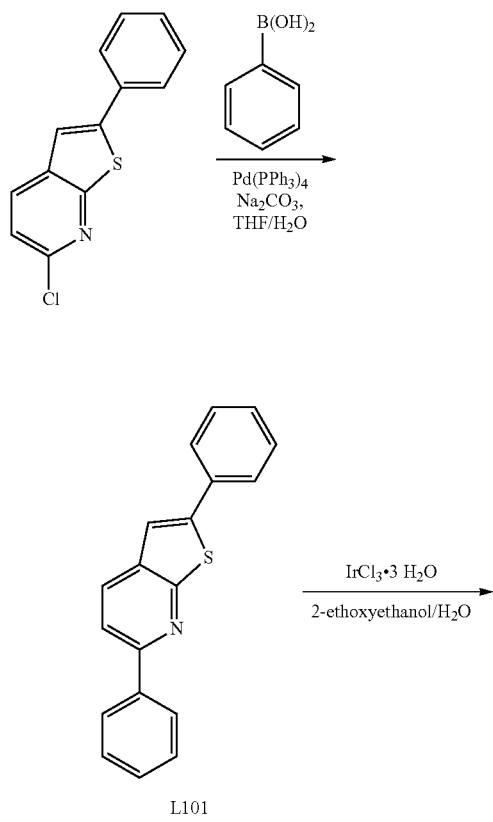

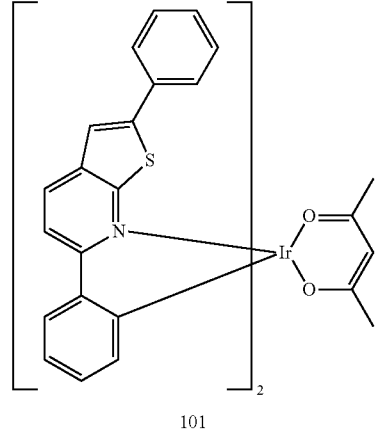

101

Synthesis of Intermediate L101

Intermediate L101 (2.08 g, 59%) was obtained in the same manner as in Synthesis of Intermediate L1 of Synthesis Example 1, except that 6-chloro-2-phenylthieno[2,3-b]pyridine (2.99 g, 12.2 mmol) was used instead of 6-chloro-2-phenylfuro[2,3-b]pyridine (2.55 g, 11.1 mmol).

LC-MS m/z=288 (M+H)$^+$.

Synthesis of Intermediate L101-dimer

Intermediate L101-dimer (2.16 g, 86%) was obtained in the same manner as in Synthesis of Intermediate L1-dimer of Synthesis Example 1, except that Intermediate L101 (1.97 g, 7.03 mmol) was used instead of Intermediate L1.

Synthesis of Compound 101

Compound 101 (0.47 g, 22%) was obtained in the same manner as in Synthesis of Compound 1 of Synthesis Example 1, except that Intermediate L101-dimer (1.95 g, 1.22 mmol) was used instead of Intermediate L1-dimer. The obtained compound was identified by MS and HPLC analysis.

HRMS(MALDI-TOF) calcd for C$_{43}$H$_{30}$IrN$_2$O$_2$S$_2$: m/z 863.1378, Found: 863.1377.

Synthesis Example 4 (Compound 116)

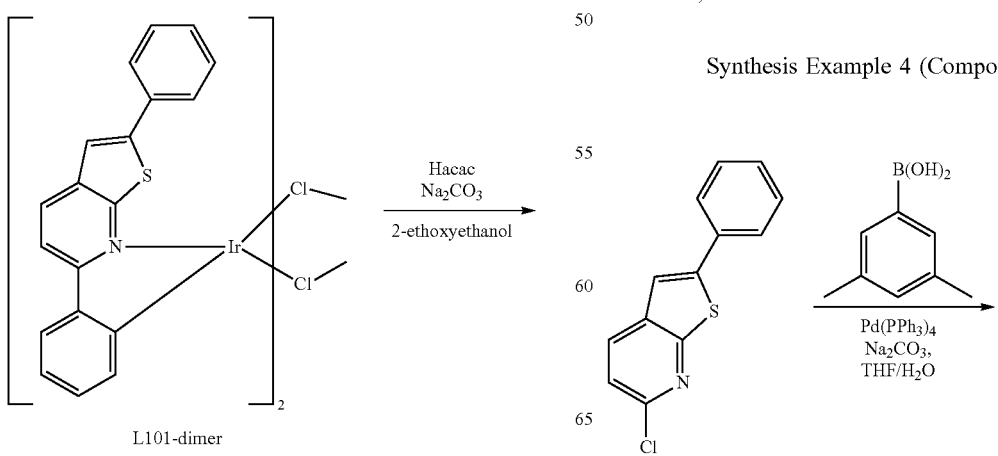

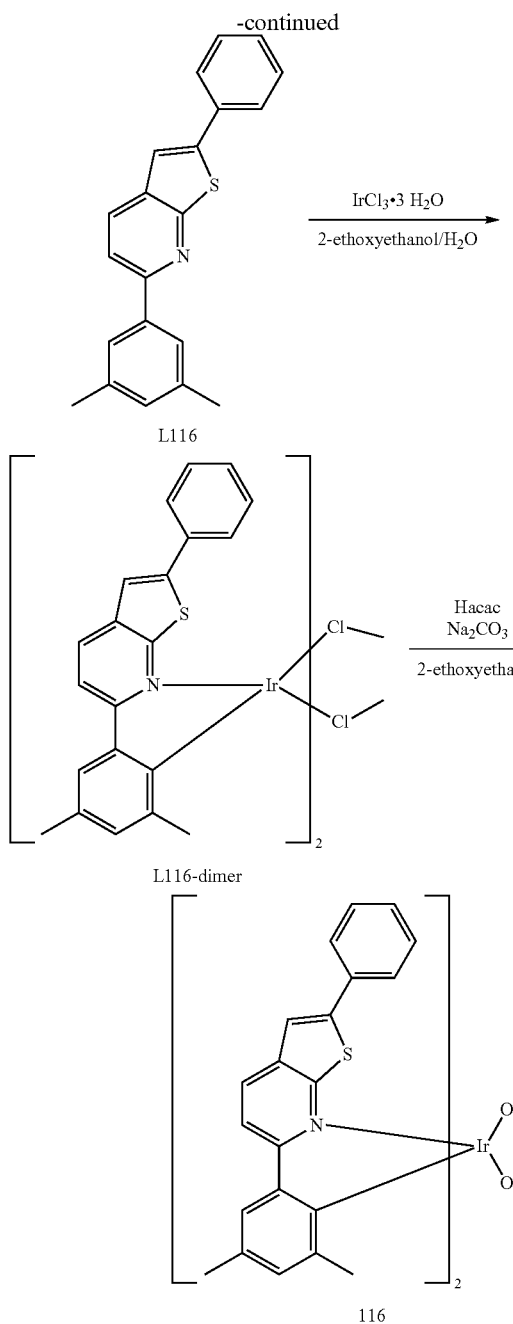

L116

L116-dimer

116

Synthesis of Intermediate L116

Intermediate L116 (3.00 g, 86%) was obtained in the same manner as in Synthesis of Intermediate L16 of Synthesis Example 2, except that 6-chloro-2-phenylthieno[2,3-b]pyridine (2.73 g, 11.1 mmol) was used instead of 6-chloro-2-phenylfuro[2,3-b]pyridine (2.69 g, 11.71 mmol).

LC-MS m/z=316 (M+H)$^+$.

Synthesis of Intermediate L116-dimer

Intermediate L116-dimer (2.16 g, 72%) was obtained in the same manner as in Synthesis of Intermediate L16-dimer of Synthesis Example 2, except that Intermediate L116 (2.48 g, 7.88 mmol) was used instead of Intermediate L16.

Synthesis of Compound 116

Compound 116 (0.47 g, 21%) was obtained in the same manner as in Synthesis of Compound 16 of Synthesis Example 2, except that Intermediate L116-dimer (2.04 g, 1.19 mmol) was used instead of Intermediate L16-dimer. The obtained compound was identified by MS and HPLC analysis.

HRMS(MALDI-TOF) calcd for $C_{47}H_{39}IrN_2O_2 S_2$: m/z 920.2082, Found: 920.2080.

Synthesis Example 5 (Compound 146)

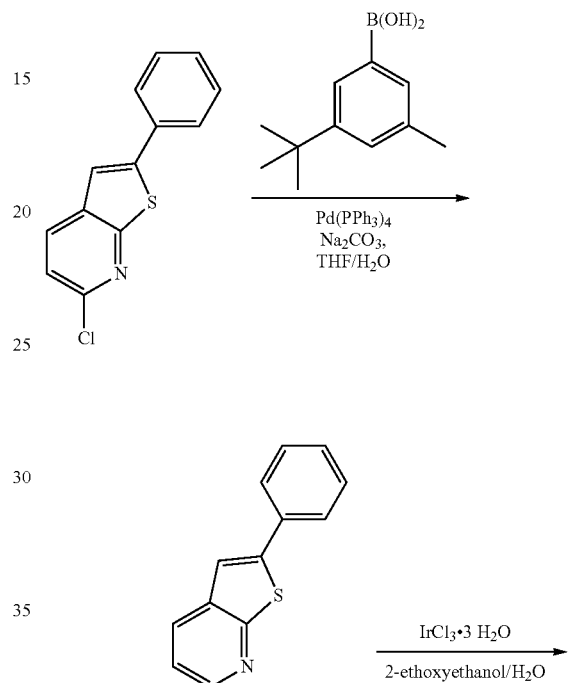

L146

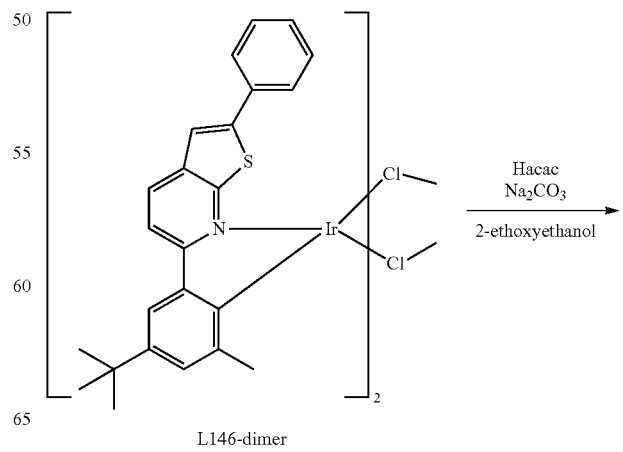

L146-dimer

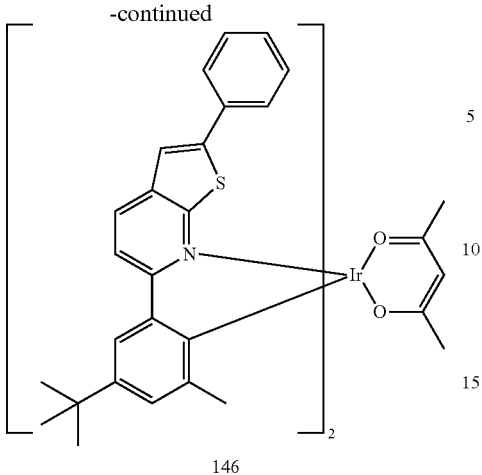

146

Synthesis of Intermediate L146

Intermediate L146 (3.30 g, 83%) was obtained in the same manner as in Synthesis of Intermediate L116 of Synthesis Example 4, except that (3-(tert-butyl)-5-methylphenyl)boronic acid (3.23 g, 16.8 mmol) was used instead of (3,5-dimethylphenyl)boronic acid (2.64 g, 17.56 mmol).

LC-MS m/z=358 (M+H)$^+$.

Synthesis of Intermediate L146-dimer

Intermediate L146-dimer (2.60 g, 74%) was obtained in the same manner as in Synthesis of Intermediate L116-dimer of Synthesis Example 4, except that Intermediate L146 (2.99 g, 8.37 mmol) was used instead of Intermediate L116.

Synthesis of Compound 146

Compound 146 (0.48 g, 20%) was obtained in the same manner as in Synthesis of Compound 116 of Synthesis Example 4, except that Intermediate L146-dimer (2.04 g, 1.19 mmol) was used instead of Intermediate L116-dimer. The obtained compound was identified by MS and HPLC analysis.

HRMS(MALDI-TOF) calcd for $C_{47}H_{38}IrN_2O_2 S_2$: m/z 919.2004, Found: 919.2003.

Synthesis Example 6 (Compound 216)

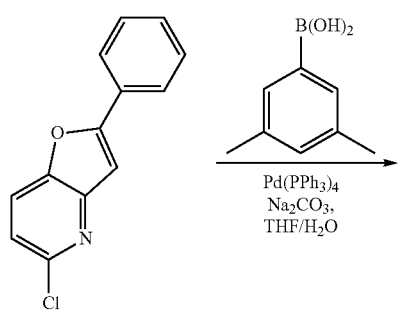

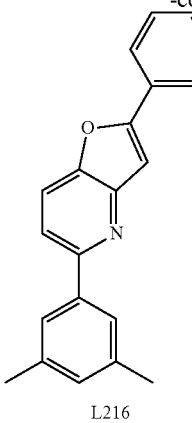

L216

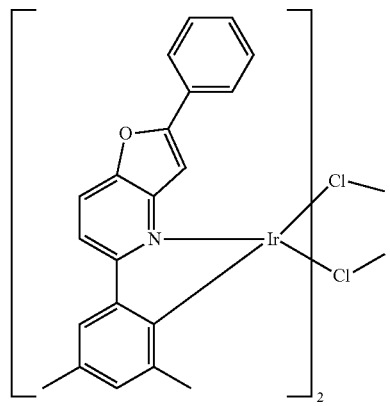

L216-dimer

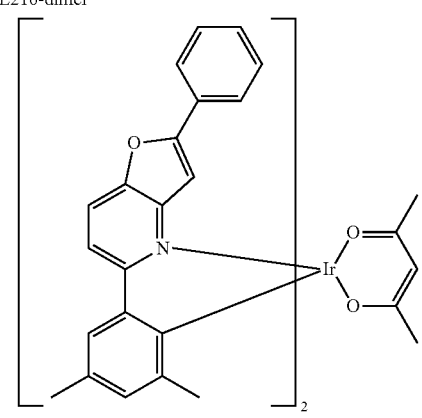

216

Synthesis of Intermediate L216

Intermediate L216 (3.00 g, 86%) was obtained in the same manner as in Synthesis of Intermediate L16 of Synthesis Example 2, except that 5-chloro-2-phenylfuro[3,2-b]pyridine (2.69 g, 11.71 mmol) was used instead of 6-chloro-2-phenylfuro[2,3-b]pyridine (2.69 g, 11.71 mmol).

LC-MS m/z=300 (M+H)$^+$.

Synthesis of Intermediate L216-dimer

Intermediate L216-dimer (3.2 g, 91%) was obtained in the same manner as in Synthesis of Intermediate L16-dimer of Synthesis Example 2, except that Intermediate L216 (2.86 g, 9.55 mmol) was used instead of Intermediate L16. The obtained compound was used in a next reaction without additional purification.

Synthesis of Compound 216

Compound 216 (0.75 g, 34%) was obtained in the same manner as in Synthesis of Compound 16 of Synthesis Example 2, except that Intermediate L216-dimer (2.04 g, 1.24 mmol) was used instead of Intermediate L16-dimer. The obtained compound was identified by MS and HPLC analysis.

HRMS(MALDI-TOF) calcd for $C_{47}H_{39}IrN_2O_4$: m/z 888.2539, Found: 888.2539.

Synthesis Example 7 (Compound 316)

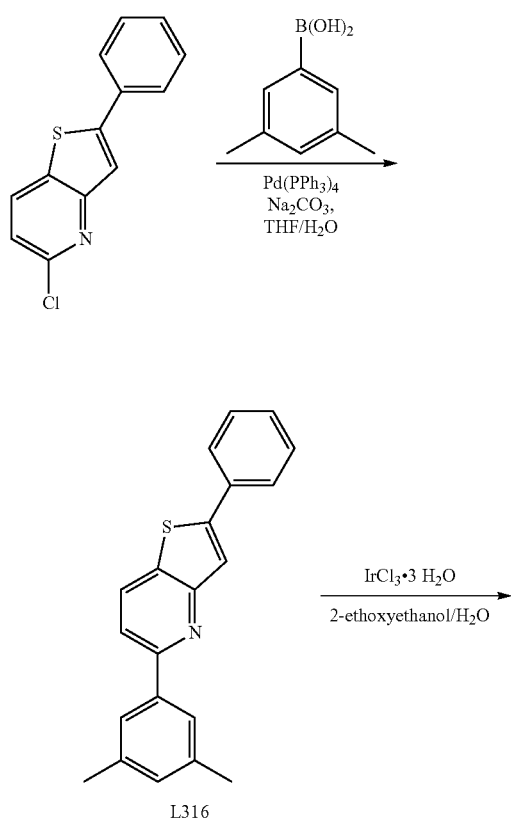

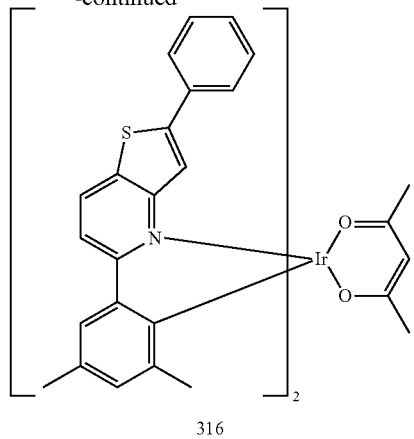

316

Synthesis of Intermediate L316

Intermediate L316 (3.01 g, 76%) was obtained in the same manner as in Synthesis of Intermediate L16 of Synthesis Example 2, except that 5-chloro-2-phenylthieno[3,2-b]pyridine (3.12 g, 12.7 mmol) was used instead of 5-chloro-2-phenylfuro[2,3-c]pyridine (2.69 g, 11.71 mmol).

LC-MS m/z=316 (M+H)$^+$.

Synthesis of Intermediate L316-dimer

Intermediate L316-dimer (2.60 g, 74%) was obtained in the same manner as in Synthesis of Intermediate L16-dimer of Synthesis Example 2, except that Intermediate L316 (2.89 g, 9.19 mmol) was used instead of Intermediate L16.

Synthesis of Compound 316

Compound 316 (0.49 g, 20%) was obtained in the same manner as in Synthesis of Compound 16 of Synthesis Example 2, except that Intermediate L316-dimer (2.23 g, 1.30 mmol) was used instead of Intermediate L16-dimer. The obtained compound was identified by MS and HPLC analysis.

HRMS(MALDI-TOF) calcd for $C_{47}H_{39}IrN_2O_2S_2$: m/z 920.2082, Found: 920.2080.

Evaluation Example 1: Evaluation of Radiative Decay Rate

CBP and Compound 16 were co-deposited at a weight ratio of 9:1 under a vacuum pressure of $10^{-7}$ torr to manufacture a film having a thickness of 40 nm.

A PL spectrum of the film was evaluated at room temperature by using a PicoQuant TRPL measurement system FluoTime 300 and a PicoQuant pumping source PLS340 (excitation wavelength=340 nm, spectral width=20 nm), a wavelength of a main peak of the spectrum was determined, and PLS340 repeatedly measured the number of photons emitted from the film at the wavelength of the main peak due to a photon pulse (pulse width=500 ps) applied to the film according to time based on time-correlated single photon counting (TCSPC), thereby obtaining a sufficiently fittable TRPL curve. A decay time $T_{decay}$ of the film was obtained by fitting one or more exponential decay functions to the result obtained therefrom. The function used for fitting is expressed by Equation 10, and the greatest value among the values obtained from each exponential decay function used for fitting was taken as $T_{decay}$. At this time, a baseline or background signal curve was obtained by repeating the same measurement once more for the same measurement time as the measurement time for obtaining the TRPL curve in a dark state (a state in which a pumping signal applied to the

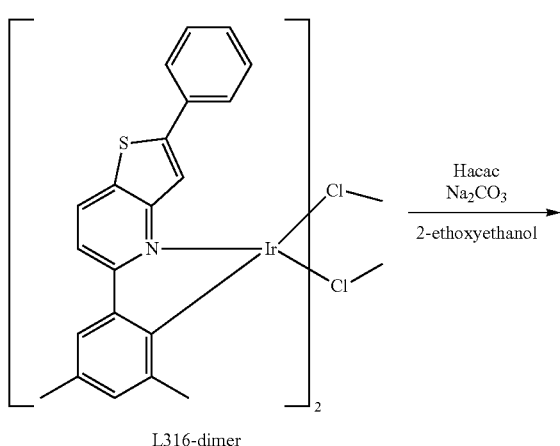

L316-dimer predetermined film was blocked), and the baseline or background signal curve was used for fitting as a baseline.

$$f(t) = \sum_{i=1}^{n} A_i \exp(-t/T_{decay,i})$$ Equation 10

Then, the quantum efficiency of the film was measured by using a Hamamatsu Quantaurus-QY Absolute PL quantum yield spectrometer (provided with a xenon light source, a monochromator, a photonic multichannel analyzer, and an integrating sphere and using PLQY measurement software (Hamamatsu Photonics, Ltd., Shizuoka, Japan)). Upon measurement of the quantum efficiency, the excitation wavelength was measured while scanning from 320 nm to 380 nm at an interval of 10 nm, and the greatest value was taken as the quantum efficiency (Φ).

The radiative decay rate ($k_r$) of Compound 1 was obtained by substituting $T_{decay}$ and Φ into Equation 11, and results thereof are shown in Table 2.

$$k_r = \Phi/T_{decay}$$ Equation 11

The measurement of the radiative decay rate was repeated on Compounds 101, 116, 146, 216, 316, A1, A2, B, C1, C2 and D, and results thereof are shown in Table 2.

TABLE 2

| Compound No. | Radiative decay rate (s$^{-1}$) |
|---|---|
| 16 | 4.72 × 10$^5$ |
| 101 | 5.68 × 10$^5$ |
| 116 | 7.09 × 10$^5$ |
| 146 | 6.72 × 10$^5$ |
| 216 | 1.22 × 10$^6$ |
| 316 | 1.56 × 10$^6$ |
| A1 | 4.08 × 10$^5$ |
| A2 | 4.15 × 10$^5$ |
| B | 4.62 × 10$^5$ |
| C1 | 1.85 × 10$^5$ |
| C2 | 3.52 × 10$^5$ |
| D | 2.13 × 10$^5$ |

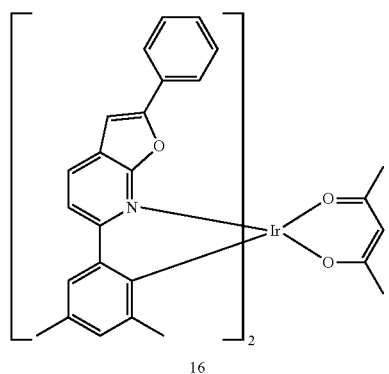

16

TABLE 2-continued

| Compound No. | Radiative decay rate (s$^{-1}$) |
|---|---|

101

116

146

216

TABLE 2-continued

| Compound No. | Radiative decay rate (s⁻¹) |
|---|---|
| 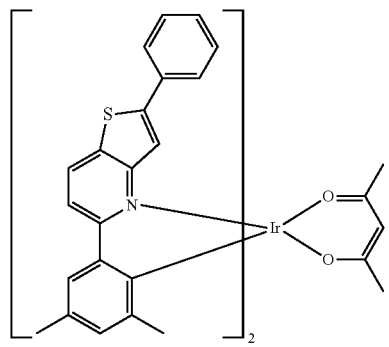 316 | |
| 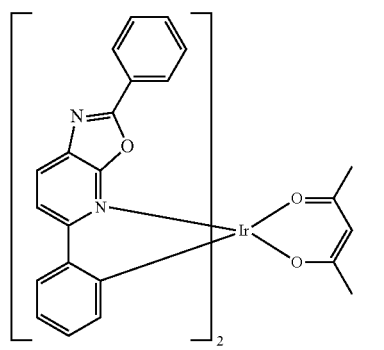 A1 | |
| 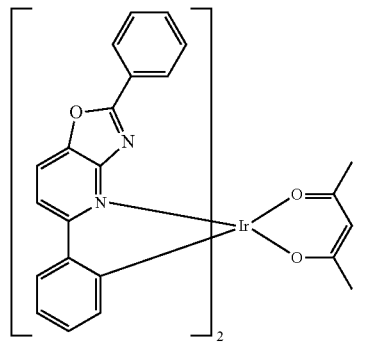 A2 | |
| 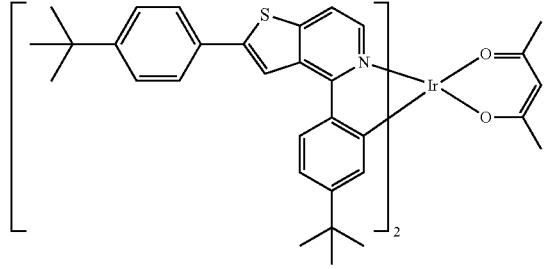 B | |

TABLE 2-continued

| Compound No. | Radiative decay rate (s⁻¹) |
|---|---|
| 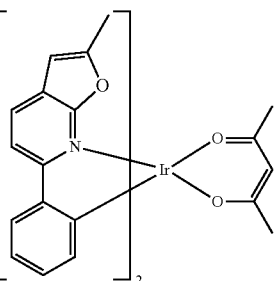 C1 | |
| 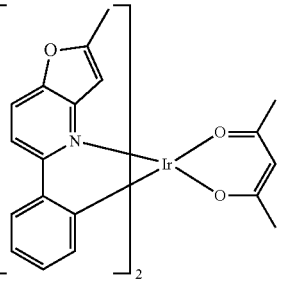 C2 | |
| 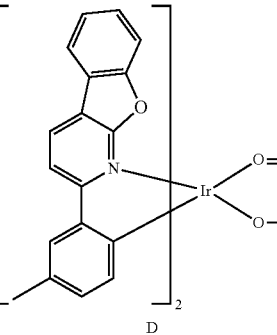 D | |

From Table 2, it is confirmed that Compounds 16, 101, 116, 146, 216, and 316 have high radiative decay rates, as compared with those of Compounds A1, A2, B, C1, C2, and D.

Example 1

As an anode, a glass substrate, on which ITO/Ag/ITO were deposited to thicknesses of 70 Å/1,000 Å/70 Å, was cut to a size of 50 mm×50 mm×0.5 mm, sonicated with isopropyl alcohol and pure water each for 5 minutes, and then cleaned by exposure to ultraviolet rays and ozone for 30 minutes. Then, the glass substrate was provided to a vacuum deposition apparatus.

2-TNATA was vacuum-deposited on the anode to form a hole injection layer having a thickness of 600 Å, and 4,4'-bis[N-(1-naphthyl)-N-phenylamino]biphenyl (NPB) was vacuum-deposited on the hole injection layer to form a hole transport layer having a thickness of 1,350 Å.

Then, CBP (host) and Compound 16 (dopant) were co-deposited on the hole transport layer at a weight ratio of 98:2 to form an emission layer having a thickness of 400 Å.

Then, BCP was vacuum-deposited on the emission layer to form a hole blocking layer having a thickness of 50 Å, Alq₃ was vacuum-deposited on the hole blocking layer to form an electron transport layer having a thickness of 350 Å, LiF was vacuum-deposited on the electron transport layer to form an electron injection layer having a thickness of 10 Å, and Mg and Ag were co-deposited on the electron injection layer at a weight ratio of 90:10 to form a cathode having a thickness of 120 Å, thereby completing the manufacture of an organic light-emitting device (which emits red light).

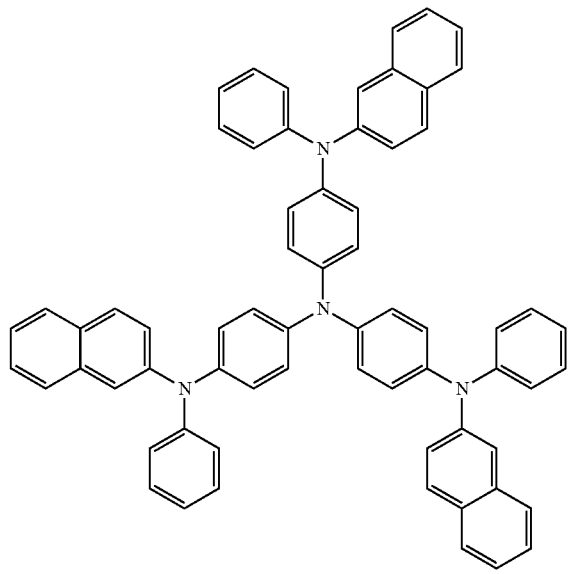

2-TNATA

NPB

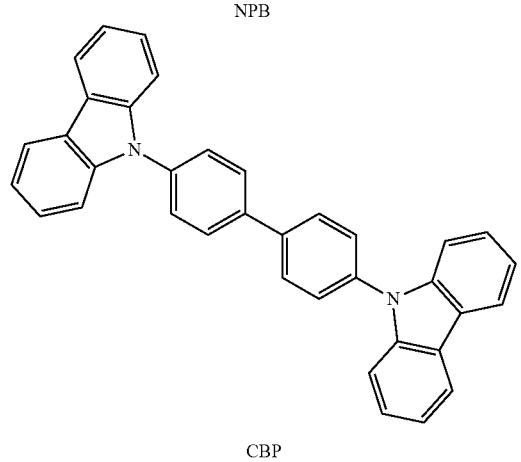

CBP

-continued

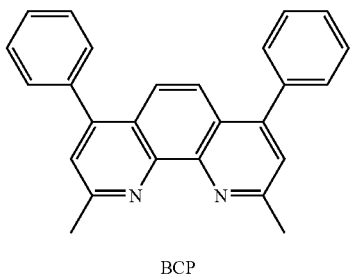

BCP

Examples 2 to 6 and Comparative Examples A1, A2, B, C1, C2, and D

Organic light-emitting devices were manufactured in the same manner as in Example 1, except that Compounds shown in Table 3 were each used instead of Compound 16 as a dopant in forming an emission layer.

Evaluation Example 2: Evaluation of Characteristics of Organic Light-Emitting Devices The driving voltage, maximum value of external quantum efficiency (Max EQE), roll-off ratio, maximum emission wavelength of main peak of EL spectrum, and lifespan ($T_{97}$) of the organic light-emitting devices manufactured according to Examples 1 to 6 and Comparative Examples A1, A2, B, C1, C2, and D were evaluated, and results thereof are shown in Table 3. A current-voltage meter (Keithley 2400) and a luminance meter (Minolta Cs-1000A) were used as the evaluation devices, and the lifespan ($T_{97}$) (at 3,500 nit) indicates an amount of time that lapsed when luminance was 97% of initial luminance (100%). The roll-off ratio was calculated by Equation 20:

Roll off ratio={1−(efficiency(at 3,500 nit)/maximum luminescence efficiency)}×100%   Equation 20

TABLE 3

| | Compound No. of dopant in emission layer | Driving voltage (V) | Max EQE (%) | Roll-Off ratio (%) | Maximum emission wavelength (nm) | $T_{97}$ (hr) (at 3,500 nit) |
|---|---|---|---|---|---|---|
| Example 1 | 16 | 3.74 | 26.5 | 10 | 606 | 144 |
| Example 2 | 101 | 3.64 | 26.9 | 11 | 555 | 107 |
| Example 3 | 116 | 3.74 | 27.6 | 10 | 581 | 157 |
| Example 4 | 146 | 4.17 | 26.4 | 11 | 557 | 156 |
| Example 5 | 216 | 4.28 | 27.9 | 5 | 581 | 181 |
| Example 6 | 316 | 4.20 | 31.5 | 2 | 576 | 258 |
| Comparative Example A1 | A1 | 5.75 | 24.1 | 19 | 575 | 85 |
| Comparative Example A2 | A2 | 5.84 | 24.7 | 14 | 614 | 86 |
| Comparative Example B | B | 4.3 | 26.0 | 12 | 580 | 60 |
| Comparative Example C1 | C1 | 5.22 | 24.4 | 32 | 514 | 48 |
| Comparative Example C2 | C2 | 5.59 | 25.4 | 15 | 505 | 48 |
| Comparative Example D | D | 4.34 | 24.6 | 28 | 555 | 69 |

TABLE 3-continued

| Compound No. of dopant in emission layer | Driving voltage (V) | Max EQE (%) | Roll-Off ratio (%) | Maximum emission wavelength (nm) | T$_{97}$ (hr) (at 3,500 nit) |
| --- | --- | --- | --- | --- | --- |
| 16 | | | | | |
| 101 | | | | | |
| 116 | | | | | |
| 146 | | | | | |
| 216 | | | | | |
| 316 | | | | | |
| A1 | | | | | |
| A2 | | | | | |

TABLE 3-continued

| Compound No. of dopant in emission layer | Driving voltage (V) | Max EQE (%) | Roll-Off ratio (%) | Maximum emission wavelength (nm) | T₉₇ (hr) (at 3,500 nit) |
|---|---|---|---|---|---|

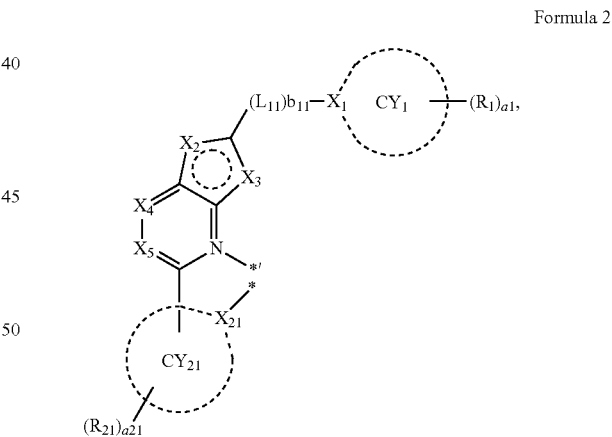

From Table 3, it is confirmed that the organic light-emitting devices of Examples 1 to 6 emit red light and have improved driving voltage, improved external quantum efficiency, improved roll-off ratio, and improved lifespan characteristics, compared with those of the organic light-emitting devices of Comparative Examples A1, A2, B, C1, C2, and D.

Since the organometallic compound has a high radiative decay rate, an electronic device, for example, an organic light-emitting device, which includes the organometallic compound represented by Formula 1, may have improved driving voltage, improved external quantum luminescence efficiency, improved roll-off ratio, and improved lifespan characteristics. In addition, since the organometallic compound has excellent phosphorescent luminescent characteristics, a diagnostic composition having high diagnostic efficiency may be provided by using the organometallic compound.

It should be understood that embodiments described herein should be considered in a descriptive sense only and not for purposes of limitation. Descriptions of features or aspects within each embodiment should typically be considered as available for other similar features or aspects in other embodiments.

While embodiments have been described with reference to the FIGURES, it will be understood by those of ordinary skill in the art that various changes in form and details may be made therein without departing from the spirit and scope as defined by the following claims.

What is claimed is:
1. An organometallic compound represented by Formula 1:

$$M(L_1)_{n1}(L_2)_{n2},\qquad \text{Formula 1}$$

wherein, in Formula 1,
M is Ir or Os, and the sum of n1 and n2 is 3 or 4; or
M is Pt, and the sum of n1 and n2 is 2,
$L_1$ is a ligand represented by Formula 2,
n1 is 1, 2, or 3, wherein, when n1 is 2 or more, two or more $L_1$ are identical to or different from each other,
$L_2$ is a monodentate ligand, a bidentate ligand, a tridentate ligand, or a tetradentate ligand,
n2 is 0, 1, 2, 3, or 4, wherein, when n2 is 2 or more, two or more $L_2$ are identical to or different from each other, and
$L_1$ and $L_2$ are different from each other:

Formula 2

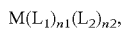

wherein, in Formula 2,
$X_1$ is C or N
$X_{21}$ is C or N,
a group represented by

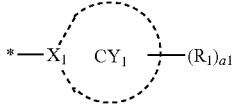

in Formula 2 is a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with $R_1$ in the number of a1, a group represented by

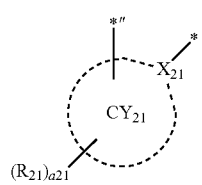

in Formula 2 is a group represented by one of Formulae CY21-1 to CY21-25:

CY21-1

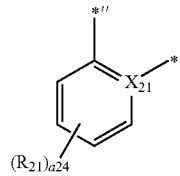

CY21-2

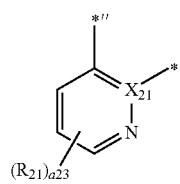

CY21-3

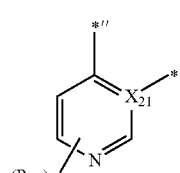

CY21-4

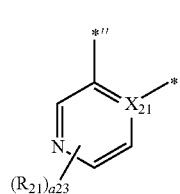

CY21-5

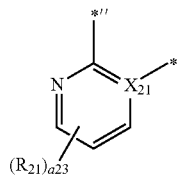

CY21-6

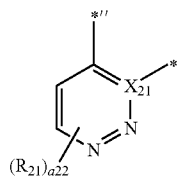

CY21-7

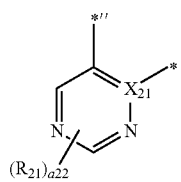

CY21-8

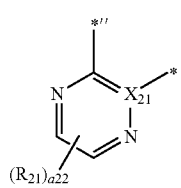

CY21-9

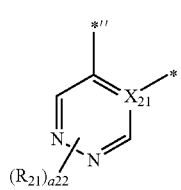

CY21-10

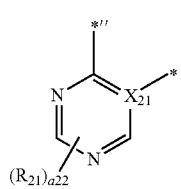

CY21-11

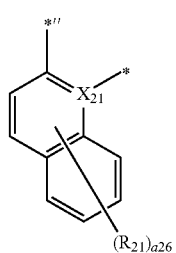

-continued
CY21-12
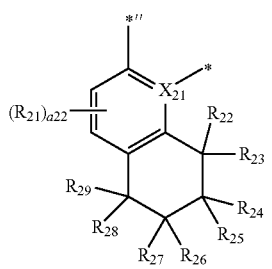
CY21-13
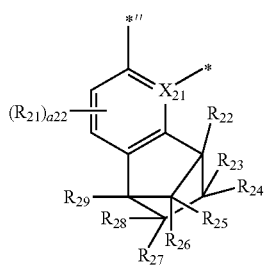
CY21-14
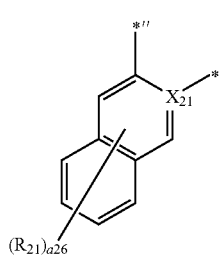
CY21-15
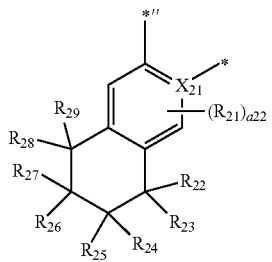
CY21-16
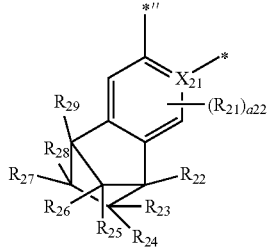
CY21-17
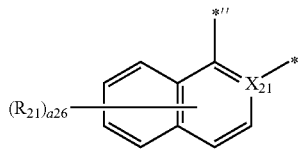
-continued
CY21-18
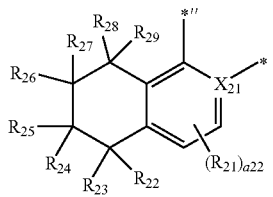
CY21-19
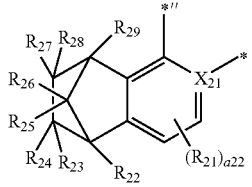
CY21-20
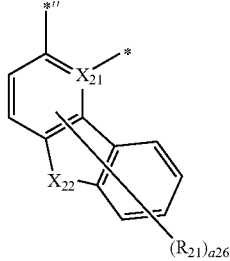
CY21-21
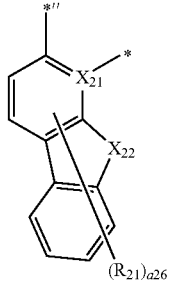
CY21-22
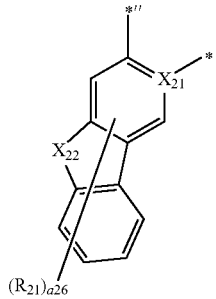
CY21-23
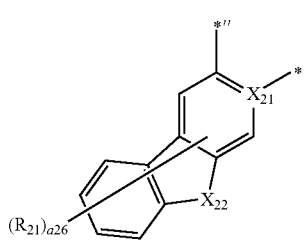

-continued

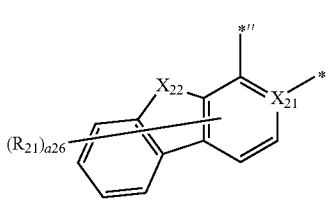

CY21-24

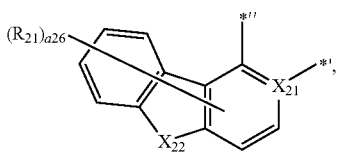

CY21-25 wherein, in Formulae CY21-1 to CY21-25, $X_{21}$ is C or N, $X_{22}$ is $C(R_{22})(R_{23})$, $N(R_{22})$, O, S, or $Si(R_{22})(R_{23})$, $R_{21}$ to $R_{29}$ are each independently hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropoly cyclic group, —N(Q$_1$)(Q$_2$), —Si(Q$_3$)(Q$_4$)(Q$_5$), —B(Q$_6$)(Q$_7$), —P(=O)(Q$_8$)(Q$_9$) or —P(Q$_8$)(Q$_9$), a26 is an integer from 0 to 6, a24 is an integer from 0 to 4, a23 is an integer from 0 to 3, a22 is an integer from 0 to 2,

*" indicates a binding site to a carbon atom of a neighboring 6-membered ring in Formula 2, and

* indicates a binding site to M in Formula 1, $X_2$ and $X_3$ are each independently O, S, Se, or $C(R_2)$, wherein one of $X_2$ or $X_3$ is O, S, or Se, $X_4$ is N or $C(R_4)$, $X_5$ is N or $C(R_5)$, $R_1$, $R_2$, $R_4$, and $R_5$ are each independently hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), —P(=O)(Q$_8$)(Q$_9$) or —P(Q$_8$)(Q$_9$), a1 is an integer from 0 to 20, ring $CY_1$ and $R_2$ are not linked to each other, and $R_1$ and $R_2$ are not linked to each other, b11 is 0, wherein, when b11 is 0, a group represented by *-$(L_{11})_{b11}$-*' is a single bond, two or more of a plurality of neighboring $R_{21}$ are optionally linked to form a $C_5$-$C_{30}$ carbocyclic group that is unsubstituted or substituted with at least one $R_{10a}$ groups or a $C_2$-$C_{30}$ heterocyclic group that is unsubstituted or substituted with at least one $R_{10a}$ group, $R_{10a}$ is the same as defined in connection with $R_{21}$,

* and *' each indicate a binding site to M in Formula 1, a substituent of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_2$-$C_{60}$ heteroarylalkyl group, the substituted monovalent non-aromatic condensed polycyclic group, and the substituted monovalent non-aromatic condensed heteropolycyclic group is:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a C$_2$-C$_{60}$ heteroarylalkyl group, a monovalent non-aromatic condensed polycyclic group, a monovalent non-aromatic condensed heteropoly cyclic group, —N(Q$_{11}$)(Q$_{12}$), —Si(Q$_{13}$)(Q$_{14}$)(Q$_{15}$), —B(Q$_{16}$)(Q$_{17}$), —P(=O)(Q$_{18}$)(Q$_{19}$), or any combination thereof;

a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, C$_2$-C$_{60}$ heteroarylalkyl group, a monovalent non-aromatic condensed polycyclic group, or a monovalent non-aromatic condensed heteropolycyclic group;

a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, C$_2$-C$_{60}$ heteroarylalkyl group, a monovalent non-aromatic condensed polycyclic group, or a monovalent non-aromatic condensed heteropolycyclic group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, C$_2$-C$_{60}$ heteroarylalkyl group, a monovalent non-aromatic condensed polycyclic group, a monovalent non-aromatic condensed heteropoly cyclic group, —N(Q$_{21}$)(Q$_{22}$), —Si(Q$_{23}$)(Q$_{24}$)(Q$_{25}$), —B(Q$_{26}$)(Q$_{27}$), —P(=O)(Q$_{28}$)(Q$_{29}$), or any combination thereof;

—N(Q$_{31}$)(Q$_{32}$), —Si(Q$_{33}$)(Q$_{34}$)(Q$_{35}$), —B(Q$_{36}$)(Q$_{37}$), or —P(=O)(Q$_{38}$)(Q$_{39}$); or any combination thereof, and Q$_1$ to Q$_9$, Q$_{11}$ to Q$_{19}$, Q$_{21}$ to Q$_{29}$, and Q$_{31}$ to Q$_{39}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryl group substituted with a C$_1$-C$_{60}$ alkyl group, a C$_6$-C$_{60}$ aryl group, or any combination thereof, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, C$_2$-C$_{60}$ heteroarylalkyl group, a monovalent non-aromatic condensed polycyclic group, or a monovalent non-aromatic condensed heteropoly cyclic group.

2. The organometallic compound of claim 1, wherein R$_1$, R$_2$, R$_4$, R$_5$, R$_{21}$ to R$_{29}$, and R$_{10a}$ are each independently:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a cyclooctenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a cyclooctenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —Si($Q_{33}$)($Q_{34}$)($Q_{35}$), or any combination thereof; or —N($Q_1$)($Q_2$), —Si($Q_3$)($Q_4$)($Q_5$), —B($Q_6$)($Q_7$), —P(=O)($Q_8$)($Q_9$), or —P($Q_8$)($Q_9$), and $Q_1$ to $Q_9$ and $Q_{33}$ to $Q_{35}$ are each independently:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, or —CD$_2$CDH$_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, or a naphthyl group, each unsubstituted or substituted with deuterium, a $C_1$-$C_{10}$ alkyl group, a phenyl group, or any combination thereof.

3. The organometallic compound of claim 1, wherein $R_1$ and $R_2$ are each independently:

hydrogen, deuterium, —F, —Cl, —Br, —I, a cyano group, or —SF$_5$; or a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonanyl group, an isononanyl group, a sec-nonanyl group, a tert-nonanyl group, an n-decanyl group, an isodecanyl group, a sec-decanyl group, a tert-decanyl group, a $C_1$-$C_{10}$ alkoxy, a cyclopentyl group, a cyclohexyl group, a cycloheptyl group, a cyclooctyl group, an adamantyl group, a norbornyl group, a norbornenyl group, a cyclopentenyl group, a cyclohexenyl group, or a cycloheptenyl group, each unsubstituted or substituted with deuterium, —F, —Cl, —Br, —I, —CD$_3$, —CD$_2$H, —CDH$_2$, —CF$_3$, —CF$_2$H, —CFH$_2$, a cyano group, a $C_1$-$C_{20}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or any combination thereof, and a1 is an integer from 0 to 5.

4. The organometallic compound of claim 1, wherein a group represented by

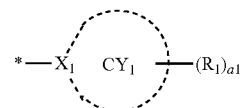

is one of Formulae 10-13(1) to 10-13(18) or 10-13:

10-13((1)

10-13(2)

10-13(3)

10-13(4)

10-13(5)

10-13(6)

10-13(7)

10-13(8)

10-13(9)

10-13(10) 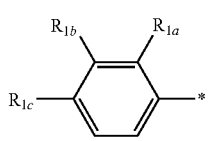
10-13(11) 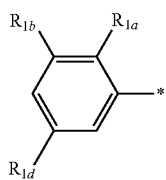
10-13(12) 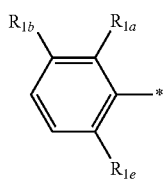
10-13(13) 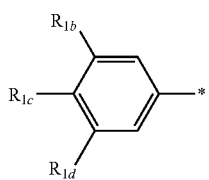
10-13(14) 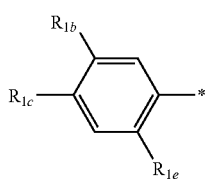
10-13(15) 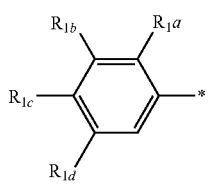
10-13(16) 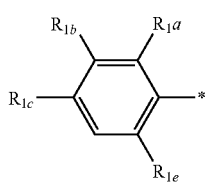
10-13(17) 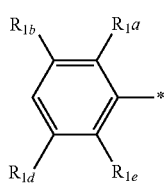
10-13(18) 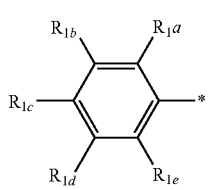
10-13 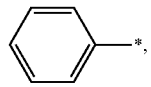
wherein, in Formulae 10-13(1) to 10-13(18) and 10-13, $R_{1a}$ to $R_{1e}$ are each independently the same as defined in connection with $R_1$ in claim 1, wherein $R_{1a}$ to $R_{1e}$ are each not hydrogen, and * indicates a binding site to a neighboring carbon atom.
5. The organometallic compound of claim 1, wherein a group represented by
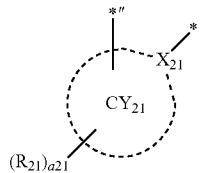
in Formula 2 is a group represented by one of Formulae CY21(1) to CY21(56):
CY21(1) 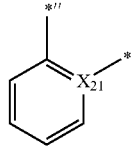
CY21(2) 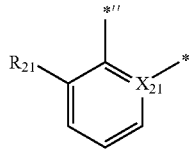
CY21(3) 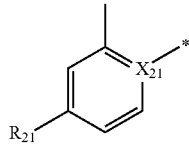
CY21(4) 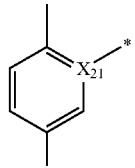
CY21(5) 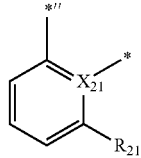

-continued
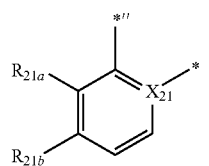
CY21(6)
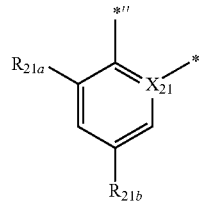
CY21(7)
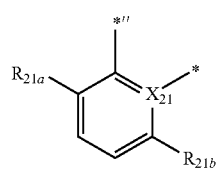
CY21(8)
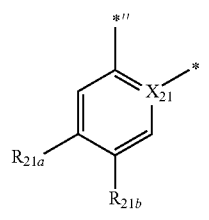
CY21(9)
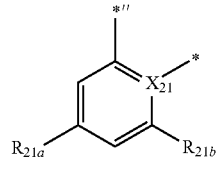
CY21(10)
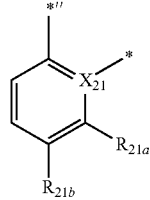
CY21(11)
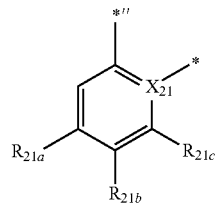
CY21(12)
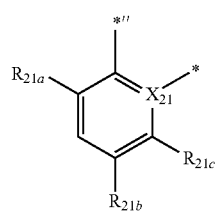
CY21(13)
-continued
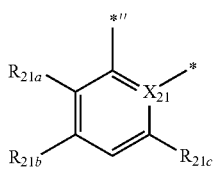
CY21(14)
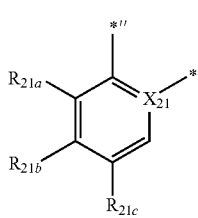
CY21(15)
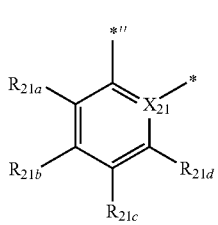
CY21(16)
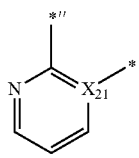
CY21(17)
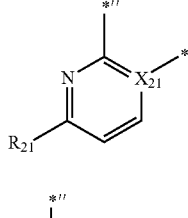
CY21(18)
CY21(19)
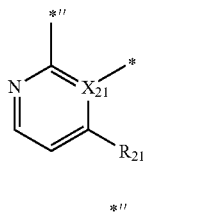
CY21(20)
CY21(21)

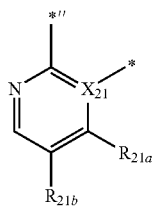 CY21(22)
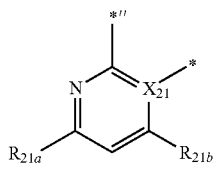 CY21(23)
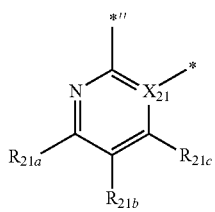 CY21(24)
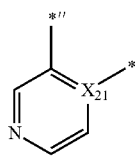 CY21(25)
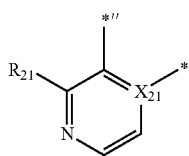 CY21(26)
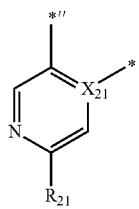 CY21(27)
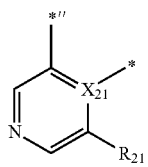 CY21(28)
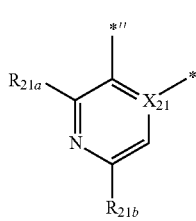 CY21(29)
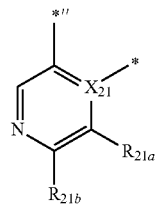 CY21(30)
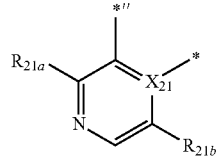 CY21(31)
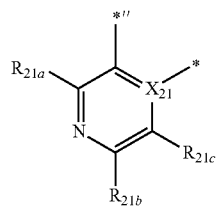 CY21(32)
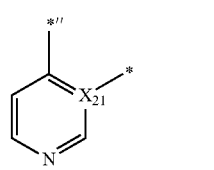 CY21(33)
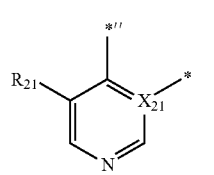 CY21(34)
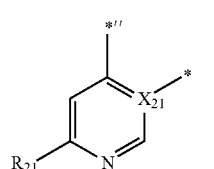 CY21(35)
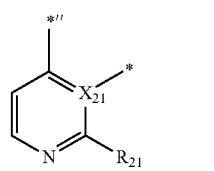 CY21(36)
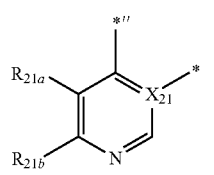 CY21(37)

-continued
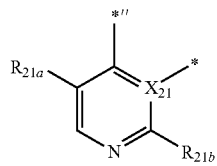
CY21(38)
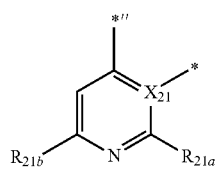
CY21(39)
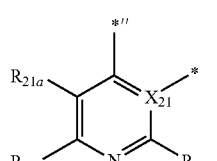
CY21(40)
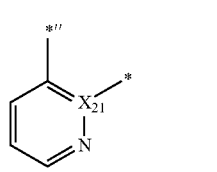
CY21(41)
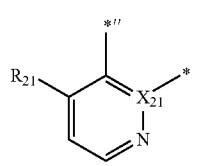
CY21(42)
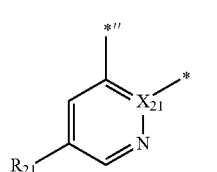
CY21(43)
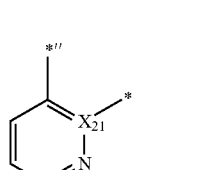
CY21(44)
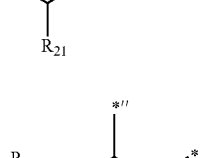
CY21(45)
-continued
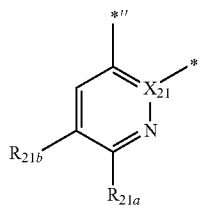
CY21(46)
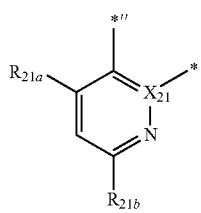
CY21(47)
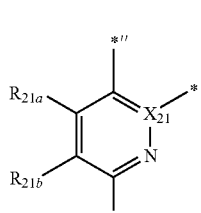
CY21(48)
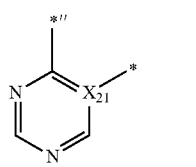
CY21(49)
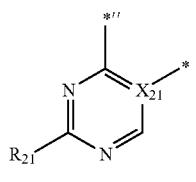
CY21(50)
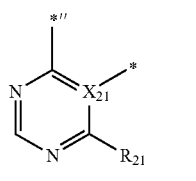
CY21(51)
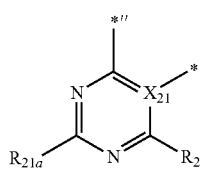
CY21(52)
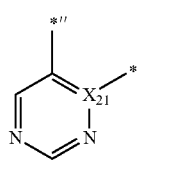
CY21(53)

-continued

CY21(54)

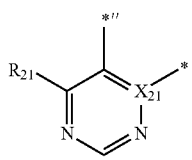

CY21(55)

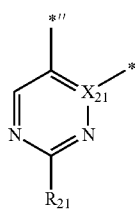

CY21(56)

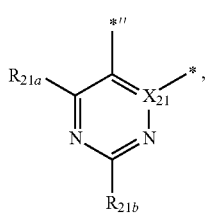

wherein, in Formulae CY21(1) to CY21(56), $X_{21}$ and $R_{21}$ are each independently the same as described in claim 1, $R_{21a}$ to $R_{21d}$ are each independently the same as defined in connection with $R_{21}$ in claim 1, wherein $R_{21}$ and $R_{21a}$ to $R_{21d}$ are each not hydrogen,

*'' indicates a binding site to a carbon atom of a neighboring 6-membered ring in Formula 2, and

* indicates a binding site to M in Formula 1.

6. The organometallic compound of claim 1, wherein $L_1$ is a ligand represented by Formula 2A or 2B:

Formula 2A

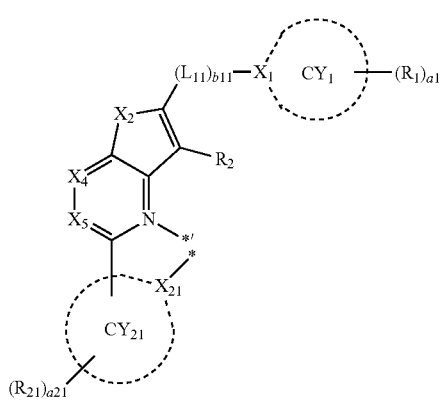

Formula 2B

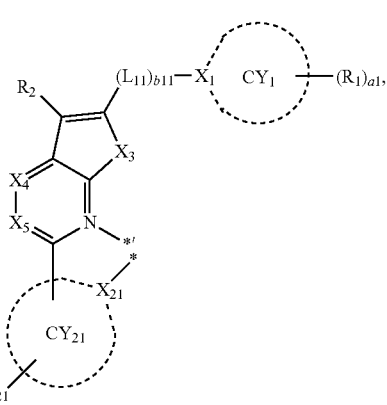

wherein, in Formulae 2A and 2B, $X_1$, $X_{21}$, ring $CY_1$, ring $CY_{21}$, $X_4$, $X_5$, $R_1$, $R_2$, $R_{21}$, a1, a21, $L_{11}$, b11, *, and *' are each independently the same as described in claim 1, wherein $X_2$ and $X_3$ are each independently O, S, or Se.

7. The organometallic compound of claim 1, wherein, in Formula 1, $L_2$ is a bidentate ligand linked to M of Formula 1 via O, S, N, C, P, Si, or As.

8. The organometallic compound of claim 1, wherein, in Formula 1, $L_2$ is a bidentate ligand represented by Formula 3:

Formula 3

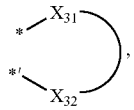

wherein, in Formula 3,
$X_{31}$ and $X_{32}$ are each independently O;
$X_{31}$ is O and $X_{32}$ is N; or
$X_{31}$ is N and $X_{32}$ is C,

indicates any atomic group linking $X_{31}$ and $X_{32}$ to each other, and

* and *' each indicate a binding site to M in Formula 1.

9. The organometallic compound of claim 1, wherein, in Formula 1, $L_2$ is a group represented by one of Formulae 3A to 3F:

3A

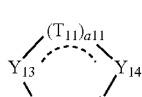

3B

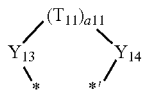

-continued

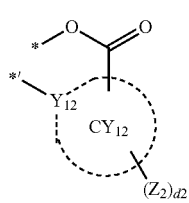
3C

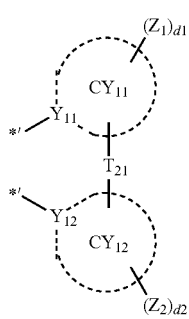
3D

*—C≡C—Z₁
3E

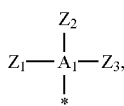
3F wherein, in Formulae 3A to 3F,
Y₁₃ is O, N, N(Z₁), P(Z₁)(Z₂), or As(Z₁)(Z₂),
Y₁₄ is O, N, N(Z₃), P(Z₃)(Z₄), or As(Z₃)(Z₄),
T₁₁ is a single bond, a double bond, *—C(Z₁₁)(Z₁₂)—*', *—C(Z₁₁)=C(Z₁₂)—*', *=C(Z₁)—*', *—C(Z₁₁)=*', *=C(Z₁)—C(Z₁₂)=C(Z₁₃)—*', *—C(Z₁₁)=C(Z₁₂)—C(Z₁₃)=*', *—N(Z₁₁)—*', or a C₅-C₃₀ carbocyclic group that is unsubstituted or substituted with at least one Zn group,
a11 is an integer from 1 to 10,
Y₁₁ and Y₁₂ are each independently C or N,
T₂₁ is a single bond, a double bond, O, S, C(Z₁₁)(Z₁₂), Si(Z₁₁)(Z₁₂), or N(Z₁₁), ring CY₁₁ and ring CY₁₂ are each independently a C₅-C₃₀ carbocyclic group or a C₂-C₃₀ heterocyclic group,
A₁ is P or As,
Z₁ to Z₄ and Zn to Z₁₃ are each independently the same as defined in connection with R₂₁ in claim 1,
d1 and d2 are each independently an integer from 0 to 10, and
* and *' each indicate a binding site to M in Formula 1.

10. The organometallic compound of claim 1, wherein, in Formula 1, L₂ is a group represented by one of Formulae 3-1(1) to 3-1(66) or 3-1(301) to 3-1(309):

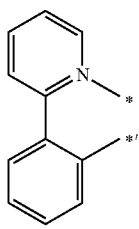
3-1(1)

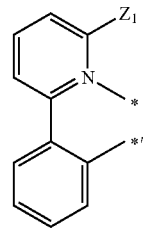
3-1(2)

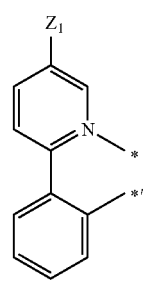
3-1(3)

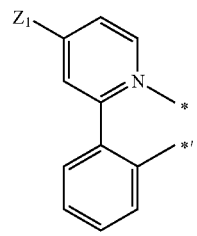
3-1(4)

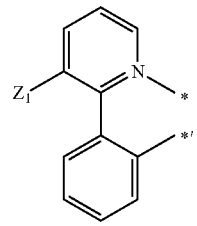
3-1(5)

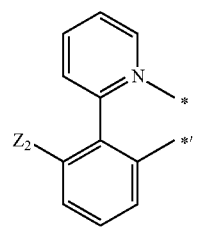
3-1(6)

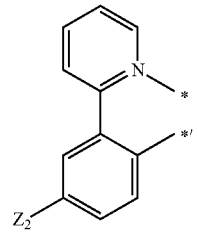
3-1(7)

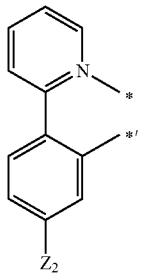
3-1(8)
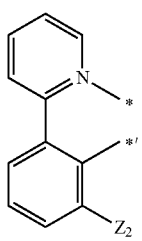
3-1(9)
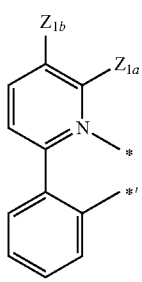
3-1(10)
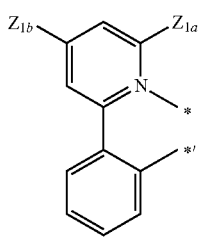
3-1(11)
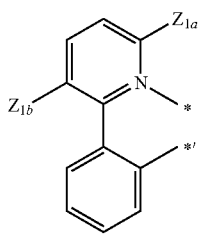
3-1(12)
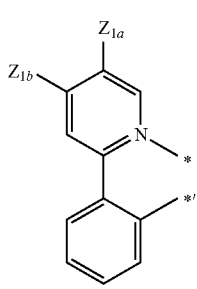
3-1(13)
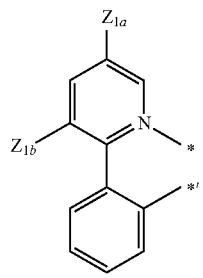
3-1(14)
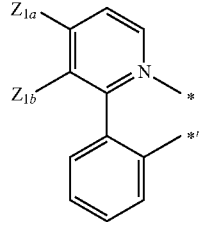
3-1(15)
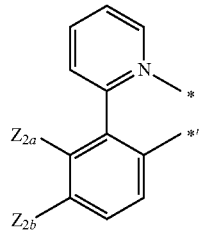
3-1(16)
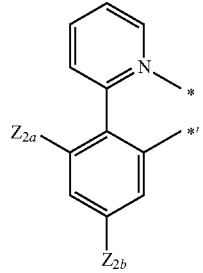
3-1(17)
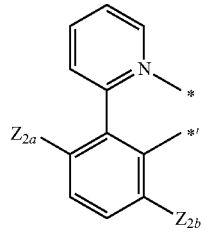
3-1(18)
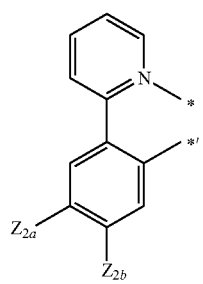
3-1(19)

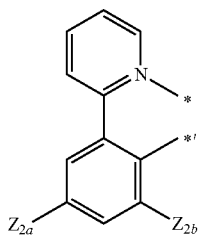
3-1(20)
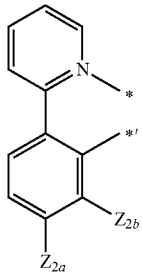
3-1(21)
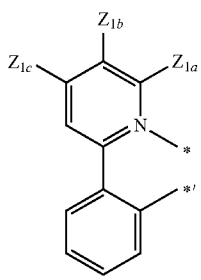
3-1(22)
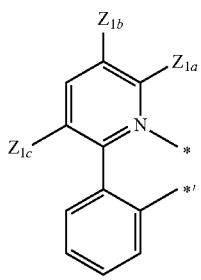
3-1(23)
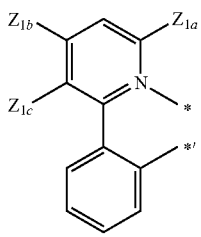
3-1(24)
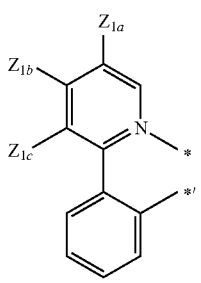
3-1(25)
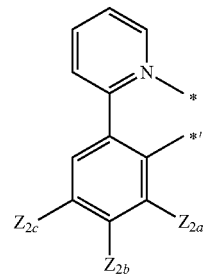
3-1(26)
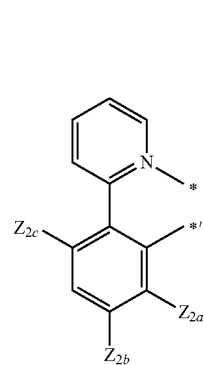
3-1(27)
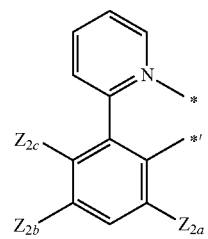
3-1(28)
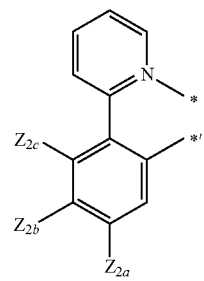
3-1(29)
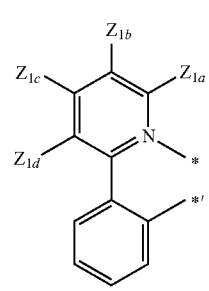
3-1(30)

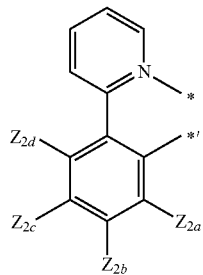 3-1(31)
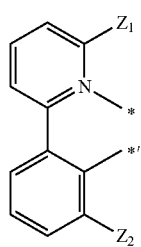 3-1(32)
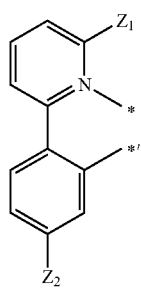 3-1(33)
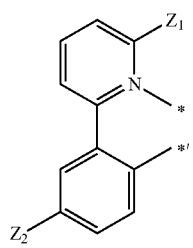 3-1(34)
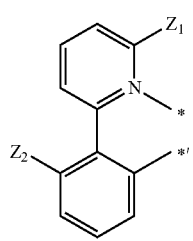 3-1(35)
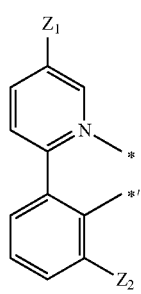 3-1(36)
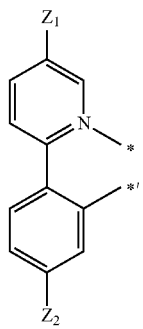 3-1(37)
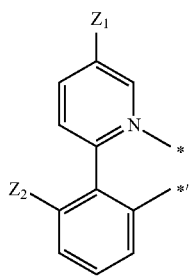 3-1(38)
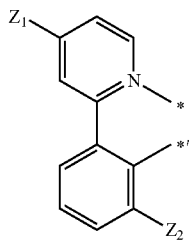 3-1(39)
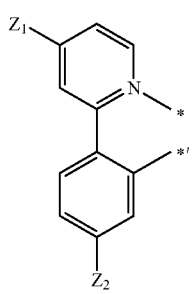 3-1(40)
3-1(41)

303
-continued
3-1(42)
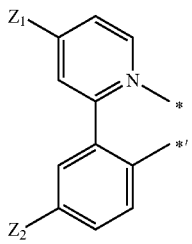
3-1(43)
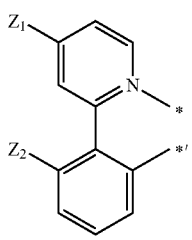
3-1(44)
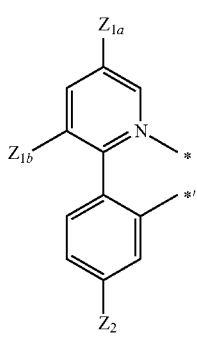
3-1(45)
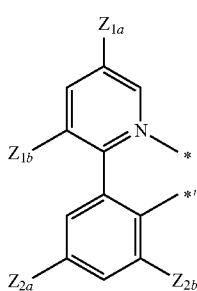
3-1(46)
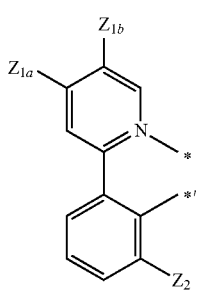
304
-continued
3-1(47)
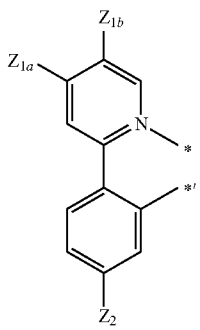
3-1(48)
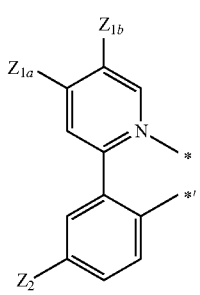
3-1(49)
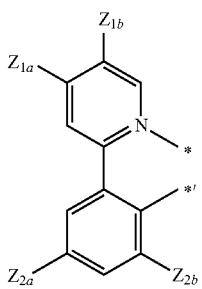
3-1(50)
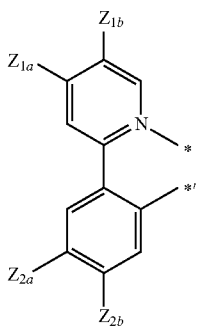
3-1(51)
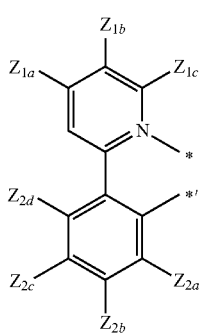

3-1(52) 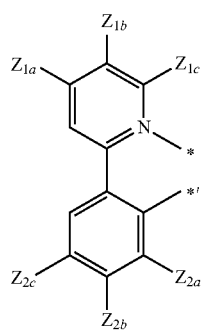
3-1(53) 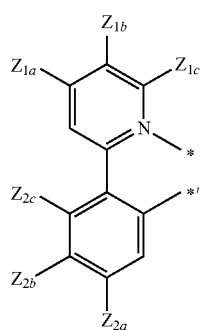
3-1(54) 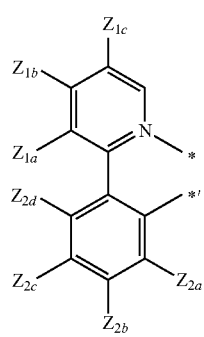
3-1(55) 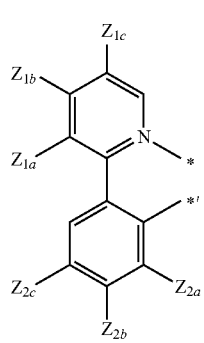
3-1(56) 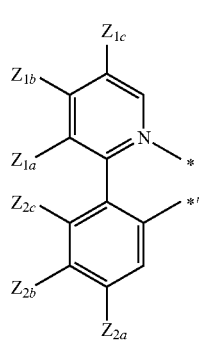
3-1(57) 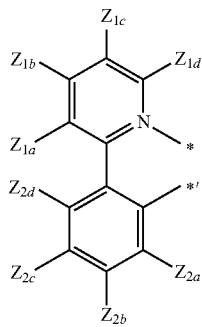
3-1(58) 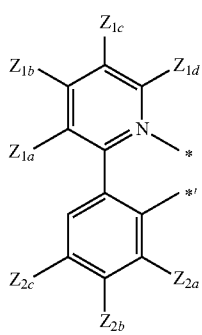
3-1(59) 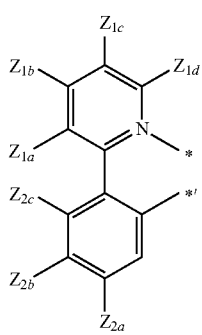
3-1(60) 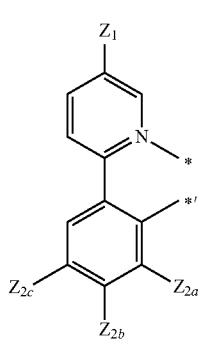

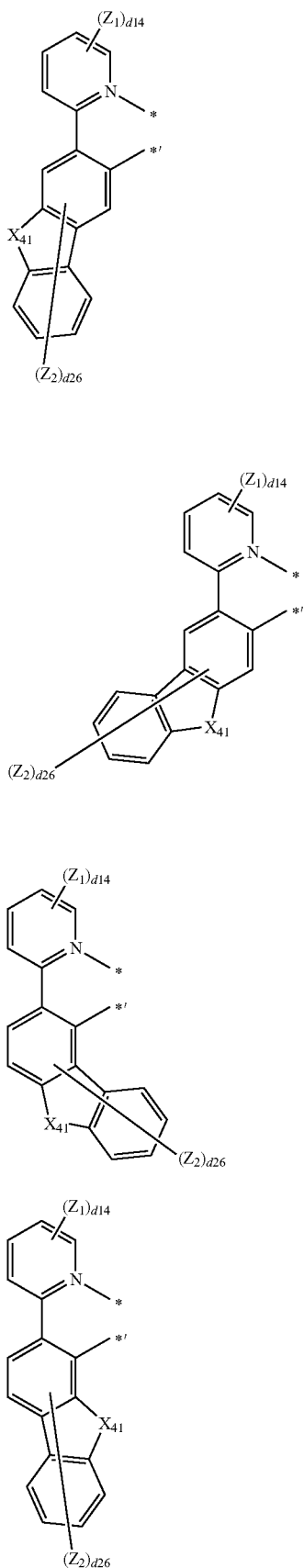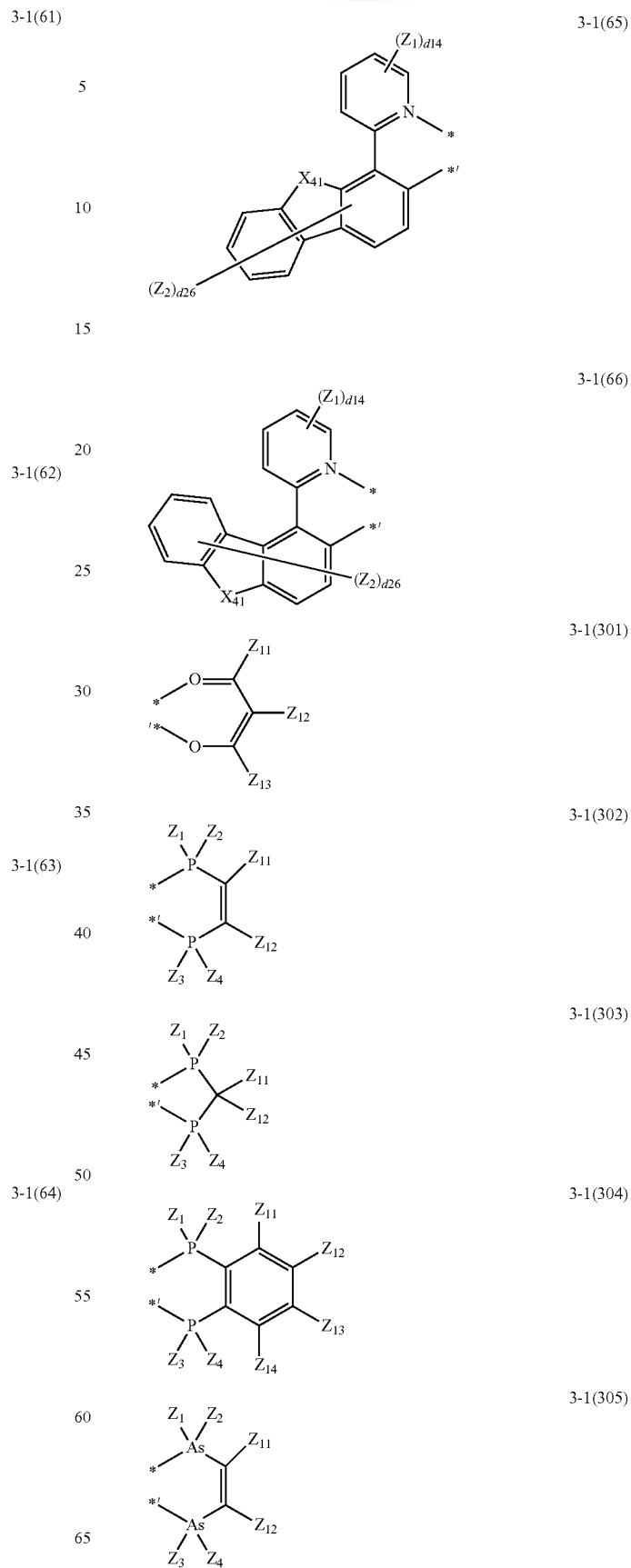

309
-continued

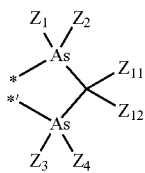
3-1(306)

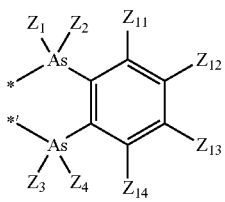
3-1(307)

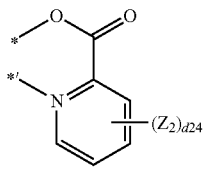
3-1(308)

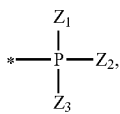
3-1(309)

wherein, in Formulae 3-1(1) to 3-1(66) and 3-1(301) to 3-1(309), $X_{41}$ is O, S, $N(Z_{21})$, $C(Z_{21})(Z_{22})$, or $Si(Z_{21})(Z_{22})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{22}$ are each independently the same as defined in connection with $R_{21}$ in claim 1, d14 and d42 are each is an integer from 0 to 4, d26 is an integer from 0 to 6, and

* and *' each indicate a binding site to M in Formula 1.

11. An organometallic compound represented by one of Compounds 1 to 420:

1

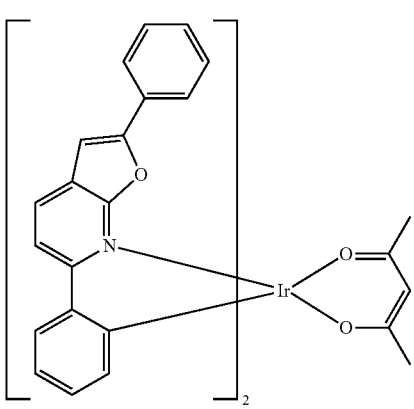

310
-continued

2

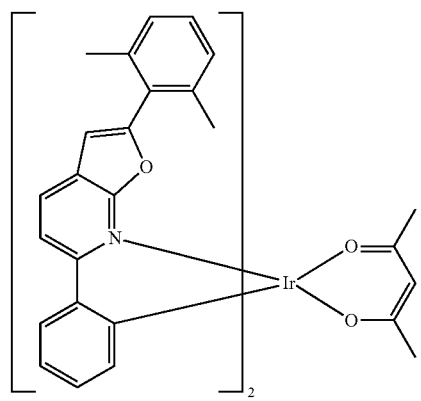

3

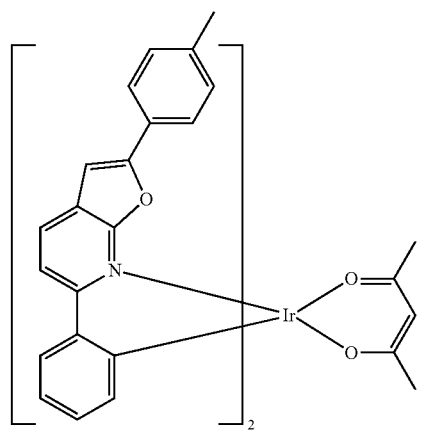

4

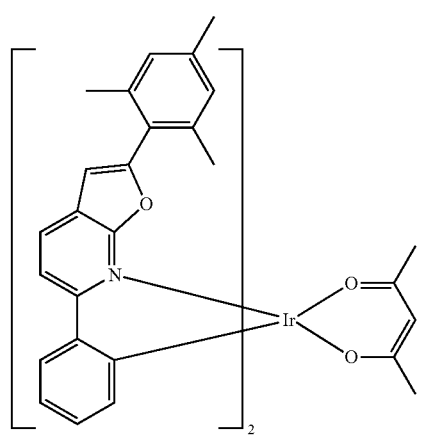

311
-continued
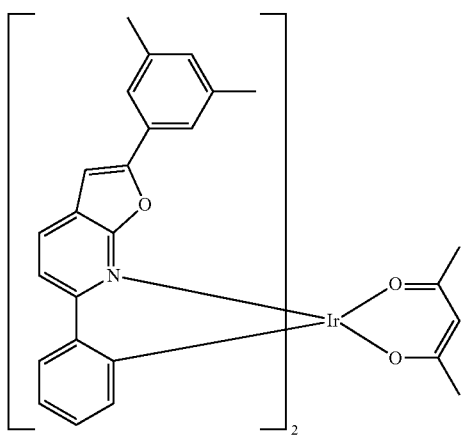
5
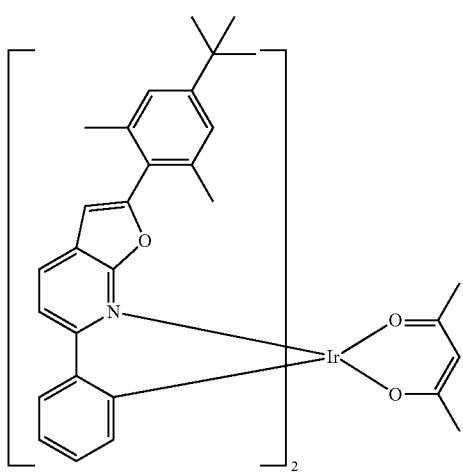
6
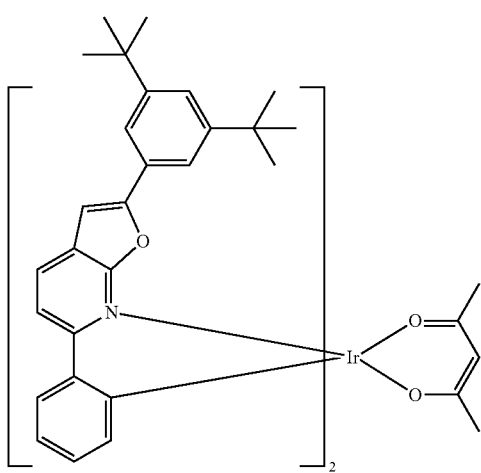
7
312
-continued
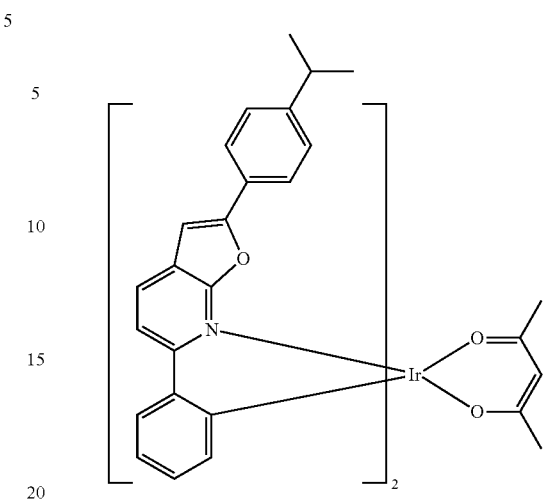
8
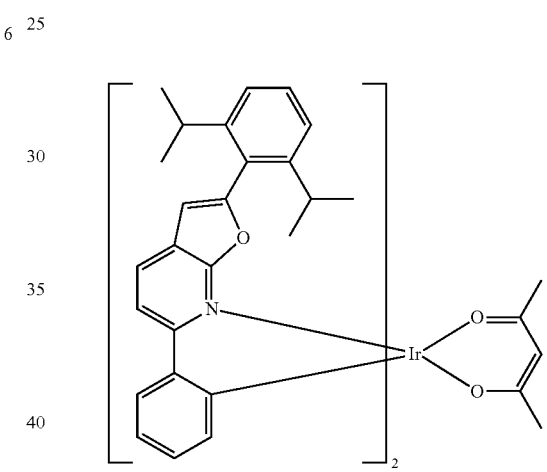
9
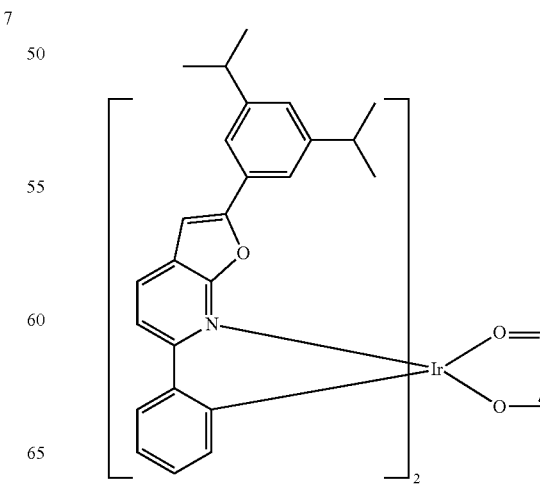
10

11
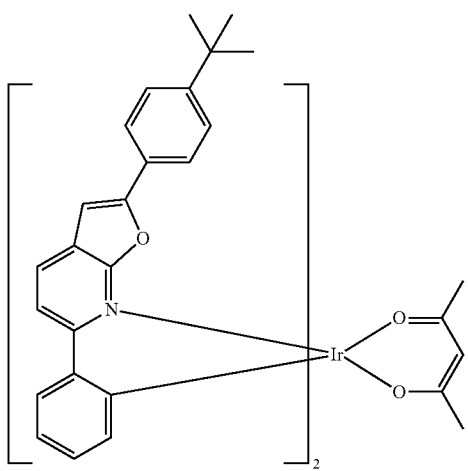
12
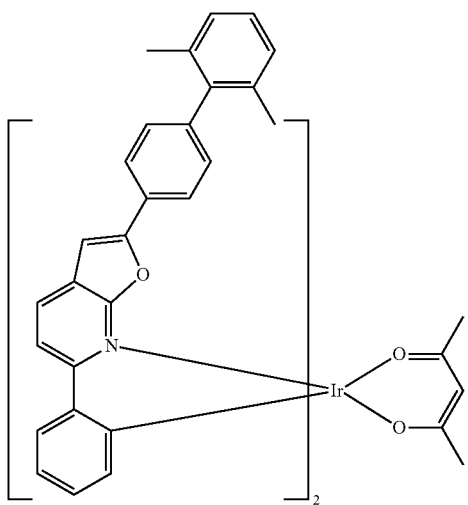
13
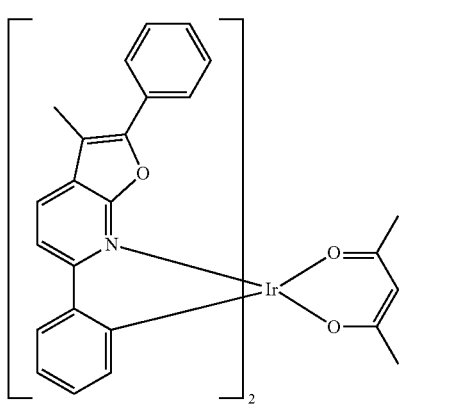
14
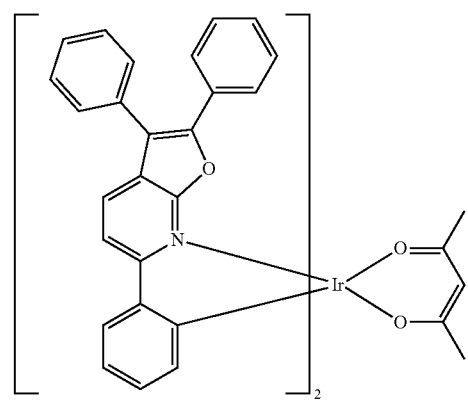
15
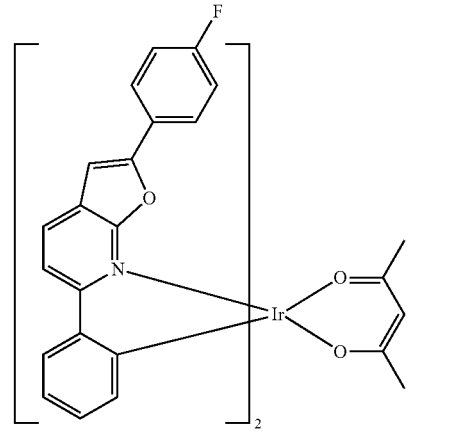
16
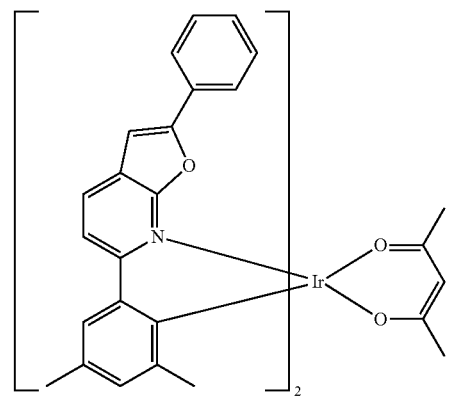
17
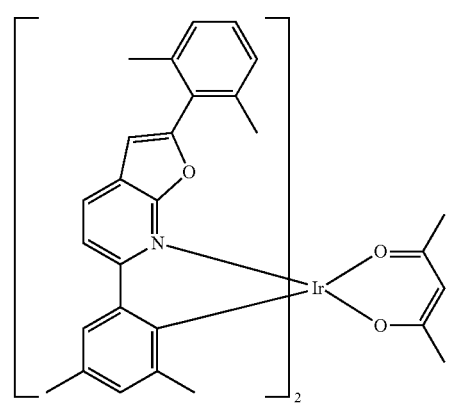

-continued
| 18 | 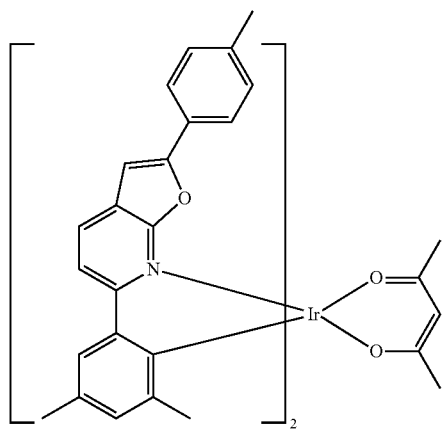 |
| --- | --- |
| 19 | 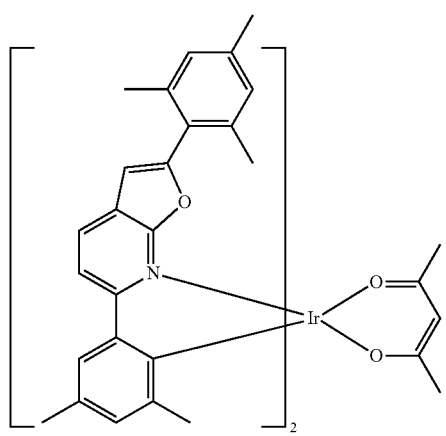 |
| --- | --- |
| 20 | 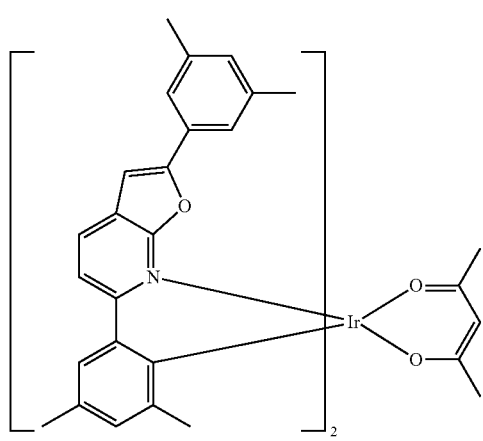 |
| --- | --- |
-continued
| 21 | 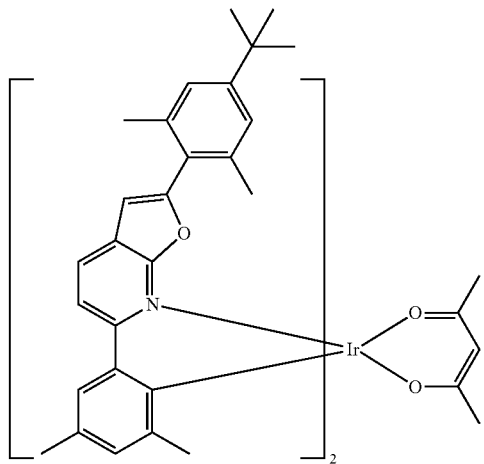 |
| --- | --- |
| 22 | 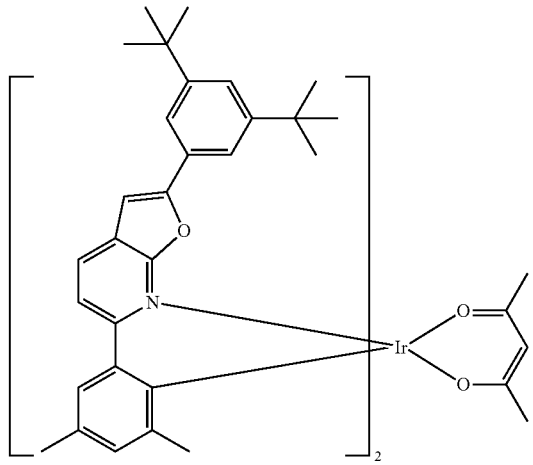 |
| --- | --- |
| 23 | 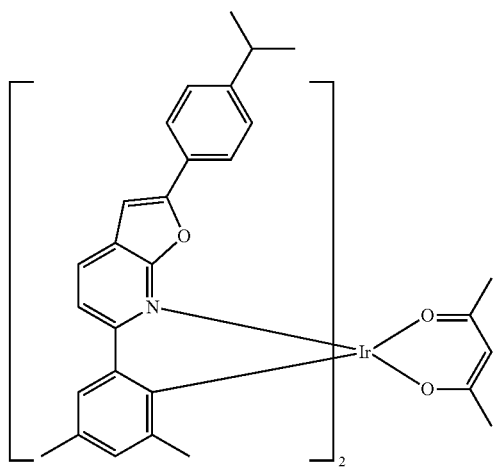 |
| --- | --- |

24
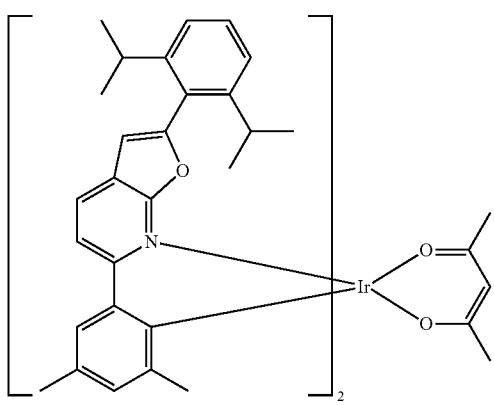
25
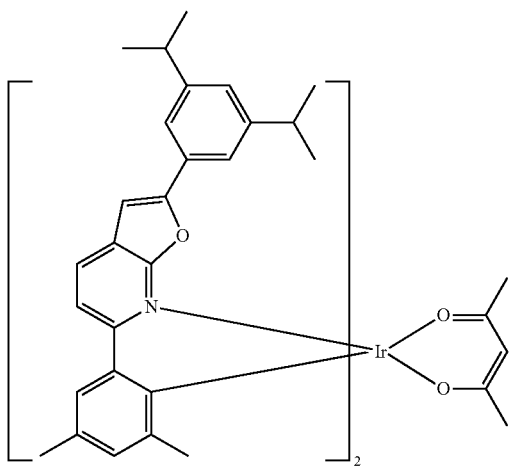
26
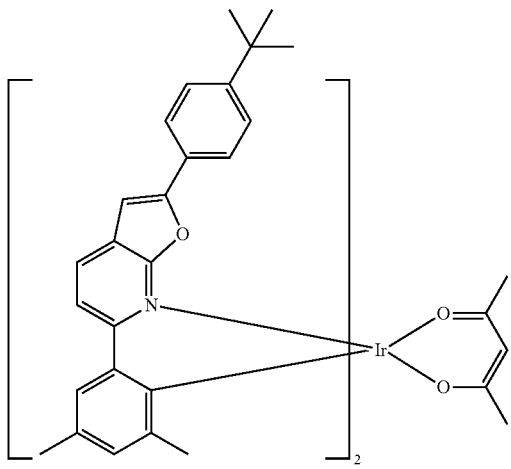
27
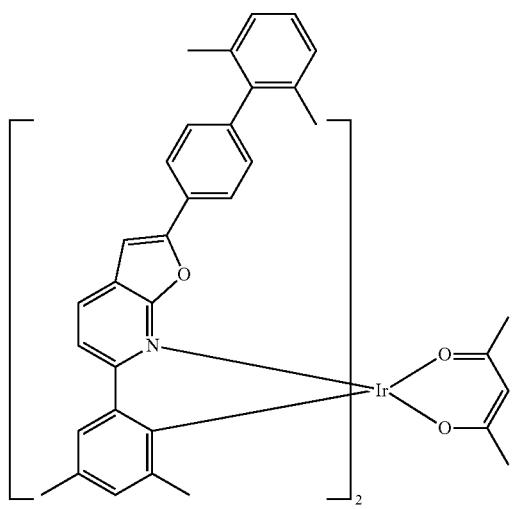
28
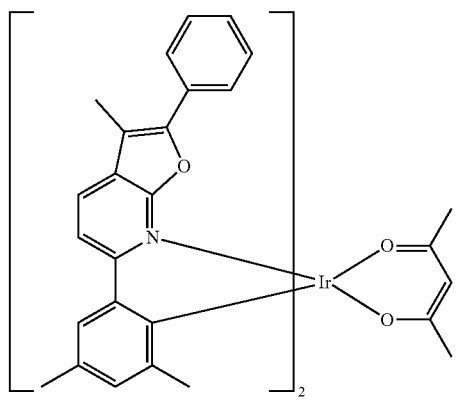
29
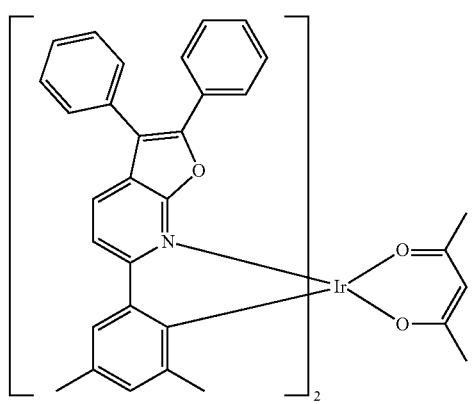

319
30
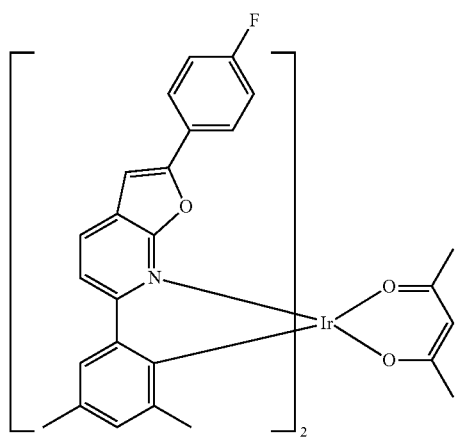
31
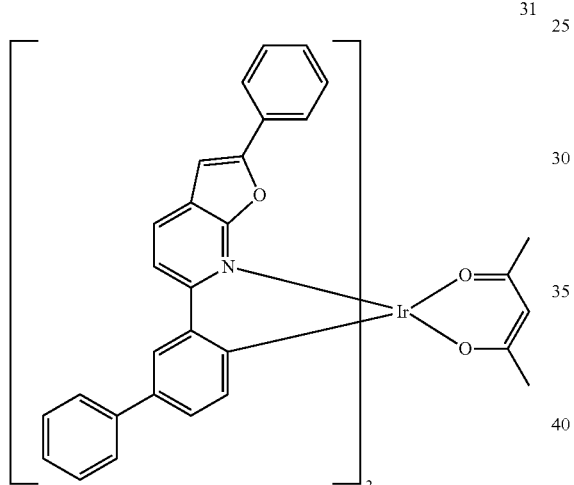
32
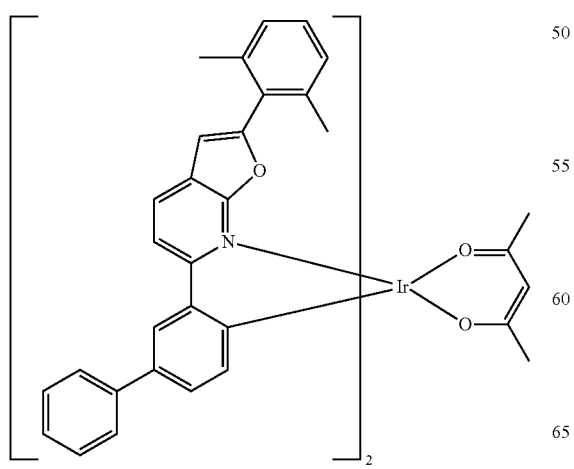
320
33
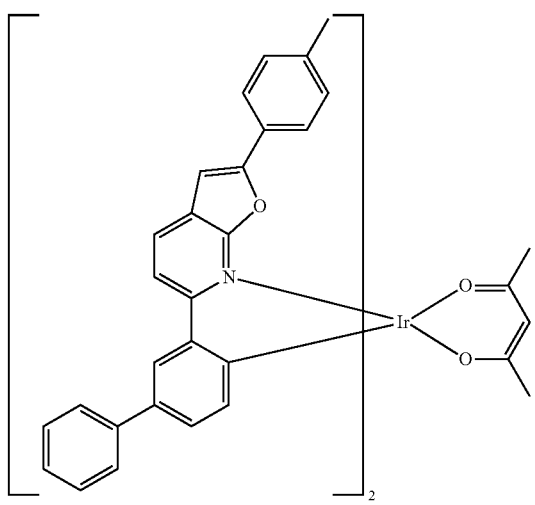
34
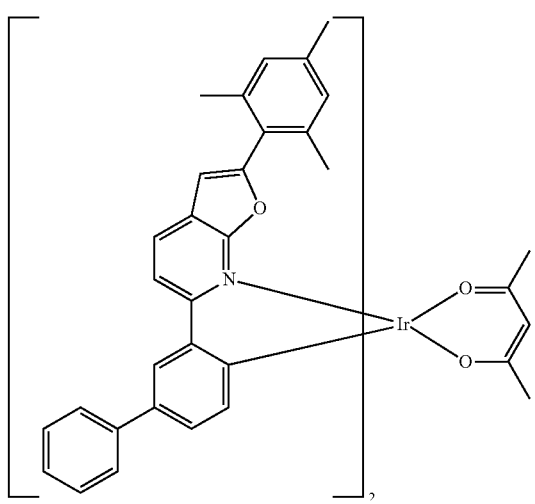
35
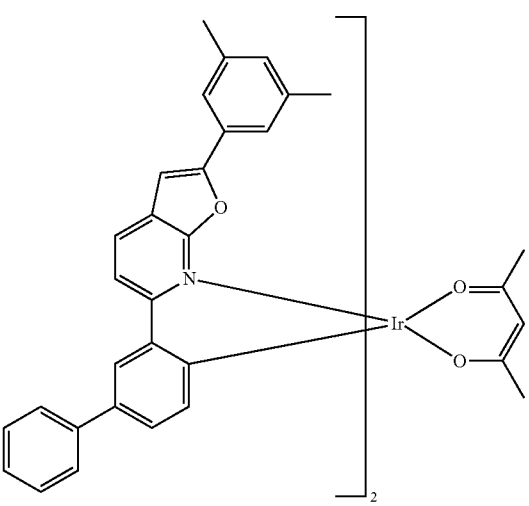

321 -continued
36
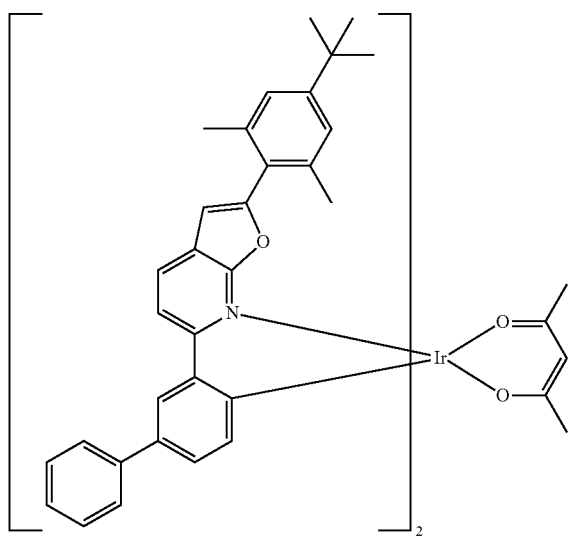
37
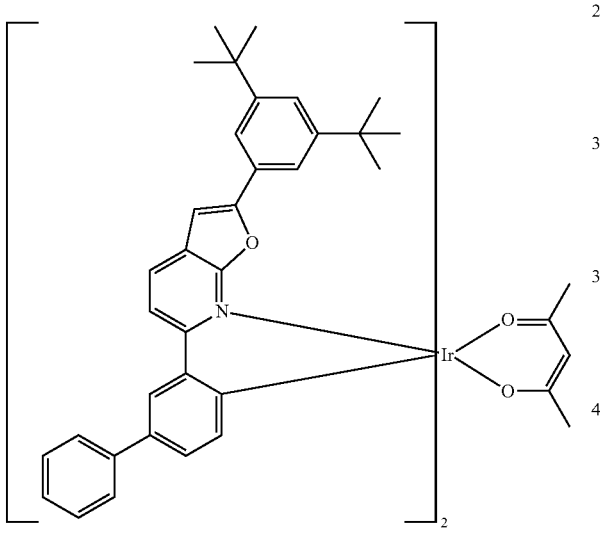
38
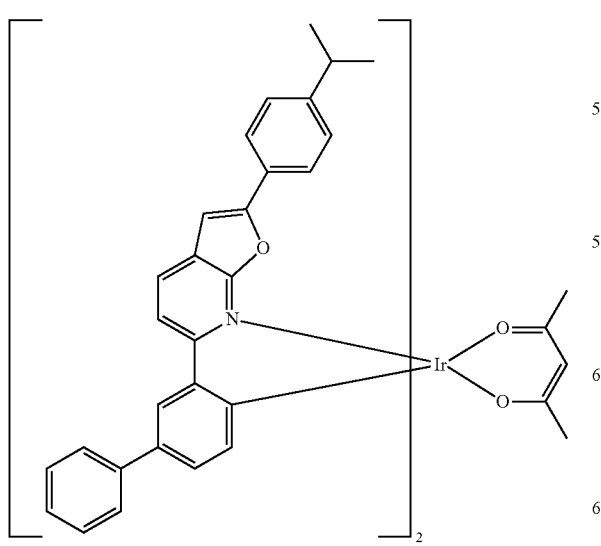
322 -continued
39
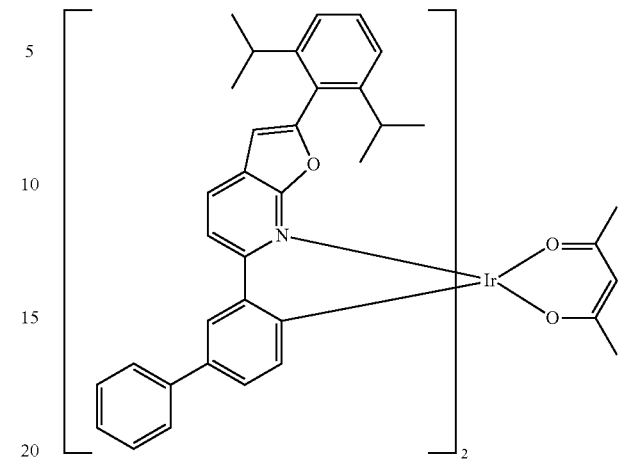
40
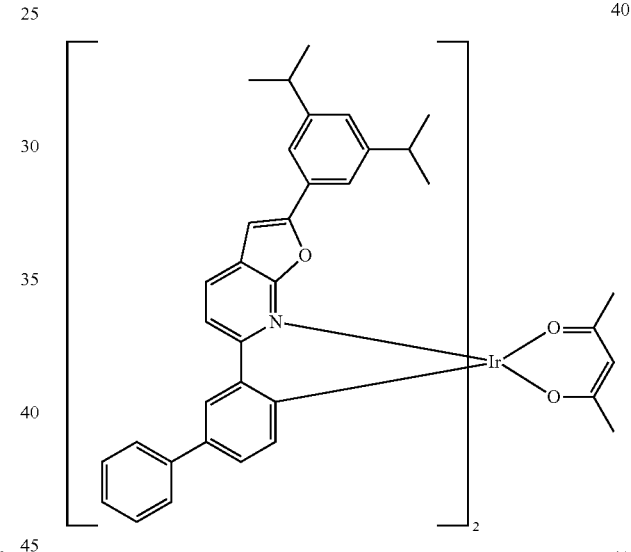
41
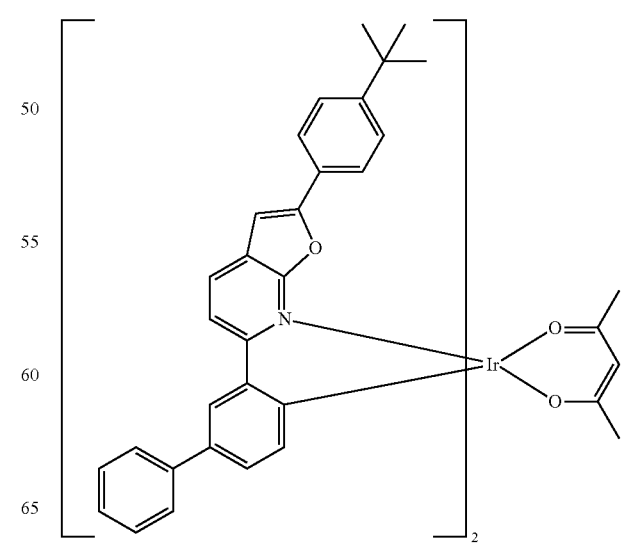

42
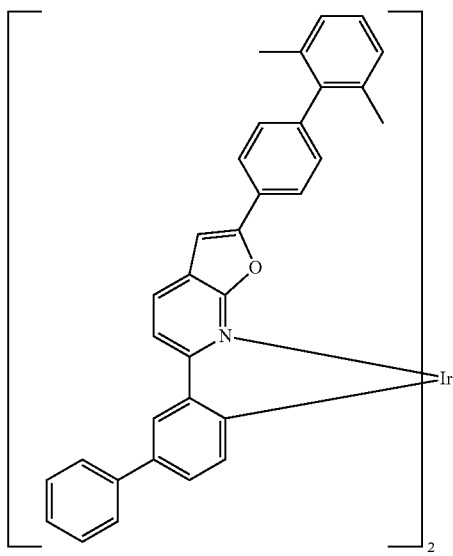
43
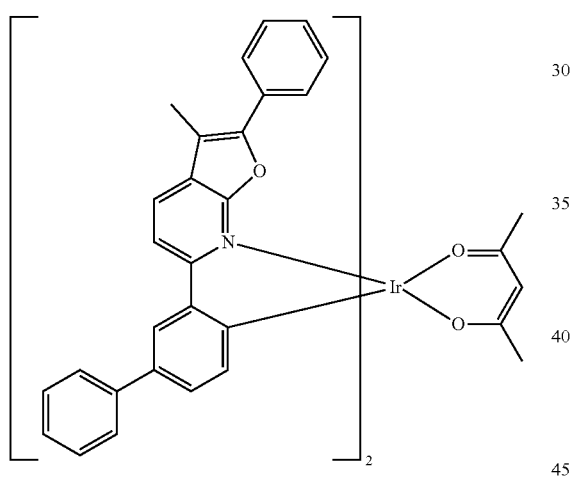
44
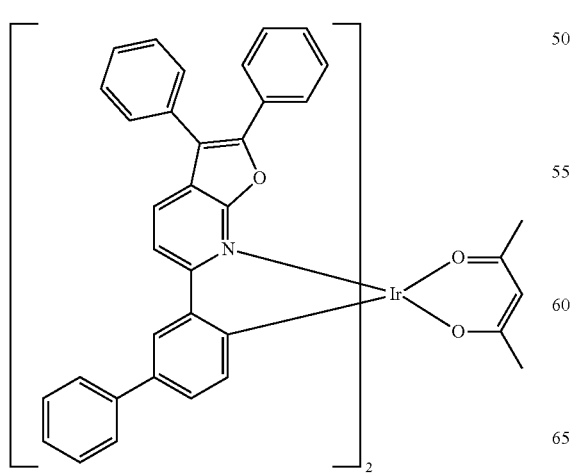
45
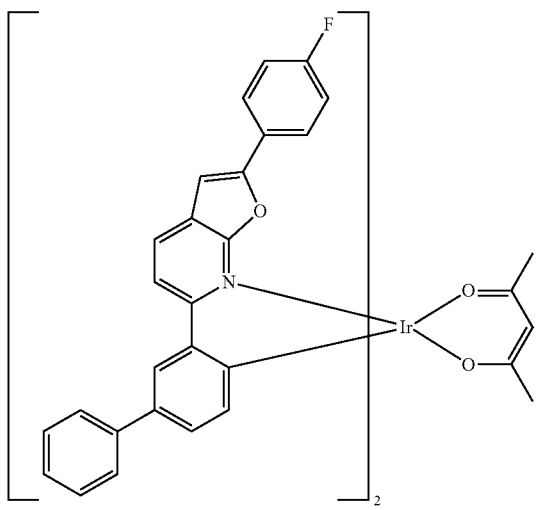
46
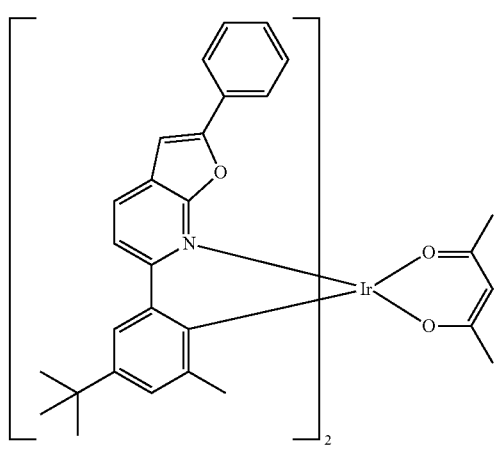
47
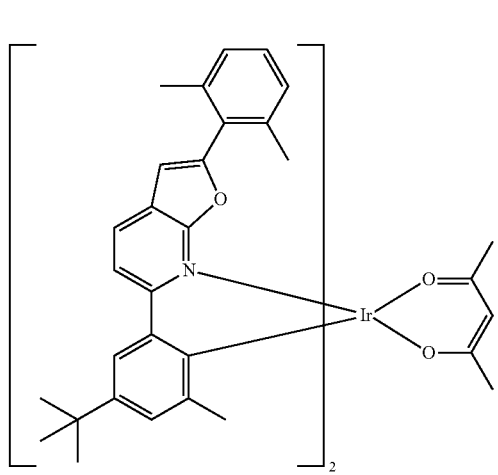

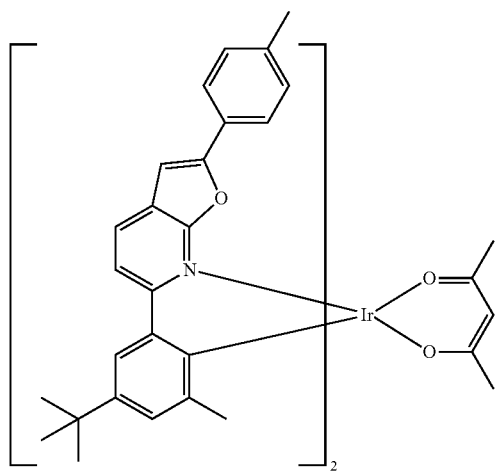
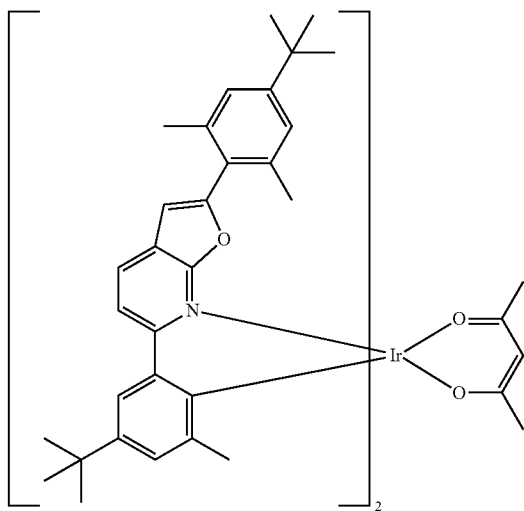
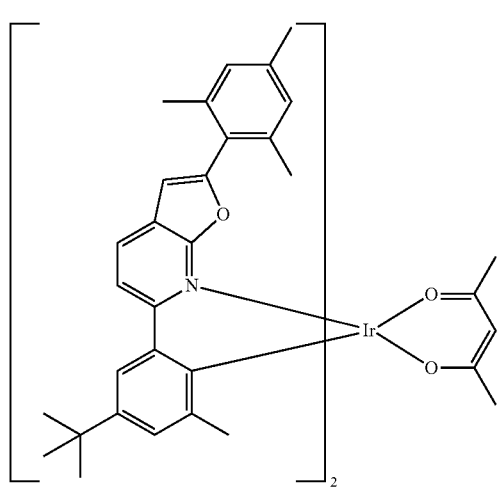
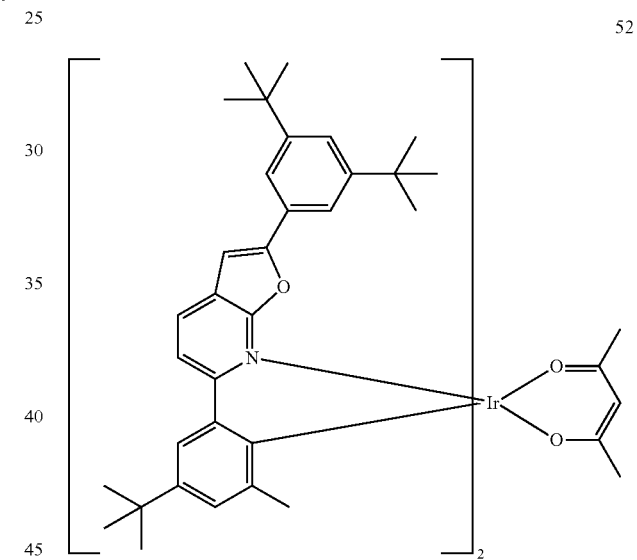
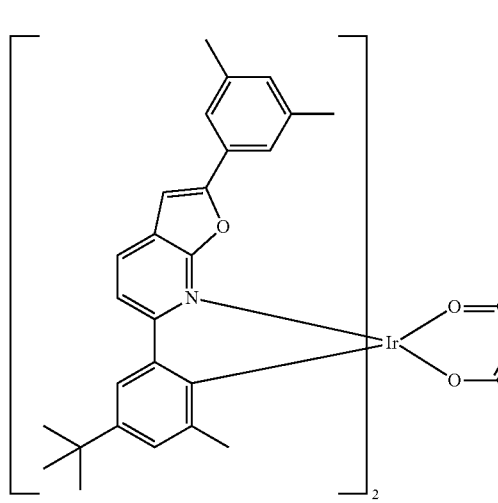
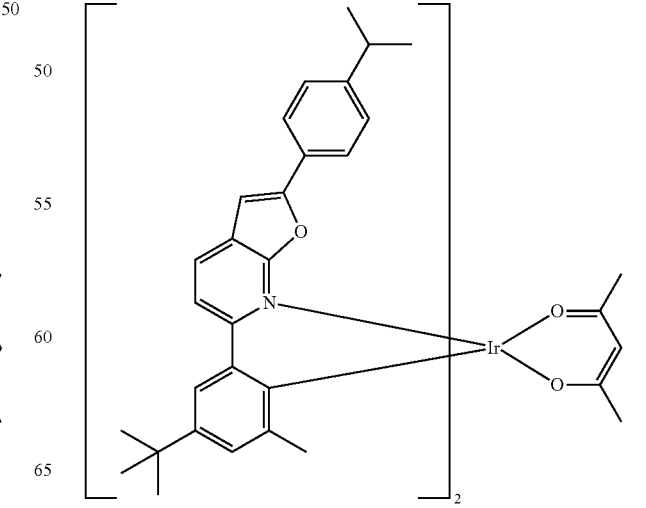

54
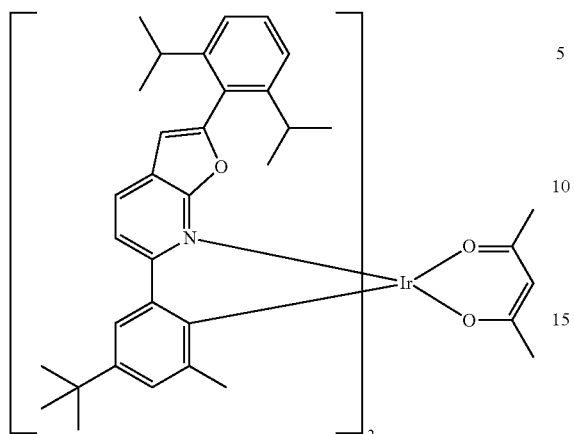
55
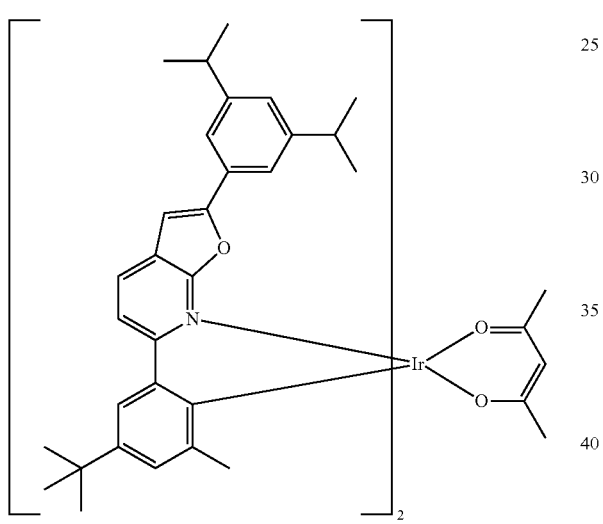
56
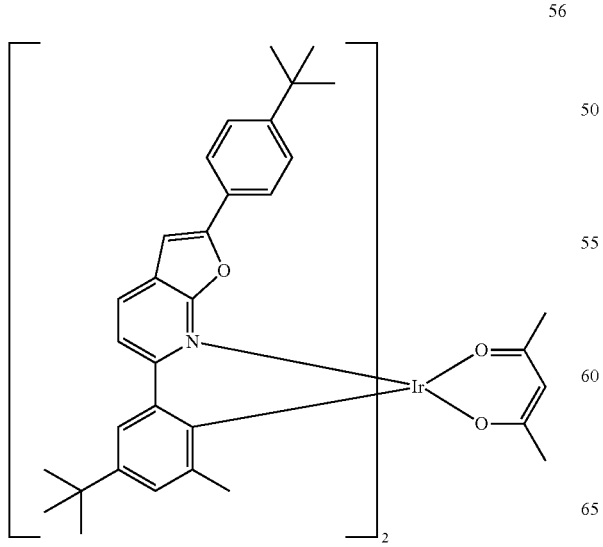
57
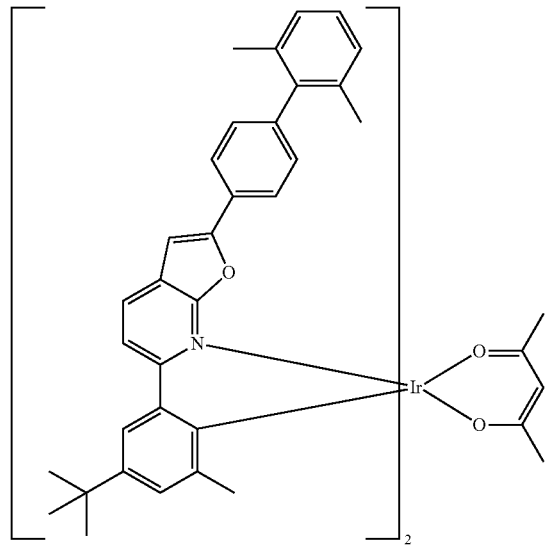
58
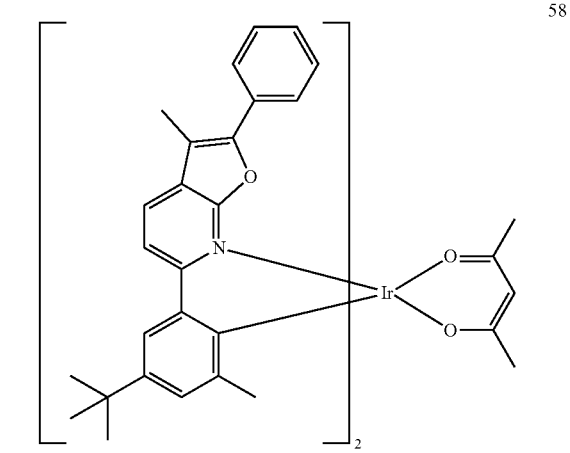
59
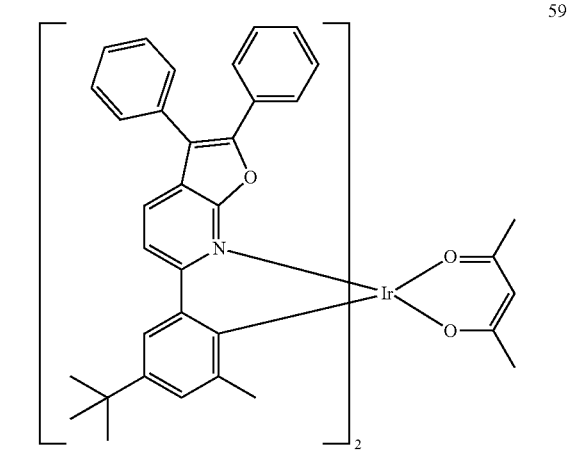

329
-continued
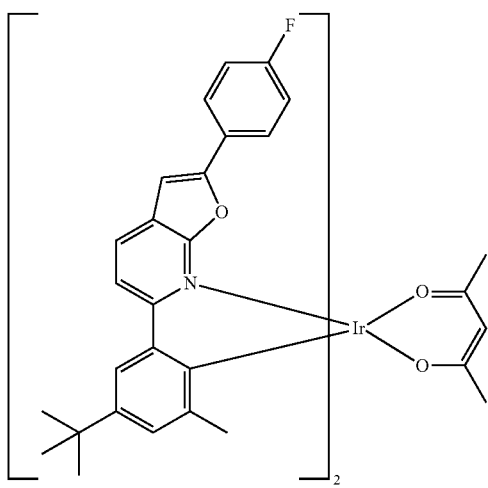
60
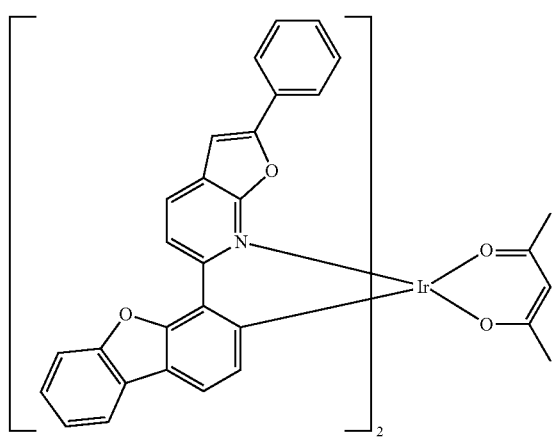
61
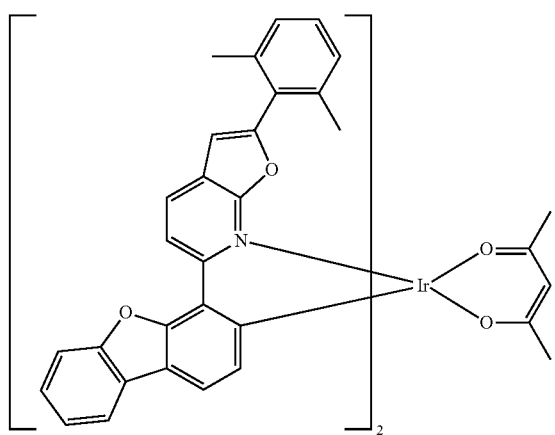
62
330
-continued
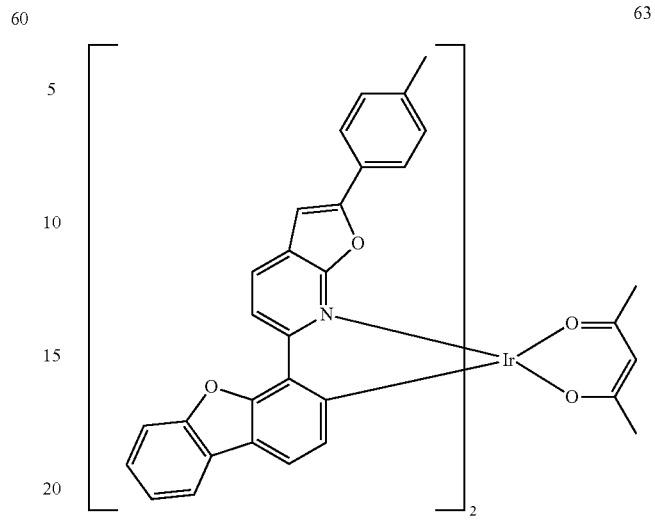
63
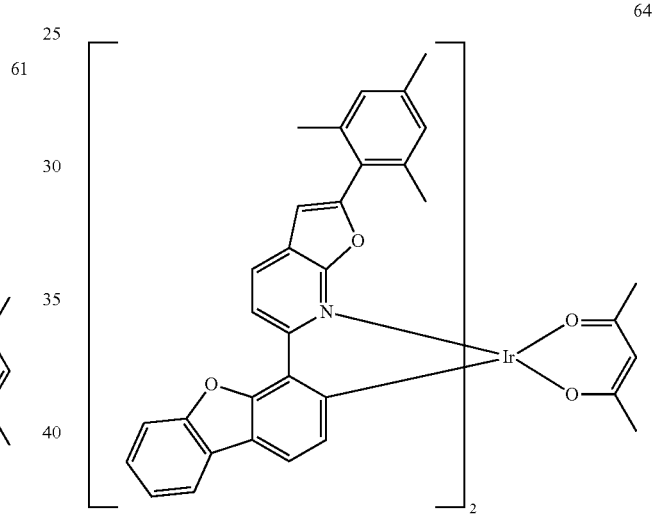
64
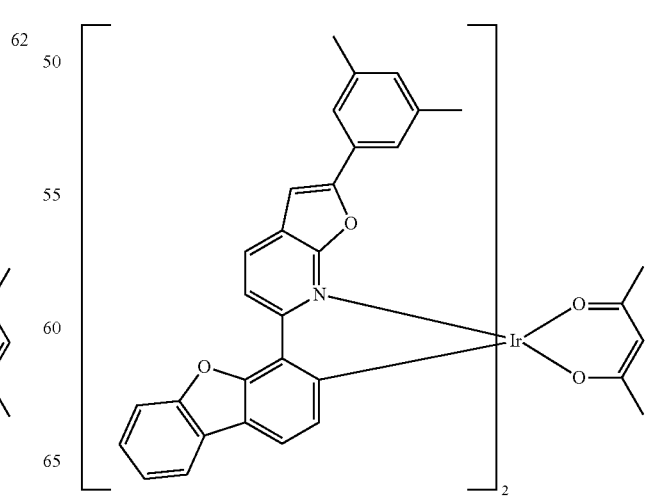
65

331
-continued
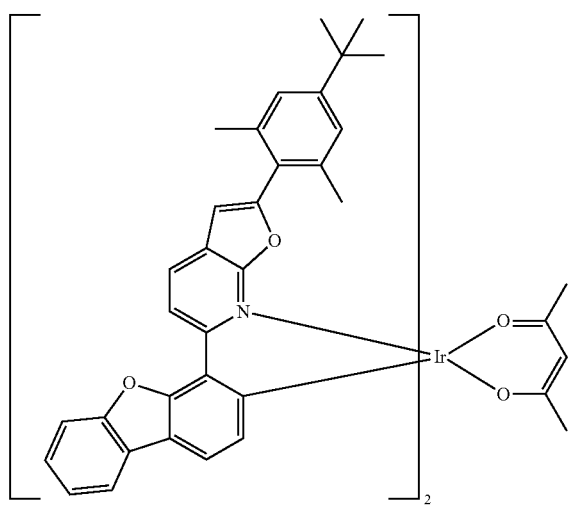
66
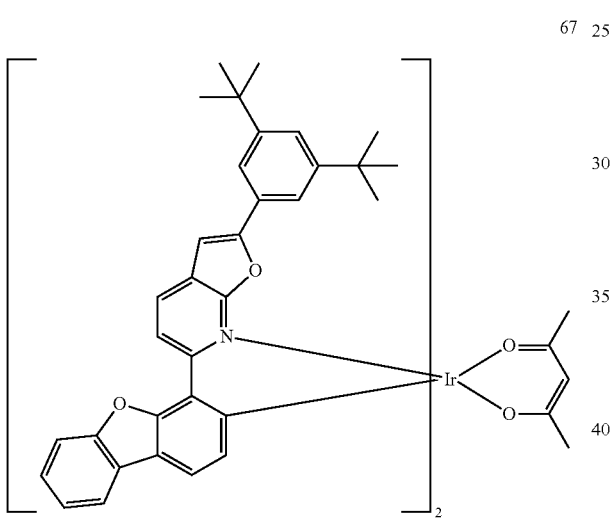
67
68
332
-continued
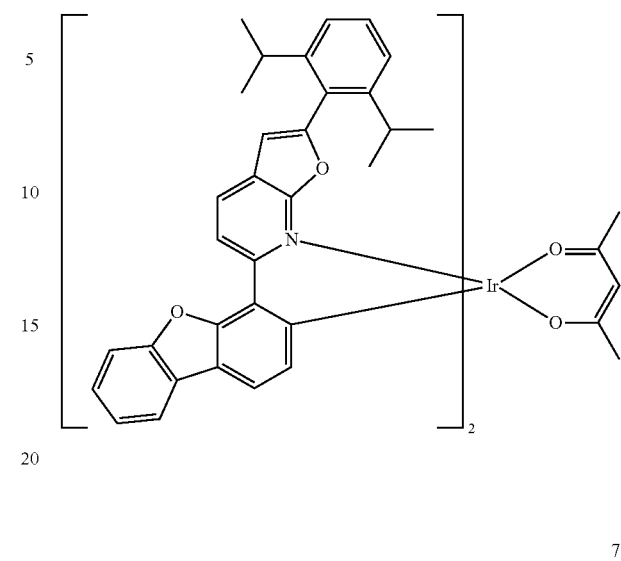
69
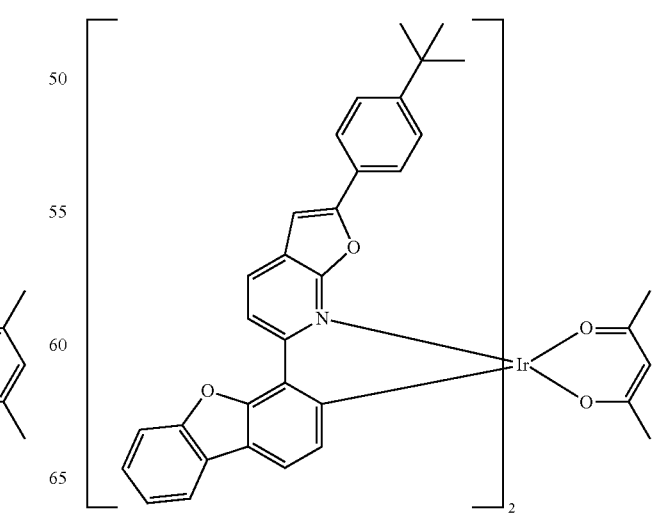
70
71

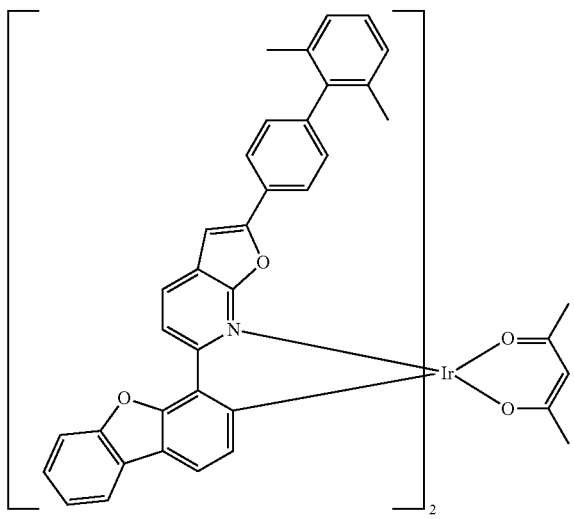
72
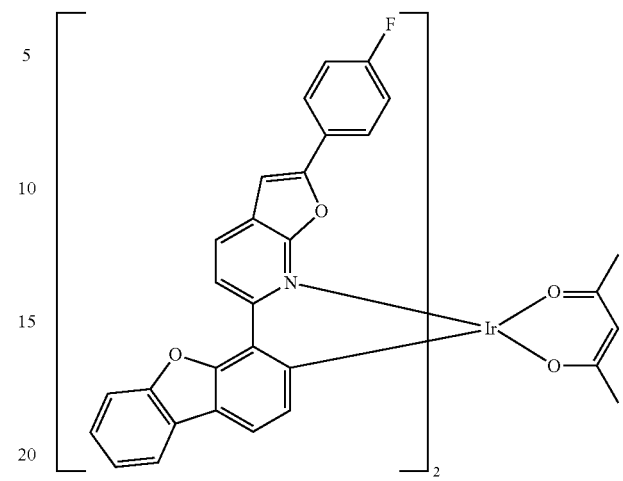
75
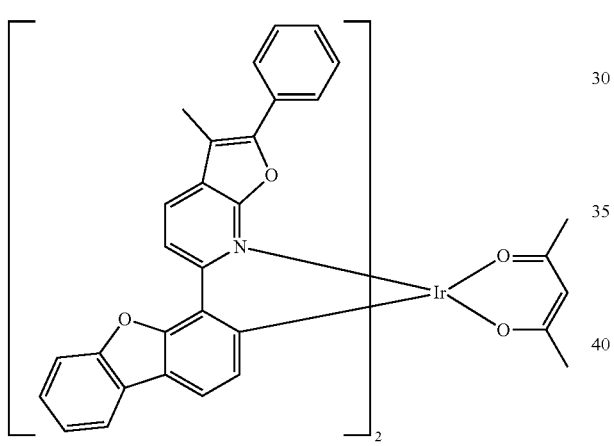
73
76
74
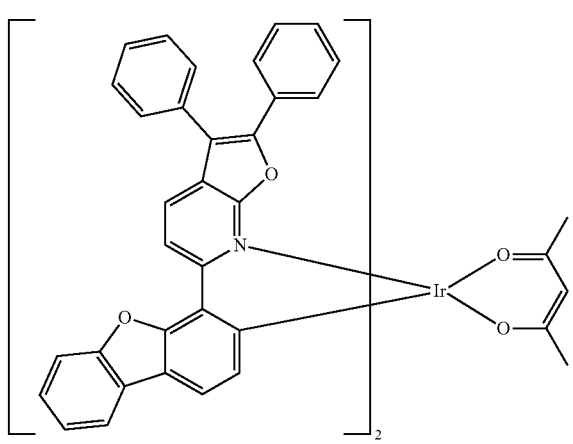
77

78
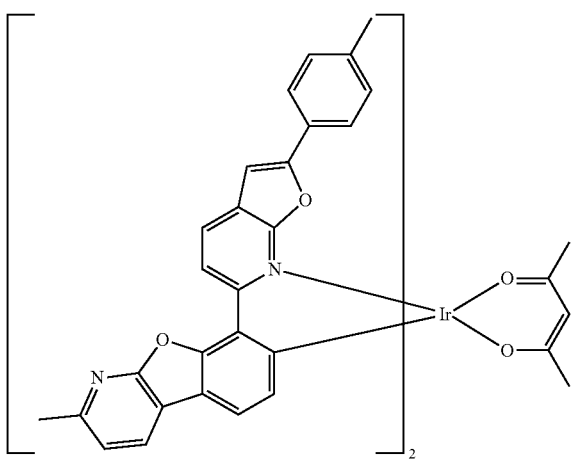
79
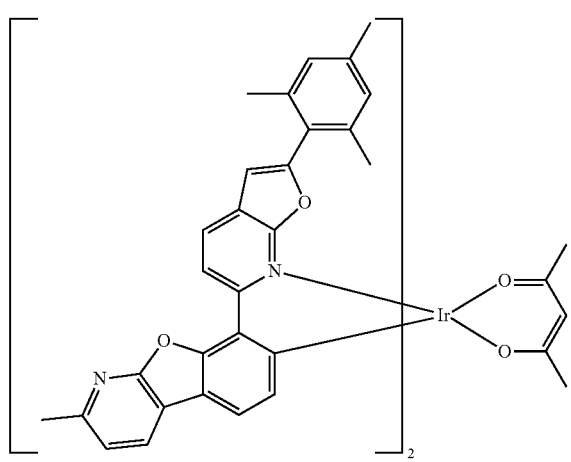
80
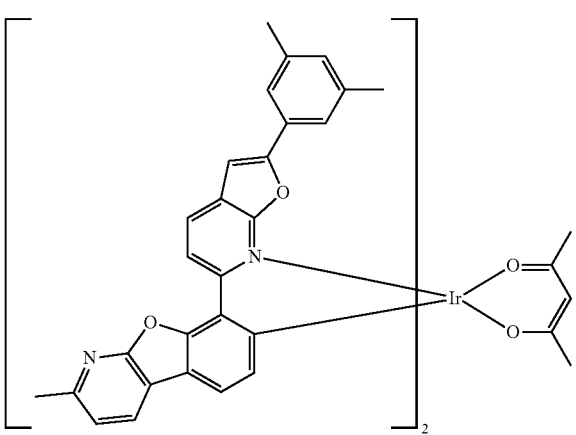
81
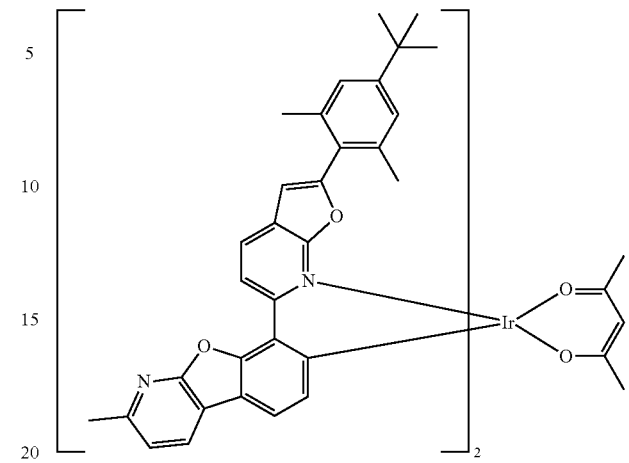
82
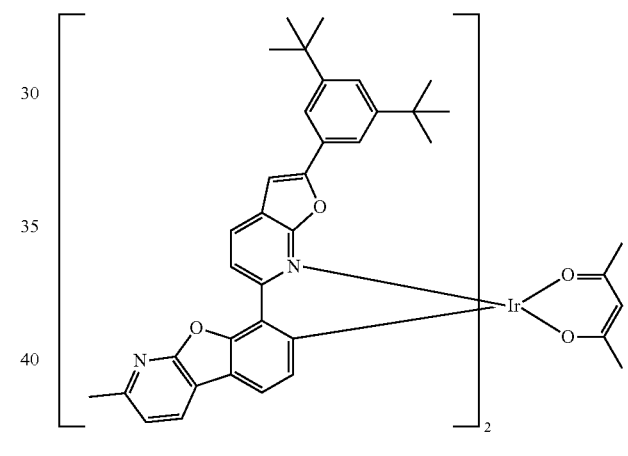
83
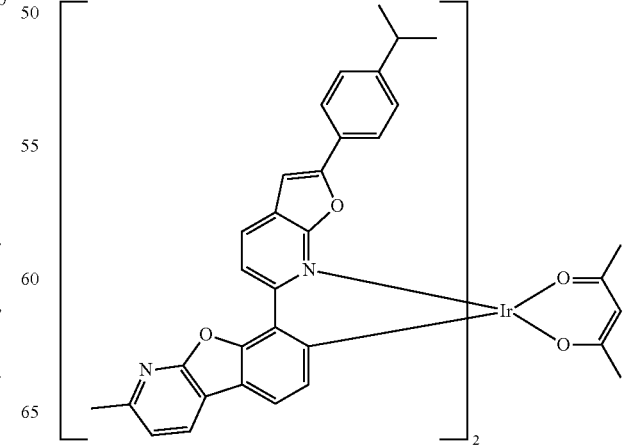

337
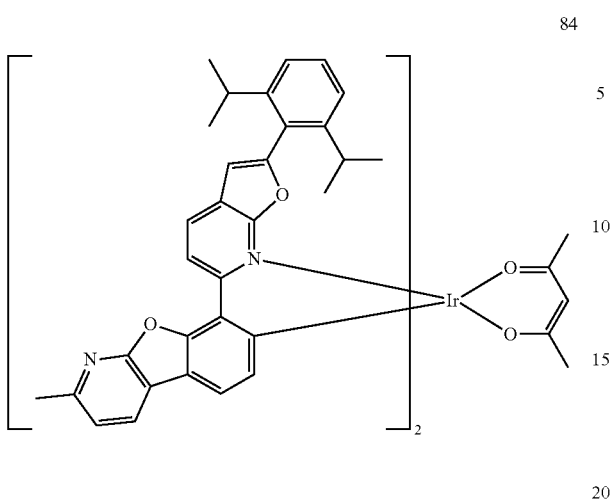
84
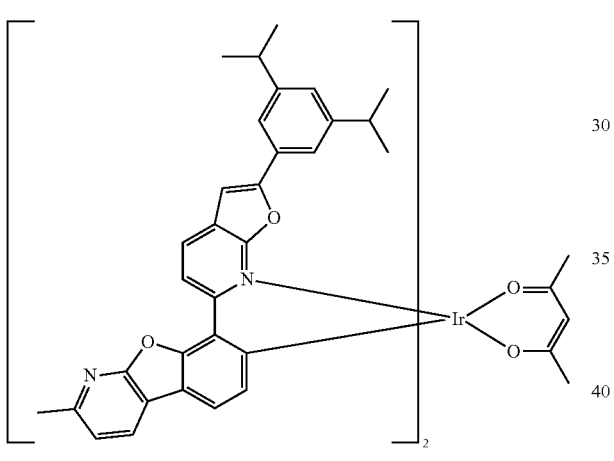
85
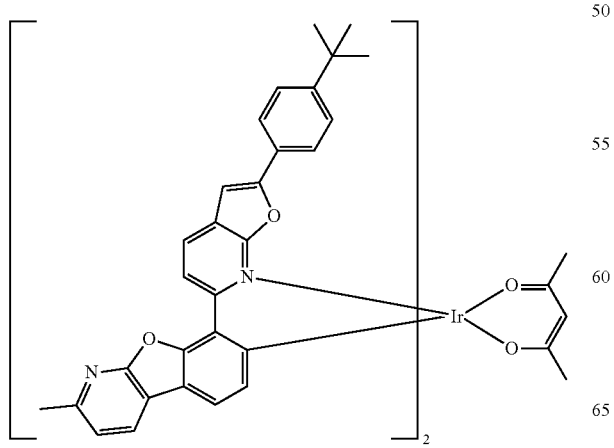
86
338
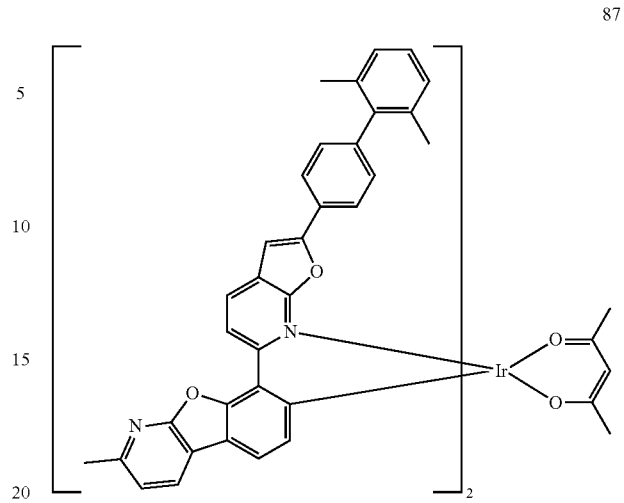
87
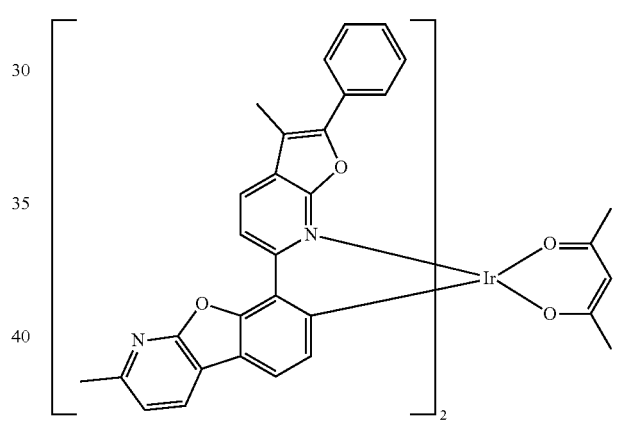
88
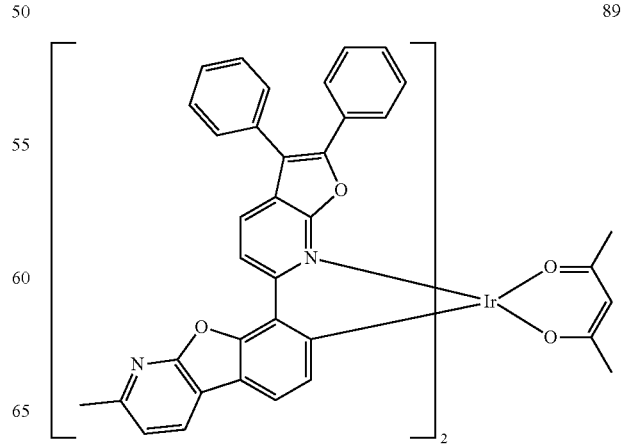
89

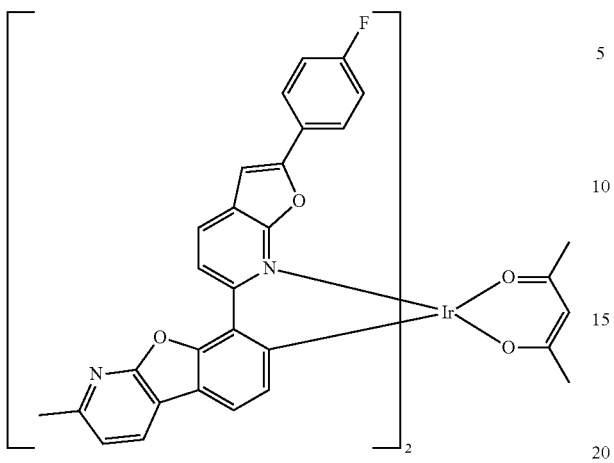
90
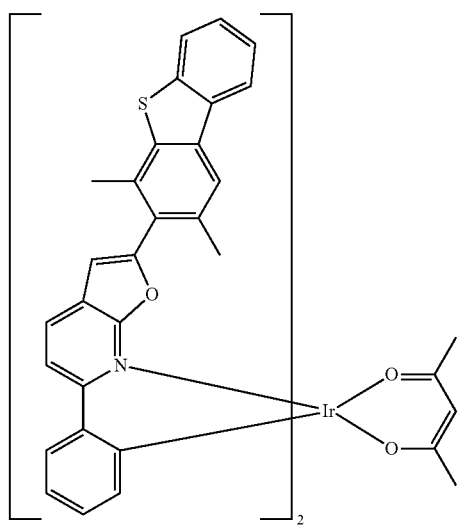
93
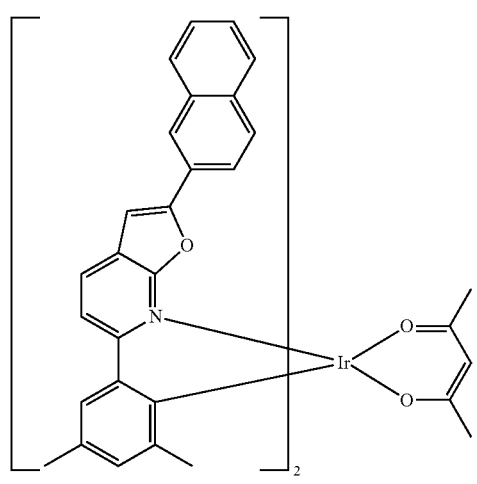
91
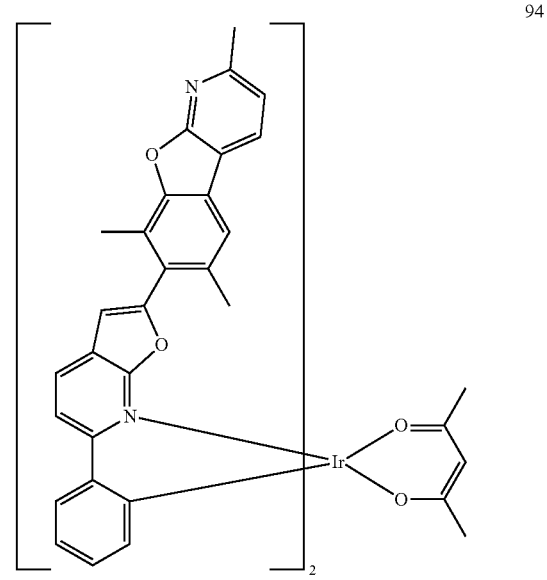
94
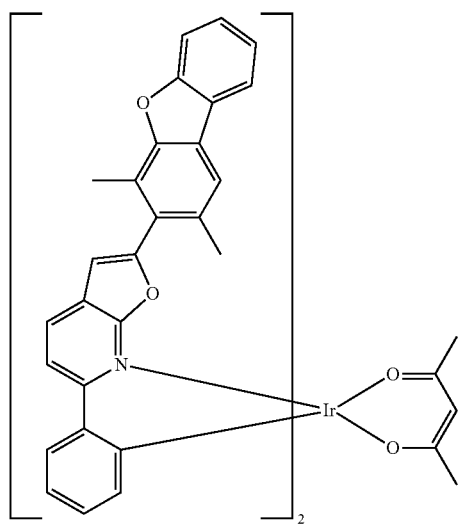
92
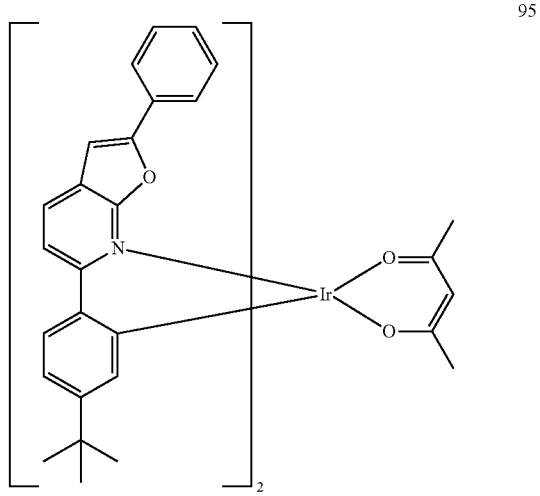
95

96
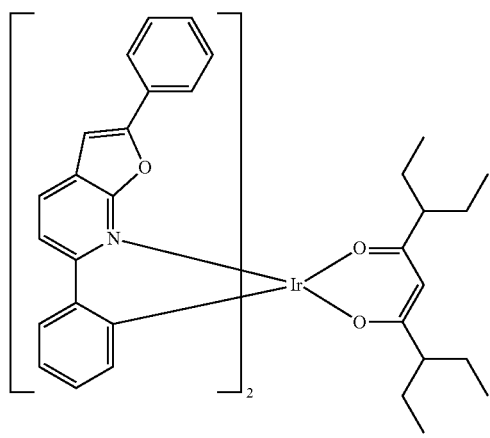
97
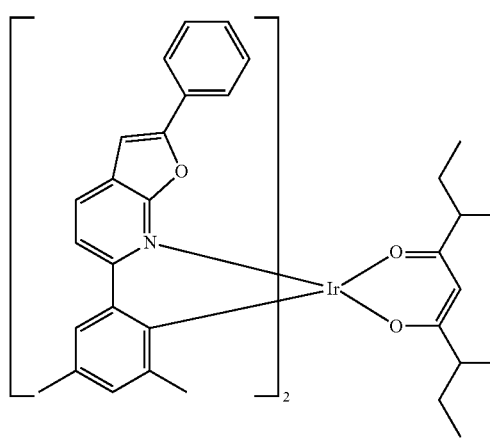
98
99
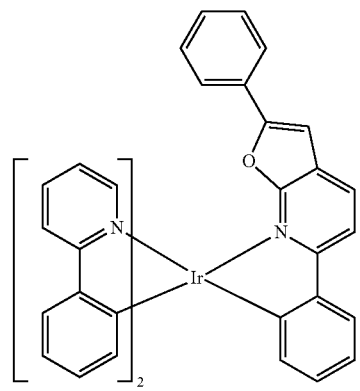
100
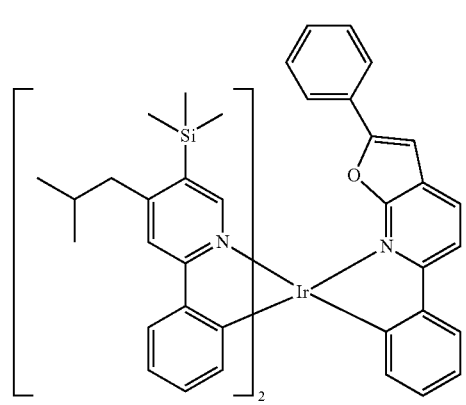
101
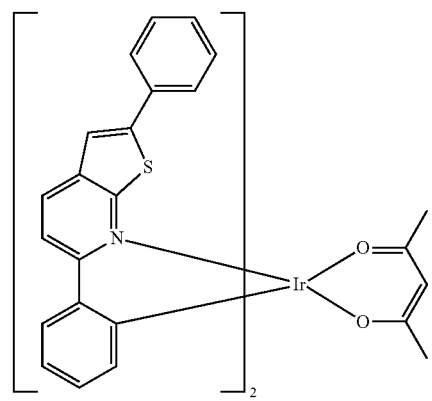
102
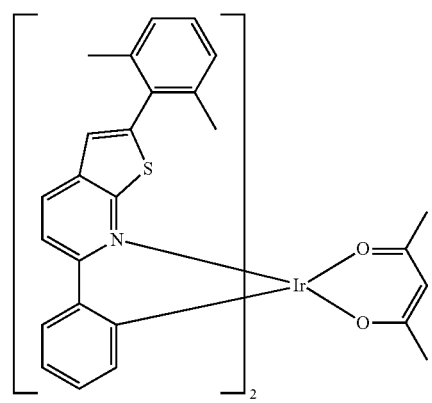

103
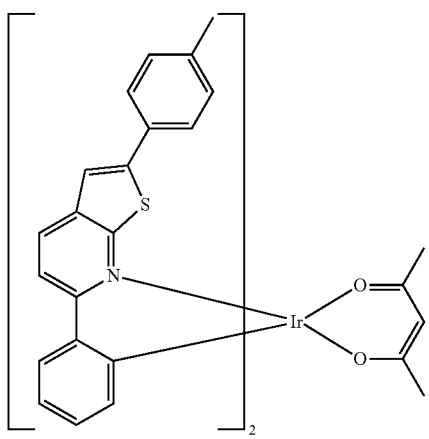
104
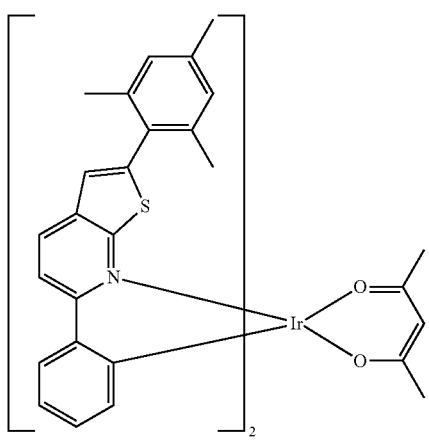
105
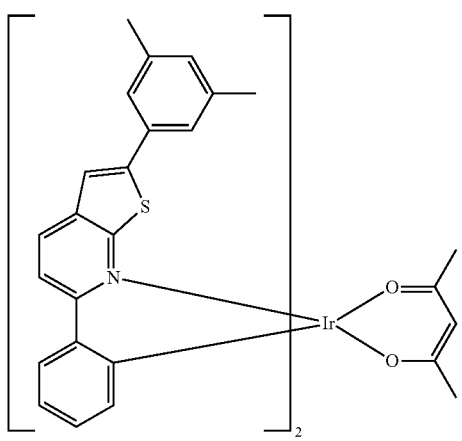
106
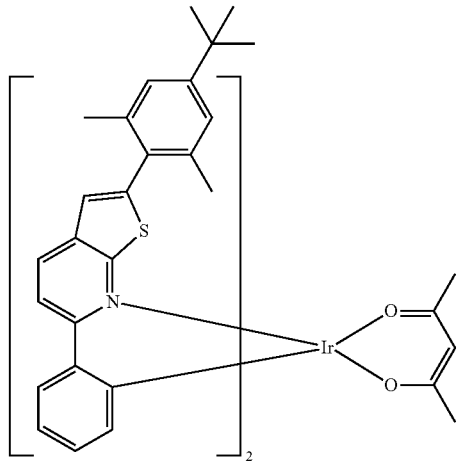
107
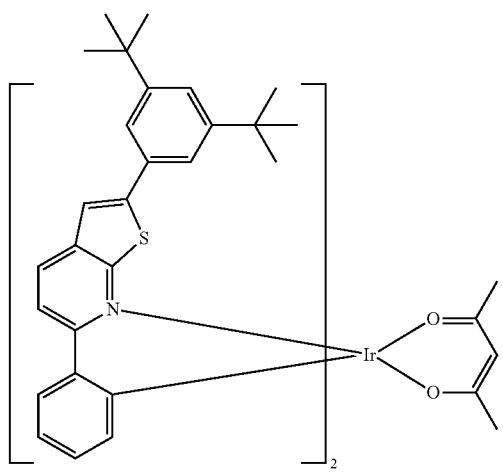
108
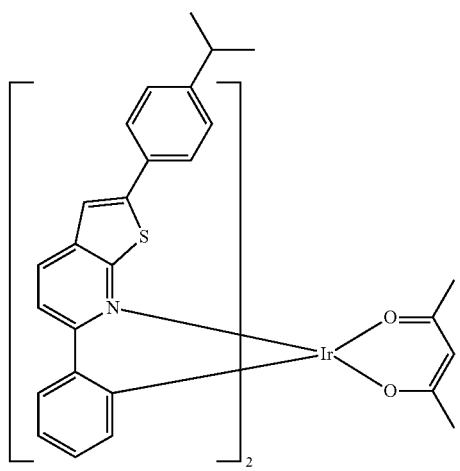

345
-continued
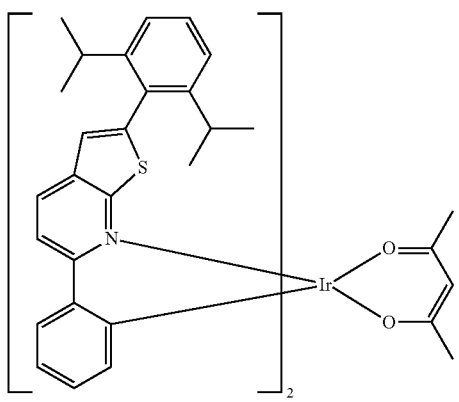
109
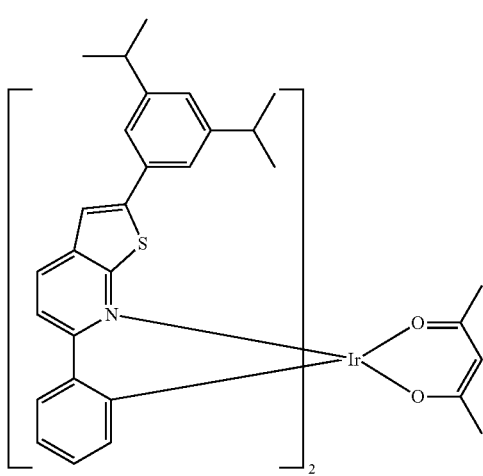
110
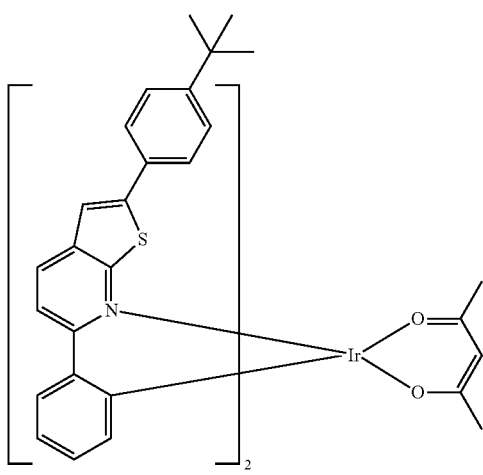
111
346
-continued
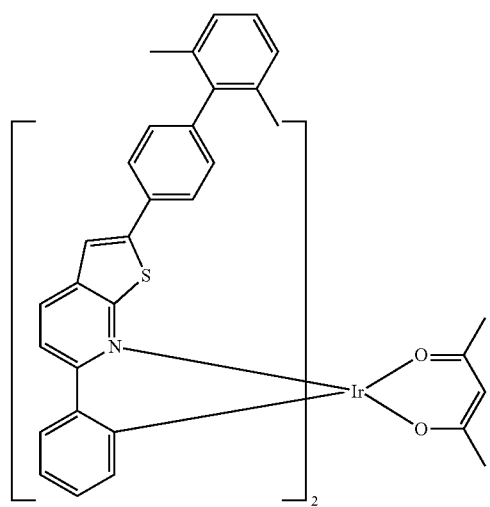
112
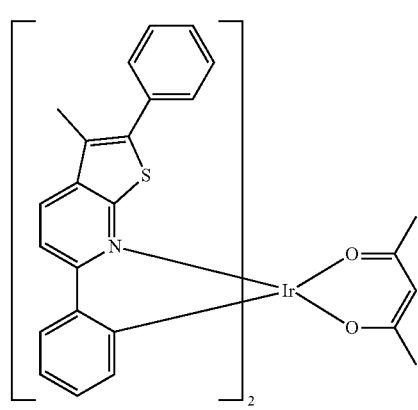
113
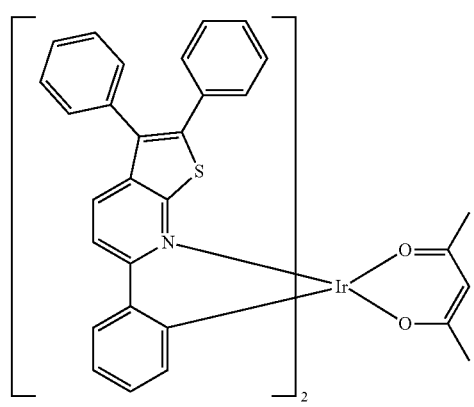
114

347
-continued
115
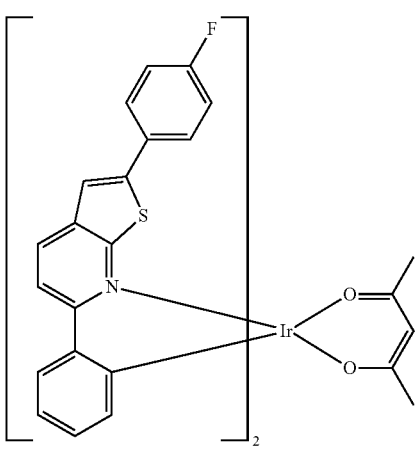
116
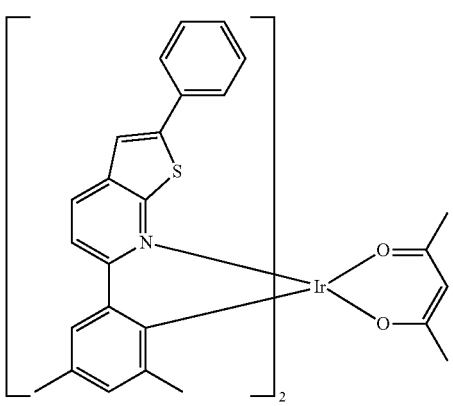
117
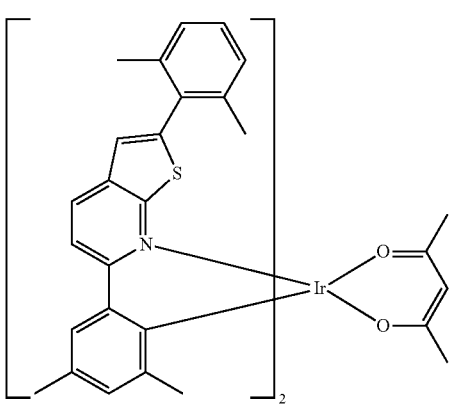
348
-continued
118
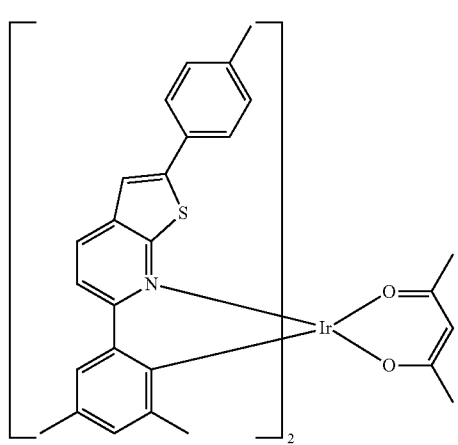
119
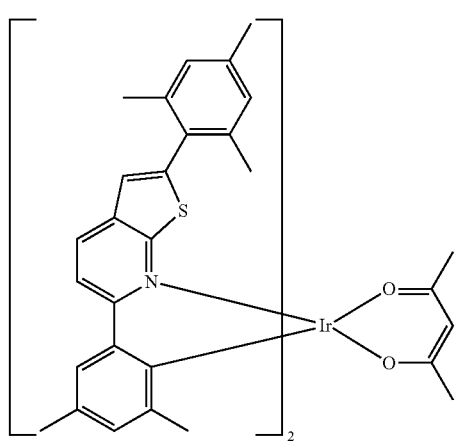
120
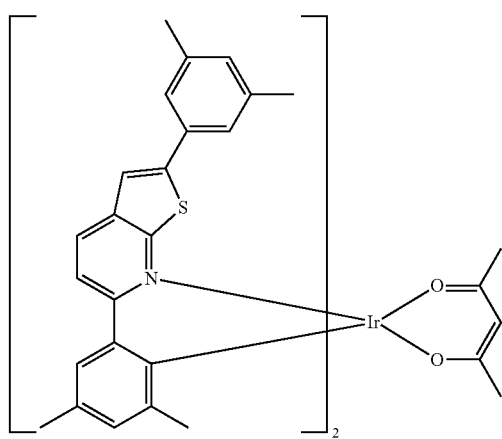

121
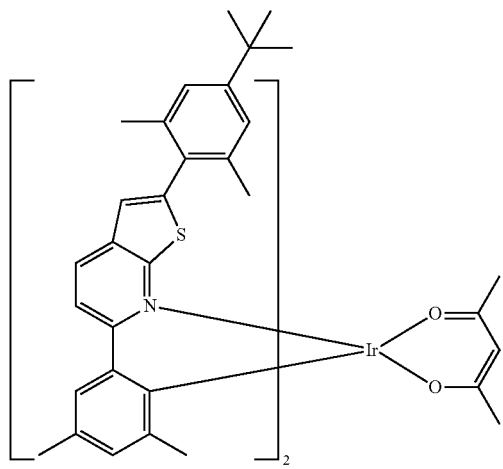
122
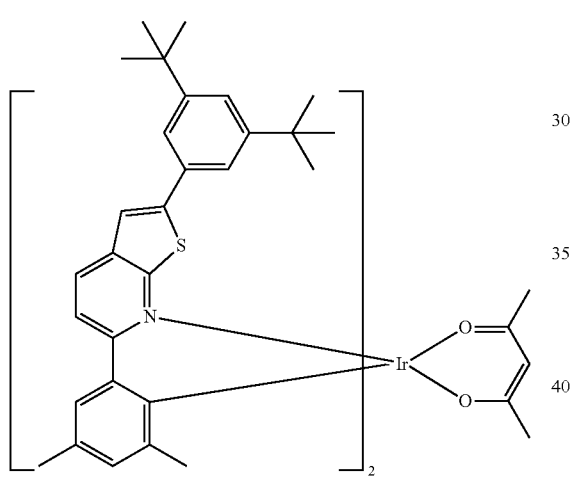
123
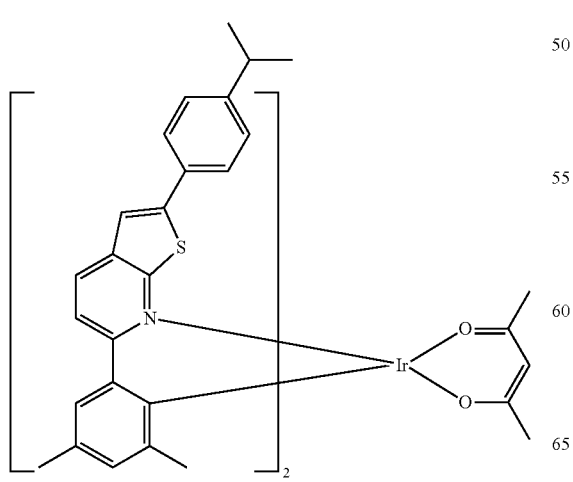
124
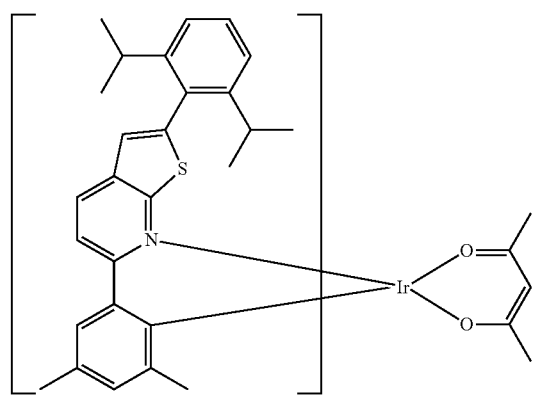
125
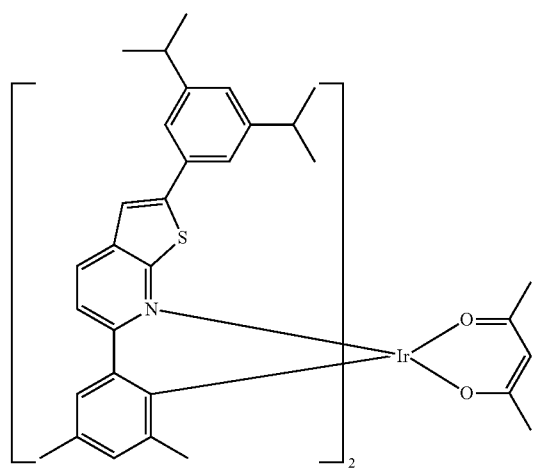
126
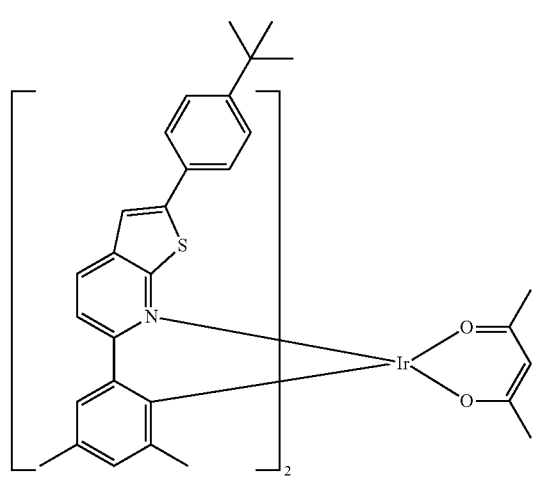

127
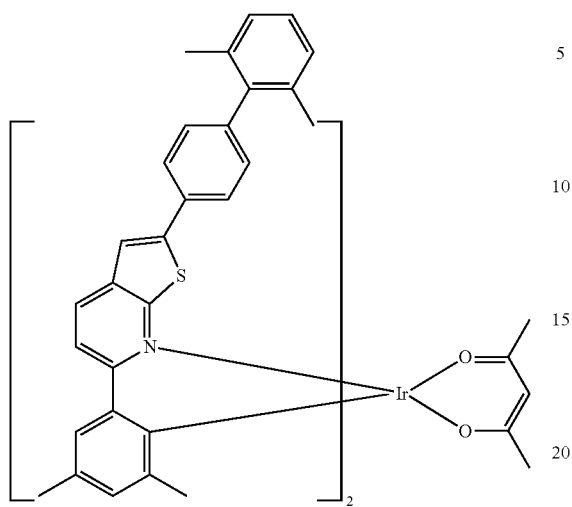
128
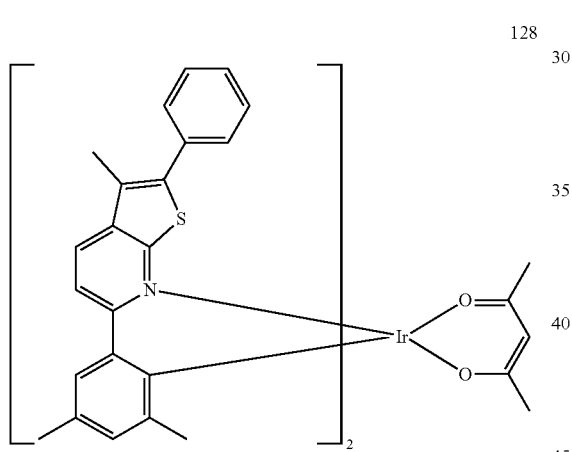
129
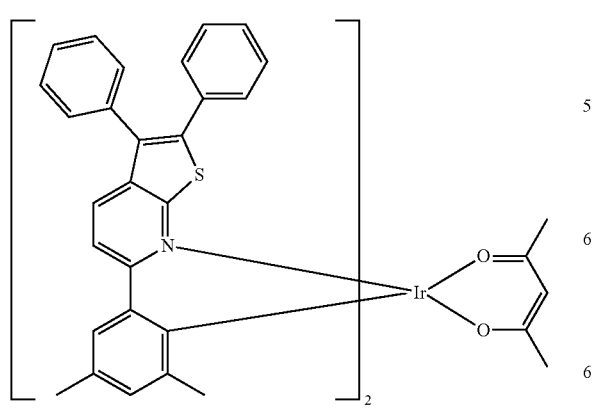
130
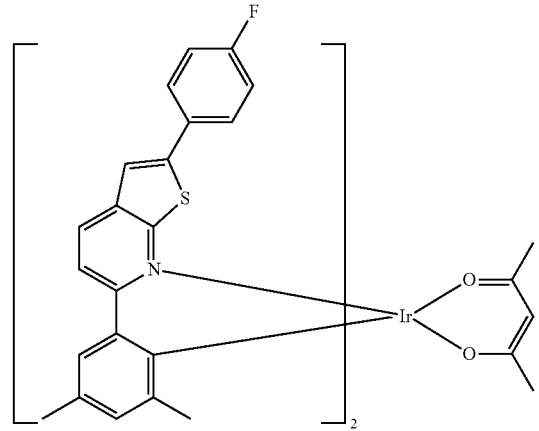
131
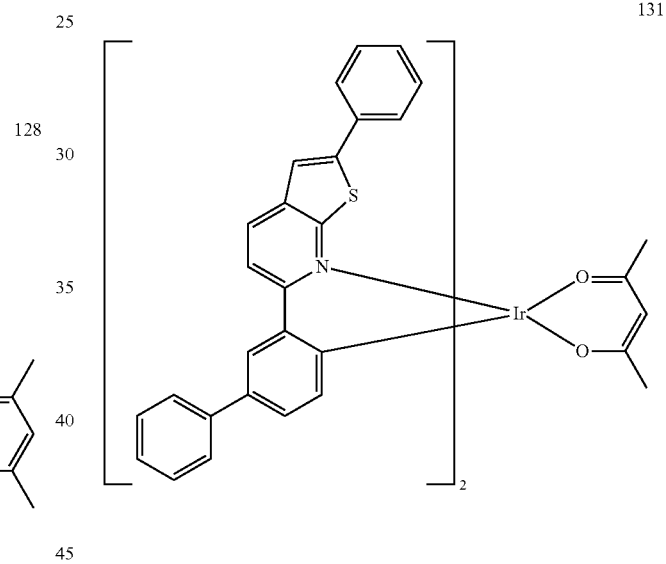
132
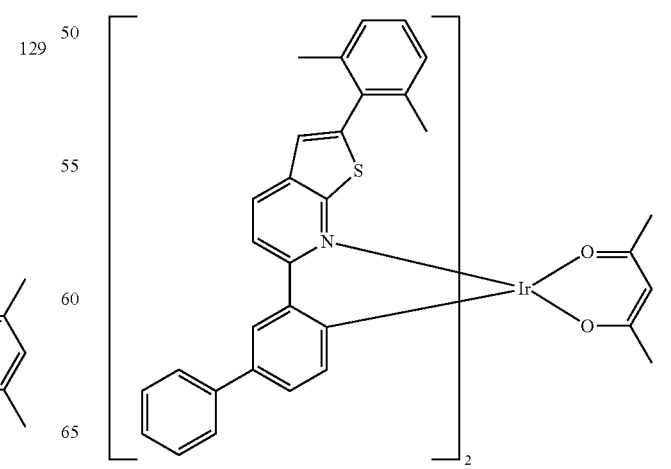

133
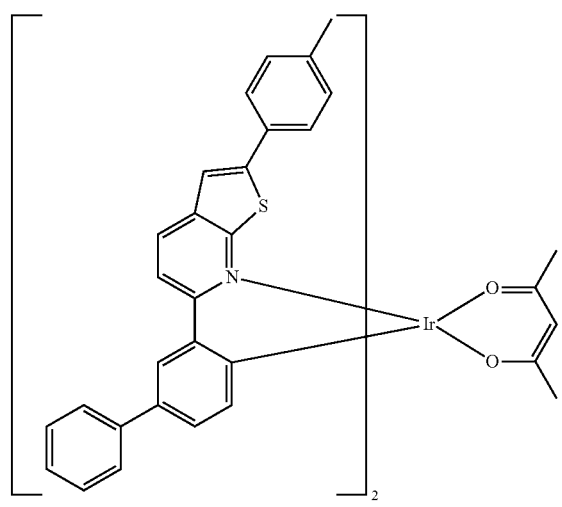
134
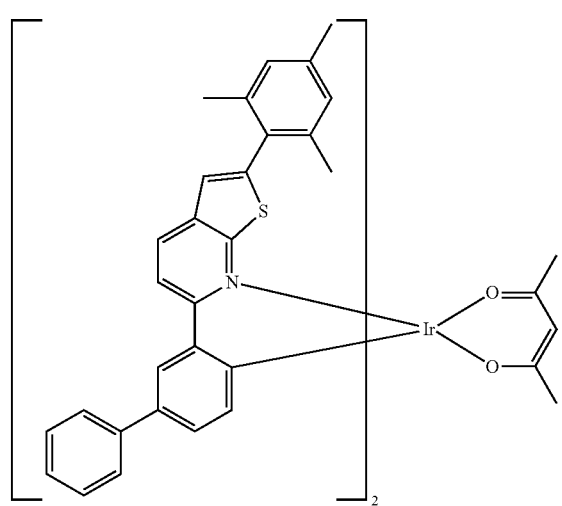
135
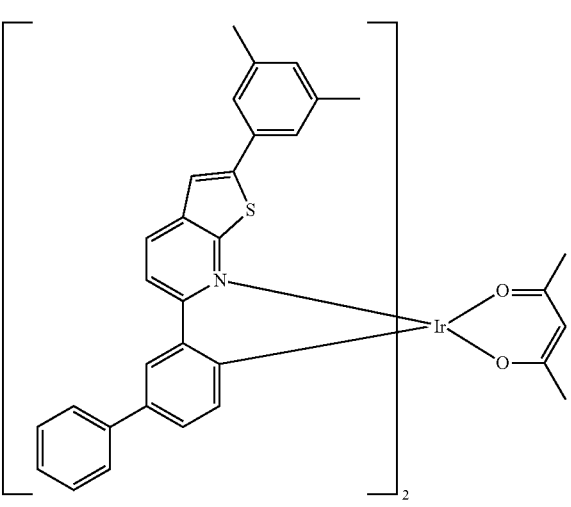
136
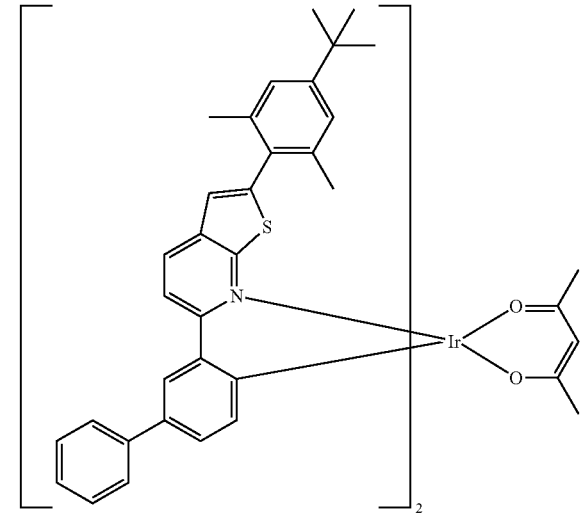
137
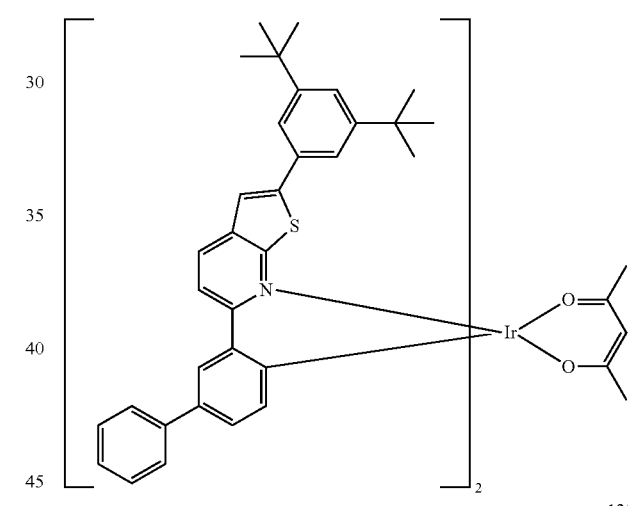
138
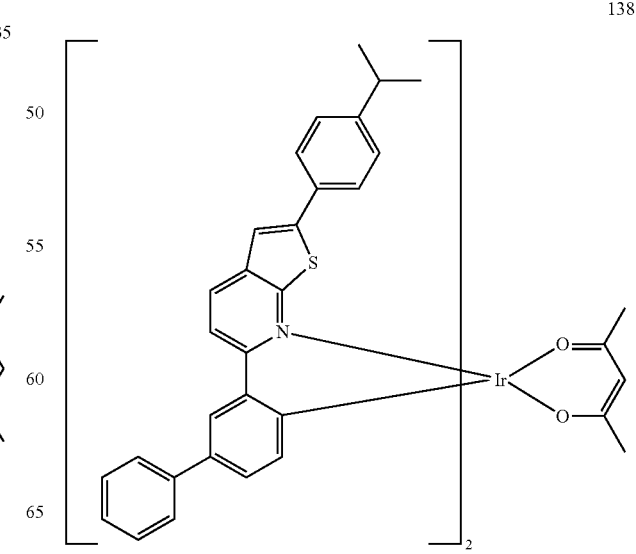

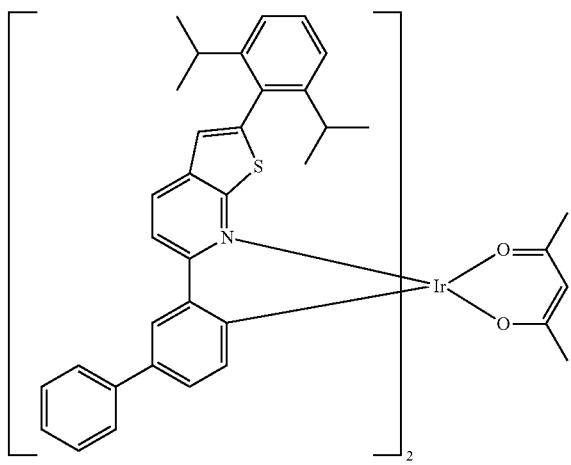
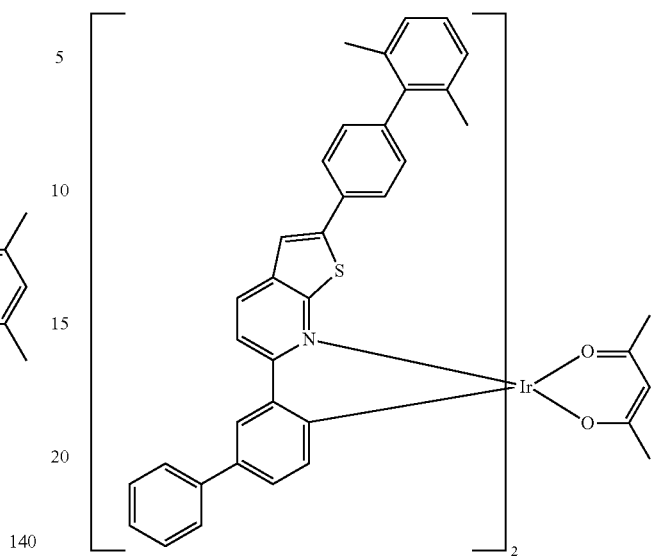
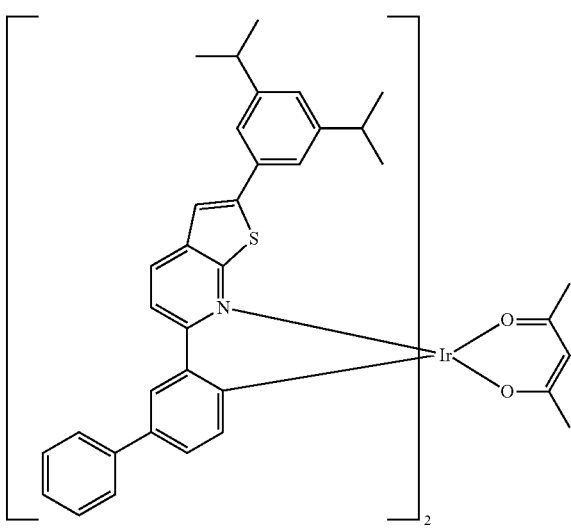
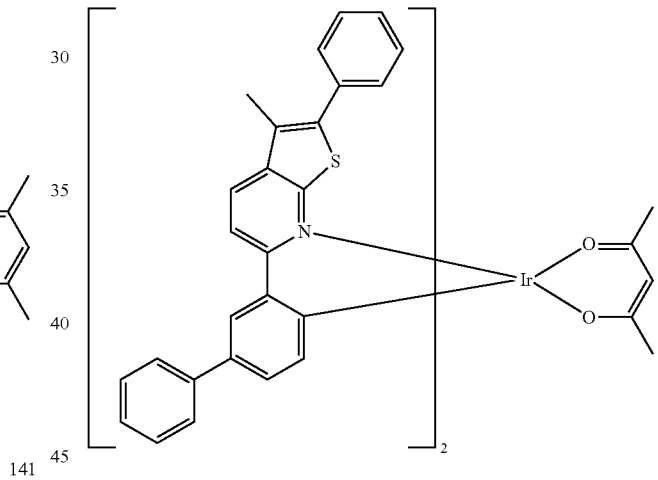
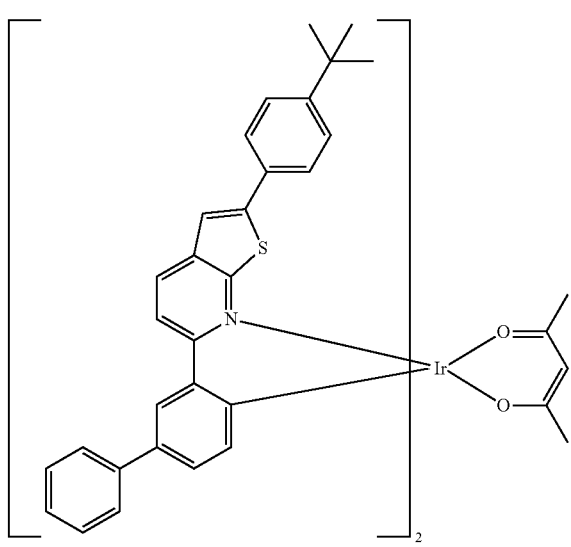
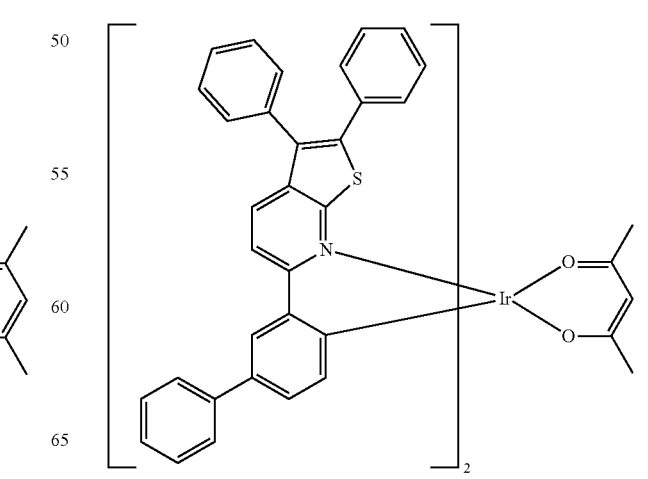

-continued
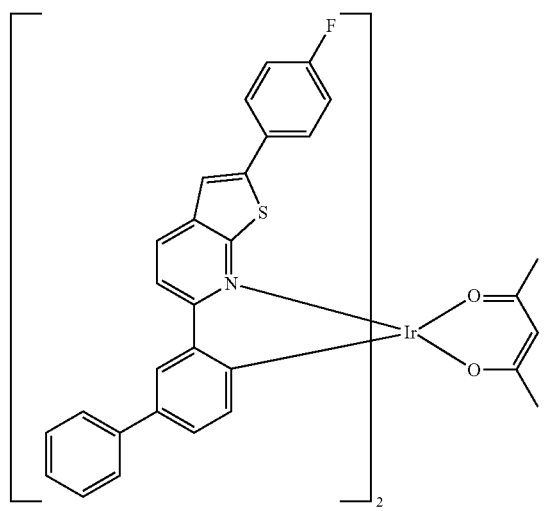
145
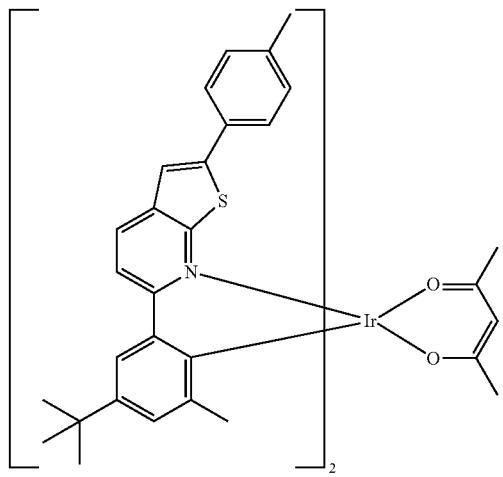
148
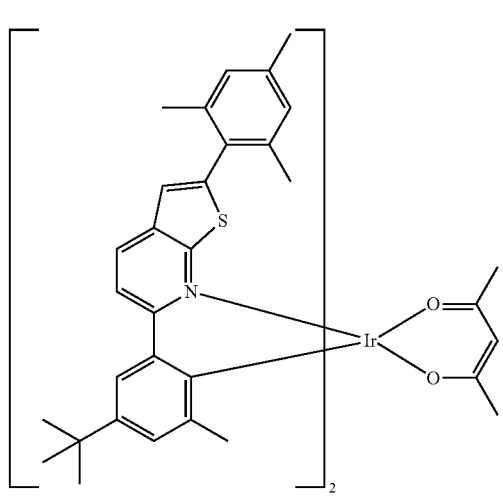
149
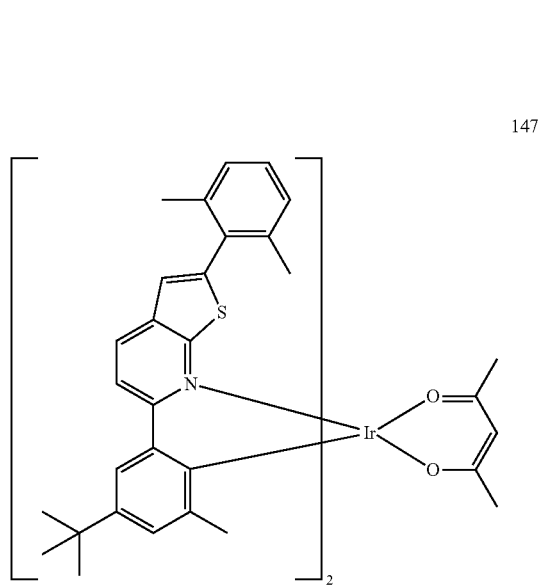
146
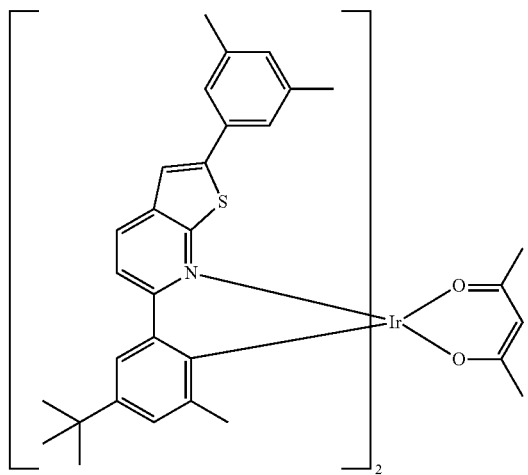
150
147

151
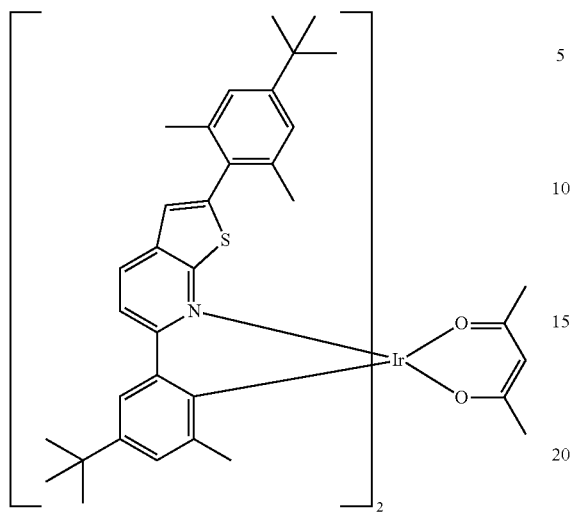
152
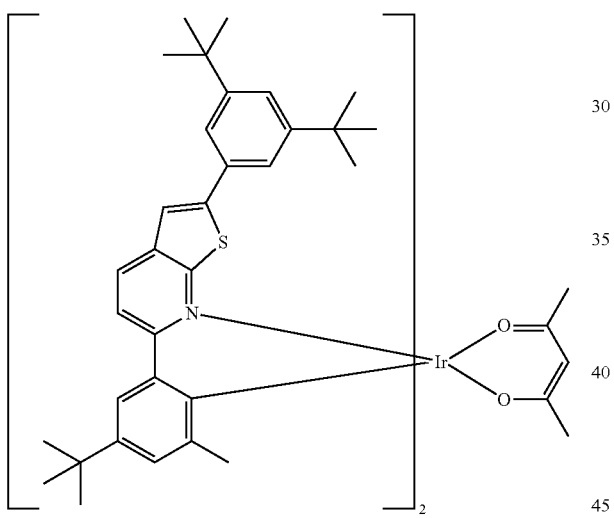
153
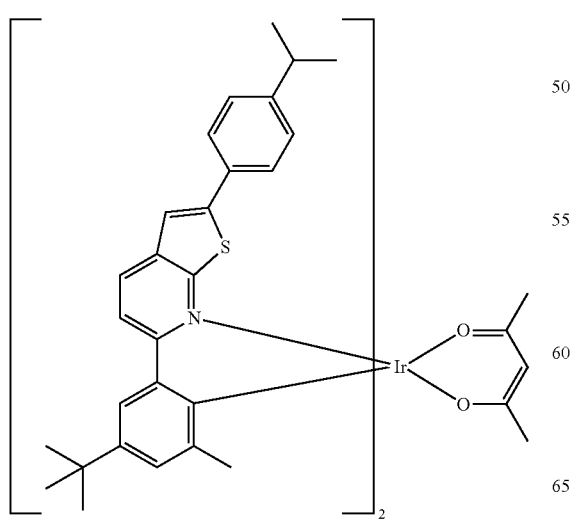
154
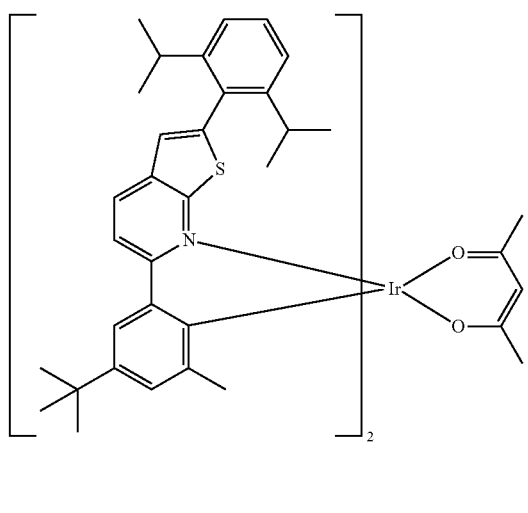
155
155
156
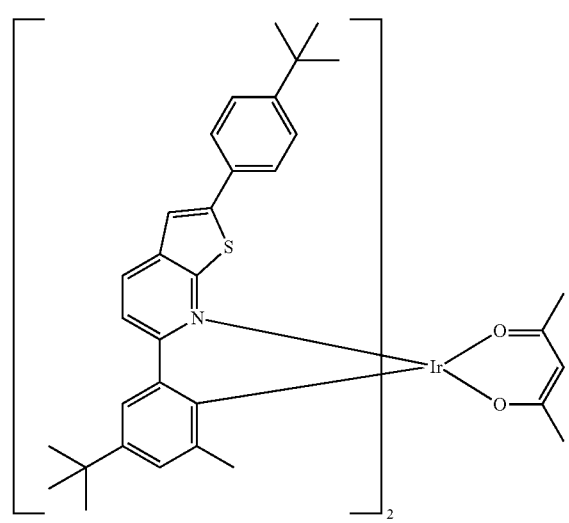

157
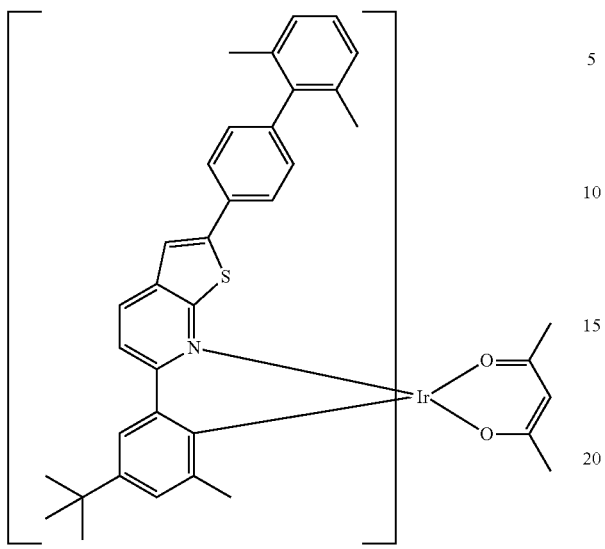
158
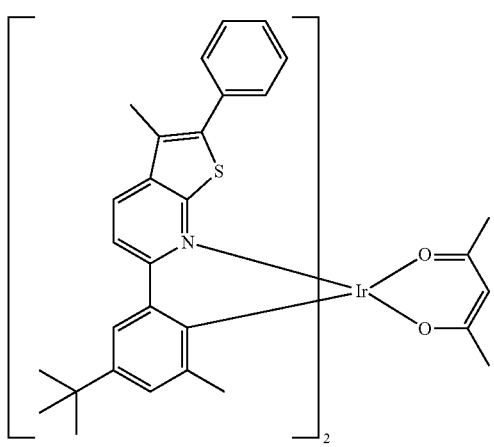
159
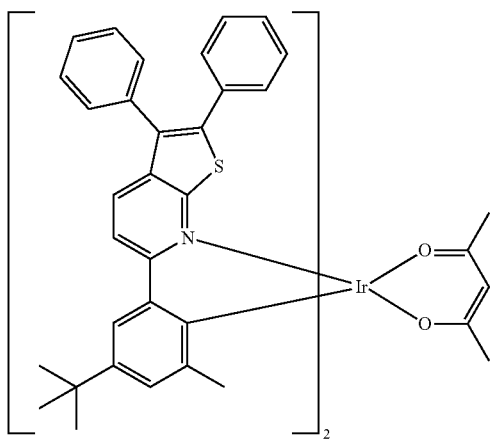
160
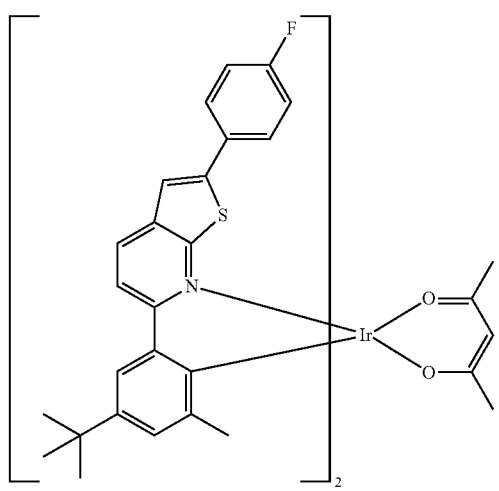
161
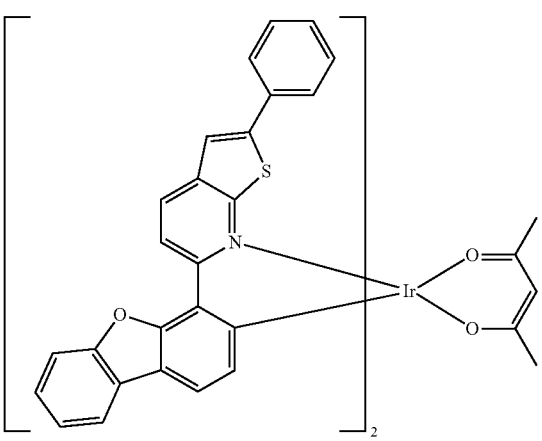
162
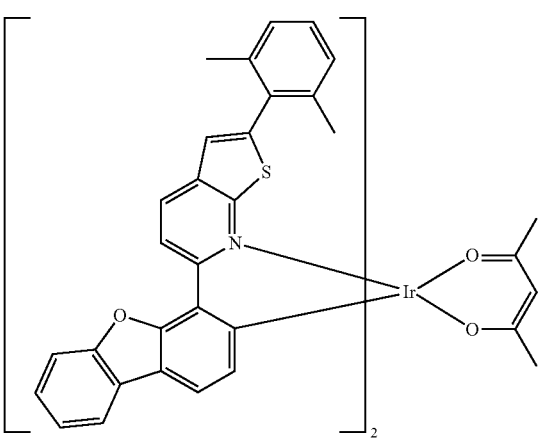

163
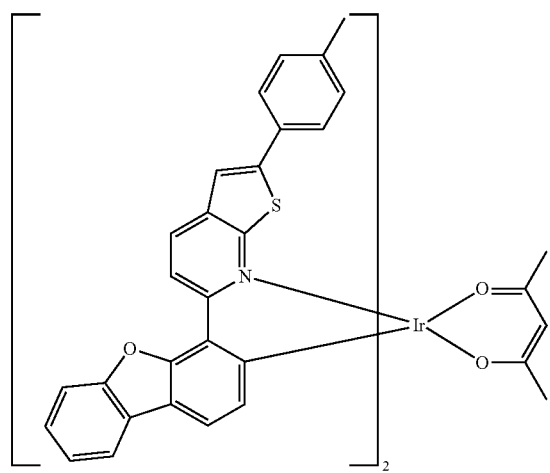
164
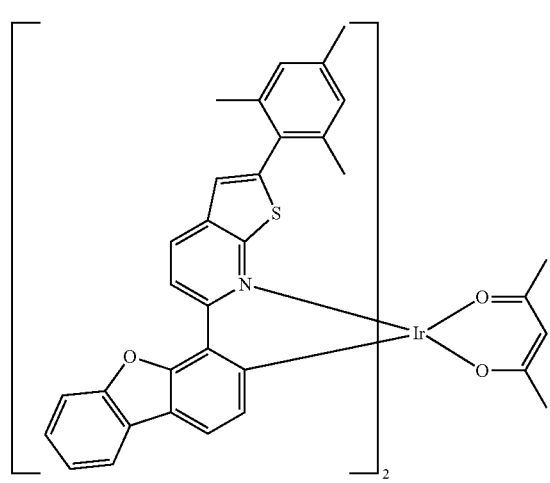
165
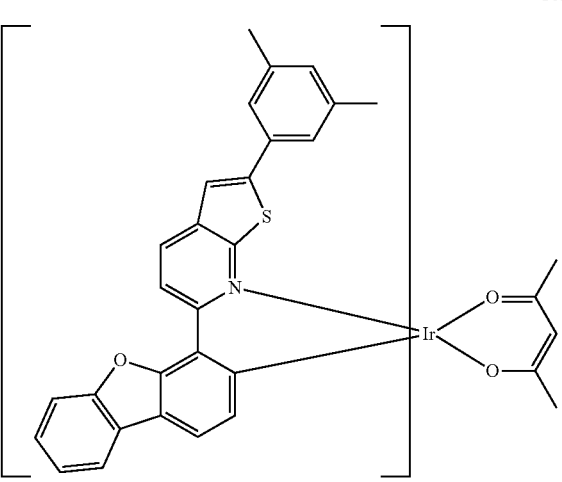
166
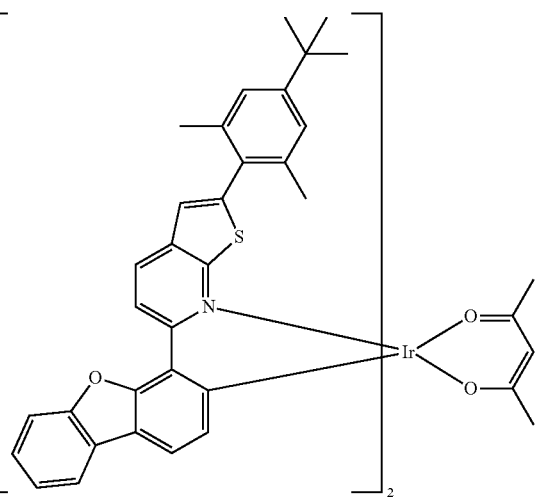
167
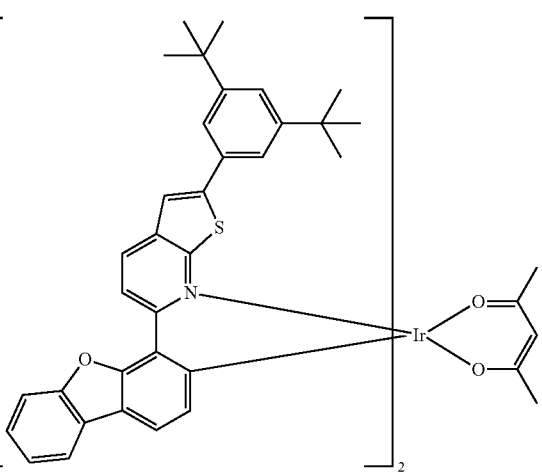
168
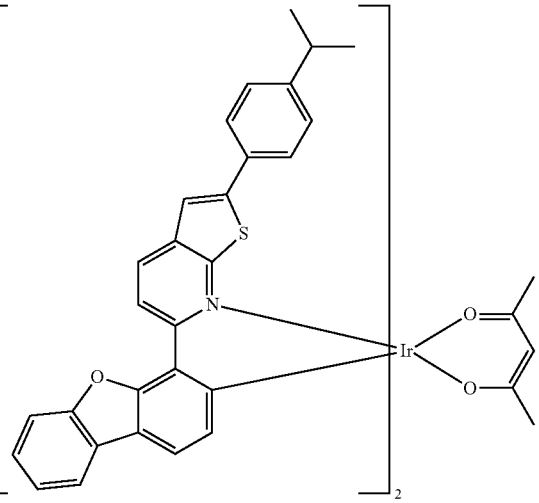

169
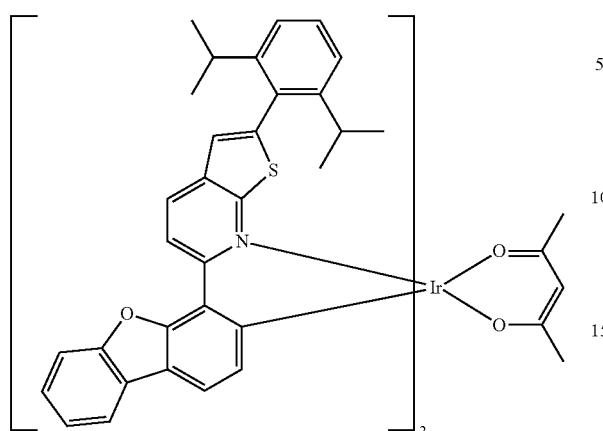
170
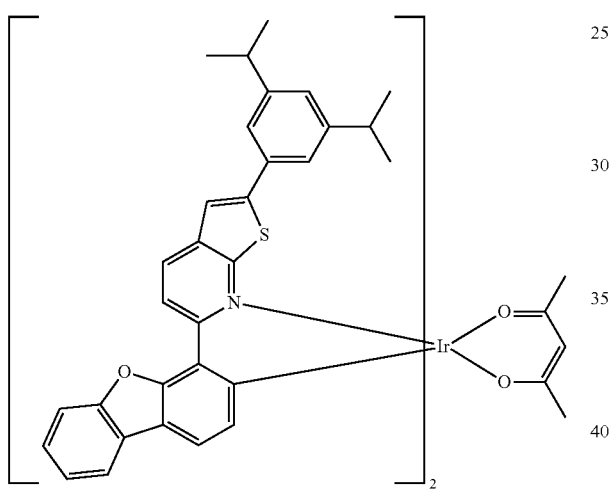
171
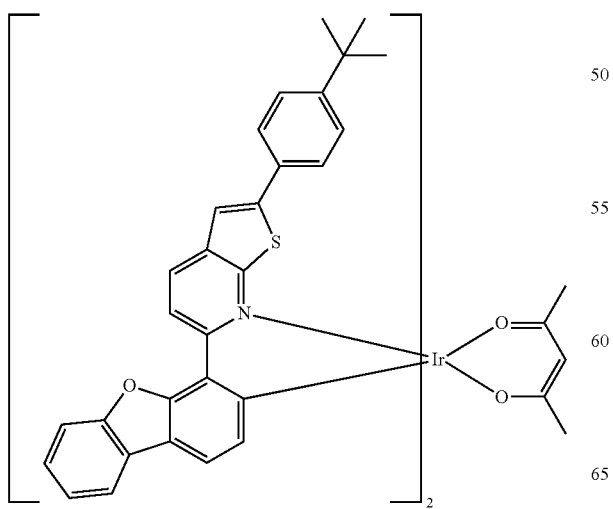
172
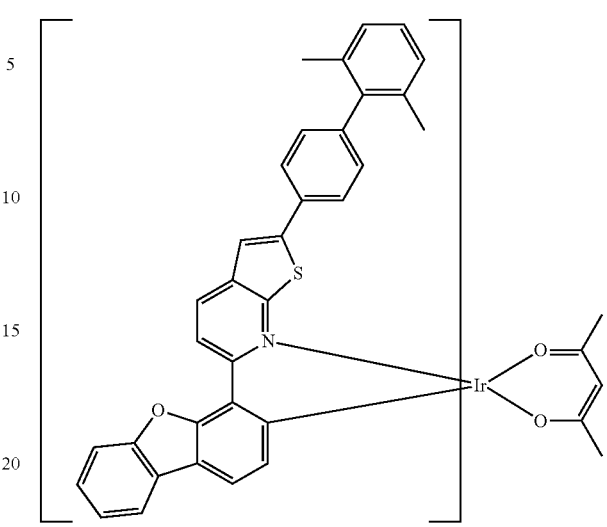
173
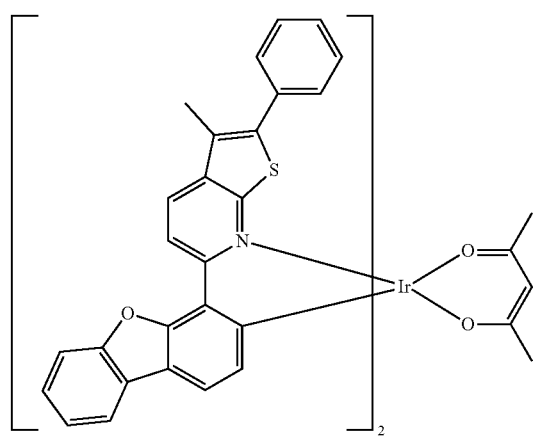
174
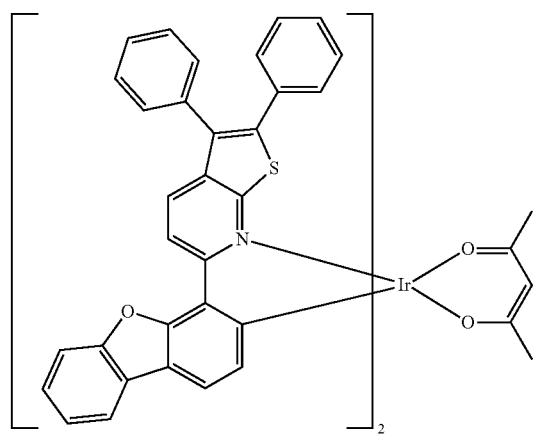

175
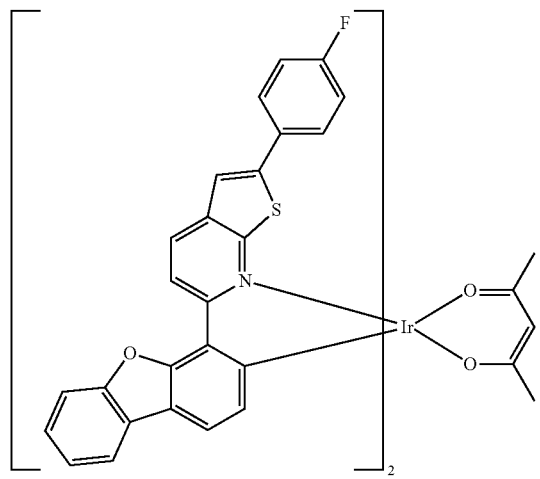
176
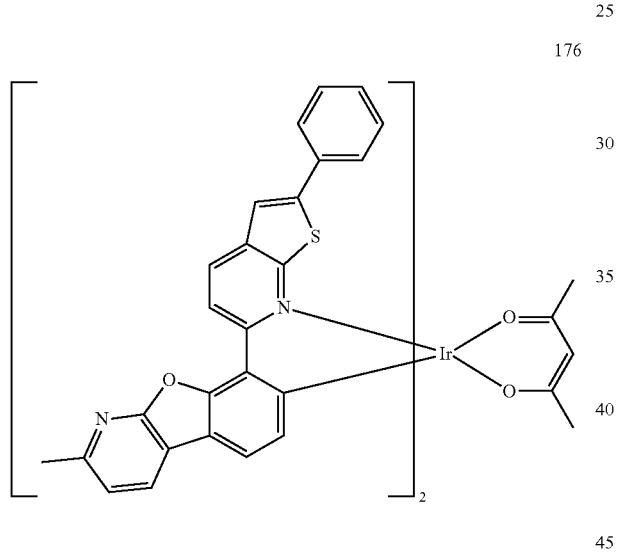
177
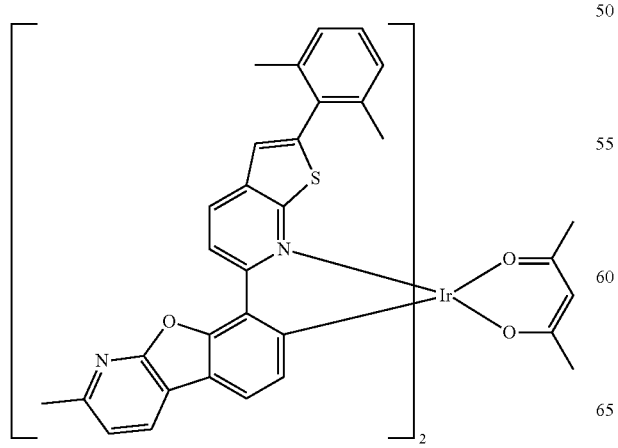
178
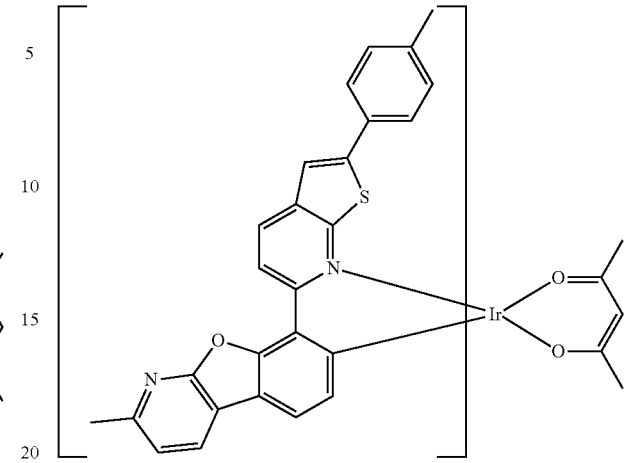
179
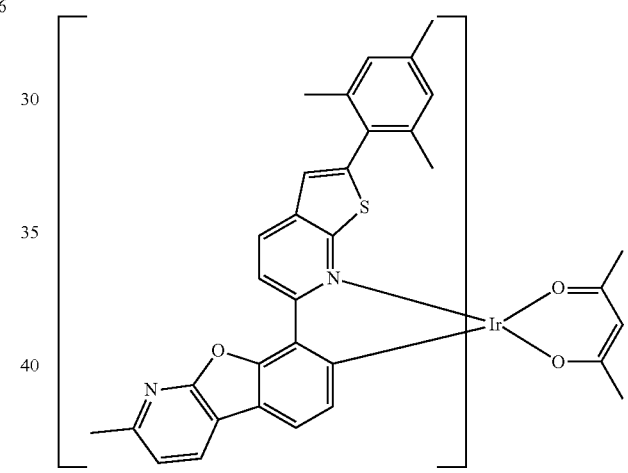
180
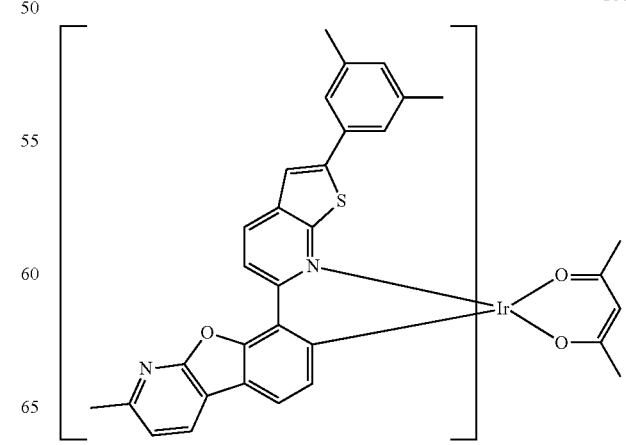

369
-continued
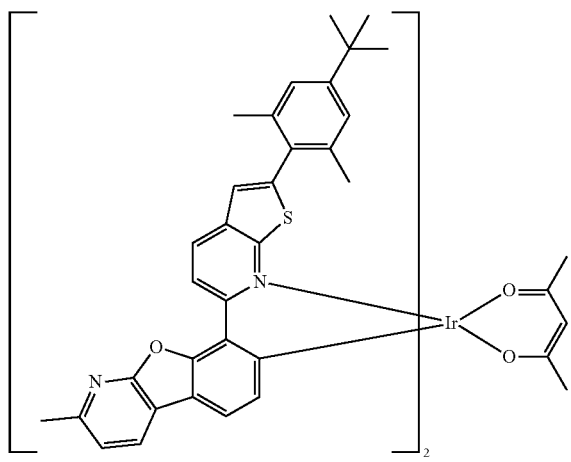
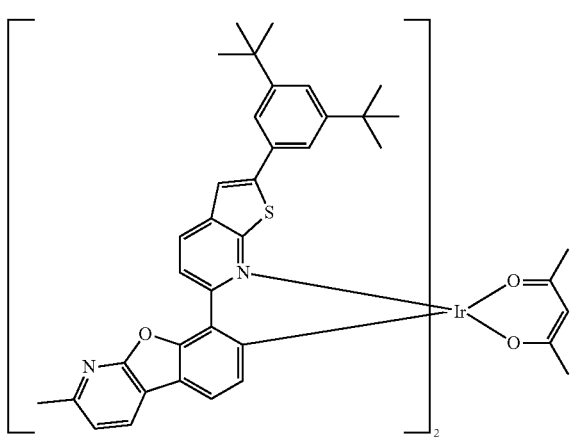
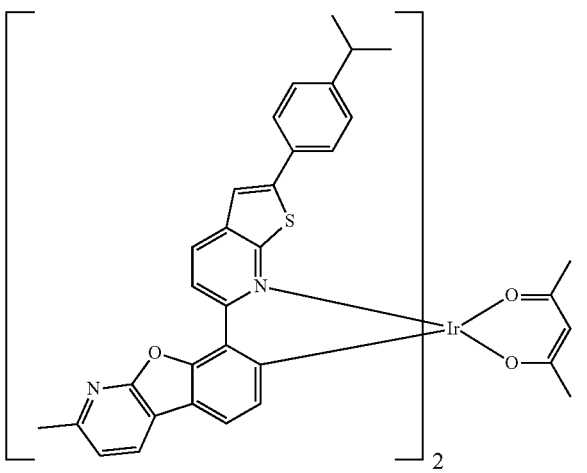
370
-continued
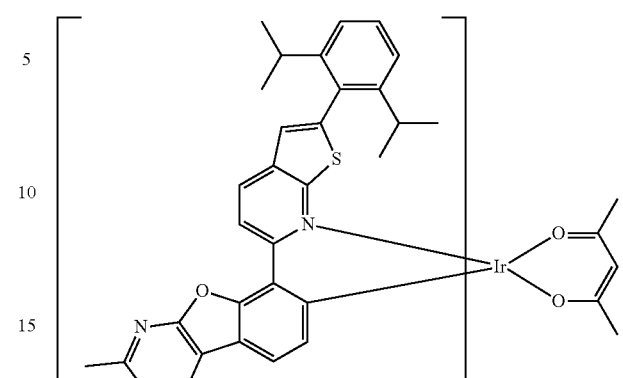

187
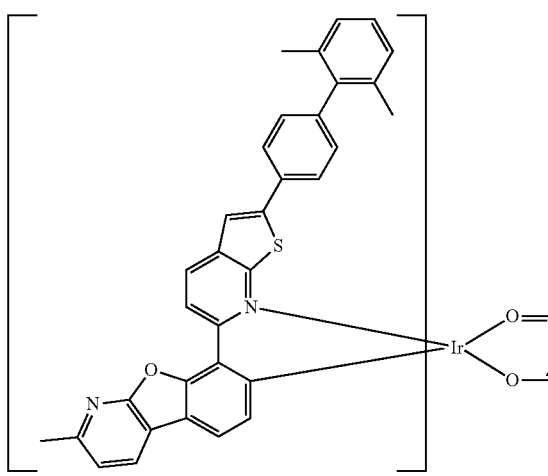
188
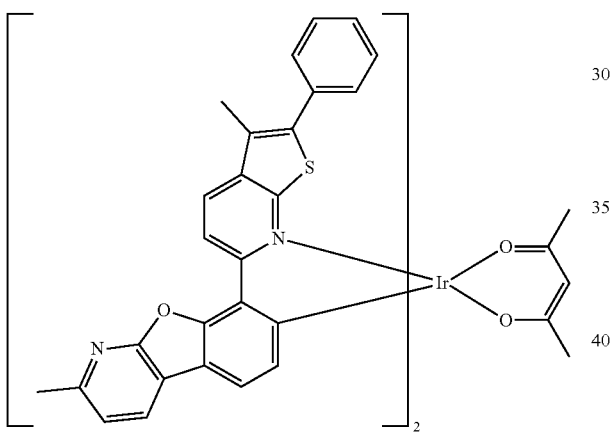
189
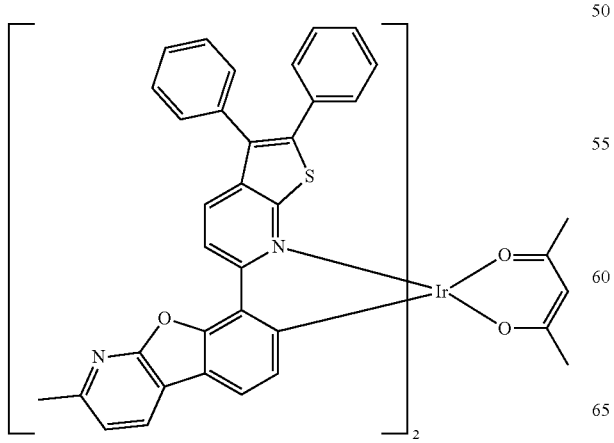
190
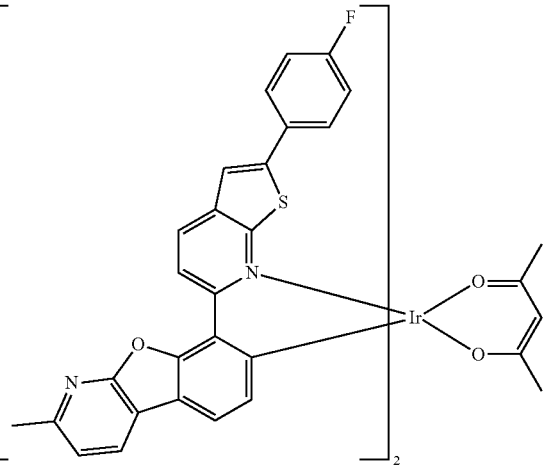
191
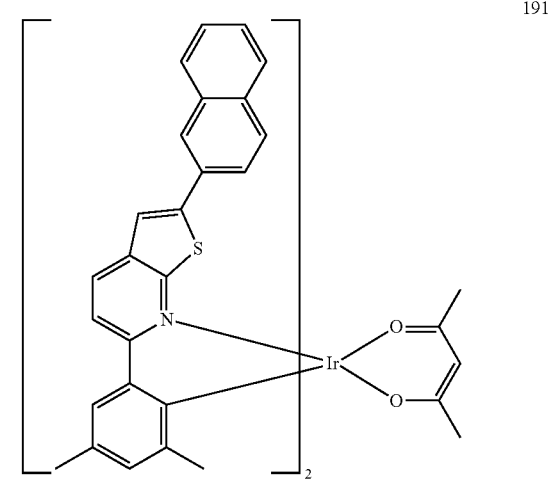
192
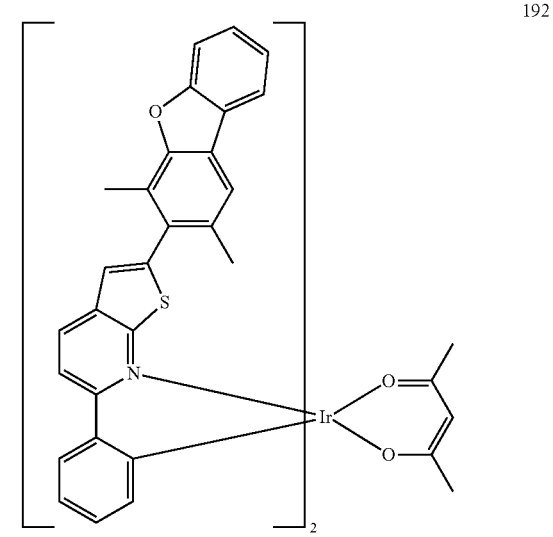

193
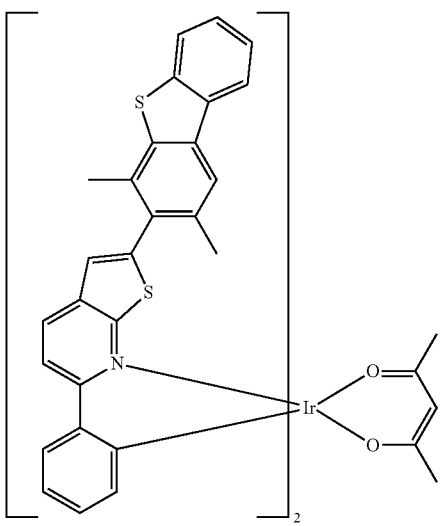
194
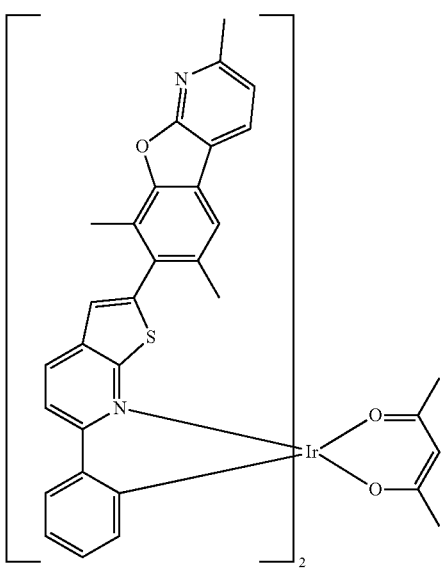
195
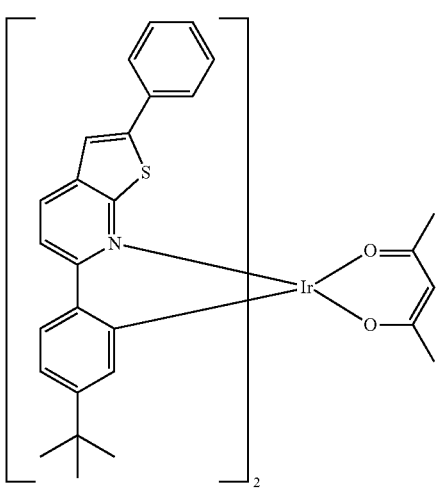
196
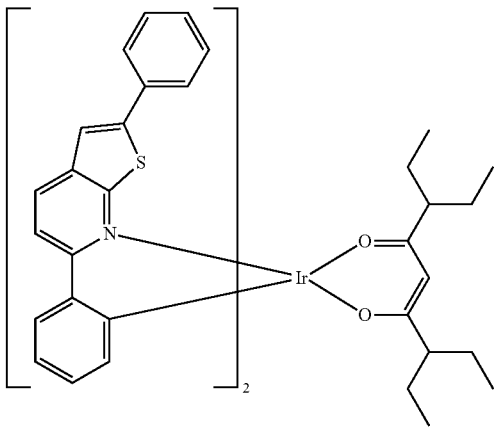
197
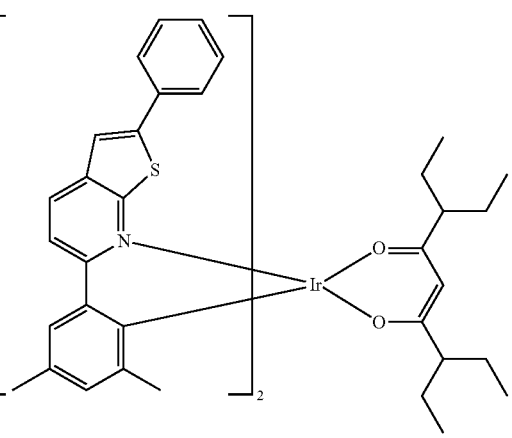
198
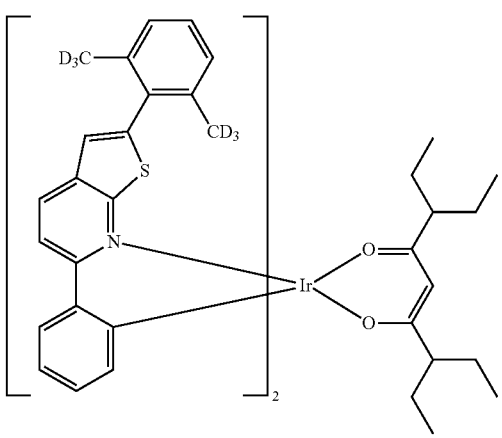

-continued
199 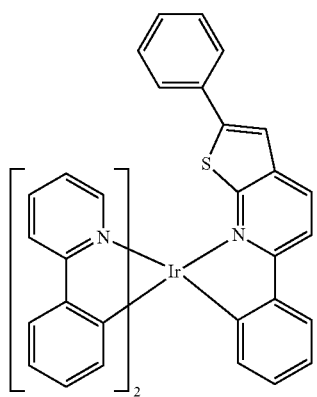
200 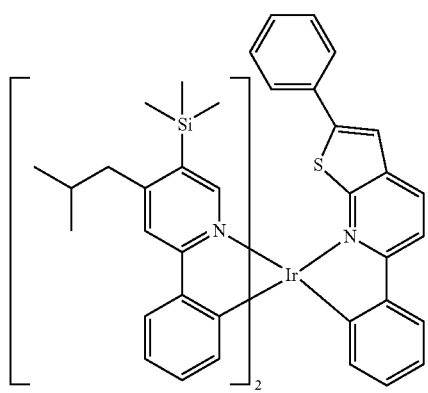
201 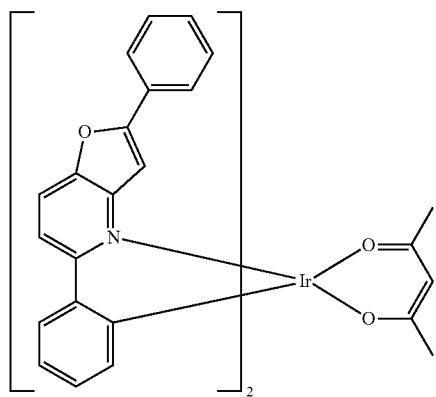
202 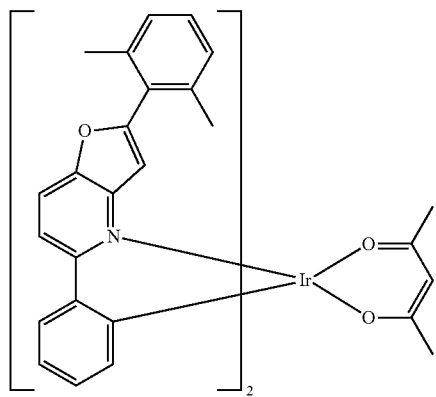
-continued
203 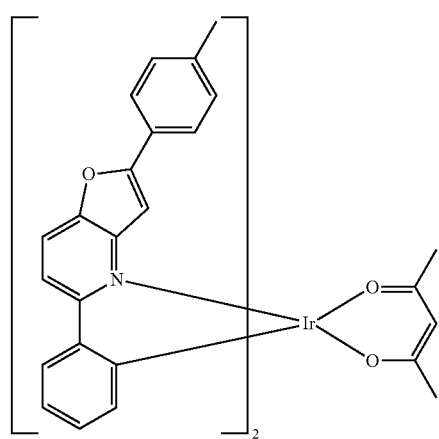
204 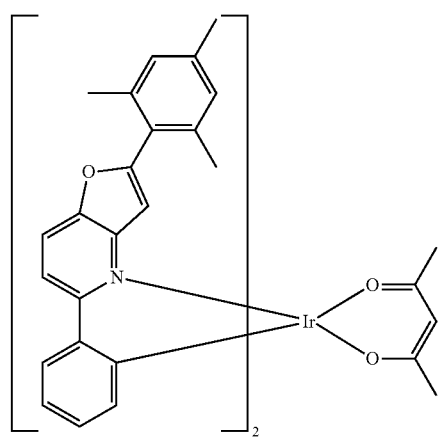
205 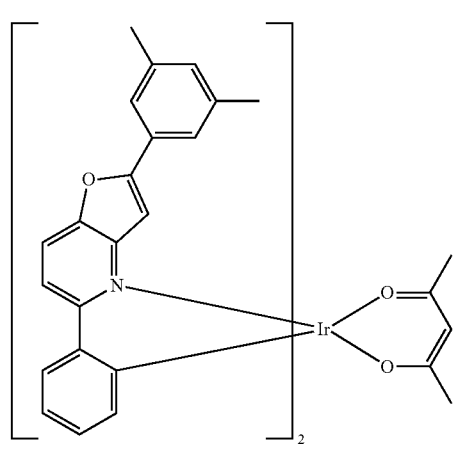

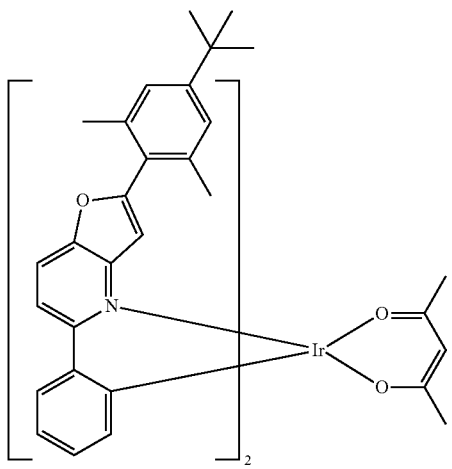
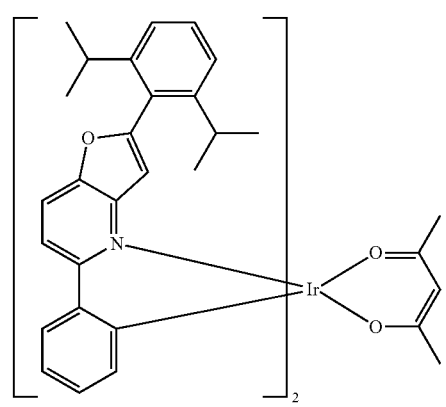

212
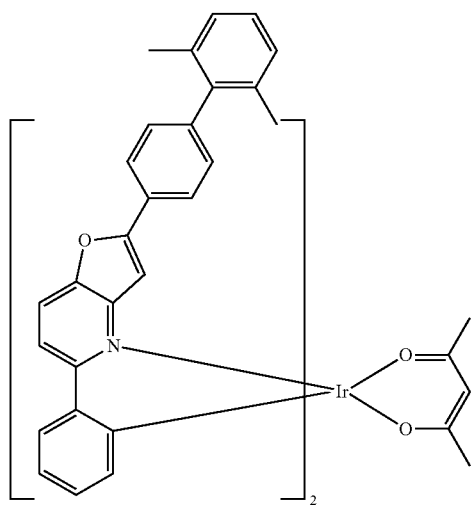
213
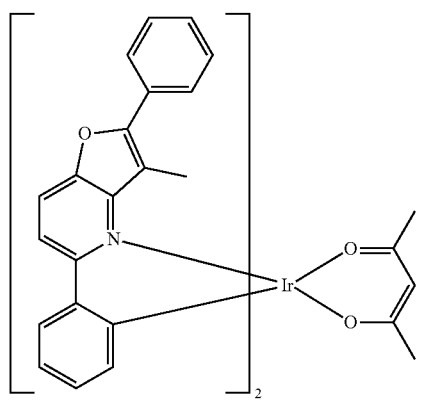
214
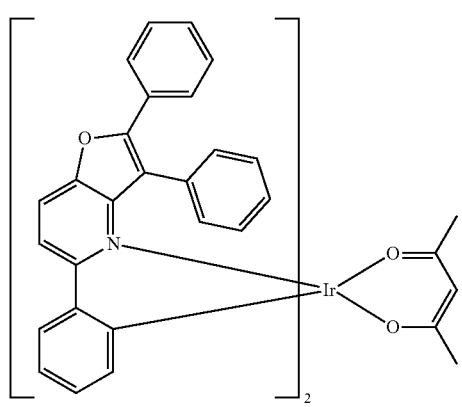
215
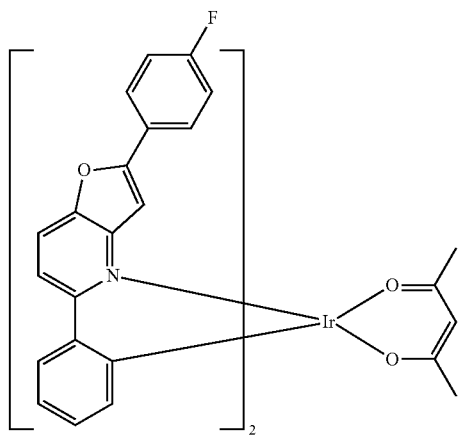
216
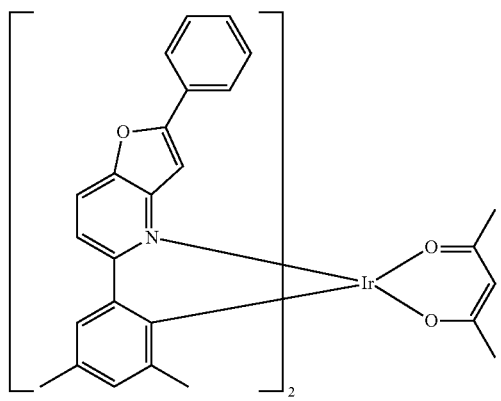
217
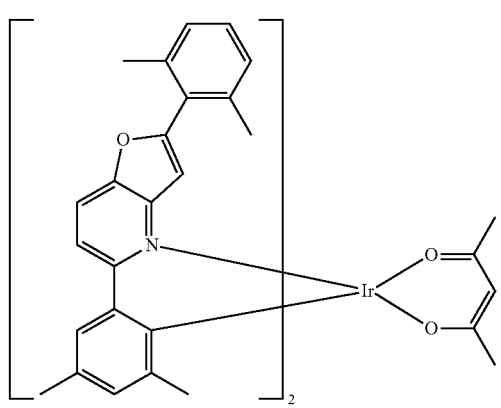

-continued
218
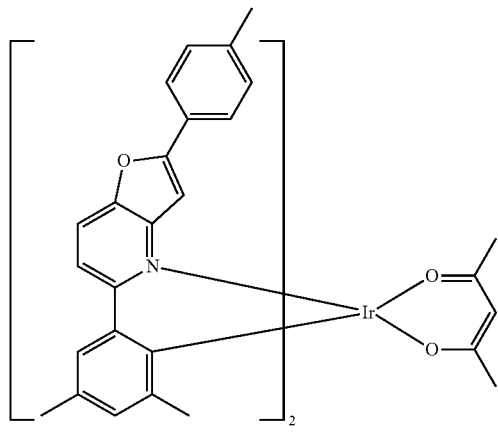
219
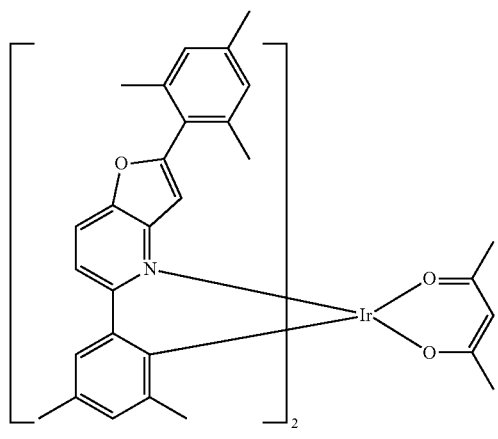
220
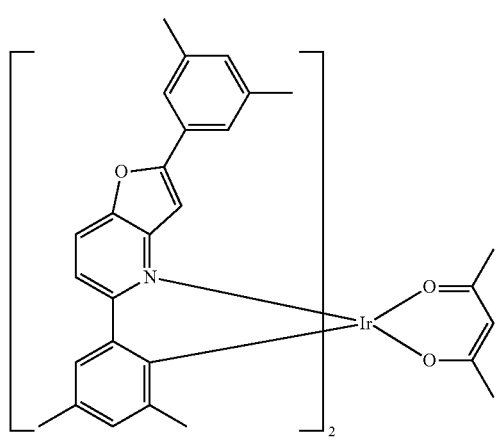
-continued
221
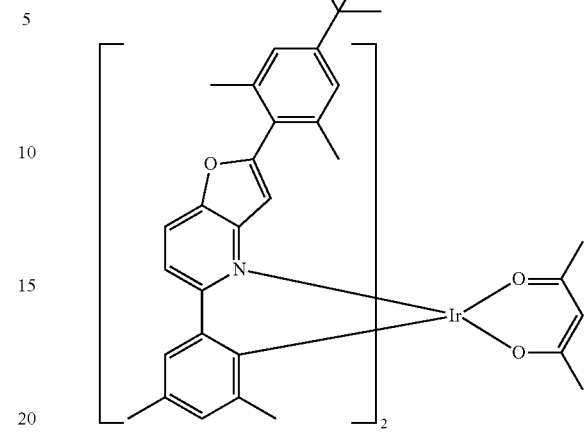
222
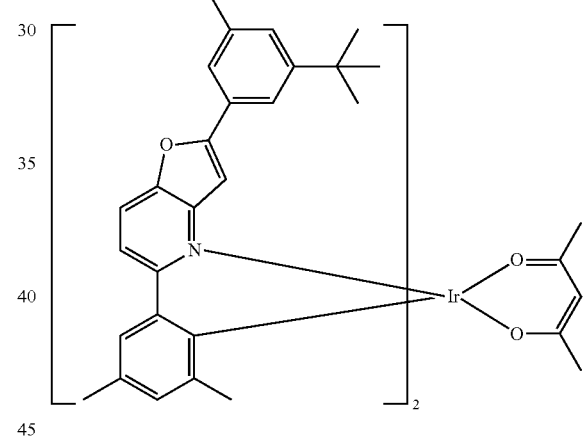
223
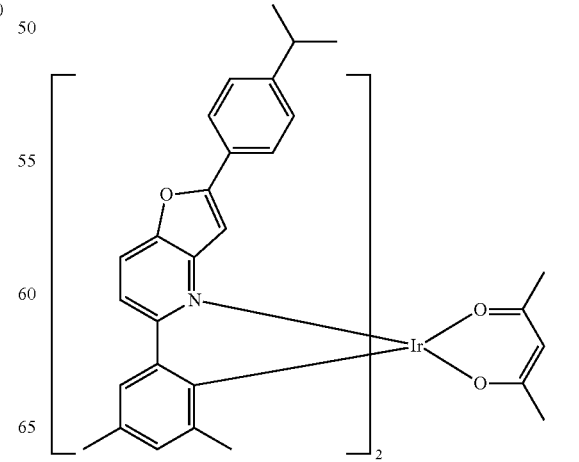

383
224
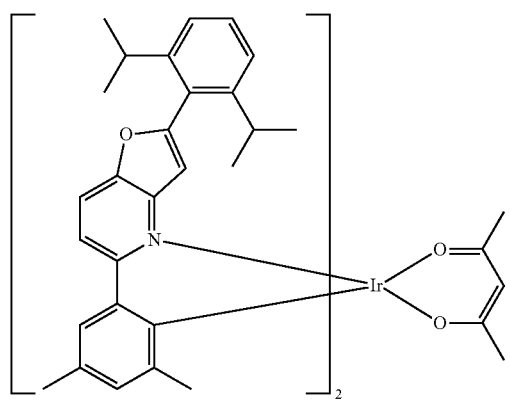
225
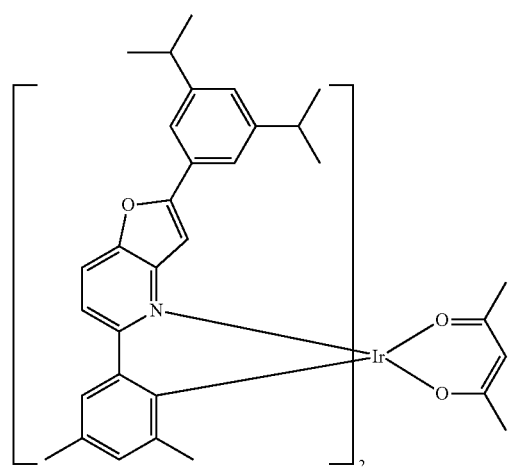
226
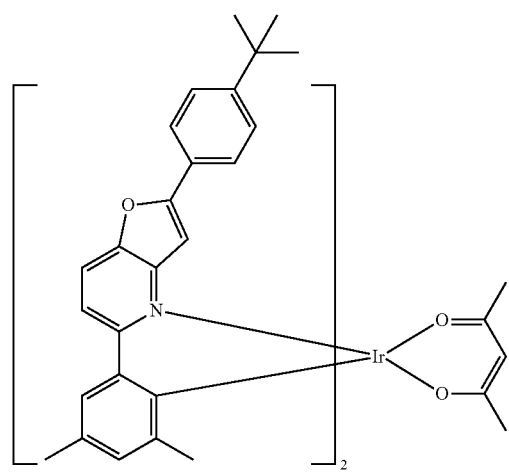
384
227
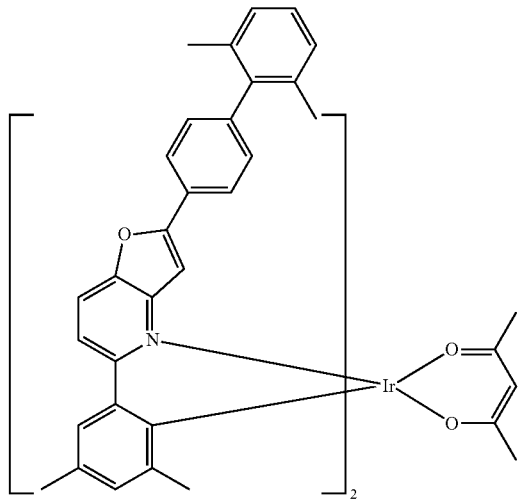
228
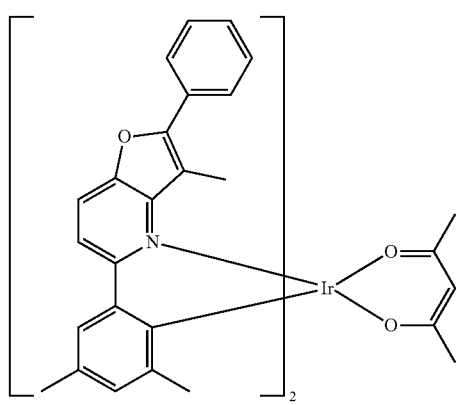
229
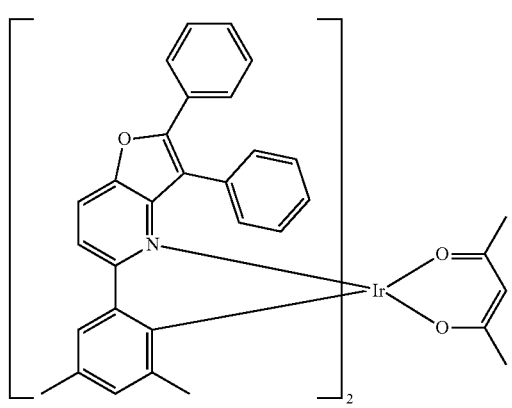

230
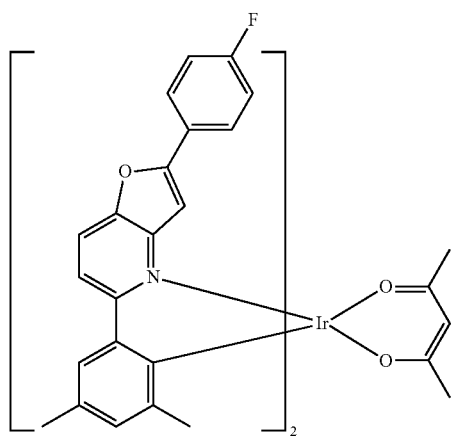
231
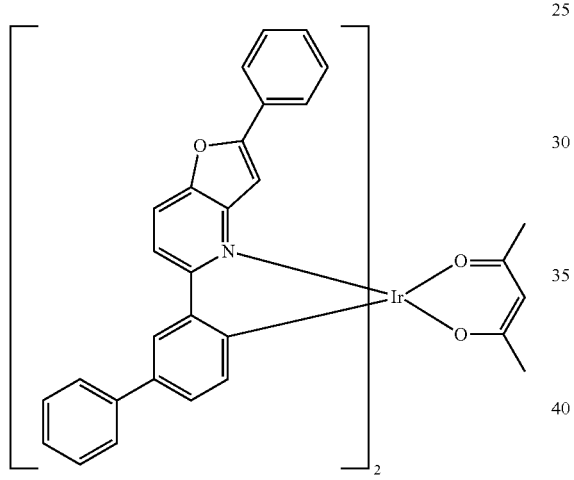
232
233
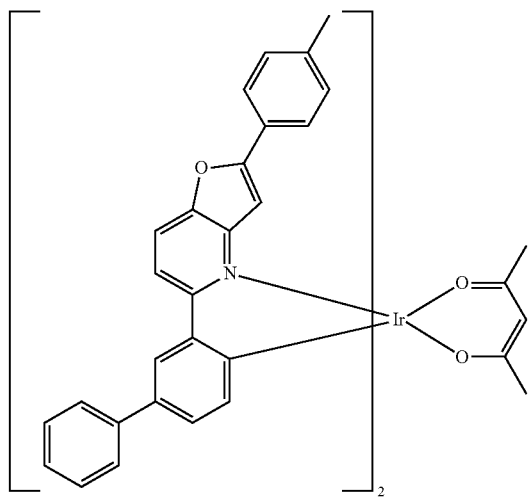
234
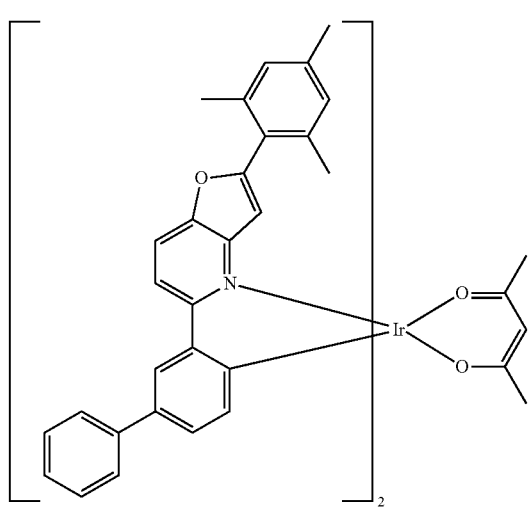
235
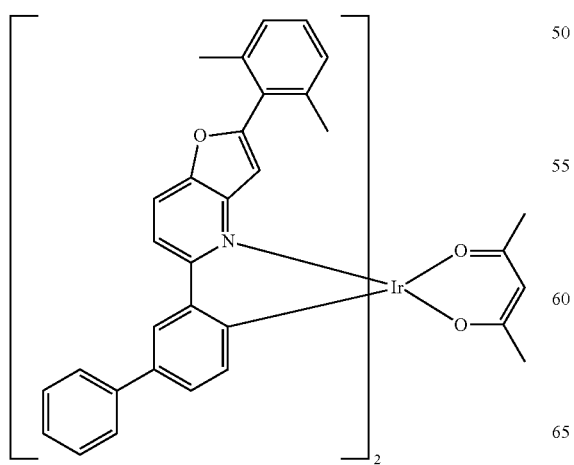

387
-continued
236
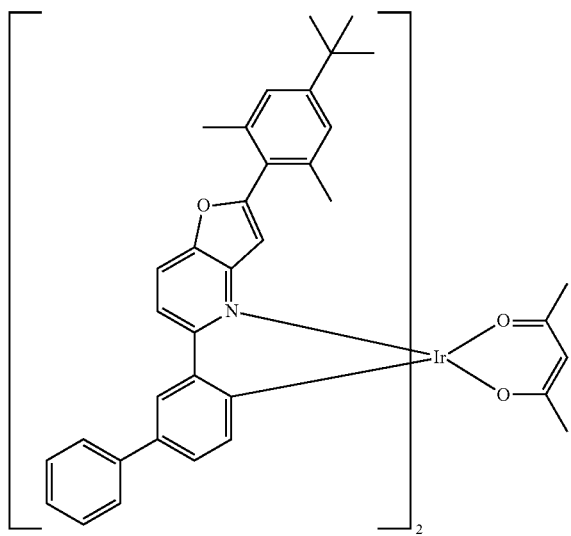
237
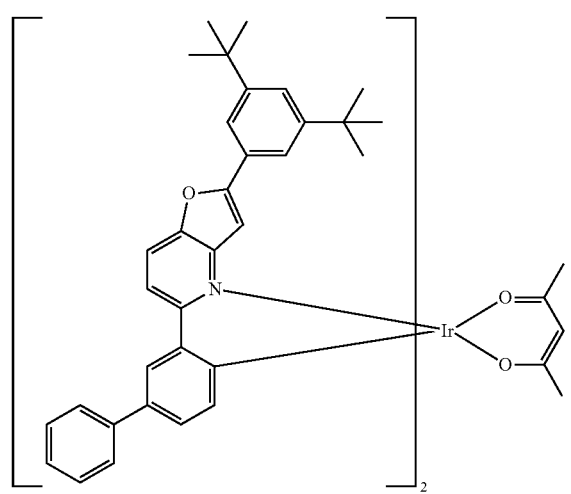
238
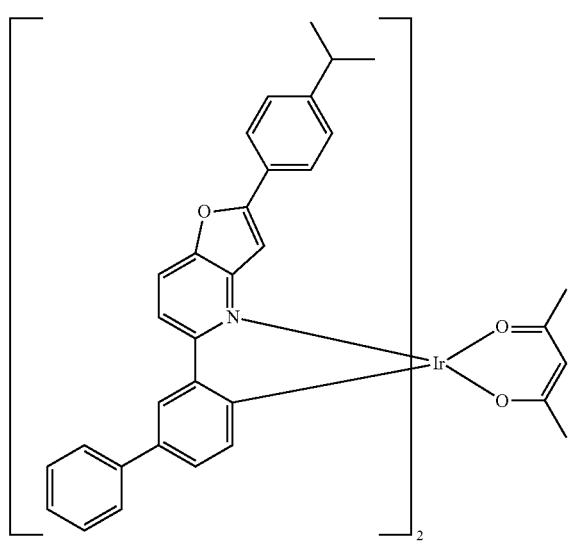
388
-continued
239
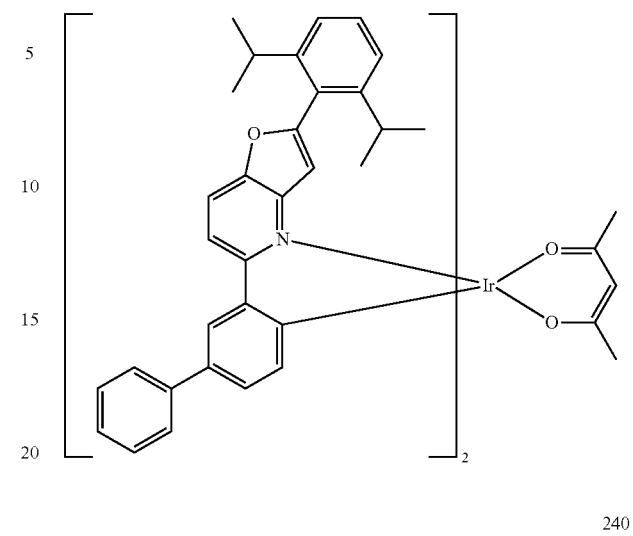
240
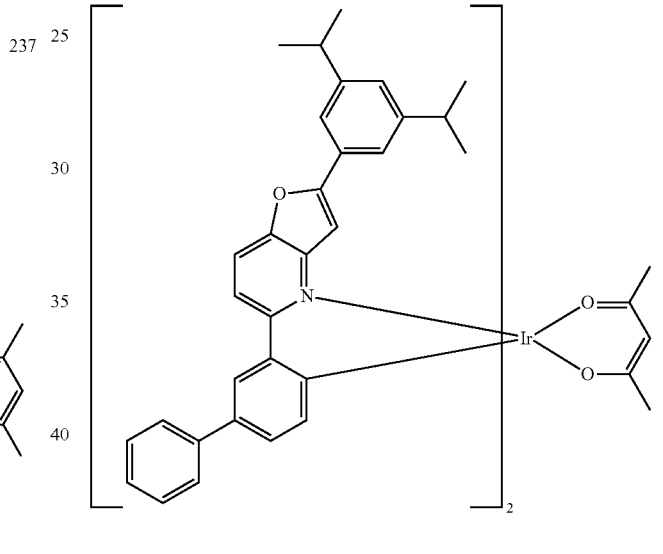
241
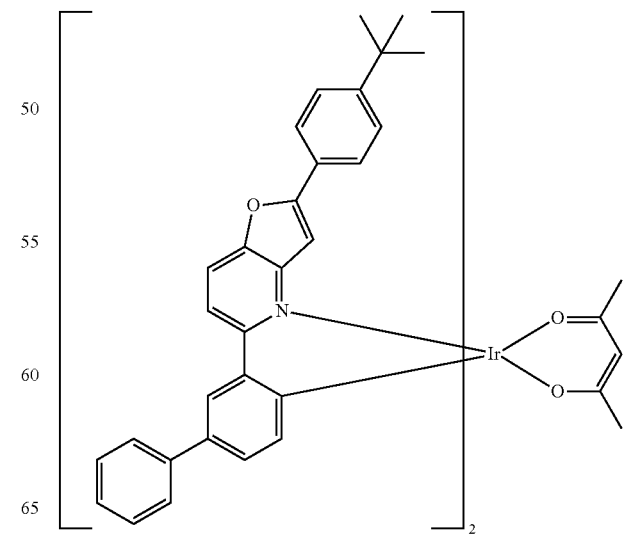

242
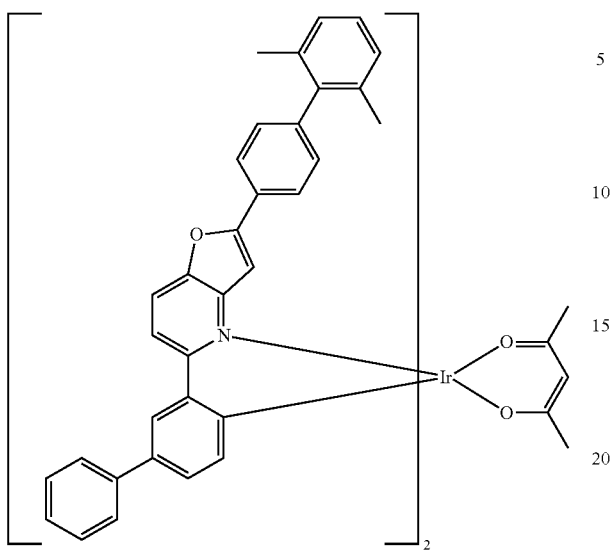
243
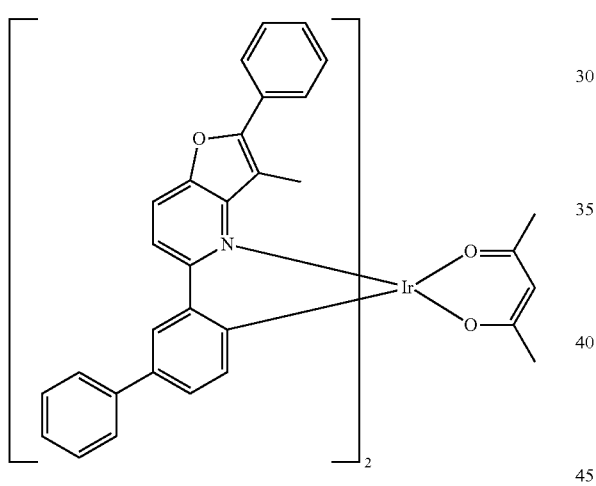
244
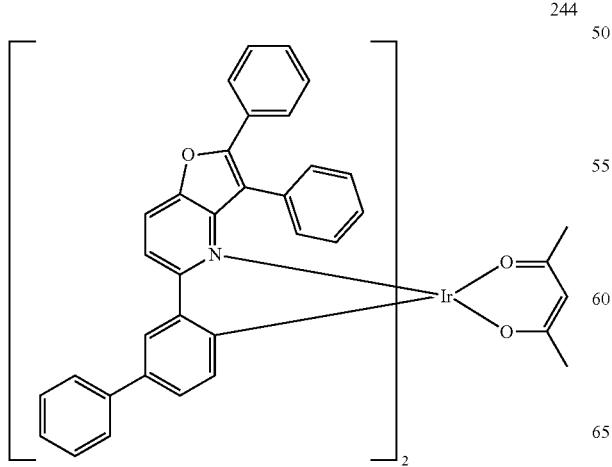
245
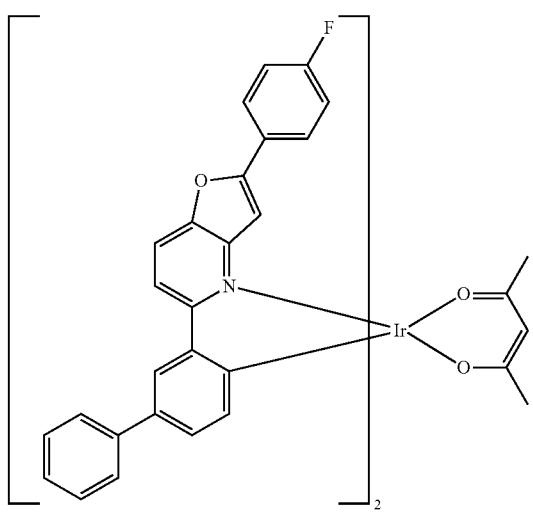
246
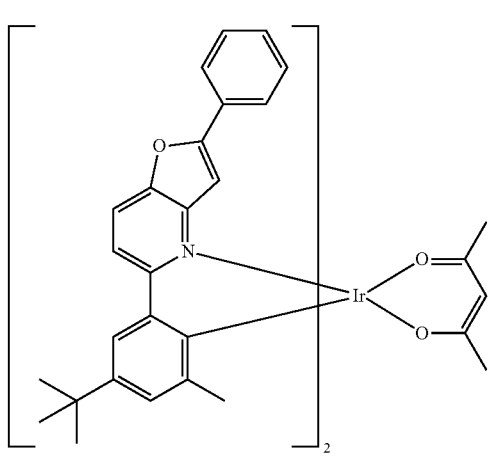
247
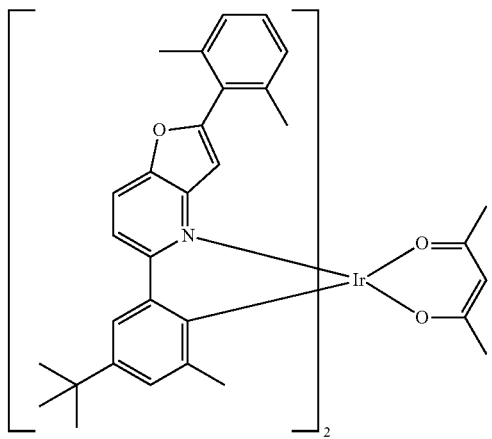

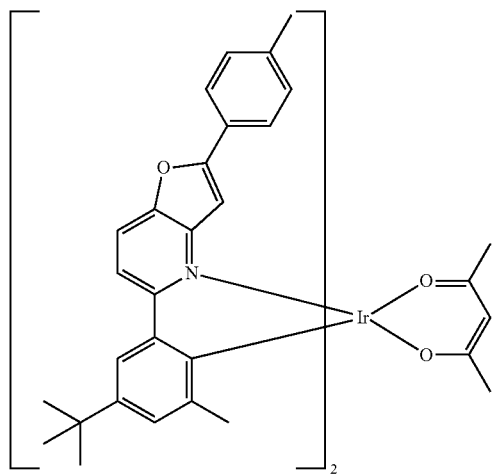
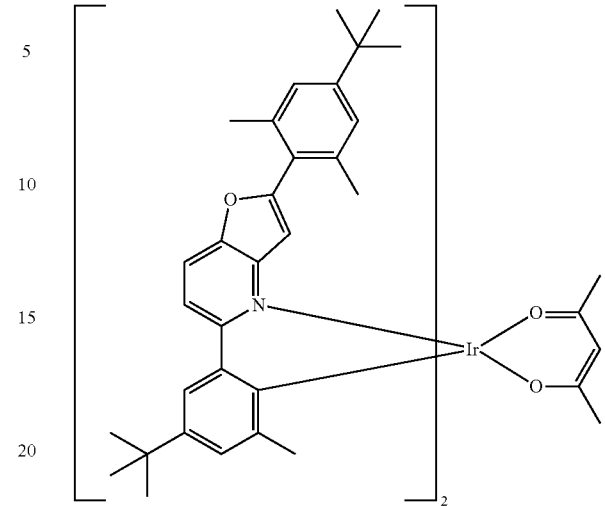
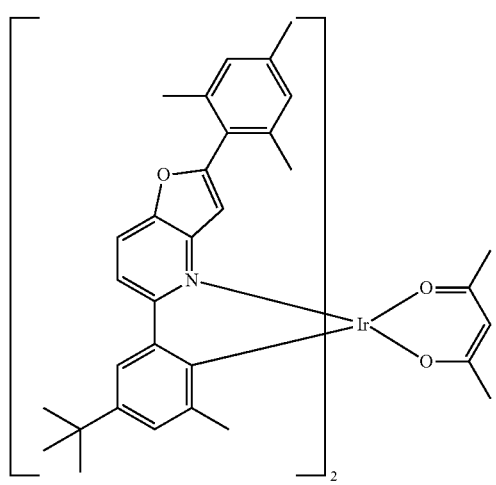
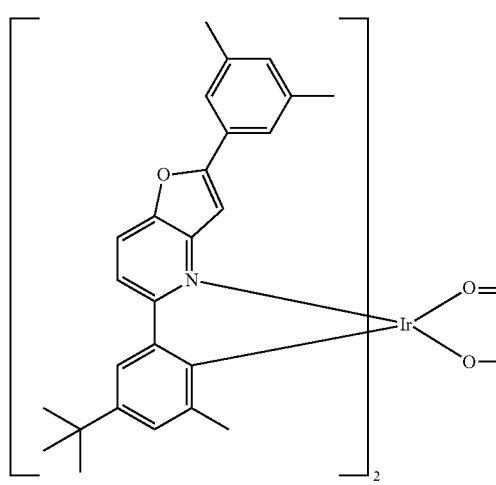

254
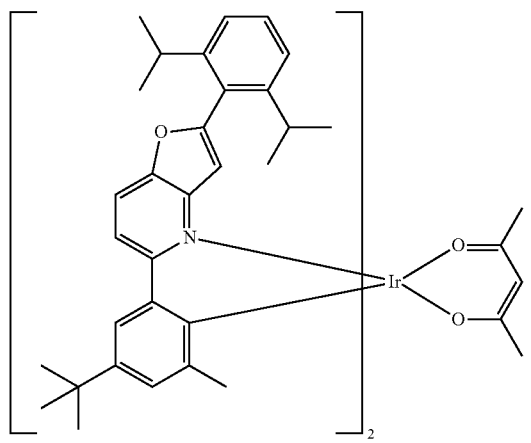
255
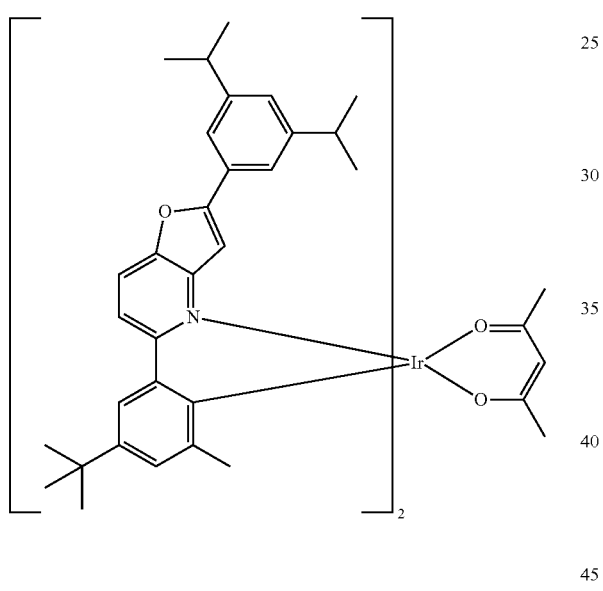
256
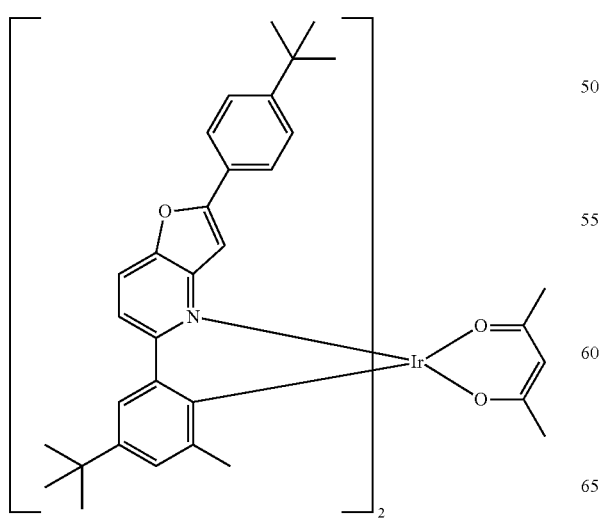
257
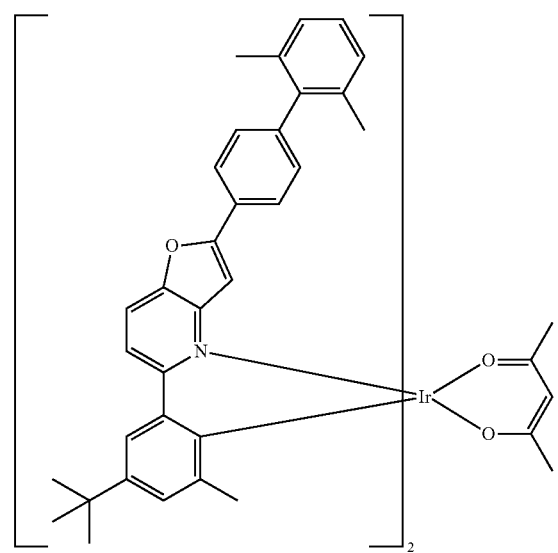
258
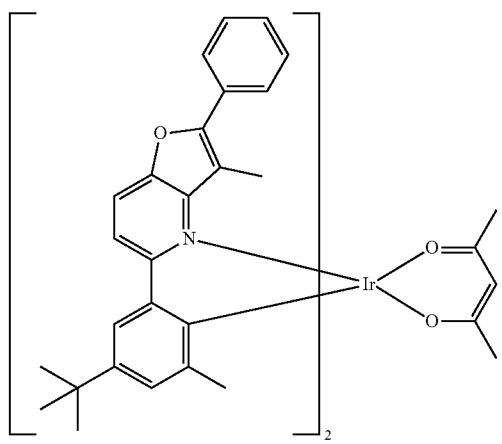
259
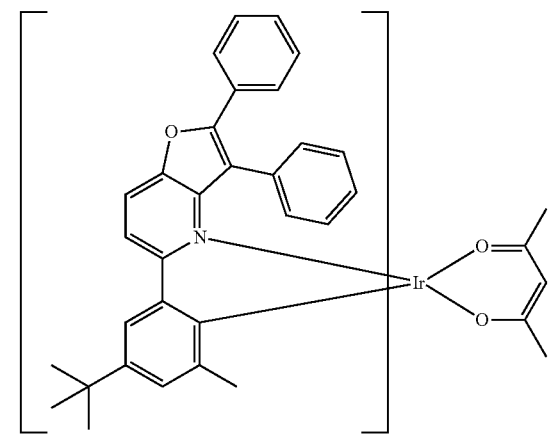

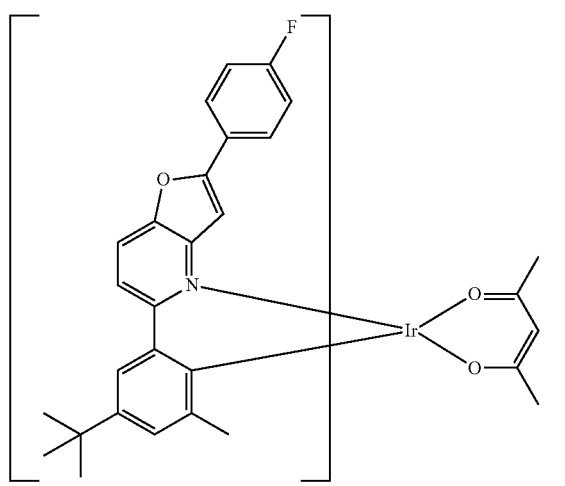
260
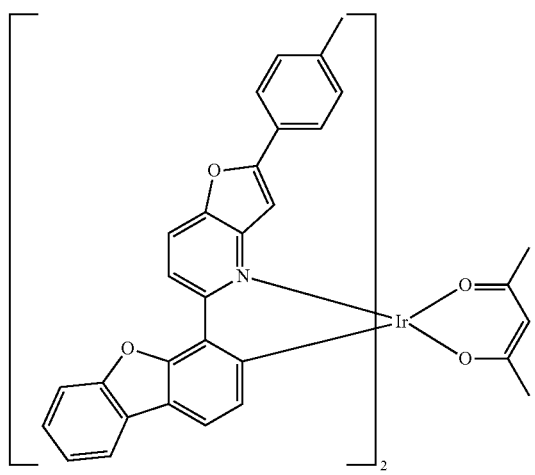
263
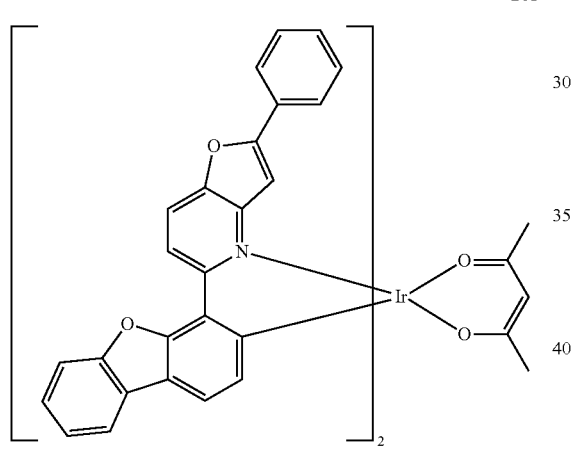
261
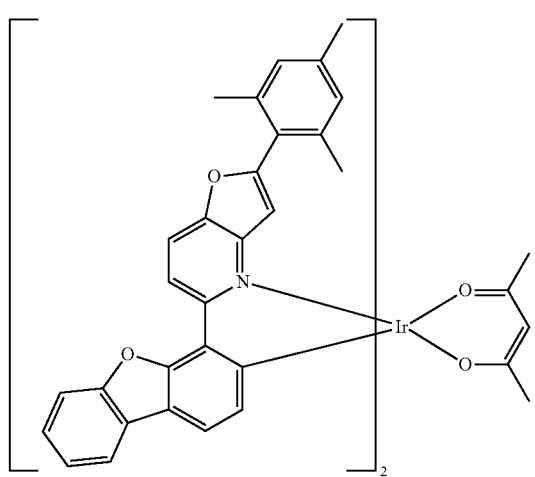
264
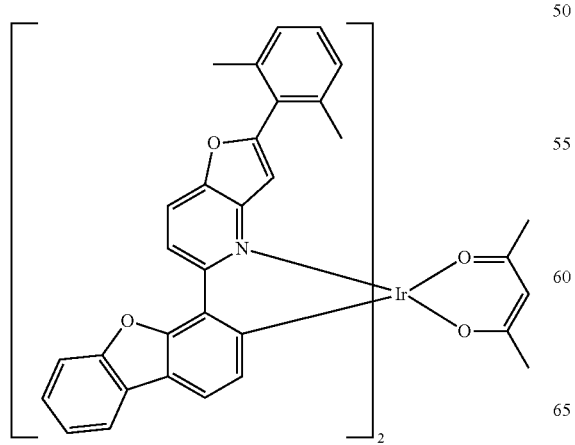
262
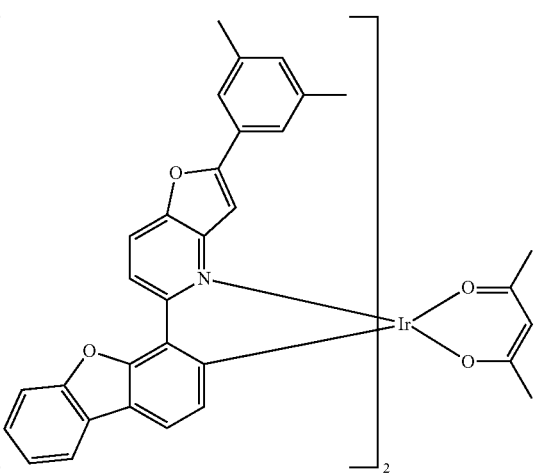
265

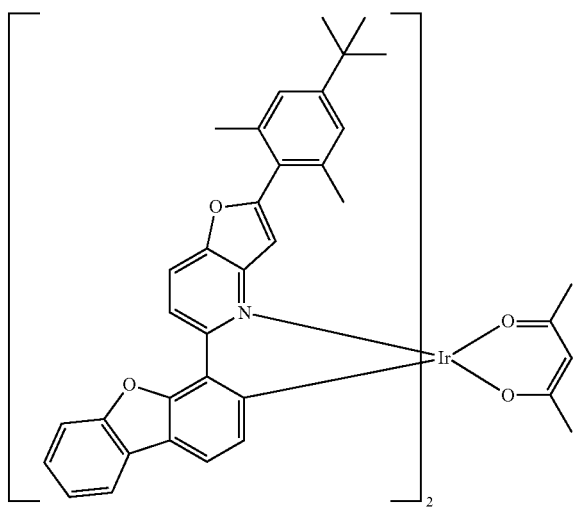
266
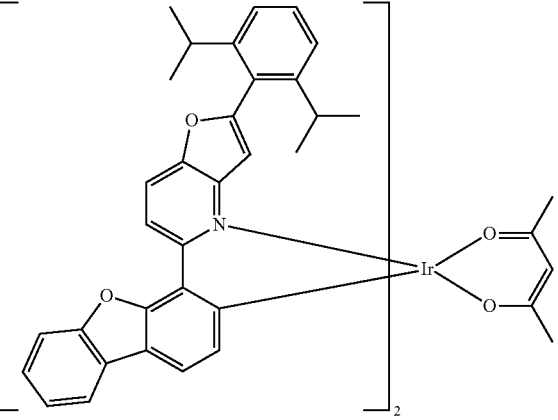
269
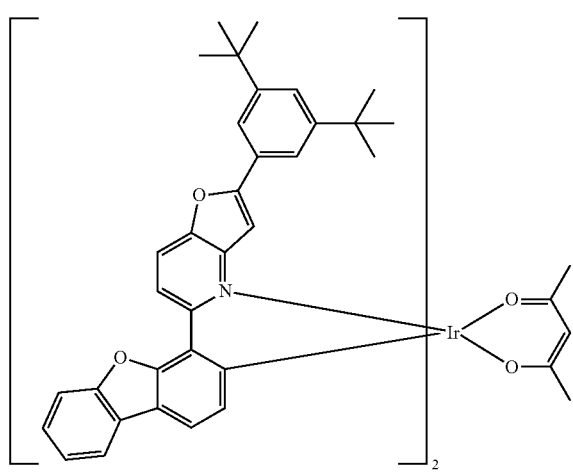
267
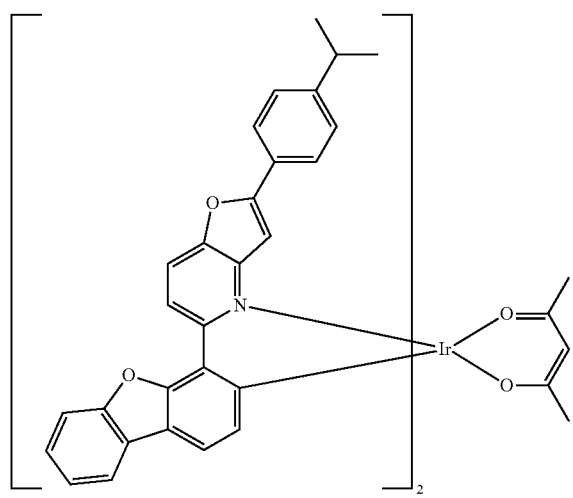
268
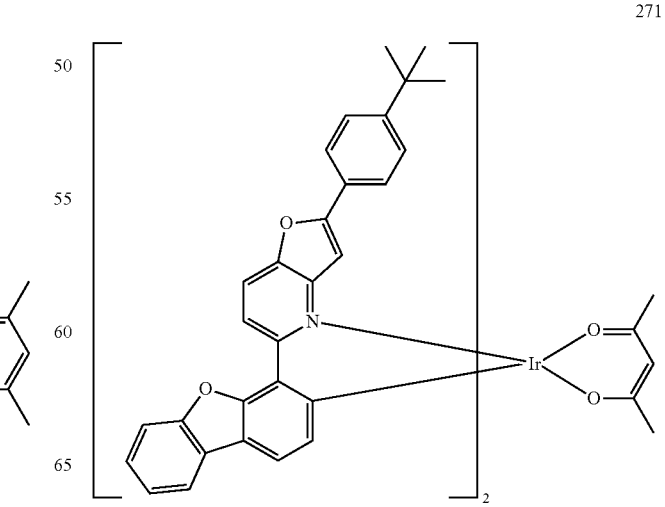
270
271

272
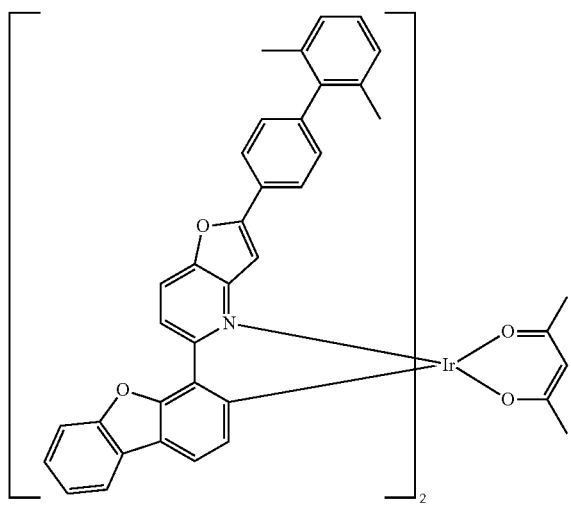
275
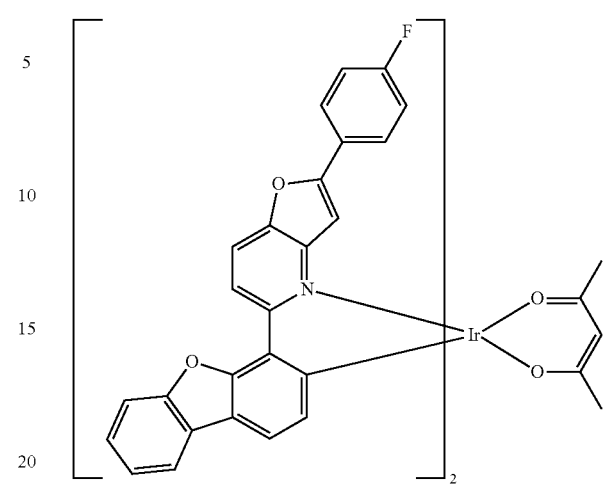
273
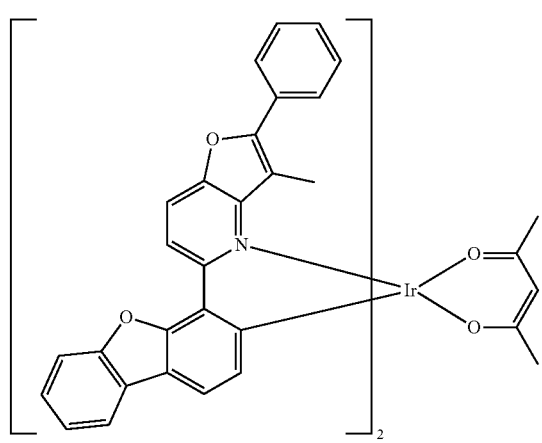
276
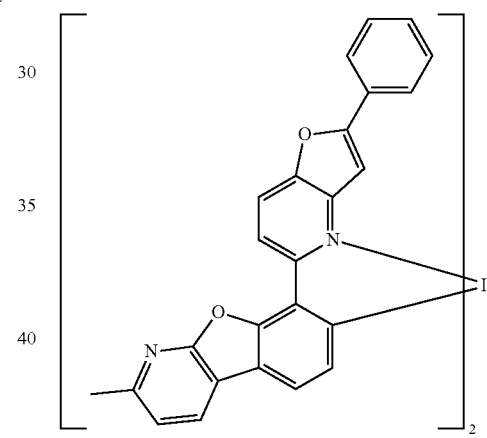
274
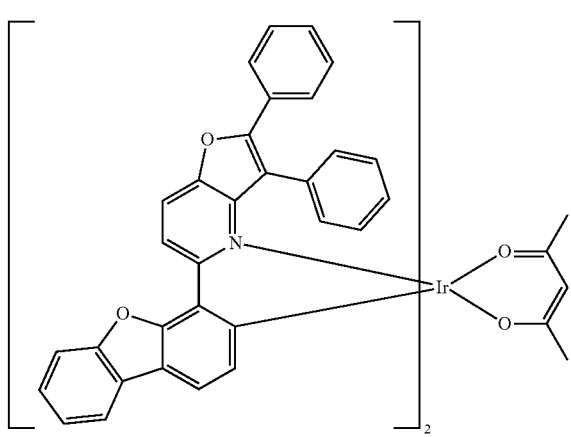
277
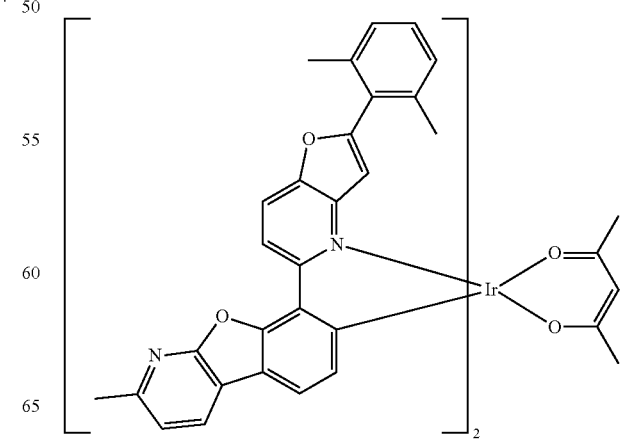

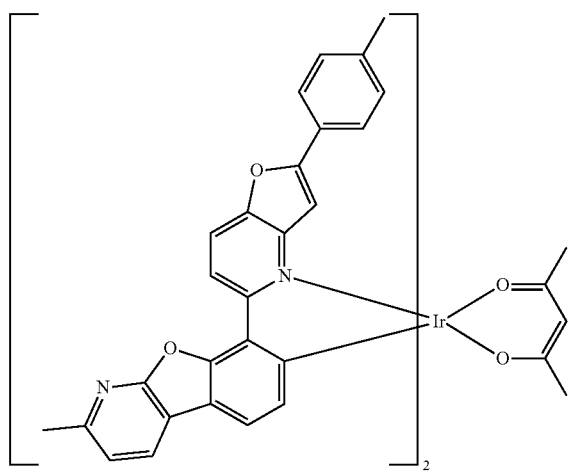
278
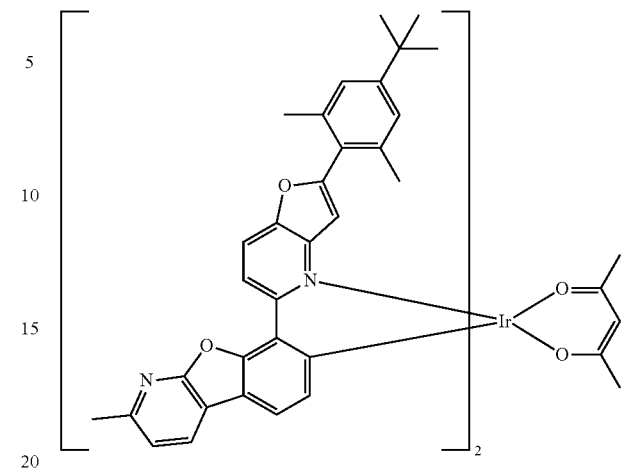
281
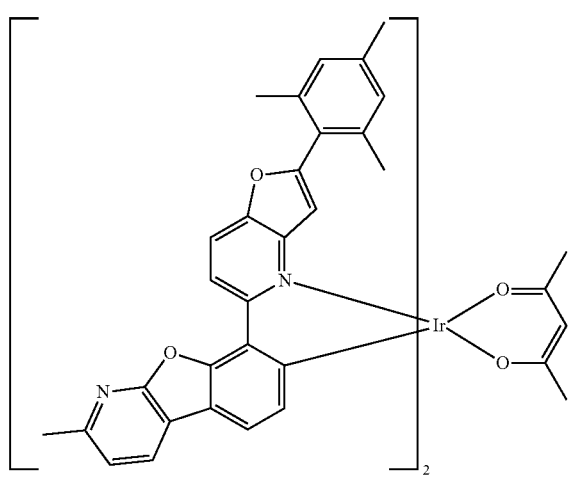
279
282
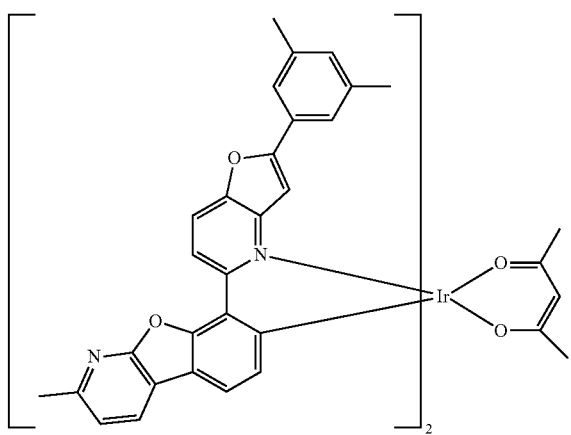
280
283

403
-continued
284
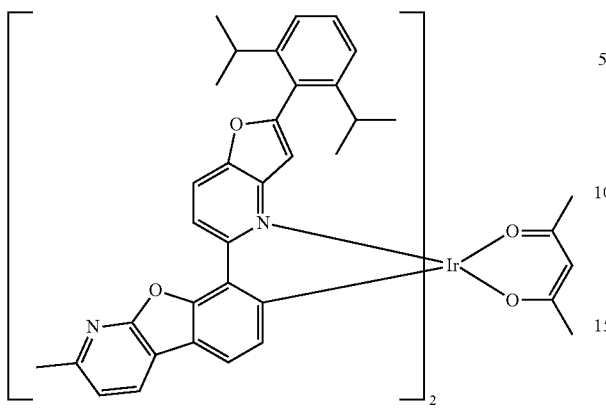
285
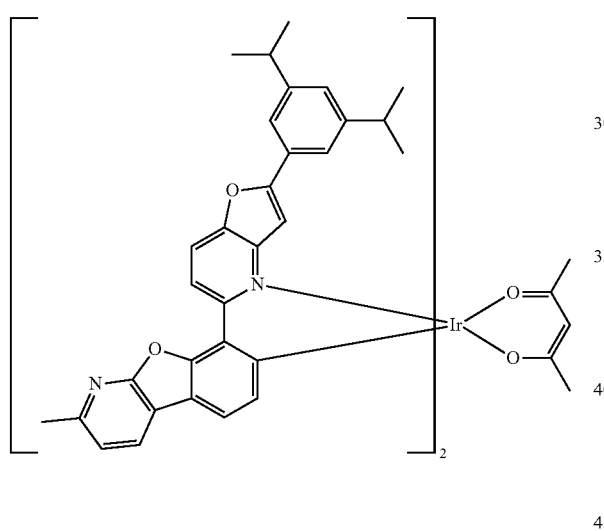
286
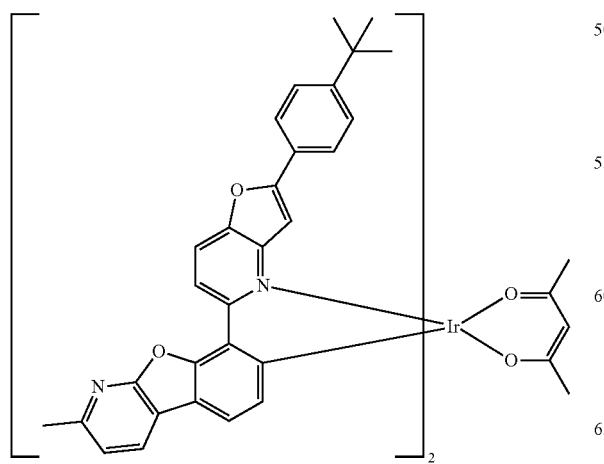
404
-continued
287
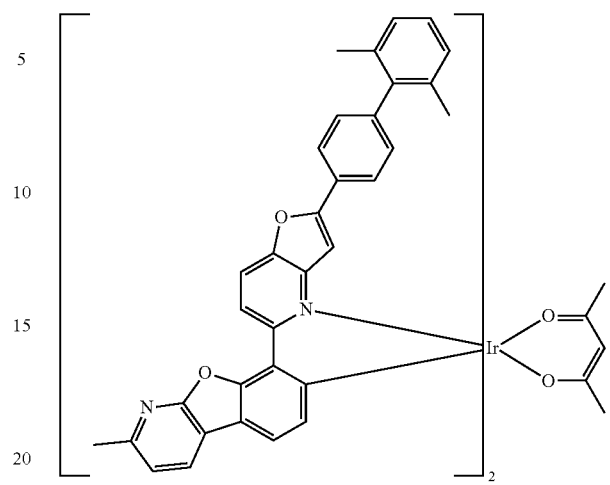
288
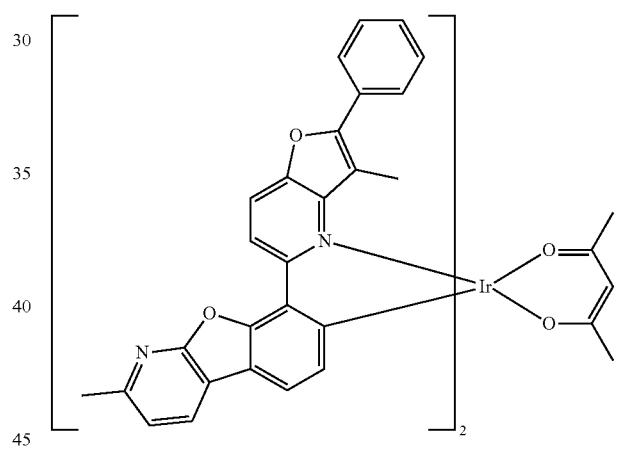
289
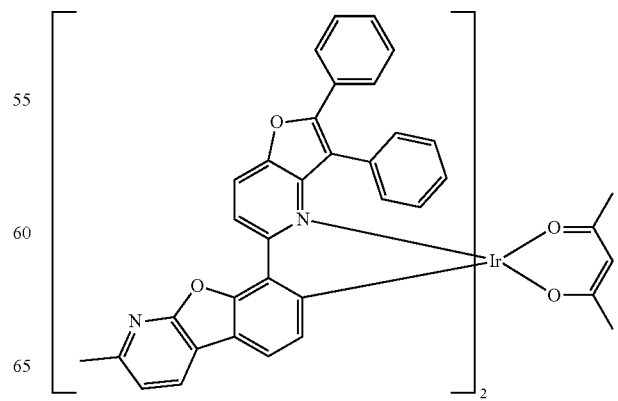

405 -continued
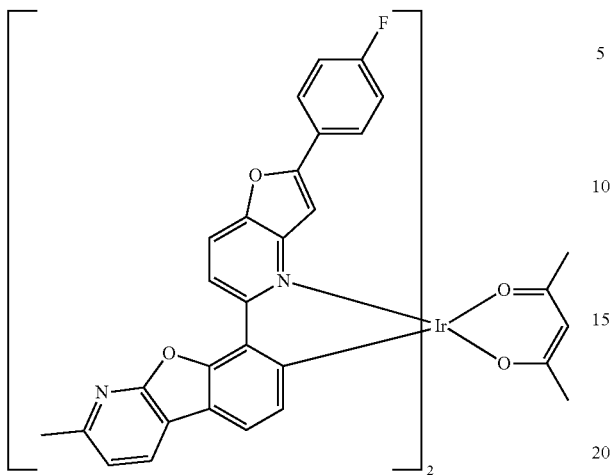
290
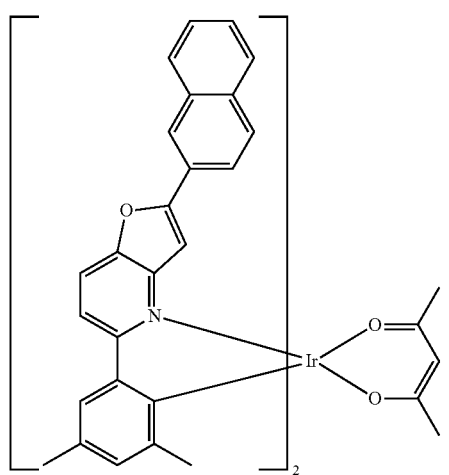
291
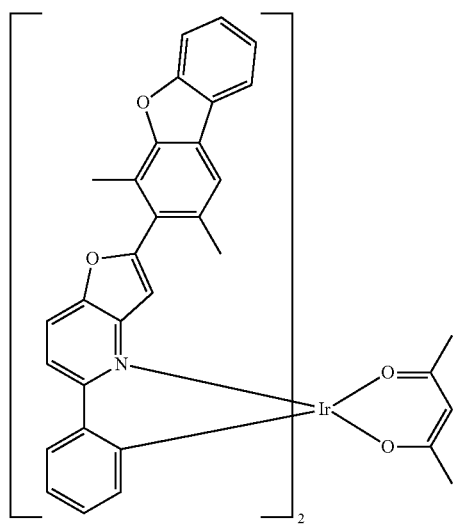
292
406 -continued
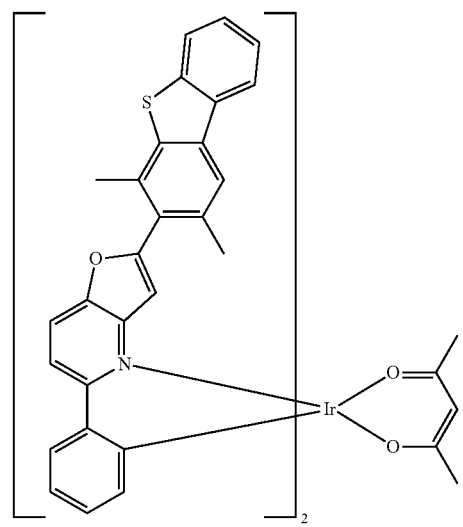
293
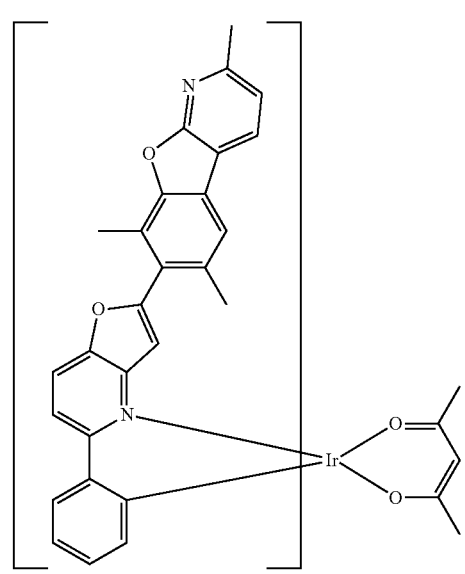
294
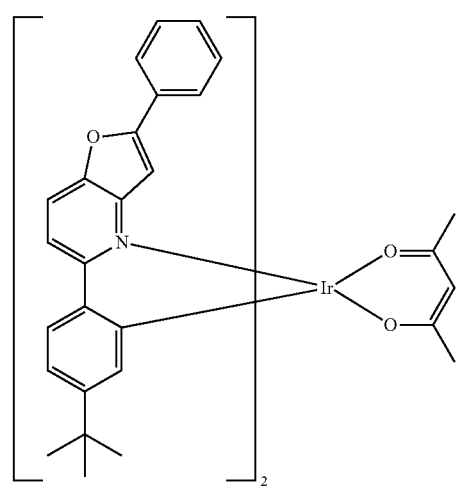
295

296
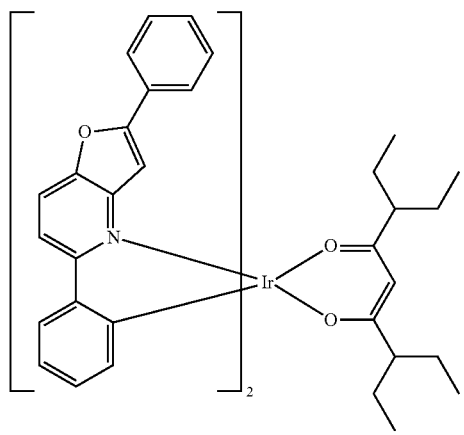
297
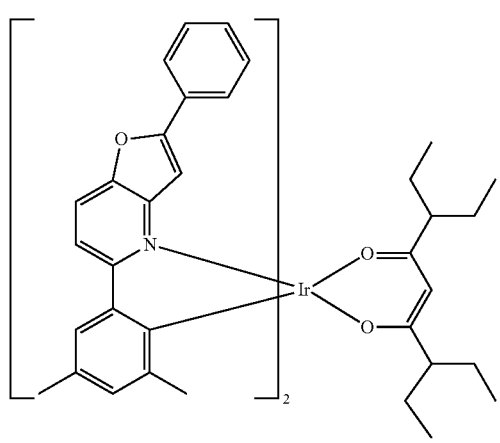
298
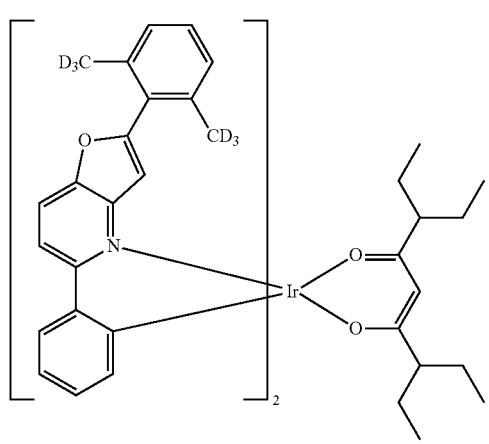
299
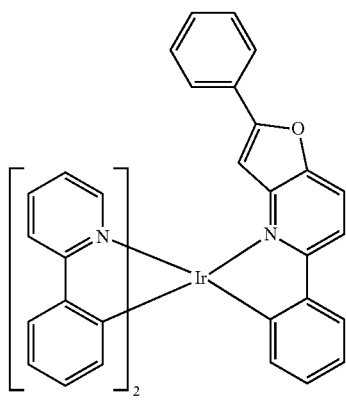
300
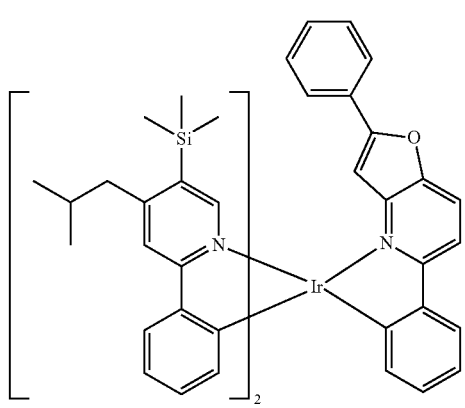
301
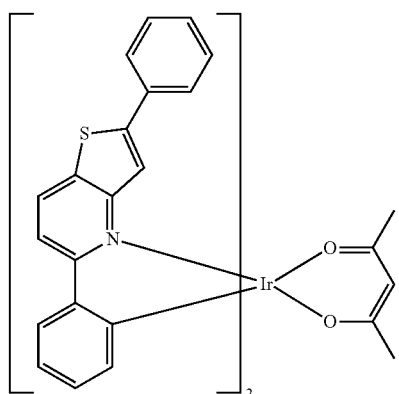
302
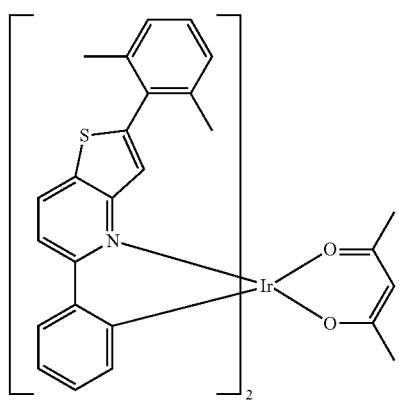

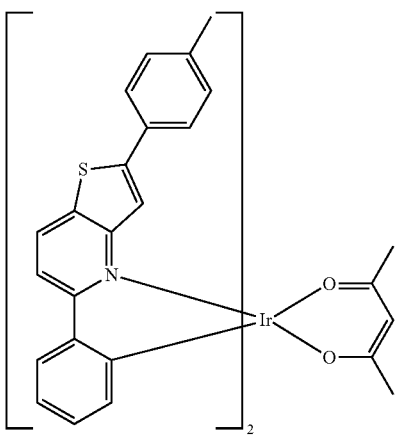
303
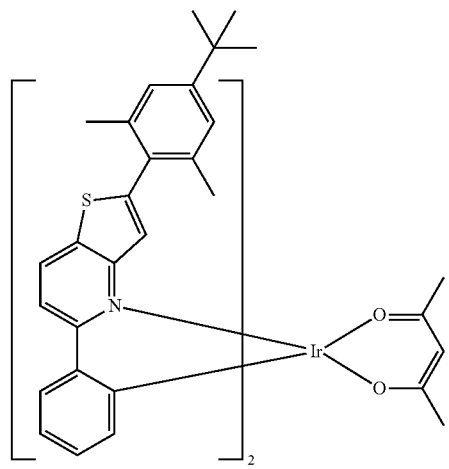
306
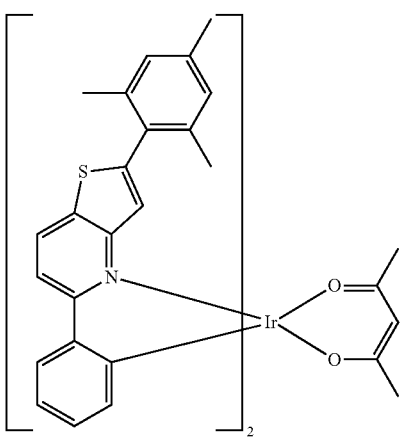
304
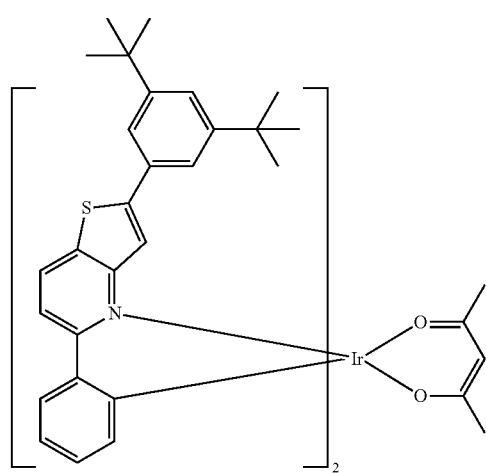
307
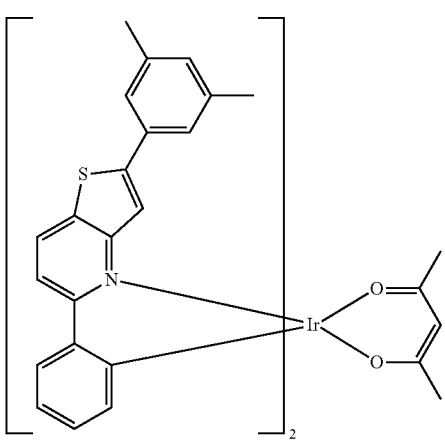
305
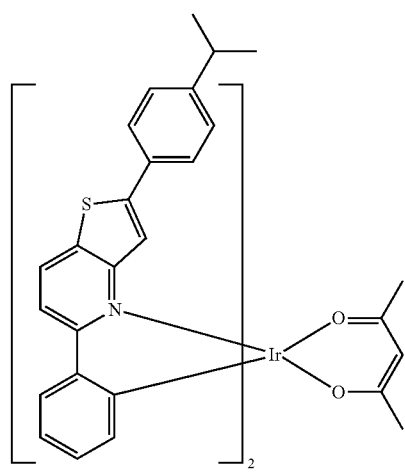
308

411
-continued
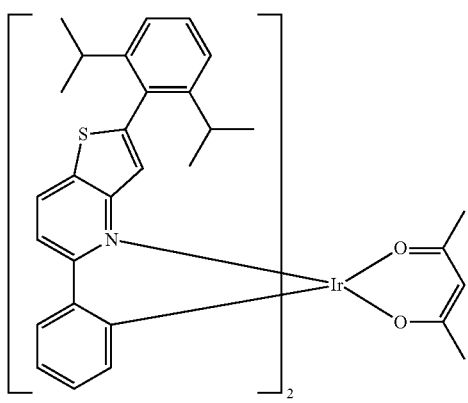
309
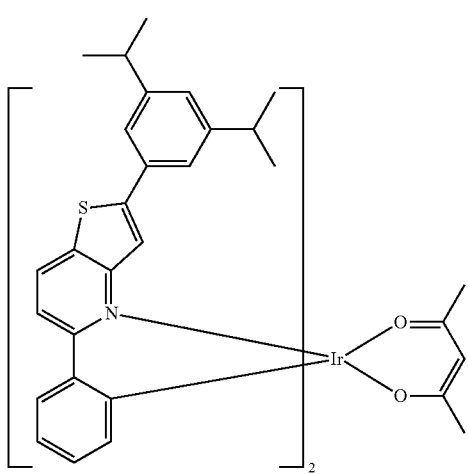
310
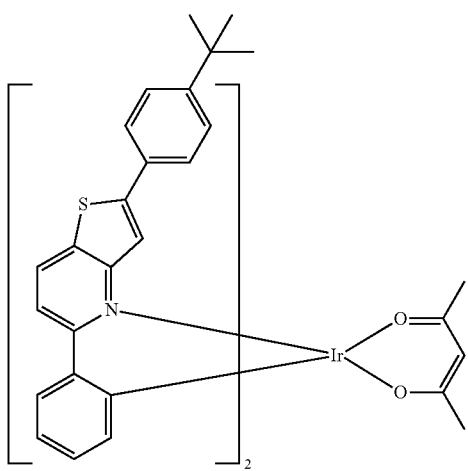
311
412
-continued
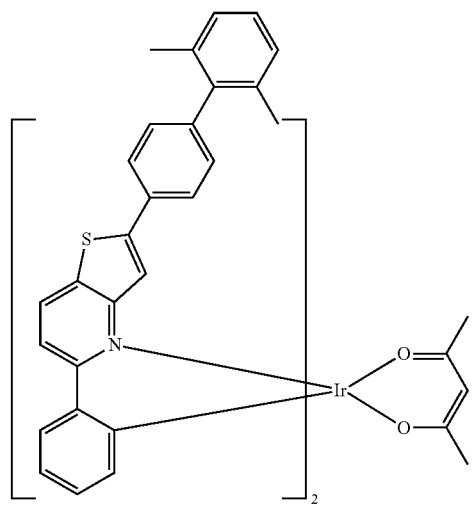
312
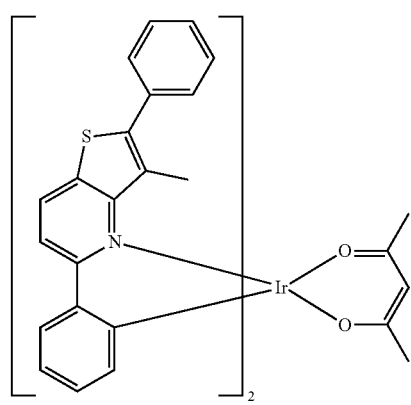
313
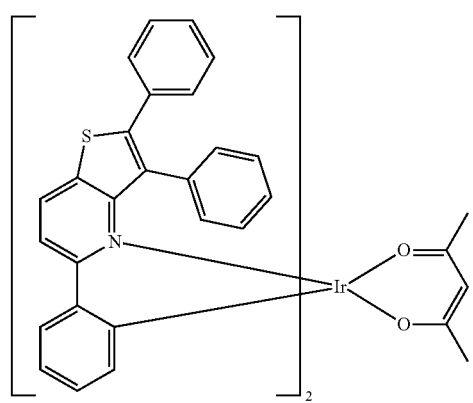
314

413
-continued
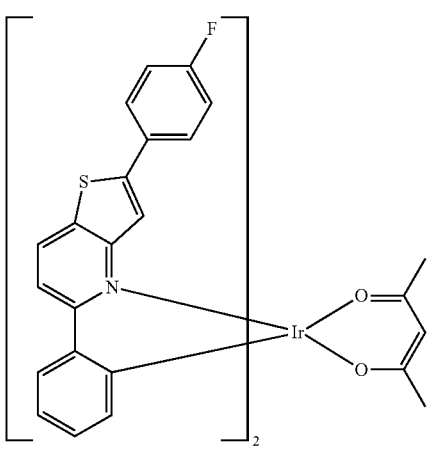
315
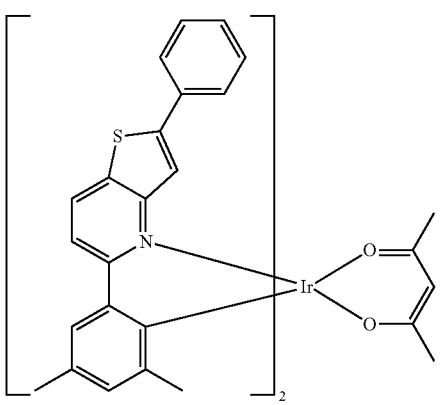
316
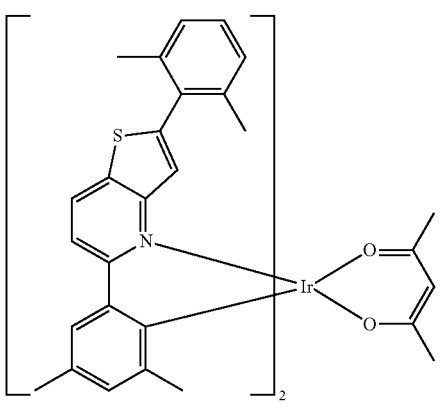
317
414
-continued
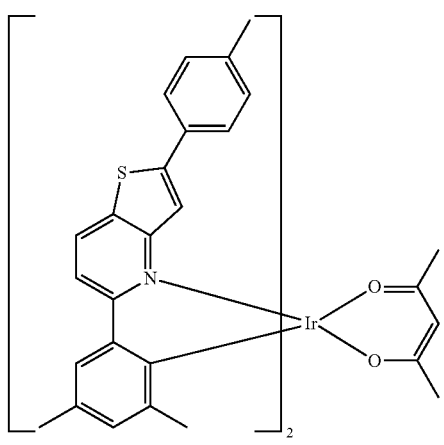
318
319
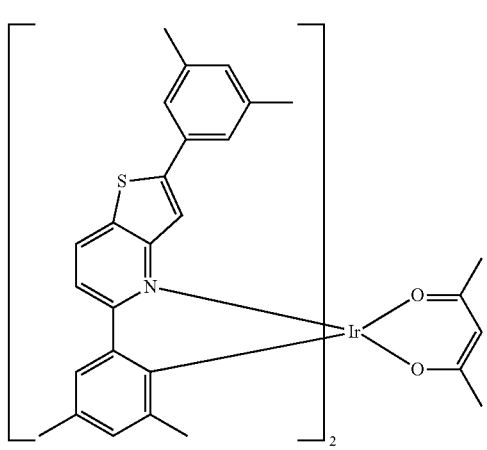
320

321
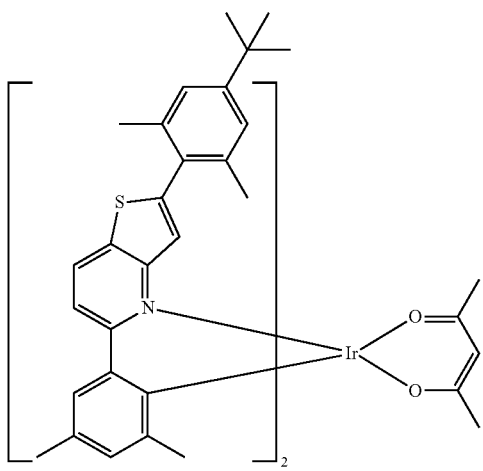
322
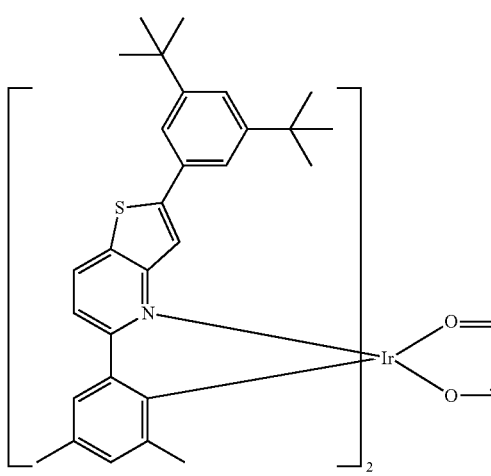
323
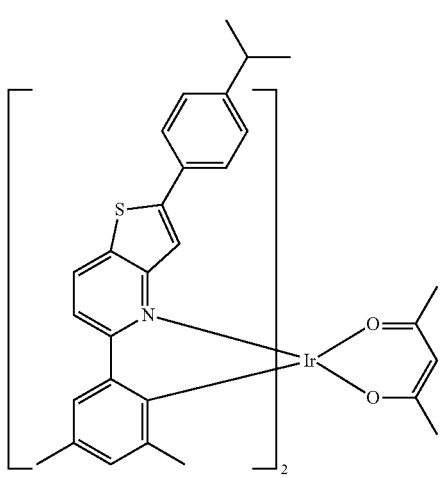
324
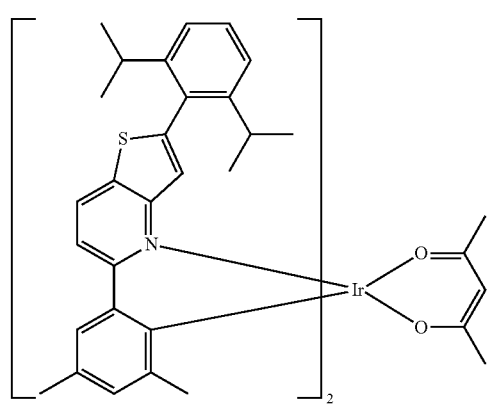
325
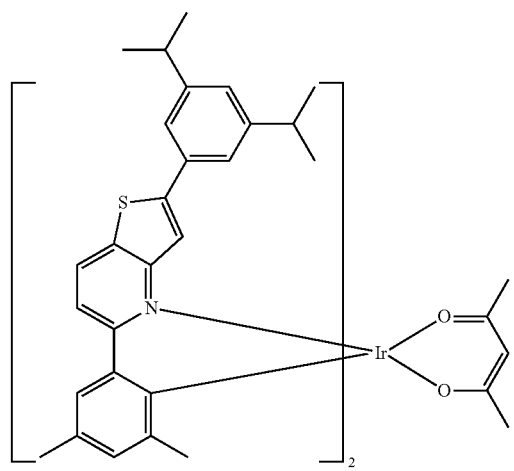
326
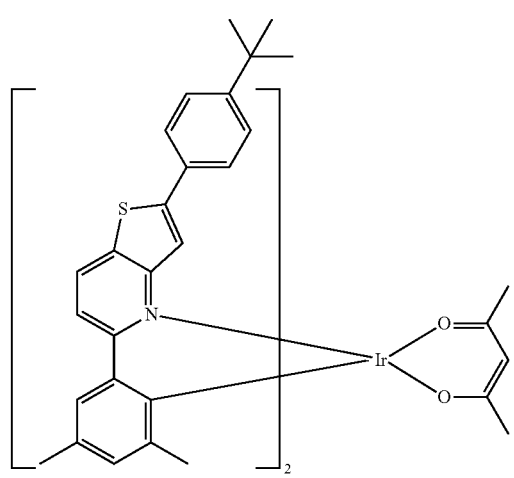

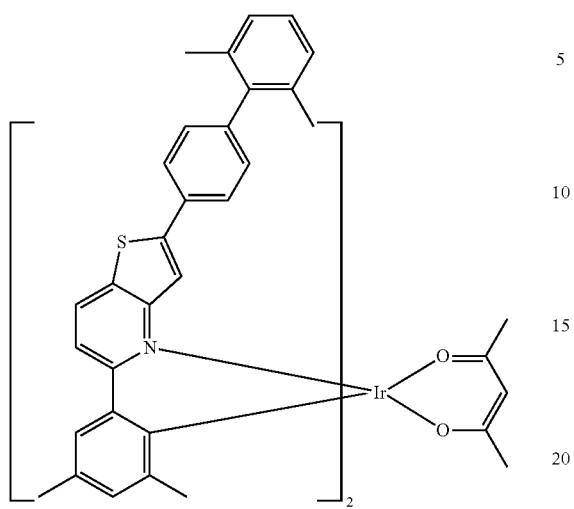
327
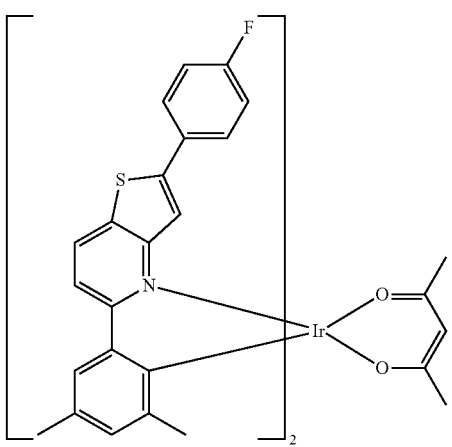
330
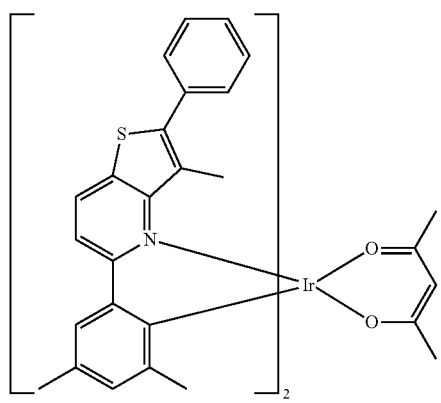
328
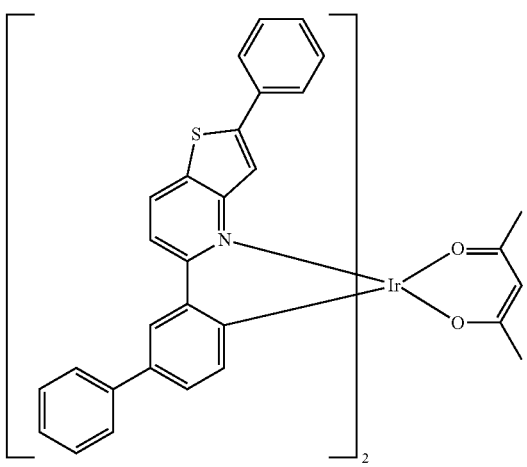
331
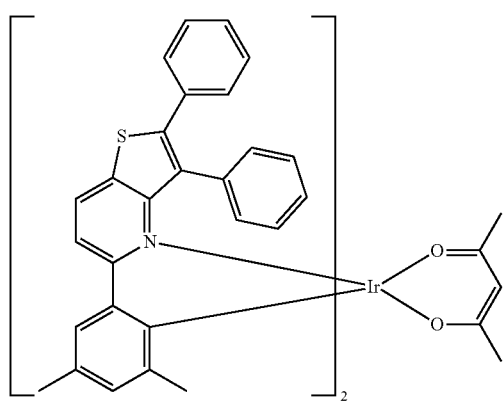
329
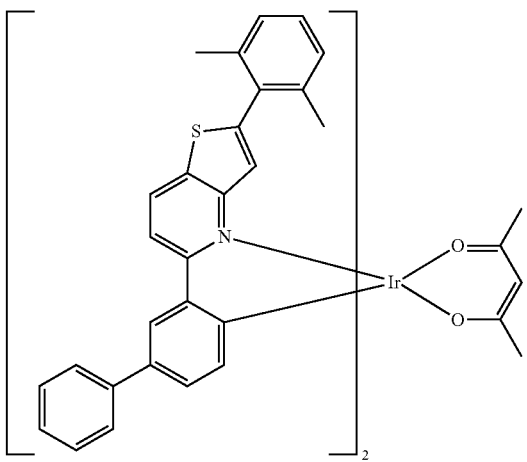
332

-continued
333
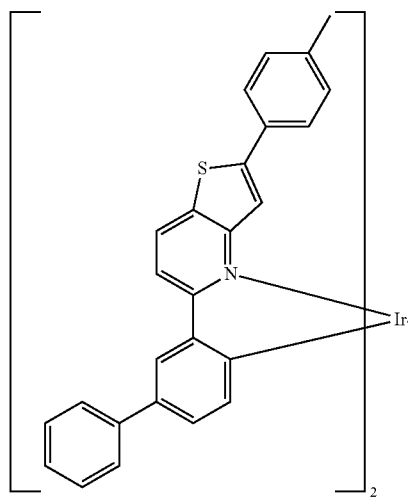
334
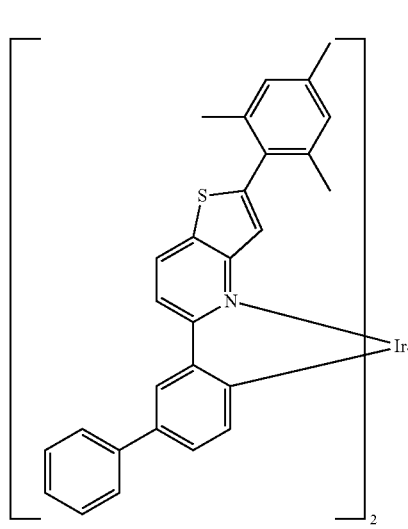
335
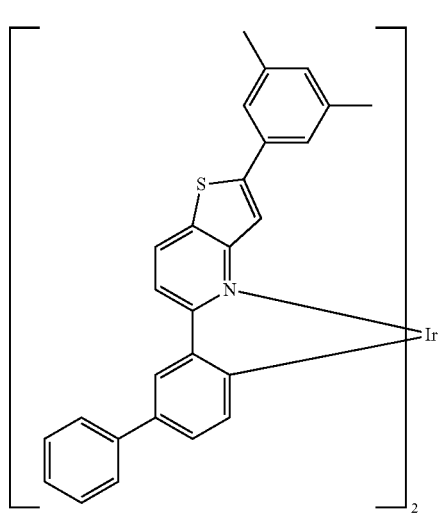
-continued
336
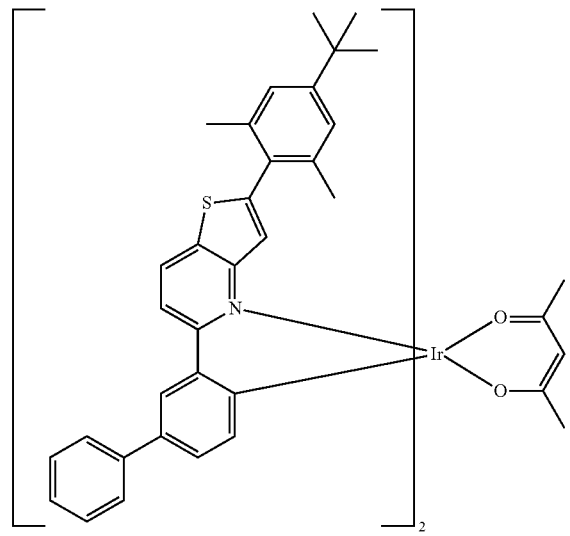
337
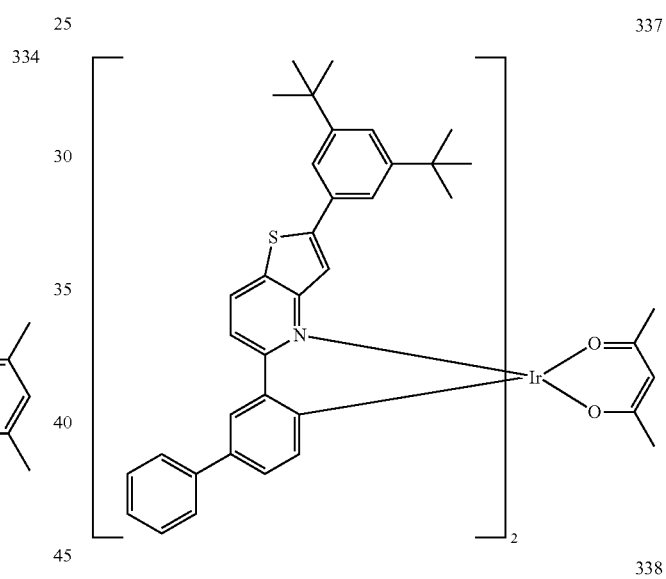
338
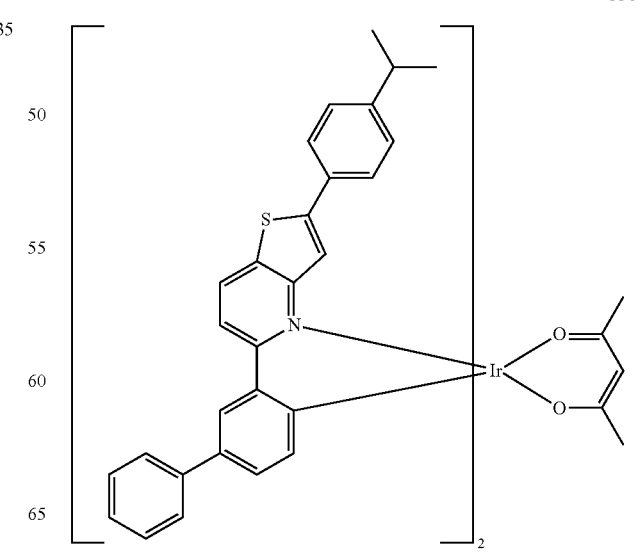

339
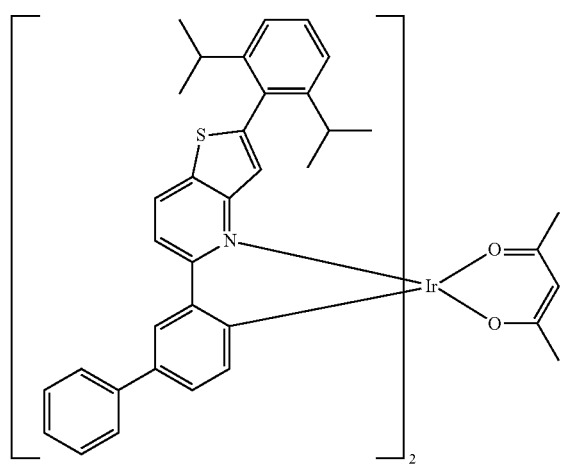
340
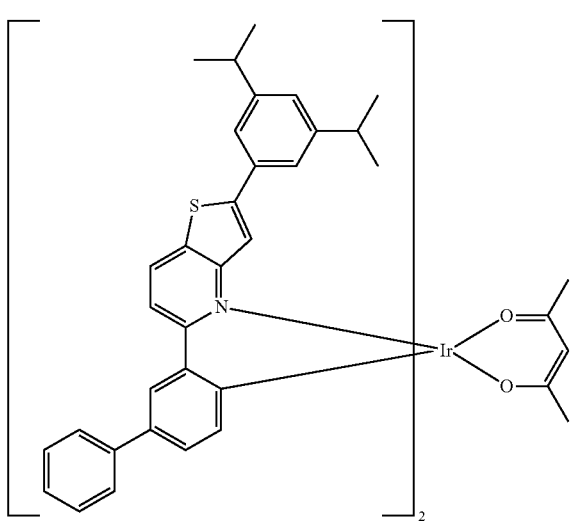
341
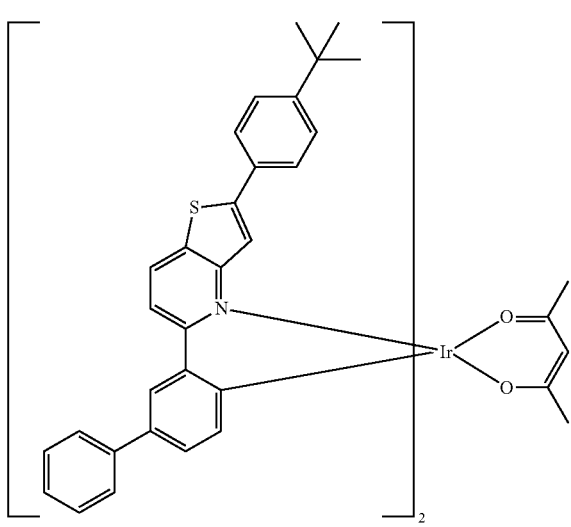
342
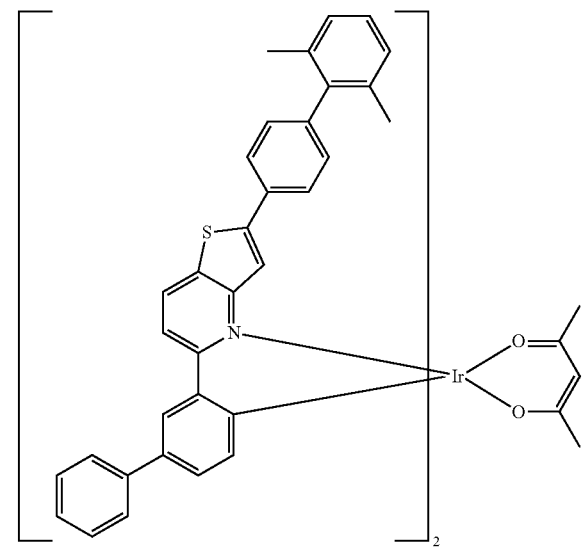
343
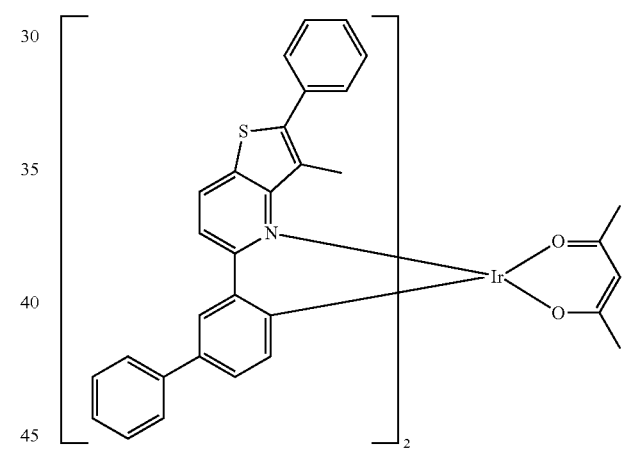
344
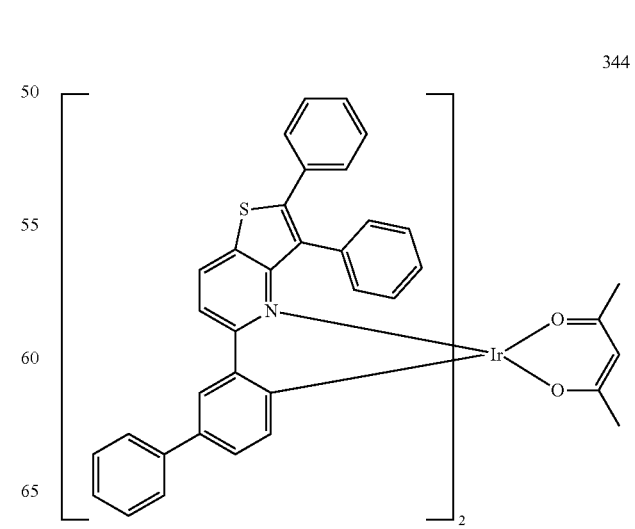

-continued
345
346
347
348
349
350
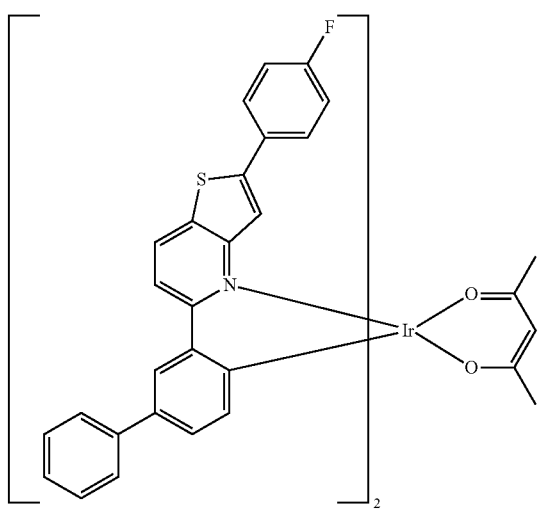
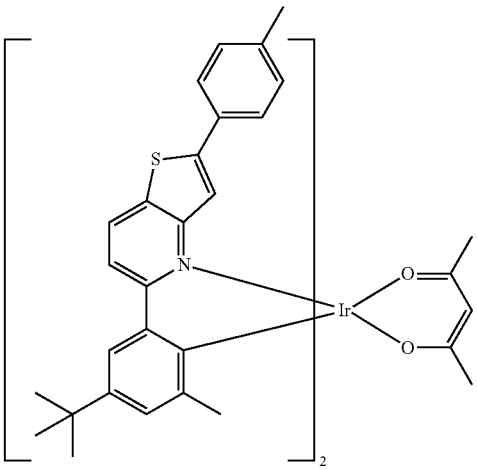
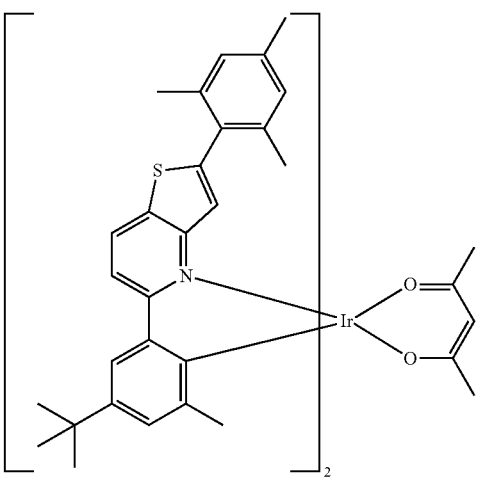
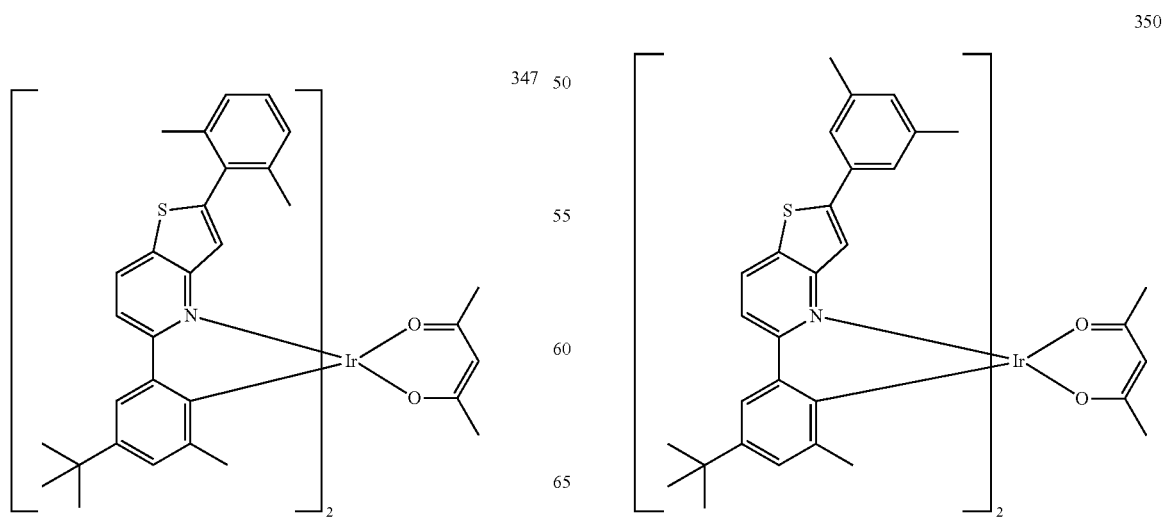

351
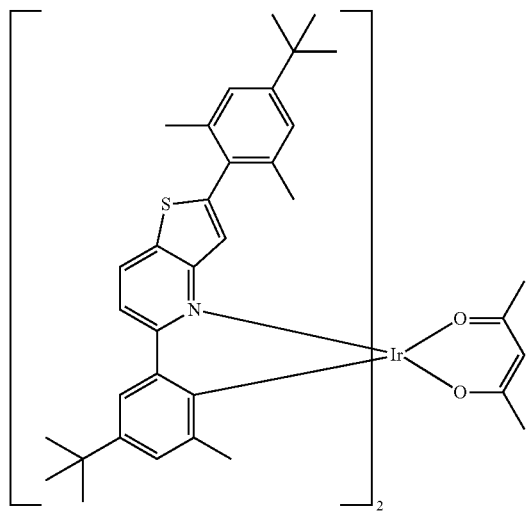
352
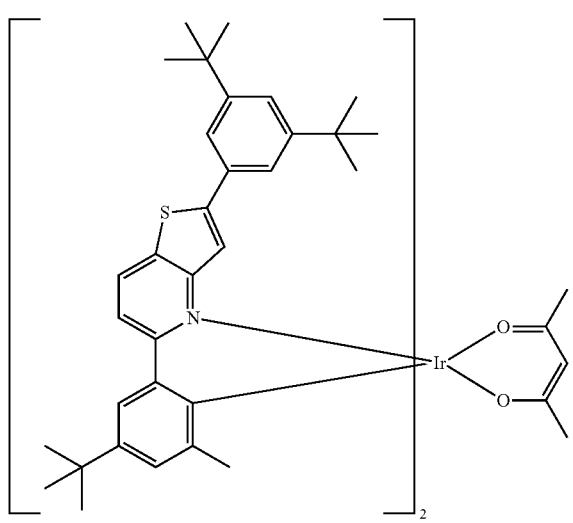
353
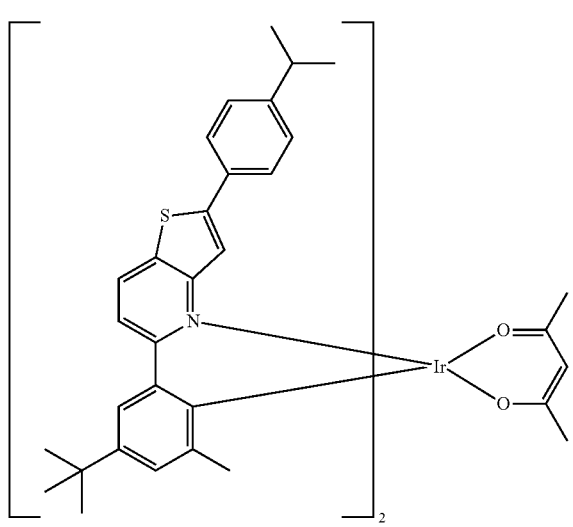
354
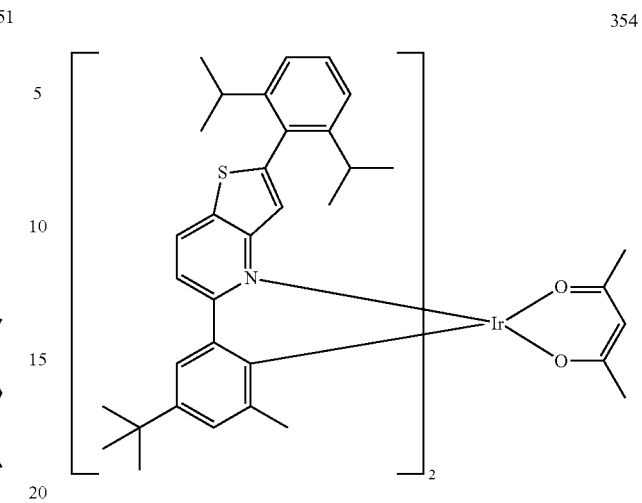
355
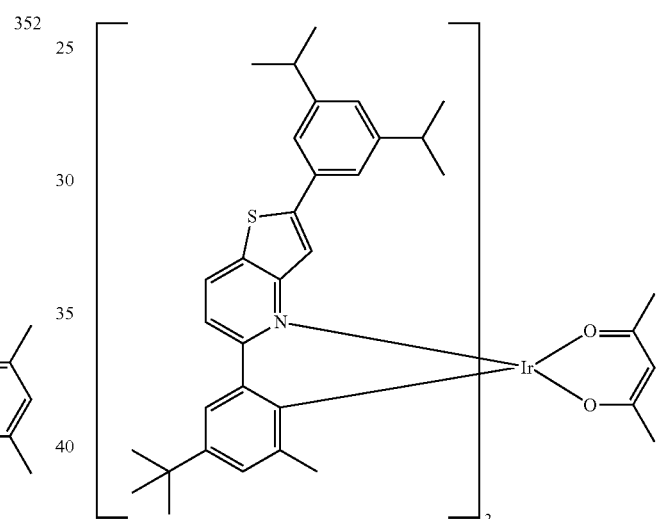
356
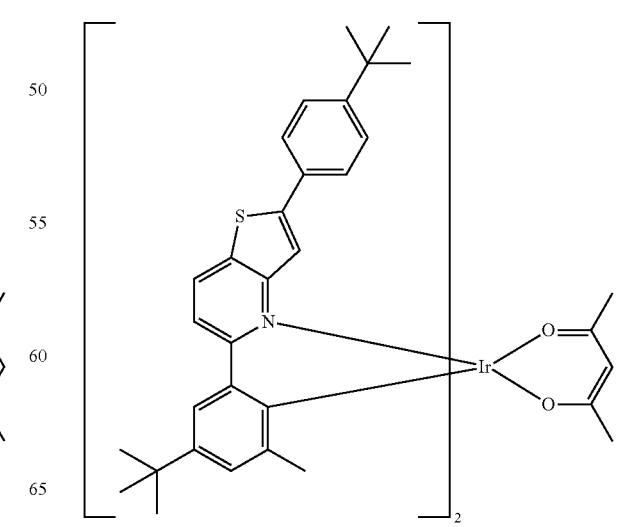

-continued
357
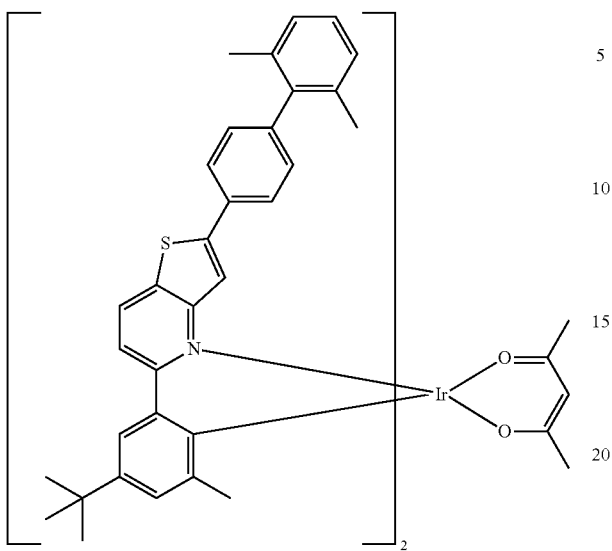
358
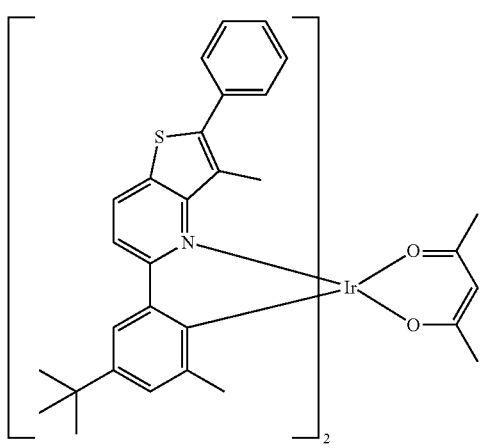
359
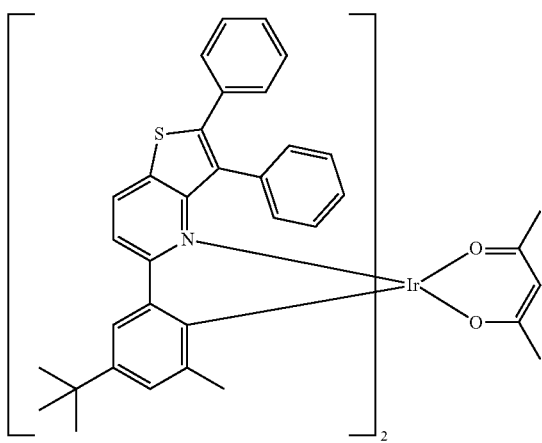
-continued
360
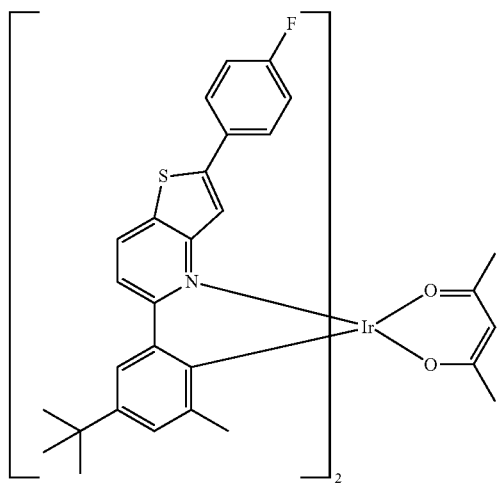
361
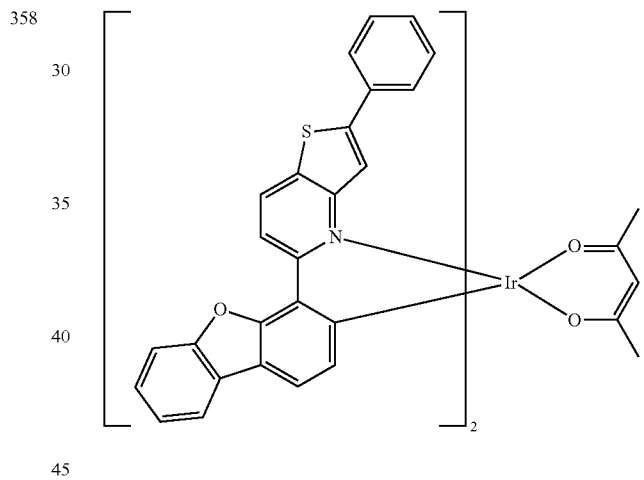
362
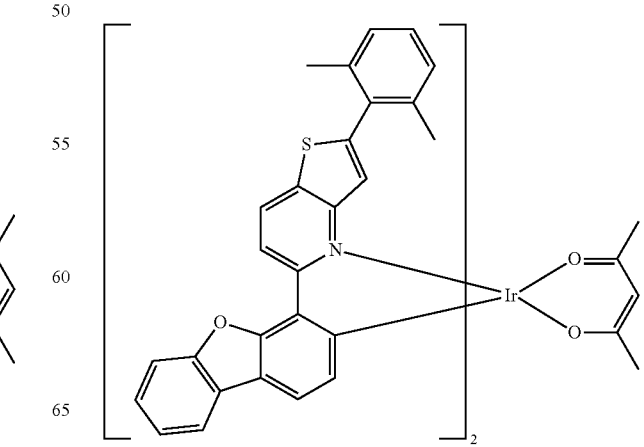

429
-continued
363
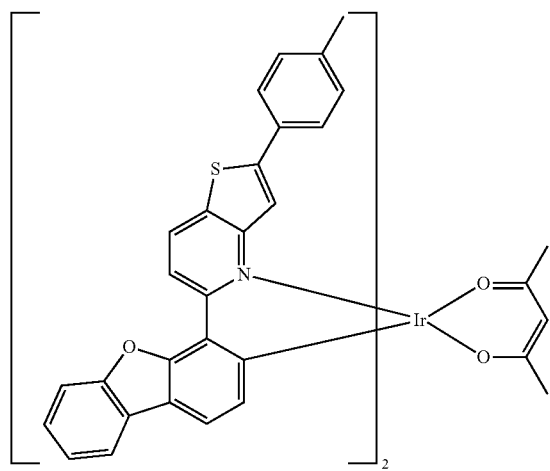
364
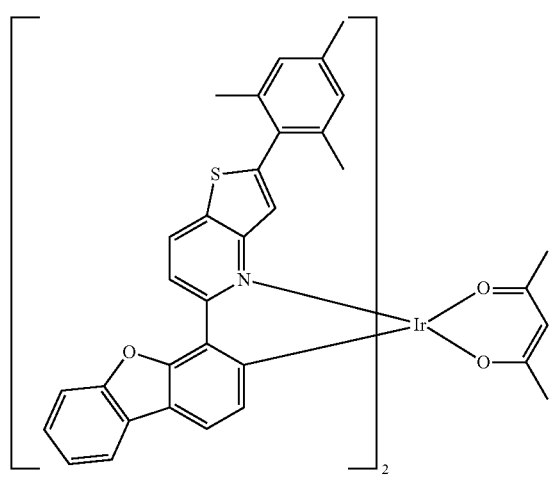
365
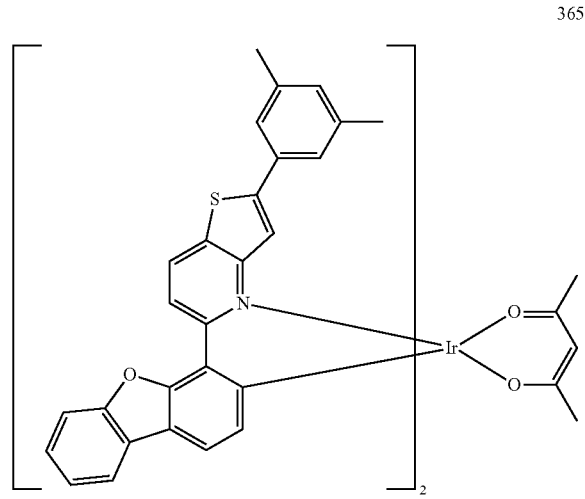
430
-continued
366
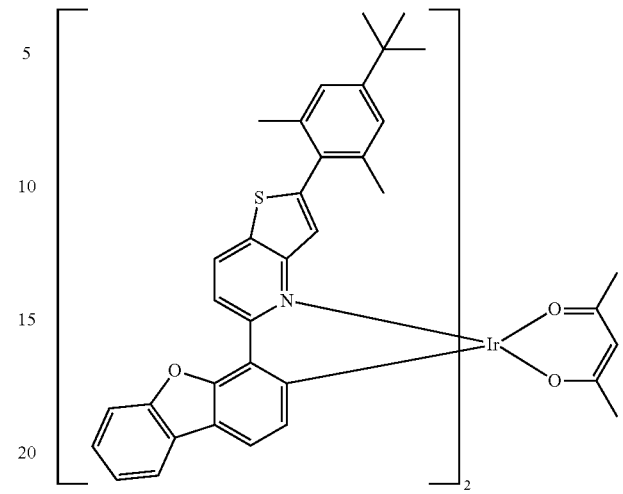
367
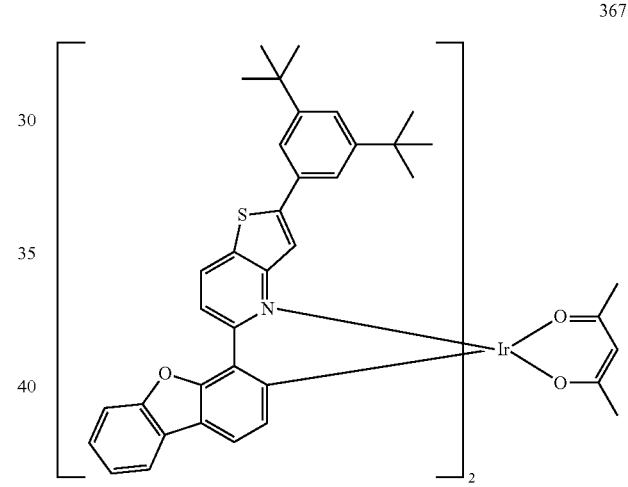
368

-continued
369
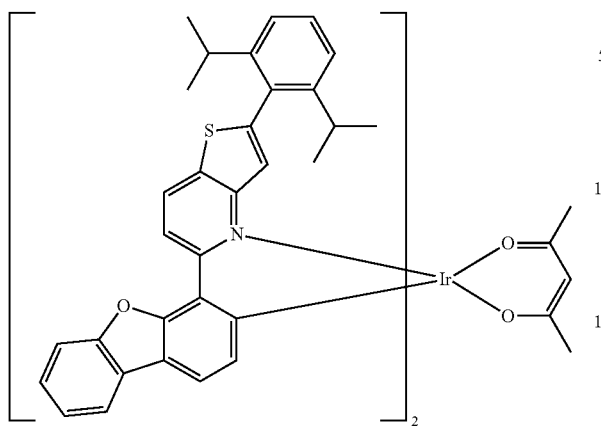
370
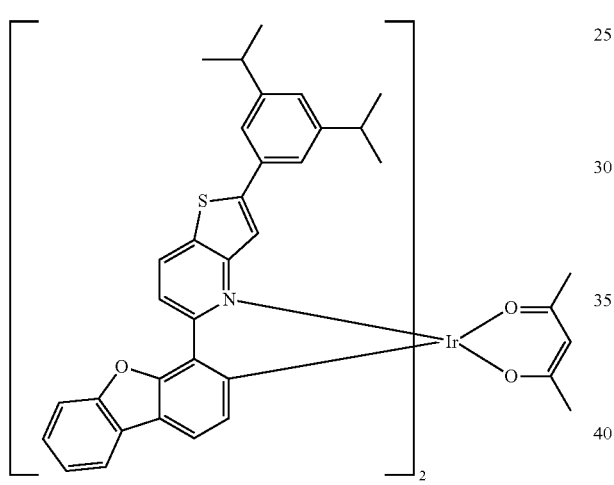
371
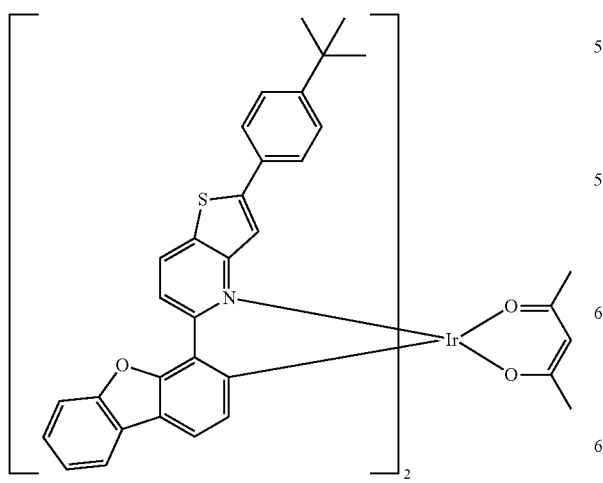
-continued
372
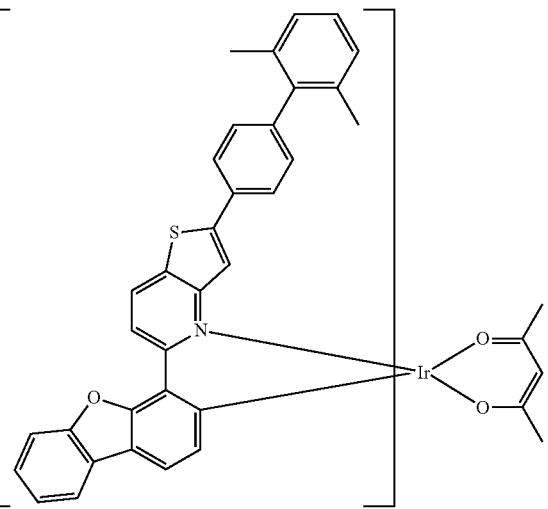
373
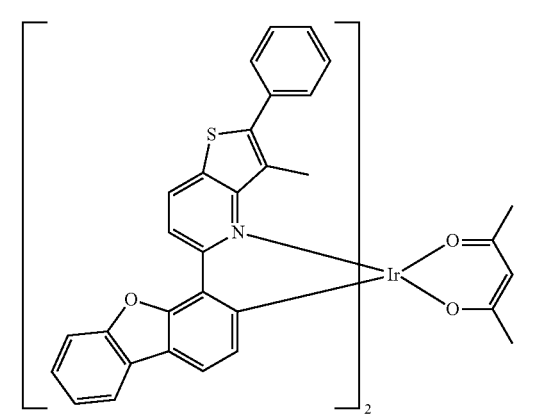
374
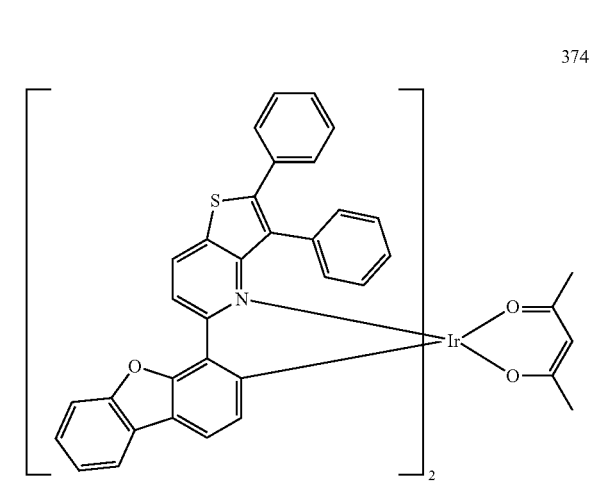

433
-continued
375
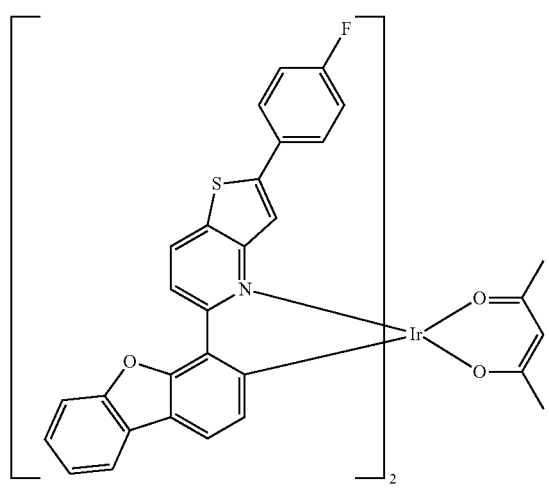
376
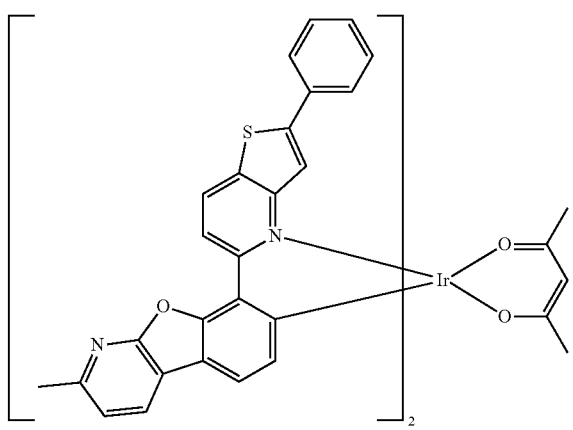
377
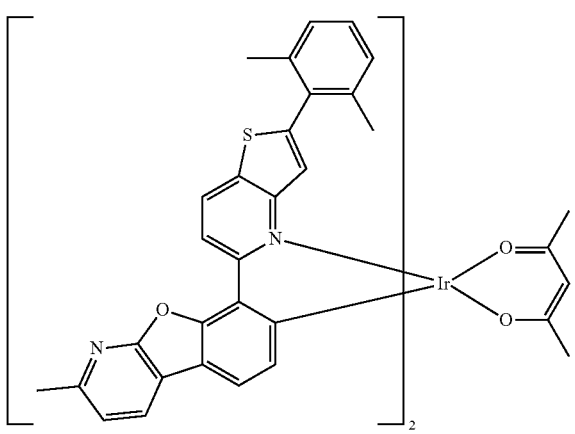
434
-continued
378
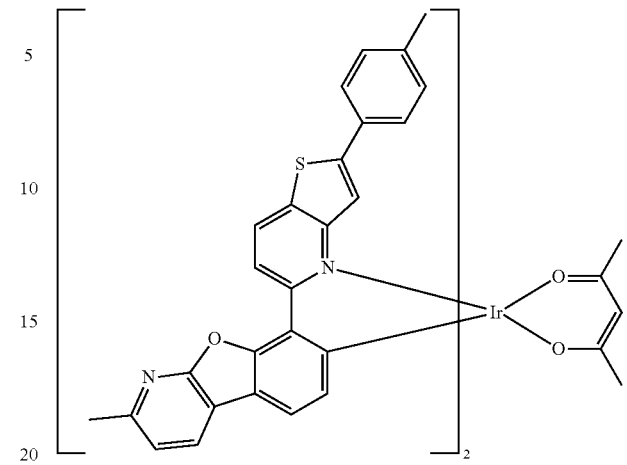
379
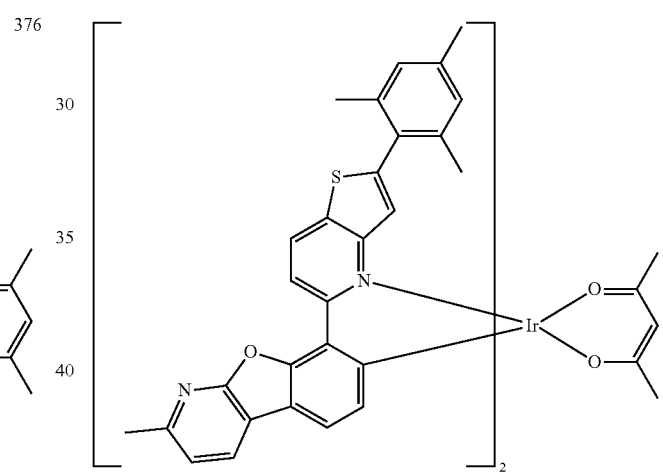
380
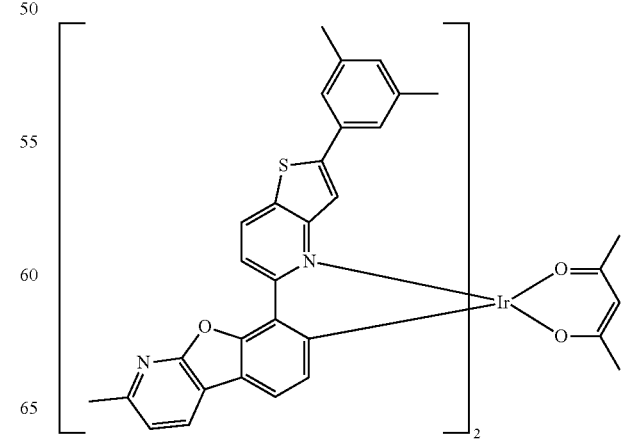

435
-continued
436
-continued
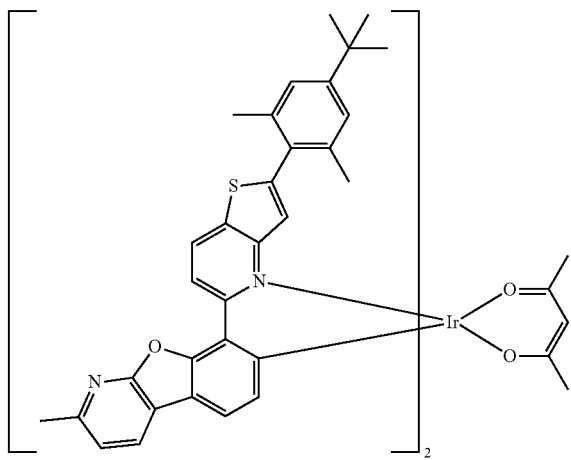
381
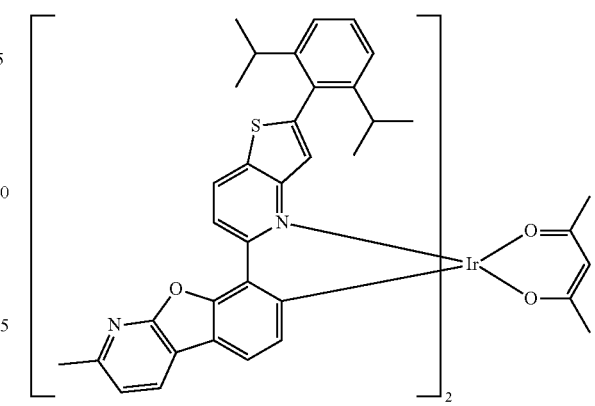
384
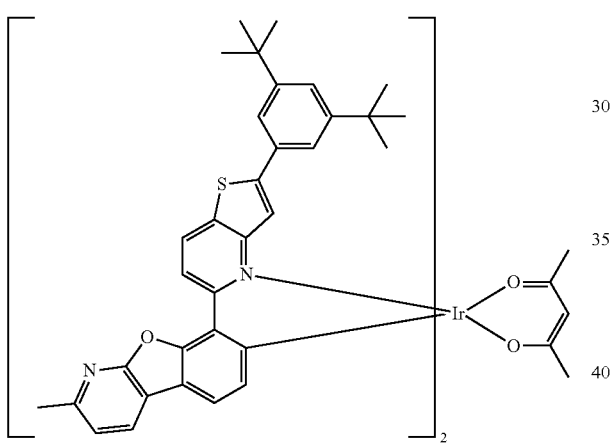
382
385
383
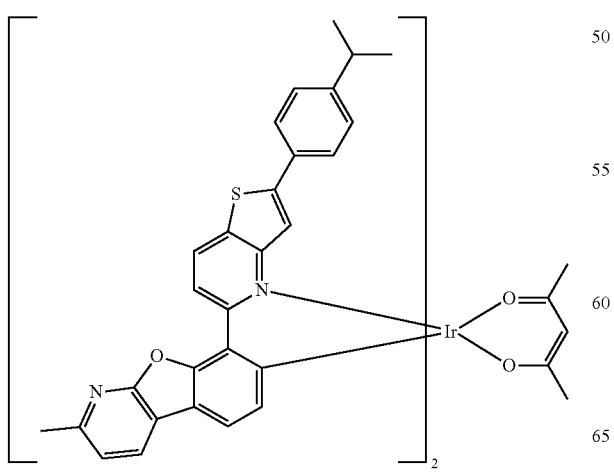
386

387
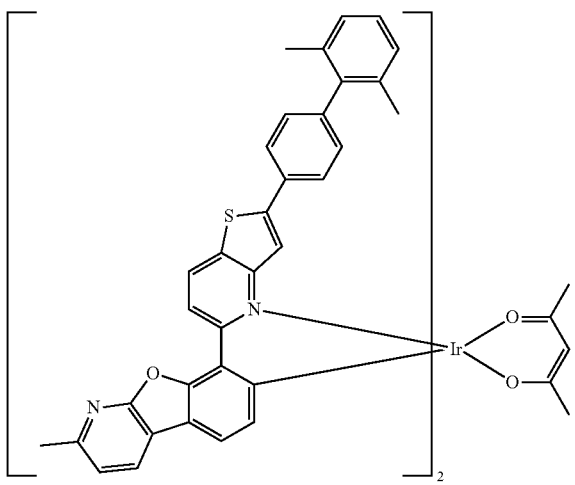
388
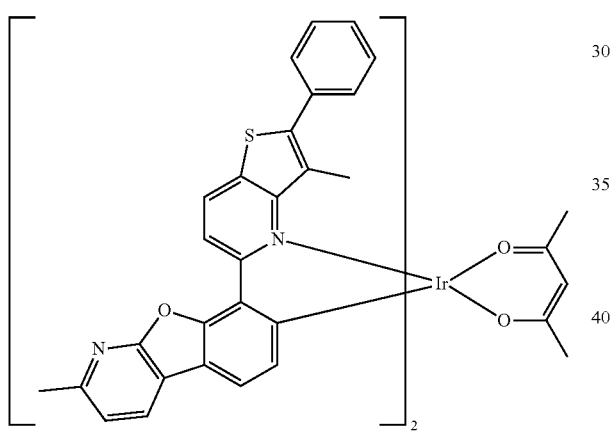
389
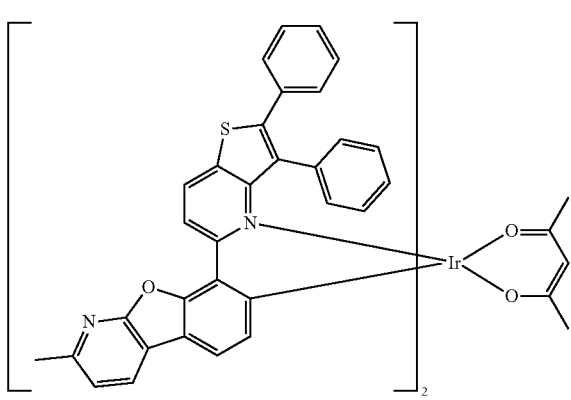
390
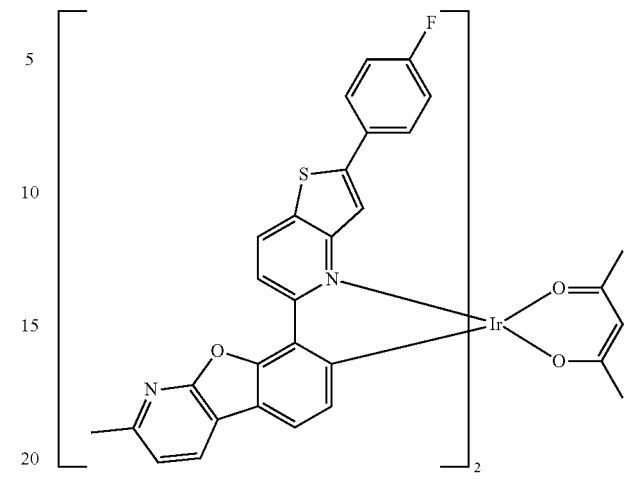
391
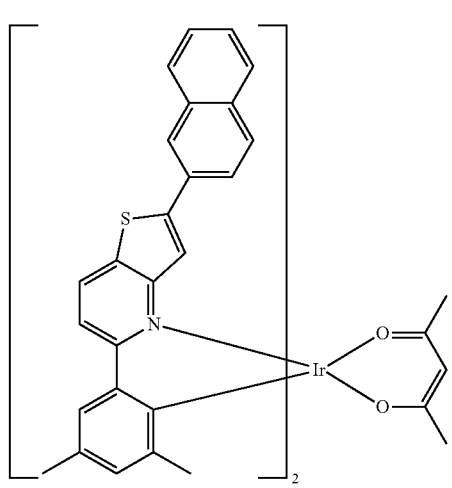
392
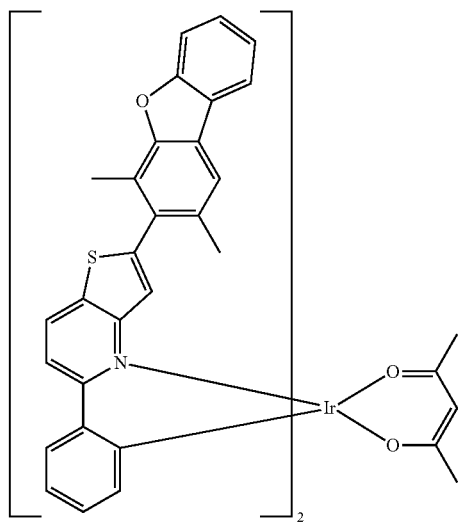

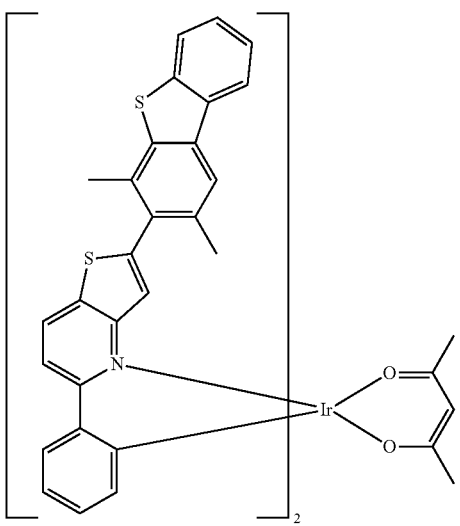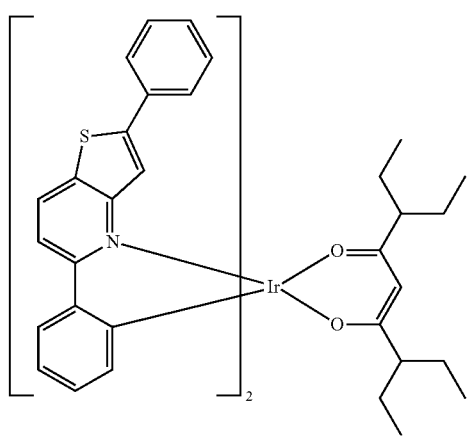

399
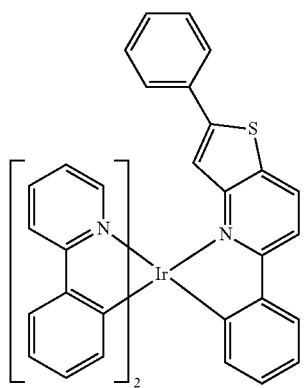
400
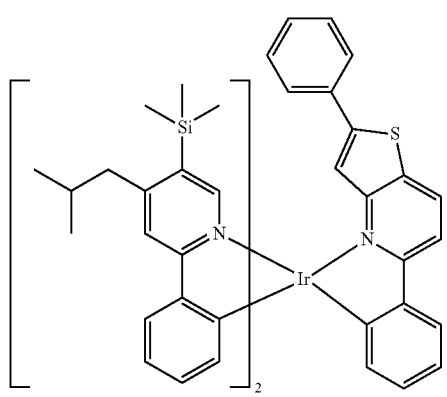
401
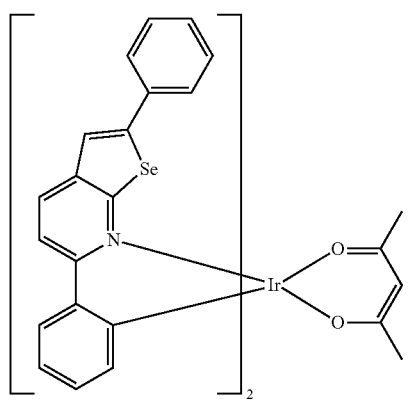
402
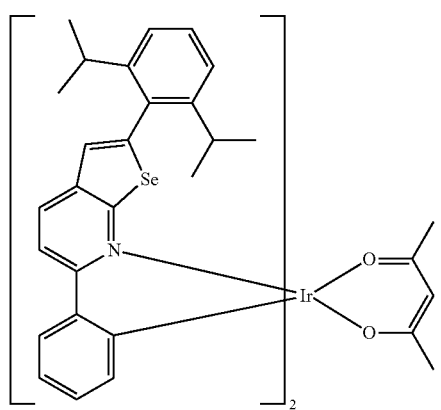
403
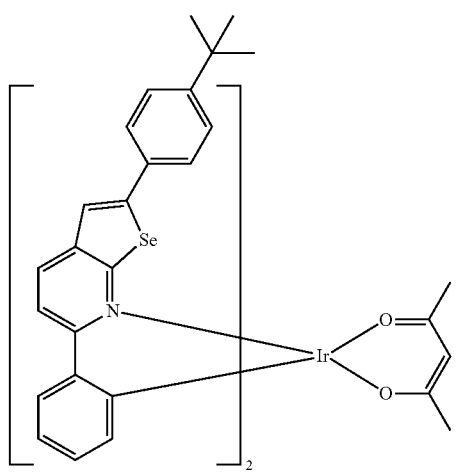
404
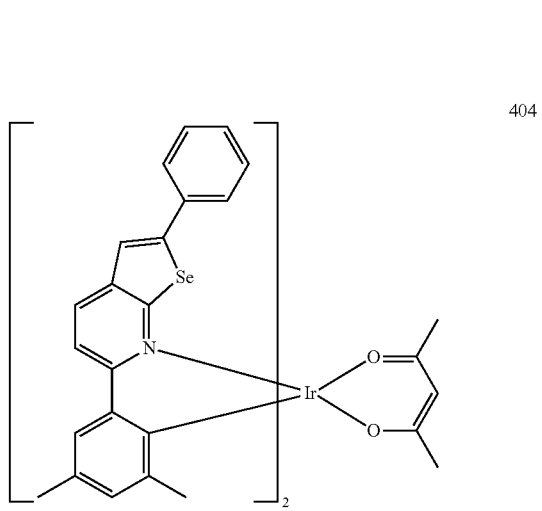
405
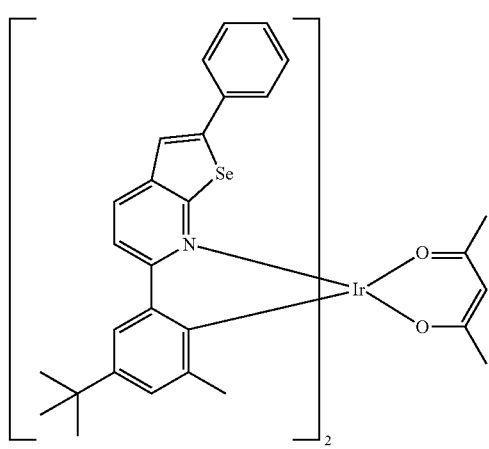

406
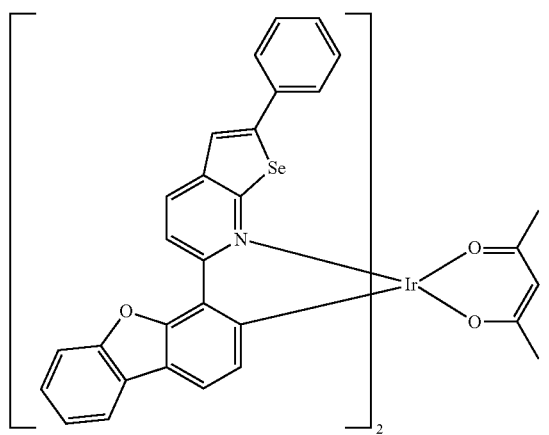
407
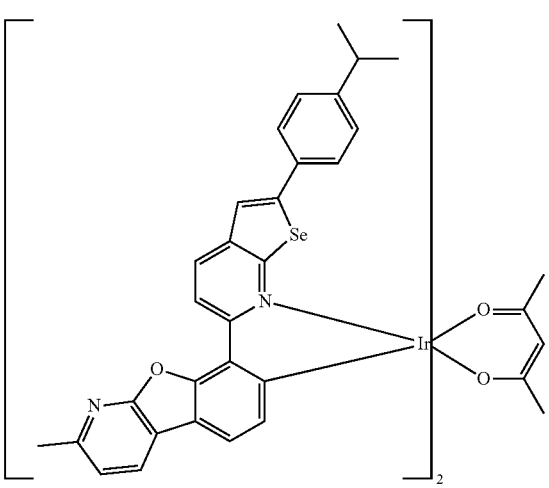
408
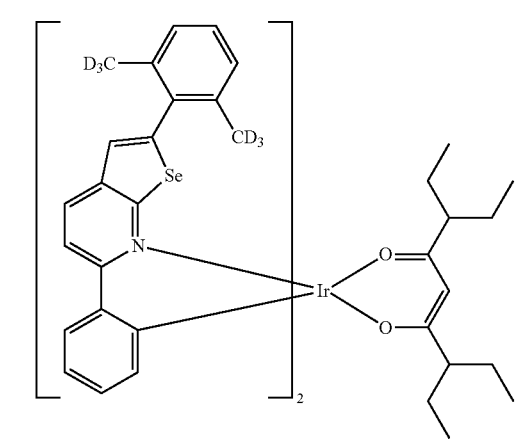
409
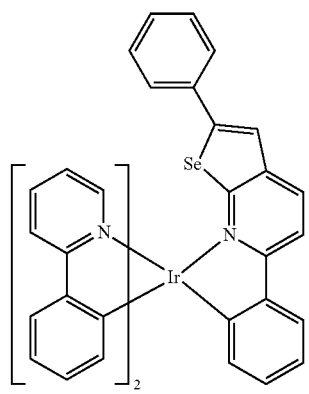
410
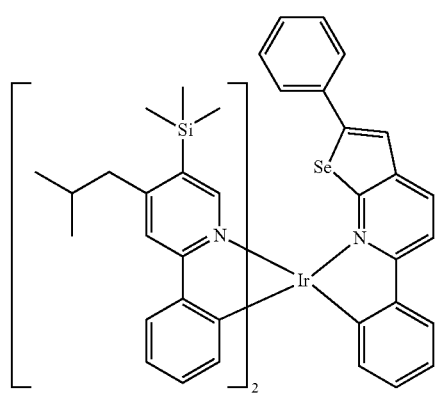
411
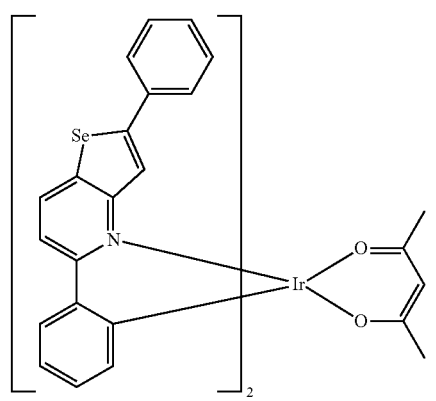
412
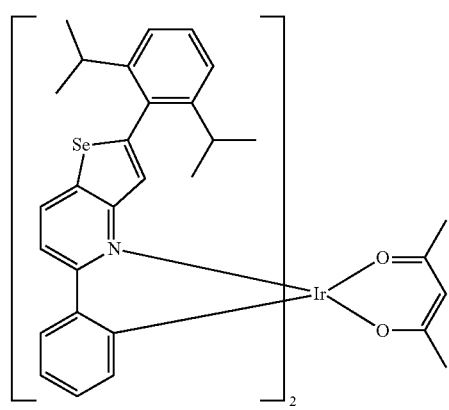

413
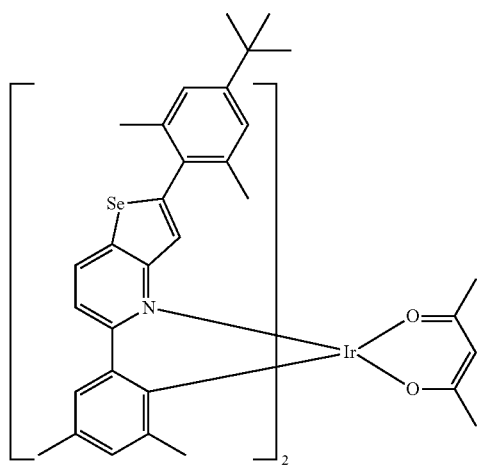
414
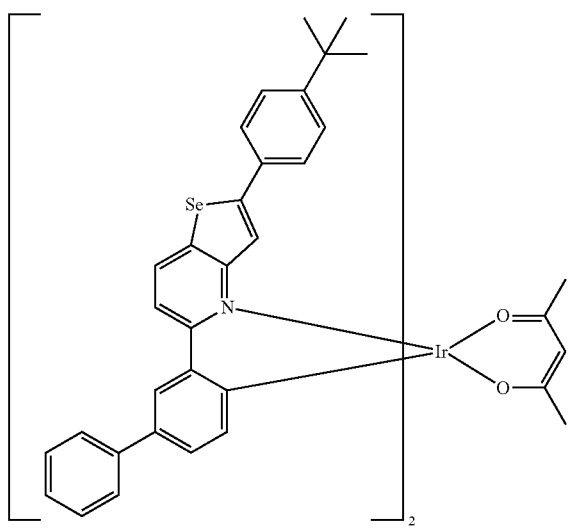
415
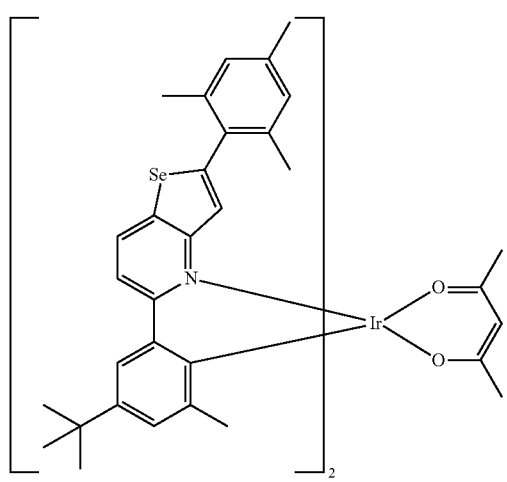
416
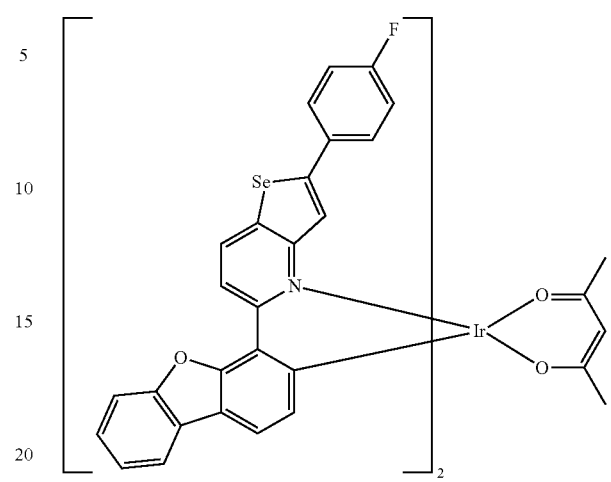
417
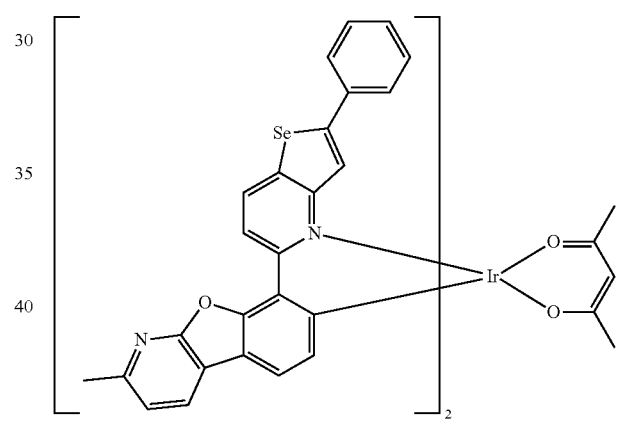
418
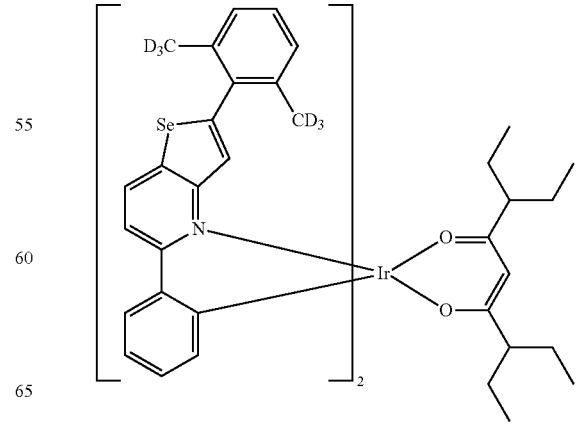

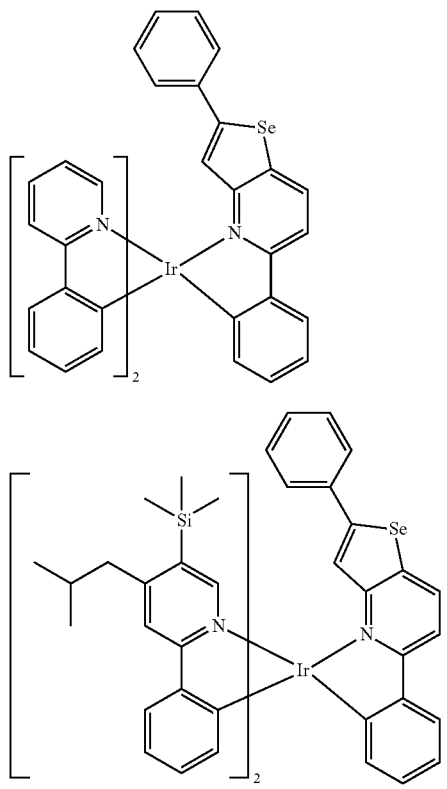

12. An organic light-emitting device comprising:
    a first electrode;
    a second electrode; and
    an organic layer disposed between the first electrode and the second electrode and comprising an emission layer,
    wherein the organic layer comprises at least one organometallic compound of claim 1.

13. The organic light-emitting device of claim 12, wherein
    the first electrode is an anode,
    the second electrode is a cathode,
    the organic layer further comprises a hole transport region disposed between the first electrode and the emission layer and an electron transport region disposed between the emission layer and the second electrode,
    the hole transport region comprises a hole injection layer, a hole transport layer, an electron blocking layer, a buffer layer, or any combination thereof, and
    the electron transport region comprises a hole blocking layer, an electron transport layer, an electron injection layer, or any combination thereof.

14. The organic light-emitting device of claim 12, wherein the emission layer comprises the organometallic compound.

15. The organic light-emitting device of claim 8, wherein the emission layer further comprises a host, and an amount of the host is larger than an amount of the organometallic compound.

16. A diagnostic composition comprising at least one organometallic compound of claim 1.

* * * * *